United States Patent
Arnaiz et al.

[11] Patent Number: 6,140,351
[45] Date of Patent: Oct. 31, 2000

[54] ORTHO-ANTHRANILAMIDE DERIVATIVES AS ANTI-COAGULANTS

[75] Inventors: Damian O. Arnaiz, Hercules; Yuo-Ling Chou, Lafayette; Brian D. Griedel, El Cerrito; Rushad E. Karanjawala, Hercules; Monica J. Kochanny, San Rafael; Wheeseong Lee, Lafayette; Amy Mei Liang, Richmond; Michael M. Morrissey, Danville; Gary B. Phillips, Pleasant Hill; Karna Lyn Sacchi, San Francisco; Steven T. Sakata, San Diego; Kenneth J. Shaw, San Rafael; R. Michael Snider, Napa, all of Calif.; Shung C. Wu, Princeton, N.J.; Bin Ye, Richmond; Zuchun Zhao, El Sobrante, both of Calif.

[73] Assignee: Berlex Laboratories, Inc., Richmond, Calif.

[21] Appl. No.: 09/187,459

[22] Filed: Nov. 5, 1998

Related U.S. Application Data

[63] Continuation-in-part of application No. 08/994,284, Dec. 19, 1997, abandoned.

[51] Int. Cl.$^7$ ............... A61K 31/44; C07D 409/00; C07D 411/00
[52] U.S. Cl. ............................ 514/336; 546/280.4
[58] Field of Search ............... 514/536; 546/280.4

[56] References Cited

U.S. PATENT DOCUMENTS

| | | |
|---|---|---|
| 4,064,169 | 12/1977 | Hamano et al. . |
| 4,734,411 | 3/1988 | Kurono .................. 514/220 |
| 5,332,822 | 7/1994 | Misra . |
| 5,451,700 | 9/1995 | Morrissey et al. . |
| 5,612,363 | 3/1997 | Mohan et al. . |
| 5,663,381 | 9/1997 | Dallas et al. . |
| 5,691,364 | 11/1997 | Buckman et al. . |
| 5,693,641 | 12/1997 | Buckman et al. . |
| 5,721,214 | 2/1998 | Marlowe et al. . |
| 5,726,173 | 3/1998 | Mohan et al. . |
| 5,726,198 | 3/1998 | Mohan et al. . |
| 5,728,697 | 3/1998 | Mohan et al. . |
| 5,731,308 | 3/1998 | Mohan et al. . |
| 5,731,311 | 3/1998 | Mohan et al. . |
| 5,753,635 | 5/1998 | Buckman et al. . |
| 5,846,970 | 12/1998 | Buckman et al. . |
| 5,846,972 | 12/1998 | Buckman et al. . |
| 5,849,759 | 12/1998 | Arnaiz et al. . |
| 5,859,005 | 1/1999 | Mohan et al. . |
| 5,863,914 | 1/1999 | Mohan et al. . |
| 5,877,181 | 3/1999 | Buckman et al. . |
| 5,883,100 | 3/1999 | Buckman et al. . |
| 5,889,005 | 3/1999 | Buckman et al. . |

FOREIGN PATENT DOCUMENTS

| | | |
|---|---|---|
| 0518818A2 | 6/1992 | European Pat. Off. . |
| 0540051A1 | 10/1992 | European Pat. Off. . |
| 0567966A1 | 4/1993 | European Pat. Off. . |
| 0601459A2 | 12/1993 | European Pat. Off. . |
| 824908 | 12/1959 | United Kingdom . |
| WO93/15756 | 8/1993 | WIPO . |
| WO94/13693 | 6/1994 | WIPO . |
| WO94/17817 | 8/1994 | WIPO . |
| WO96/10022 | 4/1996 | WIPO . |
| WO97/29067 | 8/1997 | WIPO . |
| WO98/11094 | 3/1998 | WIPO . |
| WO98/15547 | 4/1998 | WIPO . |
| WO99/00127 | 7/1999 | WIPO . |
| WO99/00128 | 7/1999 | WIPO . |

OTHER PUBLICATIONS

Tidwell, R. et al., "Strategies for Anticoagulation with Synthetic Protease Inhibitors, Xa Inhibitors Versus Thrombin Inhibitors," *Thrombosis Research*, (1980) 19:339–349.

Wagner, G. et al., "Synthese von a–a'–Bis[amidinobenzyliden]–und a–a' Bis–[amidinobenzyl]–cycloalkanonen," *Pharmazie*, (1977) 32,141–145.

Stürzebecher, J. et al., "Cyclic Amides of Nα–arysulfonylaminoacylated 4–amidinophenylalanine—Tight Binding Inhibtors of Thrombin," *Thrombosis Research*, (1983) 29:635–642.

Kikumoto, R. et al., "Selective inhibition of Thrombin by (2R,4R)–4–Methyl–1–[N²–[(3–methyl–1,2,3, 4–tetrahydro–8–quinolinyl)–sulfonyl]–L–arginyl)]–2piperidinecarboxylic Acid," *Biochemistry*, (1984) 23:85–90.

Stürzebecher, J. et al., "Synthetic Inhibitors of Serine Proteinases XXIII, Inhibition of Factor Xa by Diamidines", *Thrombosis Research*, (1980) 17:545:548.

Chauhan, P. et al., "Effect of new diamidines against *Leishmania donovani* infection," *Indian Journal of Experimental Biology*, (1993) 31:196–198.

Ashley, J. et al., "The Search for Chemotherapeutic Amidines. Part XVI. Amidinoanilino–1,3,5–triazines and Related Compounds", *J. of the Chemical Society*, (1960) 4525:4532.

Geratz, J. et al., "The Inhibition of Urokinase by Aromatic Diamidines" *Thrombos. Diathes. haemorrh. (Stuttg.)*, (1975)33:230–243.

(List continued on next page.)

*Primary Examiner*—D. Margaret Seaman
*Attorney, Agent, or Firm*—Carol J. Roth

[57] ABSTRACT

This invention is directed to compounds of formula (III):

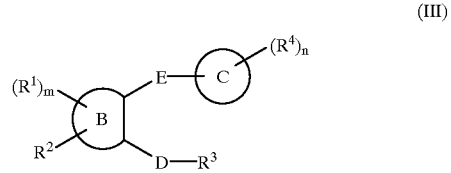

wherein B, C, D, E, R$^1$, R$^2$ and R$^3$ are disclosed herein. These compounds are disclosed as being useful as anticoagulants.

50 Claims, No Drawings-

OTHER PUBLICATIONS

Geratz, J. et al. "Novel Bis (benzamidino) Compounds with an Aromatic Central Link. Inhibitors of Thrombin, Pancreatic Kallikrein, Trypsin, and Complement" *J. of Medicinal Chemistry*, (1976) 19(5):634–639.

Chauhan, P. et al., "Antiparasitic Agents: Part VI—Synthesis of 1,2,–,1,3–&1,4–Bis(4–substituted aryloxy)benzenes & Their Biological Activities", *Indian Journal of Chemistry*, (1988) 27B:38–42.

U.S. Patent Application Serial No. 09/196,921, filed Nov. 19, 1998, entitled: *Polyhydroxylated Monocyclic N–Heterocyclic Derivatives as Anti–Coagulants*.

U.S. Patent Application Serial No. 09/205,498, filed Dec. 4, 1998, entitled: *Aryl Substituted N–Heterocyclic Derivatives as Anti–Coagulants*.

Chemical Abstracts 108:56587, El–Naggar, 1985.

Chemical Abstracts 106:196451, Kurono, abstract of EP 213956, 1987.

Chemical Abstracts 106:152850, El–Naggar, 1986.

Chemical Abstracts 101:7623, El–Naggar, 1982.

Chemical Abstracts 100:34516, Kovac, 1983.

Chemical Abstracts 90:121516, El–Zanfally, 1978.

Chemical Abstracts 71:124525, abstract of FR 1542160, 1968.

Chemical Abstracts 71:112994, abstract of ZA 6805942, 1969.

ORTHO-ANTHRANILAMIDE DERIVATIVES AS ANTI-COAGULANTS

This application is a continuation-in-part application of U.S. patent application, Ser. No. 08/994,284, filed Dec. 19, 1997, now abandoned, which is incorporated by reference in full herein.

FIELD OF THE INVENTION

The present invention is directed to ortho-anthranilamide derivatives and their pharmaceutically acceptable salts, which inhibit the enzyme, factor Xa, thereby being useful as anti-coagulants. It also relates to pharmaceutical compositions containing the derivatives or their pharmaceutically acceptable salts, and methods of their use.

BACKGROUND OF THE INVENTION

Factor Xa is a member of the trypsin-like serine protease class of enzymes. A one-to-one binding of factors Xa and Va with calcium ions and phospholipid forms the prothrombinase complex which converts prothrombin to thrombin. Thrombin, in turn, converts fibrinogen to fibrin which polymerizes to form insoluble fibrin.

In the coagulation cascade, the prothrombinase complex is the convergent point of the intrinsic (surface activated) and extrinsic (vessel injury-tissue factor) pathways (*Biochemistry* (1991), Vol. 30, p. 10363; and *Cell* (1988), Vol. 53, pp. 505–518). The model of the coagulation cascade has been refined further with the discovery of the mode of action of tissue factor pathway inhibitor (TFPI) (*Seminars in Hematology* (1992), Vol. 29, pp. 159–161). TFPI is a circulating multi-domain serine protease inhibitor with three Kunitz-type domains which competes with factor Va for free factor Xa. Once formed, the binary complex of factor Xa and TFPI becomes a potent inhibitor of the factor VIIa and tissue factor complex.

Factor Xa can be activated by two distinct complexes, by tissue factor-VIIa complex on the "Xa burst" pathway and by the factor IXa-VIIIa complex (TENase) of the "sustained Xa" pathway in the coagulation cascade. After vessel injury, the "Xa burst" pathway is activated via tissue factor (TF). Up regulation of the coagulation cascade occurs via increased factor Xa production via the "sustained Xa" pathway. Down regulation of the coagulation cascade occurs with the formation of the factor Xa-TFPI complex, which not only removes factor Xa but also inhibits further factor formation via the "Xa burst" pathway. Therefore, the coagulation cascade is naturally regulated by factor Xa.

The primary advantage of inhibiting factor Xa over thrombin in order to prevent coagulation is the focal role of factor Xa versus the multiple functions of thrombih. Thrombin not only catalyzes the conversion of fibrinogen to fibrin, factor VIII to VIIIA, factor V to Va, and factor XI to XIa, but also activates platelets, is a monocyte chemotactic factor, and mitogen for lymphocytes and smooth muscle cells. Thrombin activates protein C, the in vivo anti-coagulant inactivator of factors Va and VIIIa, when bound to thrombomodulin. In circulation, thrombin is rapidly inactivated by antithrombin III (ATIII) and heparin cofactor II (HCII) in a reaction which is catalyzed by heparin or other proteoglycan-associated glycosaminoglycans, whereas thrombin in tissues is inactivated by the protease, nexin. Thrombin carries out its multiple cellular activation functions through a unique "tethered ligand" thrombin receptor (*Cell* (1991), Vol. 64, p. 1057), which requires the same anionic binding site and active site used in fibrinogen binding and cleavage and by thrombomodulin binding and protein C activation. Thus, a diverse group of in vivo molecular targets compete to bind thrombin and the subsequent proteolytic events will have very different physiological consequences depending upon which cell type and which receptor, modulator, substrate or inhibitor binds thrombin.

Published data with the proteins antistasin and tick anticoagulant peptide (TAP) demonstrate that factor Xa inhibitors are efficacious anti-coagulants (*Thrombosis and Haemostasis* (1992), Vol. 67, pp. 371–376; and *Science* (1990), Vol. 248, pp. 593–596).

The active site of factor Xa can be blocked by either a mechanism-based or a tight binding inhibitor (a tight binding inhibitor differs from a mechanism-based inhibitor by the lack of a covalent link between the enzyme and the inhibitor). Two types of mechanism-based inhibitors are known, reversible and irreversible, which are distinguished by ease of hydrolysis of the enzyme-inhibitor link (*Thrombosis Res* (1992), Vol. 67, pp. 221–231; and *Trends Pharmacol. Sci.* (1987), Vol. 8, pp. 303–307). A series of guanidino compounds are examples of tight-binding inhibitors (*Thrombosis Res.* (1980), Vol. 19, pp. 339–349). Arylsulfonyl-arginine-piperidine-carboxylic acid derivatives have also been shown to be tight-binding inhibitors of thrombin (*Biochem.* (1984), Vol. 23, pp. 85–90), as well as a series of arylamidine-containing compounds, including 3-amidinophenylaryl derivatives (*Thrombosis Res.* (1983), Vol. 29, pp. 635–642) and bis(amidino)benzyl cycloketones (*Thrombosis Res.* (1980), Vol. 17, pp. 545–548). However, these compounds demonstrate poor selectivity for factor Xa.

Related Disclosures

European Published Patent Application 0 540 051 (Nagahara et al.) describes aromatic amidine derivatives. These derivatives are stated to be capable of showing a strong anticoagulant effect through reversible inhibition of factor Xa.

The synthesis of α,α'-bis(amidinobenzylidene) cycloalkanones and α,α'-bis(amidino-benzyl) cycloalkanones is described in *Pharmazie* (1977), Vol. 32, No. 3, pp. 141–145. These compounds are disclosed as being serine protease inhibitors.

U.S. Pat. No. 5,612,363 (Mohan et al.) describes N,N-di (aryl) cyclic urea derivatives. These compounds are stated to be factor Xa inhibitors, thereby being useful as anticoagulants.

U.S. Pat. No. 5,633,381 (Dallas et al.) describes (Z,Z), (Z,E) and (E,Z) isomers of substituted bis(phenylmethylene) cycloketones. These compounds are disclosed as being factor Xa inhibitors, thereby being useful as anticoagulants.

U.S. Pat. No. 5,691,364 (Buckman et al.) describes benzamidine derivatives. These compounds are stated to be factor Xa inhibitors, thereby being useful as anticoagulants.

PCT Published Patent Application WO/97/21437 (Arnaiz et al.) describes naphthyl-substituted benzimidazole derivatives. These compounds are disclosed as being factor Xa inhibitors, thereby being useful as anticoagulants.

PCT Published Patent Application WO/97/29067 (Kochanny et al.) describes benzamidine derivatives that are substituted by amino acid and hydroxy acid derivatives. These compounds are stated to be factor Xa inhibitors, thereby being useful as anticoagulants.

PCT Published Patent Applications WO/96/10022 (Faull et al.), WO97/29104 (Faull et al.), and WO/97/28129 describe aminoheterocyclic compounds which are disclosed as being factor Xa inhibitors, thereby being useful as anfithrombotics and anticoagulants.

The above references, published patent applications and U.S. patents are herein incorporated in full by reference.

SUMMARY OF THE INVENTION

This invention is directed to compounds or their pharmaceutically acceptable salts which inhibit human factor Xa and are therefore useful as pharmacological agents for the treatment of disease-states characterized by thrombotic activity, i.e., as anti-coagulants.

Accordingly, in one aspect, this invention provides compounds of formula (III):

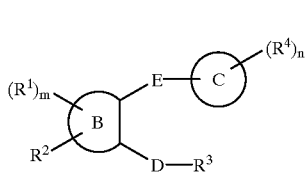

(III)

wherein
m is 1 to 3;
n is 1 to 5;

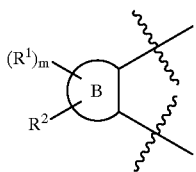

is an aryl or a heterocyclic ring substituted by $R^2$ and one or more $R^1$ groups;

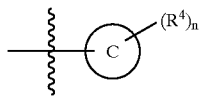

is an aryl or a heterocyclic ring substituted by one or more $R^4$ groups;

D and E are independently a linker selected from the group consisting of —N($R^5$)—C(X)—; —$R^8$—N($R^5$)—C(X)—; —N($R^5$)—C(X)—$R^8$—; —$R^8$—N($R^5$)—C(X)—$R^8$—; —N($R^5$)—S(O)$_p$—; —$R^8$—N($R^5$)—S(O)$_p$—; —N($R^5$)—S(O)$_p$—$R^8$—; and —$R^8$—N($R^5$)—S(O)$_p$—$R^8$— (where p is 0 to 2; X is oxygen, sulfur or $H_2$) where D and E can be attached to the B ring having the $R^1$ and $R^2$ substituents by either terminus of the selected linker;

each $R^1$ is independently hydrogen, alkyl, aryl, aralkyl, halo, haloalkyl, cyano, —$OR^5$, —S(O)$_p$—$R^9$ (where p is 0 to 2), —C(O)$OR^5$, —C(O)N($R^5$)$R^6$, —N($R^5$)$R^6$, —O—C(O)$R^5$, —N($R^5$)—CH($R^{12}$)—C(O)$OR^5$, heterocyclyl (optionally substituted by alkyl, aryl, aralkyl, halo, haloalkyl, oxo, —$OR^5$, —C(O)$OR^5$, —N($R^5$)$R^6$ or —C(O)N($R^5$)$R^6$) or heterocyclylalkyl (optionally substituted by alkyl, aryl, aralkyl, halo, haloalkyl, oxo, —$OR^5$, —C(O)$OR^5$, —N($R^5$)$R^6$ or —C(O)N($R^5$)$R^6$);

$R^2$ is hydrogen, alkyl, aryl, aralkyl, halo, haloalkyl, cyano, —$OR^5$, —S(O)$_p$—$R^9$ (where p is 0 to 2), —C(O)$OR^5$, —C(O)N($R^5$)$R^6$, —N($R^{10}$)$R^{11}$, —C($R^7$)H—N($R^{10}$)$R^{11}$, —C($R^7$)H—$R^8$—N($R^{10}$)$R^{11}$, —C($R^7$)H—$OR^5$, —C($R^7$)H—$R^8$—$OR^5$, —C($R^7$)H—S(O)$_p$—$R^9$ (where p is 0 to 2), —C($R^7$)H—$R^8$—S(O)$_p$—$R^9$ (where p is 0 to 2), —O—$R^8$—S(O)$_p$—$R^9$ (where p is 0 to 2), —C($R^7$)H—N($R^5$)$R^6$, —C($R^7$)H—$R^8$—N($R^5$)$R^6$, —O—$R^8$—CH(OH)—CH$_2$—N($R^{10}$)$R^{11}$, —O—$R^8$—N($R^{10}$)$R^{11}$, —O—$R^8$—O—C(O)$R^5$, —O—$R^8$—CH(OH)—CH$_2$—$OR^5$, —O—($R^8$—O)$_t$—$R^5$ (where t is 1 to 6), —O—($R^8$—O)$_t$—$R^{19}$ (where t is 1 to 6), —O—$R^8$—C(O)$R^5$, —O—$R^8$—C(O)$R^{19}$, —O—$R^8$—C(O)$OR^5$, —N($R^5$)—$R^8$—N($R^{10}$)$R^{11}$, —S(O)$_p$—$R^8$—N($R^5$)$R^6$ (where p is 0 to 2), —S(O)$_p$—$R^8$—C(O)$OR^5$ (where p is 0 to 2), or —N($R^5$)—CH($R^{12}$)—C(O)$OR^5$;

$R^3$ is aryl or heterocyclyl both substituted by one or more $R^{14}$ substituents independently selected from the group consisting of hydrogen, alkyl, halo, formyl, acetyl, cyano, —$R^8$—CN, —N($R^{10}$)$R^{11}$, —$R^8$—N($R^{10}$)$R^{11}$, —R—N$^\oplus$($R^9$)($R^{16}$)$_2$, —C(O)$OR^5$, —$R^8$—C(O)$OR^5$, —$OR^5$, —$R^8$—$OR^5$, —C($R^7$)H—O—$R^{15}$, —S(O)$_p$—$R^{15}$ (where p is 0 to 2), —$R^8$—S(O)$_p$—$R^{15}$ (where p is 0 to 2), —S(O)$_p$—N($R^5$)$R^6$ (where p is 0 to 2), —C(O)N($R^5$)$R^6$, —$R^8$—C(O)N($R^5$)$R^6$, —N($R^5$)—($R^8$—O)$_t$—$R^5$ (where t is 1 to 6), —$R^8$—N($R^5$)—($R^8$—O)$_t$—$R^5$ (where t is 1 to 6), —$R^8$—O—($R^8$—O)$_t$—$R^5$ (where t is 1 to 6), —O—$R^8$—CH(OH)—CH$_2$—$OR^5$, —C($R^7$)H—O—$R^8$—CH(OH)—CH$_2$—$OR^5$, —C($R^7$)H—N($R^5$)—$R^8$—[CH(OH)]$_t$—CH$_2$—$OR^5$ (where t is 1 to 6), —C($R^7$)H—N($R^5$)—S(O)$_2$—N($R^{10}$)$R^{11}$, —C($R^7$)H—N($R^{10}$)—C(N$R^{17}$)—N($R^{10}$)$R^{11}$, —C($R^7$)H—N($R^{10}$)—C(N$R^{17}$)—$R^{10}$, —C(N$R^{17}$)—N($R^5$)$R^6$, —C($R^7$)H—C(N$R^{17}$)—N($R^5$)$R^6$, —C($R^7$)H—O—N($R^5$)$R^6$, heterocyclyl (wherein the heterocyclyl radical is not attached to the rest of the molecule through a nitrogen atom and is optionally substituted by alkyl, aryl, aralkyl, halo, haloalkyl, oxo, —$OR^5$, —C(O)$OR^5$, —N($R^5$)$R^6$ or —C(O)N($R^5$)$R^6$), and heterocyclylalkyl (wherein the heterocyclyl radical is not attached to the alkyl radical through a nitrogen ring and is optionally substituted by one or more substituents selected from the group consisting of alkyl, aryl, aralkyl, halo, haloalkyl, oxo, —$OR^5$, —C(O)$OR^5$, —N(R—)$R^6$ and —C(O)N($R^5$)$R^6$);

each $R^4$ is independently hydrogen, alkyl, halo, haloalkyl, cyano, nitro, —$OR^5$, —C(O)$OR^5$, —N($R^5$)$R^6$, —C(O)N($R^5$)$R^6$, or —$R^8$—N($R^5$)$R^6$;

each $R^5$ and $R^6$ is independently hydrogen, alkyl, aryl or aralkyl;

each $R^7$ is independently hydrogen or alkyl;

each $R^8$ is independently a straight or branched alkylene, alkylidene or alkylidyne chain;

each $R^9$ is independently alkyl, aryl or aralkyl;

each $R^{10}$ and $R^{11}$ is independently hydrogen, alkyl, haloalkyl, aryl, aralkyl, formyl, cyano, —$R^8$—CN, —$OR^5$, —$R^8$—$OR^5$, —S(O)$_p$—$R^{15}$ (where p is 0 to 2), —$R^8$—S(O)$_p$—$R^{15}$ (where p is 0 to 2), —N($R^5$)$R^6$, —$R^8$—N($R^5$)$R^6$, —$R^8$—C(O)$OR^5$, —C(O)—$R^{15}$, —C(O)NH$_2$, —$R^8$—C(O)NH$_2$, —C(S)NH$_2$, —C(O)—S—$R^5$, —C(O)—N($R^5$)$R^{15}$, —$R^8$—C(O)—N($R^5$)$R^{15}$, —C(S)—N($R^5$)$R^{15}$, —$R^8$—N($R^5$)—C(O)H, —$R^8$—N($R^5$)—C(O)$R^{15}$, —C(O)O—$R^8$—N($R^5$)$R^6$, —C(N($R^5$)$R^6$)=C($R^{18}$)$R^{10}$, —$R^8$—N($R^5$)—P(O)(O$R^5$)$_2$, cycloalkyl (optionally substituted by one or more substituents selected from the group consisting of alkyl, halo and —$OR^5$), heterocyclyl (optionally substituted by alkyl, aryl, aralkyl, halo, haloalkyl, oxo, —$OR^5$, —$R^8$—$OR^5$, —C(O)$OR^5$, —S(O)$_p$—$R^9$ (where p is 0 to 2), —$R^8$—S(O)$_p$—$R^9$ (where p is 0 to 2), —N($R^5$)$R^6$ or —C(O)N($R^5$)$R^6$), or heterocyclylalkyl (optionally substituted by one or more substituents selected from the group consisting of alkyl, aryl, aralkyl, halo, haloalkyl, oxo, —$OR^5$, —$R^8$—$OR^5$, —C(O)$OR^5$, —S(O)$_p$—$R^9$ (where p is 0 to 2), —$R^8$—S(O)$_p$—$R^9$ (where p is 0 to 2), —N($R^5$)$R^6$ and —C(O)N($R^5$)$R^6$);

or $R^{10}$ and $R^{11}$ together with the nitrogen to which they are attached form a N-heterocyclic ring containing zero to three additional hetero atoms, where the N-heterocylic ring is optionally substituted by one or more substituents selected from the group consisting of alkyl, halo, haloalkyl, aryl, aralkyl, oxo, nitro, cyano, —$R^8$—CN, =N($R^{17}$), —$OR^5$, —C(O)OR⁵, —R⁸—C(O)OR⁵, —N(R⁵)R⁶, —R⁸—N(R⁵)R⁶, —C(O)N(R⁵)R⁶, —R⁸—C(O)N(R⁵)R⁶, —N(R⁵)—N(R⁵)R⁶, —C(O)R⁵, —C(O)—(R⁸—O)ₜ—R⁵ (where t is 1 to 6), —S(O)ₚ—R⁹ (where p is 0 to 2), —R⁸—S(O)ₚ—R⁹ (where p is 0 to 2), —(R⁸—O)ₜ—R⁵ (where t is l to 6), and heterocyclyl (optionally substituted by one or more substituents selected from the group consisting of alkyl, aryl, aralkyl, halo, haloalkyl, —OR⁵, —C(O)OR—⁵, —N(R—⁵)R⁶, and —C(O)N(R—⁵)R⁶);

R¹² is a side chain of an α-amino acid;

each R¹⁵ is independently alkyl, cycloalkyl, haloalkyl, aryl, aralkyl, —R⁸—O—C(O)—R⁵, —R—OR⁵, —N(R⁵)R⁶, —R⁸—N(R⁵)R⁶, —R⁸—C(O)OR⁵, heterocyclyl (optionally substituted by one or more substituents selected from the group consisting of alkyl, aryl, aralkyl, halo, haloalkyl, —OR⁵, —R⁸—OR⁵, —C(O)OR⁵, —N(R⁵)R⁶, and —C(O)N(R⁵)R⁶), or heterocyclylalkyl (optionally substituted by one or more substituents selected from the group consisting of alkyl, aryl, aralkyl, halo, haloalkyl, —OR⁵, —R⁸—OR⁵, —C(O)OR⁵, —N(R⁵)R⁶, and —C(O)N(R⁵)R⁶);

or R⁵ and R¹⁵ together with the nitrogen to which they are attached form a N-heterocyclic ring containing zero to three additional hetero atoms, where the N-heterocyclic ring is optionally substituted by one or more substituents selected from the group consisting of alkyl, aryl, aralkyl, amino, monoalkylamino, dialkylamino, OR⁵, —C(O)OR⁵, aminocarbonyl, monoalkylaminocarbonyl, and dialkylaminocarbonyl;

each R¹⁶ is independently alkyl, aryl, aralkyl, —R⁸—OR⁵, —R⁵—N(R⁵)R⁶, cycloalkyl (optionally substituted by one or more substituents selected from the group consisting of alkyl, halo and —OR⁵), heterocyclyl (optionally substituted by alkyl, aryl, aralkyl, halo, haloalkyl, —OR⁵, —C(O)OR⁵, —N(R⁵)R⁶ or —C(O)N(R⁵)R⁶), or heterocyclylalkyl (optionally substituted by one or more substituents selected from the group consisting of alkyl, aryl, aralkyl, halo, haloalkyl, —OR⁵, —C(O)OR⁵, —N(R⁵)R⁶ and —C(O)N(R⁵)R⁶); or both R¹⁶'s together with the nitrogen to which they are attached (and wherein the R⁹ substituent is not present) form an aromatic N-heterocyclic ring containing zero to three additional hetero atoms, where the N-heterocyclic ring is optionally substituted by one or more substituents selected from the group consisting of alkyl, aryl, aralkyl, —OR⁵, —R⁸—OR⁵, —C(O)OR⁵, —R⁸—C(O)OR⁵, —N(R⁵)R⁶, —R⁸—N(R⁵)R⁶, —C(O)R⁵, —C(O)—(R⁸—O)ₜ—R⁵ (where t is 1 to 6), and —(R⁸—O)ₜ—R⁵ (where t is 1 to 6);

each R¹⁷ is independently hydrogen, alkyl, aryl, aralkyl, cyano, —OR⁵, —R⁸—OR⁵, —C(O)OR⁵, —R⁸—C(O)OR⁵, —C(O)—N(R⁵)R⁶, or —R⁸—C(O)—N(R⁵)R⁶;

R¹⁸ is hydrogen, alkyl, aryl, aralkyl, cyano, —C(O)OR⁵, or —NO₂; and each R¹⁹ is cycloalkyl, haloalkyl, —R⁸—OR⁵, —R⁸—N(R⁵)R⁶, —R⁸—C(O)OR⁵, —R⁸—C(O)N(R⁵)R⁶, heterocyclyl (optionally substituted by alkyl, aryl, aralkyl, halo, haloalkyl, —OR⁵, —C(O)OR⁵, —N(R⁵)R⁶ or —C(O)N(R⁵)R⁶), or heterocyclylalkyl (optionally substituted by one or more substituents selected from the group consisting of alkyl, aryl, aralkyl, halo, haloalkyl, —OR⁵, —C(O)OR⁵, —N(R⁵)R⁶ and —C(O)N(R⁵)R⁶);

as a single stereoisomer or a mixture thereof; or a pharmaceutically acceptable salt thereof.

In another aspect, this invention provides compounds of formula (I):

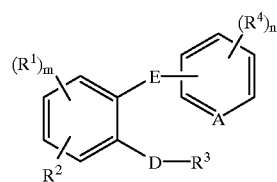

A is =CH— or =N—;
m is 1 to 3;
n is 1 to 4;
D is —N(R⁵)—C(Z)— or —N(R⁵)—S(O)ₚ— (where p is 0 to 2; Z is oxygen, sulfur or H₂; and the nitrogen atom is directly bonded to the phenyl ring having the R¹ and R² substituents);
E is —C(Z)—N(R⁵)— or —S(O)ₚ—N(R )— (where p is 0 to 2; Z is oxygen, sulfur or H₂; and the nitrogen atom can be bonded to the phenyl ring having the R¹ and the R² substituents or to the aromatic ring having the R⁴ substituent);
each R¹ is independently hydrogen, alkyl, aryl, aralkyl, halo, haloalkyl, cyano, —OR⁵, —S(O)ₚ—R⁹ (where p is 0 to 2), —C(O)OR⁵, —C(O)N(R⁵)R⁶, —N(R⁵)R⁶, —O—C(O)R⁵, or —N(R⁵)—CH(R¹²)—C(O)OR⁵;

or two adjacent R¹'s together with the carbons to which they are attached form a heterocyclic ring fused to the phenyl ring wherein the heterocyclic ring is optionally substituted by one or more substituents selected from the group consisting of alkyl, aryl and aralkyl;

R² is hydrogen, alkyl, aryl, aralkyl, halo, haloalkyl, cyano, —OR⁵, —(O)ₚ—R⁹ (where p is 0 to 2), —C(O)OR⁵, —OC(O)—R⁵, —C(O)N(R⁵)R⁶, —N(R¹⁰)R¹¹, —C(R⁷)H—N(R¹⁰)R¹¹, —C(R⁷)H—R⁸—N(R¹⁰)R¹¹, —C(R⁷)H—OR⁵, —C(R⁷)H—R⁸—OR⁵, —C(R⁷)H—S(O)ₚ—R⁹ (where p is 0 to 2), —C(R⁷)H—R⁸—S(O)ₚ—R⁹ (where p is 0 to 2), —O—R⁸—S(O)O ₚ—R⁹ (where p is 0 to 2), —C(R⁷)H—N(R⁵)R⁶, —C(R⁷)H—R⁸—N(R⁵)R⁶, —O—R⁸—CH(OH)—CH₂—N(R¹⁰)R¹¹, —O—R⁸—N(R¹⁰)R¹¹, —O—R⁸—O—C(O)R⁵, —O—R⁸—CH(OH)—CH₂—OR⁵, —O—(R⁸—O)ₜ—R⁵ (where t is 1 to 6), —O—(R⁸—O)ₜ—R¹⁹ (where t is 1 to 6), —O—R⁸—C(O)R⁵, —O—R⁸—C(O)R¹⁹, —O—R⁸—C(O)OR⁵, —N(R⁵)—R⁸—N(R¹⁰)R¹¹, —S(O)ₚR⁸—N(R⁵)R⁶ (where p is 0 to 2), —S(O)ₚ—R⁸—C(O)OR⁵ (where p is 0 to 2), or —N(R⁵)—CH(R¹²)—C(O)OR⁵;

R³ is a radical of formula (i):

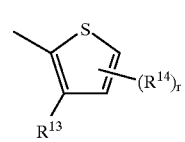

where:
r is 1 or 2;
R¹³ is hydrogen, alkyl, halo, haloalkyl, —N(R⁵)R⁶, —C(R⁷)H—N(R⁵)⁶, —OR⁵, —R⁸—OR⁵, —S(O)ₚ—R⁸—N(R⁵)R⁶ (where p is 0 to 2) or heterocyclylalky (where the heterocyclic ring is optionally substituted by one or more substituents selected from the group consisting of alkyl, halo, aralkyl, nitro and cyano); and each R¹⁴is independently hydrogen, alkyl, halo, formyl, acetyl, cyano, —R⁸—CN, —N(R¹⁰)R¹¹, —C(R⁷)H—N ($R^{10}$)$R^{11}$, —C($R^7$)H—$R^8$N($R^{10}$)$R^{11}$, —C($R^7$)H—$N^{\oplus}$($R^9$) ($R^{16}$)$_2$, —C($R^7$)H—$R^8$—$N^{\oplus}$($R^9$)($R^{16}$)$_2$, —C(O)O$R^5$, —C($R^7$)H—C(O)O$R^5$, —C($R^7$)H—$R^8$—C(O)O$R^5$, —O$R^5$, —C($R^7$)H—O$R^5$, —C($R^7$)H—$R^8$—O$R^5$, —C($R^7$)H—O—$R^{15}$, —S(O)$_p$$R^{15}$ (where p is 0 to 2), —C($R^7$)H—S(O)$_p$—$R^{15}$ (where p is 0 to 2), —C($R^7$)H—$R^8$—S(O)$_p$—$R^{15}$ (where p is 0 to 2), —S(O)$_p$—N($R^5$)$R^6$ (where p is 0 to 2), —C(O)N($R^5$)$R^6$, —C($R^7$)H—C(O)N($R^5$)$R^6$, —C($R^7$)H—$R^8$—C(O)N($R^5$)$R^6$, —C($R^7$)H—N($R^5$)—($R^8$—O)$_t$—$R^5$ (where t is 1 to 6), —C($R^7$)H—$R^8$—N($R^5$)—($R^8$—O)$_t$—$R^5$ (where t is 1 to 6), —C($R^7$)H—O—($R^8$—O)$_t$—$R^5$ (where t is 1 to 6), —C($R^7$)H—$R^8$—O—($R^8$—O)$_t$—$R^5$ (where t is 1 to 6), —O—$R^8$—CH(OH)—CH$_2$—O$R^5$, —C($R^7$)H—O—$R^8$—CH(OH)—CH$_2$—O$R^5$, —C($R^7$)H—N($R^5$)—$R^8$—[CH(OH)]$_t$—CH$_2$—O$R^5$ (where t is 1 to 6), —C($R^7$)H—N($R^5$)—S(O)$_2$—N($R^{10}$)$R^{11}$, —C($R^7$)H—N($R^{10}$)—C(N$R^{17}$)—N($R^{10}$)$R^{11}$, —C($R^7$)H—N($R^{10}$)—C(N$R^{17}$)—$R^{10}$, —C(N$R^{17}$)—N($R^5$)$R^6$, —C($R^7$)H—C(N$R^{17}$)—N($R^5$)$R^6$, —C($R^7$)H—O—N($R^5$)$R^6$, heterocyclyl (wherein the heterocyclyl radical is not attached to the radical of formula (i) through a nitrogen atom and is optionally substituted by alkyl, aryl, aralkyl, halo, haloalkyl, oxo, —O$R^5$, —C(O)O$R^5$, —N($R^5$)$R^6$ or —C(O)N($R^5$)$R^6$), or heterocyclylalkyl (wherein the heterocyclyl radical is not attached to the alkyl radical through a nitrogen atom and is optionally substituted by one or more substituents selected from the group consisting of alky, aryl, aralkyl, halo, haloalkyl, oxo, —O$R^5$, —C(O)O$R^5$,—N($R^5$)$R^6$ and —C(O)N($R^5$)$R^6$);

or $R^3$ is a radical of the formula (ii):

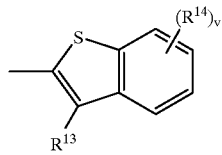

(ii)

where v is 1 to 4;

$R^{13}$ is as defined above for formula (i); and $R^{14}$ is as defined above for formula (i);

each $R^4$ is independently hydrogen, alkyl, halo, haloalkyl, cyano, nitro, —O$R^5$, —C(O)O$R^5$, —N($R^5$)$R^6$, —C(O)N($R^5$)$R^6$, or —$R^8$—N($R^5$)$R^6$;

$R^5$ and $R^6$ are each independently hydrogen, alkyl, aryl or aralkyl;

each $R^7$ is independently hydrogen or alkyl;

each $R^8$ is independently a straight or branched alkylene, alkylidene or alkylidyne chain;

each $R^9$ is independently alkyl, aryl or aralkyl;

$R^{10}$ and $R^{11}$ are each independently hydrogen, alkyl, haloalkyl, aryl, aralkyl, formyl, cyano, —$R^8$—CN, —O$R^5$, —$R^8$—O$R^5$, —S(O)$_p$—$R^{15}$ (where p is 0 to 2), —$R^8$—S(O)$_p$—$R^{15}$ (where p is 0 to 2), —N($R^5$)$R^6$, —$R^8$—N($R^5$)$R^6$, —$R^8$—C(O)O$R^5$, —C(O)—$R^{15}$, —C(O)NH$_2$, —$R^8$—C(O)NH$_2$, —C(S)NH$_2$, —C(O)—S—$R^5$, —C(O)—N($R^5$)$R^{15}$, —$R^8$—C(O)—N($R^5$)$R^{15}$, —C(S)—N($R^5$)$R^{15}$, —$R^8$—N($R^5$)—C(O)H, —$R^8$N($R^5$)—C(O)$R^{15}$, —C(O)O—$R^8$—N($R^5$)$R^6$, —C(N($R^5$)$R^6$)=C($R^{18}$)$R_{10}$, —$R^8$—N($R^5$)—P(O)(O$R^5$)$_2$, cycloalkyl (optionally substituted by one or more substituents selected from the group consisting of alkyl, halo and —O$R^5$), heterocyclyl (optionally substituted by alkyl, aryl, aralkyl, halo, haloalkyl, oxo, —O$R^5$, —$R^8$—O$R^5$, —C(O)O$R^5$, —S(O)$_p$—$R^9$ (where p is 0 to 2), —$R^8$—S(O)$_p$—$R^9$ (where p is 0 to 2), —N($R^5$)$R^6$ or —C(O)N($R^5$)$R^6$), or heterocyclylalkyl (optionally substituted by one or more substituents selected from the group consisting of alkyl, aryl, aralkyl, halo, haloalkyl, oxo, —O$R^5$, —$R^8$—O$R^5$, —C(O)O$R^5$, —S(O)$_p$—$R^9$ (where p is 0 to 2), —$R^8$—S(O)$_p$—$R^9$ (where p is 0 to 2), —N($R^5$)$R^6$ and —C(O)N($R^5$)$R^6$);

or $R^{10}$ and $R^{11}$ together with the nitrogen to which they are attached form a N-heterocyclic ring containing zero to three additional hetero atoms, where the N-heterocylic ring is optionally substituted by one or more substituents selected from the group consisting of alkyl, halo, haloalkyl, aryl, aralkyl, oxo, nitro, cyano, —$R^8$—CN, =N($R^{17}$), —O$R^5$, —C(O)O$R^5$, —$R^8$—C(O)O$R^5$, —N($R^5$)$R^6$, —$R^8$—N($R^5$)$R^6$, —C(O)N($R^5$)$R^6$, —$R^8$—C(O)N($R^5$)$R^6$, —N($R^5$)—N($R^5$)$R^6$, —C(O)$R^5$, —C(O)—($R^8$—O)$_t$—$R^5$ (where t is 1 to 6), —S(O)$_p$—$R^9$ (where p is 0 to 2), —$R^8$—S(O)$_p$—$R^9$ (where p is 0 to 2), —($R^8$—O)$_t$—$R^5$ (where t is 1 to 6), and heterocyclyl (optionally substituted by one or more substituents selected from the group consisting of alkyl, aryl, aralkyl, halo, haloalkyl, —O$R^5$, —C(O)O$R^5$, —N($R^5$)$R^6$, and —C(O)N($R^5$)$R^6$);

$R^{12}$ is a side chain of an α-amino acid;

each $R^{15}$ is independently alkyl, cycloalkyl, haloalkyl, aryl, aralkyl, —$R^8$—O—C(O)—$R^5$, —$R^8$—O$R^5$, —N($R^5$)$R^6$, —$R^8$—N($R^5$)$R^6$, —$R^8$—C(O)O$R^5$, heterocyclyl (optionally substituted by one or more substituents selected from the group consisting of alkyl, aryl, aralkyl, halo, haloalkyl, —O$R^5$, —$R^8$—O$R^5$, —C(O)O$R^5$, —N($R^5$)$R^6$, and —C(O)N($R^5$)$R^6$), or heterocyclylalkyl (optionally substituted by one or more substituents selected from the group consisting of alkyl, aryl, aralkyl, halo, haloalkyl, —O$R^5$, —$R^8$—O$R^5$, —C(O)O$R^5$, —N($R^5$)$R^6$, and —C(O)N($R^5$)$R^6$);

or $R^5$ and $R^{15}$ together with the nitrogen to which they are attached form a N-heterocyclic ring containing zero to three additional hetero atoms, where the N-heterocyclic ring is optionally substituted by one or more substituents selected from the group consisting of alkyl, aryl, aralkyl, amino, monoalkylamino, dialkylamino, —O$R^5$, —C(O)O$R^5$, aminocarbonyl, monoalkylaminocarbonyl, and dialkylaminocarbonyl;

each $R^{16}$ is independently alkyl, aryl, aralkyl, —$R^8$—O$R^5$, —$R^8$—N($R^5$)$R^6$, cycloalkyl (optionally substituted by one or more substituents selected from the group consisting of alkyl, halo and —O$R^5$), heterocyclyl (optionally substituted by alkyl, aryl, aralkyl, halo, haloalkyl, —O$R^5$, —C(O)O$R^5$, —N($R^5$)$R^6$ or —C(O)N($R^5$)$R^6$), or heterocyclylalkyl (optionally substituted by one or more substituents selected from the group consisting of alkyl, aryl, aralkyl, halo, haloalkyl, —O$R^5$, —C(O)O$R^5$, —N($R^5$)$R^6$ and —C(O)N($R^5$)$R^6$); or both $R^{16}$'s together with the nitrogen to which they are attached (and wherein the $R^9$ substituent is not present) form an aromatic N-heterocyclic ring containing zero to three additional hetero atoms, where the N-heterocyclic ring is optionally substituted by one or more substituents selected from the group consisting of alkyl, aryl, aralkyl, —O$R^5$, —C(O)O$R^5$, —$R^8$—C(O)O$R^5$, —N($R^5$)$R^6$, —$R^8$—N($R^5$)$R^6$, —C(O)$R^5$, —C(O)—($R^8$—O)$_t$—$R^5$ (where t is 1 to 6), and —($R^8$—O)$_t$—$R^5$ (where t is 1 to 6);

each $R^{17}$ is independently hydrogen, alkyl, aryl, aralkyl, cyano, —O$R^5$, —$R^8$—O$R^5$, —C(O)O$R^5$, —$R^8$—C(O)O$R^5$, —C(O)—N($R^5$)$R^6$, or —$R^8$—C(O)—N($R^5$)$R^6$;

$R^{18}$ is hydrogen, alkyl, aryl, aralkyl, cyano, —C(O)O$R^5$, or —NO$_2$; and each $R^{19}$ is cycloalkyl, haloalkyl, —$R^8$—O$R^5$, —$R^8$—N($R^5$)$R^6$, —$R^8$—C(O)O$R^5$, —$R^8$—C(O)N($R^5$)$R^6$, heterocyclyl (optionally substituted by alkyl, aryl, aralkyl, halo, haloalkyl, —O$R^5$, —C(O)O$R^5$, —N($R^5$)$R^6$ or —C(O)N($R^5$)$R^6$), or heterocyclylalkyl (optionally substituted by one or more substituents selected from the group consisting of alkyl, aryl, aralkyl, halo, haloalkyl, —OR⁵, —C(O)OR⁵, —N(R⁵)R⁶ and —C(O)N(R⁵)R⁶);

as a single stereoisomer or a mixture thereof; or a pharmaceutically acceptable salt thereof; provided that when A is =CH—, m is 1, n is 1, D is —N(H)—C(O)— (where the nitrogen atom is directly bonded to the phenyl ring having the R¹ and R² substituents), E is —C(O)—N(H)— (where the nitrogen atom is directly bonded to the phenyl ring having the R⁴ substitutent), R¹ is hydrogen and R² is in the 5-position and is methyl, R⁴ is in the 4-position and is fluoro, R³ can not be a radical of formula (ii) where v is 1, R¹⁴ is hydrogen, and R¹³ is chloro.

In another aspect, this invention provides compositions useful in treating a human having a disease-state characterized by thrombotic activity, which composition comprises a therapeutically effective amount of a compound of the invention as described above, without the proviso, or a pharmaceutically acceptable salt thereof, and a pharmaceutically acceptable excipient.

In another aspect, this invention provides a method of treating a human having a disease-state characterized by thrombotic activity, which method comprises administering to a human in need thereof a therapeutically effective amount of a compound of the invention as described above, without the proviso.

In another aspect, this invention provides a method of treating a human having a disease-state alleviated by the inhibition of factor Xa, which method comprises administering to a human in need thereof a therapeutically effective amount of a compound of the invention as described above, without the proviso.

In another aspect, this invention provides a method of inhibiting human factor Xa in vitro by the administration of a compound of the invention, without the proviso.

DETAILED DESCRIPTION OF THE INVENTION

Definitions

As used in the specification and appended claims, unless specified to the contrary, the following terms have the meaning indicated:

"Alkyl" refers to a straight or branched hydrocarbon chain radical consisting solely of carbon and hydrogen atoms, containing no unsaturation, having from one to six carbon atoms, and which is attached to the rest of the molecule by a single bond, e.g., methyl, ethyl, n-propyl, 1-methylethyl (isopropyl), n-butyl, n-pentyl, 1,1-dimethylethyl (t-butyl), and the like.

"Alkoxy" refers to a radical of the formula —OR$_a$ where R$_a$ is an alkyl radical as defined above, e.g., methoxy, ethoxy, propoxy, and the like.

"Alkoxyalkyl" refers to a radical of the formula —R$_a$—OR$_a$ where each R$_a$ is independently an alkyl radical as defined above, e.g., 2-methoxyethyl, methoxymethyl, 3-ethoxypropyl, and the like.

"Alkylene chain" refers to straight or branched chain divalent radical consisting solely of carbon and hydrogen atoms, containing no unsaturation and having from one to six carbon atoms, e.g., methylene, ethylene, propylene, n-butylene and the like.

"Alkylidene chain" refers to a straight or branched chain unsaturated divalent radical consisting solely of carbon and hydrogen atoms, having from two to six carbon atoms, wherein the unsaturation is present only as double bonds and wherein a double bond can exist between the first carbon of the chain and the rest of the molecule, e.g., ethylidene, propylidene, n-butylidene, and the like.

"Alkylidyne chain" refers to a straight or branched chain unsaturated divalent radical consisting solely of carbon and hydrogen atoms having from two to six carbon atoms, wherein the unsaturation is present only as triple bonds and wherein a triple bond can exist between the first carbon of the chain and the carbon atom of the rest of the molecule to which it is attached, e.g., propylid-2-ynyl, n-butylid-1-ynyl, and the like.

"Amino" refers to the —NH₂ radical.

"Aminocarbonyl" refers to the —C(O)NH₂ radical.

"Aryl" refers to a phenyl or naphthyl radical. Unless otherwise indicated, the term "aryl" refers to phenyl or naphthyl radicals which are optionally substituted by alkyl, halo, —OR⁵ (where R⁵ is hydrogen, alkyld aryl or aralkyl).

"Aralkyl" refers to a radical of the formula —R$_a$R$_b$ where R$_a$ is an alkyl radical, as defined above, substituted by R$_b$, an aryl radical, as defined above, e.g., benzyl.

"α-Amino Acids" refer to naturally occurring and commercially available amino acids and optical isomers thereof. Typical natural and commercially available amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, ortho-tyrosine, meta-tyrosine, para-tyrosine, tryptophan, glutamine, asparagine, proline and hydroxyproline. A "side chain of an α-amino acid" refers to the radical found on the α-carbon of an α-amino acid as defined above, for example, hydrogen (for glycine), methyl (for alanine), benzyl (for phenylalanine), and the like.

"Cycloalkyl" refers to a 3- to 7-membered monocyclic cyclic radical which is saturated, and which consists solely of carbon and hydrogen atoms, e.g., cyclopropyl, cyclobutyl, cyclopentyl, cyclohexyl, and the like.

"DMF" refers to N,N-dimethylformamide.

"DMSO" refers to dimethylsulfoxide.

"Dialkylamino" refers to a radical of the formula —N(R$_a$)R$_a$ where each R$_a$ is independently an alkyl radical as defined above, e.g., dimethylamino, diethylamino, (iso-propyl)(ethyl)amino, and the like.

"Dialkylaminocarbonyl" refers to a radical of the formula —C(O)N(R$_a$)R$_a$ where each R$_a$ is independently an alkyl radical as defined above, e.g., (dimethylamino)carbonyl, (diethylamino)carbonyl, ((iso-propyl)(ethyl)amino) carbonyl, and the like.

"Halo" refers to bromo, chloro, iodo or fluoro.

"Haloalkyl" refers to an alkyl radical, as defined above, that is substituted by one or more halo radicals, as defined above, e.g., trifluoromethyl, difluoromethyl, trichloromethyl, 2-trifluoroethyl, 1-fluoromethyl-2-fluoroethyl, 3-bromo-2-fluoropropyl, 1-bromomethyl-2-bromoethyl, and the like.

"Heterocyclic ring" refers to a stable 3- to 15-membered ring radical which consists of carbon atoms and from one to five heteroatoms selected from the group consisting of nitrogen, phosphorus, oxygen and sulfur. For purposes of this invention, the heterocyclic ring radical may be a monocyclic, bicyclic or tricyclic ring system, which may include fused or bridged ring systems; and the nitrogen, phosphorus, carbon or sulfur atoms in the heterocyclic ring radical may be optionally oxidized to various oxidation states. In addition, the nitrogen atom may be optionally quaternized; and the ring radical may be partially or fully saturated or aromatic. Examples of such heterocyclic ring radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, indanyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, dioxaphospholanyl and oxadiazolyl. For those compounds where two adjacent $R^1$'s together with the carbons to which they are attached form a heterocyclic ring fused to the phenyl ring, the most preferred heterocyclic ring is the dioxolane ring (with the phenyl ring forms a benzodioxole ring).

"Heterocyclyl" refers to a heterocyclic ring radical as defined above, except that the heterocyclyl ring radical may be attached to the main structure at any heteroatom or carbon atom that results in the creation of a stable structure.

"Heterocyclylalkyl" refers to a radical of the formula —$R_a$—$R_c$ where $R_a$ is an alkyl radical as defined above and $R_c$ is a heterocyclyl ring radical as defined above, for example, (4-methylpiperazin-1-yl)methyl, (morpholin-4-yl) methyl, 2-(oxazolin-2-yl)ethyl, and the like.

"N-heterocyclic ring" refers to those heterocyclic ring radicals defined above which contain at least one nitrogen. The N-heterocyclic ring radical is attached to the main structure through a nitrogen atom in the ring. Examples include, but are not limited to, 4—methylpiperazin-1-yl, pyrrolidin-1-yl, morpholin-4-yl, oxazolin-2-yl, and the like. The N-heterocyclic ring may contain up to three additional hetero atoms. Examples include tetrazolyl, triazolyl, thiomorpholinyl, oxazinyl, and the like.

"HPLC" refers to high pressure liquid chromatography.

"Monoalkylamino" refers to a radical of the formula —N(H)$R_a$ where $R_a$ is an alkyl radical as defined above, e.g., methylamino, ethylamino, (t-butyl)amino, and the like.

"Monoalkylaminocarbonyl" refers to a radical of the formula —C(O)N(H)$R_a$ where $R_a$ is an alkyl radical as defined above, e.g., (methylamino)carbonyl, (ethylamino) carbonyl, ((t-butyl)amino)carbonyl, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Therapeutically effective amount" refers to that amount of a compound of the invention which, when administered to a human in need thereof, is sufficient to effect treatment, as defined below, for disease-states characterized by thrombotic activity. The amount of a compound of the invention which constitutes a "therapeutically effective amount" will vary depending on the compound, the disease-state and its severity, and the age of the human to be treated, but can be determined routinely by one of ordinary skill in the art having regard to his own knowledge and to this disclosure.

"THF" refers to tetrahydrofuran.

"Treating" or "treatment" as used herein covers the treatment of a disease-state in a human, which disease-state is characterized by thrombotic activity, and includes:

(i) preventing the disease-state from occurring in a human, in particular, when such human is predisposed to the disease-state but has not yet been diagnosed as having it;

(ii) inhibiting the disease-state, ie., arresting its development; or (iii) relieving the disease-state, ie., causing regression of the disease-state.

The yield of each of the reactions described herein is expressed as a percentage of the theoretical yield.

For purposes of this invention, in the substituent "—$R^8$—$OR^5$", the "—$OR^5$" group may be attached to any carbon in the alkylene, alkylidene or alkylidyne chain.

Some of the compounds of the invention may have imino, amino, oxo or hydroxy substituents off aromatic heterocyclic ring systems. For purposes of this disclosure, it is understood that such imino, amino, oxo or hydroxy substituents may exist in their corresponding tautomeric form, i.e., amino, imino, hydroxy or oxo, respectively.

For purposes of this invention, unless otherwise indicated, the linker moieties between the B ring and the C ring ("E") and between the B ring and the $R^3$ moiety ("D") may be independently attached to the B ring on either end of the linker.

For purposes of this invention, the quaternary salts represented by "—N⁺(R⁹)(R¹⁶)₂" include aromatic rings wherein both R¹⁶'s together with the nitrogen to which they are attached form an aromatic ring and it is understood that R⁹ is not present.

The compounds of the invention, or their pharmaceutically acceptable salts, may have asymmetric carbon atoms, oxidized sulfur atoms or quaternized nitrogen atoms in their structure. The compounds of the invention and their pharmaceutically acceptable salts may therefore exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention. Methods for the preparation and/or separation and isolation of single stereoisomers from racemic mixtures or non-racemic mixtures of stereoisomers are well known in the art.

The nomenclature used herein is a modified form of the I.U.P.A.C. system wherein the compounds of the invention are named as derivatives of benzamide. For example, a compound of the invention selected from formula (I) where A is —N—; m is 1; n is 1; E is —C(O)—N(H)— where the nitrogen atom is bonded to pyridine ring; D is —N(H)—C(O)— where the nitrogen atom is bonded to the phenyl ring; $R^1$ is in the 5-position and is chloro; $R^2$ is in the 3-position and is —N(R¹⁰)R¹¹ where R¹⁰ and R¹¹ together with nitrogen to which they are attached form a morpholin-4-yl ring; $R^4$ is in the 5-position and is chloro; and $R^3$ is selected from formula (i):

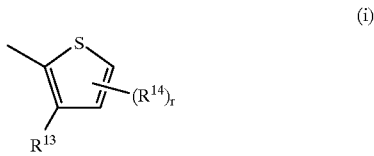

where R¹³ is chloro, r is 1 and R¹⁴ is —C(R⁷)H—N(R¹⁰)R¹¹ where R⁷ is hydrogen, R¹⁰ is methyl and R¹¹ is 1-methylpiperidin-4-yl; i.e., a compound of the following formula (with position numbers indicated):

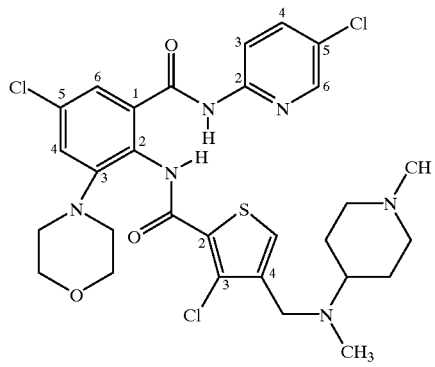

is named herein as N-(5-chloropyridin-2-yl)-2-[((4-((N'-methyl-N'-(1-methylpiperidin-4-yl)amino)methyl)-3-chlorothiophen-2-yl)carbonyl)amino]-3-(morpholin-4-yl)-5-chlorobenzamide.

For purposes of this specification, parenthesis are used to denote substituents of a main atom. For example, —C(R⁷)H—N(R¹⁰)R¹¹ refers to the radical:

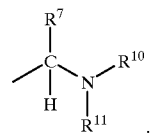

Carbonyl and thiocarbonyl groups are indicated as —C(O)— and —C(S)—, respectively, and optionally substituted imino radicals are indicated as =N(R¹⁷).

Substituents having repeating sections are indicated by brackets (or parenthesis) and the repeating integer. For example, the substituent —C(R⁷)H—R⁸—(R⁸—O)ₜ—R⁵ where t is 3 refers to the the substituent —C(R⁷)H—R⁸—R⁸—O—R⁸—O—R⁸—O—R⁵.

Utility and Administration

A. Utility

The compounds of the invention are inhibitors of the serine protease, factor Xa, and are therefore useful in disease-states characterized by thrombotic activity based on factor Xa's role in the coagulation cascade (see Background of the Invention above). Primarily, the compounds of the invention are useful as anti-coagulants. A primary indication for the compounds is prophylaxis for long term risk following myocardial infarction. Additional indications are prophylaxis of deep vein thrombosis (DVT) following orthopedic surgery or prophylaxis of selected patients following a transient ischemic attack. The compounds of the invention may also be useful for indications in which coumarin is currently used, such as for DVT or other types of surgical intervention such as coronary artery bypass graft and percutaneous transluminal coronary angioplasty. The compounds are also useful for the treatment of thrombotic complications associated with acute promyelocytic leukemia, diabetes, multiple myelomas, disseminated intravascular coagulation associated with septic shock, purpura fulminanas associated infection, adult respiratory distress syndrome, unstable angina, and thrombotic complications associated with aortic valve or vascular prosthesis. The compounds are also useful for prophylaxis for thrombotic diseases, in particular in patients who have a high risk of developing such disease.

In addition, the compounds of the invention are useful as in vitro diagnostic reagents for selectively inhibiting factor Xa without inhibiting other components of the coagulation cascade.

B. Testing

The primary bioassays used to demonstrate the inhibitory effect of the compounds of the invention on factor Xa are simple chromogenic assays involving only serine protease, the compound of the invention to be tested, substrate and buffer (see, e.g., *Thrombosis Res.* (1979), Vol. 16, pp. 245–254). For example, four tissue human serine proteases can be used in the primary bioassay, free factor Xa, prothrombinase, thrombin (IIa) and tissue plasminogen activator (tPA). The assay for tPA has been successfully used before to demonstrate undesired side effects in the inhibition of the fibrinolytic process (see, e.g., *J. Med. Chem.* (1993), Vol. 36, pp. 314–319).

Another bioassay useful in demonstrating the utility of the compounds of the invention in inhibiting factor Xa demonstrates the potency of the compounds against free factor Xa in citrated plasma. For example, the anticoagulant efficacy of the compounds of the invention will be tested using either the prothrombin time (PT), or activated partial thromboplastin time (aPTT) while selectivity of the compounds is checked with the thrombin clotting time (TCT) assay. Correlation of the $K_i$ in the primary enzyme assay with the $K_i$ for free factor Xa in citrated plasma will screen against compounds which interact with or are inactivated by other plasma components. Correlation of the $K_i$ with the extension of the PT is a necessary in vitro demonstration that potency in the free factor Xa inhibition assay translates into potency in a clinical coagulation assay. In addition, extension of the PT in citrated plasma can be used to measure duration of action in subsequent pharmacodynamic studies.

For further information on assays to demonstrate the activity of the compounds of the invention, see R. Lottenberg et al., *Methods in Enzymology* (1981), Vol. 80, pp. 341–361, and H. Ohno et al., *Thrombosis Research* (1980), Vol. 19, pp. 579–588.

C. General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally, topically, transdermally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and a compound of the invention as the/an active agent, and, in addition, may include other medicinal agents, pharmaceutical agents, carriers, adjuvants, etc.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. Preferably, the composition will be about 5% to 75% by weight of a compound(s) of the invention, or a pharmaceutically acceptable salt thereof, with the rest being suitable pharmaceutical excipients.

The preferred route of administration is oral, using a convenient daily dosage regimen which can be adjusted according to the degree of severity of the disease-state to be treated. For such oral administration, a pharmaceutically acceptable composition containing a compound(s) of the invention, or a pharmaceutically acceptable salt thereof, is formed by the incorporation of any of the normally employed excipients, such as, for example, pharmaceutical grades of mannitol, lactose, starch, pregelatinized starch, magnesium stearate, sodium saccharin, talcum, cellulose ether derivatives, glucose, gelatin, sucrose, citrate, propyl gallate, and the like. Such compositions take the form of solutions, suspensions, tablets, pills, capsules, powders, sustained release formulations and the like.

Preferably such compositions will take the form of capsule, caplet or tablet and therefore will also contain a diluent such as lactose, sucrose, dicalcium phosphate, and the like; a disintegrant such as croscarmellose sodium or derivatives thereof; a lubricant such as magnesium stearate and the like; and a binder such as starch, gum acacia, polyvinylpyrrolidone, gelatin, cellulose ether derivatives, and the like.

The compounds of the invention, or their pharmaceutically acceptable salts, may also be formulated into a suppository using, for example, about 0.5% to about 50% active ingredient disposed in a carrier that slowly dissolves within the body, e.g., polyoxyethylene glycols and polyethylene glycols (PEG), e.g., PEG 1000 (96%) and PEG 4000 (4%).

Liquid pharmaceutically administrable compositions can, for example, be prepared by dissolving, dispersing, etc., a compound(s) of the invention (about 0.5% to about 20%), or a pharmaceutically acceptable salt thereof, and optional pharmaceutical adjuvants in a carrier, such as, for example, water, saline, aqueous dextrose, glycerol, ethanol and the like, to thereby form a solution or suspension.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Actual methods of preparing such dosage forms are known, or will be apparent, to those skilled in this art; for example, see *Remington's Pharmaceutical Sciences,* 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state alleviated by the inhibition of factor Xa in accordance with the teachings of this invention.

The compounds of the invention, or their pharmaceutically acceptable salts, are administered in a therapeutically effective amount which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disease-states; and the host undergoing therapy. Generally, a therapeutically effective daily dose is from about 0.14 mg to about 14.3 mg/kg of body weight per day of a compound of the invention, or a pharmaceutically acceptable salt thereof, preferably, from about 0.7 mg to about 10 mgfkg of body weight per day; and most preferably, from about 1.4 mg to about 7.2 mg/kg of body weight per day. For example, for administration to a 70 kg person, the dosage range would be from about 10 mg to about 1.0 gram per day of a compound of the invention, or a pharmaceutically acceptable salt thereof, preferably from about 50 mg to about 700 mg per day, and most preferably from about 100 mg to about 500 mg per day.

PREFERRED EMBODIMENTS

Of the compounds disclosed in the Summary of the Invention, certain compounds are preferred.

The most preferred compounds of the invention are those compounds selected from formula (III) having the formula (I):

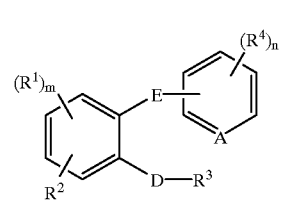

A is =CH— or =N—;

m is 1 to 3;

n is 1 to 4;

D is —N($R^5$)—C(Z)— or —N($R^5$)—S(O)$_p$— (where p is 0 to 2; Z is oxygen, sulfur or $H_2$; and the nitrogen atom is directly bonded to the phenyl ring having the $R^1$ and $R^2$ substituents);

E is —C(Z)—N($R^5$)— or —S(O)$_p$—N($R^5$)— (where p is 0 to 2; Z is oxygen, sulfur or $H_2$; and the nitrogen atom can be bonded to the phenyl ring having the $R^1$ and the $R^2$ substituents or to the aromatic ring having the $R^4$ substituent);

each $R^1$ is independently hydrogen, alkyl, aryl, aralkyl, halo, haloalkyl, cyano, —$OR^5$, —S(O)$_p$—$R^9$ (where p is 0 to 2), —C(O)$OR^5$, —C(O)N($R^5$)$R^6$, —N($R^6$)$R^6$, —O—C(O)$R^5$, or —N(R)—CH($R^{12}$)—C(O)$OR^5$;

or two adjacent $R^1$'s together with the carbons to which they are attached form a heterocyclic ring fused to the phenyl ring wherein the heterocyclic ring is optionally substituted by one or more substituents selected from the group consisting of alkyl, aryl and aralkyl;

$R^2$ is hydrogen, alkyl, aryl, aralkyl, halo, haloalkyl, cyano, —$OR^5$, —S(O)$_p$—$R^9$ (where p is 0 to 2), —C(O)$OR^5$, —OC(O)—$R^5$, —C(O)N($R^5$)$R^6$, —N($R^{10}$)$R^{11}$, —C($R^7$)H—N($R^{10}$)$R^{11}$, —C($R^7$)H—$R^8$—N($R^{10}$)$R^{11}$, —C($R^7$)H—$OR^5$, —C($R^7$)H—$R^8$—$OR^5$, —C($R^7$)H—S(O)$_p$—$R^9$ (where p is 0 to 2), —C($R^7$)H—$R^8$—S(O)$_p$—$R^9$ (where p is 0 to 2), —O—$R^8$—S(O)$_p$—$R^9$ (where p is 0 to 2), —C($R^7$)H—N($R^5$)$R^6$, —C($R^7$)H—$R^8$—N($R^5$)$R^6$, —O—$R^8$—CH(OH)—$CH_2$—N($R^{10}$)$R^{11}$, —O—$R^8$—N($R^{10}$)$R^{11}$, —O—$R^8$—O—C(O)$R^5$, —O—$R^8$—CH(OH)—$CH_2$—$OR^5$, —O—($R^8$—O)$_t$$R^5$ (where t is 1 to 6), —O—($R^8$—O)$_t$$R^{19}$ (where t is 1 to 6), —O—$R^8$—C(O)$OR^5$, —O—$R^8$—C(O)$R^{19}$, —O—$R^8$—C(O)$OR^5$, —N($R^5$)—$R^8$—N($R^{10}$)$R^{11}$, —S(O)$_p$$R^8$—N($R^5$)$R^6$ (where p is 0 to 2), —S(O)$_p$—$R^8$—C(O)$OR^5$ (where p is 0 to 2), or —N($R^5$)—CH($R^{12}$)—C(O)$OR^5$;

$R^3$ is a radical of formula (i):

(i)

where:
r is 1 or 2;
$R^{13}$ is hydrogen, alkyl, halo, haloalkyl, —N($R^5$)$R^5$, —C($R^7$)H—N($R^5$)$R^6$, —$OR^5$, —$R^8$—$OR^5$, —S(O)$_p$—$R^8$—N($R^5$)$R^6$ (where p is 0 to 2) or heterocyclylalkyl (where the heterocyclic ring is optionally substituted by one or more substituents selected from the group consisting of alkyl, halo, aralkyl, nitro and cyano); and each $R^{14}$ is independently hydrogen, alkyl, halo, formyl, acetyl, cyano, —$R^8$—CN, —N($R^{10}$)$R^{11}$, —C($R^7$)H—N($R^{10}$)$R^{11}$, —C($R^7$)H—$R^8$—N($R^{10}$)$R^{11}$, —C($R^7$)H—$N^\oplus$($R^9$)($R^{16}$)$_2$, —C($R^7$)H—$R^8$—$N^\oplus$($R^9$)($R^{16}$)$_2$, —C(O)$OR^5$, —C($R^7$)H—C(O)$OR^5$, —C($R^7$)H—$R^8$—C(O)$OR_5$, —$OR^5$, —C($R^7$)H—$OR^5$, —C($R^7$)H—$R^8$—$OR^5$, —C($R^7$)H—O—$R^{15}$, —S(O)$_p$—$R^{15}$ (where p is 0 to 2), —C($R^7$)H—S(O)$_p$—$R^{15}$ (where p is 0 to 2), —C($R^7$)H—$R^8$—S(O)$_p$—$R^{15}$ (where p is 0 to 2), —S(O)$_p$—N($R^5$)$R^6$ (where p is 0 to 2), —C(O)N($R^5$)$R^6$, —C($R^7$)H—C(O)N($R^5$)$R^6$, —C($R^7$)H—$R^8$—C(O)N($R^5$)$R^6$, —C($R^7$)H—N($R^5$)—($R^8$—O)$_t$—$R^5$ (where t is 1 to 6), —C($R^7$)H—$R^8$—N($R^5$)—($R^8$—O)$_t$—$R^5$ (where t is 1 to 6), —C($R^7$)H—O—($R^8$—O)$_t$—$R^5$ (where t is 1 to 6), —C($R^7$)H—$R^8$—O—($R^8$—O)$_t$-$R^5$ (where t is 1 to 6), —O—$R^8$—CH(OH)—$CH_2$—$OR^5$, —C($R^7$)H—O—$R^8$—CH(OH)—$CH_2$—$OR^5$, —C($R^7$)H—N($R^5$)—$R^8$—[CH(OH)]$_t$—$CH_2$—$OR^5$ (where t is 1 to 6), —C($R^7$)H—N($R^5$)—S(O)$_2$—N($R^{10}$)$R^{11}$, —C($R^7$)H—N($R^{10}$)—C(NR$^{17}$)—N($R^{10}$)$R^{11}$, —C($R^7$)H—N($R^{10}$)—C(NR$^{17}$)—$R^{10}$, —C(NR$^{17}$)—N($R^5$)$R^6$, —C($R^7$)H—C(NR$^{17}$)—N($R^5$)$R^6$, —C($R^7$)H—O—N($R^5$)$R^6$, heterocyclyl (wherein the heterocyclyl radical is not attached to the radical of formula (i) through a nitrogen atom and is optionally substituted by alkyl, aryl, aralkyl, halo, haloalkyl, oxo, —$OR^5$, —C(O)$OR^5$, —N($R^5$)$R^6$ or —C(O)N($R^5$)$R^6$), or heterocyclylalkyl (wherein the heterocyclyl radical is not attached to the alkyl radical through a nitrogen atom and is optionally substituted by one or more substituents selected from the group consisting of alkyl, aryl, aralkyl, halo, haloalkyl, oxo, —$OR^5$, —C(O)$OR^5$, —N($R^5$)$R^6$ and —C(O)N($R^5$)$R^6$);

or $R^3$ is a radical of the formula (ii):

(ii)

where v is 1 to 4;
$R^{13}$ is as defined above for formula (i); and
$R^{14}$ is as defined above for formula (i); and
each $R^4$ is independently hydrogen, alkyl, halo, haloalkyl, cyano, nitro, —$OR^5$, —C(O)$OR^5$, —N($R^5$)$R^6$, —C(O)N($R^5$)$R^6$, or —$R^8$—N($R^5$)$R^6$;

$R^5$ and $R^6$ are each independently hydrogen, alkyl, aryl or aralkyl;

each $R^7$ is independently hydrogen or alkyl;

each $R^8$ is independently a straight or branched alkylene, alkylidene or alkylidyne chain;

each $R^9$ is independently alkyl, aryl or aralkyl;

$R^{10}$ and $R^{11}$ are each independently hydrogen, alkyl, haloalkyl, aryl, aralkyl, formyl, cyano, —$R^8$—CN, —$OR^5$, —$R^8$—$OR^5$, —S(O)$_p$—$R^{15}$ (where p is 0 to 2), —$R^8$—S(O)$_p$—$R^{15}$ (where p is 0 to 2), —N($R^5$)$R^6$, —$R^8$—N($R^5$)$R^6$, —$R^8$—C(O)$OR^5$, —C(O)—$R^{15}$, —C(O)N$H_2$, —$R^8$—C(O)N$H_2$, —C(S)N$H_2$, —C(O)—S—$R^5$, —C(O)—N($R^5$)$R_{15}$, —$R^8$—C(O)—N($R^5$)$R^{15}$, —C(S)—N($R^5$)$R^{15}$, —$R^8$—N($R^5$)—C(O)H, —$R^8$—N($R^5$)—C(O)$R^{15}$, —C(O)O—$R^8$—N($R^5$)$R^6$, —C(N($R^5$)$R^6$)=C($R^{18}$)$R^{10}$, —$R^8$—N($R^5$)—P(O)(O$R^5$)$_2$, cycloalkyl (optionally substituted by one or more substituents selected from the group consisting of alkyl, halo and —$OR^5$), heterocyclyl (optionally substituted by alkyl, aryl, aralkyl, halo, haloalkyl, oxo, —$OR^5$, —$R^8$—$OR^5$, —C(O)$OR^5$, —S(O)$_p$—$R^9$ (where p is 0 to 2), —$R^8$—S(O)$_p$—$R^9$ (where p is 0 to 2), —N($R^5$)$R^6$ or —C(O)N($R^5$)$R^6$), or heterocyclylalkyl (optionally substituted by one or more substituents selected from the group consisting of alkyl, aryl, aralkyl, halo, haloalkyl, oxo, —$OR^5$, —$R^8$—$OR^5$, —C(O)$OR^5$, —S(O)$_p$—$R^9$ (where p is 0 to 2), —$R^8$—S(O)$_p$—$R^9$ (where p is 0 to 2), —N($R^5$)$R^6$ and —C(O)N($R^5$)$R^6$);

or $R^{10}$ and $R^{11}$ together with the nitrogen to which they are attached form a N-heterocyclic ring containing zero to three additional hetero atoms, where the N-heterocylic ring is optionally substituted by one or more substituents selected from the group consisting of alkyl, halo, haloalkyl, aryl, aralkyl, oxo, nitro, cyano, —$R^8$—CN, =N($R^{17}$), —$OR^5$, —C(O)$OR^5$, —$R^8$—C(O)$OR^5$, —N($R^5$)$R^6$, —$R^8$—N($R^5$)$R^6$, —C(O)N($R^5$)$R^6$, —$R^8$—C(O)N($R^5$)$R^6$, —N($R^5$)—N($R^5$)$R^6$, —C(O)$R^5$, —C(O)—($R^8$—O)$_t$—$R^5$ (where t is 1 to 6), —S(O)$_p$—$R^9$ (where p is 0 to 2), —$R^8$—S(O)$_p$—$R^9$ (where p is 0 to 2), —($R^8$—O)$_t$—$R^5$ (where t is 1 to 6), and heterocyclyl (optionally substituted by one or more substituents selected from the group consisting of alkyl, aryl, aralkyl, halo, haloalkyl, —$OR^5$, —C(O)$OR^5$, —N($R^5$)$R^6$, and —C(O)N($R^5$)$R^5$);

$R^{12}$ is a side chain of an α-amino acid;

each $R^{15}$ is independently alkyl, cycloalkyl, haloalkyl, aryl, aralkyl, —$R^8$—O—C(O)—$R^5$, —$R^8$—O$R^5$, —N($R^5$)$R^6$, —$R^8$—N($R^5$)$R^6$, —$R^8$—C(O)O$R^5$, heterocyclyl (optionally substituted by one or more substituents selected from the group consisting of alkyl, aryl, aralkyl, halo, haloalkyl, —O$R^5$, —$R^8$—O$R^5$, —C(O)O$R^5$, —N($R^5$)$R^6$, and —C(O)N($R^5$)$R^6$), or heterocyclylalkyl (optionally substituted by one or more substituents selected from the group consisting of alkyl, aryl, aralkyl, halo, haloalkyl, —O$R^5$, —$R^8$—O$R^5$, —C(O)O$R^5$, —N($R^5$)$R^6$, and —C(O)N($R^5$)$R^6$);

or $R^5$ and $R^{15}$ together with the nitrogen to which they are attached form a N-heterocyclic ring containing zero to three additional hetero atoms, where the N-heterocyclic ring is optionally substituted by one or more substituents selected from the group consisting of alkyl, aryl, aralkyl, amino, monoalkylamino, dialkylamino, —O$R^5$, —C(O)O$R^5$, aminocarbonyl, monoalkylaminocarbonyl, and dialkylaminocarbonyl;

each $R^{16}$ is independently alkyl, aryl, aralkyl, —$R^8$—O$R^5$, —$R^8$—N($R^5$)$R^6$, cycloalkyl (optionally substituted by one or more substituents selected from the group consisting of alkyl, halo and —O$R^5$), heterocyclyl (optionally substituted by alkyl, aryl, aralkyl, halo, haloalkyl, —O$R^5$, —C(O)O$R^5$, —N($R^5$)$R^6$ or —C(O)N($R^5$)$R^6$), or heterocyclylalkyl (optionally substituted by one or more substituents selected from the group consisting of alkyl, aryl, aralkyl, halo, haloalkyl, —O$R^5$, —C(O)O$R^5$, —N($R^5$)$R^6$ and —C(O)N($R^5$)$R^6$); or both $R^{16}$'s together with the nitrogen to which they are attached (and wherein the $R^9$ substituent is not present) form an aromatic N-heterocyclic ring containing zero to three additional hetero atoms, where the N-heterocyclic ring is optionally substituted by one or more substituents selected from the group consisting of alkyl, aryl, aralkyl, —O$R^5$, —C(O)O$R^5$, —$R^8$—C(O)O$R^5$, —N($R^5$)$R^6$, —$R^8$—N($R^5$)$R^6$, —C(O)$R^5$, —C(O)—($R^8$—O)$_t$—$R^5$ (where t is 1 to 6), and —($R^8$—O)$_t$—$R^5$ (where t is 1 to 6);

each $R^{17}$ is independently hydrogen, alkyl, aryl, aralkyl, cyano, —O$R^5$, —$R^8$—O$R^5$, —C(O)O$R^5$, —$R^8$—C(O)O$R^5$, —C(O)—N($R^5$)$R^6$, or —$R^8$—C(O)—N($R^5$)$R^6$;

$R^{18}$ is hydrogen, alkyl, aryl, aralkyl, cyano, —C(O)O$R^5$, or —NO$_2$; and each $R^{19}$ is cycloalkyl, haloalkyl, —$R^8$—O$R^5$, —$R^8$—N($R^5$)$R^6$, —$R^8$—C(O)O$R^5$, —$R^8$—C(O)N($R^5$)$R^6$, heterocyclyl (optionally substituted by alkyl, aryl, aralkyl, halo, haloalkyl, —O$R^5$, —C(O)O$R^5$, —N($R^5$)$R^6$ or —C(O)N($R^5$)$R^6$), or heterocyclylalkyl (optionally substituted by one or more substituents selected from the group consisting of alkyl, aryl, aralkyl, halo, haloalkyl, —O$R^5$, —C(O)O$R^5$, —N($R^5$)$R^6$ and —C(O)N($R^5$)$R^6$).

Of these compounds, a preferred group of compounds are those compounds wherein:

A is =N—;
m is 1 to 3;
n is 1 to 4;
D is —N($R^5$)—C(Z)— (where Z is oxygen, sulfur or H$_2$, and $R^5$ is hydrogen or alkyl);
E is —C(Z)—N($R^5$)— (where Z is oxygen, sulfur or H$_2$, $R^5$ is hydrogen or alkyl, and the nitrogen is attached to the pyridinyl ring);
$R^1$ is halo or haloalkyl;
$R^2$ is —N($R^{10}$)$R^{11}$, —O—$R^8$—S(O)$_p$—$R^9$ (where p is 0), —O—$R^8$—C(O)O$R^5$, —O—($R^8$—O)$_t$—$R^5$ (where t is 1) or —O—$R^8$—N($R^{10}$)$R^{11}$ where:
each $R^5$ is independently hydrogen or alkyl;

each $R^8$ is independently a straight or branched alkylene chain;
$R^9$ is alkyl; and
$R^{10}$ and $R^{11}$ are each independently hydrogen, alkyl, or —$R^8$—O—$R^5$ (where $R^8$ is a straight or branched alkylene chain and $R^5$ is hydrogen or alkyl);
or $R^{10}$ and $R^{11}$ together with the nitrogen to which they are attached form a N-heterocyclic ring containing zero to one additional hetero atoms, where the N-heterocyclic ring is optionally substituted by alkyl;
$R^3$ is a radical of the formula (i):

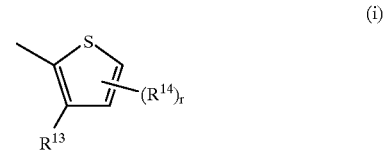

where r is 1;
$R^{13}$ is halo; and
$R^{14}$ is —C($R^7$)H—N($R^{10}$)$R^{11}$ where:
$R^7$ is hydrogen; and
$R^{10}$ and $R^{11}$ together with the nitrogen to which they are attached form piperazinyl optionally substituted by one or more substituents selected from the group consisting of alkyl and —C(O)$R^5$; and
$R^4$ is hydrogen or halo.

Of this group of compounds, a preferred subgroup of compounds are those compounds wherein:
m is 1;
n is 1;
D is —N(H)—C(O)—;
E is —C(O)—N(H)— (where the nitrogen is bonded to the 2-position of the pyridinyl ring);
$R^1$ is halo in the 5-position;
$R^2$ is —N($R^{10}$)$R^{11}$, —O—$R^8$—S(O)$_p$—$R^9$ (where p is 0), —O—$R^8$—C(O)O$R^5$, —O—($R^8$—O)$_t$—$R^5$ (where t is 1) or —O—$R^8$—N($R^{10}$)$R^{11}$ where:
each $R^5$ is independently hydrogen, methyl or ethyl;
each $R^8$ is independently a methylene, ethylene or propylene chain;
$R^9$ is methyl or ethyl; and
$R^{10}$ and $R^{11}$ are each independently hydrogen, methyl, ethyl, or —$R^8$—O—$R^5$ (where $R^8$ is ethylene and $R^5$ is hydrogen, methyl or ethyl); or
$R^{10}$ and $R^{11}$ together with the nitrogen to which they are attached form a N-heterocyclic ring containing zero to one additional hetero atoms, where the N-heterocyclic ring is optionally substituted by alkyl;
$R^3$ is a radical of the formula (i):

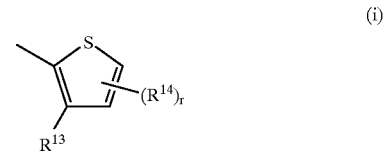

where r is 1;
$R^{13}$ is chloro; and
R is in the 4-position and is —C($R^7$)H—N($R^{10}$)$R^{11}$ where:
$R^7$ is hydrogen; and
$R^{10}$ and $R^{11}$ together with the nitrogen to which they are attached form piperazinyl optionally substituted by methyl or ethyl; and R[4] is hydrogen, bromo or chloro in the 5-position.

Of this subgroup of compounds, a preferred class of compounds are those compounds wherein:

R[1] is chloro;

R[2] is —O—R[8]—S(O)$_p$—R[9] (where p is 0), —O—R[8]—C(O)OR[5] or —O—(R[8]—O)$_t$—R[5] (where t is 1 or 2) where:

each R[5] is independently hydrogen, methyl or ethyl;

each R[8] is independently a methylene, ethylene or propylene chain; and

R[9] is methyl or ethyl.

Of this class of compounds, more preferred compounds are those compounds selected from the group consisting of:

N-(5-chloropyridin-2-yl)-2-[((4-((4-methylpiperazin-1-yl)methyl)-3-chlorothiophen-2-yl)carbonyl)amino]-3-(methylthio)methoxy-5-chlorobenzamide;

N-(5-chloropyridin-2-yl)-2-[((4-((4-methylpiperazin-1-yl)methyl)-3-chlorothiophen-2-yl)carbonyl)amino]-3-(ethoxycarbonyl)methoxy-5-chlorobenzamide;

N-(5-chloropyridin-2-yl)-2-[((4-((4-methylpiperazin-1-yl)methyl)-3-chlorothiophen-2-yl)carbonyl)amino]-3-(2-hydroxyethoxy)-5-chlorobenzamide;

N-(5-chloropyridin-2-yl)-2-[((4-((4-methylpiperazin-1-yl)methyl)-3-chlorothiophen-2-yl)carbonyl)amino]-3-(2-methoxyethoxy)-5-chlorobenzamide; and N-(5-chloropyridin-2-yl)-2-[((4-((4-methylpiperazin-1-yl)methyl)-3-chlorothiophen-2-yl)carbonyl)amino]-3-(2-ethoxyethoxy)-5-chlorobenzamide;

N-(5-chloropyridin-2-yl)-2-[((4-((4-ethylpiperazin-1-yl)methyl)-3-chlorothiophen-2-yl)carbonyl)amino]-3-(2-methoxyethoxy)-5-chlorobenzamide, and N-(5-chloropyridin-2-yl)-2-[((4-((4-ethylpiperazin-1-yl)methyl)-3-chlorothiophen-2-yl)carbonyl)amino]-3-(2-(2-methoxyethoxy)ethoxy)-5-chlorobenzamide.

Of this subgroup of compounds, another preferred class of compounds are those compounds wherein:

R[1] is chloro; and

R[2] is —N(R[10])R[11] or —O—R[8]—N(R[10])R[11] where:

R[8] is a methylene, ethylene or propylene chain; and

R[10] and R[11] are each independently hydrogen, methyl, ethyl, or —R[8]—O—R[5] (where R[8] is ethylene and R[5] is hydrogen, methyl or ethyl).

Of this class of compounds, preferred compounds are selected from the group consisting of:

N-(5-chloropyridin-2-yl)-2-[((4-((4-methylpiperazin-1-yl)methyl)-3-chlorothiophen-2-yl)carbonyl)amino]-3-(dimethyl)amino-5-chlorobenzamide;

N-(5-chloropyridin-2-yl)-2-[((4-((4-methylpiperazin-1-yl)methyl)-3-chlorothiophen-2-yl)carbonyl)amino]-3-(3-(N'-methyl-N'-(2-hydroxyethyl)amino)propoxy)-5-chlorobenzamide; and N-(5-chloropyridin-2-yl)-2-[((4-((4-methylpiperazin-1-yl)methyl)-3-chlorothiophen-2-yl)carbonyl)amino]-3-amino-5-chlorobenzamide.

Of this subgroup of compounds, another preferred class of compounds are those compounds wherein:

R[1] is chloro;

R[2] is —N(R[10])R[11] or —O—R[8]—N(R[10])R[11] where:

R[8] is methylene, ethylene or propylene; and

R[10] and R[11] together with the nitrogen to which they are attached form a N-heterocyclic ring containing zero to one additional hetero atoms, where the N-heterocyclic ring is optionally substituted by alkyl and is selected from the group consisting of morpholinyl, piperazinyl, pyrrolidinyl or imidazolyl.

Of this class of compounds, preferred compounds are selected from the group consisting of:

N-(5-chloropyridin-2-yl)-2-[((4-((4-methylpiperazin-1-yl)methyl)-3-chlorothiophen-2-yl)carbonyl)amino]-3-(morpholin4-yl)-5-chlorobenzamide;

N-(5-chloropyridin-2-yl)-2-[((4-((4-methylpiperazin-1-yl)methyl)-3-chlorothiophen-2-yl)carbonyl)amino]-3-(4-methylpiperazin-1-yl)-5-chlorobenzamide;

N-(5-chloropyridin-2-yl)-2-[((4-((4-methylpiperazin-1-yl)methyl)-3-chlorothiophen-2-yl)carbonyl)amino]-3-(3-morpholinylpropoxy)-5-chlorobenzamide;

N-(5-chloropyridin-2-yl)-2-[((4-((4-methylpiperazin-1-yl)methyl)-3-chlorothiophen-2-yl)carbonyl)amino]-3-(3-(pyrrolidin-1-yl)propoxy)-5-chlorobenzamide;

N-(5-chloropyridin-2-yl)-2-[((4-((4-methylpiperazin-1-yl)methyl)-3-chlorothiophen-2-yl)carbonyl)amino]-3-(pyrrolidin-1-yl)-5-chlorobenzamide;

N-(5-chloropyridin-2-yl)-2-[((4-((4-methylpiperazin-1-yl)methyl)-3-chlorothiophen-2-yl)carbonyl)amino]-3-(3-(imidazol-1-yl)propoxy)-5-chlorobenzamide; and N-(5-chloropyridin-2-yl)-2-[((4-((4-ethylpiperazin-1-yl)methyl)-3-chlorothiophen-2-yl)carbonyl)aminol-3-(morpholin4-yl)-5-chlorobenzamide.

Of the compounds of formula (I) described above, another preferred group of compounds are those compounds of formula (I) wherein:

A is =N—;

m is 1 to 3;

n is 1 to 4;

D is —N(R[5])—C(Z)— (where Z is oxygen, sulfur or H$_2$, and R[5] is hydrogen or alkyl);

E is —C(Z)—N(R[5])— (where Z is oxygen, sulfur or H$_2$, R[5] is hydrogen or alkyl, and the nitrogen is attached to the pyridinyl ring);

R[1] is halo or haloalkyl;

R[2] is hydrogen, haloalkyl, or —OR[5] where R[5] is hydrogen or alkyl;

R[3] is a radical of the formula (i):

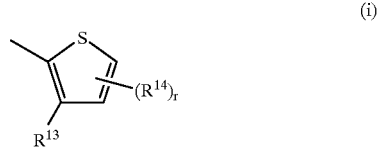

where r is 1;

R[13] is halo; and each R[14] is independently hydrogen, alkyl, halo, formyl, acetyl, cyano, —R[8]—CN, —N(R[10])R[11], —C(R[7])H—N(R[10])R[11], —C(R[7])H—R[8]—N(R[10])R[11], —C(R[7])H—N$^⊕$(R[9])(R[9])$_2$, —C(R[7])H—R[8]—N$^⊕$(R[9])(R[16])$_2$, —C(O)OR[5], —C(R[7])H—C(O)OR[5], —C(R[7])H—R[8]—C(O)OR[5], —OR[5], —C(R[7])H—OR[5], —C(R[7])H—R[8]—OR[5], —C(R[7])H—O—R[15], —S(O)$_p$—R[15] (where p is 0 to 2), —C(R[7])H—S(O)$_p$—R[15] (where p is 0 to 2), —C(R[7])H—R[8]—S(O)$_p$—R[15] (where p is 0 to 2), —S(O)$_p$—N(R[5])R[6] (where p is 0 to 2), —C(O)N(R[5])R[6], —C(R[7])H—C(O)N(R[5])R[6], —C(R[7])H—R[8]—C(O)N(R[5])R[6], —C(R[7])H—N(R[5])—(R[8]—O)$_t$—R[5] (where t is 1 to 6), —C(R[7])H—R[8]—N(R[5])—(R[8]—O)$_t$—R[5] (where t is 1 to 6), —C(R[7])H—O—(R[8]—O)$_t$—R[5] (where t is 1 to 6), —C(R[7])H—R[8]—O—(R[8]—O)$_t$—R[5] (where t is 1 to 6), —O—R[8]—CH(OH)—CH$_2$—OR[5], —C(R[7])H—O—R[8]—CH(OH)—CH$_2$—OR[5], —C(R[7])H—N(R[5])—R[8]—[CH(OH)]$_t$—CH$_2$—OR[5] (where t is 1 to 6), —C(R[7])H—N(R[5])—S(O)$_2$—N(R[10])R[11], —C(R[7])H—N(R[10])—C(NR[17])—N(R[10])R[11], —C(R[7])H—N(R[10])—C(NR[17])—R[10], —C(NR[17])—N(R[5])R[6], —C(R[7])H—C(NR[17])—N(R[5])R[6], —C(R[7])H—O—N(R[5])R[6], heterocyclyl (wherein the heterocyclyl radical is not attached to the radical of formula (i) through a nitrogen atom and is optionally substituted by alkyl, aryl, aralkyl, halo, haloalkyl, oxo, —OR$^5$, —C(O)OR$^5$, —N(R$^5$)R$^6$ or —C(O)N(R$^5$)R$^6$), or heterocyclylalkyl (wherein the heterocyclyl radical is not attached to the alkyl radical through a nitrogen atom and is optionally substituted by one or more substituents selected from the group consisting of alkyl, aryl, aralkyl, halo, haloalkyl, oxo, —OR$^5$, —C(O)OR$^5$, —N(R$^5$)R$^6$ and —C(O)N(R$^5$)R$^6$); where R$^5$ and R$^6$ are each independently hydrogen, alkyl, aryl or aralkyl;

each R$^7$ is independently hydrogen or alkyl;

each R$^8$ is independently a straight or branched alkylene, alkylidene or alkylidyne chain;

each R$^9$ is independently alkyll aryl or aralkyl;

R$^{10}$ and R$^{11}$ are each independently hydrogen, alkyl, haloalkyl, aryl, aralkyl, formyl, cyano, —R$^8$—CN, —OR$^5$, —R$^8$—OR$^5$, —S(O)$_p$—R$^{15}$ (where p is 0 to 2), —R$^8$—S(O)$_p$—R$^{15}$ (where p is 0 to 2), —N(R$^5$)R$^6$, —R$^8$—N(R$^5$)R$^6$, —R$^8$—C(O)OR$^5$, —C(O)—R$^{15}$, —C(O)NH$_2$, —R$^8$—C(O)NH$_2$, —C(S)NH$_2$, —C(O)—S—R$^5$, —C(O)—N(R$^5$)R$^{15}$, —R$^8$—C(O)—N(R$^5$)R$^{15}$, —C(S)—N(R$^5$)R$^{15}$, —R—N(R$^5$)—C(O)H, —R$^8$-N(R$^5$)—C(O)R$^{15}$, —C(O)O—R$^8$—N(R$^5$)R$^6$, —C(N(R$^5$)R$^6$)=C(R$^{18}$)R$^{10}$, —R$^8$—N(R$^5$)—P(O)(OR$^5$)$_2$, cycloalkyl (optionally substituted by one or more substituents selected from the group consisting of alkyl, halo and —OR$^5$), heterocyclyl (optionally substituted by alkyl, aryl, aralkyl, halo, haloalkyl, oxo, —OR$^5$, —R$^8$—OR$^5$, —C(O)OR$^5$, —S(O)$_p$—R$^9$ (where p is 0 to 2), —R$^8$—S(O)$_p$—R$^9$ (where p is 0 to 2), —N(R$^5$)R$^6$ or —C(O)N(R$^5$)R$^6$), or heterocyclylalkyl (optionally substituted by one or more substituents selected from the group consisting of alkyl, aryl, aralkyl, halo, haloalkyl, oxo, —OR$^5$, —R$^8$—OR$^5$, —C(O)OR$^5$, —S(O)$_p$—R$^9$ (where p is 0 to 2), —R$^8$—S(O)$_p$—R$^9$ (where p is 0 to 2), —N(R$^5$)R$^6$ and —C(O)N(R$^5$)R$^6$), where R$^5$ and R$^5$ are each independently hydrogen, alkyl, aryl or aralkyl;

each R$^8$ is independently a straight or branched alkylene, alkylidene or alkylidyne chain;

each R$^9$ is independently alkyl, aryl or aralkyl;

each R$^{15}$ is independently alkyl, cycloalkyl, haloalkyl, aryl, aralkyl, —R$^8$—O—C(O)—R$^5$, —R$^8$—OR$^5$, —N(R$^5$)R$^6$, —R$^5$—N(R$^5$)R$^6$, —R$^8$—C(O)OR$^5$, heterocyclyl (optionally substituted by one or more substituents selected from the group consisting of alkyl, aryl, aralkyl, halo, haloalkyl, —OR$^5$, —R$^8$—OR$^5$, —C(O)OR$^5$, —N(R$^5$)R$^6$, and —C(O)N(R$^5$)R$^6$), or heterocyclylalkyl (optionally substituted by one or more substituents selected from the group consisting of alkyl, aryl, aralkyl, halo, haloalkyl, —OR$^5$, —R$^8$—OR$^5$, —C(O)OR$^5$, —N(R$^5$)R$^6$, and —C(O)N(R$^5$)R$^6$), where R$^5$ and R$^6$ are independently each hydrogen, alkyl, aryl or aralkyl, and each R$^8$ is independently a straight or branched alkylene, alkylidene or alkylidyne chain;

or R$^5$ and R$^{15}$ together with the nitrogen to which they are attached form a N-heterocyclic ring containing zero to three additional hetero atoms, where the N-heterocyclic ring is optionally substituted by one or more substituents selected from the group consisting of alkyl, aryl, aralkyl, amino, monoalkylamino, dialkylamino, —OR$^5$, —C(O)OR$^5$, aminocarbonyl, monoalkylaminocarbonyl, and dialkylaminocarbonyl, where each R$^5$ is hydrogen, alkyl, aryl or aralkyl; and R$^{18}$ is hydrogen, alkyl, aryl, aralkyl, cyano, —C(O)OR$^5$, or —NO$_2$;

or R$^{10}$ and R$^{11}$ together with the nitrogen to which they are attached form a N-heterocyclic ring containing zero to three additional hetero atoms, where the N-heterocyclic ring is optionally substituted by one or more substituents selected from the group consisting of alkyl, halo, haloalkyl, aryl, aralkyl, oxo, nitro, cyano, —R$^8$—CN, =N(R$^{17}$), —OR$^5$, —C(O)OR$^5$, —R$^8$—C(O)OR$^5$, —N(R$^5$)R$^6$, —R$^8$—N(R$^5$)R$^6$, —C(O)N(R$^5$)R$^6$, —R$^8$—C(O)N(R$^5$)R$^6$, —N(R$^5$)—N(R$^5$)R$^6$, —C(O)R$^5$, —C(O)—(R$^8$—O)$_t$—R$^5$ (where t is 1 to 6), —S(O)$_p$—R$^9$ (where p is 0 to 2), —R$^8$—S(O)$_p$—R$^9$ (where p is 0 to 2), —(R$^8$—O)$_t$—R$^5$ (where t is 1 to 6), and heterocyclyl (optionally substituted by one or more substituents selected from the group consisting of alkyl, aryl, aralkyl, halo, haloalkyl, —OR$^5$, —C(O)OR$^5$, —N(R$^5$)R$^6$, and —C(O)N(R$^5$)R$^6$), where R$^5$ and R$^6$ are each independently hydrogen, alkyl, aryl or aralkyl;

each R$^8$ is independently a straight or branched alkylene, alkylidene or alkylidyne chain;

each R$^9$ is independently alkyl, aryl or aralkyl;

each R$^{17}$ is independently hydrogen, alkyl, aryl, aralkyl, cyano, —OR$^5$, —R$^8$—OR$^5$, —C(O)OR$^5$, —R$^8$—C(O)OR$^5$, —C(O)—N(R$^5$)R$^6$, or —R$^8$—C(O)—N(R$^5$)R$^6$, where R$^5$ and R$^6$ are independently each hydrogen, alkyl, aryl or aralkyl, and each R$^8$ is independently a straight or branched alkylene, alkylidene or alkylidyne chain;

each R$^{16}$ is independently alkyl, aryl, aralkyl, —R$^8$—OR$^5$, —R$^8$—N(R$^5$)R$^6$, cycloalkyl (optionally substituted by one or more substituents selected from the group consisting of alkyl, halo and —OR$^5$), heterocyclyl (optionally substituted by alkyl, aryl, aralkyl, halo, haloalkyl, —OR$^5$, —C(O)OR$^5$, —N(R$^5$)R$^6$ or —C(O)N(R$^5$)R$^6$), or heterocyclylalkyl (optionally substituted by one or more substituents selected from the group consisting of alkyl, aryl, aralkyl, halo, haloalkyl, —OR$^5$, —C(O)OR$^5$, —N(R$^5$)R$^6$ and —C(O)N(R$^5$)R$^6$), where R$^5$ and R$^6$ are independently each hydrogen, alkyl, aryl or aralkyl, and each R$^8$ is independently a straight or branched alkylene, alkylidene or alkylidyne chain; or both R$^{16}$'s together with the nitrogen to which they are attached (and wherein the R$^9$ substituent is not present) form an aromatic N-heterocyclic ring containing zero to three additional hetero atoms, where the N-heterocyclic ring is optionally substituted by one or more subsfituents selected from the group consisting of alkyl, aryl, aralkyl, —OR$^5$, —C(O)OR$^5$, —R$^8$—C(O)OR$^5$, —N(R$^5$)R$^6$, —R$^8$—N(R$^5$)R$^6$, —C(O)R$^5$, —C(O)—(R$^8$—O)$_t$—R$^5$ (where t is 1 to 6), and —(R$^8$—O)$_t$—R$^5$ (where t is 1 to 6), where R$^5$ and R$^6$ are independently each hydrogen, alksyl, aryl or aralkyl, and each R$^8$ is independently a straight or branched alkylene, alkylidene or alkylidyne chain;

each R$^{17}$ is independently hydrogen, alkyl, aryl, aralkyl, cyano, —OR$^5$, —R$^8$—OR$^5$, —C(O)OR$^5$, —R$^8$—C(O)OR$^5$, —C(O)—N(R$^5$)R$^6$, or —R$^8$—C(O)—N(R$^5$)R$^6$, where R$^5$ and R$^6$ are independently each hydrogen, alkyl, aryl or aralkyl, and each R$^8$ is independently a straight or branched alkylene, alkylidene or alkylidyne chain;

and R$^4$ is hydrogen or halo.

Of this group of compounds, a preferred subgroup of compounds are those compounds wherein:

m is 1;

n is 1;

D is —N(H)—C(O)—;

E is —C(O)—N(H)— (where the nitrogen is bonded to the 2-position of the pyridinyl ring);

R$^2$ is hydrogen, haloalkyl, or —OR$^5$ where R$^5$ is hydrogen or alkyl;

$R^3$ is a radical of the formula (i):

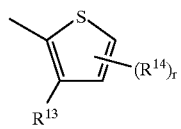

where r is 1;
$R^{13}$ is halo; and
$R^{14}$ is —C($R^7$)H—N($R^{10}$)$R^{11}$ where:
$R^7$ is hydrogen;
$R^{10}$ and $R^{11}$ are each independently hydrogen, alkyl, haloalkyl, aryl, aralkyl, formyl, cyano, —$R^8$—CN, —$OR^5$, —$R^8$—$OR^5$, —S(O)$_p$—$R^{15}$ (where p is 0 to 2), —$R^8$—S(O)$_p$—$R^{15}$ (where p is 0 to 2), —N($R^5$)$R^6$, —$R^8$—N($R^5$)$R^6$, —$R^8$—C(O)$OR^5$, —C(O)—$R^{15}$, —C(O)NH$_2$, —$R^8$—C(O)NH$_2$, —C(S)NH$_2$, —C(O)—S—$R^5$, —C(O)—N($R^5$)$R^{15}$, —$R^8$—C(O)—N($R^5$)$R^{15}$, —C(S)—N($R^5$)$R^5$, —$R^8$—N($R^5$)—C(O)H, —$R^8$—N($R^5$)—C(O)$R^{15}$, —C(O)O—$R^8$—N($R^5$)$R^6$, —C(N($R^5$)$R^6$)=C($R^{18}$)$R^{10}$, —$R^8$—N($R^5$)—P(O)(OR$^5$)$_2$, cycloalkyl (optionally substituted by one or more substituents selected from the group consisting of alkyl, halo and —$OR^5$), heterocyclyl (optionally substituted by alkyl, aryl, aralkyl, halo, haloalkyl, oxo, —$OR^5$, —$R^8$—$OR^5$, —C(O)$OR^5$, —S(O)$_p$—$R^9$ (where p is 0 to 2), —$R^8$—S(O)$_p$—$R^9$ (where p is 0 to 2), —N($R^5$)$R^6$ or —C(O)N($R^5$)$R^6$), or heterocyclylalkyl (optionally substituted by one or more substituents selected from the group consisting of alkyl, aryl, aralkyl, halo, haloalkyl, oxo, —$OR^5$, —$R^8$—$OR^5$, —C(O)$OR^5$, —S(O)$_p$—$R^9$ (where p is 0 to 2), —$R^8$—S(O)$_p$—$R^9$ (where p is 0 to 2), —N($R^5$)$R^6$ and —C(O)N($R^5$)$R^6$), where $R^5$ and $R^6$ are each independently hydrogen, alkyl, aryl or aralkyl;
each $R^8$ is independently a straight or branched alkylene, alkylidene or alkylidyne chain;
each $R^9$ is independently alkyl, aryl or aralkyl;
each $R^{15}$ is independently alkyl, cycloalkyl, haloalkyl, aryl, aralkyl, —$R^8$—O—C(O)—$R^5$, —$R^8$—$OR^5$, —N($R^5$)$R^6$, —$R^8$—N($R^5$)$R^6$, —$R^8$—C(O)$OR^5$, heterocyclyl (optionally substituted by one or more substituents selected from the group consisting of alkyl, aryl, aralkyl, halo, haloalkyl, —$OR^5$, —$R^8$—$OR^5$, —C(O)$OR^5$, —N($R^5$)$R^6$, and —C(O)N($R^5$)$R^6$), or heterocyclylalkyl (optionally substituted by one or more substituents selected from the group consisting of alkyl, aryl, aralkyl, halo, haloalkyl, —$OR^5$, —$R^8$—$OR^5$, —C(O)$OR^5$, —N($R^5$)$R^6$, and —C(O)N($R^5$)$R^6$), where
$R^5$ and $R^6$ are independently each hydrogen, alkyl, aryl or aralkyl, and
each $R^8$ is independently a straight or branched alkylene, alkylidene or alkylidyne chain;
or $R^5$ and $R^{15}$ together with the nitrogen to which they are attached form a N-heterocylic ring containing zero to three additional hetero atoms, where the N-heterocyclic ring is optionally substituted by one or more substituents selected from the group consisting of alkyl, aryl, aralkyl, amino, monoalkylamino, dialkylamino, —$OR^5$, —C(O)$OR^5$, aminocarbonyl, monoalkylaminocarbonyl, and dialkylaminocarbonyl, where
each $R^5$ is hydrogen, alkyl, aryl or aralkyl; and
$R^{18}$ is hydrogen, alkyl, aryl, aralkyl, cyano, —C(O)$OR^5$, or —NO$_2$;
or $R^{10}$ and $R^{11}$ together with the nitrogen to which they are attached form a N-heterocyclic ring containing zero to three additional hetero atoms, where the N-heterocylic ring is optionally substituted by one or more substituents selected from the group consisting of alkyl, halo, haloalkyl, aryl, aralkyl, oxo, nitro, cyano, —$R^8$—CN, =N($R^{17}$), —$OR^5$, —C(O)$OR^5$, —$R^8$—C(O)$OR^5$, —N($R^5$)$R^6$, —$R^8$—N($R^5$)$R^6$, —C(O)N($R^5$)$R^6$, —$R^8$—C(O)N($R^5$)$R^6$, —N($R^5$)—N($R^5$)$R^6$, —C(O)$R^5$, —C(O)—($R^8$—O)$_t$—$R^5$ (where t is 1 to 6), —S(O)$_p$—$R^9$ (where p is 0 to 2), —$R^8$—S(O)$_p$—$R^9$ (where p is 0 to 2), —($R^8$—O)$_t$—$R^5$ (where t is 1 to 6), and heterocyclyl (optionally substituted by one or more substituents selected from the group consisting of alkyl, aryl, aralkyl, halo, haloalkyl, —$OR^5$, —C(O)$OR^5$, —N($R^5$)$R^6$, and —C(O)N($R^5$)$R^6$), where $R^5$ and $R^6$ are each independently hydrogen, alkyl, aryl or aralkyl;
each $R^8$ is independently a straight or branched alkylene, alkylidene or alkylidyne chain;
each $R^9$ is independently alkyl, aryl or aralkyl;
each $R^{17}$ is independently hydrogen, alkyl, aryl, aralkyl, cyano, —$OR^5$, —$R^8$—$OR^5$, —C(O)$OR^5$, —$R^8$—C(O)$OR^5$, —C(O)—N($R^5$)$R^6$, or —$R^8$—C(O)—N($R^5$)$R^6$ where
$R^5$ and $R^6$ are independently each hydrogen, alkyl, aryl or aralkyl, and
each $R^8$ is independently a straight or branched alkylene, alkylidene or alkylidyne chain;
and $R^4$ is in the 5-position.

Of this subgroup of compounds, a preferred class of compounds are those compounds wherein:
$R^{10}$ and $R^{11}$ are each independently hydrogen, alkyl, haloalkyl, aryl, aralkyl, formyl, cyano, —$R^8$—CN, —$OR^5$, —$R^8$—$OR^5$, —S(O)$_p$—$R^{15}$ (where p is 0 to 2), —$R^8$—S(O)$_p$—$R^{15}$ (where p is 0 to 2), —N($R^5$)$R^6$, —$R^8$—N($R^5$)$R^6$, —$R^8$—C(O)$OR^5$, —C(O)—$R^{15}$, —C(O)NH$_2$, —$R^8$—C(O)NH$_2$, —C(S)NH$_2$, —C(O)—S—$R^5$, —C(O)—N($R^5$)$R^{15}$, —$R^8$—C(O)—N($R^5$)$R^{15}$, —C(S)—N($R^5$)$R^{15}$, —$R^8$—N($R^5$)—C(O)H, —$R^8$—N($R^5$)—C(O)$R^{15}$, —C(O)O—$R^8$—N($R^5$)$R^6$, —C(N($R^5$)$R^6$)=C($R^{18}$)$R^{10}$, —$R^8$—N($R^5$)—P(O)(OR$^5$)$_2$, cycloalkyl (optionally substituted by one or more substituents selected from the group consisting of alkyl, halo and —$OR^5$), heterocyclyl (optionally substituted by alkyl, aryl, aralkyl, halo, haloalkyl, oxo, —$OR^5$, —$R^8$—$OR^5$, —C(O)$OR^5$, —S(O)$_p$—$R^9$ (where p is 0 to 2), —$R^8$—S(O)$_p$—$R^9$ (where p is 0 to 2), —N($R^5$)$R^6$ or —C(O)N($R^5$)$R^6$), or heterocyclylalkyl (optionally substituted by one or more substituents selected from the group consisting of alkyl, aryl, aralkyl, halo, haloalkyl, oxo, —$OR^5$, —$R^8$—$OR^5$, —C(O)$OR^5$, —S(O)$_p$—$R^9$ (where p is 0 to 2), —$R^8$—S(O)$_p$—$R^9$ (where p is 0 to 2), —N($R^5$)$R^6$ and —C(O)N($R^5$)$R^8$), where $R^5$ and $R^6$ are each independently hydrogen, alkyl, aryl or aralkyl;
each R is independently a straight or branched alkylene, alkylidene or alkylidyne chain;
each $R^9$ is independently alkyl, aryl or aralkyl;
each $R^{15}$ is independently alkyl, cycloalkyl, haloalkyl, aryl, aralkyl, —$R^8$—O—C(O)—$R^5$, —$R^8$—$OR^5$, —N($R^5$)$R^6$, —$R^8$—N($R^5$)$R^6$, —$R^8$—C(O)$OR^5$, heterocyclyl (optionally substituted by one or more substituents selected from the group consisting of alkyl, aryl, aralkyl, halo, haloalkyl, —$OR^5$, —$R^8$—$OR^5$, —C(O)$OR^5$, —N($R^5$)$R^6$, and —C(O)N($R^5$)$R^6$), or heterocyclylalkyl (optionally substituted by one or more substituents selected from the group consisting of alkyl, aryl, aralkyl, halo, haloalkyl, —$OR^5$, —$R^8$—$OR^5$, —C(O)$OR^5$, —N($R^5$)$R^6$, and —C(O)N($R^5$)$R^6$) where
$R^5$ and $R^6$ are independently each hydrogen, alkyl, aryl or aralkyl, and
each $R^8$ is independently a straight or branched alkylene, alkylidene or alkylidyne chain;

or R⁵ and R¹⁵ together with the nitrogen to which they are attached form a N-heterocyclic ring containing zero to three additional hetero atoms, where the N-heterocyclic ring is optionally substituted by one or more substituents selected from the group consisting of alkyl, aryl, aralkyl, amino, monoalkylamino, dialkylamino, —OR⁵, —C(O)OR⁵, aminocarbonyl, monoalkylaminocarbonyl, and dialkylaminocarbonyl, where each R⁵ is independently hydrogen, alkyl, aryl or aralkyl; and R¹⁸ is hydrogen, alkyl, aryl, aralkyl, cyano, —C(O)OR⁵, or —NO₂.

Of this class of compounds, a preferred subclass of compounds are those compounds wherein:

R¹⁰ is hydrogen, alkyl, or —R⁸—OR⁵; and
R¹¹ is hydrogen, alkyl or —R⁸—OR⁵;

where each R⁸ is independently a straight or branched alkylene chain, and each R⁵ is hydrogen or alkyl.

Of this subclass of compounds, preferred compounds are those compounds selected from the group consisting of:

N-(5-chloropyridin-2-yl)-2-[((4-(chloromethyl)-3-chlorothiophen-2-yl)carbonyl)amino]-3-methoxy-5-chlorobenzamide;

N-(5-chloropyridin-2-yl)-2-[((4-((N'-methyl-N'-(2-hydroxyethyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(2-hydroxyethyl)amino)methyl)-3-chlorothiophen-2-yl)carbonyl)amino]-3-hydroxy-5-chlorobenzamide;

N-(5-chloropyridin-2-yl)-2-[((4-((N',N'-di(2-hydroxypropyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(3-hydroxypropyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(2-hydroxypropyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(2-hydroxyethyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(2,2-dimethyl-2-hydroxyethyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(2-hydroxyethyl)amino)methyl)-3-chlorothiophen-2-yl)carbonyl)amino]-3-ethoxy-5-chlorobenzamide;

N-(5-chloropyridin-2-yi)-2-1((4-(((2-hydroxyethyi)amino)methyl)-3-chlorothiophen-2-yl)carbonyl)amino]-3-methoxy-5-chlorobenzamide;

N-(5-chloropyridin-2-yl)-2-[((4-((methylamino)methyl)-3-chlorothiophen-2-yl)carbonyl)amino]-3-methoxy-5-chlorobenzamide;

N-(5-chloropyridin-2-yl)-2-[((4-(amino)methyl-3-chlorothiophen-2-yl)carbonyl)amino]-3-methoxy-5-chlorobenzamide;

N-(5-chloropyridin-2-yl)-2-[((4-((dimethylamino)methyl)-3-chlorothiophen-2-yl)carbonyl)amino]-3-methoxy-5-chlorobenzamide;

N-(5-chloropyridin-2-yl)-2-[((4-((N'-ethyl-N'-methylamino)methyl)-3-chlorothiophen-2-yl)carbonyl)amino]-3-methoxy-5-chlorobenzamide;

N-(5-chloropyridin-2-yl)-2-[((4-((N'-(1-methylethyl)amino)methyl)-3-chlorothiophen-2-yl)carbonyl)amino]-3-methoxy-5-chlorobenzamide;

N-(5-chloropyridin-2-yl)-2-[((4-(ethylaminomethyl-3-chlorothiophen-2-yl)carbonyl)amino]-3-methoxy-5-chlorobenzamide; and N-(5-chloropyridin-2-yl)-2-[((4-(diethylamino)methyl-3-chlorothiophen-2-yl)carbonyl)amino]-3-methoxy-5-chlorobenzamide.

Of this class of compounds, another preferred subclass of compounds are those compounds wherein:

R¹⁰ is hydrogen, alkyl, or —R⁸—N(R⁵)R⁶, and
R¹¹ is —S(O)ₚ—R¹⁵ (where p is 0 to 2) or —R⁸—N(R⁵)R⁶ where:

R⁵ and R⁶ are independently hydrogen or alkyl;

each R⁸ is independently a straight or branched alkylene, alkylidene or alkylidyne chain; and R¹⁵ is independently alkyl, cycloalkyl, haloalkyl, aryl, aralkyl, —R⁸—O—C(O)—R⁵, —R⁸—OR⁵, —N(R⁵)R⁶, —R⁸—N(R⁵)R⁶, —R⁸—C(O)OR⁵, heterocyclyl (optionally substituted by one or more substituents selected from the group consisting of alkyl, aryl, aralkyl, halo, haloalkyl, —OR⁵, —R⁸—OR⁵, —C(O)OR⁵, —N(R⁵)R⁶, and —C(O)N(R⁵)R⁶), or heterocyclylalkyl (optionally substituted by one or more substituents selected from the group consisting of alkyl, aryl, aralkyl, halo, haloalkyl, —OR⁵, —R⁸—OR⁵, —C(O)OR⁵, —N(R⁵)R⁶, and —C(O)N(R⁶)R⁶) where R⁵ and R⁶ are independently each hydrogen, alkyl, aryl or aralkyl, and each R⁸ is independently a straight or branched alkylene, alkylidene or alkylidyne chain.

Of this subclass of compounds, preferred compounds are selected from the group consisting of:

N-(5-chloropyridin-2-yl)-2-[((4-((N'-methyl-N'-(3-(dimethylamino)propyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(methylsulfonyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(2-(dimethylamino)ethyl)amino)methyl)-3-chlorothiophen-2-yl)carbonyl)amino]-3-hydroxy-5-chlorobenzamide;

N-(5-chloropyridin-2-yl)-2-[((4-((N'-(methyl)sulfonyl-N'-(2-(dimethylamino)ethyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(2-(dimethylamino)ethyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-((3,5-dimethylisoxazol-4-yl)sulfonyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(methylsulfonyl)amino)methyl)-3-chlorothiophen-2-yl)carbonyl)amino]-3-hydroxy-5-chlorobenzamide;

N-(5-chloropyridin-2-yl)-2-[((4-((N'-methyl-N'-((2-(4-hydroxypiperidin-1-yl)ethyl)sulfonyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-((2-(pyrrolidin-1-yl)ethyl)sulfonyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-((dimethylamino)sulfonyl)amino)methyl)-3-chlorothiophen-2-yl)carbonyl)amino]-3-methoxy-5-chlorobenzamide;

N-(5-chloropyridin-2-yl)-2-[((4-((N'-(2-aminoethyl)amino)methyl)-3-chlorothiophen-2-yl)carbonyl)amino]-3-methoxy-5-chlorobenzamide; and N-(5-chloropyridin-2-yl)-2-[((4-((N'-ethyl-N'-(4-(dimethylamino)but-3-yn-2-yl)amino)methyl)-3- chlorothiophen-2-yl)carbonyl)amino]-3-methoxy-5-chlorobenzamide.

Of this class of compounds, another preferred subclass of compound are those compounds wherein:

$R^{10}$ is hydrogen, alkyl or —$R^8$—$OR^5$; and $R^{11}$ is formyl, cyano, —C(O)—$R^{15}$, —C(O)$NH_2$, —C(S)$NH_2$, —C(O)—S—$R^5$, —C(O)—N($R^5$)$R^{15}$, —C(S)—N($R^5$)$R^{15}$, —$R^8$—N($R^5$)—P(O)($OR^5$)$_2$, or —C(N($R^5$)$R^6$)=C($R^{18}$)$R^{10}$, where:

each $R^5$ is hydrogen or alkyl;

$R^8$ is a straight or branched alkylene chain;

each $R^{15}$ is independently alkyl, cycloalkyl, haloalkyl, aryl, aralkyl, —$R^8$—O—C(O)—$R^5$, —$R^8$—$OR^5$, —N($R^5$)$R^6$, —$R^8$—N($R^5$)$R^6$, —$R^8$—C(O)$OR^5$, heterocyclyl (optionally substituted by one or more substituents selected from the group consisting of alkyl, aryl, aralkyl, halo, haloalkyl, —$OR^5$, —$R^8$—$OR^5$, —C(O)$OR^5$, —N($R^5$)$R^6$, and —C(O)N($R^5$)$R^6$), or heterocyclylalkyl (optionally substituted by one or more substituents selected from the group consisting of alkyl, aryl, aralkyl, halo, haloalkyl, —$OR^5$, —$R^8$—$OR^5$, —C(O)$OR^5$, —N($R^5$)$R^6$, and —C(O)N($R^5$)$R^6$) where $R^5$ and $R^6$ are independently each hydrogen, alkyl, aryl or aralkyl, and each $R^8$ is independently a straight or branched alkylene, alkylidene or alkylidyne chain; and $R^{18}$ is hydrogen, alkyl, aryl, aralkyl, cyano, —C(O)$OR^5$, or —$NO_2$.

Of this subclass of compounds, preferred compounds are those compounds selected from the group consisting of:

N-(5-chloropyridin-2-yl)-2-[((4-((N'-methyl-N"-ethylureido)methyl)-3-chlorothiophen-2-yl)carbonyl)amino]-3-methoxy-5-chlorobenzamide;

N-(5-chloropyridin-2-yl)-2-[((4-((N'-methyl-N"-(2-carboxyethyl)ureido)methyl)-3-chlorothiophen-2-yl)carbonyl)amino]-3-methoxy-5-chlorobenzamide;

N-(5-chloropyridin-2-yl)-2-[((4-((N'-methyl-N"-(4-(2-hydroxyethyl)piperazin-1-yl)carbonyl)amino)methyl)-3-chlorothiophen-2-yl)carbonyl)amino]-3-methoxy-5-chlorobenzamide;

N-(5-chloropyridin-2-yl)-2-[((4-((N'-methyl-N"-(2-(morpholin-4-yl)ethyl)thioureido)methyl)-3-chlorothiophen-2-yl)carbonyl)amino]-3-methoxy-5-chlorobenzamide;

N-(5-chloropyridin-2-yl)-2-[((4-((N'-methyl-N'-(((4-hydroxypiperidin-1-yl)methyl)carbonyl)amino)methyl)-3-chlorothiophen-2-yl)carbonyl)amino]-3-methoxy-5-chlorobenzamide;

N-(5-chloropyridin-2-yl)-2-[((4-((N'-methyl-N"-(2-hydroxyethyl)ureido)methyl)-3-chlorothiophen-2-yl)carbonyl)amino]-3-methoxy-5-chlorobenzamide;

N-(5-chloropyridin-2-yl)-2-[((4-(N'-methylureido)methyl)-3-chlorothiophen-2-yl)carbonyl)amino]-3-methoxy-5-chlorobenzamide; and N-(5-chloropyridin-2-yl)-2-[((4-((N'-(2-hydroxyethyl)ureido)methyl)-3-chlorothiophen-2-yl)carbonyl)amino]-3-methoxy-5-chlorobenzamide;

N-(5-chloropyridin-2-yl)-2-[((4-((N'-methyl-N"-(2-(chloro)ethyl)ureido)methyl)-3-chlorothiophen-2-yl)carbonyl)amino]-3-methoxy-5-chlorobenzamide;

N-(5-chloropyridin-2-yl)-2-[((4-((N'-methyl-N"-(2-(acetoxy)ethyl)ureido)methyl)-3-chlorothiophen-2-yl)carbonyl)amino]-3-methoxy-5-chlorobenzamide;

N-(5-chloropyridin-2-yl)-2-[((4-((N'-methyl-N"-(2-(pyrrotidin-1-yl)ethyl)ureido)methyl)-3-chlorothiophen-2-yl)carbonyl)amino]-3-methoxy-5-chlorobenzamide;

N-(5-chloropyridin-2-yl)-2-[((4-((N'-(2-(chloro)ethyl)ureido)methyl)-3-chlorothiophen-2-yl)carbonyl)amino]-3-methoxy-5-chlorobenzamide;

N-(5-chloropyridin-2-yl)-2-[((4-((N'-methyl-N"-(2-(((2-hydroxyphenyl)carbonyl)oxy)ethyl)ureido)-methyl)-3-chlorothiophen-2-yl)carbonyl)amino]-3-methoxy-5-chlorobenzamide;

N-(5-chloropyridin-2-yl)-2-[((4-((N'-methyl-N"-cyanoamino)methyl)-3-chlorothiophen-2-yl)carbonyl)amino]-3-methoxy-5-chlorobenzamide;

N-(5-chloropyridin-2-yl)-2-[((4-((N'-(2-((fluoromethylcarbonyl)amino)ethyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-((2-aminoethoxy)carbonyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-((methylthio)carbonyl)amino)methyl)-3-chlorothiophen-2-yl)carbonyl)amino]-3-methoxy-5-chlorobenzamide;

N-(5-chloropyridin-2-yl)-2-[((4-((N'-ethyl-N'-((phenylthio)carbonyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(2-nitro-1-(methylamino)ethenyl)amino)methyl)-3-chlorothiophen-2-yl)carbonyl)amino]-3-methoxy-5-chlorobenzamide;

N-(5-chloropyridin-2-yl)-2-[((4-(((2-dimethylphosphoramidoethyl)amino)methyl)-3-chlorothiophen-2-yl)carbonyl)amino]-3-methoxy-5-chlorobenzamide.

Of the class of compounds, another preferred subclass of compounds are those compounds wherein:

$R^{10}$ is hydrogen, alkyl, haloalkyl, or —$R^8$—$OR^5$;

$R^{11}$ is cycloalkyl (optionally substituted by one or more substituents selected from the group consisting of alkyl, halo and —$OR^5$), heterocyclyl (optionally substituted by alkyl, aryl, aralkyl, halo, haloalkyl, oxo, —$OR^5$, —$R^8$—$OR^5$, —C(O)$OR^5$, —S(O)$_p$—$R^9$ (where p is 0 to 2), —$R^8$—S(O)$_p$—$R^9$ (where p is 0 to 2), —N($R^5$)$R^6$ or —C(O)N($R^5$)$R^6$), or heterocyclylalkyl (optionally substituted by one or more substituents selected from the group consisting of alkyl, aryl, aralkyl, halo, haloalkyl, oxo, —$OR^5$, —$R^8$—$OR^5$, —C(O)$OR^5$, —S(O)$_p$—$R^9$ (where p is 0 to 2), —$R^8$—S(O)$_p$—$R^9$ (where p is 0 to 2), —N($R^5$)$R^5$ and —C(O)N($R^5$)$R^6$), where $R^5$ and $R^6$ are each independently hydrogen, alkyl, aryl or aralkyl;

each $R^8$ is independently a straight or branched alkylene, alkylidene or alkylidyne chain;

each $R^9$ is independently alkyl, aryl or aralkyl;

each $R^{15}$ is independently alkyl, cycloalkyl, haloalkyl, aryl, aralkyl, —$R^8$—O—C(O)—$R^5$, —$R^8$—$OR^5$, —N($R^5$)$R^6$, —$R^8$—N($R^5$)$R^6$, —$R^8$—C(O)$OR^5$, heterocyclyl (optionally substituted by one or more substituents selected from the group consisting of alkyl, aryl, aralkyl, halo, haloalkyl, —$OR^5$, —$R^8$—$OR^5$, —C(O)$OR^5$, —N($R^5$)$R^6$, and —C(O)N($R^5$)$R^6$), or heterocyclylalkyl (optionally substituted by one or more substituents selected from the group consisting of alkyl, aryl, aralkyl, halo, haloalkyl, —$OR^6$, —$R^8$—$OR^5$, —C(O)$OR^5$, —N($R^5$)$R^6$, and —C(O)N($R^5$)$R^6$) where $R^5$ and $R^6$ are independently each hydrogen, alkyl, aryl or aralkyl, and each $R^8$ is independently a straight or branched alkylene, alkylidene or alkylidyne chain.

Of this subclass of compounds, preferred compounds are selected from the group consisting of:

N-(5-chloropyridin-2-yl)-2-[((4-((N'-(2-(morpholin-4-yl)ethyl)amino)methyl)-3-chlorothiophen-2-yl)carbonyl)amino]-5-chlorobenzamide;

N-(5-chloropyridin-2-yl)-2-[((4-((N'-methyl-N'-(2-(pyrrolidin-1-yl)ethyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(1-methylpiperidin-4-yl)amino)methyl)-3-chlorothiophen-2-yl)carbonyl)amino]-3-hydroxy-5-chlorobenzamide;

N-(5-chloropyridin-2-yl)-2-[((4-((N'-methyl-N'-(4-hydroxycyclohexyl)amino)methyl)-3-chlorothiophen-2-yl)carbonyl)amino]-3-methoxy-5-chlorobenzamide;

N-(6-chloropyridin-2-yl)-2-[((4-((N'-methyl-N'-(pyridin-2-yl)methyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-oxazolin-2-yl)amino)methyl)-3-chlorothiophen-2-yl)carbonyl)aminol-3-methoxy-5-chlorobenzamide;

N-(5-chloropyridin-2-yl)-2-[((4-((N'-methyl-N'-(thiazolin-2-yl)amino)methyl)-3-chlorothiophen-2-yl)carbonyl)amino]-3-methoxy-5-chlorobenzamide;

N-(5-chloropyridin-2-yl)-2-[((4-((N'-ethyl-N'-(oxazolin-2-yl)amino)methyl)-3-chlorothiophen-2-yl)carbonyl)amino]-3-methoxy-5-chlorobenzamide;

N-(5-chloropyrldin-2-yl)-2-[((4-((N'-ethyl-N'-(thiazolin-2-yl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(4-(oxo)oxazolin-2-yl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(pyridin-2-yl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(dihydro-4(H)-1,3-oxazin-2-yl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(oxazolin-2-yl)amino)methyl)-3-chlorothiophen-2-yl)carbonyl)amino]-5-chlorobenzamide;

N-(5-chloropyridin-2-yl)-2-[((4-((N'-methyl-N'-(oxazolin-2-yl)amino)methyl)-3-chlorothiophen-2-yl)carbonyl)amino]-3-hydroxy-5-chlorobenzamide;

N-(5-chloropyridin-2-yl)-2-[((4-((N'-(t-butyl)-N'-(oxazolin-2-yl)amino)methyl)-3-chlorothiophen-2-yl)carbonyl)amino]-3-methoxy-5-chlorobenzamide;

N-(5-chloropyridin-2-yl)-2-[((4-(((thiazol-2-yl)amino)methyl)-3-chlorothiophen-2-yl)carbonyl)amino]-3-methoxy-5-chlorobenzamide;

N-(5-chloropyridin-2-yl)-2-[((4-((N'-(2-methoxyethyl)-N'-(oxazolin-2-yl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(oxazol-2-yl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(4-trifluoromethyl-5-(methoxycarbonyl)pyrimidin-2-yl)amino)methyl)-3-chlorothiophen-2-yl)carbonyl)amino]-3-methoxy-5-chlorobenzamide;

N-(5-chloropyridin-2-yl)-2-[((4-((N'-ethyl-N'-(dihydro-4(H)-1,3-oxazin-2-yl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(5-methyloxazolin-2-yl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(tetrazol-5-yl)amino)methyl)-3-chlorothiophen-2-yl)carbonyl)amino]-3-methoxy-5-chlorobenzamide;

N-(5-chloropyridin-2-yl)-2-[((4-((N'-ethyl-N'-(tetrazol-5-yl)amino)methyl-3-chlorothiophen-2-yl)carbonyl)amino]-3-methoxy-5-chlorobenzamide;

N-(5-chloropyridin-2-yl)-2-[((4-((N'-ethyl-N'-(4-methyloxazolin-2-yl)amino)methyl-3-chlorothiophen-2-yl)carbonyl)amino]-3-methoxy-5-chlorobenzamide;

N-(5-chloropyridin-2-yl)-2-[((4-((N'-(pyrazol-3-yl)amino)methyl)-3-chlorothiophen-2-yl)carbonyl)amino]-3-methoxy-5-chlorobenzamide;

N-(5-chloropyridin-2-yl)-2-[((4-((N'-(2,2,2-trifluoroethyl)-N'-(oxazolin-2-yl)amino)methyl)-3-chlorothiophen-2-yl)carbonyl)amino]-3-methoxy-5-chlorobenzamide;

N-(5-chloropyridin-2-yl)-2-[((4-((N'-(4-(ethoxycarbonyl)oxazolin-2-yl)amino)methyl)-3-chlorothiophen-2-yl)carbonyl)amino]-3-methoxy-5-chlorobenzamide;

N-(5-chloropyridin-2-yl)-2-[((4-((N'-(3,4-dihydro-2H-pyrrol-5-yl)amino)methyl)-3-chlorothiophen-2-yl)carbonyl)amino]-3-methoxy-5-chlorobenzamide;

N-(5-chloropyridin-2-yl)-2-[((4-((N'-(1,2,4-triazol-4-yl)amino)methyl)-3-chiorothiophen-2-yl)carbonyl)amino]-3-methoxy-5-chlorobenzamide;

N-(5-chloropyridin-2-yl)-2-[((4-((N'-methyl-N'-(3,4-dihydro-2H-pyrrol-5-yl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(pyridin-4-yl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(2-amino-6-methylpyrimidin-4-yl)amino)methyl)-3-chlorothiophen-2-yl)carbonyl)amino]-3-methoxy-5-chlorobenzamide;

N-(5-chloropyridin-2-yl)-2-[((4-((N'-methyl-N'-((1,2,4-oxadiazol-3-yl)methyl)amino)methyl)-3-chlorothiophen-2-yl)carbonyl)amino]-3-methoxy-5-chlorobenzamide;

N-(5-chloropyridin-2-yl)-2-[((4-((N'-(2-(imidazol-4-yl)ethyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(3,4,5,6-tetrahydropyridin-2-yl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(2-chloropyrimidin4-yl)amino)methyl)-3-chlorothiophen-2-yl)carbonyl)amino]-3-methoxy-5-chlorobenzamide;

N-(5-chloropyridin-2-yl)-2-[((4-((N'-ethyl-N'-(imidazol-2-yl)methyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(4-aminopyrimidin-2-yl)amino)methyl)-3-chlorothiophen-2-yl)carbonyl)amino]-3-methoxy-5-chlorobenzamide;

N-(5-chloropyridin-2-yl)-2-[((4-((N'-(4-aminopyrimidin-2-yl)amino)methyl)-3-chiorothiophen-2-yl)carbonyl)amino]-3-methoxy-5-chlorobenzamide;

N-(5-chloropyridin-2-yl)-2-[((4-((N'-(4-(methylamino)pyrimidin-2-yl)amino)methyl)-3-chlorothiophen-2-yl)carbonyl)amino]-3-methoxy-5-chlorobenzamide;

N-(5-chloropyridin-2-yl)-2-[((4-((N'-methyl-N'-((3-(methoxymethyl)-1,2,4-oxadiazol-5-yl)methyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-((3-((methylthio)methyl)-1,2,4-oxadiazol-5-yl)methyl)amino)methyl)-3-chlorothiophen-2-yl)carbonyl)amino]-3-methoxy-5-chlorobenzamide; and N-(5-chloropyridin-2-yl)-2-[((4-((N'-methyl-N'-(1,3,2-dioxaphospholan-2-yl)amino)methyl)-3-chlorothiophen-2-yl)carbonyl)amino]-3-methoxy-5-chlorobenzamide.

Of the subgroup of compounds, another preferred class of compounds are those compounds wherein:

$R^{10}$ and $R^{11}$ together with the nitrogen to which they are attached form a N-heterocyclic ring containing zero to three additional hetero atoms, where the N-heterocylic ring is optionally substituted by one or more substituents selected from the group consisting of alkyl, halo, haloalkyl, aryl, aralkyl, oxo, nitro, cyano, —$R^8$—CN, =$N(R^{17})$, —$OR^5$, —$C(O)OR^5$, —$R^8$—$C(O)OR^5$, —$N(R^6)R^6$, —$R^8$—$N(R^5)R^6$, —$C(O)N(R^5)R^6$, —$R^8$—$C(O)N(R^5)R^5$, —$N(R^5)$—N($R^5$)$R^6$, —$C(O)R^5$, —C(O)—($R^8$—O)$_t$—$R^5$ (where t is 1 to 6), —$S(O)_p$—$R^9$ (where p is 0 to 2), —$R^8$—$S(O)_p$—$R^9$ (where p is 0 to 2), —($R^8$—O)$_t$—$R^5$ (where t is 1 to 6), and heterocyclyl (optionally substituted by one or more substituents selected from the group consisting of alkyl, aryl, aralkyl, halo, haloalkyl, —$OR^5$, —$C(O)OR^5$, —$N(R^5)R^6$, and —$C(O)N(R^5)R^6$), where $R^5$ and $R^6$ are each independently hydrogen, alkyl, aryl or aralkyl;

each $R^8$ is independently a straight or branched alkylene, alkylidene or alkylidyne chain;

each $R^9$ is independently alkyl, aryl or aralkyl;

each $R^{17}$ is independently hydrogen, alkyl, aryl, aralkyl, cyano, —$OR^5$, —$R^8$—$OR^5$, —$C(O)OR^5$, —$R^8$—$C(O)OR^5$, —$C(O)$—$N(R^5)R^6$, or —$R^8$—$C(O)$—$N(R^5)R^6$ where $R^5$ and $R^6$ are independently each hydrogen, alkyl, aryl or aralkyl, and each $R^8$ is independently a straight or branched alkylene, alkylidene or alkylidyne chain.

Of this class of compounds, a preferred subclass of compounds are those compounds wherein the N-heterocylic ring is optionally substituted by one or more substituents selected from the group consisting of alkyl, halo, haloalkyl, aryl, aralkyl, and nitro.

Of this subclass of compounds, preferred compounds are selected from the group consisting of:

N-(5-chloropyridin-2-yl)-2-[((4-((4,5-dihydropyrazolin-1-yl)methyl)-3-chlorothiophen-2-yl)carbonyl)amino]-3-methoxy-5-chlorobenzamide;

N-(5-chloropyridin-2-yl)-2-[((4-((imidazol-1-yl)methyl)-3-chlorothiophen-2-yl)carbonyl)amino]-3-methoxy-5-chlorobenzamide;

N-(5-chloropyridin-2-yl)-2-[((4-((morpholin-4-ylmethyl)-3-chlorothiophen-2-yl)carbonyl)amino]-3-methoxy-5-chlorobenzamide;

N-(5-chloropyridin-2-yl)-2-[((4-((pyrazol-1-yl)methyl)-3-chlorothiophen-2-yl)carbonyl)amino]-3-methoxy-5-chlorobenzamide;

N-(5-chloropyridin-2-yl)-2-[((4-((hydantoin-3-yl)methyl)-3-chlorothiophen-2-yl)carbonyl)amino]-3-methoxy-5-chlorobenzamide;

N-(5-chloropyridin-2-yl)-2-[((4-((1,4,5,6-tetrahydropyrimidin-1-yl)methyl)-3-chlorothiophen-2-yl)carbonyl)amino]-3-methoxy-5-chlorobenzamide;

N-(5-chloropyridin-2-yl)-2-[((4-((imidazolin-1-yl)methyl)-3-chlorothiophen-2-yl)carbonyl)amino]-3-methoxy-5-chlorobenzamide;

N-(5-chloropyridin-2-yl)-2-[((4-((pyrrolidin-1-yl)methyl)-3-chlorothiophen-2-yl)carbonyl)amino]-3-methoxy-5-chlorobenzamide;

N-(5-chloropyridin-2-yl)-2-[((4-((2,3,4,5,6,7-hexahydro-3,7-dimethyl-2,6-dioxo-1H-purin-1-yl)methyl)-3-chlorothiophen-2-yl)carbonyl)amino]-3-methoxy-5-chlorobenzamide;

N-(5-chloropyridin-2-yl)-2-[((4-((4-methylpiperazin-1-yl)methyl)-3-chlorothiophen-2-yl)carbonyl)amino]-3-methoxy-5-chlorobenzamide;

N-(5-chloropyridin-2-yl)-2-[((4-((4-methylpiperazin-1-yl)methyl)-3-chlorothiophen-2-yl)carbonyl)amino]-3-hydroxy-5-chlorobenzamide;

N-(5-chloropyridin-2-yl)-2-[((4-((4-methylpiperazin-1-yl)methyl)-3-chlorothiophen-2-yl)carbonyl)amino]-5-chlorobenzamide;

N-(pyridin-2-yl)-2-[((4-((4-methylpiperazin-1-yl)methyl)-3-chlorothiophen-2-yl)carbonyl)amino]-5-chlorobenzamide;

N-(5-bromopyridin-2-yl)-2-[((4-((4-methylpiperazin-1-yl)methyl)-3-chlorothiophen-2-yl)carbonyl)aminol-5-chlorobenzamide;

N-(5-chloropyridin-2-yl)-2-[((4-((4-ethylpiperazin-1-yl)methyl)-3-chlorothiophen-2-yl)carbonyl)amino]-3-methoxy-5-chlorobenzamide;

N-(5-chloropyridin-2-yl)-2-[((4-((2-methylimidazol-1-yl)methyl)-3-chlorothiophen-2-yl)carbonyl)amino]-3-methoxy-5-chlorobenzamide;

N-(5-chloropyridin-2-yl)-2-[((4-((4-methylimidazol-1-yl)methyl)-3-chlorothiophen-2-yl)carbonyl)amino]-3-methoxy-5-chlorobenzamide;

N-(5-chloropyridin-2-yl)-2-[((4-((5-methylimidazol-1-yl)methyl)-3-chlorothiophen-2-yl)carbonyl)amino]-3-methoxy-5-chlorobenzamide;

N-(5-chloropyridin-2-yl)-2-[((4-((2-methylimidazolin-1-yl)methyl)-3-chlorothiophen-2-yl)carbonyl)amino]-3-methoxy-5-chlorobenzamide;

N-(5-chloropyridin-2-yl)-2-[((4-((2,4-dimethylimidazol-1-yl)methyl)-3-chlorothiophen-2-yl)carbonyl)amino]-3-methoxy-5-chlorobenzamide;

N-(5-chloropyridin-2-yl)-2-[((4-((2,5-dimethylimidazol-1-yl)methyl)-3-chlorothiophen-2-yl)carbonyl)aminol-3-methoxy-5-chlorobenzamide;

N-(5-chloropyridin-2-yl)-2-[((4-((2-methyl-4-nitroimidazol-1-yl)methyl)-3-chlorothiophen-2-yl)carbonyl)amino]-3-methoxy-5-chlorobenzamide;

N-(5-chloropyridin-2-yl)-2-[((4-((4,5-dichloroimidazol-1-yl)methyl)-3-chlorothiophen-2-yl)carbonyl)amino]-3-methoxy-5-chlorobenzamide;

N-(5-chloropyridin-2-yl)-2-[((4-((2-(chloromethyl)imidazolin-1-yl)methyl)-3-chlorothiophen-2-yl)carbonyl)amino]-3-methoxy-5-chlorobenzamide; and N-(5-chloropyridin-2-yl)-2-[((4-((2-(fluoromethyl)imidazolin-1-yl)methyl)-3-chlorothiophen-2-yl)carbonyl)amino]-3-methoxy-5-chlorobenzamide.

Of the class of compounds, another preferred subclass of compounds are those compounds wherein the N-heterocylic ring is substituted by one or more substituents selected from the group consisting of alkyl, nitro, —$R^8$—CN, —$OR^5$, —$N(R^5)$—$N(R^5)R^6$, —$C(O)R^5$, —$S(O)_p$—$R^9$ (where p is 0 to 2), —($R^8$—O)$_t$—$R^5$ (where t is 1 to 6), and heterocyclyl (optionally substituted by one or more substituents selected from the group consisting of alkyl, aryl, aralkyl, halo, haloalkyl, —$OR^5$, —$C(O)OR^5$, —$N(R^5)R^6$, and —$C(O)N(R^5)R^6$), where $R^5$ and $R^6$ are each independently hydrogen, alkyl, aryl or aralkyl;

each $R^8$ is independently a straight or branched alkylene, alkylidene or alkylidyne chain;

each $R^9$ is independently alkyl, aryl or aralkyl.

Of this subclass of compounds, preferred compounds are those compounds selected from the group consisting of:

N-(5-chloropyridin-2-yl)-2-[((4-((4-(hydroxymethyl)imidazol-1-yl)methyl)-3-chlorothiophen-2-yl)carbonyl)amino]-3-methoxy-5-chlorobenzamide;

N-(5-chloropyridin-2-yl)-2-[((4-((5-(hydroxymethyl)imidazol-1-yl)-3-chlorothiophen-2-yl)carbonyl)amino]-3-methoxy-5-chlorobenzamide;

N-(5-chloropyridin-2-yl)-2-[((4-((2-(methoxymethyl)imidazolin-1-yl)methyl)-3-chlorothiophen-2-yl)carbonyl)amino]-3-methoxy-5-chlorobenzamide;

N-(5-chloropyridin-2-yl)-2-[((4-((2-(hydroxymethyl)imidazol-1-yl)methyl)-3-chlorothiophen-2-yl)carbonyl)amino]-3-methoxy-5-chlorobenzamide;

N-(5-chloropyridin-2-yl)-2-[((4-((4-formylpiperazin-1-yl)methyl)-3-chlorothiophen-2-yl)carbonyl)amino]-3-methoxy-5-chlorobenzamide;

N-(5-chloropyridin-2-yl)-2-[((4-((2-(N'-amino-N-methyl)amino)imidazolin-1-yl)methyl)-3-chlorothiophen-2-yl)carbonyl)amino]-3-methoxy-5-chlorobenzamide;

N-(5-chloropyridin-2-yl)-2-[((4-((4-hydroxypiperidin-1-yl)methyl)-3-chlorothiophen-2-yl)carbonyl)amino]-3-methoxy-5-chlorobenzamide;

N-(5-chloropyridin-2-yl)-2-[((4-((2-(methylthio)imidazolin-1-yl)methyl)-3-chlorothiophen-2-yl)carbonyl)amino]-3-methoxy-5-chlorobenzamide;

N-(5-chloropyridin-2-yl)-2-[((4-((4-(methylsulfonyl)piperazin-1-yl)methyl)-3-chlorothiophen-2-yl)carbonyl)amino]-3-methoxy-5-chlorobenzamide;

N-(5-chloropyridin-2-yl)-2-[((4-((2-methyl4-nitroimidazol-1-yl)methyl)-3-chlorothiophen-2-yl)carbonyl)amino]-3-methoxy-5-chlorobenzamide;

N-(5-chloropyridin-2-yl)-2-[((4-((2-(cyanomethyl)imidazolin-1-yl)methyl)-3-chlorothiophen-2-yl)carbonyl)amino]-3-methoxy-5-chlorobenzamide; and N-(5-chloropyridin-2-yl)-2-[((4-((4-(pyrimidin-2-yl)piperazin-1-yl)methyl)-3-chlorothiophen-2-yl)carbonyl)amino]-3-methoxy-5-chlorobenzamide.

Of the class of compounds, another preferred subclass of compounds are those compounds wherein the N-heterocylic ring is substituted by one or more substituents selected from the group consisting of alkyl, oxo, $=N(R^{17})$, $-C(O)OR^5$, $-N(R^5)R^6$, $-C(O)N(R^5)R^6$, $-(R^8-O)_t-R^5$, and heterocyclyl (optionally substituted by one or more substituents selected from the group consisting of alkyl, aryl, aralkyl, halo, haloalkyl, $-OR^5$, $-C(O)OR^5$, $-N(R^5)R^6$, and $-C(O)N(R^5)R^6$), where $R^5$ and $R^6$ are each independently hydrogen, alkyl, aryl or aralkyl;

each $R^8$ is independently a straight or branched alkylene, alkylidene or alkylidyne chain;

each $R^{17}$ is independently hydrogen, alkyl, aryl, aralkyl, cyano, $-OR^5$, $-R^8-OR^5$, or $-C(O)OR^5$, $-R^8-C(O)OR^5$, $-C(O)-N(R^5)R^6$, $-R^8-C(O)-N(R^5)R^6$ where $R^5$ and $R^6$ are independently each hydrogen, alkyl, aryl or aralkyl, and each $R^8$ is independently a straight or branched alkylene, alkylidene or alkylidyne chain.

Of this subclass of compounds, preferred compounds are those wherein the N-heterocylic ring is substituted by $=N(R^{17})$ and is optionally substituted by one or more substituents selected from the group consisting of alkyl, oxo, $-C(O)OR^5$, $-N(R^5)R^6$, $-C(O)N(R^5)R^6$, and $-(R^8-O)_t-R^5$, where $R^5$ and $R^6$ are each independently hydrogen, alkyl, aryl or aralkyl;

each $R^8$ is independently a straight or branched alkylene, alkylidene or alkylidyne chain;

each $R^{17}$ is independently hydrogen, alkyl, aryl, aralkyl, cyano, $-OR^5$, $-R^8-OR^5$, $-C(O)OR^5$, $-R^8-C(O)OR^5$, $-C(O)-N(R^5)R^6$, or $-R^8-C(O)-N(R^5)R^6$ where $R^5$ and $R^6$ are independently each hydrogen, alkyl, aryl or aralkyl, and each $R^8$ is independently a straight or branched alkylene, alkylidene or alkylidyne chain.

Of these compounds, preferred compounds are selected from the group consisting of:

N-(5—chloropyridin-2-yl)-2-[((4-((2-imino-5-methyltetrahydrooxazol-3-yl)methyl)-3-chlorothiophen-2-yl)carbonyl)amino]-3-methoxy-5-chlorobenzamide;

N-(5-chloropyridin-2-yl)-2-[((4-((2-imino-5,5-(dimethyl)tetrahydrooxazol-3-yl)methyl)-3-chlorothiophen-2-yl)carbonyl)amino]-3-methoxy-5-chlorobenzamide;

N-(5-chloropyridin-2-yl)-2-[((4-((2-ethylimino-5,5-(dimethyl)tetrahydrooxazol-3-yl)methyl)-3-chlorothiophen-2-yl)carbonyl)amino]-3-methoxy-5-chlorobenzamide;

N-(5-chloropyridin-2-yl)-2-[((4-((2-imino-5(S)-methyltetrahydrooxazol-3-yl)methyl)-3-chlorothiophen-2-yl)carbonyl)amino]-3-methoxy-5-chlorobenzamide;

N-(5-chloropyridin-2-yl)-2-[((4-((2-imino-5(R)-methyltetrahydrooxazol-3-yl)methyl)-3-chlorothiophen-2-yl)carbonyl)amino]-3-methoxy-5-chlorobenzamide;

N-(5-chloropyridin-2-yl)-2-[((4-((24iminotetrahydrooxazol-3-yl)methyl)-3-chiorothiophen-2-yl)carbonyl)amino]-3-methoxy-5-chlorobenzamide;

N-(5-chloropyridin-2-yl)-2-[((4-((2-imino-5-(methoxymethyl)tetrahydrooxazol-3-yl)methyl)-3-chlorothiophen-2-yl)carbonyl)amino]-3-methoxy-5-chlorobenzamide;

N-(5-chloropyridin-2-yl)-2-[((4-((2-imino-4-methyltetrahydrooxazol-3-yl)methyl)-3-chlorothiophen-2-yl)carbonyl)amino]-3-methoxy-5-chlorobenzamide;

N-(5-chloropyridin-2-yl)-2-[((4-((trans4,5-dimethyl-2-iminotetrahydrooxazol-3-yl)methyl)-3-chlorothiophen-2-yl)carbonyl)amino]-3-methoxy-5-chlorobenzamide;

N-(5-chloropyridin-2-yl)-2-[((4-((cis-4,5-dimethyl-2-iminotetrahydrooxazol-3-yl)methyl)-3-chlorothiophen-2-yl)carbonyl)amino]-3-methoxy-5-chlorobenzamide;

N-(5-chloropyridin-2-yl)-2-[((4-((3-methyl-2-imino-2,3-dihydroimidazol-1-yl)methyl)-3-chlorothiophen-2-yl)carbonyl)amino]-3-methoxy-5-chlorobenzamide;

N-(5-chloropyridin-2-yl)-2-[((4-((2-iminotetrahydroimidazol-1-yl)methyl)-3-chlorothiophen-2-yl)carbonyl)amino]-3-methoxy-5-chlorobenzamide;

N-(5-chloropyridin-2-yl)-2-[((4-((2-imino-1,2-dihydropyrimidin-1-yl)methyl)-3-chlorothiophen-2-yl)carbonyl)amino]-3-methoxy-5-chlorobenzamide;

N-(5-chloropyridin-2-yl)-2-[((4-((2-imino-4-(hydroxymethyl)tetrahydrooxazol-3-yl)methyl)-3-chlorothiophen-2-yl)carbonyl)amino]-3-methoxy-5-chlorobenzamide;

N-(5-chloropyridin-2-yl)-2-[((4-((2-iminotetrahydrothiazol-3-yl)methyl)-3-chlorothiophen-2-yl)carbonyl)amino]-3-methoxy-5-chlorobenzamide;

N-(5-chloropyridin-2-yl)-2-[((4-((2-imino-4-oxoimidazolin-1-yl)methyl)-3-chlorothiophen-2-yl)carbonyi)amino]-3-methoxy-5-chlorobenzamide;

N-(5-chloropyridin-2-yl)-2-[((4-(( tetrahydro-2-imino-2H-pyrimidin-1-ylpyrimidin-1-yl)methyl)-3-chlorothiophen-2-yl)carbonyl)amino]-3-methoxy-5-chlorobenzamide;

N-(5-chloropyridin-2-yl)-2-[((4-((2-(methoxycarbonylamino)imidazolin-1-yl)methyl)-3-chlorothiophen-2-yl)carbonyl)amino]-3-methoxy-5-chlorobenzamide;

N-(5-chloropyridin-2-yl)-2-[((4-((2-(cyanoimino)tetrahydroimidazol-1-yl)methyl)-3-chlorothiophen-2-yl)carbonyl)amino]-3-methoxy-5-chlorobenzamide;

N-(5-chloropyridin-2-yl)-2-[((4-((2-imino-3-((phenylamino)carbonyl)tetrahydroimidazol-1-yl)methyl)-3-chlorothiophen-2-yl)carbonyl)amino]-3-methoxy-5-chlorobenzamide;

N-(5-chloropyridin-2-yl)-2-((4-((cis-4,5-dimethoxy-2-iminotetrahydroimidazol-1-yl)methyl)-3-chlorothiophen-2-yl)carbonyl)amino]-3-methoxy-5-chlorobenzamide;

N-(5-chloropyridin-2-yl)-2-[((4-((2-amino-4-imino-1,4-dihydropyrimidin-1-yl)methyl)-3-chlorothiophen-2-yl)carbonyl)amino]-3-methoxy-5-chlorobenzamide;

N-(5-chloropyridin-2-yl)-2-[((4-((2-((2-hydroxyethyl)imino)tetrahydroimidazol-1-yl)methyl)-3-chlorothiophen-2-yl)carbonyl)amino]-3-methoxy-5-chlorobenzamide;

N-(5-chloropyridin-2-yl)-2-[((4-((2-iminopiperidin-1-yl)methyl)-3-chlorothiophen-2-yl)carbonyl)amino]-3-methoxy-5-chlorobenzamide;

N-(5-chloropyridin-2-yl)-2-[((4-((4-imino-1(4H)-pyridinyl)methyl)-3-chlorothiophen-2-yl)carbonyl)amino]-3-methoxy-5-chlorobenzamide;

N-(5-chloropyridin-2-yl)-2-[((4-((2-imino-1(2H)-pyridin-1-yl)methyl)-3-chlorothiophen-2-yl)carbonyl)amino]-3-methoxy-5-chlorobenzamide;

N-(5-chloropyridin-2-yl)-2-[((4-((2-(ethylimino)pyrrolidin-1-yl)methyl)-3-chlorothiophen-2-yl)carbonyl)amino]-3-methoxy-5-chlorobenzamide; and N-(5-chloropyridin-2-yl)-2-[((4-((2-(((aminocarbonyl)methyl)imino)tetrahydroimidazol-1-yl)methyl)-3-chlorothiophen-2-yl)carbonyl)amina]-3-methoxy-5-chlorobenzamide.

Of the class of compounds, another preferred subclass of compounds are those compounds wherein the N-heterocylic ring is substituted by —N($R^5$)$R^6$ and optionally substituted by one or more substituents selected from the group consisting of alkyl, oxo, —N($R^5$)$R^6$, —O$R^5$, and —C(O)N($R^5$)$R^6$, where $R^5$ and $R^6$ are each independently hydrogen, alkyl, aryl or aralkyl.

Of this subclass of compounds, preferred compounds are selected from the group consisting of:

N-(5-chloropyridin-2-yl)-2-[((4-((2-aminoimidazol-1-yl)methyl)-3-chlorothiophen-2-yl)carbonyl)amino]-3-methoxy-5-chlorobenzamide;

N-(5-chloropyridin-2-yl)-2-[((4-((5-aminotetrazol-1-yl)methyl)-3-chlorothiophen-2-yl)carbonyl)amino]-3-methoxy-5-chlorobenzamide;

N-(5-chloropyridin-2-yl)-2-[((4-((3-amino-1,2,4-triazol-1-yl)methyl)-3-chlorothiophen-2-yl)carbonyl)amino]-3-methoxy-5-chlorobenzamide;

N-(5-chloropyridin-2-yl)-2-[((4-((3,5-diamino-4H-1,2,4-triazol-4-yl)methyl)-3-chlorothiophen-2-yl)carbonyl)amino]-3-methoxy-5-chlorobenzamide;

N-(5-chloropyridin-2-yl)-2-[((4-((4-amino-5-(aminocarbonyl)imidazol-1-yl)methyl)-3-chlorothiophen-2-yl)carbonyl)amino]-3-methoxy-5-chlorobenzamide;

N-(5-chloropyridin-2-yl)-2-[((4-((2,6-diaminopurin-9-yl)methyl)-3-chlorothiophen-2-yl)carbonyl)amino]-3-methoxy-5-chlorobenzamide;

N-(5-chloropyridin-2-yl)-2-[((4-((2,6-diaminopurin-7-yl)methyl)-3-chlorothiophen-2-yl)carbonyl)amino]-3-methoxy-5-chlorobenzamide;

N-(5-chlordpyridin-2-yl)-2-[((4-((5-amino-2-oxo-2H-pyrimidin-1-yl)methyl)-3-chlorothiophen-2-yl)carbonyl)amino]-3-methoxy-5-chlorobenzamide;

N-(6-chloropyridin-2-yl)-2-[((4-((6-aminopurin-9-yl)methyl)-3-chlorothiophen-2-yl)carbonyl)amino]-3-methoxy-5-chlorobenzamide;

N-(5-chloropyridin-2-yl)-2-[((4-((6-aminopurin-7-yl)methyl)-3-chlorothiophen-2-yl)carbonyl)amino]-3-methoxy-5-chlorobenzamide;

N-(5-chloropyridin-2-yl)-2-[((4-((2-amino-6-oxopurin-9-yl)methyl)-3-chlorothiophen-2-yl)carbonyl)amino]-3-methoxy-5-chlorobenzamide;

N-(5-chloropyridin-2-yl)-2-[((4-((2-amino-6-oxopurin-7-yl)methyl)-3-chlorothiophen-2-yl)carbonyl)amino]-3-methoxy-5-chlorobenzamide;

N-(5-chloropyridin-2-yl)-2-[((4-((5-(dimethylamino)-1,2,4-oxadiazol-3-yl)methyl)-3-chlorothiophen-2-yl)carbonyl)amino]-3-methoxy-5-chlorobenzamide;

N-(5-chloropyridin-2-yl)-2-[((4-((5-amino-1,2,4-oxadiazol-3-yl)methyl)-3-chlorothiophen-2-yl)carbonyl)amino]-3-methoxy-5-chlorobenzamide;

N-(5-chloropyridin-2-yl)-2-[((4-((2-(methylamino)imidazol-1-yl)methyl)-3-chlorothiophen-2-yl)carbonyl)amino]-3-methoxy-5-chlorobenzamide;

N-(5-chloropyridin-2-yl)-2-[((4-((2,4-diamino-6-hydroxypyrimidin-5-yl)methyl)-3-chlorothiophen-2-yl)carbonyl)amino]-3-methoxy-5-chlorobenzamide;

N-(5-chloropyridin-2-yl)-2-[((4-((2-(ethylamino)imidazol-1-yl)methyl)-3-chlorothiophen-2-yl)carbonyl)amino]-3-methoxy-5-chlorobenzamide;

N-(5-chloropyridin-2-yl)-2-[((4-((2-(1-methylethyl)imidazol-1-yl)methyl)-3-chlorothiophen-2-yl)carbonyl)amino]-3-methoxy-5-chlorobenzamide;

N-(5-chloropyridin-2-yl)-2-[((4-((3-dimethylamino-5-methylpyrazol-1-yl)methyl)-3-chlorothiophen-2-yl)carbonyl)amino]-3-methoxy-5-chlorobenzamide; and N-(5-chloropyridin-2-yl)-2-[((4-((3-dimethylamino-5-methylpyrazol-2-yl)methyl)-3-chlorothiophen-2-yl)carbonyl)amino]-3-methoxy-5-chlorobenzamide.

Of the group of compounds described above, another preferred subgroup of compounds are those compounds wherein:

each $R^{14}$ is independently alkyl, —$R^8$—CN, —C($R^7$)H—$R^8$—N($R^{10}$)$R^{11}$, —C($R^7$)H—$R^8$—N$^\oplus$($R^9$)($R^{16}$)$_2$, —C($R^7$)H—O$R^5$, —C($R^7$)H—$R^8$—O$R^5$, —C($R^7$)H—O—$R^{15}$, —C($R^7$)H—S(O)$_p$—$R^{15}$ (where p is 0 to 2), —C($R^7$)H—N($R^5$)—($R^8$—O)$_t$—$R^5$ (where t is 1 to 6), —C($R^7$)H—N($R^5$)—$R^8$—[CH(OH)]$_t$—CH$_2$—O$R^5$ (where t is 1 to 6), —C($R^7$)H—N($R^5$)—S(O)$_2$—N($R^{10}$)$R^{11}$, —C($R^7$)H—O—N($R^5$)$R^6$, or heterocyclyl (wherein the heterocyclyl radical is not attached to the radical of formula (i) through a nitrogen atom and is optionally substituted by alkyl, aryl, aralkyl, halo, haloalkyl, oxo, —O$R^5$, —C(O)O$R^5$, —N($R^5$)$R^6$ or —C(O)N($R^5$)$R^6$), where $R^5$ and $R^6$ are each independently hydrogen, alkyl, aryl or aralkyl;

each $R^7$ is independently hydrogen or alkyl;

each $R^8$ is independently a straight or branched alkylene, alkylidene or alkylidyne chain;

$R^{10}$ and $R^{11}$ are each independently hydrogen, alkyl, haloalkyl, aryl, aralkyl, formyl, cyano, —$R^8$—CN, —O$R^5$, —$R^8$—O$R^5$, —S(O)$_p$—$R^{15}$ (where p is 0 to 2), —$R^8$—S(O)$_p$—$R^{15}$ (where p is 0 to 2), —N($R^5$)$R^6$, —$R^8$—N($R^5$)$R^6$, —$R^8$—C(O)O$R^5$, —C(O)—$R^{15}$, —C(O)NH$_2$, —$R^8$—C(O)NH$_2$, —C(S)NH$_2$, —C(O)—S—$R^5$, —C(O)—N($R^5$)$R^{15}$, —$R^8$—C(O)—N($R^5$)$R^{15}$, C(S)—N($R^5$)$R^{15}$, —$R^8$—N($R^5$)—C(O)H, —$R^8$—N($R^5$)—C(O)$R^{15}$, —C(O)O—$R^8$—N($R^5$)$R^6$, —C(N($R^5$)$R^6$)=C($R^{18}$)$R^{10}$, —$R^8$—N($R^5$)—P(O)(O$R^5$)$_2$, cycloalkyl (optionally substituted by one or more substituents selected from the group consisting of alkyl, halo and —O$R^5$), heterocyclyl (optionally substituted by alkyl, aryl, aralkyl, halo, haloalkyl, oxo, —O$R^5$, —$R^8$—O$R^5$, —C(O)O$R^5$, —S(O)$_p$—$R^9$ (where p is 0 to 2), —$R^8$—S(O)$_p$—$R^9$ (where p is 0 to 2), —N($R^5$)$R^6$ or —C(O)N($R^5$)$R^6$), or heterocyclylalkyl (optionally substituted by one or more substituents selected from the group consisting of alkyl, aryl, aralkyl, halo, haloalkyl, oxo, —O$R^5$, —$R^8$—O$R^5$, —C(O)O$R^5$, —S(O)$_p$—$R^9$ (where p is 0 to 2), —$R^8$—S(O)$_p$—$R^9$ (where p is 0 to 2), —N($R^5$)$R^6$ and —C(O)N($R^5$)$R^6$), where $R^5$ and $R^6$ are each independently hydrogen, alkyl, aryl or aralkyl;

each $R^8$ is independently a straight or branched alkylene, alkylidene or alkylidyne chain;

each $R^9$ is independently alkyl, aryl or aralkyl;

each $R^{15}$ is independently alkyl, cycloalkyl, haloalkyl, aryl, aralkyl, —$R^8$—O—C(O)—$R^5$, —$R^8$—O$R^5$, —N($R^5$)$R^6$, —$R^8$—N($R^5$)$R^6$, —$R^8$—C(O)O$R^5$, heterocyclyl (optionally substituted by one or more substituents selected from the group consisting of alkyl, aryl, aralkyl, halo, haloalkyl, —OR$^5$, —R$^8$—OR$^5$, —C(O)OR$^5$, —N(R$^5$)R$^6$, and —C(O)N(R$^5$)R$^6$), or heterocyclylalkyl (optionally substituted by one or more substituents selected from the group consisting of alkyl, aryl, aralkyl, halo, haloalkyl, —OR$^5$, —R$^8$—OR$^5$, —C(O)OR$^5$, —N(R$^5$)R$^6$, and —C(O)N(R$^5$)R$^6$), where R$^5$ and R$^6$ are independently each hydrogen, alkyl, aryl or aralkyl, and each R$^8$ is independently a straight or branched alkylene, alkylidene or alkylidyne chain;

or R$^5$ and R$^{15}$ together with the nitrogen to which they are attached form a N-heterocyclic ring containing zero to three additional hetero atoms, where the N-heterocyclic ring is optionally substituted by one or more substituents selected from the group consisting of alkyl, aryl, aralkyl, amino, monoalkylamino, dialkylamino, —OR$^5$, —C(O)OR$^5$, aminocarbonyl monoalkylaminocarbonyl, and dialkylaminocarbonyl, where each R$^5$ is hydrogen, alkyl, aryl or aralkyl; and R$^{18}$ is hydrogen, alkyl, aryl, aralkyl, cyano, —C(O)OR$^5$, or —NO$_2$;

or R$^{10}$ and R$^{11}$ together with the nitrogen to which they are attached form a N-heterocyclic ring containing zero to three additional hetero atoms, where the N-heterocyclic ring is optionally substituted by one or more substituents selected from the group consisting of alkyl, halo, haloalkyl, aryl, aralkyl, oxo, nitro, cyano, —R$^8$—CN, =N(R$^{17}$), —OR$^5$, —C(O)OR$^5$, —R$^8$—C(O)OR$^5$, —N(R$^5$)R$^6$, —R$^8$—N(R$^5$)R$^6$, —C(O)N(R$^5$)R$^6$, —R$^8$—C(O)N(R$^5$)R$^6$, —N(R$^5$)—N(R$^5$)R$^6$, —C(O)R$^5$, —C(O)—(R$^8$—O)$_t$—R$^5$ (where t is 1 to 6), —S(O)$_p$—R$^9$ (where p is 0 to 2), —R$^8$—S(O)$_p$—R$^9$ (where p is 0 to 2), —(R$^8$—O)$_t$—R$^5$ (where t is 1 to 6), and heterocyclyl (optionally substituted by one or more substituents selected from the group consisting of alkyl, aryl, aralkyl, halo, haloalkyl, —OR$^5$, —C(O)OR$^5$, —N(R$^5$)R$^6$, and —C(O)N(R$^5$)R$^6$), where R$^5$ and R$^5$ are each independently hydrogen, alkyl, aryl or aralkyl;

each R$^8$ is independently a straight or branched alkylene, alkylidene or alkylidyne chain;

each R$^9$ is independently alkyl, aryl or aralkyl;

each R$^{17}$ is independently hydrogen, alkyl, aryl, aralkyl, cyano, —OR$^5$, —R$^8$—OR$^5$, —C(O)OR$^5$, —R$^8$—C(O)OR$^5$, —C(O)—N(R$^5$)R$^6$, or —R$^8$—C(O)—N(R$^5$)R$^6$, where R$^5$ and R$^6$ are independently each hydrogen, alkyl, aryl or aralkyl, and each R$^8$ is independently a straight or branched alkylene, alkylidene or alkylidyne chain;

each R$^{16}$ is independently alkyl, aryl, aralkyl, —R$^8$—OR$^5$, —R$^8$—N(R$^5$)R$^6$, cycloalkyl (optionally substituted by one or more substituents selected from the group consisting of alky, halo and —OR$^5$), heterocyclyl (optionally substituted by alkyl, aryl, aralkyl, halo, haloalkyl, —OR$^5$, —C(O)OR$^6$, —N(R$^5$)R$^6$ or —C(O)N(R$^5$)R$^6$), or heterocyclylalkyl (optionally substituted by one or more substituents selected from the group consisting of alkyl, aryl, aralkyl, halo, haloalkyl, —OR$^5$, —C(O)OR$^5$, —N(R$^5$)R$^6$ and —C(O)N(R$^5$)R$^6$), where R$^5$ and R$^6$ are independently each hydrogen, alkyl, aryl or aralkyl, and each R$^8$ is independently a straight or branched alkylene, alkylidene or alkylidyne chain; or both R$^{16}$'s together with the nitrogen to which they are attached (and wherein the R$^9$ substituent is not present) form an aromatic N-heterocyclic ring containing zero to three additional hetero atoms, where the N-heterocylic ring is optionally substituted by one or more substituents selected from the group consisting of alkyl, aryl, aralkyl, —OR$^5$, —R$^8$—OR$^5$, —C(O)OR$^5$, —R—C(O)OR$^5$, —N(R$^5$)R$^6$, —R—N(R$^5$)R$^6$, —C(O)R$^5$, —C(O)—(R$^8$—O)$_t$—R$^5$ (where t is 1 to 6), and —(R$^8$—O)$_t$—R$^5$ (where t is 1 to 6), where R$^5$ and R$^6$ are independently each hydrogen, alkyl, aryl or aralkyl, and each R$^8$ is independently a straight or branched alkylene, alkylidene or alkylidyne chain.

Of this subgroup of compounds, preferred compounds are selected from the group consisting of:

N-(5-chloropyridin-2-yl)-2-[((4-((pyridinium-1-yl)methyl)-3-chlorothiophen-2-yl)carbonyl)amino]-3-hydroxy-5-chlorobenzamide, N-(5-chloropyridin-2-yl)-2-[((4-((N'-methyl-N'-(2-(hydroxyethoxy)ethyl)amino)methyl)-3-chlorothiophen-2-yl)carbonyl)amino]-3-methoxy-5-chlorobenzamide;

N-(5-chloropyridin-2-yl)-2-[((4-((methylsulfinyl)methyl)-3-chlorothiophen-2-yl)carbonyl)amino]-3-methoxy-5-chlorobenzamide;

N-(5-chloropyridin-2-yl)-2-[((4-((N'-methyl-N'-(2,3-dihydroxypropyl)amino)methyl)-3-chlorothiophen-2-yl)carbonyl)amino]-3-methoxy-5-chlorobenzamide;

N-(5-chloropyridin-2-yl)-2-[((4-(((2-hydroxyethyl)sulfinyl)methyl)-3-chlorothiophen-2-yl)carbonyl)amino]-3-methoxy-5-chlorobenzamide;

N-(5-chloropyridin-2-yl)-2-[((4-((pyridinium-1-yl)methyl)-3-chlorothiophen-2-yl)carbonyl)amino]-3-methoxy-5-chlorobenzamide;

N-(5-chloropyridin-2-yl)-2-[((4-methyl-3-chlorothiophen-2-yl)carbonyl)amino]-3-methoxy-5-chlorobenzamide;

N-(5-chloropyridin-2-yl)-2-[((4-cyanomethyl-3-chlorothiophen-2-yl)carbonyl)amino]-3-methoxy-5-chlorobenzamide;

N-(5-chloropyridin-2-yl) -2-[((4-(2-methylaminoethyl)-3-chlorothiophen-2-yl)carbonyl)amino]-3-methoxy-5-chlorobenzamide;

N-(5-chloropyridin-2-yl)-2-[((4-(hydroxy)methyl-3-chlorothiophen-2-yl)carbonyl)amino]-3-methoxy-5-chlorobenzamide;

N-(5-chloropyridin-2-yl)-2-[((4-(((imidazol-2-yl)thio)methyl)-3-chlorothiophen-2-yl)carbonyl)amino]-3-methoxy-5-chlorobenzamide;

N-(5-chloropyridin-2-yl)-2-[((4-((imidazolin-2-yl)thio)methyl)-3-chlorothiophen-2-yl)carbonyl)amino]-3-methoxy-5-chlorobenzamide;

N-(5-chloropyridin-2-yl)-2-[((4-(((5-hydroxymethyl-1-methylimidazol-2-yl)thio)methyl)-3-chlorothiophen-2-yl)carbonyl)amino]-3-methoxy-5-chlorobenzamide;

N-(5-chloropyridin-2-yl)-2-[((4-(((diethylamino)oxy)methyl)-3-chlorothiophen-2-yl)carbonyl)amino]-3-methoxy-5-chlorobenzamide; and N-(5-chioropyridin-2-yl)-2-[((4-(imidazolin-2-yl)-3-chlorothiophen-2-yl)carbonyl)amino]-3-methoxy-5-chlorobenzamide.

Of the group of comounds described above, another preferred subgroup of compounds are those compounds wherein:

each R$^{14}$ is independently —C(R$^7$)H—N(R$^{10}$)—C(NR$^{17}$)—N(R$^{10}$)R$^{11}$, —C(R$^7$)H—N(R$^{10}$)—C(NR$^{17}$)—R$^{10}$, or —C(R$^7$)H—C(NR$^{17}$)—N(R$^5$)R$^6$, where R$^5$ and R$^6$ are each independently hydrogen, alkyl, aryl or aralkyl;

each R$^7$ is independently hydrogen or alkyl;

each R$^9$ is independently alkyl, aryl or aralkyl;

R$^{10}$ and R$^{11}$ are each independently hydrogen, alkyl, haloalkyl, aryl, aralkyl, formyl, cyano, —R$^8$—CN, —OR$^5$, —$R^8$—$OR^5$, —$S(O)_p$—$R^{15}$ (where p is 0 to 2), —$R^8$—$S(O)_p$—$R^{15}$ (where p is 0 to 2), —$N(R^5)R^6$, —$R^8$—$N(R^5)R^6$, 13 $R^8$—$C(O)OR^5$, —$C(O)$—$R^{15}$, —$C(O)NH_2$, —$R^8$—$C(O)NH_2$, —$C(S)NH_2$, —$C(O)$—$S$—$R^5$, —$C(O)$—$N(R^5)R^{15}$, —$R^8$—$C(O)$—$N(R^5)R^{15}$, —$C(S)$—$N(R^5)R^{15}$, —$R^8$—$N(R^5)$—$C(O)H$, —$R^8$—$N(R^5)$—$C(O)R^{15}$, —$C(O)O$—$R^8$—$N(R^5)R^6$, —$C(N(R^5)R^6)$=$C(R^{18})R^{10}$, —$R^8$—$N(R^5)$—$P(O)(OR^5)_2$, cycloalkyl (optionally substituted by one or more substituents selected from the group consisting of alkyl, halo and —$OR^5$), heterocyclyl (optionally substituted by alkyl, aryl, aralkyl, halo, haloalkyl, oxo, —$OR^5$, —$R^8$—$OR^5$, —$C(O)OR^5$, —$S(O)_p$—$R^9$ (where p is 0 to 2), —$R^8$—$S(O)_p$—$R^9$ (where p is 0 to 2), —$N(R^5)R^6$ or —$C(O)N(R^5)R^6$), or heterocyclylalkyl (optionally substituted by one or more substituents selected from the group consisting of alkyl, aryl, aralkyl, halo, haloalkyl, oxo, —$OR^5$, —$R^8$—$OR^5$, —$C(O)OR^5$, —$S(O)_p$—$R^9$ (where p is 0 to 2), —$R^8$—$S(O)_p$—$R^9$ (where p is 0 to 2), —$N(R^5)R^6$ and —$C(O)N(R^5)R^6$), where $R^5$ and $R^6$ are each independently hydrogen, alkyl, aryl or aralkyl;

each $R^8$ is independently a straight or branched alkylene, alkylidene or alkylidyne chain;

each $R^9$ is independently alkyl, aryl or aralkyl;

each $R^{15}$ is independently alkyl, cycloalkyl, haloalkyl, aryl, aralkyl, —$R^8$—$O$—$C(O)$—$R^5$, —$R^8$—$OR^5$, —$N(R^5)R^6$, —$R^8$—$N(R^5)R^6$, —$R^8$—$C(O)OR^5$, heterocyclyl (optionally substituted by one or more substituents selected from the group consisting of alkyl, aryl, aralkyl, halo, haloalkyl, —$OR^5$, —$R^8$—$OR^5$, —$C(O)OR^5$, —$N(R^5)R^6$, and —$C(O)N(R^5)R^6$), or heterocyclylalkyl (optionally substituted by one or more substituents selected from the group consisting of alkyl, aryl, aralkyl, halo, haloalkyl, —$OR^5$, —$R^8$—$OR^5$, —$C(O)OR^5$, —$N(R^5)R^6$, and —$C(O)N(R^5)R^6$), where $R^5$ and $R^6$ are independently each hydrogen, alkyl, aryl or aralkyl, and each $R^8$ is independently a straight or branched alkylene, alkylidene or alkylidyne chain;

or $R^5$ and $R^{15}$ together with the nitrogen to which they are attached form a N-heterocyclic ring containing zero to three additional hetero atoms, where the N-heterocyclic ring is optionally substituted by one or more substituents selected from the group consisting of alkyl, aryl, aralkyl, amino, monoalkylamino, dialkylamino, —$OR^5$, —$C(O)OR^5$, aminocarbonyl, monoalkylaminocarbonyl, and dialkylaminocarbonyl, where each $R^5$ is hydrogen, alkyl, aryl or aralkyl; and $R^{18}$ is hydrogen, alkyl, aryl, aralkyl, cyano, —$C(O)OR^5$, or —$NO_2$;

or $R^{10}$ and $R^{11}$ together with the nitrogen to which they are attached form a N-heterocyclic ring containing zero to three additional hetero atoms, where the N-heterocyclic ring is optionally substituted by one or more substituents selected from the group consisting of alkyl, halo, haloalkyl, aryl, aralkyl, oxo, nitro, cyano, —$R^8$—$CN$, =$N(R^7)$, —$OR^5$, —$C(O)OR^5$, —$R^8$—$C(O)OR^5$, —$N(R^5)R^6$, —$R^8$—$N(R^5)R^6$, —$C(O)N(R^5)R^6$, —$R^8$—$C(O)N(R^5)R^6$, —$N(R^5)$—$N(R^5)R^6$, —$C(O)R^5$, —$C(O)$—$(R^8$—$O)_tR^5$ (where t is 1 to 6), —$S(O)_p$—$R^9$ (where p is 0 to 2), —$R^8$—$S(O)_p$—$R^9$ (where p is 0 to 2), —$(R^8$—$O)_t$—$R^5$ (where t is 1 to 6), and heterocyclyl (optionally substituted by one or more substituents selected from the group consisting of alkyl, aryl, aralkyl, halo, haloalkyl, —$OR^5$, —$C(O)OR^5$, —$N(R^5)R^6$, and —$C(O)N(R^5)R^6$), where $R^5$ and $R^6$ are each independently hydrogen, alkyl, aryl or aralkyl;

each $R^8$ is independently a straight or branched alkylene, alkylidene or alkylidyne chain;

each $R^9$ is independently alkyl, aryl or aralkyl;

each $R^{17}$ is independently hydrogen, alkyl, aryl, aralkyl, cyano, —$OR^5$, —$R^8$—$OR^5$, —$C(O)OR^5$, —$R^8$—$C(O)OR^5$, —$C(O)$—$N(R^5)R^6$, or —$R^8$—$C(O)$—$N(R^5)R^6$, where $R^5$ and $R^6$ are independently each hydrogen, alkyl, aryl or aralkyl, and each $R^8$ is independently a straight or branched alkylene, alkylidene or alkylidyne chain;

each $R^{17}$ is independently hydrogen, alkyl, aryl, aralkyl, cyano, —$OR^5$, —$R^8$—$OR^5$, —$C(O)OR^5$, —$R^8$—$C(O)OR^5$, —$C(O)$—$N(R^5)R^6$, or —$R^8$—$C(O)$—$N(R^5)R^6$, where $R^5$ and $R^6$ are independently each hydrogen, alkyl, aryl or aralkyl, and each $R^8$ is independently a straight or branched alkylene, alkylidene or alkylidyne chain.

Of this subgroup of compounds, preferred compounds are selected from the group consisting of:

N-(5-chloropyridin-2-yl)-2-[((4-(((amidino)(methyl)amino)methyl)-3-chlorothiophen-2-yl)carbonyl)amino]-3-methoxy-5-chlorobenzamide;

N-(5-chloropyridin-2-yl)-2-[((4-((N'-(1-iminoethyl)-N'-methylamino)methyl)-3-chlorothiophen-2-yl)carbonyl)amino]-3-methoxy-5-chlorobenzamide;

N-(5-chloropyridin-2-yl)-2-[((4-(N'-N''-dimethyl-N'''-cyanoguanidino)methyl-3-chlorothiophen-2-yl)carbonyl)amino]-3-methoxy-5-chlorobenzamide;

N-(5-chloropyridin-2-yl)-2-[((4-(N'-methyl-N''-hydroxyguanidino)methyl-3-chlorothiophen-2-yl)carbonyl)amino]-3-methoxy-5-chlorobenzamide;

N-(5-chloropyridin-2-yl)-2-[((4-(N'-methyl-N''-(2-aminoethyl)-N'''-cyanoguanidino)methyl-3-chlorothiophen-2-yl)carbonyl)amino]-3-methoxy-5-chlorobenzamide;

N-(5-chloropyridin-2-yl)-2-[((4-(N'-methyl-N''-aminoguanidino)methyl-3-chlorothiophen-2-yl)carbonyl)amino]-3-methoxy-5-chlorobenzamide;

N-(5-chloropyridin-2-yl)-2-[((4-(N'-N''-dimethyl-N'''-(aminocarbonyl)guanidino)methyl-3-chlorothiophen-2-yl)carbonyl)amino]-3-methoxy-5-chlorobenzamide;

N-(5-chloropyridin-2-yl)-2-[((4-((N'-(imino(phenyl)methyl)amino)methyl)-3-chlorothiophen-2-yl)carbonyl)amino]-3-methoxy-5-chlorobenzamide;

N-(5-chloropyridin-2-yl)-2-[((4-((N'-(1-imino-2-(aminocarbonyl)ethyl)amino)methyl)-3-chlorothiophen-2-yl)carbonyl)amino]-3-methoxy-5-chlorobenzamide;

N-(5-chloropyridin-2-yl)-2-[((4-((N'-(1-imino-4,4,4-trifluorobutyl)amino)methyl)-3-chlorothiophen-2-yl)carbonyl)amino]-3-methoxy-5-chlorobenzamide;

N-(5-chloropyridin-2-yl)-2-[((4-((N'-(imino(pyridin4-yl)methyl)amino)methyl)-3-chlorothiophen-2-yl)carbonyl)amino]-3-methoxy-5-chlorobenzamide;

N-(5-chloropyridin-2-yl)-2-[((4-((N'-(imino(thiophen-2-yl)methyl)amino)methyl)-3-chlorothiophen-2-yl)carbonyl)amino]-3-methoxy-5-chlorobenzamide;

N-(5-chloropyridin-2-yl)-2-[((4-((N'-(imino(pyrazin-2-yl)methyl)amino)methyl)-3-chlorothiophen-2-yl)carbonyl)amino]-3-methoxy-5-chlorobenzamide;

N-(5-chloropyridin-2-yl)-2-[((4-((N'-(cyclopropyl(imino)methyl)amino)methyl)-3-chlorothiophen-2-yl)carbonyl)amino]-3-methoxy-5-chlorobenzamide;

N-(5-chloropyridin-2-yl)-2-[((4-((N'-ethyl-N'-(3-cyano-1-iminopropyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(1-imino-4,4,4-trifluorobutyl)amino)methyl)-3-chlorothiophen-2-yl)carbonyl)amino]-3-methoxy-5-chlorobenzamide; and N-(5-chloropyridin-2-yl)-2-[((4-(2-amino-2-(hydroxyimino)ethyl)-3-chlorothiophen-2-yl)carbonyl)amino]-3-methoxy-5-chlorobenzamide.

Of the compounds of formula (I) described above, another preferred group of compounds are those compounds of formula (I) wherein:
A is =N—;
m is 1;
n is 1;
D is —N(H)—C(O)—;
E is —C(O)—N(H)— (where the nitrogen is bonded to the 2-position of the pyridinyl ring);
$R^2$ is —N($R^{10}$)$R^{11}$ where:
$R^{10}$ and $R^{11}$ are each independently hydrogen, alkyl or —$R^8$—O—$R^5$ where $R^8$ is an alkylene chain, and $R^5$ is hydrogen or alkyl; or
$R^{10}$ and $R^{11}$ together with the nitrogen to which they are attached form a N-heterocyglic ring containing zero to three additional hetero atoms, where the N-heterocylic ring is optionally substituted by one or more substituents selected from the group consisting of alkyl and —C(O)O$R^5$ where $R^5$ is hydrogen or alkyl;
$R^3$ is a radical of the formula (i):

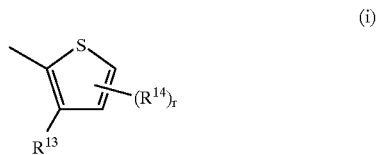

where r is 1;
$R^{13}$ is halo; and
$R^{14}$ is —C($R^7$)H—N($R^{10}$)$R^{11}$ or —C($R^7$)H—N($R^5$)—$R^8$—[CH(OH)]$_t$—CH$^2$—O$R^5$ (where t is 1 to 3)
where:
each $R^5$ is independently hydrogen or alkyl;
$R^7$ is hydrogen;
$R^8$ is a straight or branched alkylene chain;
$R^{10}$ and $R^{11}$ are each independently hydrogen, alkyl, formyl, —$R^8$—O$R^5$, —S(O)$_p$—$R^{15}$ (where p is 0 to 2), —$R^8$—N($R^5$)$R^6$, —$R^8$—C(O)O$R^5$, —C(O)—$R^{15}$, —C(O)NH$_2$, —C(S)NH$_2$, —C(O)—N($R^5$)$R^{15}$, —C(S)—N($R^5$)$R^{15}$, cycloalkyl (optionally substituted by —O$R^5$), heterocyclyl (optionally substituted by one or more substituents selected from the group consisting of alkyl, haloalkyl, oxo, —O$R^5$, and —C(O)O$R^5$), or heterocyclylalkyl (optionally substituted by one or more substituents selected from the group consisting of alkyl, haloalkyl, oxo, —O$R^5$, and —C(O)O$R^5$), where:
each $R^5$ and $R^6$ is independently hydrogen or alkyl;
each $R^8$ is independently a straight or branched alkylene chain; and
each $R^{15}$ is alkyl, —$R^8$—O$R^5$, —$R^8$—C(O)O$R^5$, heterocyclyl (optionally substituted by —$R^8$—O$R^5$), or heterocyclylalkyl (optionally substituted by —O$R^5$);
or $R^{10}$ and $R^{11}$ together with the nitrogen to which they are attached form a N-heterocyclic ring containing zero to three additional hetero atoms, where the N-heterocyclic ring is optionally substituted by one or more substituents selected from the group consisting of alkyl, oxo, =N($R^{17}$), —O$R^5$, —$R^8$—O$R^5$, and —N($R^5$)$R^6$; where
each $R^5$ and $R^6$ is independently hydrogen or alkyl;
$R^8$ is a straight or branched alkylene chain; and
each $R^{17}$ is independently hydrogen, alkyl, aryl, aralkyl, cyano, —O$R^5$, —$R^8$—O$R^5$, —C(O)O$R^5$, —$R^8$—C(O)O$R^5$, —C(O)—N($R^5$)$R^6$, or —$R^8$—C(O)—N($R^5$)$R^6$;
and $R^4$ is in the 5-position and is hydrogen or halo.
Of this group of compound, a preferred subgroup of compounds are those compounds wherein:

$R^2$ is —N($R^{10}$)$R^{11}$ where:
$R^{10}$ and $R^{11}$ are each independently hydrogen, alkyl or —$R^8$—O—$R^5$ where $R^8$ is an alkylene chain, and $R^5$ is hydrogen or alkyl.
Of this subgroup of compounds, a preferred class of compounds are those compounds wherein:
$R^{14}$ is —C($R^7$)H—N($R^{10}$)$R^{11}$ where:
$R^7$ is hydrogen;
$R^{10}$ and $R^{11}$ are each independently hydrogen, alkyl, formyl, —$R^8$—O$R^5$, —S(O)$_p$—$R^{15}$ (where p is 0 to 2), —$R^8$—N($R^5$)$R^6$, —$R^8$—C(O)O$R^5$, —C(O)—$R_{15}$, —C(O)NH$_2$, —C(S)NH$_2$, —C(O)—N($R^5$)$R^{15}$, —C(S)—N($R^5$)$R^{15}$, cycloalkyl (optionally substituted by —O$R^5$), heterocyclyl (optionally substituted by one or more substituents selected from the group consisting of alkyl, haloalkyl, oxo, —O$R^5$, and —C(O)O$R^5$), or heterocyclylalkyl (optionally substituted by one or more substituents selected from the group consisting of alkyl, haloalkyl, oxo, —O$R^5$, and —C(O)O$R^5$); where:
each $R^5$ and $R^6$ is hydrogen or alkyl;
each $R^8$ is independently a straight or branched alkylene chain; and
each $R^{15}$ is alkyl, —$R^8$—O$R^5$, —$R^8$—C(O)O$R^5$, heterocyclyl (optionally substituted by —$R^8$—OR5), or heterocyclylalkyl (optionally substituted by —O$R^5$);
or $R^{10}$ and $R^{11}$ together with the nitrogen to which they are attached form a N-heterocyclic ring containing zero to three additional hetero atoms, where the N-heterocylic ring is optionally substituted by one or more substituents selected from the group consisting of alkyl, oxo, =N($R^{17}$), —O$R^5$, —$R^8$—O$R^5$, and —N($R^5$)$R^6$; where:
each $R^5$ is hydrogen or alkyl;
$R^8$ is straight or branched alkylene chain; and
each $R^{17}$ is independently hydrogen, alkyl, aryl, aralkyl, cyano, —O$R^5$, —$R^8$—O$R^5$, —C(O)O$R^5$, $R^8$—C(O)O$R^5$, —C(O)—N($R^5$)$R^6$, or —$R^8$—C(O)—N($R^5$)$R^6$.
Of this class of compounds, preferred compounds are selected from the group consisting of:
N-(5-chloropyridin-2-yl)-2-[((4-((N'-methyl-N'-(3-(dimethylamino)propyl)amino)methyl)-3-chlorothiophen-2-yl)carbonyl)amino]-3-(dimethyl)amino-5-chlorobenzamide;
N-(5-chloropyridin-2-yl)-2-[((4-((N'-methyl-N'-(2-(dimethylamino)ethyl)amino)methyl)-3-chlorothiophen-2-yl)carbonyl)amino]-3-(dimethyl)amino-5-chlorobenzamide;
N-(5-chloropyridin-2-yl)-2-[((4-((N'-methyl-N'-(1-methylpiperidin-4-yl)amino)methyl)-3-chlorothiophen-2-yl)carbonyl)amino]-3-(dimethyl)amino-5-chlorobenzamide; and
N-(5-chloropyridin-2-yl)-2-[((4-((N'-methyl-N'-(2-hydroxyethyl)amino)methyl)-3-chlorothiophen-2-yl)carbonyl)amino]-3-(di(2-methoxyethyl)amino)-5-chlorobenzamide.
Of this group of compounds, another preferred subgroup of compounds are those compounds wherein:
$R^2$ is —N($R^{10}$)$R^{11}$ where:
$R^{10}$ and $R^{11}$ together with the nitrogen to which they are attached form a N-heterocyclic ring containing zero to three additional hetero atoms, where the N-heterocyclic ring is optionally substituted by one or more substituents selected from the group consisting of alkyl and —C(O)O$R^5$ where $R^5$ is hydrogen or alkyl.
Of this subgroup of compounds, preferred compounds are selected from the group consisting of:
N-(5-chloropyridin-2-yl)-2-[((4-((N'-methyl-N'-(2-(dimethylamino)ethyl)amino)methyl)-3-chlorothiophen-2-yl)carbonyl)amino]-3-(morpholin-4-yl)-5-chlorobenzamide;

N-(5-chloropyridin-2-yl)-2-[((4-((N'-(2-hydroxyethyl) amino)methyl)-3-chlorothiophen-2-yl)carbonyl)amino]-3- (morpholin-4-yl)-5-chlorobenzamide;

N-(5-chloropyridin-2-yl)-2-[((4-((N'-methyl-N'-(2-hydroxyethyl)amino)methyl)-3-chlorothiophen-2-yl) carbonyl)amino]-3-(morpholin-4-yl)-5-chlorobenzamide;

N-(5-chloropyridin-2-yl)-2-[((4-((N'-methyl-N'-(-methylpiperidin-4-yl)amino)methyl)-3-chlorothiophen-2-yl)carbonyl)amino]-3-(morpholin-4-yl)-5-chlorobenzamide;

N-(5-chloropyridin-2-yl)-2-g((4-((N'-methyl-N'-(2-(morpholin-4-yl)ethyl)amino)methyl)-3-chlorothiophen-2-yl)carbonyl)amino]-3-(morpholin-4-yl)-5-chlorobenzamide;

N-(5-chloropyridin-2-yl)-2-[((4-((N'-methyl-N'-(methylsulfonyl)amino)methyl)-3-chlorothiophen-2-yl) carbonyl)amino]-3-(morpholin-4-yl)-5-chlorobenzamide;

N-(5-chloropyridin-2-yl)-2-[((4-((N'-methyl-N'-(3-(dimethylamino)propyl)amino)methyl)-3-chlorothiophen-2-yl)carbonyl)amino]-3-(morpholin-4-yl)-5-chlorobenzamide;

N-(5-chloropyridin-2-yl)-2-[((4-((N'-methyl-N'-(2-(pyrrolidin-1-yl)ethyl)amino)methyl)-3-chlorothiophen-2-yl)carbonyl)amino]-3-(morpholin-4-yl)-5-chlorobenzamide;

N-(5-chloropyridin-2-yl)-2-[((4-((N'-methyl-N'-(2-methoxyethyl)amino)methyl)-3-chlorothiophen-2-yl) carbonyl)amino]-3-(morpholin4-yl)-5-chlorobenzamide;

N-(5-chloropyridin-2-yl)-2-[((4-((N'-methylsulfonyl-N'-(2-(pyrrolidin-1-yl)ethyl)amino)methyl)-3-chlorothiophen-2-yl)carbonyl)amino]-3-(morpholin-4-yl)-5-chlorobenzamide;

N-(5-chloropyridin-2-yl)-2-[((4-((N''-methyl-N'-(2-(pyrrolidin-1-yl)ethyl)ureido)methyl)-3-chlorothiophen-2-yl)carbonyl)amino]-3-(morpholin-4-yl)-5-chlorobenzamide;

N-(5-chloropyridin-2-yl)-2-[((4-((N'-methyl-N'-(methylsulfonyl)amino)methyl)-3-chlorothiophen-2-yl) carbonyl)amino]-3-(4-methylpiperazin-1-yl)-5-chlorobenzamide;

N-(5-chloropyridin-2-yl)-2-[((4-((N'-methyl-N'-(2-hydroxyethyl)amino)methyl)-3-chlorothiophen-2-yl) carbonyl)amino]-3-(4-methylpiperazin-1-yl)-5-chlorobenzamide;

N-(5-chloropyridin-2-yl)-2-[((4-((N'-methyl-N'-(2-hydroxyethyl)amino)methyl)-3-chlorothiophen-2-yl) carbonyl)amino]-3-(pyrrolidin-1-yl)-5-chlorobenzamide;

N-(5-chloropyridin-2-yl)-2-[((4-((N'-(1-methylethyl)-N'-(2-(pyrrolidin-1-yl)ethyl)amino)methyl)-3-chlorothiophen-2-yl)carbonyl)amino]-3-(morpholin-4-yl)-5-chlorobenzamide;

N-(5-chloropyridin-2-yl)-2-[((4-((N'-methyl-N'-(2-hydroxyethyl)amino)methyl)-3-chlorothiophen-2-yl) carbonyl)amino]-3-(4-(ethoxycarbonyl)piperidin-1-yl)-5-chlorobenzamide;

N-(5-chloropyridin-2-yl)-2-[((4-((N'-methyl-N'-(2-hydroxyethyl)amino)methyl)-3-chlorothiophen-2-yl) carbonyl)amino]-3-(4-(carboxy)piperidin-1-yl)-5-chlorobenzamide;

N-(5-chloropyridin-2-yl)-2-1((4-((N'-methyl-N'-(2,3-dihydroxypropyl)amino)methyl)-3-chlorothiophen-2-yl) carbonyl)amino]-3-(morpholin-4-yl)-5-chlorobenzamide;

N-(5-chloropyridin-2-yl)-2-[((4-((N'-methyl-N''-ethylureido)methyl)-3-chlorothiophen-2-yl)carbonyl) amino]-3-(4-ethylpiperazin-1-yl)-5-chlorobenzamide;

N-(5-chloropyridin-2-yl)-2-[((4-((N'-methyl-N'-(oxazolin-2-yl)amino)methyl)-3-chlorothiophen-2-yl) carbonyl)amino]-3-(morpholin4-yl)-5-chlorobenzamide;

N-(5-chloropyridin-2-yl)-2-[((4-((N'-ethyl-N'-(oxazolin-2-yl)amino)methyl)-3-chlorothiophen-2-yl)carbonyl) amino]-3-(morpholin-4-yl)-5-chlorobenzamide;

N-(5-chloropyridin-2-yl)-2-[((4-((N'-methyl-N'-(4-trifluoromethyl-5-(methoxycarbonyl)pyrimidin-2-yl)amino) methyl)-3-chlorothiophen-2-yl)carbonyl)amino]-3-(morpholin-4-yl)-5-chlorobenzamide;

N-(5-chloropyridin-2-yl)-2-[((4-((N'-methyl-N'-(4-trifluoromethyl-5-carboxypyrimidin-2-yl)amino)methyl)-3-chlorothiophen-2-yl)carbonyl)amino]-3-(morpholin-4-yl)-5-chlorobenzamide;

N-(5-chloropyridin-2-yl)-2-[((4-((2-iminotetrahydrooxazol-3-yl)methyl)-3-chlorothiophen-2-yl) carbonyl)amino]-3-(morpholin-4-yl)-5-chlorobenzamide; and N-(5-chloropyridin-2-yl)-2-[((4-((N'-methyl-N'-(tetrazol-5-yl)amino)methyl)-3-chlorothiophen-2-yl)carbonyl) amino]-3-(morpholin4-yl)-5-chlorobenzamide.

Of the compounds of formula (I) described above, another preferred group of compounds are those compounds of formula (I) wherein:

A is =N—;
m is 1;
n is 1;
D is —N(H)—C(O)—;
E is —C(O)—N(H)— (where the nitrogen is bonded to the 2-position of the pyridinyl ring);
$R^2$ is —O—$(R^8$—O$)_t$—$R^5$ (where t is 1 to 3) or —O—$(R^8$—O$)_t$—$R^{19}$ where $R^5$ is hydrogen or alkyl, each $R^8$ is independently a straight or branched alkylene chain, and $R^{19}$ is heterocyclyl (optionally substituted by alkyl, aryl, aralkyl, halo, or haloalkyl);
$R^3$ is a radical of the formula (i):

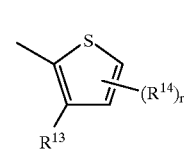

where r is 1;
$R^{13}$ is halo; and
$R^{14}$ is —C($R^7$)H—N($R^{10}$)$R^{11}$ where:
$R^7$ is hydrogen;
$R^{10}$ and $R^{11}$ are each independently hydrogen, alkyl, formyl, —$R^8$—O$R^5$, —S(O)$R_p$—$R^{15}$ (where p is 0 to 2), —$R^8$—N($R^5$)$R^6$, —$R^8$—C(O)O$R^5$, —C(O)—$R^{15}$, —C(O) NH$_2$, —C(S)NH$_2$, —C(O)—N($R^5$)$R^{15}$, —C(S)—N($R^5$)$R^{15}$, cycloalkyl (optionally substituted by —O$R^5$), heterocyclyl (optionally substituted by one or more substituents selected from—the group consisting of alkyl, haloalkyl, oxo, —O$R^5$, and —C(O)O$R^5$), or heterocyclylalkyl (optionally substituted by one or more substituents selected from the group consisting of alkyl, haloalkyl, oxo, —O$R^5$, and —C(O) O$R^5$); where:

each $R^5$ and $R^6$ is hydrogen or alkyl;
each $R^8$ is independently a straight or branched alkylene chain; and
each $R^{15}$ is alkyl, —$R^8$—O$R^5$, —$R^8$—C(O)O$R^5$, heterocyclyl (optionally substituted by —$R^8$—O$R^5$), or heterocyclylalkyl (optionally substituted by —O$R^5$);

or $R^{10}$ and $R^{11}$ together with the nitrogen to which they are attached form a N-heterocyclic ring containing zero to three additional hetero atoms, where the N-heterocylic ring is optionally substituted by one or more substituents selected from the group consisting of alkyl, oxo, =N($R^{17}$), —O$R^5$, —$R^8$—O$R^5$, and —N($R^5$)$R^6$; where

47 each $R^5$ is hydrogen or alkyl;

$R^8$ is straight or branched alkylene chain; and each $R^{17}$ is independently hydrogen, alkyl, aryl, aralkyl, cyano, —$OR^5$, —$R^8$—$OR^5$, —$C(O)OR^5$, —$R^8$—$C(O)OR^5$, —$C(O)$—$N(R^5)R^6$, or —$R^8$—$C(O)$—$N(R^5)R^6$; and $R^4$ is in the 5-position and is hydrogen or halo.

Of this group of compounds, preferred compounds are selected from the group consisting of:

N-(5-chloropyridin-2-yl)-2-[((4-((N'-methyl-N'-(2-(dimethylamino)ethyl)amino)methyl)-3-chlorothiophen-2-yl)carbonyl)amino]-3-(2-hydroxyethoxy)-5-chlorobenzamide;

N-(5-chloropyridin-2-yl)-2-[((4-((N'-methyl-N'-(1-methylpiperidin-4-yl)amino)methyl)-3-chlorothiophen-2-yl)carbonyl)amino]-3-(2-hydroxyethoxy)-5-chlorobenzamide;

N-(5-chloropyridin-2-yl)-2-[((4-((N'-methyl-N'-(2-(pyrrolidin-1-yl)ethyl)amino)methyl)-3-chlorothiophen-2-yl)carbonyl)amino]-3-(2-methoxyethoxy)-5-chlorobenzamide N-(5-chloropyridin-2-yl)-2-[((4-((N'-methyl-N'-(2-(pyrrolidin-1-yl)ethyl)amino)methyl)-3-chlorothiophen-2-yl)carbonyl)amino]-3-(2-hydroxyethoxy)-5-chlorobenzamide;

N-(5-chloropyridin-2-yl)-2-[((4-((N'-methyl-N'-(2,3-dihydroxypropyl)amino)methyl)-3-chlorothiophen-2-yl)carbonyl)amino]-3-(2-methoxyethoxy)-5-chlorobenzamide;

N-(5-chloropyridin-2-yl)-2-[((4-((N'-ethyl-N'-(2-hydroxyethyl)amino)methyl)-3-chlorothiophen-2-yl)carbonyl)amino]-3-(2-methoxyethoxy)-5-chlorobenzamide, N-(5-chloropyridin-2-yl)-2-[((4-((N'-methyl-N'-(2-hydroxyethyl)amino)methyl)-3-chlorothiophen-2-yl)carbonyl)amino]-3-(2-methoxyethoxy)-5-chlorobenzamide;

N-(5-chloropyridin-2-yl)-2-[((4-((N'-methyl-N'-(oxazolin-2-yl)amino)methyl)-3-chlorothiophen-2-yl)carbonyl)amino]-3-((2-(2-methoxyethoxy)ethoxy)-5-chlorobenzamide;

N-(5-chloropyridin-2-yl)-2-[((4-((N'-methyl-N'-(methylsulfonyl)amino)methyl)-3-chlorothiophen-2-yl)carbonyl)amino]-3-((2-(2-methoxyethoxy)ethoxy)-5-chlorobenzamide; and N-(5-chloropyridin-2-yl)-2-[((4-((N'-methyl-N'-(2-hydroxyethyl)amino)methyl)-3-chlorothiophen-2-yl)carbonyl)amino]-3-(3-(pyridin-3-yloxy)propoxy)-5-chlorobenzamide.

Of the compounds of formula (I) described above, another preferred group of compounds are those compounds of formula (I) wherein:

A is =N—;

m is 1;

n is 1;

D is —N(H)—C(O)—;

E is —C(O)—N(H)— (where the nitrogen is bonded to the 2-position of the pyridinyl ring);

$R^2$ is —O—$R^8$—$N(R^{10})R^{11}$ where:

$R^8$ is a straight or branched alkylene chain; and $R^{10}$ and $R^{11}$ are each independently hydrogen, alkyl or —$R^8$—O—$R^5$ where $R^8$ is an alkylene chain, and $R^5$ is hydrogen or alkyl; or $R^{10}$ and $R^{11}$ together with the nitrogen to which they are attached form a N-heterocyclic ring containing zero to three additional hetero atoms, where the N-heterocylic ring is optionally substituted by one or more substituents selected from the group consisting of alkyl and —$C(O)OR^5$ where $R^5$ is hydrogen or alkyl;

48

$R^3$ is a radical of the formula (i):

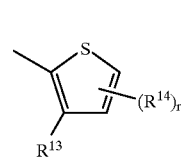

where r is 1;

$R^{13}$ is halo; and $R^{14}$ is —$C(R^7)H$—$N(R^{10})R^{11}$ where:

$R^7$ is hydrogen;

$R^{10}$ and $R^{11}$ are each independently hydrogen, alkyl, formyl, —$R^8$—$OR^5$, —$S(O)_p$—$R^{15}$ (where p is 0 to 2), —$R^8$—$N(R^5)R^6$, —$R^8$—$C(O)OR^5$, —$C(O)$—$R^{15}$, —$C(O)NH_2$, —$C(S)NH_2$, —$C(O)$—$N(R^5)R^{15}$, —$C(S)$—$N(R^5)R^{15}$, cycloalkyl (optionally substituted by —$OR^5$), heterocyclyl (optionally substituted by one or more substituents selected from the group consisting of alkyl, haloalkyl, oxo, —$OR^5$, and —$C(O)OR^5$), or heterocyclylalkyl (optionally substituted by one or more substituents selected from the group consisting of alkyl, haloalkyl, oxo, —$OR^5$, and —$C(O)OR^5$), where:

each $R^5$ and $R^6$ is hydrogen or alkyl;

each $R^8$ is independently a straight or branched alkylene chain; and each $R^{15}$ is alkyl, —$R^8$—$OR^5$, —$R^8$—$C(O)OR^5$, heterocyclyl (optionally substituted by —$R^8$—$OR^5$), or heterocyclylalkyl (optionally substituted by —$OR^5$); and $R^4$ is in the 5-position and is hydrogen or halo.

Of this group of compounds, preferred compounds are selected from the group consisting of:

N-(5-chloropyridin-2-yl)-2-[((4-((N'-methyl-N'-(1-methylpiperidin-4-yl)amino)methyl)-3-chlorothiophen-2-yl)carbonyl)amino]-3-(3-(morpholin-4-yl)propoxy)-5-chloroberizamide;

N-(5-chloropyridin-2-yl)-2-[((4-((N'-methyl-N'-(2-hydroxyethyl)amino)methyl)-3-chlorothiophen-2-yl)carbonyl)amino]-3-(3-(pyrrolidin-1-yl)propoxy)-5-chlorobenzamide;

N-(5-chloropyridin-2-yl)-2-[((4-((N'-methyl-N'-(2-hydroxyethyl)amino)methyl)-3-chlorothiophen-2-yl)carbonyl)amino]-3-(3-(morpholin-4-yl)propoxy)-5-chlorobenzamide;

N-(5-chloropyridin-2-yl)-2-[((4-((N'-methyl-N'-(2-hydroxyethyl)amino)methyl)-3-chlorothiophen-2-yl)carbonyl)amino]-3-(2-(imidazol-1-yl)ethoxy)-5-chlorobenzamide;

N-(5-chloropyridin-2-yl)-2-[((4-((N'-methyl-N'-(2-hydroxyethyl)amino)methyl)-3-chlorothiophen-2-yl)carbonyl)amino]-3-(3-(imidazol-1-yl)propoxy)-5-chlorobenzamide;

N-(5-chloropyridin-2-yl)-2-[((4-((N'-methyl-N'-(methylsulfonyl)amino)methyl)-3-chlorothiophen-2-yl)carbonyl)amino]-3-(2-(pyrrolidin-1-yl)ethoxy)-5-chlorobenzamide;

N-(5-chloropyridin-2-yl)-2-[((4-((N'-methyl-N'-(methylsulfonyl)amino)methyl)-3-chlorothiophen-2-yl)carbonyl)amino]-3-(2-(imidazol-1-yl)ethoxy)-5-chlorobenzamide;

N-(5-chloropyridin-2-yl)-2-[((4-((N'-methyl-N'-(2-hydroxyethyl)amino)methyl)-3-chlorothiophen-2-yl)carbonyl)amino]-3-(2-(pyrrolidin-1-yl)ethoxy)-5-chlorobenzamide;

N-(5-chloropyridin-2-yl)-2-[((4-((N'-methyl-N'-(methylsuffonyl)amino)methyl)-3-chlorothiophen-2-yl)

carbonyl)amino]-3-(3-(4-ethylpiperazin-1-yl)propoxy)-5-chlorobenzamide; and

N-(5-chloropyridin-2-yl)-2-[((4-((N'-methyl-N'-(methylsulfonyl)amino)methyl)-3-chlorothiophen-2-yl)carbonyl)amino]-3-(2-aminoethoxy)-5-chlorobenzamide.

Of the compounds of formula (I) described above, another preferred group of compounds are those compounds of formula (I) wherein:

A is =N—;
m is 1;
n is 1;
D is —N(H)—C(O)—;
E is —C(O)—N(H)— (where the nitrogen is bonded to the 2-position of the pyridinyl ring);
$R^2$ is —O—$R^8$—O—C(O)$R^5$, —O—$R^8$—CH(OH)—CH$_2$—N($R^{10}$)$R^{11}$, or —O—$R^8$—CH(OH)—CH$_2$—O$R^5$ where
each $R^5$ is hydrogen or alkyl;
$R^8$ is a straight or branched alkylene chain; and
$R^{10}$ and $R^{11}$ are each independently hydrogen, alkyl or —$R^8$—O—$R^5$ where $R^8$ is an alkylene chain, and $R^5$ is hydrogen or alkyl; or
$R^{10}$ and $R^{11}$ together with the nitrogen to which they are attached form a N-heterocyclic ring containing zero to three additional hetero atoms, where the N-heterocylic ring is optionally substituted by one or more substituents selected from the group consisting of alkyl and —C(O)O$R^5$ where $R^5$ is hydrogen or alkyl;
$R^3$ is a radical of the formula (i):

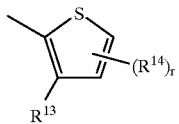

(i)

where r is 1;
$R^{13}$ is halo; and
$R^{14}$ is —C($R^7$)H—N($R^{10}$)$R^{11}$ or —C($R^7$)H—N($R^5$)—S(O)$_2$—N($R^{10}$)$R^{11}$ where:
$R^5$ is hydrogen or alkyl;
$R^7$ is hydrogen;
$R^{10}$ and $R^{11}$ are each independently hydrogen, alkyl, formyl, —$R^8$—O$R^5$, —S(O)$_p$—$R^{15}$ (where p is 0 to 2), —$R^8$—N($R^5$)$R^6$, —$R^8$—C(O)O$R^5$, —C(O)—$R^{15}$, —C(O)NH$_2$, —C(S)NH$_2$, —C(O)—N($R^5$)$R^{15}$, —C(S)—N($R^5$)$R^{15}$, cycloalkyl (optionally substituted by —O$R^5$), heterocyclyl (optionally substituted by one or more substituents selected from the group consisting of alkyl, haloalkyl, oxo, —O$R^5$, and —C(O)O$R^5$), or heterocyclylalkyl (optionally substituted by one or more substituents selected from the group consisting of alkyl, haloalkyl, oxo, —O$R^5$, and —C(O)O$R^5$); where:
each $R^5$ and $R^6$ is hydrogen or alkyl;
each $R^8$ is independently a straight or branched alkylene chain; and
each $R^{15}$ is alkyl, —$R^8$—O$R^5$, —$R^8$—C(O)O$R^5$, heterocyclyl (optionally substituted by —$R^8$—O$R^5$), or heterocyclylalkyl (optionally substituted by —O$R^5$); and
$R^4$ is in the 5-position and is hydrogen or halo.

Of this group of compounds, preferred compounds are selected from the group consisting of:

N-(5-chloropyridin-2-yl)-2-[((4-((N'-methyl-N'-(2-(pyrrolidin-1-yl)ethyl)amino)methyl)-3-chlorothiophen-2-yl)carbonyl)amino]-3-(2-acetoxyethoxy)-5-chlorobenzamide;

N-(5-chloropyridin-2-yl)-2-[((4-((N'-methyl-N'-(methylsulfonyl)amino)methyl)-3-chlorothiophen-2-yl)carbonyl)amino]-3-(2-hydroxy-3-(pyrrolidin-1-yl)propoxy)-5-chlorobenzamide;

N-(5-chloropyridin-2-yl)-2-[((4-((N'-methyl-N'-((dimethylamino)sulfonyl)amino)methyl)-3-chlorothiophen-2-yl)carbonyl)amino]-3-(2-hydroxy-3-(pyrrolidin-1-yl)propoxy)-5-chlorobenzamide;

N-(5-chloropyridin-2-yl)-2-[((4-((N'-methyl-N'-(methylsulfonyl)amino)methyl)-3-chlorothiophen-2-yl)carbonyl)amino]-3-(2-hydroxy-3-(imidazol-1-yl)propoxy)-5-chlorobenzamide; and N-(5-chloropyridin-2-yl)-2-[((4-((N'-methyl-N'-(methylsulfonyl)amino)methyl)-3-chlorothiophen-2-yl)carbonyl)amino]-3-(2-hydroxy-3-methoxypropoxy)-5-chlorobenzamide.

Of the compounds of formula (I) described above, another preferred group of compounds are those compounds of formula (I) wherein:

A is =N—;
m is 1 to 3;
n is 1;
D is —N($R^5$)—C(Z)— (where Z is oxygen and $R^5$ is hydrogen or alkyl);
E is —C(Z)—N($R^5$)— (where Z is oxygen, $R^5$ is hydrogen or alkyl, and the nitrogen is attached to the pyridinyl ring);
each $R^1$ is independently hydrogen, halo or —O$R^5$; or two adjacent $R^1$'s together with the carbons to which they are attached form a dioxole ring fused to the phenyl ring wherein the dioxole ring is optionally substituted by alkyl;
$R^2$ is hydrogen;
$R^3$ is a radical of the formula (i):

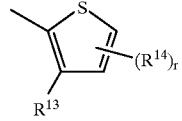

(i)

where r is 1;
$R^{13}$ is halo; and
$R^{14}$ is —C($R^7$)H—N($R^{10}$)$R^{11}$ where:
$R^7$ is hydrogen; and
$R^{10}$ and $R^{11}$ are each independently hydrogen, alkyl, formyl, —$R^8$—O$R^5$, —S(O)$_p$—$R^{15}$ (where p is 0 to 2), —$R^8$—N($R^5$)$R^6$, —$R^8$—C(O)O$R^5$, —C(O)—$R^{15}$, —C(O)NH$_2$, —C(S)NH$_2$, —C(O)—N($R^5$)$R^{15}$, —C(S)—N($R^5$)$R^{15}$, cycloalkyl (optionally substituted by —O$R^5$), heterocyclyl (optionally substituted by one or more substituents selected from the group consisting of alkyl, haloalkyl, oxo, —O$R^5$, and —C(O)O$R^5$), or heterocyclylalkyl (optionally substituted by one or more substituents selected from the group consisting of alkyl, haloalkyl, oxo, —O$R^5$, and —C(O)O$R^5$); where:
each $R^5$ and $R^6$ is hydrogen or alkyl;
each $R^8$ is independently a straight or branched alkylene chain; and
each $R^{15}$ is alkyl, —$R^8$—O$R^5$, —$R^8$—C(O)O$R^5$, heterocyclyl (optionally substituted by —$R^8$—O$R^5$), or heterocyclylalkyl (optionally substituted by —O$R^5$); and
$R^4$ is in the 5-position and is hydrogen or halo.

Of this group of compounds, preferred compounds are selected from the group consisting of:

N-(5-chloropyridin-2-yl)-2-[((4-((N'-methyl-N'-(2-hydroxyethyl)amino)methyl)-3-chlorothiophen-2-yl)carbonyl)amino]-3,4,5-trimethoxybenzamide;

(N-(5-chloropyridin-2-yl)amino)carbonyl-6-[4-((N'-methyl-N'-(oxazolin-2-yl)amino)methyl)-3-chlorothiophen-2-yl)carbonyl]amino-1,3-benzodioxole;

5-(N-(5-chloropyridin-2-yl)amino)carbonyl-6-[4-((N'-methyl-N'-(2-hydroxyethyl)amino)methyl)-3-chlorothiophen-2-yl)carbonyl]amino-1,3-benzodioxole; and 5-(N-(5-chloropyridin-2-yl)amino)carbonyl-6-[4-((N'-(2-methoxyethyl)-N'-(oxazolin-2-yl)amino)methyl)-3-chlorothiophen-2-yl)carbonyl]amino-1,3-benzodioxole.

Of the compounds of formula (I) described above, another preferred group of compounds are those compounds of formula (I) wherein:

A is —CH—;
m is 1;
n is 1;
D is —N($R^5$)—C(Z)— (where Z is oxygen and $R^5$ is hydrogen or alkyl);
E is —C(Z)—N($R^5$)— (where Z is oxygen, $R^5$ is hydrogen or alkyl, and the nitrogen is attached to the phenyl ring having the $R^4$ substituent);
$R^1$ is alkyl or halo;
$R^2$ is hydrogen, alkyl, aryl, aralkyl, halo, haloalkyl, cyano, —$OR^5$, —$S(O)_p$—$R^9$ (where p is 0 to 2), —C(O)$OR^5$, —C(O)N($R^5$)$R^6$, —N($R^{10}$)$R^{11}$, —C($R^7$)H—$OR^5$, —C($R^7$)H—$S(O)_p$—$R^9$ (where p is 0 to 2), —O—$R^8$—S(O)$_p$—$R^9$ (where p is 0 to 2), —C($R^7$)H—N($R^5$)$R^6$, —O—$R^8$—CH(OH)—$CH_2$—N($R^{10}$)$R^{11}$, —O—$R^8$—N($R^{10}$)$R^{11}$, —O—$R^8$—O—C(O)$R^5$, —O—$R^8$—CH(OH)—$CH_2$—$OR^5$; O—($R^8$—O)$_t$—$R^5$ (where t is 1 to 6), —O—$R^8$—C(O)$R^5$, —O—$R^8$—C(O)$OR^5$, —N($R^5$)—$R^8$—N($R^{10}$)$R^{11}$, —$S(O)_p R^8$—N($R^5$)$R^6$ (where p is 0 to 2), —$S(O)_p$—$R^8$—C(O)$OR^5$ (where p is 0 to 2), —N($R^5$)—CH($R^{12}$)—C(O)$OR^5$;
$R^3$ is a radical of formula (i):

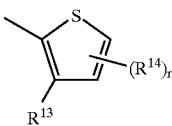

(i)

where:
r is 1 or 2;
$R^{13}$ is hydrogen, alkyl, halo, haloalkyl, —N($R^5$)$R^6$, —C($R^7$)H—N($R^5$)$R^6$, —$OR^5$, —$S(O)_p$—$R^8$—N($R^5$)$R^6$ (where p is 0 to 2) or heterocyclylalkyl (where the heterocyclic ring is optionally substituted by one or more substituents selected from the group consisting of alkyl, halo, aralkyl, nitro and cyano); and
each $R^{14}$ is independently hydrogen, alkyl, halo, formyl, acetyl, —N($R^{10}$)$R^{11}$, —C($R^7$)H—N($R^{10}$)$R^{11}$, —C($R^7$)H—$N^⊕$($R^9$)($R^{16}$)$_2$, —N($R^5$)—$R^8$—C(O)$OR^5$, —C($R^7$)H—N($R^5$)—$R^8$—C(O)$OR^5$, —C(O)$OR^5$, —$OR^5$, —C($R^7$)H—$OR^5$, —$S(O)_p R^{15}$ (where p is 0 to 2), —C($R^7$)H—$S(O)_p$—$R^{15}$ (where p is 0 to 2), —$S(O)_p$—N($R^5$)$R^6$ (where p is 0 to 2), —C(O)N($R^5$)$R^6$, —C($R^7$)H—N($R^5$)—($R^8$—O)$_t R^5$ (where t is 1 to 6), —C($R^7$)H—O—($R^8$—O)$_t$—$R^5$ (where t is 1 to 6), —O—$R^8$—CH(OH)—$CH_2$—$OR^5$, —C($R^7$)H—N($R^5$)—$R^8$—[CH(OH)]$_t$—$CH_2$—$OR^5$ (where t is 1 to 6), —C($R^7$)H—N($R^5$)—$S(O)_2$—N($R^{10}$)$R^{11}$, —C($R^7$)H—N($R^{10}$)—C(N$R^{17}$)—N($R^{10}$)$R^{11}$, or —C($R^7$)H—N($R^{10}$)—C(N$R^{17}$)—$R^{10}$;
$R^4$ is halo;
$R^5$ and $R^6$ are each independently hydrogen, alkyl, aryl or aralkyl;

$R^7$ is hydrogen or alkyl;
each $R^8$ is independently a straight or branched alkylene or alkylidene chain;
each $R^9$ is independently alkyl, aryl or aralkyl;
$R^{10}$ and $R^{11}$ are each independently hydrogen, alkyl, aryl, aralkyl, formyl, —$OR^5$, —$R^8$—$OR^5$, —$S(O)_p$—$R^{15}$ (where p is 0 to 2), —$R^8$—N($R^5$)$R^6$, —$R^8$—C(O)$OR^5$, —C(O)—$R^{15}$, —C(O)$NH_2$, —C(S)$NH_2$, —C(O)—N($R^5$)$R^{15}$, —C(S)—N($R^5$)$R^{15}$, cycloalkyl (optionally substituted by one or more substituents selected from the group consisting of alkyl, halo and —$OR^5$), heterocyclyl (optionally substituted by alkyl, aryl, aralkyl, halo, haloalkyl, oxo, —$OR^5$, —C(O)$OR^5$, —N($R^5$)$R^6$ or —C(O)N($R^5$)$R^6$), or heterocyclylalkyl (optionally substituted by one or more substituents selected from the group consisting of alkyl, aryl, aralkyl, halo, haloalkyl, oxo, —$OR^5$, —C(O)$OR^5$, —N($R^5$)$R^5$, and —C(O)N($R^5$)$R^6$);
or $R^{10}$ and $R^{11}$ together with the nitrogen to which they are attached form a N-heterocyclic ring containing zero to three additional hetero atoms, where the N-heterocylic ring is optionally substituted by one or more substituents selected from the group consisting of alkyl, aryl, aralkyl, oxo, =N($R^{17}$), —$OR^5$, —C(O)$OR^5$, —$R^8$—C(O)$OR^5$, —N($R^5$)$R^6$, —$R^8$—N($R^5$)$R^6$, —C(O)$OR^5$, —C(O)—($R^8$—O)$_t R^5$ (where t is 1 to 6), and —($R^8$—O)$_t R^5$ (where t is 1 to 6);
$R^{12}$ is a side chain of an α-amino acid;
each $R^{15}$ is independently alkyl, haloalkyl, aryl, aralkyl, —R —$OR^5$, —$R^8$—N($R^5$)$R^6$, —$R^8$—C(O)$OR^5$, heterocyclyl (optionally substituted by one or more substituents selected from the group consisting of alkyl, aryl, aralkyl, halo, haloalkyl, —$OR^5$, —C(O)$OR^5$, —N($R^5$)$R^6$, and —C(O)N($R^5$)$R^6$), or heterocyclylalkyl (optionally substituted by one or more substituents selected from the group consisting of alkyl, aryl, aralkyl, halo, haloalkyl, —$OR^5$, —C(O)$OR^5$, —N($R^5$)$R^6$, and —C(O)N($R^5$)$R^6$);
or $R^5$ and $R^{15}$ together with the nitrogen to which they are attached form a N-heterocyclic ring containing zero to three additional hetero atoms, where the N-heterocyclic ring is optionally substituted by one or more substituents selected from the group consisting of alkyl, aryl, aralkyl, amino, monoalkylamino, dialkylamino, —$OR^5$, —C(O)$OR^5$, aminocarbonyl, monoalkylaminocarbonyl, and dialkylaminocarbonyl; and
each $R^{16}$ is independently alkyl, aryl, aralkyl, —$R^8$—$OR^5$, —$R^8$—N($R^5$)$R^6$, cycloalkyl (optionally substituted by one or more substituents selected from the group consisting of alkyl, halo and —$OR^5$), heterocyclyl (optionally substituted by alkyl, aryl, aralkyl, halo, haloalkyl, —$OR^5$, —C(O)$OR^5$, —N($R^5$)$R^6$ or —C(O)N($R^5$)$R^6$), or heterocyclylalkyl (optionally substituted by one or more substituents selected from the group consisting of alkyl, aryl, aralkyl, halo, haloalkyl, —$OR^5$, —C(O)$OR^5$, —N($R^5$)$R^6$ and —C(O)N($R^5$)$R^6$), or
both $R^{16}$'s together with the nitrogen to which they are attached (and wherein the $R^9$ substituent is not present) form an aromatic N-heterocyclic ring containing zero to three additional hetero atoms, where the N-heterocylic ring is optionally substituted by one or more substituents selected from the group consisting of alkyl, aryl, aralkyl, —$OR^5$, —C(O)$OR^5$, —$R^8$—C(O)$OR^5$, —N($R^5$)$R^6$, —$R^8$—N($R^5$)$R^6$, —C(O)$R^5$, —C(O)—($R^8$—O)$_t$—$R^5$ (where t is 1 to 6), and —($R^8$—O)$_t$—$R^5$ (where t is 1 to 6).

Of this group of compounds, a preferred subgroup of compounds are those compounds wherein:
D is —N(H)—C(O)—;
E is —C(O)—N(H)—;
$R^1$ is halo;

$R^2$ is hydrogen, —$OR^5$, —$N(R^{10})R^{11}$, —O—$R^8$—S(O)$_p$—$R^9$ (where p is 0 to 2), —O—$R^8$—N($R^{10}$)$R^{11}$, —O—$R^8$—O—C(O)$R^5$ or —O—$R^8$—C(O)O$R^5$
where:
  each $R^5$ is hydrogen or alkyl;
  each $R^8$ is independently a straight or branched alkylene chain;
  $R^9$ is alkyl;
  $R^{10}$ and $R^{11}$ together with the nitrogen to which they are attached form a N-heterocyclic ring containing zero to three additional hetero atoms;
  $R^3$ is a radical of formula (i):

where:
  r is 1;
  $R^{13}$ is halo; and
  $R^{14}$ is in the 4-position and is —C($R^7$)H—N($R^{10}$)$R^{11}$
where:
  $R^7$ is hydrogen or alkyl; and
  $R^{10}$ and $R^{11}$ are each independently hydrogen, alkyl, —$R^8$—O$R^5$ or heterocyclyl;
  or $R^{10}$ and $R^{11}$ together with the nitrogen to which they are attached form a piperazine ring optionally substituted by alkyl; and
  $R^4$ is chloro.

Of this subgroup of compounds, preferred compounds are selected from the group consisting of:

N-(4-chlorophenyl)-2-[((4-((4-methylpiperazin-1-yl)methyl)-3-chlorothiophen-2-yl)carbonyl)amino]-3-methoxy-5-chlorobenzamide;

N-(4-chlorophenyl)-2-[((4-((4-methylpiperazin-1-yl)methyl)-3-chlorothiophen-2-yl)carbonyl)amino]-3-hydroxy-5-chlorobenzamide;

N-(4-chlorophenyl)-2-[((4-((4-methylpiperazin-1-yl)methyl)-3-chlorothiophen-2-yl)carbonyl)amino]-5-fluorobenzamide;

N-(4-chlorophenyl)-2-[((4-((4-methylpiperazin-1-yl)methyl)-3-chlorothiophen-2-yl)carbonyl)amino]-3-(ethoxycarbonyl)methoxy-5-chlorobenzamide;

N-(4-chlorophenyl)-2-[((4-((4-methylpiperazin-1-yl)methyl)-3-chlorothiophen-2-yl)carbonyl)amino]-3-((acetoxy)ethoxy)-5-chlorobenzamide;

N-(4-chlorophenyl)-2-[((4-((4-methylpiperazin-1-yl)methyl)-3-chlorothiophen-2-yl)carbonyl)amino]-3-(2-(morpholin-4-yl)ethoxy)-5-chlorobenzamide;

N-(4-chlorophenyl)-2-[((4-((4-methylpiperazin-1-yl)methyl)-3-chlorothiophen-2-yl)carbonyl)amino]-3-((methylthio)methoxy)-5-chlorobenzamide;

N-(4-chlorophenyl)-2-[((4-((4-methylpiperazin-1-yl)methyl)-3-chlorothiophen-2-yl)carbonyl)amino]-3-(3-(morpholin-4-yl)propoxy)-5-chlorobenzamide;

N-(4-chlorophenyl)-2-[((4-((N'-methyl-N'-(2-hydroxyethyl)amino)methyl)-3-chlorothiophen-2-yl)carbonyl)amino]-3-(morpholin-4-yl)-5-chlorobenzamide;

N-(4-chlorophenyl)-2-[((4-((N'-methyl-N'-(oxazolin-2-yl)amino)methyl)-3-chlorothiophen-2-yl)carbonyl)amino]-3-(morpholin-4-yl)-5-chlorobenzamide; and N-(4-chlorophenyl)-2-[((4((N'-methyl-N'-(oxazolin-2-yl)amino)methyl)-3-chlorothiophen-2-yl)carbonyl)amino]-3-methoxy-5-chlorobenzamide.

Of the group of compounds described above, another preferred subgroup of compounds are those compounds wherein:

D is —N(H)—C(O)—;
E is —C(O)—N(H)—;
$R^1$ is methyl or chloro;
$R^2$ is hydrogen or —$OR^5$;
$R^3$ is a radical of formula (i):

where:
  r is 1 or 2;
  $R^{13}$ is alkyl, halo, $OR^5$ (where $R^5$ is alkyl) or heterocyclylalkyl (where the heterocyclic ring is optionally substituted by alkyl); and
  each $R^{14}$ is independently hydrogen, alkyl, halo, formyl, —N($R^{10}$)$R^{11}$, —C($R^7$)H—N($R^{10}$)$R^{11}$, —C($R^7$)H—N$^{\oplus}$($R^9$)($R^{16}$)$_2$, —C(O)O$R^5$, —C($R^7$)H—O$R^5$, —S(O)$_p$—$R^{15}$ (where p is 0 to 2), —C($R^7$)H—S(O)$_p$—$R^{15}$ (where p is 0 to 2), —C(O)N($R^5$)$R^6$, —C($R^7$)H—N($R^5$)—($R^8$—O)$_t$—$R^5$ (where t is 1 to 6), —C($R^7$)H—O—($R^8$—O)$_t$—$R^5$ (where t is 1 to 6),
—C($R^7$)H—O—$R^8$—CH(OH)—CH$_2$—O$R^5$, or —C($R^7$)H—N($R^5$)—$R^8$—[CH(OH)]$_t$—CH$_2$—O$R^5$ (where t is 1 to 6);
  $R^4$ is halo;
  $R^5$ and $R^6$ are each independently hydrogen or alkyl;
  each $R^7$ is independently hydrogen or alkyl;
  each $R^8$ is independently a straight or branched alkylene chain;
  $R^9$ is alkyl;
  $R^{10}$ and $R^{11}$ are each independently hydrogen, alkyl, aryl, aralkyl, formyl, —$OR^5$, —$R^8$—$OR^5$, —S(O)$_p R^{15}$ (where p is 0 to 2), —$R^8$—N($R^5$)$R^6$, —$R^8$—C(O)O$R^5$, —C(O)—$R^{15}$, —C(O)NH$_2$, —C(S)NH$_2$, —C(O)—N($R^5$)$R^{15}$, —C(S)—N($R^5$)$R^{15}$, heterocyclyl (optionally substituted by alkyl, aryl, aralkyl, halo, haloalkyl, oxo, —$OR^5$, —C(O)O$R^5$, —N($R^5$)$R^6$ or—C(O)N($R^5$)$R^6$), or heterocyclylalkyl (optionally substituted by one or more substituents selected from the group consisting of alkyl, aryl, aralkyl, halo, haloalkyl, oxo, —$OR^5$, —C(O)O$R^5$, —N($R^5$)$R^6$ and —C(O)N($R^5$)$R^6$);

or $R^{10}$ and $R^{11}$ together with the nitrogen to which they are attached form a N-heterocyclic ring containing zero to three additional hetero atoms, where the N-heterocylic ring is optionally substituted by one or more substituents selected from the group consisting of alkyl, oxo, —N($R^5$)$R^6$, —$R^8$—C(O)O$R^5$, —C(O)$R^5$, and —C(O)—($R^8$—O)$_t$—$R^5$ (where t is 1 to 6);

$R^{15}$ is alkyl, haloalkyl, aryl, aralkyl, —$R^8$—O$R^5$, —N($R^5$)$R^6$, —$R^8$—N($R^5$)$R^6$—$R^8$—C(O)O$R^5$, heterocyclyl (optionally substituted by one or more substituents selected from the group consisting of alkyl, aryl, aralkyl, halo, haloalkyl, —$OR^5$, —C(O)O$R^6$, —N($R^5$)$R^6$), and—C(O)N($R^5$)$R^6$), or heterocyclylalkyl (optionally substituted by one or more substituents selected from the group consisting of alkyl, aryl, aralkyl, halo, haloalkyl, —$OR^5$, —C(O)O$R^5$, —N($R^5$)$R^6$, and —C(O)N($R^5$)$R^6$);

or $R^5$ and $R^{15}$ together with the nitrogen to which they are attached form a N-heterocyclic ring containing zero to three additional hetero atoms, where the N-heterocyclic ring is optionally substituted by one or more substituents selected from the group consisting of alkyl, aryl, aralkyl, amino, monoalkylamino, dialkylamino, —$OR^5$, —C(O)O$R^5$, aminocarbonyl, monoalkylaminocarbonyl, and dialkylaminocarbonyl; and each $R^{16}$ is independently alkyl, aryl, aralkyl, —$R^8$—$OR^5$, —$R^8$—$N(R^5)R^6$, cycloalkyl (optionally substituted by one or more substituents selected from the group consisting of alkyl, halo and —$OR^5$), heterocyclyl (optionally substituted by alkyl, aryl, aralkyl, halo, haloalkyl, —$OR^5$, —C(O)$OR^5$, —$N(R^5)R^6$ or —C(O)$N(R^5)R^6$), or heterocyclylalkyl (optionally substituted by one or more substituents selected from the group consisting of alkyl, aryl, aralkyl, halo, haloalkyl, —$OR^5$, —C(O)$OR^5$, —$N(R^5)R^6$ and —C(O)$N(R^5)R^6$), or both $R^{16}$'s together with the nitrogen to which they are attached (and wherein the $R^9$ substituent is not present) form an aromatic N-heterocyclic ring containing zero to three additional hetero atoms, where the N-heterocylic ring is optionally substituted by one or more substituents selected from the group consisting of alkyl, aryl, aralkyl, —$OR^5$, —C(O)$OR^5$, —$R^8$—C(O)$OR^5$, —$N(R^5)R^6$, —$R^8$—$N(R^5)R^6$, —C(O)$R^5$, —C(O)—($R^8$—O)$_t$—$R^5$ (where t is 1 to 6), and —($R^8$—O)$_t$—$R^5$ (where t is 1 to 6).

Of this subgroup of compounds, a preferred class of compounds are those compounds wherein:

$R^3$ is a radical of formula (i):

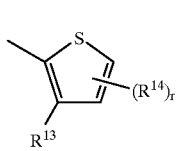

(i)

where:
r is 1 or 2;
$R^{13}$ is halo, alkyl or 4-methylpiperazin-1-yl, and
each $R^{14}$ is independently hydrogen or —C($R^7$)H—N($R^{10}$)$R^{11}$ where:
$R^7$ is hydrogen or alkyl;
$R^{10}$ and $R^{11}$ are each independently hydrogen, alkyl, aryl, aralkyl, formyl, —$OR^5$, —$R^8$—$OR^5$, —S(O)$_p$—$R^{15}$ (where p is 0 to 2), —$R^8$—$N(R^5)R^6$, —$R^8$—C(O)$OR^5$, —C(O)—$R^{15}$, —C(O)$NH_2$, —C(S)$NH_2$, —C(O)—$N(R^5)R^{15}$, —C(S)—$N(R^5)R^{15}$, heterocyclyl (optionally substituted by alkyl, aryl, aralkyl, halo, haloalkyl, oxo, —$OR^5$, —C(O)$OR^5$, —$N(R^5)R^6$ or —C(O)$N(R^5)R^6$), or heterocyclylalkyl (optionally substituted by one or more substituents selected from the group consisting of alkyl, aryl, aralkyl, halo, haloalkyl, oxo, —$OR^5$, —C(O)$OR^5$, —$N(R^5)R^6$ and —C(O)$N(R^5)R^6$) where:
each $R^5$ and $R^6$ are independently hydrogen or alkyl;
each $R^8$ is independently a straight or branched alkylene chain; and
each $R^{15}$ is alkyl, haloalkyl, aryl, aralkyl, —$R^8$—$OR^5$, —$R^8$—$N(R^5)R^6$, —$R^8$—C(O)$OR^5$, heterocyclyl (optionally substituted by one or more substituents selected from the group consisting of alkyl, aryl, aralkyl, halo, haloalkyl, —$OR^5$, —C(O)$OR^5$, —$N(R^5)R^6$, and —C(O)$N(R^5)R^6$), or heterocyclylalkyl (optionally substituted by one or more substituents selected from the group consisting of alkyl, aryl, aralkyl, halo, haloalkyl, —$OR^5$, —C(O)$OR^5$, —$N(R^5)R^6$, and —C(O)$N(R^5)R^6$).

Of this class of compounds, preferred compounds are selected from the group consisting of:

N-(4-chlorophenyl)-2-[((3-methylthiophen-2-yl)carbonyl)amino]-5-chlorobenzamide;

N-(4-chlorophenyl)-2-[((3-((4-methylpiperazin-1-yl)methyl)thiophen-2-yl)carbonyl)amino]-5-chlorobenzamide;

N-(4-chlorophenyl)-2-[((5-((dimethylamino)methyl)-3-chlorothiophen-2-yl)carbonyl)amino]-5-chlorobenzamide;

N-(4-chlorophenyl)-2-[((3-chloro-5-(N'-methyl-N'-(2-hydroxyethyl)amino)methylthiophen-2-yl)carbonyl)amino]-5-chlorobenzamide;

N-(4-chlorophenyl)-2-[((3-chloro-5-(N'-methyl-N'-(ethoxycarbonylmethyl)amino)methylthiophen-2-yl)carbonyl)amino]-5-chlorobenzamide;

N-(4-chlorophenyl)-2-[((3-chloro-5-(N'-methyl-N'-(carboxymethyl)amino)methylthiophen-2yl)carbonyl)amino]-5-chlorobenzamide;

N-(4-chlorophenyl)-2-[((3-chloro-5-(N',N'-di(2-hydroxyethyl)amino)methyl)thiophen-2-yl)carbonyl)amino]-5-chlorobenzamide;

N-(4-chlorophenyl)-2-[((3-chloro-5-(((N'-(3-dimethylaminophenyl)amino)methyl)thiophen-2-yl)carbonyl)amino]-5-chlorobenzamide;

N-(4-chlorophenyl)-2-[((3-chloro-4,5-di((n-propyl)aminomethyl)thiophen-2-yl)carbonyl)amino]-5-chlorobenzamide;

N-(4-chlorophenyl)-2-[((3-chloro-5-((N'-methyl-N'-(2-dimethylaminoethyl)amino)methyl)thiophen-2-yl)carbonyl)amino]-5-chlorobenzamide;

N-(4-chlorophenyl)-2-[((3-chloro-4-((N'-methyl-N'-(2-hydroxyethyl)amino)methyl)thiophen-2-yl)carbonyl)amino]-5-chlorobenzamide;

N-(4-chlorophenyl)-2-[((3-chloro-4-((N'-methyl-N'-(ethoxycarbonylmethyl)amino)methyl)thiophen-2-yl)carbonyl)amino]-5-chlorobenzamide;

N-(4-chlorophenyl)-2-[((3-chloro-4-((N'-methyl-N'-(2-dimethylaminoethyl)amino)methyl)thiophen-2-yl)carbonyl)amino]-5-chlorobenzamide;

N-(4-chlorophenyl)-2-[((3-chloro-4-((N'-(3-(imidazol-1-yl)propyl)amino)methyl)thiophen-2-yl)carbonyl)amino]-5-chlorobenzamide;

N-(4-chlorophenyl)-2-[((3-chloro-4-((N'-methyl-N'-(3-(dimethylamino)propyl)amino)methyl)thiophen-2-yl)carbonyl)amino]-5-chlorobenzamide;

N-(4-chlorophenyl)-2-[((3-chloror-((N'-(2-methylpropyl)amino)methyl)thiophen-2-yl)carbonyl)amino]-5-chlorobenzamide;

N-(4-chlorophenyl)-2-[((3-chloro-4-((N'-methyl-N'-(1-methylpiperidin4-yl)amino)methyl)thiophen-2-yl)carbonyl)amino]-5-chlorobenzamide;

N-(4-chlorophenyl)-2-[((3-chloro-4-((N'-(2-(morpholin-4-yl)ethyl)amino)methyl)thiophen-2-yl)carbonyl)amino]-5-chlorobenzamide;

N-(4-chlorophenyl)-2-[((3-chloro-4-((N'-methyl-N'-hydroxyamino)methyl)thiophen-2-yl)carbonyl)amino]-5-chlorobenzamide;

N-(4-chlorophenyl)-2-[((3-chloro-4-((N'-methyl-N'-(2-diethylaminoethyl)amino)methyl)thiophen-2-yl)carbonyl)amino]-5-chlorobenzamide;

N-(4-chlorophenyl)-2-[((3-chloro-4-((N'-(2-hydroxyethyl)1-N'-(2-(morpholin-4-yl)ethyl)amino)methyl)thiophen-2-yl)carbonyl)amino]-5-chlorobenzamide; and N-(4-chlorophenyl)-2-[((3-chloro-4-((N'-methyl-N'-(2-(pyrrolidin-1-yl)ethyl)amino)methyl)thiophen-2-yl)carbonyl)amino]-5-chlorobenzamide.

Of the subgroup of compounds described above, another preferred class of compounds are those compounds wherein:

$R^3$ is a radical of formula (i):

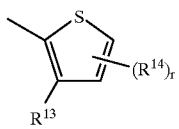

where:
r is 1 or 2;
$R^{13}$ is halo or alkyl, and
each $R^{14}$ is independently hydrogen, alkyl or —C($R^7$)H—N($R^{10}$)$R^{11}$ where:
$R^7$ is hydrogen or alky; and
$R^{10}$ and $R^{11}$ together with the nitrogen to which they are attached form a N-heterocyclic ring containing zero to three additional hetero atoms, where the N-heterocylic ring is optionally substituted by one or more substituents selected from the group consisting of alkyl, oxo, —N($R^5$)$R^6$, —$R^8$—C(O)O$R^5$, —C(O)$R^5$, and —C(O)—($R^8$—O)$_t R^5$
(where t is 1 to 6) where
each $R^5$ is hydrogen or alkyl; and
$R^8$ is a straight or branched alkylene chain.

Of this class of compounds, preferred compounds are selected from the group consisting of:

N-(4-chlorophenyl)-2-[((4-methyl-3-chlorothiophen-2-yl)carbonyl)amino]-5-chlorobenzamide;

N-(4-chlorophenyl)-2-[((3-chloro-5-((4-(carboxymethyl)piperazin-1-yl)methyl)thiophen-2-yl)carbonyl)amino]-5-chlorobenzamide;

N-(4-chlorophenyl)-2-[((4-((4-methylpiperazin-1-yl)methyl)-3-chlorothiophen-2-yl)carbonyl)amino]-5-chlorobenzamide;

N-(4-chlorophenyl)-2-[((5-((4-methylpiperazin-1-yl)methyl)-3-chlorothiophen-2-yl)carbonyl)amino]-5-chlorobenzamide;

N-(4-chlorophenyl)-2-[((3-chloro-5-((4-(ethoxycarbonylmethyl)piperazin-1-yl)methyl)thiophen-2-yl)carbonyl)amino]-5-chlorobenzamide;

N-(4-chlorophenyl)-2-[((3-chloro-5-(thiomorpholin-4-yl)methylthiophen-2-yl)carbonylamino]-5-chlorobenzamide;

N-(4-chlorophenyl)-2-[((3-chloro-5-(morpholin-4-yl)methylthiophen-2-yl)carbonyl)amino]-5-chlorobenzamide;

N-(4-chlorophenyl)-2-[((3-chloro-5-(1-(oxo)thiomorpholin-4-yl)methylthiophen-2-yl)carbonyl)amino]-5-chlorobenzamide;

N-(4-chlorophenyl)-2-[((3-chloro-5-((4-(((2-(2-methoxyethoxy)ethoxy)methyl)carbonyl)piperazin-1-yl)methyl)thiophen-2-yl)carbonyl)amino]-5-chlorobenzamide;

N-(4-chlorophenyl)-2-[((4-(morpholin-4-yl)methyl-3-chlorothiophen-2-yl)carbonyl)amino]-5-chlorobenzamide;

N-(4-chlorophenyl)-2-[((3-chloro-5-(1,1,4-tri(oxo)thiomorpholin-4-yl)methylthiophen-2-yl)carbonyl)amino]-5-chlorobenzamide;

N-(4-chlorophenyl)-2-[((3-chloro-4-(thiomorpholin-4-yl)methylthiophen-2-yl)carbonyl)amino]-5-chlorobenzamide;

N-(4-chlorophenyl)-2-[((3-chloro-5-((imidazol-1-yl)methyl)thiophen-2-yl)carbonyl)amino]-5-chlorobenzamide;

N-(4-chlorophenyl)-2-[((3-chloro-5-methyl-4-((4-methylpiperazin-1-yl)methyl)thiophen-2-yl)carbonyl)amino]-5-chlorobenzamide;

N-(4-chlorophenyl)-2-[((3-chloro4-methyl-5-((4-methylpiperazin-1-yl)methyl)thiophen-2-yl)carbonyl)amino]-5-chlorobenzamide;

N-(4-chlorophenyl)-2-[((3-chloro-4-((4H-1,2,4-triazol-1-yl)methyl)thiophen-2-yl)carbonyl)amino]-5-chlorobenzamide;

N-(4-chlorophenyl)-2-[((3-chloro-4-((imidazol-1-yl)methyl)thiophen-2-yl)carbonyl)amino]-5-chlorobenzamide;

N-(4-chlorophenyl)-2-[((3-chloro-4-((tetrazol-1-yl)methyl)thiophen-2-yl)carbonyl)amino]-5-chlorobenzamide;

N-(4-chlorophenyl)-2-[((3-chloro-4-((tetrazol-2-yl)methyl)thiophen-2-yl)carbonyl)amino]-5-chlorobenzamide;

N-(4-chlorophenyl)-2-[((3-chloro-4-((pyrazol-1-yl)methyl)thiophen-2-yl)carbonyl)amino]-5-chlorobenzamide;

N-(4-chlorophenyl)-2-[((3-chloro-4-((1,2,3-triazol-1-yl)methyl)thiophen-2-yl)carbonyl)amino]-5-chlorobenzamide;

N-(4-chlorophenyl)-2-[((3-chloro-4-((4-(2-(2-hydroxyethoxy)ethyl)piperazin-1-yl)methyl)thiophen-2-yl)carbonyl)amino]-5-chlorobenzamide;

N-(4-chlorophenyl)-2-[((3-chloro-4-((1,2,3-triazol-2-yl)methyl)thiophen-2-yl)carbonyl)amino]-5-chlorobenzamide;

N-(4-chlorophenyl)-2-[((3-chloro-4-((4-ethylpiperazin-1-yl)methyl)thiophen-2-yl)carbonyl)amino]-5-chlorobenzamide;

N-(4-chlorophenyl)-2-[((3-chloro-4-((4-oxomorpholin-4-yl)methyl)thiophen-2-yl)carbonyle)amino]-5-chlorobenzamide;

N-(4-chlorophenyl)-2-[((3-chloro-4-((4-acetylpiperazin-1-yl)methyl)thiophen-2-yl)carbonyl)amino]-5-chlorobenzamide; and N-(4-chlorophenyl)-2-[((4-((2-aminoimidazol-1-yl)methyl)-3-chlorothiophen-2-yl)carbonyl)amino]-3-methoxy-5-chlorobenzamide.

Of this subgroup of compounds described above, another preferred class of compounds are those compounds wherein:
$R^3$ is a radical of formula (i):

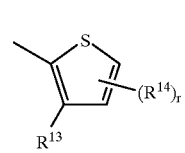

where:
r is 1 or 2;
$R^{13}$ is halo or alkyl, and
each $R^{14}$ is independently —C($R^7$)H—S(O)$_p$—$R^{15}$ where:
p is 0 to 2;
$R^7$ is hydrogen or alkyl; and
$R^{15}$ is alkyl, —$R^8$—N($R^5$)$R^6$ or —$R^8$—C(O)O$R^5$ where:
$R^5$ and $R^6$ are each independently hydrogen or alkyl; and
each $R^8$ is independently a straight or branched alkylene chain.

Of this class of compounds, preferred compounds are selected from the group consisting N-(4-chlorophenyl)-2-[((3-chloro-5-((methylthio)methyl)thiophen-2-yl)carbonyl)amino]-5-chlorobenzamide;

N-(4-chlorophenyl)-2-[((3-chloro-5-(((methoxycarbonylmethyl)thio)methyl)thiophen-2-yl)carbonyl)amino]-5-chlorobenzamide;

N-(4-chlorophenyl)-2-[((3-chloro-5-(((methoxycarbonylmethyl)sulfinyl)methyl)thiophen-2-yl)carbonyl)amino]-5-chlorobenzamide;

N-(4-chlorophenyl)-2-[((3-chloro-5-((methylsulfinyl)methyl)thiophen-2-yl)carbonyle)amino]-5-chlorobenzamide;

N-(4-chlorophenyl)-2-[((3-chloro-5-(((carboxymethyl)thio)methyl)thiophen-2-yl)carbonyl)amino]-5-chlorobenzamide;

N-(4-chlorophenyl)-2-[((3-chloro-5-((methylsulfonyl)methyl)thiophen-2-yl)carbonyl)amino]-5-chlorobenzamide;

N-(4-chlorophenyl)-2-[((3-chloro-5-(((2-(dimethylamino)ethyl)thio)methyl)thiophen-2-yl)carbonyl)amino]-5-chlorobenzamide;

N-(4-chlorophenyl)-2-[((3-chloro-5-(((2-(dimethylamino)ethyl)sulfinyl)methyl)thiophen-2-yl)carbonyl)amino]-5-chlorobenzamide;

N-(4-chlorophenyl)-2-[((3-chloro-4-((methylthio)methyl)thiophen-2-yl)carbonyl)amino]-5-chlorobenzamide;

N-(4-chlorophenyl)-2-[((3-chloro-4-(((methoxycarbonylmethyl)thio)methyl)thiophen-2-yl)carbonyl)amino]-5-chlorobenzamide;

N-(4-chlorophenyl)-2-[((3-chloro-4-(((2-(dimethylamino)ethyl)thio)methyl)thiophen-2-yl)carbonyl)amino]-5-chlorobenzamide;

N-(4-chlorophenyl)-2-[((3-chloro-4-((methylsulfonyl)methyl)thiophen-2-yl)carbonyl)amino]-5-chlorobenzamide; and N-(4-chlorophenyl)-2-[((3-chloro-4-((methylsulfinyl)methyl)thiophen-2-yl)carbonyl)amino]-5-chlorobenzamide.

Of the subgroup of compounds described above, another preferred class of compounds are those compounds wherein:

$R^3$ is a radical of formula (i):

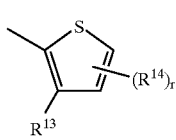

(i)

where:
r is 1 or 2;
$R^{13}$ is halo or alkyl, and
each $R^{14}$ is independently formyl, —N($R^{10}$)$R^{11}$, —C(O)O$R^5$, —C($R^7$)H—O$R^5$ or —C(O)N($R^5$)$R^6$ where:

$R^5$ and $R^6$ are each independently hydrogen or alkyl;
$R^7$ is hydrogen or alkyl; and
$R^{10}$ and $R^{11}$ are independently hydrogen or alkyl.

Of this class of compounds, preferred compounds are selected from the group consisting of:

N-(4-chlorophenyl)-2-[((3-chloro-5-carboxythiophen-2-yl)carbonyl)amino]-5-chlorobenzamide; and N-(4-chlorophenyl)-2-[((3-chloro-4-(hydroxymethyl)thiophen-2-yl)carbonyl)amino]-5-chlorobenzamide.

Of the subgroup of compounds described above, another preferred class of compounds are those compounds wherein:

$R^3$ is a radical of formula (i):

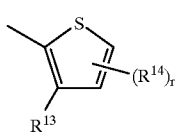

(i)

where:
r is 1 or 2;
$R^{13}$ is alkyl, halo or —O$R^5$ (where $R^5$ is alkyl), and
each $R^{14}$ is independently hydrogen, halo, —C($R^7$)H—N$^{\oplus}$($R^9$)($R^{16}$)$_2$, —S(O)$_p$—$R^{15}$, —C($R^7$)H—N($R^5$)—($R^8$—O)$_t$—$R^5$ (where t is 1 to 6), —C($R^7$)H—O—($R^8$—O)$_t$—$R^5$ (where t is 1 to 6), —C($R^7$)H—O—$R^8$—CH(OH)—CH$_2$—O$R^5$, or —C($R^7$)H—N($R^5$)—$R^8$—[CH(OH)]$_t$—CH$_2$—O$R^5$ (where t is 1 to 6) where:

$R^5$ and $R^6$ are independently hydrogen or alkyl;
$R^7$ is hydrogen or alkyl;

each $R^8$ is independently a straight or branched alkylene chain;

$R^{10}$ and $R^{11}$ are independently hydrogen, alkyl or —$R^8$—O$R^5$ where $R^8$ is a straight or branched alkylene chain and $R^5$ is hydrogen or alkyl; and $R^{15}$ is alkyl or —N($R^5$)$R^6$; and each $R^{16}$ is independently alkyl, aryl, aralkyl, —$R^8$—O$R^5$, —$R^8$—N($R^5$)$R^6$, cycloalkyl (optionally substituted by one or more substituents selected from the group consisting of alkyl, halo and —O$R^5$), heterocyclyl (optionally substituted by alkyl, aryl, aralkyl, halo, haloalkyl, —O$R^5$, —C(O)O$R^5$, —N($R^5$)$R^6$ or —C(O)N($R^5$)$R^6$), or heterocyclylalkyl (optionally substituted by one or more substituents selected from the group consisting of alkyl, aryl, aralkyl, halo, haloalkyl, —O$R^5$, —C(O)O$R^5$, —N($R^5$)$R^6$ and —C(O)N($R^5$)$R^6$), or both $R^{16}$'s together with the nitrogen to which they are attached (and wherein the $R^9$ substituent is not present) form an aromatic N-heterocyclic ring containing zero to three additional hetero atoms, where the N-heterocylic ring is optionally substituted by one or more substituents selected from the group consisting of alkyl, aryl, aralkyl, —O$R^5$, —C(O)O$R^5$, —$R^8$—C(O)O$R^5$, —N($R^5$)$R^6$, —$R^8$—N($R^5$)$R^6$, —C(O)$R^5$, —C(O)—($R^8$—O)$_t$—$R^5$ (where t is 1 to 6), and —($R^8$—O)$_t$—$R^5$ (where t is 1 to 6).

Of this class of compounds, preferred compounds are selected from the group consisting of:

N-(4-chlorophenyl)-2-[((3-chloro-4-((N',N'-dimethyl-N'-(2-hydroxyethyl)ammonio)methyl)thiophen-2-yl)carbonyl)amino]-5-chlorobenzamide;

N-(4-chlorophenyl)-2-[((3-chloro-4-((((2-hydroxyethoxy)ethyl)amino)methyl)thiophen-2-yl)carbonyl)amino]-5-chlorobenzamide;

N-(4-chlorophenyl)-2-[((3-chloro-4-((2-(2-methoxyethoxy)ethoxy)methyl)thiophen-2-yl)carbonyl)amino]-5-chlorobenzamide;

N-(4-chlorophenyl)-2-[((3-chloro-4-((2-(2-methoxyethoxy)ethoxy)ethoxy)methyl)thiophen-2-yl)carbonyl)amino]-5-chlorobenzamide;

N-(4-chlorophenyl)-2-[((3-chloro-4-((2-methoxyethoxy)methyl)thiophen-2-yl)carbonyl)amino]-5-chlorobenzamide;

N-(4-chlorophenyl)-2-[((3-chloro-4-((N',N'-dimethyl-N'-(3-hydroxypropyl)ammonio)methyl)thiophen-2-yl)carbonyl)amino]-5-chlorobenzamide;

N-(4-chlorophenyl)-2-[((3-chloro-4-((N'-methyl-N'-(2,3-dihydroxypropyl)amino)methyl)thiophen-2-yl)carbonyl)amino]-5-chlorobenzamide;

N-(4-chlorophenyl)-2-[((3-chloro-4-((N'-methyl-N'-(2,3,4,5,6-pentahydroxyhexyl)amino)methyl)thiophen-2-yl)carbonylamino]-5-chlorobenzamide;

N-(4-chlorophenyl)-2-[((3-chloro-4-((N'-methyl-N'-(2-(hydroxyethoxy)ethyl)amino)methyl)thiophen-2-yl)carbonyl)amino]-5-chlorobenzamide;

N-(4-chlorophenyl)-2-[((3-chloro-4-(methylsulfonyl)thiophen-2-yl)carbonyl)amino]-5-methylbenzamide;

N-(4-chlorophenyl)-2-[((3-chlorothiophen-2-yl)carbonyl)amino]-5-methylbenzamide;

N-(4-chlorophenyl)-2-[((3-bromothiophen-2-yl)carbonyl)amino]-5-methylbenzamide;

N-(4-chlorophenyl)-2-[((3-chloro4-((1-methylethyl)sulfonyl)thiophen-2-yl)carbonyl)amino]-5-methylbenzamide;

N-(4-chlorophenyl)-2-[((4-(methylamino)sulfonyl-3-methylthiophen-2-yl)carbonyl)amino]-5-methylbenzamide; and N-(4-chlorophenyl)-2-[((3-methoxythiophen-2-yl)carbonyl)amino]-5-methylbenzamide.

Of the compounds of formula (I) described above, another preferred group of compounds are those compounds of formula (I) wherein:

A is —CH— or =N—;
m is 1 to 3;
n is 1 to 4;
D is —N(H)—C(O)— or —N(H)—CH$_2$—;
E is —C(O)—N(H)—; (where the nitrogen atom is bonded to the aromatic ring containing the R$^4$ substituent);
each R$^1$ is independently hydrogen, alkyl, aryl, aralkyl, halo, haloalkyl, cyano, —OR$^5$, —S(O)$_p$—R$^9$ (where p is 0 to 2), —C(O)OR$^5$, —C(O)N(R$^5$)R$^6$, —N(R$^5$)R$^6$, —O—C(O)R$^5$, or —N(R$^5$)—CH(R$^{12}$)—C(O)OR$^5$;
R$^2$ is hydrogen, alkyl, aryl, aralkyl, halo, haloalkyl, cyano, —OR$^5$, —S(O)$_p$—R$^9$ (where p is 0 to 2), —C(O)OR$^5$, —OC(O)—R$^5$, —C(O)N(R$^5$)R$^6$, —N(R$^{10}$)R$^{11}$, —C(R$^7$)H—OR$^5$, —C(R$^7$)H—S(O)$_p$—R$^9$ (where p is 0 to 2), —O—R$^8$—S(O)$_p$—R$^9$ (where p is 0 to 2), —C(R$^7$)H—N(R$^5$)R$^6$, —O—R$^8$—CH(OH)—CH$_2$—N(R$^{10}$)R$^{11}$ —O—R$^8$—N(R$^{10}$)R$^{11}$, —O—R$^8$—O—C(O)R$^5$, —O—R$^8$—CH(OH)—CH$_2$—OR$^5$; —O—(R$^8$—O)$_t$—R$^5$ (where t is 1 to 6), —O—R$^8$—C(O)R$^5$, —O—R$^8$—C(O)OR$^5$, —N(R$^5$)—R$^8$—N(R$^{10}$)R$^{11}$, —S(O)$_p$R$^8$—N(R$^5$)R$^6$ (where p is 0 to 2), —S(O)$_p$—R$^8$—C(O)OR$^5$ (where p is 0 to 2), or —N(R$^5$)—CH(R$^{12}$)—C(O)OR$^5$;
R$^3$ is a radical of formula (ii):

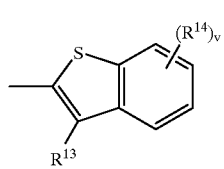

where v is 1 to 4;
R$^{13}$ is hydrogen, alkyl, halo, haloalkyl, —N(R$^5$)R$^6$, —C(R$^7$)H—N(R$^5$)R$^6$, —OR$^5$, —S(O)$_p$—R$^8$—N(R$^5$)R$^6$ (where p is 0 to 2) or heterocyclylalkyl (where the heterocyclic ring is optionally substituted by one or more substituents selected from the group consisting of alkyl, halo, aralkyl, nitro and cyano); and
each R$^{14}$ is independently hydrogen, alkyl, halo, formyl, acetyl, —N(R$^{10}$)R$^{11}$, —C(R$^7$)H—N(R$^{10}$)R$^{11}$, —C(R$^7$)H—N$^\oplus$(R$^9$)(R$^{16}$)$_2$, —N(R$^5$)—R$^8$—C(O)OR$^5$, —C(R$^7$)H—N(R$^5$)—R$^8$—C(O)OR$^5$, —C(O)OR$^5$, —OR$^5$, —C(R$^7$)H—OR$^5$, —S(O)$_p$—R$^{15}$ (where p is 0 to 2), —C(R$^7$)H—S(O)$_p$—R$^{15}$ (where p is 0 to 2), —S(O)$_p$—N(R$^5$)R$^6$ (where p is 0 to 2), —C(O)N(R$^5$)R$^6$, —C(R$^7$)H—N(R$^5$)—(R$^8$—O)$_t$—R$^5$ (where t is 1 to 6), —C(R$^7$)H—O—(R$^8$—O)$_t$—R$^5$ (where t is 1 to 6), —O—R$^8$—CH(OH)—CH$_2$—OR$^5$, —C(R$^7$)H—O—R$^8$—CH(OH)—CH$_2$—OR$^5$, —C(R$^7$)H—N(R$^5$)—R$^8$—[CH(OH)]$_t$—CH$_2$—OR$^5$(where t is 1 to 6), —C(R$^7$)H—N(R$^5$)—S(O)$_2$—N(R$^{10}$)R$^{11}$, —C(R$^7$)H—N(R$^{10}$)—C(NR$^{17}$)—N(R$^{10}$)R$^{11}$, or —C(R$^7$)H—N(R$^{10}$)—C(NR$^{17}$)—R$^{10}$;
each R$^4$ is independently hydrogen, alkyl, halo, haloalkyl, cyano, nitro, —OR$^5$, —C(O)OR$^5$, —N(R$^5$)R$^6$, —C(O)N(R$^5$)R$^6$, or —R$^8$—N(R$^5$)R$^6$;
R$^5$ and R$^6$ are each independently hydrogen, alky, aryl or aralkyl;
each R$^7$ is independently hydrogen or alkyl;
each R$^8$ is independently a straight or branched alkylene or alkylidene chain;
each R$^9$ is independently alkyl, aryl or aralkyl;
R$^{10}$ and R$^{11}$ are each independently hydrogen, alkyl, aryl, aralkyl, formyl, —OR$^5$, —R$^8$—OR$^5$, —S(O)$_p$—R$^{15}$ (where p is 0 to 2), —R$^8$—N(R$^5$)R$^6$, —R$^8$—C(O)OR$^5$, —C(O)—R$^{15}$, —C(O)NH$_2$, —C(S)NH$_2$, —C(O)—N(R$^5$)R$^{15}$, —C(S)—N(R$^5$)R$^{15}$, cycloalkyl (optionally substituted by one or more substituents selected from the group consisting of alkyl, halo and —OR$^5$), heterocyclyl (optionally substituted by alkyl, aryl, aralkyl, halo, haloalkyl, oxo, —OR$^5$, —C(O)OR$^5$, —N(R$^5$)R$^6$ or —C(O)N(R$^5$)R$^6$), or heterocyclylalkyl (optionally substituted by one or more substituents selected from the group consisting of alkyl, aryl, aralkyl, halo, haloalkyl, oxo, —OR$^5$, —C(O)OR$^5$, —N(R$^5$)R$^6$ and —C(O)N(R$^5$)R$^6$);
or R$^{10}$ and R$^{11}$ together with the nitrogen to which they are attached form a N-heterocyclic ring containing zero to three additional hetero atoms, where the N-heterocylic ring is optionally substituted by one or more substituents selected from the group consisting of alkyl, aryl, aralkyl, oxo, =N(R$^{17}$), —OR$^5$, —C(O)OR$^5$, —R$^8$—C(O)OR$^5$, —N(R$^5$)R$^5$, —R$^8$—N(R$^5$)R$^6$, —C(O)R$^5$, —C(O)—(R$^8$—O)$_t$R$^5$ (where t is 1 to 6), and —(R$^8$—O)$_t$—R$^5$ (where t is 1 to 6);
R$^{12}$ is a side chain of an α-amino acid;
R$^{15}$ is alkyl, haloalkyl, aryl, aralkyl, —R$^8$—OR$^5$, —N(R$^5$)R$^6$, —R$^8$—N(R$^5$)R$^6$, —R$^8$—C(O)OR$^5$ heterocyclyl (optionally substituted by one or more substituents selected from the group consisting of alky, aryl, aralkyl, halo, haloalkyl, —OR$^5$, —C(O)OR$^5$, —N(R$^5$)R$^6$, and —C(O)N(R$^5$)R$^6$), or heterocyclylalkyl (optionally substituted by one or more substituents selected from the group consisting of alkyl, aryl, aralkyl, halo, haloalkyl, —OR$^5$, —C(O)OR$^5$, —N(R$^5$)R$^6$, and —C(O)N(R$^5$)R$^6$);
or R$^5$ and R$^{15}$ together with the nitrogen to which they are attached form a N-heterocyclic ring containing zero to three additional hetero atoms, where the N-heterocyclic ring is optionally substituted by one or more substituents selected from the group consisting of alkyl, aryl, aralkyl, amino, monoalkylamino, dialkylamino, —OR$^5$, —C(O)OR$^5$, aminocarbonyl, monoalkylaminocarbonyl, and dialkylaminocarbonyl; and
each R$^{16}$ is independently alkyl, aryl, aralkyl, —R$^8$—OR$^5$, —R—N(R$^5$)R$^6$, cycloalkyl (optionally substituted by one or more substituents selected from the group consisting of alkyl, halo and —OR$^5$), heterocyclyl (optionally substituted by alkyl, aryl, aralkyl, halo, haloalkyl, —OR$^5$, —C(O)OR$^5$, —N(R$^5$)R$^6$ or —C(O)N(R$^5$)R$^6$), or heterocyclylalkyl (optionally substituted by one or more substituents selected from the group consisting of alkyl, aryl, aralkyl, halo, haloalkyl, —OR$^5$, —C(O)OR$^5$, —N(R$^5$)R$^6$ and —C(O)N(R$^5$)R$^6$), or
both R$^{16}$'s together with the nitrogen to which they are attached (and wherein the R$^9$ substituent is not present) form an aromatic N-heterocyclic ring containing zero to three additional hetero atoms, where the N-heterocylic ring is optionally substituted by one or more substituents selected from the group consisting of alkyl, aryl, aralkyl, —OR$^5$, —C(O)OR$^5$, —R$^8$—C(O)OR$^5$, —N(R$^5$)R$^6$, —R$^8$—N(R$^5$) R$^6$, —C(O)R$^5$, —C(O)—(R$^8$—O)$_t$—R$^5$ (where t is 1 to 6), and —(R$^8$—O)$_t$—R$^5$ (where t is 1 to 6); and
each R is independently hydrogen, alkyl, aryl, aralkyl, cyano, —OR$^5$, —R$^8$—OR$^5$, —C(O)OR$^5$, —R$^8$—C(O)OR$^5$, —C(O)—N(R$^5$)R$^6$, or —R$^8$—C(O)—N(R$^5$)R$^6$.
Of this group of compounds, preferred compounds are selected from the group consisting of:
N-phenyl-2-[((3-chicrobenzo[b]thien-2-yl)carbonyl)amino]-5-methylbenzamide;
N-(pyridin-3-yl)-2-[((3-chlorobenzo[b]thien-2-yl)carbonyl)amino]-5-methylbenzamide;
N-(pyridin-2-yl)-2-[((3-chlorobenzo[b]thien-2-yl)carbonyl)amino]-5-methylbenzamide;

N-(4-methoxyphenyl)-2-[((3-chlorobenzo[b]thien-2-yl)carbonyl)amino]-5-methylbenzamide;

N-(3-fluorophenyl)-2-[((3-chlorobenzo[b]thien-2-yl)carbonyl)amino]-5-methylbenzamide;

N-(4-chlorophenyl)-2-[((3-chlorobenzo[b]thien-2-yl)carbonyl)amino]-5-methylbenzamide;

N-(4-bromophenyl)-2-[((3-chlorobenzor[b]thien-2-yl)carbonyl)amino]-5-methylbenzamide;

N-(5-chloropyridin-2-yl)-2-[((3-chlorobenzo[b]thien-2-yl)carbonyl)amino]-5-methylbenzamide;

N-(3-chlorophenyl)-2-[((3-chlorobenzo[b]thien-2-yl)carbonyl)amino]-5-methylbenzamide;

N-(3-methylphenyl)-2-[((3-chlorobenzo[b]thien-2-yl)carbonyl)amino]-5-methylbenzamide;

N-(4-chloro-2-methylphenyl)-2-[((3-chlorobenzo[b]thien-2-yl)carbonyl)amino]-5-methylbenzamide;

N-(4-cyanophenyl)-2-[((3-chlorobenzo[b]thien-2-yl)carbonyl)amino]-5-methylbenzamide;

N-(4-fluorophenyl)-2-[((benzo[b]thien-2-yl)carbonyl)amino]-5-methylbenzamide;

N-(4-fluorophenyl)-2-[((3-methylbenzo[b]thien-2-yl)carbonyl)amino]-5-methylbenzamide;

N-(4-chlorophenyl)-2-[((3-methoxybenzo[b]thien-2-yl)carbonyl)amino]-5-methylbenzamide;

N-(4-fluorophenyl)-2-[((3-chlorobenzo[b]thien-2-yl)carbonyl)amino]benzamide;

N-(4-fluorophenyl)-2-[((3-chlorobenzo[b]thien-2-yl)carbonyl)amino]-5-methoxybenzamide;

N-(4-bromophenyl)-2-[((3-chlorobenzo[b]thien-2-yl)carbonyl)amino]-5-chlorbenzamide;

N-phenyl-2-[((3-chlorobenzo[b]thien-2-yl)carbonyl)amino]-3-methylbenzamide;

N-(4-fluorophenyl)-2-[((3-chlorobenzo[b]thien-2-yl)carbonyl)amino]-5-(pyrrolidin-1-yl)methylbenzamide;

N-(4-chlorophenyl)-2-[((3-chlorobenzo[b]thien-2-yl)carbonyl)amino]-4-(trifuoromethyl)benzamide;

N-(4-fluorophenyl)-2-[((3-chlorobenzo[b]thien-2-yl)carbonyl)amino]-5-(dimethylamino)methylbenzamide;

N-(4-chlorophenyl)-2-[((3-chlorobenzo[b]thien-2-yl)carbonyl)amino]-5-(4-methylpiperazin-1 -yl)benzamide;

N-(4-fluorophenyl)-2-[((3-chlorobenzo[b]thien-2-yl)carbonyl)amino]-5-(amino)methylbenzamide;

N-(4-chlorophenlyl)-2-[((3-chlorobenzo[b]thien-2-yl)carbonyl)amino]-5-hydroxybenzamide;

N-phenyl-2-[((3-chlorobenzo[b]thien-2-yl)carbonyl)amino]-4,5-dimethoxybenzamide;

N-phenyl-2-[((3-chlorobenzo[b]thien-2-yl)carbonyl)amino]-4,5-dihydroxybenzamide;

N-(4-chlorophenyl)-2-[((3-chlorobenzo[b]thien-2-ylcarbonyl)amino]-5-fluorobenzamide;

N-(4-chlorophenyl)-2-[((3-chlorobenzo[b]thien-2-yl)carbonyl)amino]-3-chlorobenzamide;

N-phenyl-2-[((3-chlorobenzo[b]thien-2-yl)carbonyl)amino]-3-methoxybenzamide;

N-phenyl-2-[((3-chlorobenzo[b]thien-2-yl)carbonyl)amino]-3-hydroxybenzamide;

N-(4-chlorophenyl)-2-[((3-chlorobenzo[b]thien-2-yl)carbonyl)amino]-4-fluorobenzamide;

N-(4-chlorophenyl)-2-[((3-chlorobenzo[b]thien-2-yl)carbonyl)amino]-4-chlorobenzamide;

N-(4-chlorophenyl)-2-[((3-chlorobenzo[b]thien-2-yl)carbonyl)amino]-3-methoxybenzamide;

N-(4-chlorophenyl)-2-[((3-chlorobenzo[b]thien-2-yl)carbonyl)amino]-6-fluorobenzamide;

N-(4-chlorophenyl)-2-[((3-chlorobenzo[b]thien-2-yl)carbonyl)amino]-3-hydroxybenzamide;

N-(4-chlorophenyl)-2-[((3-chlorobenzo[b]thien-2-yl)carbonyl)amino]4-methylbenzamide;

N-(4-chlorophenyl)-2-[((3-chlorobenzo[b]thien-2-yl)carbonyl)amino]-3-(ethoxycarbonyl)methoxybenzamide;

N-(4-chlorophenyl)-2-[((3-chlorobenzo[b]thien-2-yl)carbonyl)amino]-4,5-dihydroxybenzamide;

N-(4-chlorophenyl)-2-[((3-chlorobenzo[b]thien-2-yl)carbonyt)amino]-4,5-dimethoxybenzamide;

N-(4-chlorophenyl)-2-[((3-chlorobenzo[b]thien-2-yl)carbonyl)amino]benzamide;

N-(4-chlorophenyl)-2-[((3-chlorobenzo[b]thien-2-yl)carbonyl)amino]-5-aminobenzamide;

N-(4-chlorophenyl)-2-[((3-chlorobenzo[b]thien-2-yl)carbonyl)amino]-4-methyl-5-chlorobenzamide;

N-(4-chlorophenyl)-2-[((3-chlorobenzo[b]thien-2-yl)carbonyl)amino]-3-methoxy-5-chlorobenzamide;

N-(4-chlorophenyl)-2-[((3-chlorobenzo[b]thien-2-yl)carbonyl)amino]-3-methylbenzamide;

N-(4-chlorophenyl)-2-[((3-chlorobenzo[b]thien-2-yl)carbonyl)amino]-3-methyl-5-chlorobenzamide;

N-(4-chlorophenyl)-2-[((3-chlorobenzo[b]thien-2-yl)carbonyl)amino]-4-fluoro-5-chlorobenzamide;

N-(4-chlorophenyl)-2-[((3-chlorobenzo[b]thien-2-yl)carbonyl)amino]-3-hydroxy-5-chlorobenzamide;

N-(4-chlorophenyl)-2-[((3-chlorobenzo[b]thien-2-yl)carbonyl)amino]-4,5-difiuorobenzamide;

N-(4-chlorophenyl)-2-[((3-chlorobenzo[b]thien-2-yl)carbonyl)amino]-4-(N'-methyl-N'-(3-(dimethylamino)propylamino-5-fluorobenzamide;

N-(4-chlorophenyl)-2-[((3-chlorobenzo[b]thien-2-yl)carbonyl)amino]-4-(4-methylpiperazin-1-yl)-5-fluorobenzamide;

N-(4-chlorophenyl)-2-[((3-chlorobenzo[b]thien-2-yl)carbonyl)amino]-4-((3-(4-methylpiperazin-1-yl)propyl)amino)-5-fluorobenzamide;

N-(4-chlorophenyl)-2-[((3-chloro-6-methylbenzo[b]thien-2-yl)carbonyl)amino]-5-chlorobenzamide;

N-(4-chlorophenyl)-2-[((3-methylbenzo[b]thien-2-yl)carbonyl)amino]-5-chlorobenzamide;

N-(4-chlorophenyl)-2-[((3-(dimethylamino)methylbenzo[b]thien-2-yl)carbonyl)amino]-5-chlorobenzamide;

N-(4-chlorophenyl)-2-[((3-chloro-6-(dimethylamino)methylbenzo[b]thien-2-yl)carbonyl)amino]-5-chlorobenzamide;

N-(4-chlorophenyl)-2-[((3-(4-methylpiperazin-1-yl)methylbenzo[b]thien-2-yl)carbonyl)amino]-5-chlorobenzamide;

N-(4-chlorophenyl)-2-[((3-chloro-6-(4-methylpiperazin-1-yl)methylbenzo[b]thien-2-yl)carbonyl)amino]-5-chlorobenzamide;

N-(4-chlorophenyl)-2-[((3-chloro-6-(4-(carboxymethyl)piperazin-1-yl)methylbenzo[b]thien-2-yl)carbonyl)amino]-5-chlorobenzamide;

N-(4-chlorophenyl)-2-[((3-chloro-6-((methoxycarbonyl)methylthio)methylbenzo[b]thien-2-yl)carbonyl)amino]-5-chlorobenzamide;

N-(4-chlorophenyl)-2-[((3-chlorobenzo[b]thien-2-ylcarbonyl)amino]-5-chlorobenzamide;

N-(5-chloropyridin-2-yl)-2-[((4-((4-methylpiperazin-1-yl)methyl)-3-chlorothiophen-2-yl)carbonyl)amino]-3-chloro-5-(N'-methyl-N'-(ethoxycarbonyl)methylamino)benzamide;

N-(5-chloropyridin-2-yl)-2-[((4-(N'-methyl-N'-(2-(dimethylamino)ethyl)amino)-3-chlorothiophen-2-yl)carbonyl)amino]-3-chloro-5-(N'-methyl-N'-(ethoxycarbonyl)methylamino)benzamide;

N-phenyl-2-[((3-chlorobenzo[b]thien-2-yl)carbonyl)amino]-5-hdyroxy-4-((1,1-dimethylethyl)carbonyl)oxybenzamide; and N'-(4-chlorophenyl)-2-((3-methylbenzo[b]thien-2yl) methyl)amino-5-benzamide.

Of the compounds disclosed above, the following compounds are the most preferred compounds of the invention:

N-(5-chloropyridin-2-yl)-2-[((4-((N'-methyl-N'-(2-hydroxyethyl)amino)methyl)-3-chlorothiophen-2-yl) carbonyl)amino]-3-(morpholin-4yl)-5-chlorobenzamide;

N-(5-chloropyridin-2-yl)-2-[((4-((N'-methyl-N'-(2,3-dihydroxypropyl)amino)methyl)-3-chlorothiophen-2-yl) carbonyl)amino]-3-methoxy-5-chlorobenzamide;

N-(5-chloropyridin-2-yl)-2-[((4-((N'-methyl-N'-(2-hydroxyethyl)amino)methyl)-3-chlorothiophen-2-yl) carbonyl)amino]-3-methoxy-5-chlorobenzamide;

N-(5-chloropyridin-2-yl)-2-[((4-((4-ethylpiperazin-1-yl) methyl)-3-chlorothiophen-2-yl)carbonyl)amino]-3-methoxy-5-chlorobenzamide;

N-(5-chloropyridin-2-yl)-2-[((4-((4-methylpiperazin-1-yl)methyl)-3-chlorothiophen-2-yl)carbonyl)amino]-3-(2-methoxyethoxy)-5-chlorobenzamide, N-(5-chloropyridin-2-yl)-2-[((4-((N'-methyl-N''-(2-(pyrrolidin-1-yl)ethyl)ureido)methyl)-3-chlorothiophen-2-yl)carbonyl)amino]-3-methoxy-5-chlorobenzamide;

N-(5-chloropyridin-2-yl)-2-[((4-((N'-methyl-N'-oxazolin-2-yl)amino)methyl)-3-chlorothiophen-2-yl)carbonyl) amino]-3-methoxy-5-chlorobenzamide;

N-(5-chloropyridin-2-yl)-2-[((4-((4-ethylpiperazin-1-yl) methyl)-3-chlorothiophen-2-yl)carbonyl)amino]-3-(2-(2-methoxyethoxy)ethoxy)-5-chlorobenzamide, N-(5-chloropyridin-2-yl)-2-[((4-((N'-methyl-N'-(methylsulfonyl)amino) methyl)-3-chlorothiophen-2-yl) carbonyl)amino]-3-(2-hydroxy-3-(pyrrolidin-1-yl) propoxy)-5-chlorobenzamide, N-(5-chloropyridin-2-yl)-2-[((4-((2-aminoimidazol-1-yl) methyl)-3-chlorothiophen-2-yl)carbonyl)amino]-3-methoxy-5-chlorobenzamide, N-(5-chloropyddin-2-yl)-2-[((4-(chloromethyl)-3-chlorothiophen-2-yl)carbonyl)amino]-3-methoxy-5-chlorobenzamide;

N-(5-chloropyridin-2-yl)-2-[((4-((methylamino)methyl)-3-chlorothiophen-2-yl)carbonyl)amino]-3-methoxy-5-chlorobenzamide N-(5-chloropyridin-2-yl)-2-[((4-((2-imino-5(S)-methyltetrahydrooxazol-3-yl)methyl)-3-chlorothiophen-2-yl)carbonyl)amino]-3-methoxy-5-chlorobenzamide, N-(5-chloropyridin-2-yl)-2-[((4-((dimethylamino) methyl)-3-chlorothiophen-2-yl)carbonyl)amino]-3-methoxy-5-chlorobenzamide;

N-(5-chloropyridin-2-yl)-2-[((4-((2-methylimidazol-1-yl) methyl)-3-chlorothiophen-2-yl)carbonyl)amino]-3-methoxy-5-chlorobenzamide;

N-(5-chloropyridin-2-yl)-2-[((4-((2-methylimidazolin-1-yl)methyl)-3-chlorothiophen-2-yl)carbonyl)amino]-3-methoxy-5-chlorobenzamide;

N-(5-chloropyridin-2-yl)-2-[((4-((N'-methyl-N'-(3,4-dihydro-2H-pyrrol-5-yl)amino)methyl)-3-chlorothiophen-2-yl)carbonyl)amino]-3-methoxy-5-chlorobenzamide;

N-(5-chloropyridin-2-yl)-2-[((4-((2-(methylamino) imidazol-1-yl)methyl)-3-chlorothiophen-2-yl)carbonyl) amino]-3-methoxy-5-chlorobenzamide;

N-(5-chloropyridin-2-yl)-2-[((4-(imidazolin-2-yl)-3-chlorothiophen-2-yl)carbonyl)amino]-3-methoxy-5-chlorobenzamide;

N-(5-chloropyridin-2-yl)-2-[((4-((N'-methyl-N'-(pyridin-4-yl)amino)methyl)-3-chlorothiophen-2-yl)carbonyl) amino]-3-methoxy-5-chlorobenzamide; and N-(5-chloropyridin-2-yl)-2-[((4-((2-(ethylamino) imidazol-1-yl)methyl)-3-chlorothiophen-2-yl)carbonyl) amino]-3-methoxy-5-chlorobenzamide.

Preparation of Compounds of The Invention

It is understood that in the following description, combinations of substituents and/or variables on the depicted formulae are permissible only if such combinations result in stable compounds.

For purposes of illustration only and unless otherwise indicated, the following Reaction Schemes are directed to the preparation of the compounds of the invention as set forth above in the Summary of the Invention as compounds of formula (I). In particular, for purposes of illustration only and unless otherwise indicated, the compounds prepared in the following Reaction Schemes are compounds of formula (I) wherein D is —N($R^5$)—C(O)— (where the nitrogen is bonded to the phenyl ring having the $R^1$ and $R^2$ substituents), and E is —C(O)—N($R^5$)— (where the nitrogen is bonded at the 2-position of the pyridinyl (if A is =N—) or to the phenyl (if A is =CH—) having the $R^4$ substituent) and $R^3$ is a radical of the formula (i):

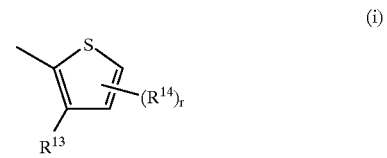

where each $R^{13}$ and each $R^{14}$ are as described in each following Reaction Scheme. It is understood that the other compounds of the invention may be prepared by similar methods as described herein.

A. Preparation of Compounds of Formula (Ia)

Compounds of formula (Ia) are compounds of the invention wherein $R^{13}$ is chloro and the $R^{14}$ substituent is in the 4-position of the thienyl radical. These compounds are prepared as described below in Reaction Scheme 1 where A is =CH— or =N—, each $R^{1a}$ is independently hydrogen, alkyl, aryl, aralkyl, halo, cyano, —$OR^5$, —S(O)$_p$—$R^9$ (where p is 0 to 2), —C(O)$OR^5$, —O—C(O)—$R^5$, —C(O) N($R^5$)$R^6$, —N($R^5$)$R^6$; $R^{2a}$ is hydrogen, alkyl, aryl, aralkyl, halo, cyano, —$OR^5$, —S(O)$_p$—$R^9$ (where p is 0 to 2), —C(O)$OR^5$, —C(O)N($R^5$)$R^6$, —N($R^{10}$)$R^{11}$, —C($R^7$)H—N($R^{10}$)$R^{11}$, —C($R^7$)H—$R^8$—N($R^{10}$)$R^{11}$, —C($R^7$)H—$OR^5$, —C($R^7$)H—$R^8$—$OR^5$, —C($R^7$)H—S(O)$_p$—$R^9$ (where p is 0 to 2), —C($R^7$)H—$R^8$—S(O)$_p$—$R^9$ (where p is 0 to 2), —O—$R^8$—S(O)$_p$—$R^9$ (where p is 0 to 2), —C($R^7$)H—N($R^5$)$R^6$, —C($R^7$)H—$R^8$—N($R^5$)$R^6$, —O—$R^8$—CH(OH)—CH$_2$—N($R^{10}$)$R^{11}$, —O—$R^8$—N($R^{10}$)$R^{11}$, —O—$R^8$—O—C(O)$R^5$, —O—$R^8$—CH(OH)—CH$_2$—$OR^5$, —O—($R^8$—O)$_t R^5$ (where t is 1 to 6), —O—($R^8$—O)$_t$—$R^{19}$ (where t is 1 to 6), —O—$R^8$—C(O)$R^5$, —O—$R^8$—C(O)$R^{19}$, —O—$R^8$—C(O)$OR^5$, —N($R^5$)—$R^8$—N($R^{10}$)$R^{11}$, —S(O)$_p$—$R^8$—N($R^5$)$R^6$ (where p is 0 to 2), or —S(O)$_p$—$R^8$—C(O)$OR^5$ (where p is 0 to 2); each $R^4$ is independently hydrogen, alkyl, halo, cyano, —$OR^5$, —C(O)$OR^5$, —N($R^5$)$R^6$, —C(O)N($R^5$)$R^6$, or —$R^8$—N($R^5$)$R^6$; each $R^5$ and $R^6$ is as described above in the Summary of the Invention for compounds of formula (I); $R^{5a}$ is hydrogen; $R^7$ is hydrogen or alkyl; each $R^8$ and $R^9$ are as described above in the Summary of the Invention for compounds of formula (I); each $R^{10}$ and $R^{11}$ is independently hydrogen, alkyl, aryl, aralkyl, formyl, cyano, —$R^8$—CN, —$OR^5$, —$R^8$—$OR^5$, —S(O)$_p$—$R^{15}$ (where p is 0 to 2), —$R^8$—S(O)$_p$—$R^{15}$ (where p is 0 to 2), —N($R^5$)$R^6$, —$R^8$—N($R^5$)$R^6$, —$R^8$—C(O)$OR^5$, —C(O)—$R^{15}$, —C(O)NH$_2$, —$R^8$—C(O)NH$_2$, —C(S)NH$_2$, —C(O)—S—$R^5$, —C(O)—N($R^5$)$R^{15}$, —$R^8$—C(O)—N($R^5$)$R^{15}$, —C(S)—N($R^5$)$R^{15}$, —$R^8$—N($R^5$)—C (O)H, —R⁸—N(R⁵)—C(O)R¹⁵, —C(O)O—R⁸—N(R⁵)R⁶, —C(N(R⁵)R⁶)=C(R¹⁸)R¹⁰, —R⁸—N(R⁵)—P(O)(OR⁵)₂, cycloalkyl (optionally substituted by one or more substituents selected from the group consisting of alkyl, halo and —OR⁵), heterocyclyl (optionally substituted by one or more substituents selected from the group consisting of alkyl, aryl, aralkyl, halo, —OR⁵, —C(O)OR⁵, —N(R⁵)R⁶ and —C(O)N(R⁵)R⁶), or heterocyclylalkyl (optionally substituted by one or more substituents selected from the group consisting of alkyl, aryl, aralkyl, halo, —OR⁵, —R⁸—OR⁵, —C(O)OR⁵, —S(O)ₚR⁹ (where p is 0 to 2), —R⁸—S(O)ₚ—R⁹ (where p is 0 to 2), —N(R⁵)R⁶ and —C(O)N(R⁵)R⁶); or R¹⁰ and R¹¹ together with the nitrogen to which they are attached form a N—heterocyclic ring containing zero to three additional hetero atoms, where the heterocylic ring is optionally substituted by one or more substituents selected from the group consisting of alkyl, aryl, aralkyl, oxo, nitro, cyano, —R⁸—CN, =N(R¹⁷), —OR⁵, —C(O)OR⁵, —R⁸—C(O)OR⁵, —N(R⁵)R⁶, —R⁸—N(R⁵)R⁶, —C(O)N(R⁵)R⁶, —R⁸—C(O)N(R⁵)R⁶, —N(R⁵)—N(R⁵)R⁶, —C(O)R⁵, —C(O)—(R⁸—O)ₜ—R⁵ (where t is 1 to 6), —S(O)ₚ—R⁹ (where p is 0 to 2), —R⁸—S(O)ₚ—R⁹ (where p is 0 to 2), —(R⁸—O)ₜ—R⁵ (where t is 1 to 6), and heterocyclyl (optionally substituted by one or more substituents selected from the group consisting of alkyl, aryl, aralkyl, halo, —OR⁵, —C(O)OR⁵, —N(R⁵)R⁶, and —C(O)N(R⁵)R⁶); R¹⁴ᵃ is cyano, —N(R¹⁰)R¹¹, —N⊕(R⁹)(R¹⁶)₂, —N(R⁵)—R⁸—C(O)OR⁵, —S—R¹⁵, —S—R⁸—C(O)OR⁵, —S—R⁸—N(R⁵)R⁶, —N(R⁵)—(R⁸—O)ₜ—R⁵ (where t is 1 to 6), —N(R⁵)—R⁸—[CH(OH)]ₜ—CH₂—OR⁵ (where t is 1 to 6), —S—R⁸—OR¹⁵; or R¹⁴ᵃ is heterocyclyl wherein the heterocyclic ring is optionally substituted by alkyl, aryl, aralkyl, oxo, —OR⁵, —C(O)OR⁵, —N(R⁵)R⁶ or —C(O)N(R⁵)R⁶; where each R¹⁵ and R¹⁶ are as described above in the Summary of the Invention for compounds of formula (I) except that neither can be or contain haloalkyl; R¹⁷ is as described in the Summary of the Invention for compounds of formula (I); and X is chloro or bromo:

Reaction Scheme 1

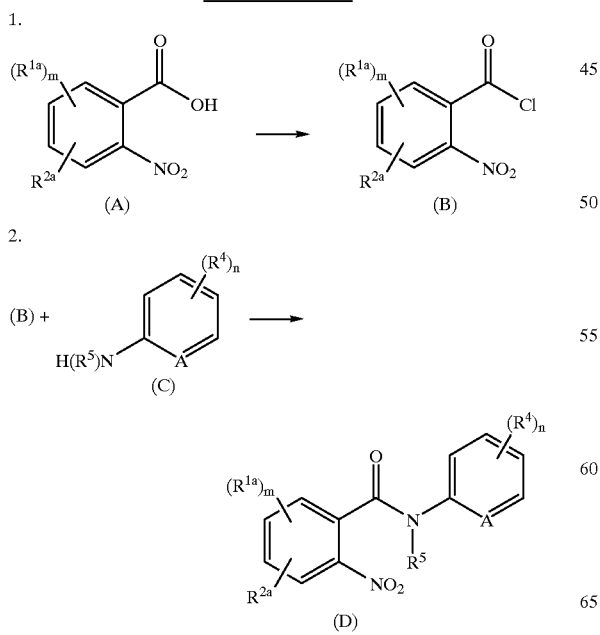

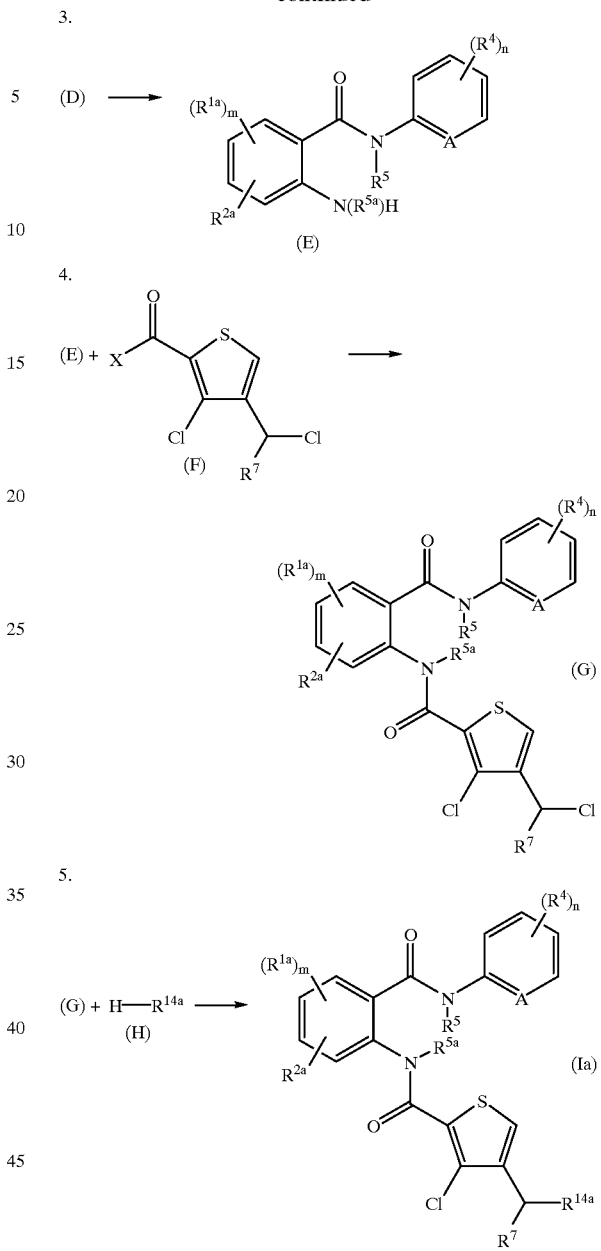

Compounds of formula (A), formula (C), and formula (H) are commercially available, for example, from Aldrich Co. Compounds of formula (F) are commercially available or may be prepared according to methods described herein.

In general, compounds of formula (Ia) are prepared by first reacting a compound of formula (A) in an aprotic solvent, for example, methylene chloride, at temperatures of between about −10° C. to about 10° C., preferably at 0° C., with a halogenating agent, for example, oxalyl chloride. The reaction mixture is allowed to warm to ambient temperature and stirred for about 8 to 20 hours, preferably for about 16 hours, to produce a compound of formula (B), which is isolated from the reaction mixture by standard techniques (such as removal of solvents).

The compound of formula (B) in an aprotic solvent, for example, methylene chloride, at temperatures of between about −10° C. to about 10° C., preferably at 0° C., is then treated with a compound of formula (C) in the presence of a base, for example, triethylamine. The reaction mixture is then stirred for about 20 to 30 minutes, preferably for about 20 minutes, at temperatures of between about —10C to about 10IC, preferably at 0° C, then warmed to ambient temperature, and stirred for about 1 to about 20 hours, preferably for about 16 hours. The compound of formula (D) is then isolated from the reaction mixture by standard isolation techniques, such as evaporation of solvents, extraction and concentration.

The compound of formula (D) is then reduced by treatment with a reducing agent, such as tin(II) chloride under standard reducing conditions to produce a compound of formula (E), which is isolated from the reaction mixture by standard techniques.

The compound of formula (E) in an aprotic solvent, for example, methylene chloride, at temperatures of between about –10° C. to about 100° C., preferably at 0° C., is then treated with a compound of formula (F) in the presence of a base, for example, pyridine. The compound of formula (G) is then isolated from the reaction mixture by standard isolation techniques, such as concentration and trituration with water.

The compound of formula (G) in an aprotic solvent, such as DMF, at temperatures of between about –10° C. to about 10° C., preferably at 0° C., is then treated with a compound of formula (H). The reaction mixture is stirred for about 20 minutes to an hour, preferably for about 30 minutes, and then allowed to warm to ambient temperature. After stirring for about 6 to about 20 hours, preferably for about 7 hours, the compound of formula (Ia) is isolated from the reaction mixture by standard isolation techniques, such as filtration and purification by flash chromatography.

The compound of formula (H) may be present as an acid salt, wherein the corresponding free base is formed in situ by the addition of a base to the reaction mixture, or is treated with a base prior to the reaction with the compounds of formula (G) to form the free base.

Any unprotected amino substituent must be protected prior to Step 4 to avoid acylation. Any carboxy substituent must also be esterified prior to Step 1. The resulting compounds may be deprotected when needed by appropriate methods known to those skilled in the art to afford compounds having an unsubstituted amino or carboxy subsfituent thereon.

Compounds of the invention where D is —N($R^5$)—S(O)$_p$— (where p is 2) may be prepared by methods disclosed above by reacting a compound of formula (E) with the sulfonyl chloride of the substituted thiophene or benzothiophene radical.

Compounds of the invention where E is —N($R^5$)—(O)$_p$— (where p is 2), can be formed by reacting a substituted benzene sulfonyl chloride with a compound of formula (C) and then proceeding with Steps 3–5 above.

Compounds of formula (E) where $R^{5a}$ is hydrogen may be reacted with an appropriate alkylating agent prior to Step 4 to produce compounds where $R^{5a}$ is alkyl, aryl or aralkyl.

Compounds of the invention where $R^{13}$ is —S(O)$_p$— $R^8$—N($R^5$)$R^6$ (where p is 0) may be prepared from the corresponding halo as described herein. Compounds where $R^{13}$ is heterocyclylalkyl may be made from substitution from the corresponding haloalkyl.

Compounds of formula (G) may be reacted with tertiary amines of the formula N($R^9$)($R^{16}$)$_2$ where $R^9$ and $R^{16}$ are as described above in the Summary of the Invention for compounds of formula (I) by methods similar to those described above to prepare compounds of the invention wherein $R^{4a}$ is —N$^\oplus$($R^9$)($R^{16}$)$_2$.

Any unoxidized sulfur and nitrogen may be oxidized after the final step in Reaction Scheme 1 by methods known to those skilled in the art to produce the desired oxidized substituents.

Compounds of formula (Ia) where $R^{14a}$ contains a —N(H)$R^{10}$ group may be reacted with a heterocyclic compound having a reactive halogen to form compounds where $R^{14a}$ contains a —N($R^{10}$)$R^{11}$ group wherein $R^{11}$ is heterocyclyl.

Compounds of formula (Ia) where $R^{14a}$ contains a secondary amino substituent may be reacted with an aldehyde in an aprotic solvent, such as acetonitrile, in the presence of a reducing agent such as sodium cyanoborohydride to form compounds wherein the amino substituent is further substituted by an alkyl or aralkyl group.

Compounds of formula (Ia) where $R^{14a}$ is —N($R^{10}$)$R^{11}$ where $R^{10}$ is hydrogen and $R^{11}$ is —$R^8$—O$R^5$ (where $R^5$ is hydrogen and $R^8$ is ethyl or propyl optionally substituted by alkyl or alkoxyalkyl) can be reacted with cyanogen bromide to form compounds of the invention where $R^{14}$ is —C($R^7$)H—N($R^{10}$)$R^{11}$ where $R^{10}$ and $R^{11}$ together with the nitrogen to which they are attached form optionally substituted 2-iminooxazolidin-3-yl or optionally substituted tetrahydro-2-amino-1,3-oxazinyl.

Compounds of formula (Ia) where $R^{14a}$ is —N($R^{10}$)$R^{11}$ where $R^{11}$ is hydrogen and $R^{10}$ is alkyl, aryl or aralkyl can be reacted with a cyano halide under basic conditions to form compounds of the invention where $R^{14}$ is —C($R^7$)H—N($R^{10}$)—CN, which can then be reacted with an azide in the presence of tributyl tin chloride in an aprotic solvent to form a compound of the invention where $R^{14}$ is —C($R^7$)H—N($R^{10}$)$R^{11}$ where $R^{11}$ is tetrazolyl attached to the nitrogen through a carbon atom in the heterocyclic ring.

Compounds of formula (G) may be treated with an oxidizing agent to form the corresponding N-oxide when A is =N—, and then treated with compounds of formula (H) to form other compounds of the invention where the pyridinyl ring is oxidized.

Compounds of formula (Ia) where $R^{14a}$ is —N($R^{10}$)$R^{11}$ where $R^{10}$ is hydrogen and $R^{11}$ is —$R^8$—N($R^5$)$R^6$ where $R^8$ is ethyl or propyl and at least one $R^5$ or $R^6$ is hydrogen may be further treated with an ortho ester under mild acidic conditions to form compounds of the invention where $R^{14}$ is —C($R^7$)H—N($R^{10}$)$R^{11}$ where $R^{10}$ and $R^{11}$ together with the nitrogen form an optionally substituted imidazolinyl. Other compounds of the invention may be similarly made. Such compounds wherein the imidazolinyl is substituted with an appropriate haloalkyl may be further treated with a compound of formula (H) in an aprouic solvent to form compounds wherein the imidazolinyl is substituted by the corresponding $R^{14a}$ group.

Compounds of formula (Ia) where $R^{14a}$ is —N($R^{10}$)$R^{11}$ where $R^{10}$ and $R^{11}$ together with the nitrogen form a 2-aminoimidazolyl in a protic solvent of the formula $R^5$—OH may be further treated with a halogenating agent, such as N-chlorosuccinimide (NCS) in the presence of a strong acid to form compounds of the invention where $R^{14}$ is —C($R^7$)H—N($R^{10}$)$R^{11}$ where $R^{10}$ and $R^{11}$ form a 2-iminoimidazolidinyl substituted at the 4- and 5-position with —O$R^5$. Other compounds of the invention may be similarly made.

Compounds of formula (Ia) where $R^{14a}$ is —N($R^{10}$)$R^{11}$ where $R^{10}$ is hydrogen and $R^{11}$ is —$R^8$—N($R^5$)$R^6$ where either $R^5$ or $R^6$ is hydrogen may be further treated with phosphoryl chloride in the presence of a base, followed by treatment with a compound of the formula $R^5$—OH to form compounds of the invention where $R^{14}$ is —C($R^7$)H—N($R^5$)—P(O)(O$R^5$)$_2$.

Compounds of formula (I*a*) where $R^{14a}$ is —N($R^{10}$)$R^{11}$ where $R^{10}$ and $R^{11}$ together with the nitrogen form 2-methylthioimidazolinyl may be further treated with N($R^5$)H—$R^8$—O$R^5$ or with NH$_2$—$R^8$—C(O)—N($R^5$)$R^6$ to form compounds of the invention where $R^{14}$ is —C($R^7$)H—N($R^{10}$)$R^{11}$ where $R^{10}$ and $R^{11}$ together with the nitrogen form a imidazolinyl substituted at the 2-position with —N($R^5$)—$R^8$—O$R^5$ or with =N$R^{17}$ where $R^{17}$ is —$R^8$—C(O)—N($R^5$)$R^6$, respectively.

Compounds of formula (I*a*) where $R^{14a}$ is —N($R^{10}$)$R^{11}$ where $R^{10}$ and $R^{11}$ together with the nitrogen form a N-heterocyclic substituted with formyl may be treated under standard reducing conditions to form compounds of the invention where $R^{14}$ is —C($R^7$)H—N($R^{10}$)$R^{11}$ where $R^{10}$ and $R^{11}$ together with the nitrogen form a N-heterocyclic substituted with hydroxymethyl. Other compounds of the invention may be similarly made.

Compounds of formula (I*a*) where $R^{14a}$ is —N($R^{10}$)$R^{11}$ where $R^{10}$ is alkyl and $R^{11}$ is oxazolin-2-yl may be treated with compounds of the formula $R^5$—C(O)OH to form compounds of the invention where $R^{14}$ is —N($R^{10}$)$R^{11}$ where $R^{10}$ is alkyl and $R^{11}$ is —C(O)—N($R^5$)$R^{15}$ where $R^5$ is hydrogen and $R^{15}$ is —$R^8$—O—C(O)$R^5$ where $R^8$ is ethyl.

Other compounds of formula (I*a*) may be prepared according to the methods described herein according to methods known to those skilled in the art.

B. Preparation of Compounds of Formula (I*b*)

Compounds of formula (I*b*) are compounds of the invention and are prepared as follows in Reaction Scheme 2 wherein A is =CH— or =N—, each $R^{1a}$ is as defined in Reaction Scheme 1 above; $R^{2a}$ is as defined in Reaction Scheme 1 above; $R^5$ is as defined in the Summary of the Invention for compounds of formula (I); $R^{5a}$ is hydrogen; each $R^4$ and $R^{13}$ is as defined in the Summary of the Invention for compounds of formula (I), $R^{14}$ is as described above in the Summary of the Invention for compounds of formula (I); and X is chloro or bromo:

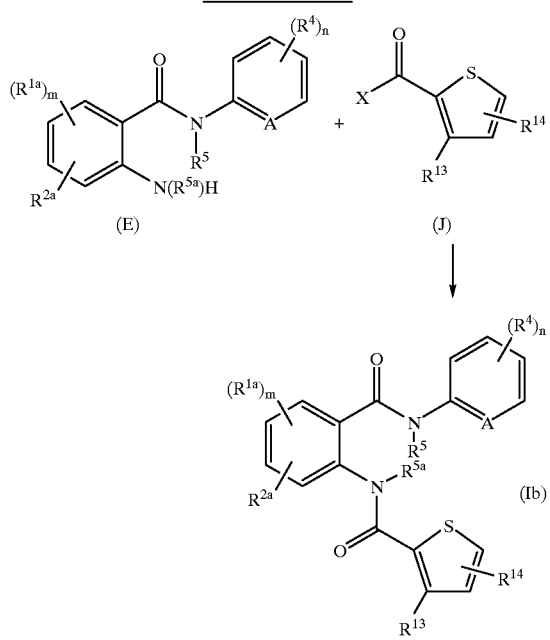

Reaction Scheme 2

Compounds of formula (E) are prepared above in Reaction Scheme 1. Compounds of formula (J) are commercially available, e.g., from Lancaster, or may be prepared by methods known to those skilled in the art from compounds of formula (J) where X is —OCH$_3$ (and where $R^{13}$ or $R^{14}$ do not contain a hydrolyzable group such as an ester), which is hydrolyzed to the acid and then converted to the acid chloride to form a compound of formula (J). In addition, compounds of formula (J) may be prepared according to methods disclosed herein.

In general, compounds of formula (I*b*) are prepared by treating a compound of formula (E) with a compound of formula (J) in the presence of a base, preferably pyridine, at temperatures of between about –10° C. to about 10° C., preferably at 0° C. The reaction mixture is allowed to warm to ambient temperature and then stirred for about 8 to 20 hours, preferably for about 16 hours. The compound of formula (I*b*) is then isolated from the reaction mixture by standard isolation techniques, such as filtration and recrystallization.

Compounds of formula (I*b*) where $R^{14}$ is hydrogen, halo, formyl, acetyl, —N($R^{10}$)$R^{11}$, —N($R^5$)—$R^8$—C(O)O$R^5$, —C(O)O$R^5$, —O$R^5$, —S(O)$_p$—$R^{15}$ (where p is 0 to 2), —S(O)$_p$—N($R^5$)$R^6$, or —C(O)N($R^5$)$R^6$; and $R^{1a}$, $R^{2a}$ or $R^{13}$ is alkyl, may be treated under standard halogenating conditions to form compounds where $R^{1a}$, $R^{2a}$ or $R^{13}$ is haloalkyl. The resulting compounds may then be treated with HN($R^{10}$)$R^{11}$ or HN($R^5$)$R^6$ to form compounds where $R^{1a}$, $R^{2a}$ or $R^{13}$ is —C($R^7$)H—N($R^{10}$)$R^{11}$ or —C($R^7$)H—N($R^5$)$R^6$.

Compounds of formula (I*b*) where $R^{14}$ is cyano may be treated with methanol or ethanol to form the corresponding imidate, which can then be treated with a compound of formula NH$_2$—$R^8$—N($R^5$)$R^6$ where at least one $R^5$ or $R^6$ is hydrogen to form compounds of the invention where $R^{14}$ is heterocyclyl containing at least two nitrogen atoms. Alternatively, the imidate so formed can be treated with a compound of formula N(H)($R^5$)$R^6$ to form compounds of the invention where $R^{14}$ is —C(NH)—N($R^5$)$R^6$ which can be further treated under conditions similar to those described herein to form compounds of the invention where $R^{14}$ is —C(N$R^{17}$)—N($R^5$)$R^6$ where $R^{17}$ is as described above in the Summary of the Invention for compounds of formula (I).

Compounds of formula (I*b*) where one or more $R^{1a}$'s is hydroxy and $R^2$ is hydrogen may be further treated with a compound of formula $R^5$—C(O)—X where X is chloro or bromo to produce compounds of the invention where one or more $R^{1a}$'s is —O—C(O)—$R^5$.

Compounds of formula (I*b*) where $R^{14}$ is —N($R^{10}$)$R^{11}$ where at least one $R^{10}$ or $R^{11}$ is hydrogen can be treated with the appropriate X—C(O)—$R^{15}$ where X is bromo or chloro and $R^{15}$ is as described above in the Summary of the Invention for compounds of formula (I) to form compounds of the invention where $R^{14}$ is —N($R^{10}$)($R^{11}$) where $R^{10}$ is hydrogen, alkyl, aryl or aralkyl and $R^{11}$ is —C(O)—$R^{15}$. During this process, other substitutents of compounds of formula (I*b*) which contain a reactive hydroxy, amino or carboxy group may also be acylated.

C. Preparation of Compounds of Formula (I*c*)

Compounds of formula (I*c*) are compounds of the invention. They are prepared from compounds of formula (I*b*) where A is =CH— or =N—, $R^{14b}$ is —CH$_2$—$R^7$ where $R^7$ is hydrogen or alkyl as illustrated below in Reaction Scheme 3 wherein each $R^{1a}$, $R^{2a}$, $R^4$, $R^5$, $R^{5a}$ and $R^{14a}$ are as defined above in Reaction Scheme 1, and $R^{13}$ is as defined above in the Summary of the Invention for compounds of formula (I), and X is bromo and chloro:

Reaction Scheme 3

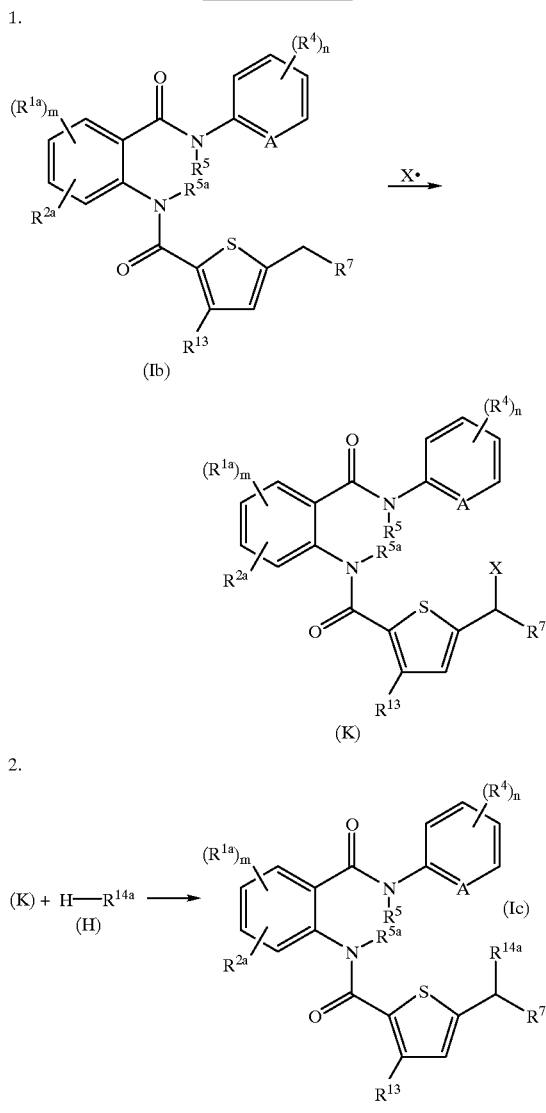

Compounds of formula (Ib) are prepared herein. Compounds of formula (H) are commercially available or may be prepared according to methods known to those skilled in the art or by methods disclosed herein.

In general, compounds of formula (Ic) are prepared by first treating a compound of formula (Ib) in an organic solvent, such as benzene, with an halogenating agent under conditions to form the halide radical (such as irradiation). The compound of formula (K) is then isolated from the reaction mixture by standard techniques, such as concentration and trituration with solvent.

The compound of formula (K) in an aprotic solvent, such as methylene chloride, is treated with a compound of formula (H). The reaction mixture is stirred at ambient temperature for about 8 to about 20 hours, preferably for about 18 hours. The compound of formula (Ic) is then isolated from the reaction mixture by standard isolation techniques, such as extraction, concentration and purification by HPLC.

Compounds of the invention where $R^{13}$ is haloalkyl may be prepared by halogenating the corresponding alkyl substituent according to methods known to those skilled in the art. The compounds so formed can then be treated with the appropriate $HN(R^5)R^6$ group under conditions similar to those described above for preparing compounds of formula (Ic) to produce compounds of the invention where $R^{13}$ is —C($R^7$)H—N($R^5$)$R^6$.

For better yield in the above Reaction Scheme, it is recommended that $R^{1a}$, $R^{2a}$, $R^4$, and $R^{13}$ do not contain an alkyl group, since this alkyl will also be halogenated and will subsequently react with compound of formula (H) during the reaction.

Compounds of formula (K) where X is bromo may be treated under standard substitution conditions to form compounds of formula (Ic) where $R^{14a}$ is hydroxy. These compounds may be further oxidized under standard oxidizing conditions to form compounds of the invention where $R^{14}$ is formyl, which can further oxidized to form compounds of the invention where $R^{14}$ is —C(O)O$R^5$.

D. Preparation of Compounds of Formula (Id)

Compounds of formula (Id) are compounds of the invention where $R^{13}$ is chloro. They are prepared from compounds of formula (M) which are compounds of either formula (G) or (K) as illustrated below in Reaction Scheme 4 where A is =CH— or =N—, each $R^{1a}$, $R^{2a}$, each $R^4$, $R^5$, $R^{5a}$ and $R^7$ are as defined above in Reaction Scheme 1; $R^{14c}$ is —O$R^5$, —S—$R^{15}$, —S—$R^8$—C(O)O$R^5$, —S—$R^8$—N($R^5$)$R^6$, —O—($R^8$—O)$_t$—$R^5$ (where t is 1 to 6), —S—$R^8$—O$R^5$, —CN or —N($R^{10}$)$R^{11}$ (where $R^{10}$ and $R^{11}$ together with the nitrogen to which they are attached form a a N-heterocyclic ring containing zero to three additional hetero atoms, where the N-heterocyclic ring is optionally substituted by one or more substituents selected from the group consisting of alkyl, halo, haloalkyl, aryl, aralkyl, oxo, nitro, cyano, —$R^8$—CN, =N($R^{17a}$), —O$R^{5b}$, —C(O)O$R^{5b}$, —$R^8$—C(O)O$R^{5b}$, —N($R^{5b}$)$R^{6b}$, —$R^8$—N($R^{5b}$)$R^{6b}$, —C(O)N($R^{5b}$)$R^{6b}$, —$R^8$—C(O)N($R^{5b}$)$R^{6b}$, —N($R^{5b}$)—N($R^{5b}$)$R^{6b}$, —C(O)$R^{5b}$, —C(O)—($R^8$—O)$_t$—$R^{5b}$ (where t is 1 to 6), —S(O)$_p$—$R^9$ (where p is 0 to 2), —$R^8$—S(O)$_p$—$R^9$ (where p is 0 to 2), —$R^8$—O)$_t$—$R^{5b}$ (where t is 1 to 6), and heterocyclyl (optionally substituted by one or more substituents selected from the group consisting of alkyl, aryl, aralkyl, halo, haloalkyl, —O$R^{5b}$, —C(O)O$R^{5b}$, —N($R^5$)$R^{6b}$, and —C(O)N($R^{5b}$)$R^{6b}$) where $R^{5b}$ and $R^{6b}$ are alkyl, aryl or aralkyl and $R^{17a}$ is as defined for $R^{17}$ in the Summary of the Invention for compounds of formula (I) except $R^{17a}$ can not be hydrogen; and where each $R^8$, $R^9$ and $R^{15}$ are as defined above in the Summary of the Invention for compounds of formula (I); and Y is a metal cation:

Reaction Scheme 4

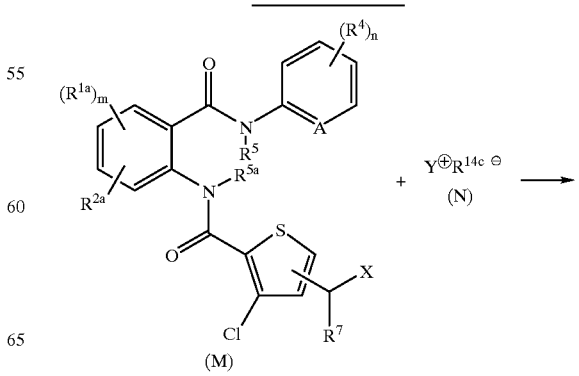

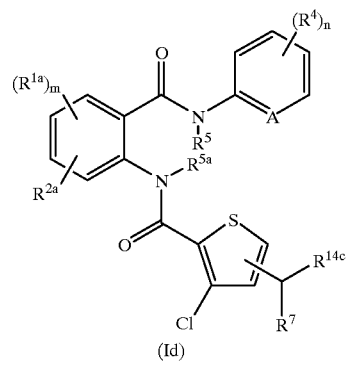

(Id)

Compounds of formula (N) are commercially available or may be prepared according to methods known to those skilled in the art.

In general, the compounds of formula (Id) are prepared by reacting a compound of formula (M) in an aprotic solvent with a compound of formula (N). The reaction mixture is stirred at ambient temperature for about 8 to about 20 hours, preferably for about 16 hours. The compound of formula (Id) is then isolated from the reaction mixture by standard isolation techniques, such as extraction, concentration of product, and flash chromatography.

Alternatively, a compound of formula $HR^{14c}$ in an aprotic solvent, such as DMF, is treated with a strong base, such as sodium hydride, at ambient temperature to form the corresponding salt. The compound of formula (M) in an aprotic solvent, such as DMF, is then added to the reaction mixture containing the salt. The reaction mixture is stirred at ambient temperature for about 10 to 20 hours, preferably for about 18 hours. The compound of formula (Id) is then isolated from the reaction mixture by standard isolation techniques, such as extraction, concentration and flash chromatography.

In general, this reaction scheme is used for those amines, alcohols and mercapto compounds of formula $HR^{14c}$ which are not reactive enough to be used in Reaction Schemes 1 or 2 above. The salt can be formed in situ or can be isolated.

Compounds of formula (Ia) where $R^{14c}$ is cyano may be further treated with hydroxylamine under basic conditions in a protic solvent to form compounds of the invention where $R^{14}$ is $-C(R^7)H-C(NR^{17})-R^{10}$ where $R^{17}$ is $-OH$.

E. Preparation of Compounds of Formula (If)

Compounds of formula (If) are compounds of the invention wherein a $R^{14}$ substituent is $-C(R^7)H-N(R^{10})R^{11}$ where $R^7$ is hydrogen or alkyl, $R^{10}$ is hydrogen, alkyl, aryl, aralkyl, $-OR^5$ (where $R^5$ is not hydrogen), $-R^8-OR^5$ (where $R^5$ is not hydrogen), $-R^8-N(R^5)R^6$, cycloalkyl (optionally substituted as described above in the Summary of the Invention for compounds of formula (I) except that $R^5$ can not be hydrogen), and heterocyclylalkyl (optionally substituted as described above in the Summary of the Invention for compounds of formula (I) except that $R^5$ can not be hydrogen), and $R^{11}$ is $-S(O)_2-R^{15a}$ where $R^{15a}$ is alkyl, haloalkyl, aryl, aralkyl, $-R^8-O-C(O)-R^5$, $-R^8-OR^5$, $-R^8-N(R^5)R^6$, $-R^8-C(O)OR^5$, heterocyclyl (optionally substituted by one or more substituents selected from the group consisting of alkyl, aryl, aralkyl, halo, haloalkyl, $-OR^{5b}$, $-R^8-OR^{5b}$, $-C(O)OR^{5b}$, $-N(R^{5b})R^{6b}$ and $-C(O)N(R^{5b})R^{6b}$ where each $R^{5b}$ and $R^{6b}$ is alkyl, aryl or aralkyl), or heterocyclylalkyl (optionally substituted by one or more substituents selected from the group consisting of alkyl, aryl, aralkyl, halo, haloalkyl, $-OR^{5b}$, $-R^8-OR^{5b}$, $-C(O)OR^{5b}$, $-N(R^{5b})R^{6b}$ or $-C(O)N(R^{5b})R^{6b}$ where each $R^{5b}$ or $R^{6b}$ is alkyl, aryl or aralkyl). They are prepared from compounds of formula (M) as illustrated below in Reaction Scheme 5 where A is =CH— or =N—; $R^{1a}$, $R^{2a}$, $R^4$, $R^5$ and $R^{5a}$ are as described above in Reaction Scheme 1; $R^{10}$ and $R^{15a}$ are as described above; and X is chloro or bromo:

Reaction Scheme 5

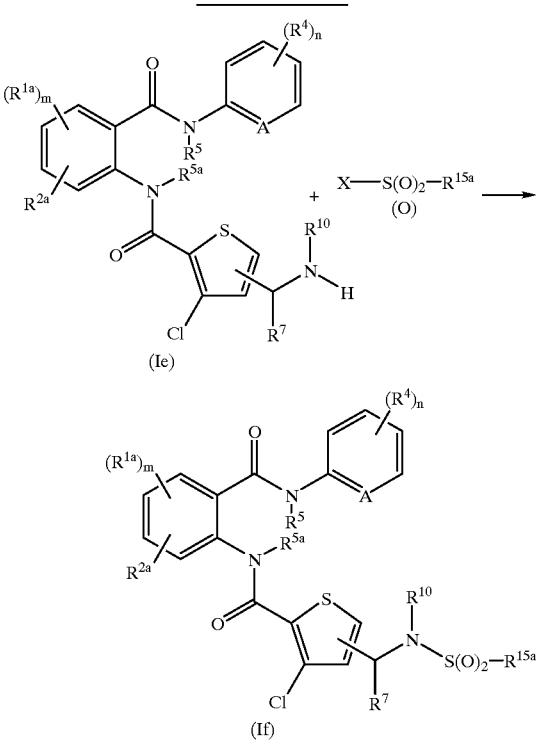

Compounds of formula (O) are commercially available or may be prepared according to methods known to those of ordinary skill in the art. The compound of formula (Ie) is a compound of formula (Ia) where $R^{14a}$ is $-N(R^{10})R^{11}$ and is prepared herein.

In general, compounds of formula (If) are prepared by treating a compound of formula (Ie) in the presence of base, such as pyridine, at temperatures of between about $-10°$ C. to about $10°$ C., preferably at $0°$ C., with a compound of formula (O). The reaction mixture is allowed to warm to ambient temperature and then stirred for about 8 to about 20 hours, preferably for about 16 hours. The compound of formula (If) is then isolated from the reaction mixture by standard isolation techniques, such as removal of solvents in vacuo and purification by flash chromatography.

This reaction scheme can also be used with compounds of the formula $X-S(O)_2-N(R^{10})R^{11}$ to make compounds of the invention where $R^{14}$ is $-C(R^7)H-N(R^{10})-S(O)_2-N(R^{10})R^{11}$.

F. Preparation of Compounds of Formula (Ig)

Compounds of formula (Ig) are compounds of the invention wherein a $R^{14}$ is $-C(R^7)H-N(R^{10})R^{11}$ where $R^7$ is hydrogen or alkyl, $R^{10}$ is hydrogen, alkyl, aryl, aralkyl, $-OR^5$ (where $R^5$ is not hydrogen), $-R^8-OR^5$, $-R^8-N(R^5)R^6$, cycloalkyl (optionally substituted as described above in the Summary of the Invention for compounds of formula (I) except that $R^5$ can not be hydrogen), and heterocyclylalkyl (optionally substituted as described above in the Summary of the Invention for compounds of formula (I) except that $R^5$ can not be hydrogen); and $R^{11}$ is either —C(O)—N(R$^5$)R$^{15b}$ or —C(S)—N(R$^5$)R$^{15b}$ where each R$^5$ is hydrogen and each R$^{15b}$ is hydrogen, alkyl, aryl, aralkyl, —R$^8$—OR$^5$, —R$^8$—C(O)OR$^5$ or heterocyclylalkyl (optionally substituted by alkyl, aryl, aralkyl, halo, haloalkyl, —OR$^5$, —C(O)OR$^5$, —N(R$^5$)R$^6$ or —C(O)N(R$^5$)R$^6$). They are prepared as described below in Reaction Scheme 6 wherein A is =CH— or =N—; R$^{1a}$, R$^{2a}$, R$^4$, R$^5$, and R$^{5a}$ are as described above in Reaction Scheme 1; and R$^{15b}$ is as described above; and Z is either oxygen or sulfur:

Reaction Scheme 6

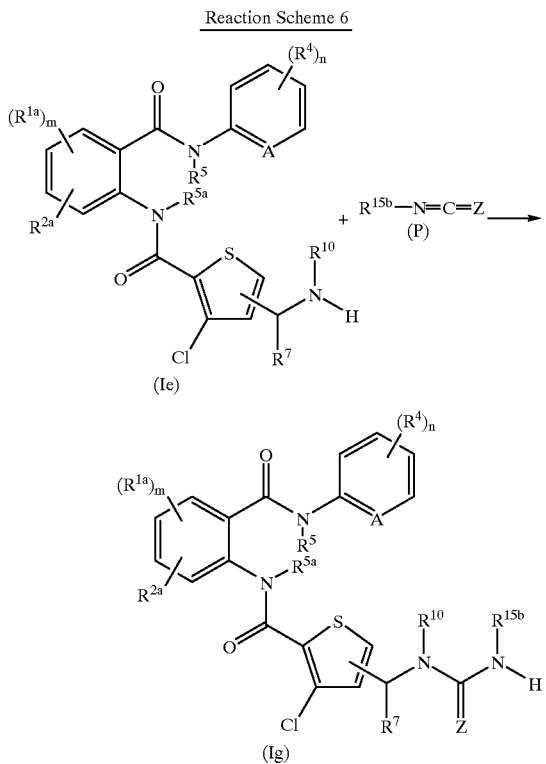

Compounds of formula (P) are commercially available, or may be prepared according to methods known to those skilled in the art. The compounds of formula (Ie) are compounds of formula (Ia) where R$^{14a}$ is —N(R$^{10}$)R$^{11}$ and are prepared by methods disclosed herein.

In general, compounds of formula (Ig) are prepared by treating a compound of formula (Ie) in an aprotic solvent, such as dioxane, with a compound of formula (P). The reaction mixture is stirred at ambient temperature for about 8 to about 20 hours, preferably for about 16 hours. The compound of formula (Ig) is isolated from the reaction mixture by standard isolation techniques, such as concentration of product and purification by flash chromatography.

Alternatively, to produce compounds of formula (Ig) where R$^{15b}$ is hydrogen, compounds of formula (Ie) may be reacted with potassium isocyanate (K—N=C=O). Alternatively, compounds of formula (Ie) may be reacted first with phosgene or equivalent, followed by reacting the resulting product with a disubstituted amine or a cyclic amine to form compounds of the invention where R$^{14}$ is —C(R$^7$)H—N(R$^{10}$)R$^{11}$ where R$^{10}$ is as described above for the compounds of formula (Ig) and R$^{11}$ is —C(O)—N(R$^5$)R$^{15}$ where R$^5$ and R$^{15}$ are independently alkyl, aryl or aralkyl, or R$^5$ and R$^{15}$ together with the nitrogen to which they are attached form a N-heterocyclic ring as defined in the Summary of the Invention for compounds of formula (I).

Compounds of formula (Ig) where R$^{15b}$ is hydrogen can be further reacted with a halocetaldehyde dialkylacetal in the presence of a protic solvent, preferably an alkanol, to form compounds of the invention where R$^{14}$ is —C(R$^7$)H—N(R$^{10}$)R$^{11}$ where R$^7$ is hydrogen or alkyl, and R$^{10}$ is as described above for the Reaction Scheme and R$^{11}$ is an oxazol-2-yl substituent.

G. Preparation of Compounds of Formula (Ih) and (Ij)

Compounds of formula (Ih) and (Ij) are compounds of the invention where R$^{14}$ is —C(R$^7$)H—N(R$^{10}$)R$^{11}$ where R$^7$ is hydrogen or alkyl, R$^{10}$ is hydrogen, alkyl, aryl or aralkyl, and R$^{11}$ is —C(O)—R$^{15}$ where R$^{15}$ is —R$^8$—OR$^5$, —R$^8$—N(R$^5$)R$^6$ or heterocyclylalkyl (optionally substituted by alkyl, aryl, aralkyl, halo, haloalkyl, —OR$^5$, —C(O)OR$^5$, —N(R$^5$)R$^6$ or —C(O)N(R$^5$)R$^6$ (where R$^5$ and R$^6$ are as described above in the Summary of the Invention for compounds of formula (I))). These compounds are prepared as described below where A is =CH— or =N—; R$^{1a}$, R$^{2a}$, R$^4$, R$^5$, R$^{5a}$ are as described above in Reaction Scheme 1; and R$^7$ and R$^8$ are as described in the Summary of the Invention for compounds of formula (I); and R$^{15c}$ is —OR$^5$, —N(R$^5$)R$^6$ or heterocyclyl (optionally substituted by alkyl, aryl, aralkyl, halo, haloalkyl, —OR$^5$, —C(O)OR$^5$, —N(R$^5$)R$^6$ or —C(O)N(R$^5$)R$^6$ (where R$^5$ and R$^6$ are as described above in the Summary of the Invention for compounds of formula (I))), for example, 4-methylpiperidine; and each X is independently bromo or chloro:

Reaction Scheme 7

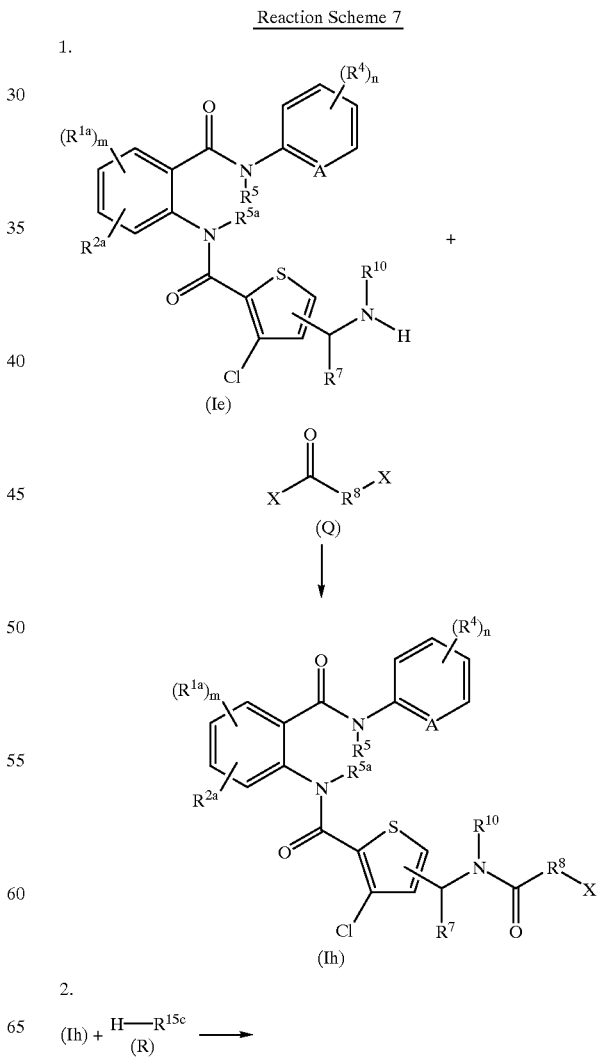

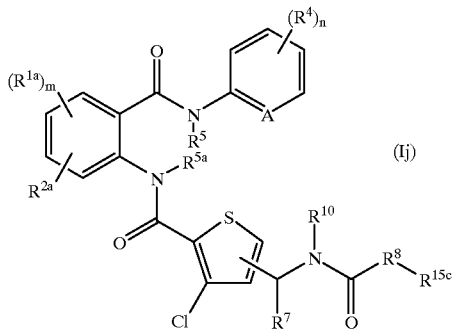

(Ij)

Compounds of formula (Q) and formula (R) are commercially available or may be prepared by methods known to those skilled in the art.

In general, the compounds of formula (Ij) are prepared by first treating a compound of formula (Ie) in an aprotic solvent, such as methylene chloride, in the presence of a base, such as diisopropylethylamine, at temperatures of between about −10° C. and about 10° C., preferably at about 0° C., with a compound of formula (Q). The reaction mixture was allowed to warm to ambient temperature and stirred for about 4 to about 10 hours, preferably for about 7 hours. A compound of formula (R) is then added to the reaction mixture and the resulting reaction mixture is stirred about 10 to about 20 hours, preferably for about 16 hours. The compound of formula (Ij) is isolated from the reaction mixture by standard isolation techniques, such as concentration and purification by HPLC.

Alternatively, the compound of formula (Q) could be phosgene (Cl—C(O)—Cl). Under these circumstances, the final product would have the $R^{15c}$ substituent directly attached to the carbonyl in the compound of formula (Ij). Alternatively, the compound of formula (Q) could also be X—S(O)$_2$—$R^8$—X to produce compounds of the invention where $R^{14}$ is —C($R^7$)H—N($R^{10}$)$R^{11}$ where $R^{10}$ is as described above for compounds of formula (Ij) and $R^{11}$ is —S(O)$_2$—$R^{15}$ where $R^{15}$ is as described above for $R^{15}$.

H. Preparation of Compounds of Formula (Ik)

Compounds of formula (Ik) are compounds of the invention where $R^{14}$ is —C($R^7$)H—N($R^{10}$)—C(N$R^{17}$)—N($R^5$)$R^6$ where each $R^5$ is as described in the Summary of the Invention for compounds of formula (I), where $R^6$ and $R^7$ are as described in the Summary of the Invention for compounds of formula (I), $R^{10}$ is hydrogen, alkyl, aryl or aralkyl, and $R^{17}$ is hydrogen, alkyl, aryl or aralkyl. They are prepared as illustrated below in Reaction Scheme 8 where A is =CH— or =N—; $R^{1a}$, $R^{2a}$, $R^4$, $R^5$ and $R^{5a}$ are as described above in Reaction Scheme 1; $R^6$ and $R^7$ are as described in the Summary of the Invention for compounds of formula (I); $R^{10}$ is hydrogen, alkyl, aryl or aralkyl; $R^{17}$ is hydrogen, alkyl, aryl or aralkyl; and X is bromo or chloro, or X can also be other leaving groups such as alkylthio (methylthio) or pyrazolyl:

Reaction Scheme 8

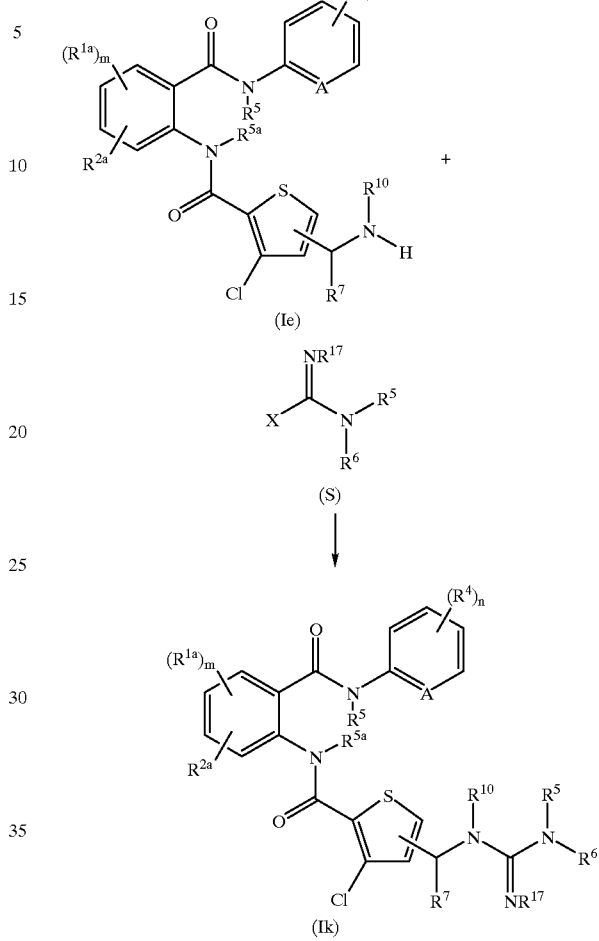

Compounds of formula (S) are commercially available, or may be prepared according to methods known to those skilled in the art.

In general, compounds of formula (Ik) are prepared by treating a compound of formula (Ie) in an aprotic solvent, such as DMF, in the presence of a base, such as triethylamine, with a compound of formula (S). The reaction mixture is stirred at ambient temperature to about 50° C., preferably at about 45° C., for about 2 to about 4 hours, preferably for about 3 hours. The reaction mixture is allowed to cool to ambient temperature and acidified, preferably with trifluoroacetic acid. The compound of formula (Ik) is isolated from the reaction mixture by standard isolation techniques, such as purification by HPLC.

I. Preparation of Compounds of Formula (Im)

Compounds of formula (Im) are compounds of the invention where $R^{14}$ is —C($R^7$)H—N($R^{10}$)—C(N$R^{17}$)—$R^{10}$ where $R^7$ is as described in the Summary of the Invention for compounds of formula (I) and each $R^{10}$ and $R^{17}$ are independently hydrogen, alkyl, aryl or aralkyl. They are prepared as illustrated below in Reaction Scheme 9 where A is =CH— or =N—; $R^{1a}$, $R^{2a}$, $R^4$, each $R^5$ and $R^{5a}$ are as described above in Reaction Scheme 1; $R^7$ is as described in the Summary of the Invention for compounds of formula (I); $R^{10}$ and $R^{17}$ are each independently hydrogen, alkyl, aryl or aralkyl; and $R^{20}$ is alkyl:

Reaction Scheme 9

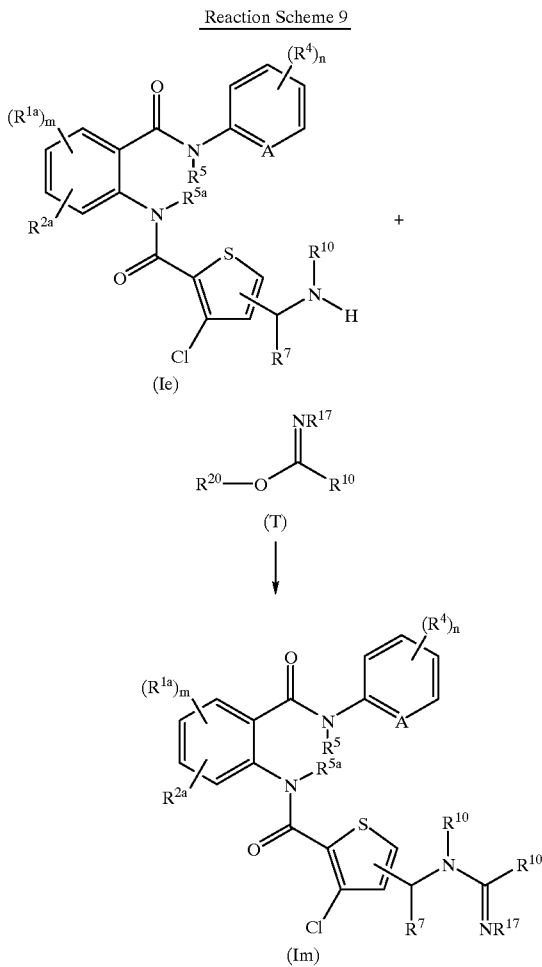

Reaction Scheme 10

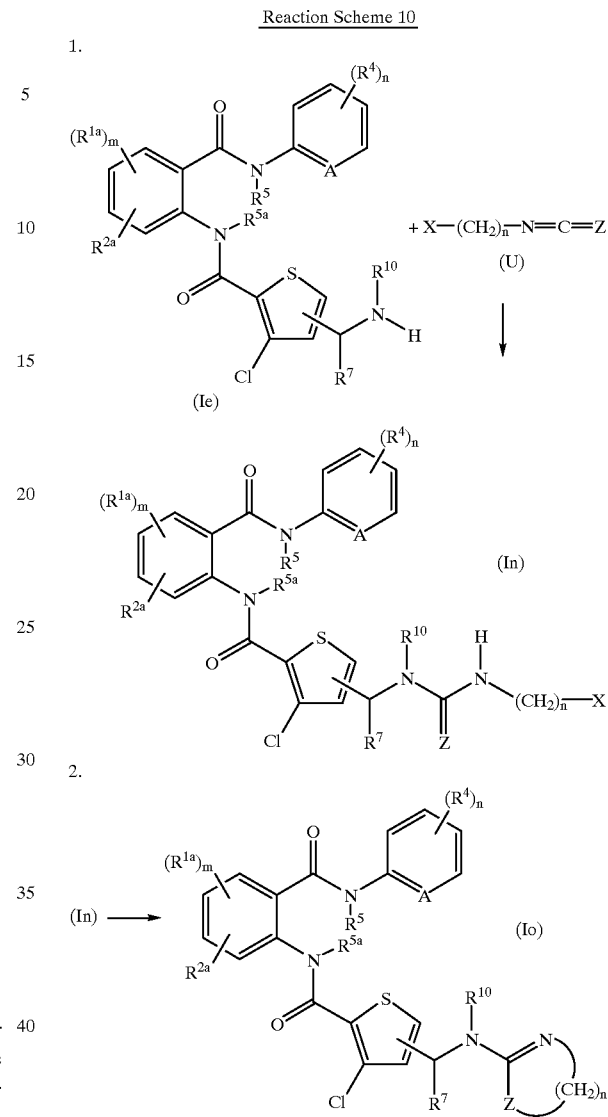

Compounds of formula (T) are commercially available or may be prepared according to methods known to those skilled in the art, or by methods described herein. Compounds of formula (Ie) are prepared herein.

In general, compounds of formula (Im) are prepared by treating a compound of formula (Ie) in a protic solvent, such as methanol, with a compound of formula (T). The reaction mixture is stirred at ambient temperature for about 8 to about 20 hours, preferably for about 16 hours. The compound of formula (Im) is then isolated from the reaction mixture by standard isolation techniques, such as concentration and purification by HPLC.

J. Preparation of Compounds of Formula (In) and (Io)

Compounds of formula (In) are compounds of the invention where $R^{14}$ is —C($R^7$)H—N($R^{10}$)$R^{11}$ where $R^7$ is hydrogen or alkyl, $R^{10}$ is hydrogen, alkyl, aryl or aralkyl and $R^{11}$ is —C(O)—N($R^5$)$R^{15}$ or —C(S)—N($R^5$)$R^{15}$; and compounds of formula (Io) are compounds of the invention where $R^{14}$ is —C($R^7$)H—N($R^{10}$)$R^{11}$ where $R^7$ is hydrogen or alkyl and $R^{10}$ is hydrogen, alkyl, aryl or aralkyl, and $R^{11}$ is heterocyclyl (optionally substituted by alkyl or oxo). They are prepared as illustrated below where A is =CH— or =N—; $R^{1a}$, $R^{2a}$, $R^4$, each $R^5$ and $R^{5a}$ are as described above in Reaction Scheme 1; $R^7$ is as described in the Summary of the Invention for compounds of formula (I); $R^{10}$ is hydrogen, alkyl, aryl or aralkyl; Z is oxygen or sulfur; n is 2 or 3; and X is bromo or chloro:

Compounds of formula (U) are commercially available or may be prepared according to methods known to those skilled in the art. Compounds of formula (Ie) are prepared herein.

In general, compounds of formula (Io) are prepared by first treating a compound of formula (Ie) in an aprotic solvent, such as tetrahydrofuran, at temperatures of about −10° C. to about 10° C., preferably at about 0° C., with an excess molar amount of a compound of formula (U). The reaction mixture is stirred at ambient temperature for about 4 to 10 hours, preferably for about 7 hours to form a compound of formula (In). The reaction mixture is cooled to a temperature of about −10° C. to about 10° C., preferably to about 0° C., and a mild base, preferably triethylamine, is added to the reaction mixture. The resulting reaction mixture is then warmed to ambient temperature and stirred for about 20 to 30 hours, preferably for about 24 hours. The compound of formula (Io) is then isolated from the reaction mixture by standard isolation techniques, such as concentration of volatiles and purification by flash chromatography.

Other compounds of formula (U) may be used to produce compounds of formula (Io) wherein the heterocyclyl ring so formed is substituted by alkyl or by oxo. For example, if the nitrogen of the isocyanate is substituted by a branched alkyl with the terminal halo atom being 2 to 3 carbons away from the nitrogen, the compound so formed would have an alkyl substituent off the heterocyclic ring in the compound of formula (Io). Also, if the nitrogen is substituted by —C(O)—$R^{17}$ where $R^{17}$ is a haloalkyl (where the halo is on the terminal carbon of the haloalkyl group), one would end up with a heterocyclic ring with an oxo substituent next to the nitrogen atom of the heterocyclic.

K. Preparation of Compounds of Formula (Z)

Compounds of formula (Z) are intermediates in the preparation of the compounds of the invention and are prepared as illustrated below where $R^{5a}$ is alkyl, $R^7$ is hydrogen or alkyl, $R^{13a}$ hydrogen, halo, —$OR^5$ (where $R^5$ is alkyl, aryl or aralkyl); and $R^{14a}$ is as described above in Reaction Scheme 1; and each X is bromo or chloro:

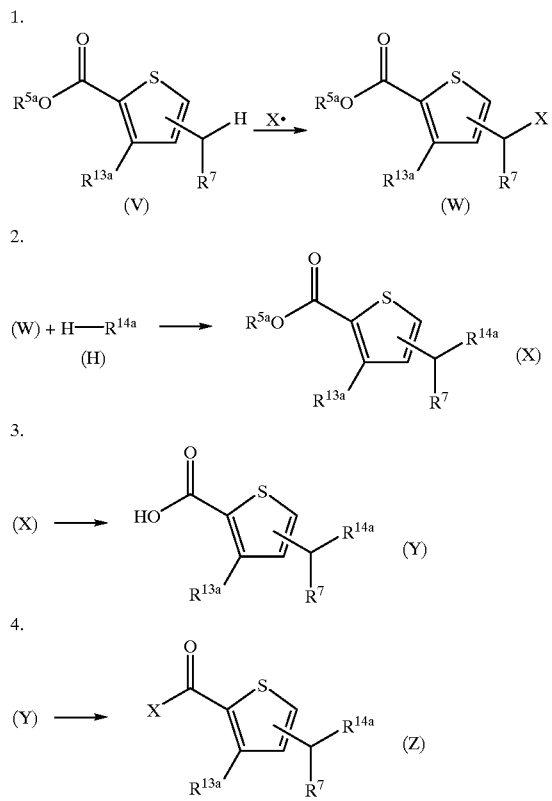

Compounds of formula (V) and formula (H) are commercially available or may be prepared according to methods known to those skilled in the art or methods disclosed herein.

In general, compounds of formula (Z) are prepared by first reacting a compound of formula (V) in an aprotic solvent, such as carbon tetrachloride, with a halogenating agent, such as sulfuryl chloride, in the presence of a catalytic agent, such as benzoyl peroxide. The reaction mixture is heated at reflux for about 12 to about 20 hours, preferably for about 17 hours, then cooled to ambient temperature. The compound of formula (W) is then isolated from the reaction mixture by standard isolation techniques, such as concentration of volatiles and purification by flash chromatography.

The compound of formula (W) in an aprotic solvent, such as methylene chloride, is then treated with a compound of formula (H). The resulting reaction mixture is then stirred at ambient temperature for about 10 to about 20 hours, preferably for about 16 hours. The compound of formula (X) is then isolated from the reaction mixture by standard isolation techniques, such as concentration of the product and purification by flash chromatography.

The compound of formula (X) in a protic solvent, such as ethanol, is then hydrolyzed under basic hydrolysis conditions (for example, by the addition of a strong base, such as sodium hydroxide) at ambient temperature. The compound of formula (Y) is then isolated from the reaction mixture by standard isolation techniques, such as concentration of volatiles, dissolution of product in water, acidification of the aqueous solution with a strong acid and filtration.

The compound of formula (Y) is then converted to a compound of formula (Z) by standard techniques.

Alternatively, the compound of formula (Y) can be isolated as the metal salt and then converted as is to a compound of formula (Z) by standard techniques.

Compounds of formula (Z) may be then be reacted with compounds of formula (E) to prepare compounds of the invention as described above in Reaction Scheme 1.

L. Preparation of Compounds of Formula (Iq)

Compounds of formula (Iq) are compounds of the invention wherein $R^2$ is —O—$R^8$—N($R^{10}$)$R^{11}$ where $R^8$ is as defined in the Summary of the Invention for compounds of formula (I) and $R^{10}$ and $R^{11}$ are as defined in the Summary of the Invention for compounds of formula (I) except that neither can be —$OR^5$, —S(O)$_2$—$R^{15}$, —C(O)—$R^{15}$, —C(O)—N($R^5$)$R^{15}$ or —C(S)—N($R^5$)$R^{15}$. They are prepared as illustrated below in Reaction Scheme 12 where A is =CH— or =N—; $R^{1a}$, $R^4$ and $R^{14}$ are as described in the Summary of the Invention for compounds of formula (I) except that none can be hydroxy, amino, carboxy or contain a nucleophilic amine; and $R^5$ and $R^8$ are as described in the Summary of the Invention for compounds of formula (I); and $R^{2b}$ is —N($R^{10}$)$R^{11}$ where $R^{10}$ and $R^{11}$ are as defined above; and $R^{13}$ is as described in the Summary of the Invention for compounds of formula (I) except that $R^{13}$ can not be haloalkyl where the alkyl is substituted by only one halogen atom or $R^{13}$ can not contain a nucleophilic nitrogen, and each X is bromo or chloro:

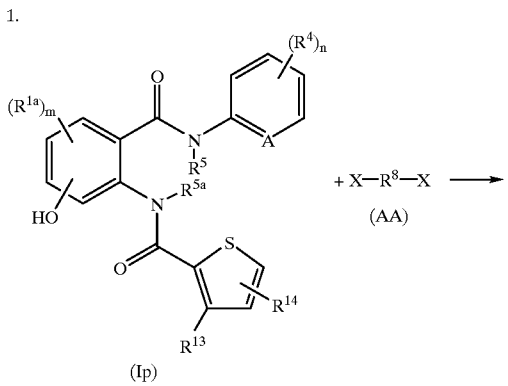

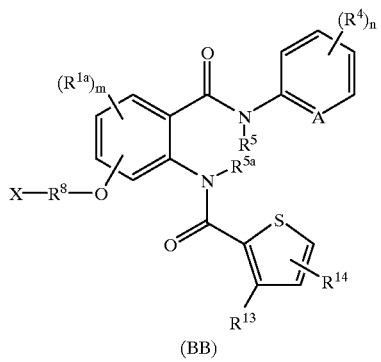

(BB)

2.

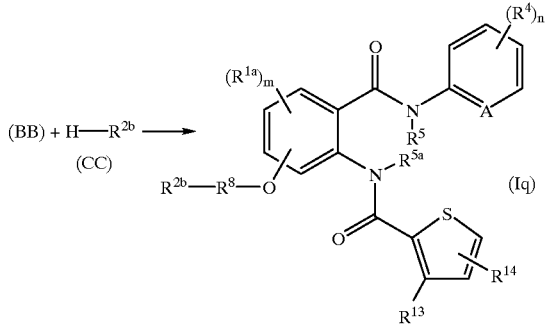

Compounds of formula (AA) and (CC) are commercially available. Compounds of formula (Ip) are prepared by methods disclosed herein.

In general, compounds of formula (Iq) are prepared by treating a compound of formula (Ip) in an aprotic solvent, such as DMF, in the presence of a base, such as cesium carbonate, with a compound of formula (AA). The reaction mixture is stirred at ambient temperature for about 16 to about 20 hours to make the compound of formula (BB). A compound of formula (CC) is added to the reaction mixture and the resulting reaction mixture is heated to temperatures of between about 60° C. and 70° C., preferably to about 65° C. The reaction mixture is maintained at that temperature for about 10 to about 14 hours, preferably for about 12 hours. The reaction mixture is then cooled to ambient temperature and the compound of formula (Iq) is isolated from the reaction mixture by standard isolation techniques, such as filtration and purification by HPLC.

When the compound of formula (CC) is a non-reactive amine, the anion of the amine may be prepared prior to reacting with the compound of formula (BB) to form the compound of formula (Iq). Such non-reactive amines include, but are not limited to, imidazole, tetrazole, and pyrazole.

M. Preparation of Compounds of Formula (Ir)

Compounds of formula (Ir) are compounds of the invention wherein $R^2$ is —O—$R^8$—S(O)$_p$—$R^9$ (where p is 0 to 2), —O$R^9$, —O—($R^8$—O)$_t$—$R^5$ (where t is 1 to 6), —O—$R^8$—C(O)O$R^5$, —O—$R^8$—N($R^{10}$)$R^{11}$, —O—C(O)—$R^5$ where each $R^5$, $R^9$ and $R^8$ are as defined above in the Summary of the Invention for compounds of formula (I); and $R^{10}$ and $R^{11}$ are as defined above in the Summary of the Invention for compounds of formula (I). They are prepared as illustrated below in Reaction Scheme 13 where A is =CH— or =N—; $R^{1a}$, $R^4$ and $R^{14}$ are as described in the Summary of the Invention for compounds of formula (I) except that none can be hydroxy, amino, carboxy or contain a nucleophilic amine; and $R^5$ and $R^8$ are as defined in the Summary of the Invention for compounds of formula (I), and $R^{13}$ is as described in the Summary of the Invention for compounds of formula (I) except that $R^{13}$ can not be haloalkyl where the alkyl is substituted by only one halogen atom or $R^{13}$ can not contain a nucleophilic nitrogen, and $R^{2c}$ is —$R^8$—S(O)$_p$—$R^9$ (where p is 0 to 2), —$R^5$, —($R^8$—O)$_t$—$R^5$ (where t is 1 to 6), —$R^8$—C(O)O$R^5$, —$R^8$—N($R^{10}$)$R^{11}$, —C(O)—$R^9$ where each $R^5$, $R^8$, $R^9$, $R^{10}$ and $R^{11}$ are as defined above; and X is chloro or bromo:

Reaction Scheme 13

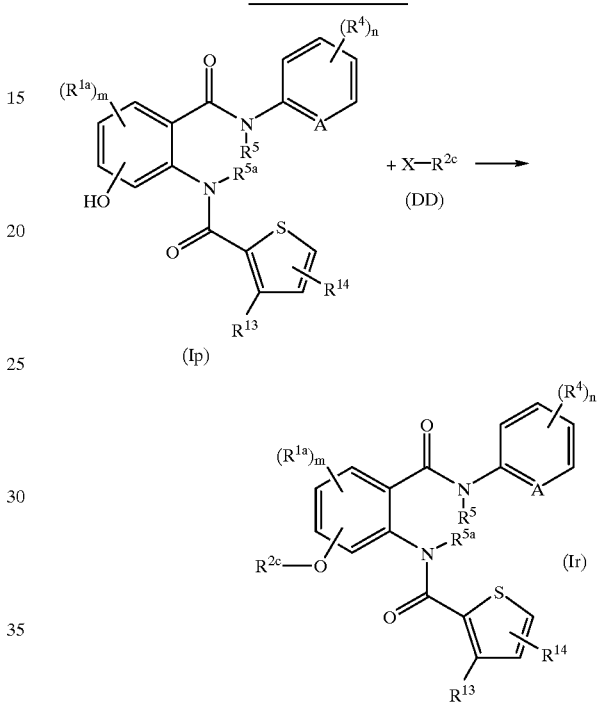

Compounds of formula (DD) are commercially available or may be prepared according to methods known to those of ordinary skill in the art. Compounds of formula (Ip) are prepared herein.

In general, compounds of formula (Ir) are prepared by treating a compound of formula (Ip) in an aprotic solvent, such as DMF, in the presence of a strong base, such as sodium hydride, at ambient temperature with a compound of formula (DD). The reaction mixture is stirred for about 1 hour to about 4 hours, preferably for about 3 hours, and then cooled to temperatures of between about -10° C. and 10° C., preferably to 0° C. The reaction mixture is then acidified with a mild acid, such as trifluoroacetic acid. The compound of formula (Ir) is then isolated from the reaction mixture by standard isolation techniques, such as purification by HPLC.

Alternatively, compounds of formula (Ir) may be prepared by treating a compound of formula (Ip) in an aprotic solvent, such as DMF, in the presence of a strong base, such as cesium carbonate, at ambient temperature with a compound of formula (DD). The reaction mixture is then heated to between about 50° C. and about 65° C., preferably to about 60° C. and stirred at that temperature for about 10 to about 20 hours, preferably for about 16 hours. The reaction mixture is then allowed to cool to ambient temperature and filtered. The resulting filtrate is then acidified by a mild acid, such as trifluoroacetic acid, and the compound of formula (Ir) is isolated from the reaction mixture by standard isolation techniques, such as purification by HPLC.

N. Preparation of Compounds of Formula (Is)

Compounds of formula (Is) are compounds of the invention wherein $R^2$ is —O—$R^8$—CH(OH)—$CH_2$—N($R^{10}$)$R^{11}$ where $R^{10}$ and $R^{11}$ are as defined above in the Summary of the Invention for compounds of formula (I) except that neither can be —$OR^5$, —S(O)$_2$—$R^{15}$, —C(O)—$R^{15}$, —C(O)—N($R^5$)$R^{15}$ or —C(S)—N($R^5$)$R^{15}$. They are prepared as illustrated below in Reaction Scheme 14 where A is =CH— or =N—; $R^{1a}$, $R^4$ and $R^{14}$ are as described in the Summary of the Invention for compounds of formula (I) except that none can be hydroxy, amino, carboxy or contain a nucleophilic amine; and $R^5$ and $R^8$ are as described in the Summary of the Invention for compounds of formula (I); and $R^{2b}$ is —N($R^{10}$)$R^{11}$ where $R^{10}$ and $R^{11}$ are as defined above; and $R^{13}$ is as described in the Summary of the Invention for compounds of formula (I) except that $R^{13}$ can not be haloalkyl where the alkyl is substituted by only one halogen atom or $R^{13}$ can not contain a nucleophilic nitrogen; and each X is bromo or chloro:

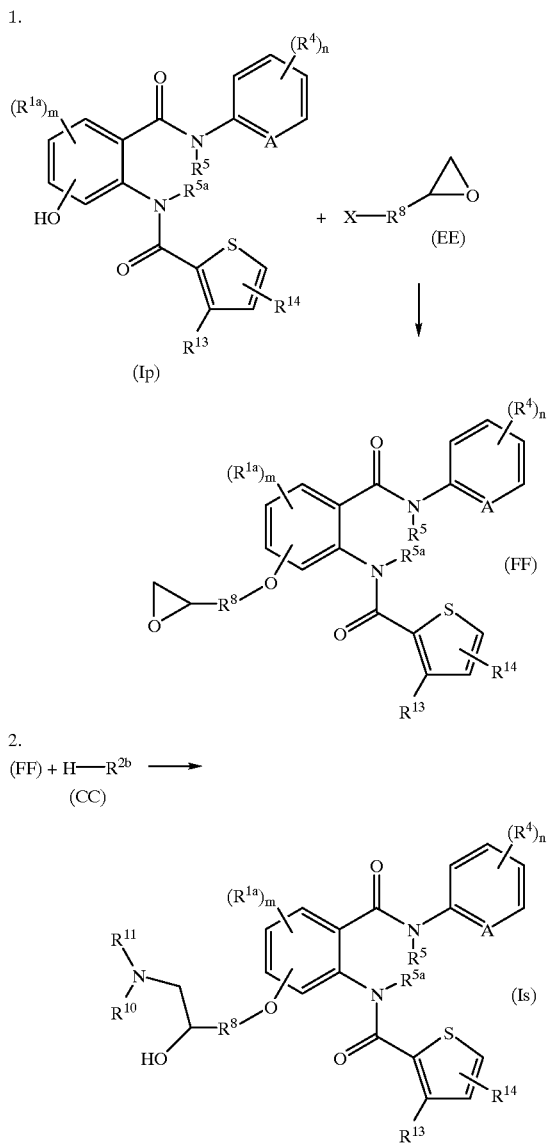

Compounds of formula (EE) and (CC) are commercially available or may be prepared according to methods known to those skilled in the art. Compounds of formula (Ip) are prepared herein.

In general, compounds of formula (Is) are prepared by first treating a compound of formula (Ip) in an aprotic solvent, such as DMF, with a compound of formula (EE) in the presence of strong base, such as cesium carbonate. The reaction mixture is stirred at ambient temperature for about 3 days. The compound of formula (FF) is then isolated from the reaction mixture by standard isolation techniques such as filtration and concentration.

The compound of formula (FF) in an aprotic solvent, preferably DMF, is then treated with salt of a compound of formula (CC). The reaction mixture is stirred at ambient temperature for about 16 to about 20 hours, preferably for about 18 hours. The compound of formula (Is) is then isolated from the reaction mixture by standard isolation techniques, such as concentration of volatiles and purification by HPLC.

O. Preparation of Compounds of Formula (It)

Compounds of formula (It) are compounds of the invention wherein $R^2$ is —O—$R^8$—CH(OH)—$CH_2$—$OR^5$ where $R^5$ and $R^8$ are as defined in the Summary of the Invention for compounds of formula (I). They are prepared as illustrated in the following Reaction Scheme 15 where A is =CH— or =N—; $R^{1a}$, $R^4$ and $R^{14}$ are as described in the Summary of the Invention for compounds of formula (I) except that none can be hydroxy, amino, carboxy or contain a nucleophilic amine; and $R^5$, and $R^8$ are as described in the Summary of the Invention for compounds of formula (I); and $R^{13}$ is as described in the Summary of the Invention for compounds of formula (I) except that $R^{13}$ can not be haloalkyl where the alkyl is substituted by only one halogen atom or $R^{13}$ can not contain a nucleophilic nitrogen; and each X is bromo or chloro:

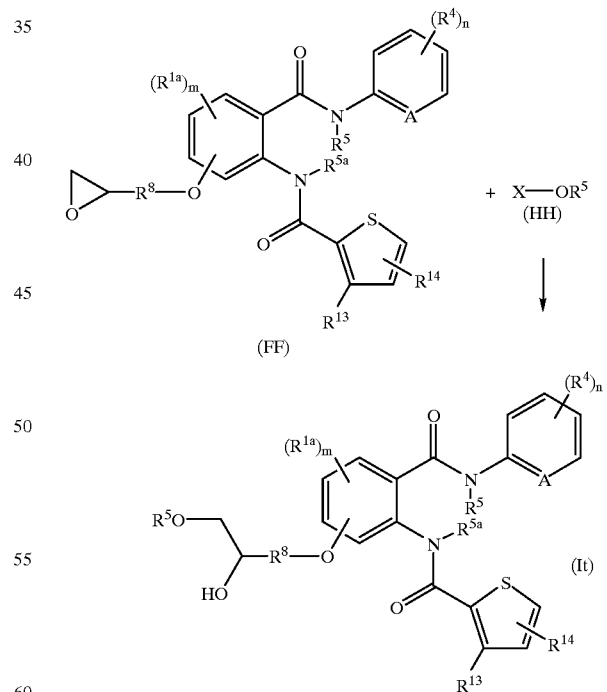

Compounds of formula (FF) are prepared herein. Compounds of formula (HH) are commercially available or may be prepared according to methods known to those skilled in the art.

In general, compounds of formula (It) are prepared by treating a compound of formula (FF) in an aprotic solvent, such as methylene chloride, with an excess amount of a compound of formula (HH) in the presence of an oxidant, such as dichlorodicyanobenzoquinone. The reaction mixture is stirred at ambient temperature for about 24 to about 48 hours, preferably for about 48 hours. The reaction is then quenched with the addition of a mild base, such as aqueous sodium bicarbonate. The compound of formula (It) is isolated from the reaction mixture by standard isolation techniques, such as extraction, concentration of volatiles and purification by flash chromatography.

P. Preparation of Compounds of Formula (Iv)

Compounds of formula (Iv) are compounds of the invention wherein the $R^2$ substituent is in the 4-position and is —S—$R^9$, —N($R^{10}$)$R^{11}$, —N($R^5$)—$R^8$—N($R^{10}$)$R^{11}$, —S—$R^8$—N($R^5$)$R^6$, —S—$R^8$—C(O)O$R^5$, or —N($R^5$)—CH($R^{12}$)—C(O)O$R^5$ (where $R^5$, $R^6$, $R^8$, $R^9$ and $R^{12}$ are as defined in the Summary of the Invention for compounds of formula (I) and $R^{10}$ and $R^{11}$ are as defined in the Summary of the Invention for compounds of formula (I) except that neither can be —O$R^5$, —S(O)$_2$—$R^{15}$, —C(O)—$R^{15}$, —C(O)N($R^5$)$R^{15}$ or —C(S)—N($R^5$)$R^{15}$ when $R^2$ is —N($R^{10}$)$R^{11}$). They are prepared as illustrated below in Reaction Scheme 16 wherein $R^{1a}$ is halo; and $R^4$ and $R^{14}$ are as described in the Summary of the Invention for compounds of formula (I) except that neither can contain a nucleophilic amine; and $R^5$ is as described in the Summary of the Invention for compounds of formula (I); and $R^{13}$ is as described in the Summary of the Invention for compounds of formula (I) except that $R^{13}$ can not be haloalkyl where the alkyl is substituted by only one halogen atom or $R^{13}$ can not contain a nucleophilic nitrogen; and $R^{2d}$ is —S—$R^9$, —N($R^{10}$)$R^{11}$, —N($R^5$)—$R^8$—N($R^{10}$)$R^{11}$, —S—$R^8$—N($R^5$)$R^6$, —S—$R^8$—C(O)O$R^5$, or —N($R^5$)—CH($R^{12}$)—C(O)O$R^5$ (where $R^5$, $R^6$, $R^8$, $R^9$, $R^{10}$, $R^{11}$ and $R^{12}$ are as defined above for $R^2$):

Reaction Scheme 16

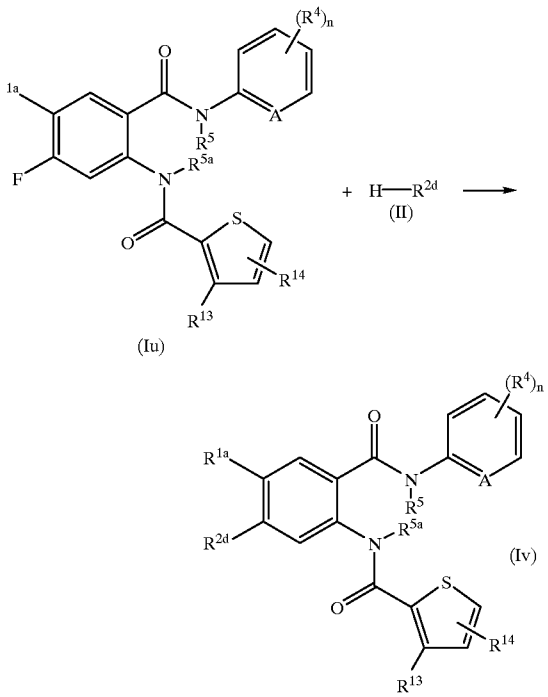

Compounds of formula (II) are commercially available, or may be prepared according to methods known to those skilled in the art. Compounds of formula (Iu) may be prepared according to methods disclosed herein.

In general, compounds of formula (Iv) are prepared by treating a compound of formula (Iu) with a compound of formula (II) in the presence of a base. The reaction mixture is heated to temperatures of between about 80° C. and about 105° C., preferably at about 85° C., for about 10 to about 20 hours, preferably for about 15 hours. The compound of formula (Iv) is then isolated from the reaction mixture by standard isolation techniques, such as concentration and purification by HPLC.

Q. Preparation of Compounds of Formula (Ip)

Compounds of formula (Ip) are compounds of the invention wherein $R^2$ is hydroxy. These compounds are prepared as illustrated below where A is =CH— or =N—; and $R^1$, $R^4$, $R^5$, $R^{13}$, $R^{14}$, m and n are as defined above in the Summary of the Invention for compounds of formula (I):

Reaction Scheme 17

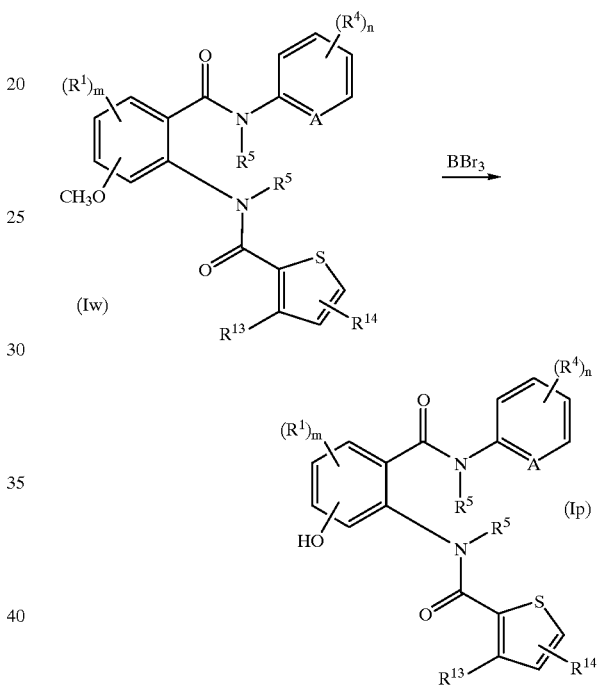

Compounds of formula (Iw) are compounds of the invention which are prepared by the methods disclosed herein.

In general, compounds of formula (Ip) are prepared by treating a compound of formula (Iw) in an aprotic solvent, such as methylene chloride, with boron tribromide at ambient temperature. The reaction mixture is stirred for about 10 to about 20 hours, preferably for about 18 hours. The compound of formula (Ip) is then isolated from the reaction mixture by standard isolation techniques, such as extraction and concentration.

During this reaction, if any of the other substituents, such as $R^1$, $R^4$, etc., contain an ester group or a lower alkyl ether group, the ester group will also be hydrolyzed to the corresponding acid and the ether group will be hydrolyzed to the corresponding alcohol.

R. Preparation of Compounds of Formula (Eb)

Compounds of formula (Eb) are compounds of formula (E) wherein $R^{1a}$ is in the 5-position and is halo. These compounds, which are intermediates in the preparation of the compounds of the invention, may be prepared as illustrated below in Reaction Scheme 18 where A is =CH— or =N—; $R^2$, $R^4$, and $R^5$ are as described above in the Summary of the Invention for compounds of formula (I); and $R^{5a}$ is hydrogen, and X is chloro or bromo:

Reaction Scheme 18

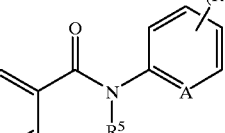

Compounds of formula (Ea) are prepared by methods disclosed herein.

In general; compounds of formula (Eb) are prepared by treating a compound of Ea in an organic solvent, such as benzene, with a halogenating agent. The reaction mixture is heated to temperatures of about 45° C. to about 55° C., preferably to about 50° C. to about 55° C. The reaction mixture is allowed to cool to ambient temperature and the compound of formula (Eb) is then isolated from the reaction mixture by standard isolation techniques, such as concentration, extraction and recrystallization.

S. Preparation of Compounds of Formula (Db)

Compounds of formula (Db) are compounds of formula (D) where the $R^{1a}$ substituent is in the 5-position and is chloro and $R^2$ is in the 3-position and is —$N(R^{10})R^{11}$, —$N(R^5)$—$R^8$—$N(R^{10})R^{11}$, —$N(R^5)$—$CH(R^{12})$—$C(O)OR^5$ (where $R^5$, $R^8$, $R^{10}$, $R^{11}$ and $R^{12}$ are as defined in the Summary of the Invention for compounds of formula (I) except that $R^{10}$ and $R^{11}$ can not be —$S(O)_2$—$R^{15}$, —$C(O)$—$R^{15}$, —$C(O)N(R^5)R^{15}$ or —$C(S)N(R^5)R^{15}$ when $R^2$ is —$N(R^{10})R^{11}$). These compounds, which are intermediates in the preparation of the compounds of the invention, are prepared as illustrated below in Reaction Scheme 19 where A is =CH— or =N—; $R^4$ and $R^5$ are as described in the Summary of the Invention for compounds of formula (I); and $R^{2e}$ is —$N(R^{10})R^{11}$, —$N(R^5)$—$R^8$—$N(R^{10})R^{11}$, or —$N(R^5)$—$CH(R^{12})$—$C(O)OR^5$ (where $R^5$, $R^8$, $R^{10}$, $R^{11}$, and $R^{12}$ are as defined above for $R^2$):

Reaction Scheme 19

Compounds of formula (Da) are prepared by methods described herein. Compound of formula (JJ) are commercially available or may be prepared according to methods known to those skilled in the art.

In general, compounds of formula (Db) are prepared by treating a compound of formula (Da) in a polar aprotic solvent, such as DMSO, with a compound of formula (JJ) in the presence of a base, such as diisopropylethylamine. The reaction mixture is heated to temperatures of between about 100° C. to about 120° C., preferably to about 110° C. to about 120° C. and maintained at that temperature for about 3 to about 5 hours, preferably for about 4 hours. The reaction mixture is then cooled to ambient temperature and the compound of formula (Db) is isolated from the reaction mixture by standard isolation techniques such as extraction, concentration and purification by flash chromatography.

T. Preparation of Compounds of Formula (Ec)

Compounds of formula (Ec) are compounds of formula (E) where $R^{1a}$ is hydrogen. These compounds, which are intermediates in the preparation of the compounds of the invention, may be prepared as illustrated below in Reaction Scheme 20 where A is =CH— or =N—; $R^{1a}$ is hydrogen, alkyl, aryl, aralkyl, halo, cyano, —$OR^5$, —$S(O)_p$—$R^9$ (where p is 0 to 2), —$C(O)OR^5$, —$C(O)$—$N(R^5)R^6$ and —$N(R^5)R^6$ (where each $R^5$ and $R^6$ can not be hydrogen and $R^9$ is alkyl, aryl, or aralkyl); and $R^{2a}$ is as defined above in Reaction Scheme 1, and $R^4$ and $R^5$ are as defined above in the Summary of the Invention for compounds of formula (I):

Reaction Scheme 20

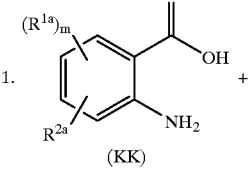

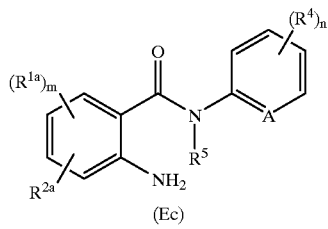

(Ec)

Compounds of formula (KK) and formula (C) and phosgene are commercially available or may be prepared according to methods known to those skilled in the art.

In general, compounds of formula (Ec) are prepared by first treating a compound of formual (KK) with phosgene in an aprotic solvent, such as dioxane. The reaction mixture is stirred at ambient temperature to about 70° C., preferably at about 65° C., for about 8 to about 12 hours, preferably for about 10 hours. The reaction mixture is cooled to ambient temperature and the compound of formula (LL) is then isolated from the reaction mixture by standard isolation techniques, such as filtration and evaporation of solvents.

The compound of formula (LL) in a polar aprotic solvent, such as dioxane, is treated with a compound of formula (C). The reaction mixture is heated at reflux for about 10 to about 20 hours, preferably for about 15 hours. The reaction mixture is allowed to cool to ambient temperature and the compound of formula (Ec) is then isolated from the reaction mixture by standard isolation techniques, such as filtration and concentration.

U. Preparation of Compounds of Formula (F)

Compounds of formula (F) are intermediates used to prepare compounds of the invention and may be prepared as illustrated below in Reaction Scheme 21 wherein each $R^5$ is alkyl, $R^7$ is hydrogen or alkyl; and M is a metal cation and X is bromo or chloro:

Reaction Scheme 21

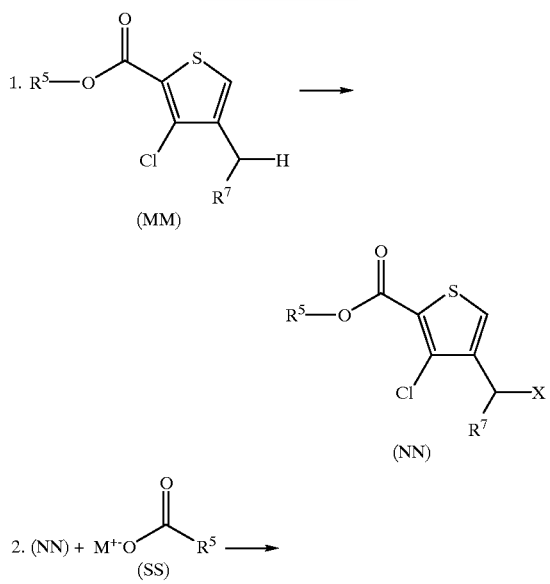

Compounds of formula (MM) are commercially available or may be prepared according to methods disclosed herein or by standard methods known to those of ordinary skill in the art.

In general, compounds of formula (F) are prepared by first treating a compound of formula (MM) in a similar manner as that described herein for the preparation of compounds of formula (W) to prepare a compound of formula (NN).

The compound of formula (NN) in a mild acidic aqueous solution is then treated with a compound of formula (SS). The reaction mixture is heated to reflux for about 20 hours to about 30 hours, preferably for about 24 hours. The reaction mixture is then cooled to ambient temperature and the compound of formula (OO) is then isolated from the reaction mixture by standard isolation techniques, such as concentration and extraction.

The compound of formula (OO) is then hydrolyzed under standard basic conditions to produce the compound of formula (PP). The compound of formula (PP) may be isolated as the metal salt and may be used as such in the next step.

The compound of formula (PP) is then converted to the acid halide by treatment with the appropriate agent, such as thionyl chloride or thionyl bromide. The resulting compound of formula (F) is isolated from the reaction mixture by standard isolation techniques.

V. Preparation of the Compound of Formula (RR)

The compound of formula (RR) is an intermediate in the preparation of compounds of the invention and is prepared as illustrated below in Reaction Scheme 22:

Reaction Scheme 22

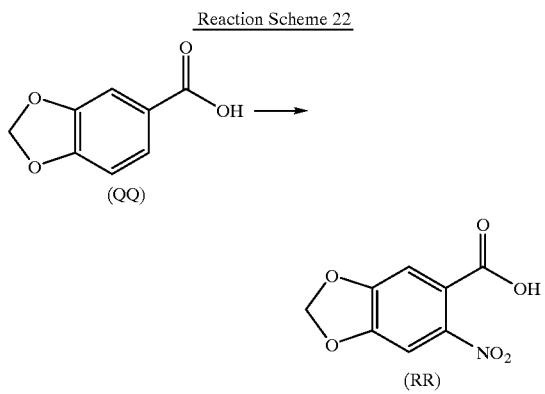

The compound of formula (QQ) is commercially available.

In general, the compound of formula (RR) is prepared by treating the compound of formula (QQ) in the presence of a mild acid, such as trifluoroacetic acid, with nitric acid. The reaction mixture is stirred at temperatures of between about −10° C. and 10° C., preferably at about 0° C., for about 30 minutes to an hour, preferably for about 1 hour. The reaction mixture is warmed to ambient temperature and stirred for about 2 to about 4 hours, preferably for about 3 hours. The compound of formula (RR) is then isolated from the reaction mixture by standard isolation techniques, such as precipitation and filtration.

All compounds of the invention as prepared above which exist in free base or acid form may be converted to their pharmaceutically acceptable salts by treatment with the appropriate inorganic or organic base or acid. Salts of the compounds prepared above may be converted to their free base or acid form by standard techniques.

The following specific preparations and examples are provided as a guide to assist in the practice of the invention, and are not intended as a limitation on the scope of the invention.

PREPARATION 1

Compounds of Formula (B)

A. To a suspension of 5-chloro-2-nitrobenzoic acid (21 g, 100 mmol) in dry methylene chloride (200 mL) at 0° C. were added several drops of DMF, followed by oxalyl chloride (13 mL, 150 mmol). The reaction was warmed to ambient temperature. After 16 hours the solvents were removed and the viscous oil dried in vacuo to afford 23 g (quantitative yield) of 5-chloro-2-nitrobenzoyl chloride; NMR (CDCl$_3$) 8.1 (d, 1), 7.7 (m, 2) ppm.

B. In a similar manner, the following compounds were made:
3,5-dichloro-2-nitrobenzoyl chloride;
5-methyl-2-nitrobenzoyl chloride;
5-(chloro)carbonyl-6-nitro-1,3-benzodioxole;
3-methoxy-2-nitrobenzoyl chloride; and
4,5-dimethoxy-2-nitrobenzoyl chloride.

C. In a similar manner, other compounds of formula (B) and corresponding intermediates of the compounds of the invention may be prepared.

PREPARATION 2

Compounds of Formula (D)

A. To a solution of 5-chloro-2-nitrobenzoyl chloride (23 g, 100 mmol) in methylene chloride (200 mL) at 0° C. was added triethylamine (16 mL, 115 mmol), followed by 4-chloroaniline (14 g, 110 mmol). The mixture was stirred for 20 minutes at 0° C., then warmed to ambient temperature. After 5 hours, the mixture was concentrated of all volatiles in vacuo. The residual solid was dissolved in ethyl acetate (400 mL) and washed with water (200 mL), 1M hydrochloric acid (2×200 mL), 1M sodium bicarbonate (200 mL) and brine (200 mL) and dried over MgSO$_4$. Concentration and drying in vacuo afforded 30 g (93% yield) of N-(4-chlorophenyl)-5-chloro-2-nitrobenzamide; NMR (CDCl$_3$) 8.1 (d, 1), 7.7 (br, 1), 7.6 (m, 2), 7.5 (d, 2), 7.3 (d, 2) ppm.

B. In a similar manner, the following compounds were made:
N-(5-chloropyridin-2-yl)-3,5-dichloro-2-nitrobenzamide; NMR (CDCl$_3$) 8.4 (s, 1), 8.0–8.2 (m, 3), 7.9 (m, 1) ppm;
N-(4-chlorophenyl)-4,5-dimethoxy-2-nitrobenzamide; NMR (DMSO-d$_6$/TFA) 10.6 (s, 1), 7.7 (d, 2), 7.6 (s, 1), 7.4 (d, 2), 7.2 (s, 1), 4.0 (s, 3), 3.9 (s, 3) ppm;
N-(4-chlorophenyl)-3-methoxy-2-nitrobenzamide; NMR (DMSO-d$_6$/TFA) 10.8 (s, 1), 7.7 (m, 3), 7.5 (d, 1), 7.4 (t, 2), 3.9 (s, 3), 3.4 (br s, 1) ppm;
N-(5-chloropyridin-2-yl)-3-methoxy-2-nitrobenzamide; NMR (CDCl$_3$) 8.8 (br, 1), 8.3 (d, 1), 8.1 (s, 1), 7.7 (d, 1), 7.5 (t, 1), 7.3 (m, 2), 3.9 (s, 3) ppm;
N-(5-chloropyridin-2-yl)-5-chloro-2-nitrobenzamide;
N-(5-bromopyridin-2-yl)-5-chloro-2-nitrobenzamide;
N-(4-chlorophenyl)-5-methyl-2-nitrobenzamide;
N-(4-bromophenyl)-5-methyl-2-nitrobenzamide;
N-(pyridin-2-yl)-5-chloro-2-nitrobenzamide;
5-(N-(5-chloropyridin-2-yl)amino)carbonyl-6-nitro-1,3-benzodioxole; and
N-(4-chlorophenyl)-3-nitro-pyridin-2-amide.

C. In a similar manner, other compounds of formula (D) and corresponding intermediates of the compounds of the invention may be prepared.

PREPARATION 3

Compounds of Formula (E)

A. N-(4-Chlorophenyl)-5-chloro-2-nitrobenzamide (13.2 g, 42.4 mmol) and tin(II) chloride dihydrate (48 g, 213 mmol) were combined in ethyl acetate (90 mL) and the mixture was heated at 70° C. under a nitrogen atmosphere. After 15 minutes, the mixture was cooled to ambient temperature, then poured onto water (750 mL) and ethyl acetate (750 mL). The aqueous layer was adjusted to pH 8 with by addition of 1 N NaOH and a saturated NaHCO$_3$ solution, and the layers were separated. The aqueous layer was further extracted with 500 mL of ethyl acetate. The combined organic extracts were washed with water (1 L), then brine (500 mL), dried over MgSO$_4$, filtered, and concentrated in vacuo to afford 11.6 g (97% yield) of N-(4-chlorophenyl)-2-amino-5-chlorobenzamide as an off-white solid; NMR (CDCl$_3$) 7.7 (br s, 1), 7.2–7.5 (m, 6), 6.7 (d, 1), 5.5 (br s, 2) ppm.

B. In a similar manner, the following compounds were made:
N-(5-chloropyridin-2-yl)-2,3-diamino-5-chlorobenzamide; NMR (DMSO-d$_6$/TFA) 10.6 (s, 1), 8.4 (dd, 1), 8.0 (dd, 1), 7.8 (m, 1), 7.8 (d, 1), 7.2 (dd, 1), 7.1 (m, 1), 6.8 (d, 1), 6.5 (s, 2) ppm;
N-(5-chloropyridin-2-yl)-2-amino-3-dimethylamino-5-chlorobenzamide; NMR (CDCl$_3$) 8.5 (s, 1), 8.3 (d, 1), 8.2 (d, 1), 7.7 (dd, 1), 7.3 (d, 1), 7.1 (d, 1), 6.0 (br s, 2), 2.7 (s, 6) ppm;
N-(5-chloropyridin-2-yl)-2-amino-3-(morpholin-4-yl)-5-chlorobenzamide; NMR (CDCl$_3$) 8.3 (m, 1), 7.5 (m, 1), 7.1–7.4 (m, 3), 3.9 (m, 4), 3.2 (m, 4) ppm;

N-(5-chloropyridin-2-yl)-2-amino-5-chlorobenzamide;
N-(5-bromopyridin-2-yl)-2-amino-5-chlorobenzamide;
N-(4-chlorophenyl)-2-amino-5-methylbenzamide;
N-(4-bromophenyl)-2-amino-5-methylbenzamide;
N-(5-chloropyridin-2-yl)-2-amino-3-(4-methylpiperazin-1-yl)-5-chlorobenzamide;
N-(4-chlorophenyl)-2-amino-5-chloro-3-(morpholin-4-yl)benzamide;
N-(5-chloropyridin-2-yl)-2-amino-3-(4-ethylpiperazin-1-yl)-5-chlorobenzamide;
N-(5-chloropyridin-2-yl)-2-amino-3-(4-(ethoxycarbonylpiperidin-1-yl)-5-chlorobenzamide;
N-(5-chloropyridin-2-yl)-2-amino-5-(N'-methyl-N'-(ethoxycarbonylmethyl)amino)-3-chlorobenzamide;
N-(5-chloropyridin-2-yl)-2-amino-3-(N',N'-di(2-methoxyethyl)amino)-5-chlorobenzamide;
N-(5-chloropyridin-2-yl)-2-amino-3-(pyrrolidin-1-yl)-5-chlorobenzamide;
5-(N-(5-chloropyridin-2-yl)amino)carbonyl-6-amino-1,3-benzodioxole.

C. In a manner similar to that described in Paragraph A above, N-(5-chloropyridin-2-yl)-2-nitro-3-(4-(tert-butoxycarbonyl)piperazin-1-yl)-5-chlorobenzamide (13 g, 26 mmol) was reacted with tin(II) chloride dihydrate (29 g, 130 mmol) in pyridine (100 mL) to afford 7.1 g (60% yield) of N-(5-chloropyridin-2-yl)-2-amino-3-(4-(tert-butoxycarbonyl)piperazin-1-yl)-5-chlorobenzamide, as a yellow solid; NMR (DMSO-d$_6$) 10.8 (s, 1), 8.4 (d, 1), 8.1 (d, 1), 7.9 (dd, 1), 7.6 (d, 1), 7.1 (d, 1), 6.2 (d, 2), 3.3 (m, 4), 2.7 (br, 4), 1.4 (s, 9) ppm.

D. To a solution of sodium hydrosulfite (300 g, 1.7 mol) in water (4 L) was added N-(5-chloropyridin-2-yl)-2-nitro-3-methoxybenzamide (140 g, 0.45 mol). Tetrahydrofuran (2 L) and 1,4-dioxane (2 L) were added and the resulting mixture stirred at ambient temperature. After 16 hours, the solution was made basic by addition of potassium carbonate and the phases separated. The organic phase was concentrated of all volatiles in vacuo to give an off-white solid. The solid was washed with water, filtered, and dried under vacuum to afford 111 g (88% yield) of N-(5-chloropyridin-2-yl)-2-amino-3-methoxybenzamide; NMR (CDCl$_3$) 8.8 (br, 1), 8.3 (d, 1), 8.1 (s, 1), 7.7 (dd, 1), 7.1 (dd, 1), 6.8 (d, 1), 6.6 (t, 1), 5.9 (br, 1), 3.9 (s, 3) ppm.

E. In a similar manner, the following compound was made:
N-(4-chlorophenyl)-2-amino-3-methoxybenzamide.

F. To a suspension of N-(4-bromophenyl)-2-nitro-5-chlorobenzamide (0.50 g, 1.4 mmol) in methanol (20 mL) was added 5% platinum on carbon (Degussa type, 50% water, 0.20 g), and the mixture stirred under hydrogen (balloon). After 0.5 hours, the mixture was filtered and concentrated of all volatiles in vacuo to afford 0.45 g (99% yield) of N-(4-bromophenyl)-2-amino-5-chlorobenzamide as a white solid; NMR (DMSO-d$_6$) 10.2 (s, 1), 7.5–7.7 (m, 5), 7.2 (dd, 1), 6.8 (d, 1) ppm.

G. In a similar manner, the following compounds were made:
N-phenyl-2-amino-4,5-dimethoxybenzamide;
N-(5-chloropyridin-2-yl)-2-amino-5-methylbenzamide;
N-phenyl-2-amino-5-methylbenzamide;
N-(4-chlorophenyl)-3-aminopyridin-2-amide.

H. In a manner similar to those methods described above, other compounds of formula (E) and corresponding intermediates of the compounds of the invention may be prepared.

PREPARATION 4

Compounds of Formula (G)

A. To a solution of 3-chloro-4-chloromethyl-2-(chlorocarbonyl)thiophene (3.1 g, 13.5 mmol) in methylene chloride (40 mL) at 0° C. was added N-(4-chlorophenyl)-2-amino-5-chlorobenzamide (3.8 g, 13.5 mmol), followed after 5 minutes by pyridine (1.6 mL, 16 mmol). The mixture was warmed to ambient temperature. After 17 hours, the mixture was concentrated of all volatiles in vacuo. The resulting solid was triturated with water and a small amount of acetonitrile and dried in vacuo to afford 5.1 g (80% yield) of N-(4-chlorophenyl)-2-[((4-(chloromethyl)-3-chlorothiophen-2-yl)carbonyl)amino]-5-chlorobenzamide as a tan powder: NMR (DMSO-d$_6$) 11.1 (s, 1), 10.8 (s, 1), 8.3 (d, 1), 8.2 (s, 1), 7.9 (s, 1), 7.7 (d, 2), 7.6 (dd, 1), 7.4 (d, 2), 4.8 (s, 2) ppm.

B. In a similar manner, the following compounds were made:
N-(5-chloropyridin-2-yl)-2-[((4-(chloromethyl)-3-chlorothiophen-2-yl)carbonyl)amino]-3-methoxy-5-chlorobenzamide; NMR (CDCl$_3$) 9.3 (br, 1), 9.1 (br, 1), 8.3 (d, 1), 8.0 (d, 1), 7.7 (d, 1), 7.6 (s, 1), 7.2 (d, 1), 7.0 (d, 1), 4.6 (s, 2), 3.9 (s, 3) ppm;
N-(5-chloropyridin-2-yl)-2-[((4-(chloromethyl)-3-chlorothiophen-2-yl)carbonyl)amino]-3-(morpholin-4-yl)-5-chlorobenzamide; NMR (CDCl$_3$) 10.9 (s, 1), 9.5 (s, 1), 8.4 (s, 1), 7.8–8.2 (m, 3), 7.4 (m, 2), 4.7 (s, 2), 3.7 (m, 4), 2.9 (m, 4) ppm;
N-(5-chloropyridin-2-yl)-2-[((4-(chloromethyl)-3-chlorothiophen-2-yl)carbonyl)amino]-3-(4-methylpiperazin-1-yl)-5-chlorobenzamide; NMR (CDCl$_3$) 10.8 (s, 1), 9.5 (s, 1), 8.4 (s, 1), 7.8–8.2 (m, 3), 7.4 (m, 2), 4.7 (s, 2), 3.4 (m, 8), 2.9 (s, 3) ppm;
N-(5-chloropyridin-2-yl)-2-[((4-(chloromethyl)-3-chlorothiophen-2-yl)carbonyl)amino]-3-(4-ethylpiperazin-1-yl)-5-chlorobenzamide; NMR (CDCl$_3$) 10.7 (s, 1), 9.6 (s, 1), 8.3 (s, 1), 7.8–8.2 (m, 3), 7.5 (m, 2); 4.6 (s, 2), 3.2–3.5 (m, 10), 1.4 (m, 3) ppm;
N-(5-chloropyridin-2-yl)-2-[((4-(chloromethyl)-3-chlorothiophen-2-yl)carbonyl)amino]-3-(4-(ethoxycarbonyl)piperidin-1-yl)-5-chlorobenzamide; NMR (CDCl$_3$) 10.8 (s, 1), 9.5 (s, 1), 7.1–8.4 (m, 6), 4.5 (s, 2), 3.0–3.5 (m, 7), 1.8–2.2 (m, 4), 1.2 (t, 3) ppm;
N-(5-chloropyridin-2-yl)-2-[((4-(chloromethyl)-3-chlorothiophen-2-yl)carbonyl)amino]-3-chloro-5-(N'-methyl-N'-(ethoxycarbonyl)methylamino)benzamide; NMR (CDCl$_3$) 10.9 (s, 1), 9.5 (s, 1), 8.5 (s, 1), 7.8–8.2 (m, 3), 7.5 (m, 2), 4.6 (s, 2), 3.0–3.6 (m, 4), 2.9 (s, 3), 1.1 (t, 3);
N-(5-chloropyridin-2-yl)-2-[((4-(chloromethyl)-3-chlorothiophen-2-yl)carbonyl)amino]-3-(N',N'-di(2-methoxyethyl)amino)-5-chlorobenzamide; NMR (CDCl$_3$) 10.8 (s, 1), 9.5 (s, 1), 7.3–8.6 (m, 6), 4.4 (s, 2), 2.8–3.5 (m, 11) ppm;
N-(5-chloropyridin-2-yl)-2-[((4-(chloromethyl)-3-chlorothiophen-2-yl)carbonyl)amino]-3-amino-5-chlorobenzamide; NMR (CDCl$_3$) 10.9 (s, 1), 9.7 (s, 1), 7.4–8.6 (m, 6), 4.2 (s, 2) ppm;
N-(5-chloropyridin-2-yl)-2-[((4-(chloromethyl)-3-chlorothiophen-2-yl)carbonyl)amino]-5-chlorobenzamide; NMR (DMSO-d$_6$) 11.4 (s, 1), 11.0 (s, 1), 7.6–8.4 (m, 7), 4.8 (s, 2) ppm;
N-(4-chlorophenyl)-2-[((4,5-di(chloromethyl)-3-chlorothiophen-2-yl)carbonyl)amino]-5-chlorobenzamide; NMR (DMSO-d$_6$) 11.2 (s, 1), 10.7 (s, 1), 8.3 (d, 1), 7.4–7.9 (m, 6), 5.1 (s, 2), 4.8 (s, 2) ppm;
N-(5-chloropyridin-2-yl)-2-[((4-(chloromethyl)-3-chlorothiophen-2-yl)carbonyl)amino]-3-dimethylamino-5-chlorobenzamide; NMR (DMSO-d$_6$/TFA) 11.5 (s, 1), 9.6 (s, 1), 8.3 (s, 1), 8.1 (d, 1), 8.0 (s, 2), 7.8 (dd, 1), 7.7 (d, 1), 4.6 (s, 2), 3.0 (s, 6) ppm;

N-(pyridin-2-yl)-2-[((4-(chloromethyl)-3-chlorothiophen-2-yl)carbonyl)amino]-5-chlorobenzamide; NMR (DMSO-d$_6$/TFA) 10.6 (s, 1), 8.4 (d, 1), 8.3 (t, 1), 8.0 (d, 1), 7.9 (s, 1), 7.8 (s, 1), 7.7 (d, 1), 7.6 (dd, 1), 7.5 (t, 1), 4.6 (s, 2) ppm;

N-(4-chlorophenyl)-2-[((4-(chloromethyl)-3-chlorothiophen-2-yl)carbonyl)amino]-3-(morpholin-4-yl)-5-chlorobenzamide;

N-(5-chloropyridin-2-yl)-2-[((4-(chloromethyl)-3-chlorothiophen-2-yl)carbonyl)amino]-3-(pyrrolidin-1-yl)-5-chlorobenzamide;

N-(5-chloropyridin-2-yl)-2-[((4-(chloromethyl)-3-chlorothiophen-2-yl)carbonyl)amino]-3-hydroxy-5-chlorobenzamide;

N-(4-chlorophenyl)-2-[((4-(chloromethyl)-3-chlorothiophen-2-yl)carbonyl)amino]-3-hydroxy-5-chlorobenzamide;

N-(5-chloropyridin-2-yl)-2-[((4-(chloromethyl)-3-chlorothiophen-2-yl)carbonyl)amino]-3-(4-(tert-butoxycarbonyl)piperazin-1-yl)-5-chlorobenzamide;

5-(N-(5-chloropyridin-2-yl)amino)carbonyl-6-[4-(chloromethyl)-3-chlorothiophen-2-yl)carbonyl]amino-1,3-benzodioxole;

N-(4-chlorophenyl)-2-[((4-(chloromethyl)-3-chlorothiophen-2-yl)carbonyl)amino]-5-fluorobenzamide;

N-(4-chlorophenyl)-2-[((4-(chloromethyl)-3-chlorothiophen-2-yl)carbonyl)amino]-3-methoxy-5-chlorobenzamide; NMR (DMSO-d$_6$/TFA) 10.4 (s, 1), 9.5 (s, 1), 8.1 (s, 1), 7.7 (d, 2), 7.3–7.4 (m, 4), 4.8 (s, 2), 3.9 (s, 3) ppm.

C. In a manner similar to those methods described above, other compounds of formula (G) and corresponding intermediates of the compounds of the invention may be prepared.

PREPARATION 5

Compounds of Formula (K)

A. To a suspension of N-(4-chlorophenyl)-2-[((5-methyl-3-chlorothiophen-2-yl)carbonyl)amino]-5-chlorobenzamide (2.6 g, 6.0 mmol) in dry benzene (250 mL) were added N-bromosuccinimide (1.2 g, 6.6 mmol) and benzoyl peroxide (0.15 g, 0.6 mmol). The mixture was refluxed while irradiating with a 250 Watt lamp. After 28 hours the reaction was concentrated of all volatiles in vacuo and the resulting solid triturated with benzene. Purification by flash chromatography on silica gel afforded 2.3 g (75% yield) of N-(4-chlorophenyl)-2-[((5-bromomethyl-3-chlorothiophen-2-yl)carbonyl)amino]-5-chlorobenzamide as a white solid; NMR (DMSO-d$_6$) 11.1 (s, 1), 10.7 (s, 1), 8.3 (d, 1), 7.9 (s, 1), 7.7 (d, 2), 7.6 (d, 1), 7.4 (d, 2), 7.3 (s, 1), 4.9 (s, 2) ppm.

B. In a similar manner, the following compounds were made:

N-(4-chlorophenyl)-2-[((3-(bromomethyl)benzo[b]thien-2-yl)carbonyl)amino]-5-chlorobenzamide; NMR (DMSO-d$_6$) 11.4 (s, 1), 10.8 (s, 1), 8.4 (d, 1), 7.4–8.2 (m, 10), 5.3 (s, 2) ppm;

N-(4-chlorophenyl)-2-[((6-(bromomethyl)benzo[b]thien-2-yl)carbonyl)amino]-5-chlorobenzamide; NMR (DMSO-d$_6$) 11.4 (s, 1), 10.8 (s, 1), 8.4 (d, 1), 7.4–8.2 (m, 10), 4.9 (s, 2) ppm.

C. In a similar manner, other compounds of formula (K) and corresponding intermediates of the compounds of the invention may be prepared.

PREPARATION 6

Compounds of Formula (T)

A. A mixture of 3,3,3-trifluoropropyl bromide (10.0 g, 56.5 mmol), potassium cyanide (5.2 g, 79.8 mmol), tetrabutylammonium iodide (0.1 g, 0.3 mmol) and DMSO (10 mL) was heated at 60° C. for 15 hours. After cooling, the mixture was extracted with ethyl ether (80 mL) and water (100 mL). The organic layer was washed with water (3×100 mL), dried (Na$_2$SO$_4$) and filtered. Ethanol (10 mL) was added, and the solution was cooled to 0° C., and saturated with HCl gas. The vessel was sealed and allowed to stand at ambient temperature for 15 hours. The mixture was then added to a solution of hexane (200 mL) and ethyl ether (40 mL). The precipitate was collected and dried in vacuo to give 3.2 g of ethyl (2,2,2-trifluoroethyl)acetimidate hydrochloride; NMR (DMSO-d$_6$/TFA) 4.4 (q, 3), 2.9 (t, 2) 2.6 (m, 2), 1.3 (t, 3) ppm.

B. In a similar manner, other compounds of formula (T) and corresponding intermediates of the compounds of the invention may be prepared.

PREPARATION 7

Compounds of Formula (W)

A. To 2-methoxycarbonyl-3-chloro-4-methylthiophene (100 g, 0.53 mol) in dry carbon tetrachloride (1.5 L) were added sulfuryl chloride (65 mL, 0.81 mol) and benzoyl peroxide (2.5 g, 10 mmol). The reaction was heated at reflux for 17 hours, then cooled to ambient temperature and concentrated of all volatiles in vacuo. Purification of the resulting oil by flash chromatography on silica gel afforded 63 g (54% yield) of 2-methoxycarbonyl-3-chloro-4-(chloromethyl)thiophene as a yellow oil which crystallized to fine needles upon standing; NMR (CDCl$_3$) 7.6 (s, 1), 4.6 (s, 2), 3.9 (s, 3) ppm.

B. To 2-methoxycarbonyl-3-chloro-4-methylthiophene (0.25 g, 1.3 mmol) in dry benzene (25 mL) were added N-bromosuccinimide (0.28 g, 1.6 mmol) and benzoyl peroxide (0.03 g, 0.13 mmol). The mixture was refluxed while irradiating with a 250 Watt lamp. After 2 hours the reaction was cooled and concentrated of all volatiles in vacuo. Purification by flash chromatography on silica gel afforded 0.20 g (58% yield) of 2-methoxycarbonyl-3-chloro-4-(bromomethyl)thiophene as a white solid; NMR (CDCl$_3$) 7.6 (s, 1), 4.4 (s, 2), 3.9 (s, 3) ppm.

C. In a similar manner, other compounds of formula (W) and corresponding intermediates of the compounds of the invention may be prepared.

PREPARATION 8

Compounds of Formula (X)

A. To 2-methoxycarbonyl-3-chloro-4-(bromomethyl)thiophene (0.20 g, 0.74 mmol) in methylene chloride (7.5 mL) was added 1-methylpiperazine (0.095 mL, 0.86 mmol) and the mixture was stirred at ambient temperature. After 16 hours, the mixture was poured onto methylene chloride (20 mL) and washed with dilute aqueous NaHCO$_3$, water and brine, dried over Na$_2$SO$_4$ and concentrated in vacuo. Purification by flash chromatography on silica gel afforded 0.085 g (40% yield) of 2-methoxycarbonyl-3-chloro-4-((4-methylpiperazin-1-yl)methyl)thiophene as a tan solid; NMR (CDCl$_3$) 7.4 (s, 1), 3.9 (s, 3), 3.5 (s, 2), 2.3–2.7 (br m, 8), 2.2 (s, 3) ppm.

B. In a similar manner, the following compounds were made:

2-methoxycarbonyl-3-chloro-4-((morpholin-4-yl)methyl)thiophene;

2-methoxycarbonyl-3-chloro-4-((thiomorpholin-4-yl)methyl)thiophene.

C. In a similar manner, other compounds of formula (X) and corresponding intermediates of the compounds of the invention may be prepared.

PREPARATION 9

Compounds of Formula (Y)

A. To a solution of 2-methoxycarbonyl-3-chloro-5-methylthiophene (1.3 g, 6.8 mmol) in ethanol (16 mL) was added aqueous sodium hydroxide (1 N, 16 mL, 16 mmol) and the mixture stirred at ambient temperature. After 3 hours the mixture was concentrated of all volatiles in vacuo. The residual solid was dissolved in water (60 mL), acidified with 1 N HCl and the solid collected by filtration to afford 1.2 g (95% yield) of 2-carboxy-3-chloro-5-methylthiophene as a white solid; NMR (CDCl$_3$) 6.8 (s, 1), 2.5 (s, 3) ppm.

B. In a similar manner, the following compounds were made:
2-carboxy-3-methoxybenzo[b]thiophene;
2-carboxy-3-chloro-4-((4-methylpiperazin-1-yl)methyl) thiophene, hydrochloride salt;
2-carboxy-3-chloro-4-cyanothiophene.

C. In a similar manner, other compounds of formula (Y) and corresponding intermediates of the compounds of the invention may be prepared.

PREPARATION 10

Compounds of Formula (FF)

A. To a solution of N-(5-chloropyridin-2-yl)-2-[((4-((N'-methyl-N'-(methylsulfonyl)amino)methyl)-3-chlorothiophen-2-yl)carbonyl)amino]-3-hydroxy-5-chlorobenzamide (4.5 g, 8.0 mmol) in DMF (200 mL) was added cesium carbonate (18 g, 55 mmol), followed by epibromohydrin (1.4 mL, 16 mmol). The mixture was stirred at ambient temperature for 3 days, then filtered. The filtrate was concentrated in vacuo to afford a quantitative yield of N-(5-chloropyridin-2-yl)-2-[((4-((N'-methyl-N'-(methylsulfonyl)amino)methyl)-3-chlorothiophen-2-yl) carbonyl)amino]-3-(2,3-epoxypropoxy)-5-chlorobenzamide; NMR (CDCl$_3$) 9.2 (s, 1), 8.8 (s, 1), 8.2 (d, 1), 8.1 (s, 1), 7.7 (d, 1), 7.6 (s, 1), 7.3 (s, 1), 7.1 (s, 1), 4.4 (d, 1), 4.3 (s, 2), 4.0 (m, 1), 3.4 (br m, 1), 3.0 (br m, 1), 2.9 (s, 3), 2.8 (s, 3), 2.7 (br m, 1) ppm.

B. In a similar manner, the following compound was made:
N-(5-chloropyridin-2-yl)-2-[((4-((N'-methyl-N'-((dimethylamino)sulfonyl)amino)methyl)-3-chlorothiophen-2-yl)carbonyl)amino]-3-(2,3-epoxypropoxy)-5-chlorobenzamide.

C. In a similar manner, other compounds of formula (FF) and corresponding intermediates of the compounds of the invention may be prepared.

PREPARATION 11

Compounds of Formula (Eb)

A. To N-(5-chloropyridin-2-yl)-2-amino-3-methoxybenzamide (39 g, 140 mmol) in benzene (2 L) was added N-chlorosuccinimide (20 g, 148 mmol) and the reaction heated at 50–55° C. After 24 hours the reaction was cooled to ambient temperature and concentrated of all volatiles in vacuo. The resulting solid was dissolved in ethyl acetate (1 L), washed with water (3×100 mL), dried over sodium sulfate, and concentrated. Recrystallization from benzene afforded 40 g (90% yield) of N-(5-chloropyridin-2-yl)-2-amino-3-methoxy-5-chlorobenzamide as off-white needles; NMR (CDCl$_3$) 8.6 (br, 1), 8.3 (m, 2), 7.7 (dd, 1), 7.1 (d, 1), 6.8 (d, 1), 5.9 (br, 1), 3.9 (s, 3) ppm.

B. In a similar manner, the following compound was made:
N-(4-chlorophenyl)-2-amino-3-methoxy-5-chlorobenzamide.

C. To a solution of N-(4-chlorophenyl)-2-amino-3-methylbenzamide (0.40 g, 1.5 mmol) in chloroform (3 mL) at 0° C. was added SO$_2$Cl$_2$ (0.31 g, 2.3 mmol). The mixture was warmed to ambient temperature and stirred for 1 hour. Concentration of all volatiles in vacuo afforded N-(4-chlorophenyl)-2-amino-3-methyl-5-chlorobenzamide as a yellow solid; NMR (DMSO-d$_6$) 10.2 (s, 1), 7.8 (d, 2), 7.6 (s, 1), 7.4 (d, 2), 7.2 (s, 1), 6.2 (br, 2), 2.1 (s, 3) ppm.

D. In a similar manner, the following compound was made:
N-(4-chlorophenyl)-2-amino-4-fluoro-5-chlorobenzamide.

E. In a manner similar to those methods described above, other compounds of formula (Eb) and corresponding intermediates of the compounds of the invention may be prepared.

PREPARATION 12

Compounds of Formula (Db)

A. To a solution of N-(5-chloropyridin-2-yl)-2-nitro-3,5-dichlorobenzamide (12 g, 34 mmol) in DMSO (50 mL) was added morpholine (3.6 g, 41 mmol) followed by N,N-diisopropylethylamine (8.9 g, 69 mmol). The mixture was heated at 110–120° C. for 4 hours, then cooled to ambient temperature, quenched with water (50 mL) and extracted with ethyl acetate (3×100 mL). The combined organics were washed with brine (2×30 mL), dried over Na$_2$SO$_4$ and concentrated in vacuo. Purification by flash chromatography on silica gel afforded 6.3 g (46% yield) of N-(5-chloropyridin-2-yl)-2-nitro-3-(morpholin-4-yl)-5-chlorobenzamide; NMR (CDCl$_3$) 8.2 (m, 1), 7.7 (m, 1), 7.2–7.4 (m, 3), 3.8 (m, 4), 3.0 (m, 4) ppm.

B. In a similar manner, the following compounds were made:
N-(5-chloropyridin-2-yl)-2-nitro-3-(4-methylpiperazin-1-yl)-5-chlorobenzamide; NMR (DMSO-d$_6$/TFA) 9.8 (br s, 1), 8.4 (d, 1), 8.0 (d, 1), 7.8 (dd, 1), 7.6 (d, 2), 3.4 (d, 2), 3.3 (d, 2), 3.2 (m, 4), 2.8 (s, 3) ppm;
N-(5-chloropyridin-2-yl)-2-nitro-3-(4-(tert-butoxycarbonyl) piperazin-1-yl)-5-chlorobenzamide; NMR (DMSO-d$_6$) 11.5 (br, 1), 8.4 (d, 1), 8.1 (d, 1), 7.9 (dd, 1), 7.7 (s, 1), 7.6 (d, 1), 3.4 (br, 4), 2.9 (m, 4), 1.4 (s, 9) ppm;
N-(4-chlorophenyl)-2-nitro-3-(morpholin-4-yl)-5-chlorobenzamide;
N-(5-chloropyridin-2-yl)-2-nitro-3-(4-ethylpiperazin-1-yl)-5-chlorobenzamide;
N-(5-chloropyridin-2-yl)-2-nitro-3-(4-(ethoxycarbonyl) piperidin-1-yl)-5-chlorobenzamide;
N-(5-chloropyridin-2-yl)-2-nitro-3-chloro-5-(N'-methyl-N'-(ethoxycarbonyl)methylamino)benzamide;
N-(5-chloropyridin-2-yl)-2-nitro-3-(N',N'-di(2-methoxyethyl)amino)-5-chlorobenzamide;
N-(5-chloropyridin-2-yl)-2-nitro-3-(pyrrolidin-1-yl)-5-chlorobenzamide.

C. Into a solution of N-(5-chloropyridin-2-yl)-2-nitro-3,5-dichlorobenzamide (4.0 g, 12 mmol) in dimethyl sulfoxide (60 mL) was bubbled an excess of dimethyl amine gas. The mixture was sealed in a pressure tube and heated at 50° C. After 3 hours, the mixture was cooled to ambient temperature, then poured into water, and extracted with methylene chloride. The combined organic extracts were dried over MgSO$_4$, and concentrated in vacuo to afford 3.8 g (93% yield) of N-(5-chloropyridin-2-yl)-2-nitro-3-dimethylamino-5-chlorobenzamide; NMR (CDCl$_3$) 9.6 (s, 1), 8.2 (d, 1), 7.8 (d, 1), 7.7 (dd, 1), 7.1 (d, 1), 6.9 (d, 1), 2.8 (s, 6) ppm.

D. In a similar manner, the following compound was made:

N-(5-chloropyridin-2-yl)-2-nitro-3-amino-5-chlorobenzamide.

E. In a manner similar to those methods described above, other compounds of formula (Db) and corresponding intermediates of the compounds of the invention may be prepared.

PREPARATION 13

Compounds of Formula (LL)

A. A mixture of anthranilic acid (10 g, 73 mmol), and phosgene (1.9 M solution in toluene, 50 mL, 94 mmol) in 1,4-dioxane (120 mL) was stirred at ambient temperature. After 50 hours, the mixture was heated at 65° C. for 10 hours then cooled to ambient temperature. The solid was collected by filtration, washed with ethyl ether and dried in vacuo to afford 11 g (92% yield) of benzoxazine-2,4-dione as tan solid; NMR (DMSO-d$_6$) 11.7 (s, 1), 7.9 (d, 1), 7.7 (t, 1), 7.2 (t, 1), 7.1 (d, 1) ppm.

B. In a similar manner, the following compounds were made:

6,7-difluorobenzoxazine-2,4-dione; NMR (DMSO-d$_6$) 11.9 (s, 1), 8.0 (t, 1), 7.0 (dd, 1) ppm;
6-fluorobenzoxazine-2,4-dione;
7-fluorobenzoxazine-2,4-dione;
8-methylbenzoxazine-2,4-dione;
7-azabenzoxazine-2,4-dione.

C. In a similar manner, other compounds of formula (LL) and corresponding intermediates of the compounds of the invention may be prepared.

PREPARATION 14

Compounds of Formula (Ec)

2-Amino-(N-4-Chlorophenyl)Benzamide

A. A mixture of benzoxazine-2,4-dione (1.6 g, 10 mmol) and 4-chloroaniline (2.5 g, 20 mmol) in 1,4-dioxane (30 mL) was heated at reflux for 15 hours. After cooling the solid was filtered, and the filtrate was concentrated, washed with ethyl ether. The washing was concentrated further to a solid. Additional washing with cold ethyl ether (10 mL) afforded N-(4-chlorophenyl)-2-aminobenzamide as a tan solid; NMR (DMSO-d$_6$) 10.1 (s, 1), 7.8 (d, 2), 7.6 (d, 1), 7.4 (d, 2), 7.2 (t, 1), 6.8 (d, 1), 6.6 (t, 1), 6.3 (s, 2) ppm.

B. In a similar manner, the following compounds were made:

N-(4-chlorophenyl)-2-amino-4,5-difluorobenzamide; NMR (DMSO-d$_6$) 10.1 (s, 1), 7.8 (m, 3), 7.4 (d, 2), 6.7 (dd, 1), 6.6 (br s, 2) ppm;
N-(4-chlorophenyl)-2-amino-5-fluorobenzamide;
N-(4-chlorophenyl)-2-amino-4-fluorobenzamide;
N-(4-chlorophenyl)-2-amino-3-methylbenzamide; and
N-(4-chlorophenyl)-3-aminopyridin-4-amide.

C. In a similar manner, other compounds of formula (Ec) and corresponding intermediates of the compounds of the invention may be prepared.

PREPARATION 15

Compound of Formula (OO)

A. To 2-methoxycarbonyl-3-chloro-4-(chloromethyl) thiophene (48 g, 0.21 mol) in glacial acetic acid (500 mL) was added sodium acetate (35 g, 0.42 mol). The reaction was heated at reflux for 24 hours, then cooled and concentrated in vacuo. The residual oil was made basic by addition of saturated aqueous sodium bicarbonate, and the resulting solution extracted with ethyl acetate (4×150 mL). The combined extracts were dried over sodium sulfate and concentrated to afford 47 g (90% yield) of 2-methoxycarbonyl-3-chloro-4-(acetoxymethyl)thiophene as a light brown oil; NMR (CDCl$_3$) 7.6 (s, 1), 5.1 (s, 2), 3.9 (s, 3), 2.1 (s, 3) ppm.

B. In a similar manner, other compounds of formula (OO) and corresponding intermediates of the compounds of the invention may be prepared.

PREPARATION 16

Compounds of Formula (PP)

A. To a solution of 2-methoxycarbonyl-3-chloro-4-(acetoxymethyl)thiophene (83 g, 0.33 mol) in 1,4-dioxane (350 mL) was added a solution of sodium hydroxide (26.5 g, 0.66 mol) in water (200 mL) and the mixture stirred at ambient temperature. After 1 hour the dioxane was removed in vacuo and the aqueous solution washed with ethyl acetate (2×100 mL). The aqueous layer was brought to pH 2 by addition of concentrated HCl, then extracted with n-butanol (4×200 mL). The combined extracts were concentrated and the resulting solid dried in vacuo to afford 63 g (90% yield) of 2-carboxy-3-chloro-4-(hydroxymethyl)thiophene as a tan powder; NMR (DMSO-d$_6$) 7.7 (s, 1), 4.4 (s, 2) ppm.

B. In a similar manner, the following compound was prepared:

2-carboxy-3-chloro-4-(2-(N-methyl-N-tert-butoxycarbonylamino)ethyl)thiophene.

C. In a manner similar to that described above in Paragraph A, 2-methoxycarbonyl-3-chloro-4-((morpholin-4-yl) methyl)thiophene (2.0 g, 8.2 mmol) was reacted with aqueous sodium hydroxide (1 M, 8.2 mL, 8.2 mmol) in 1,4-dioxane (20 mL). Concentration of all volatiles in vacuo afforded 2.0 g (86% yield) of the sodium salt of 2-carboxy-3-chloro-4-((morpholin-4-yl)methyl)thiophene; NMR (DMSO-d$_6$) 7.3 (s, 1), 3.5 (m, 4), 3.3 (d, 2), 2.3 (m, 4) ppm.

D. In a similar manner, the following compound was made:

2-carboxy-3-chloro-4-((thiomorpholin-4-yl)methyl) thiophene sodium salt.

E. In a manner similar to that described above, other compounds of formula (PP) and corresponding intermediates of the compounds of the invention may be prepared.

PREPARATION 17

Compounds of Formula (F)

A. 2-carboxy-3-chloro-4-(hydroxymethyl)thiophene (83 g, 0.43 mmol) was added to thionyl chloride (200 mL) and the mixture heated at reflux for 4–6 hours. After cooling to ambient temperature, the mixture was concentrated of all volatiles in vacuo followed by repeated concentration from 1,2-dichloroethane. The residual oil was dissolved in methylene chloride (250 mL), filtered and concentrated to afford 100 g (89% yield) of 2-chlorocarbonyl-3-chloro-4-(chloromethyl)thidphene as a tan waxy solid; NMR (CDCl$_3$) 7.8 (s, 1), 4.6 (s, 2) ppm.

B. In a similar manner, other compounds of formula (F) and corresponding intermediates of the compounds of the invention may be prepared.

PREPARATION 18

Compounds of Formula (RR)

A. To 5-carboxy-1,3-benzodioxole (50 g, 300 mmol) in trifluoroacetic acid (400 mL) at 0° C. was added HNO$_3$ (38 mL, 900 mmol) dropwise. The reaction mixture was stirred at 0° C. for 1 hour, then warmed to ambient temperature and stirred for 3 hours. The mixture was poured into ice water and the resulting precipitate was collected by filtration. The solid was air dried overnight to afford 58 g (92% yield) of 5-carboxy-6-nitro-1,3-benzodioxole as a yellow solid; NMR (DMSO-$d_6$) 7.6 (s, 1), 7.3 (s, 1), 6.3 (s, 2) ppm.

B. In a similar manner, other compounds of formula (RR) and corresponding intermediates of the compounds of the invention may be prepared.

PREPARATION 19

A. To a suspension of 2-carboxy-3-chloro-5-methylthiophene (1.2 g, 6.6 mmol) in methylene chloride (16 mL) at 0° C. were added oxalyl chloride (0.6 mL, 7.3 mmol) and a drop of DMF. The mixture was stirred at ambient temperature for 5 hours, then concentrated of all volatiles and dried in vacuo to afford 1.3 g (quantitative yield) of 2-chlorocarbonyl-3-chloro-5-methylthiophene as a pale yellow solid; NMR (DMSO-$d_6$/TFA) 7.4 (s, 1), 2.5 (s, 3) ppm.

B. In a similar manner, the following compounds were made:
2-chlorocarbonyl-3-methoxybenzo[b]thiophene;
2-chlorocarbonyl-3-chloro-4-cyanothiophene;
2-chlorocarbonyl-3-methyl-5-nitrothiophene;
2-chlorocarbonyl)-3-methyl-4-nitrothiophene; and
2-chlorocarbonyl-3-chloro-4-(2-(N-methyl-N-tert-butoxycarbonylamino)ethyl)thiophene.

C. In a similar manner, other corresponding intermediates of the compounds of the invention may be prepared.

PREPARATION 20

A. To a solution of 3,5-dichlorobenzoic acid (50 g, 0.26 mol) in sulfuric acid (250 mL) at 0° C. was added nitric acid (18 g, 0.28 mol) dropwise, and the mixture warmed slowly to ambient temperature. After 5 hours the mixture was poured onto ice, and the white precipitate collected by filtration. The solid was washed with water (3×30 mL), and dried in vacuo to afford 55 g (90% yield) of 3,5-dichloro-2-nitrobenzoic acid; NMR (CDCl$_3$) 8.3 (s, 1), 8.0 (s, 1) ppm.

B. In a similar manner, other corresponding intermediates of the compounds of the invention may be prepared.

PREPARATION 21

A. To a solution of (R)-(−)-1-amino-2-propanol (0.40 g, 5.3 mmol) in methanol (10 mL) at 0° C. were added sodium acetate (0.82 g, 10 mmol) and cyanogen bromide (5 M in acetonitrile, 1 mL, 5.0 mmol). The reaction was allowed to warm slowly to ambient temperature and stirred for 2 hours. The mixture was concentrated in vacuo. A small amount of water was added and the solution made basic by addition of a saturated aqueous K$_2$CO$_3$ solution. The mixture was extracted with methylene chloride, dried over K$_2$CO$_3$, and concentrated in vacuo to afford 0.3 g (60% yield) of 2-imino-5(R)-methyloxazolidine; NMR (DMSO-$d_6$/TFA) 5.7 (br s, 2), 4.5 (m, 1), 3.6 (dd, 1). 3.0 (dd, 1), 1.2 (d, 3) ppm.

B. In a similar manner, the following compounds were made:
2-imino-5(S)-methyloxazolidine; NMR (DMSO-$d_6$/TFA) 5.7 (br s, 2), 4.5 (m, 1), 3.6 (dd, 1). 3.0 (dd, 1), 1.2 (d, 3) ppm;
2-imino-5-methyloxazolidine; NMR (DMSO-$d_6$/TFA) 5.7 (br s, 2), 4.5 (m, 1), 3.6 (dd, 1), 3.0 (dd, 1), 1.2 (d, 3) ppm;
2-imino-5,5-dimethyloxazolidine; NMR (DMSO-$d_6$/TFA) 3.3 (s, 2), 1.3 (s, 6) ppm; and 2-imino-4-methyloxazolidine.

C. In a similar manner, other corresponding intermediates of the compounds of the invention may be prepared.

PREPARATION 22

A. To a solution of 1-amino-2-methyl-2-propanol (4.0 g, 45 mmol) in CH$_2$Cl$_2$ (25 mL) at 0° C. was added a solution of ethyl isocyanate (3.2 g, 45 mmol) in CH$_2$Cl$_2$ (5 mL) dropwise. The mixture was stirred at ambient temperature for 18 hours, then concentrated of all volatiles in vacuo to afford a quantitative yield of N-(2-methyl-2-hydroxypropyl)-N'-ethylurea as a yellow solid; NMR (DMSO-$d_6$/TFA) 5.9 (m. 1), 5.7 (m, 1), 3.0 (m, 2), 2.9 (d, 2), 1.0 (s, 6), 0.9 (t, 3) ppm.

B. In a similar manner, other corresponding intermediates of the compounds of the invention may be prepared.

PREPARATION 23

A. To a solution of N-(2-methyl-2-hydroxypropyl)-N'-ethylurea (7.2 g, 45 mmol) in CH$_2$Cl$_2$ (100 mL) at 0° C. was added a solution of thionyl chloride (5.4 g, 45 mmol) in CH$_2$Cl$_2$ (20 mL). The mixture was warmed to ambient temperature. After 2 hours, the mixture was concentrated in vacuo, and the resulting solid triturated with boiling water. The mixture was cooled to ambient temperature and made basic by addition of saturated aqueous K$_2$CO$_3$. The mixture was extracted with methylene chloride, dried over K$_2$CO$_3$, and concentrated in vacuo to afford 3.2 g (50% yield) of 2-ethylamino-5,5-dimethyloxazoline; NMR (DMSO-$d_6$/TFA) 3.2 (s, 2), 3.0 (q, 2), 1.3 (s, 6), 1.0 (t, 3) ppm.

B. In a similar manner, other corresponding intermediates of the compounds of the invention may be prepared.

PREPARATION 24

A. To a solution of 1-amino-2-propanol (2.0 g, 27 mmol) in tetrahydrofuran (20 mL) was added a solution of thiocarbonyldiimidazole (5.3 g, 27 mmol) in tetrahydrofuran (5 mL). The mixture was stirred at ambient temperature for 3 hours, then concentrated in vacuo. Purification by flash chromatography on silica gel afforded 2.9 g (93% yield) of 5-methyl-2-thioxooxazolidine; NMR (CDCl$_3$) 8.4 (br s, 1), 5.0 (m, 1), 3.8 (t, 1). 3.4 (t, 1), 1.5 (d, 3) ppm;

B. In a similar manner, the following compound was made:
4-methyl-2-thioxooxazolidine.

C. In a similar manner, other corresponding intermediates of the compounds of the invention may be prepared.

PREPARATION 25

A. To a solution of 5-methyl-2-thioxooxazolidine (2.7 g, 23 mmol) in POCl$_3$ (40 mL) was added PCl$_5$ (4.8 g, 23 mmol). The mixture was heated at 100° C. for 3 hours, then cooled to ambient temperature and concentrated in vacuo. The resulting yellow oil was dissolved in methylene chloride, filtered through silica gel and concentrated to afford a quantitative yield of 2-chloro-5-methyl-2-oxazoline.

B. In a similar manner, the following compound was made:
2-chloro-4-methyl-2-oxazoline.

C. In a similar manner, other corresponding intermediates of the compounds of the invention may be prepared.

PREPARATION 26

A. To a solution of 2-carboxy-3-chlorothiophene (2.0 g, 12.3 mmol) in chloromethyl methyl ether (10 mL) was added TiCl$_4$ (4.0 mL, 6.9 g, 36 mmol) at 0° C. under N$_2$. The resulting dark orange suspension was warmed to ambient temperature. After 5 hours the reaction mixture was poured onto methylene chloride (75 mL) and ice water (100 mL) with vigorous stirring. The layers were separated and the aqueous layer was extracted with ethyl acetate (100 mL) and the combined organics extracted with 3 portions of aqueous NaHCO$_3$ (100 mL, 25–50% saturated). The combined aqueous extracts were made acidic by addition of concentrated HCl and the resulting precipitate extracted into ethyl acetate (3×100 mL). The combined organic extracts were dried over MgSO$_4$ and concentrated of all volatiles in vacuo. The resulting solid was dissolved in acetonitrile, water and trifluoroacetic acid and purified by HPLC on a C18 Dynamax column with 30–55% acetonitrile in water gradient with 0.1% trifluoroacetic acid to afford 0.83 g (26% yield) of 2-carboxy-3-chloro-4,5-di(chloromethyl)thiophene as a white solid: NMR (CDCl$_3$) 4.8 (s, 2), 4.6 (s, 2) ppm.

B. In a similar manner, other corresponding intermediates of the compounds of the invention may be prepared.

PREPARATION 27

A. N-(5-Chloropyridin-2-yl)-2-[((4-((methylamino)methyl)-3-chlorothiophen-2-yl)carbonyl)amino]-3-methoxy-5-chlorobenzamide (0.054 g, 0.11 mmol) and 1,1-di(methylthio)-2-nitroethene (0.092 g, 0.56 mmol) were dissolved in DMF (1 mL) and stirred at 50,° C. under nitrogen for 16 hours. The reaction mixture was then partitioned between water (25 mL) and ethyl acetate (60 mL), the layers were separated and the aqueous layer extracted with ethyl acetate (30 mL). The combined organic layers were washed with water (3×30 mL), brine (30 mL), dried over magnesium sulfate, concentrated in vacuo, and dried under vacuum. The crude product was purified by flash chromatography on silica gel, eluting with 70% ethyl acetate/hexanes to give N-(5-chloropyridin-2-yl)-2-[((4-((N'-methyl-N'-(2-nitro-1-methylthioethenyl)amino)methyl)-3-chlorothiophen-2-yl)carbonyl)amino]-3-methoxy-5-chlorobenzamide as a yellow foam.

B. In a similar manner, the following compound was made:
N-(5-chloropyridin-2-yl)-2-[((4-((N'-methyl-N'-(methylthio(cyanoimino)methyl)amino)methyl)-3-chlorothiophen-2-yl)carbonyl)amino]-3-methoxy-5-chlorobenzamide.

C. In a similar manner, other corresponding intermediates of the compounds of the invention may be prepared.

PREPARATION 28

A. N-(5-Chloropyridin-2-yl)-2-[((4-(2-amino-2-(hydroxyimino)ethyl)-3-chlorothiophen-2-yl)carbonyl)amino]-3-methoxy-5-chlorobenzamide (3.06 g, 5.8 mmol) was dissolved in trichloroacetic acid (3.8 g, 23 mmol) and the mixture heated to 85° C. Trichloroacetyl chloride (1.3 mL, 11.6 mmol) was added, and the temperature was increased to 94° C. After one hour the reaction mixture was allowed to cool to room temperature, diluted with water (150 mL) and a small amount of ethyl acetate, and adjusted to basic pH with 1 N NaOH. The aqueous layer was extracted with ethyl acetate (300 mL). The organic phase was washed with 1 M sodium bicarbonate (150 mL), dried over magnesium sulfate, concentrated in vacuo, and dried under vacuum. The crude product was purified by flash chromatography on silica gel eluting with 25% ethyl acetate/hexanes to afford N-(5-chloropyridin-2-yl)-2-[((4-((5-trichloromethyl-1,2,4-oxadiazol-3-yl)methyl)-3-chlorothiophen-2-yl)carbonyl)amino]-3-methoxy-5-chlorobenzamide.

B. In a similar manner, other corresponding intermediates of the compounds of the invention may be prepared.

PREPARATION 29

A. To a solution of 2-carboxy-3-methylthiophene (10 g, 70.3 mmol) in 80 mL of trifluoroacetic acid at 0° C. was added HNO$_3$ (1.2 mL, 1.0 eq.) dropwise. The reaction mixture was warmed to ambient temperature and after 4 hours another 1.0 eq. of HNO$_3$ was added. The reaction mixture was made basic with aqueous sodium bicarbonate and washed with ethyl acetate. The aqueous layer was acidified with concentrated HCl and extracted with ethyl acetate. The organic layer was dried over sodium sulfate and concentrated in vacuo to afford 5.75 g (53%) of 2-carboxy-3-methyl-5-nitrothiophene and 2-carboxy-3-methyl-4-nitrothiophene, as a yellow solid.

B. In a similar manner, other corresponding intermediates of the compounds of the invention may be prepared.

PREPARATION 30

A. N-tert-Butoxycarbonylpiperazine (2.94 g, 16.0 mmol) was dissolved in pyridine (8 mL) under nitrogen and the solution cooled to 0° C. Methanesulfonyl chloride (1.5 mL, 19.3 mmol) was added. After 5 minutes, more pyridine was added (5 mL) and the reaction mixture was allowed to warm to ambient temperature. After 40 minutes, the pyridine was removed in vacuo. The residue was dissolved in ethyl acetate (250 mL), washed with 0.1M citric acid (3×125 mL), dried over magnesium sulfate, concentrated in vacuo, and dried under vacuum to give 3.84 g (92%) of N-tert-butoxycarbonyl-N'-methylsulfonylpiperazine.

B. N-tert-butoxycarbonyl-N'-methylsulfonylpiperazine (3.84 g, 14.5 mmol) was suspended in methylene chloride (100 mL) under nitrogen and trifluoroacetic acid (10 mL) was added. After 3 hours, the reaction mixture was concentrated in vacuo and the residue dissolved in water (150 mL). The aqueous layer was washed with ether (2×75 mL). The pH of the aqueous layer was then adjusted to 10 and it was extracted with methylene chloride (3×120 mL). The methylene chloride layers were dried over magnesium sulfate, and concentrated in vacuo to give 0.99 g of N-methylsulfonylpiperazine. Further extraction of the aqueous layer with 10% methanol/methylene chloride (3×120 mL) afforded 0.44 g of N-methylsulfonylpiperazine, for a total of 1.43 g (59%).

C. In a similar manner, other corresponding intermediates of the compounds of the invention may be prepared.

PREPARATION 31

A. Hydroxylamine hydrochloride (6.12 g, 88 mmol) was added to a solution of sodium methoxide prepared by dissolving sodium (2.02 g) in methanol (25 mL). Additional methanol (50 mL) was added, followed by (methylthio)acetonitrile (6.0 mL, 71.5 mmol). The reaction mixture was refluxed for 5 hours, filtered while hot, concentrated in vacuo, and dried under vacuum to give 1-amino-1-hydroxyimino-2-methylthioethane in quantitative yield.

B. In a similar manner, 1-amino-1-hydroxyimino-2-methoxyethane was prepared.

C. 1-Amino-1-hydroxyimino-2-methylthioethane (11.32 g, 94.2 mmol) was suspended in dry chloroform (60 mL) under nitrogen. A solution of chloroacetyl chloride (7.5 mL, 94.2 mmol) in chloroform (20 mL) was added dropwise. After stirring for 1 hour, a solution of triethylamine (15.8 mL, 113 mmol) in chloroform (20 mL) was added dropwise.

The reaction mixture was stirred for 15 minutes, then washed with water (2×70 mL), dried over sodium sulfate, concentrated in vacuo, and dried under vacuum to yield 11.4 g (62% yield) of 1-amino-1-((chloromethyl)carbonyloxy) imino-2-methylthioethane, as a brown semi-solid.

D. In a similar manner, 1-amino-1-((chloromethyl) carbonyloxy)imino-2-methoxyethane was prepared.

E. 1-Amino-1-((chloromethyl)carbonyloxy)imino-2-methylthioethane (3.04 g, 15.5 mmol) was dissolved in xylenes (15 mL) under nitrogen. The reaction mixture was refluxed for 3 hours, concentrated in vacuo, and dried under vacuum. The crude product was purified by flash chromatography on silica eluting with 10% ethyl acetate/hexanes to give 1.14 g (41% yield) of 5-chloromethyl-3-methylthiomethyl-1,2,4-oxadiazole.

F. In a similar manner, 5-chloromethyl-3-methylthiomethyl-1,2,4-oxadiazole was prepared.

G. In a manner similar to those methods described above, other corresponding intermediates of the compounds of the invention may be prepared.

PREPARATION 32

A. Acetic anhydride (30.91 g, 0.303 mol) was cooled to 0° C. and formic acid (20.6 g, 0.394 mol) was added dropwise. After stirring for 30 minutes at 0° C., the reaction mixture was warmed to room temperature then heated to 50° C. The reaction mixture was stirred for 5 hours, then cooled to ambient temperature. The product, acetic formic anhydride, was used in the next step without further purification.

B. To a solution of acetic formic anhydride (26.7 g, 0.303 mol) in THF (100 mL) was added 2-aminoimidazole (25.2 g, 0.303 mol) in THF (200 mL) at ambient temperature. After stirring for 16 hours, the reaction mixture was concentrated and the resulting solid was suspended in methylene chloride. $NH_3$ (g) was bubbled into the suspension and the reaction mixture was concentrated. The resulting white slurry was loaded onto a silica column and eluted with 0–10% methanol in methylene chloride gradient to afford 25.9 g of 2-(formylamino)imidazole as a white solid.

C. In a similar manner the following compound was prepared:
2-(acetylamino)imidazole.

D. To a suspension of 2-(formylamino)imidazole (25.9 g, 0.233 mol) in THF (200 mL) was added $BH_3$-THF (900 mL of a 1 M solution in THF, 0.9 mol) at ambient temperature. The resulting white turbid solution was stirred at ambient temperature for 16 hours. The reaction was quenched with methanol and adjusted to pH 2 with 3 N HCl in ethyl acetate. The solution was heated to reflux for an hour and then was concentrated. The resulting solid was dissolved in THF and $NH_3$ (g) was bubbled into the solution. The resulting white solid was removed by filtration and the filtrate was concentrated to afford 2-(methylamino)imidazole as a dark oil.

E. In a similar manner the following compound was prepared:
2-(ethylamino)imidazole.

F. In a manner similar to those methods described above, other corresponding intermediates of the compounds of the invention may be prepared.

PREPARATION 33

A. To a solution of 2-methoxycarbonyl-3-chloro-4-hydroxymethylthiophene (6 g, 29 mmol) in methylene chloride (100 mL) were added triethylamine (8.1 mL, 58 mmol) and methanesulfonyl chloride (2.5 mL, 32 mmol) at ambient temperature. After stirring for 6 hours, the reaction mixture was concentrated to afford 2-methoxycarbonyl-3-chloro-4-(methylsulfonyloxy)methylthiophene. The crude product was dissolved in DMF (150 mL) and excess potassium cyanide was added to the solution. The reaction mixture was stirred at ambient temperature for 16 hours, then poured into water, and extracted with methylene chloride. The combined extracts were dried over $Na_2SO_4$, filtered, and concentrated in vacuo to afford 2-methoxycarbonyl-3-chloro-4-cyanomethylthiophene.

B. 2-Methoxycarbonyl-3-chloro-4-cyanomethylthiophene (2 g, 9.27 mmol) was dissolved in THF (100 mL) and $BH_3$-THF (18.6 mL of a 1 M solution in THF, 18.6 mmol) was added. After stirring for 16 hours at ambient temperature, the reaction was quenched with water followed by 1 M NaOH. Potassium carbonate was added to afford two layers. The organic layer was separated and concentrated in vacuo to afford 2-methoxycarbonyl-3-chloro-4-(2-aminoethyl)thiophene.

C. 2-Methoxycarbonyl-3-chloro-4-(2-aminoethyl) thiophene was dissolved in THF (50 mL), and di-tert-butyl dicarbonate (2.23 g, 10.2 mmol) was added at ambient temperature. After 1 hour, water was added, and the reaction mixture was extracted with methylene chloride. The combined extracts were dried over $Na_2SO_4$, filtered, concentrated in vacuo, and purified by flash chromatography on gel to afford 1.42 g of 2-methoxycarbonyl-3-chloro-4-(2-(tert-butoxycarbonylamino)-ethyl)thiophene.

D. To a solution of 2-methoxycarbonyl-3-chloro-4-(2-(N-methyl-N-tert-butoxycarbonylamino)ethyl)-thiophene (0.93 g, 2.91 mmol) in DMF (10 mL) were added NaH (0.23 g, 5.82 mmol) and iodomethane (0.36 mL, 5.82 mmol) at ambient temperature. After stirring for 48 hours, water was added, and the reaction mixture was extracted with methylene chloride. The combined extracts were dried over $Na_2SO_4$, filtered, concentrated in vacuo, and purified by flash chromatography on silica to afford 2-methoxycarbonyl-3-chloro-4-(2-(N-methyl-N-tert-butoxycarbonylamino)ethyl)thiophene (0.45 g).

E. In a manner similar to those methods described above, other corresponding intermediates of the compounds of the invention may be prepared.

PREPARATION 34

A. To a solution of 2-chloro-3-nitropyridine (5 g, 31.6 mmol, 1.0 eq.) in 50 mL of DMF was added copper cyanide (2.47 g, 38 mmol, 1.2 eq.) and the reaction heated to 100° C. for 16 hours. The reaction mixture was cooled to ambient temperature and poured into 100 mL of water. The mixture was extracted with ethyl acetate (3×50 mL) and the combined ethyl acetate portions were dried over soduim sulfate and concentrated. The crude material was chromatographed on silica with 3:7 ethyl acetate/hexanes to give 2-cyano-3-nitropyridine as a yellow solid.

B. To a solution of 2-cyano-3-nitropyridine (0.5 g, 3.4 mmol, 1 eq.) in 50 mL of ethanol was added HCl gas. The reaction was stirred at ambient temperature for 16 hours and concentrated. The residue was dissolved in 50 mL of water and the solution neutralized with saturated aqueous sodium bicarbonate and extracted with ethyl actetate (3×50 mL). The combined ethyl acetate extractions were dried over sodium sulfate and concentrated. The residue was chromatographed to give 2-ethoxycarbonyl-3-nitropyridine (0.5 g, 90% yield) as a pale yellow oil.

C. To a solution of 2-ethoxycarbonyl-3-nitropyridine (0.5 g, 2.5 mmoL, 1 eq.) in 20 mL of methanol and 5 mL of water was added lithium hydroxide (0.2 g, 4.5 mmoL, 1.8 eq.) and the mixture stirred for 16 hours at ambient temperature. The reaction was concentrated and 50 mL of 1N KOH was were added. The solution was washed with 25 mL of ethyl actetate, acidified with 1 N HCl, and extracted with ethyl acetate (3×50 mL). The combined ethyl acetate extractions were dried over sodium sulfate and concentrated to give 2-carboxy-3-nitropyridine as a yellow solid (0.4 g, 95% yield).

D. In a manner similar to those methods described above, other intermediates for compounds of the invention where the B ring is a heterocyclic may be prepared.

EXAMPLE 1

Compounds of Formula (Ia)

A. To a solution of N-(4-chlorophenyl)-2-[((4-(chloromethyl)-3-chlorothiophen-2-yl)carbonyl)amino]-3-methoxy-5-chlorobenzamide (1.0 g, 2.1 mmol) in DMF (40 mL) at 0° C. was added 1-methylpiperazine (1.2 mL, 1.1 g, 11 mmol), and the mixture stirred for 0.5 hours at 0° C., then warmed to ambient temperature. After 7 hours the reaction mixture was poured into water (150 mL) and the resulting solid collected by filtration, washed with water (50 mL) and acetonitrile (10 mL). Purification by flash chromatography on silica gel afforded 0.77 g (64% yield) of N-(4-chlorophenyl)-2-[((4-((4-methylpiperazin-1-yl)methyl)-3-chlorothiophen-2-yl)carbonyl)amino]-3-methoxy-5-chlorobenzamide, as a white foam: NMR (DMSO-$d_6$/TFA) 10.4 (s, 1), 9.4 (s, 1), 7.2–8.1 (m, 7), 4.4 (s, 2), 3.8 (s, 3), 3.0–3.8 (br m, 8), 2.8 (s, 3) ppm.

B. In a similar manner, the following compounds were made:

N-(5-chloropyridin-2-yl)-2-[((4-((4-methylpiperazin-1-yl)methyl)-3-chlorothiophen-2-yl)carbonyl)amino]-3-(dimethyl)amino-5-chlorobenzamide; NMR (DMSO-$d_6$/TFA) 11.0 (s, 1), 9.7 (s, 1), 8.3 (d, 1), 8.2 (s, 1), 8.1 (s, 1), 7.8 (dd, 1), 7.7 (d, 1), 7.5 (d, 1), 4.4 (s, 2), 3.6–3.3 (br m, 8), 2.9 (s, 6), 2.8 (s, 3) ppm;

N-(5-chloropyridin-2-yl)-2-[((4-((N'-methyl-N'-(3-(dimethylamino)propyl)amino)methyl)-3-chlorothiophen-2-yl)carbonyl)amino]-3-(dimethyl)amino-5-chlorobenzamide; NMR (DMSO-$d_6$/TFA) 11.0 (s, 1), 9.7 (s, 1), 8.3 (d, 1), 8.2 (s, 1), 8.1 (d, 1), 7.8 (dd, 1), 7.6 (d, 1), 7.5 (d, 1), 4.4–4.3 (br m, 2), 3.2–3.0 (br m, 4), 2.9 (s, 6), 2.8 (d, 6), 2.7 (s, 3), 2.3 (br s, 2) ppm;

N-(5-chloropyridin-2-yl)-2-[((4-((N'-methyl-N'-(2-(dimethylamino)ethyl)amino)methyl)-3-chlorothiophen-2-yl)carbonyl)amino]-3-(dimethyl)amino-5-chlorobenzamide; NMR (DMSO-$d_6$/TFA) 11.0 (s, 1), 9.7 (s, 1), 8.3 (d, 1), 8.2 (s, 1), 8.1 (d, 1), 7.8 (dd, 1), 7.6 (d, 1), 7.4 (d, 1), 4.4 (br s, 2), 3.5 (br s, 4), 2.9 (s, 12), 2.8 (s, 3) ppm;

N-(5-chloropyridin-2-yl)-2-[((4-((N'-methyl-N'-(1-methylpiperidin-4-yl)amino)methyl)-3-chlorothiophen-2-yl)carbonyl)amino]-3-(dimethyl)amino-5-chlorobenzamide; NMR (DMSO-$d_6$/TFA) 11.0 (s, 1), 9.7 (s, 1), 8.3 (d, 1), 8.2 (s, 1), 8.1 (d, 1), 7.9 (dd, 1), 7.7 (d, 1), 7.5 (d, 1), 4.5–4.3 (br m, 2), 3.65–3.5 (br m, 3), 3.1–3.0 (br m, 2), 2.9 (s, 6), 2.8 (s, 3), 2.7 (s, 3), 2.4–2.3 (br m, 2), 2.1–1.9 (br m, 2) ppm;

N-(pyridin-2-yl)-2-[((4-((4-methylpiperazin-1-yl)methyl)-3-chlorothiophen-2-yl)carbonyl)amino]-5-chlorobenzamide; NMR (DMSO-$d_6$/TFA) 10.9 (s, 1), 8.5 (d, 1), 8.3 (t, 1), 8.2 (s, 1), 8.1 (d, 1), 7.9 (s, 1), 7.8 (d, 1), 7.6 (d, 1), 7.5 (t, 1), 4.4 (s, 2), 3.6–3.2 (br m, 8), 2.9 (s, 3) ppm;

N-(4-chlorophenyl)-2-[((3-chloro-4-((N'-(3-(imidazol-1-yl)propyl)amino)methyl)thiophen-2-yl)carbonyl)amino]-5-chlorobenzamide; NMR (DMSO-$d_6$/TFA) 11.2 (s, 1), 10.8 (s, 1), 9.1 (s, 1), 8.4 (d, 1), 8.2 (s, 1), 7.9 (d, 1), 7.8–7.6 (m, 5), 7.4 (d, 2), 4.3 (t, 2), 4.2 (br s, 2), 3.0 (br s, 2), 2.2 (m, 3) ppm;

N-(4-chlorophenyl)-2-[((3-chloro-4-((N'-(2-(morpholin-4-yl)ethyl)amino)methyl)thiophen-2-yl)carbonyl)amino]-5-chlorobenzamide; NMR (DMSO-$d_6$/TFA) 7.4–8.5 (m, 7), 3.3–3.7 (m, 8), 2.4–2.7 (m, 6) ppm;

N-(5-chloropyridin-2-yl)-2-[((4-((N'-(2-(morpholin-4-yl)ethyl)amino)methyl)-3-chlorothiophen-2-yl)carbonyl)amino]-5-chlorobenzamide; NMR (DMSO-$d_6$/TFA) 7.4–8.6 (m, 7), 3.6 (s, 2), 3.0–3.7 (m, 8), 2.2–2.7 (m, 6) ppm; /TFA)

N-(5-chloropyridin-2-yl)-2-[((4-((4-hydroxypiperidin-1-yl)methyl)-3-chlorothiophen-2-yl)carbonyl)amino]-3-methoxy-5-chlorobenzamide; NMR (DMSO-$d_6$/TFA) 10.9 (s, 1), 9.5 (s, 1), 9.4 (s, 1), 8.3 (s, 1), 8.2 (d, 1), 8.1 (s, 1), 7.8 (d, 1), 7.4 (s, 1), 7.3 (s, 1), 4.3 (m, 2), 3.9 (s, 3), 3.8 (br s, 1), 3.4 (m, 1), 3.2 (m, 2), 3.0 (m, 1), 1.8 (m, 4) ppm;

N-(5-chloropyridin-2-yl)-2-[((4-((N'-methyl-N'-(2-(pyrrolidin-1-yl)ethyl)amino)methyl)-3-chlorothiophen-2-yl)carbonyl)amino]-3-methoxy-5-chlorobenzamide; NMR (DMSO-$d_6$/TFA) 11.2 (s, 1), 10.8 (s, 1), 10.1 (br s, 1), 8.4 (d, 1), 8.3 (s, 1), 7.9 (s, 1), 7.7 (d, 2), 7.6 (d, 1), 7.4 (d, 2), 4.4 (s, 2), 3.6 (m, 2), 3.4 (br s, 6), 2.8 (s, 3), 2.0 (br s, 4) ppm;

N-(5-chloropyridin-2-yl)-2-[((4-((N'-methyl-N'-(2,3-dihydroxypropyl)amino)methyl)-3-chlorothiophen-2-yl)carbonyl)amino]-3-methoxy-5-chlorobenzamide; NMR (DMSO-$d_6$/TFA) 10.9 (s, 1), 9.5 (br s, 1), 9.4 (s, 1), 8.3 (s, 1), 8.2 (m, 1), 8.1 (d, 1), 7.9 (d, 1), 7.4 (s, 1), 7.3 (s, 1), 4.4 (m, 2), 4.0 (m, 1), 3.9 (s, 3), 3.4 (m, 2), 3.1 (m, 2), 2.8 (s, 3) ppm;

N-(5-chloropyridin-2-yl)-2-[((4-((N'-ethyl-N'-(2-hydroxyethyl)amino)methyl)-3-chlorothiophen-2-yl)carbonyl)amino]-3-methoxy-5-chlorobenzamide; NMR (DMSO-$d_6$/TFA) 10.9 (s, 1), 9.5 (s, 1), 9.4 (br s, 1), 8.4 (s, 1), 8.2 (s, 1), 8.1 (d, 1), 7.9 (d, 1), 7.4 (s, 1), 7.3 (s, 1), 4.4 (br s, 2), 3.9 (s, 3), 3.8 (m, 2), 3.2 (m, 4), 1.3 (m, 3) ppm;

N-(4-chlorophenyl)-2-[((3-chloro-4-((N'-methyl-N'-(2-(pyrrolidin-1-yl)ethyl)amino)methyl)thiophen-2-yl)carbonyl)amino]-5-chlorobenzamide; NMR (DMSO-$d_6$/TFA) 11.2 (s, 1), 10.8 (s, 1), 10.0 (br s, 1), 8.4 (d, 1), 8.3 (s, 1), 8.0 (s, 1), 7.8 (d, 2), 7.7 (d, 1), 7.4 (d, 2), 4.4 (s, 2), 3.6 (m, 4), 3.3 (br s, 2), 2.8 (s, 3), 2.0 (br s, 4) ppm;

N-(5-chloropyridin-2-yl)-2-[((4-((4-methylpiperazin-1-yl)methyl)-3-chlorothiophen-2-yl)carbonyl)amino]-3-(pyrrolidin-1-yl)-5-chlorobenzamide; NMR (DMSO-$d_6$) 10.9 (s, 1), 9.4 (s, 1), 8.4 (s, 1), 8.2 (d, 1), 8.1 (s, 1), 7.9 (d, 1), 7.0 (s, 1), 6.9 (s, 1) 4.3 (s, 2), 3.5 (br s, 4), 3.4 (br s, 8), 2.9 (s, 3), 1.9 (br s, 4) ppm;

N-(4-chlorophenyl)-2-[((3-chloro-4-((N'-methyl-N'-(2-hydroxyethyl)amino)methyl)thiophen-2-yl)carbonyl)amino]-5-chlorobenzamide; NMR (CDCl$_3$) 11.1 (s, 1), 8.7 (s, 1), 8.3 (d, 1), 7.7 (d, 2), 7.5 (s, 2), 7.4 (d, 2), 7.3 (dd, 1), 3.7 (t, 2), 3.6 (s, 2), 2.7 (t, 2), 2.3 (s, 3) ppm;

N-(4-chlorophenyl)-2-[((4-((4-methylpiperazin-1-yl)methyl)-3-chlorothiophen-2-yl)carbonyl)amino]-5-chlorobenzamide; NMR (DMSO-$d_6$) 11.1 (s, 1), 10.8 (s, 1), 8.3 (d, 1), 7.9 (s, 1), 7.8 (s, 1), 7.7 (d, 2), 7.6 (d, 1), 7.4 (d, 2), 3.4 (s, 2), 2.4 (m, 4), 2.3 (m, 4), 2.1 (s, 3) ppm;

N-(4-chlorophenyl)-2-[((3-chloro-4-((N'-methyl-N'-(2-dimethylaminoethyl)amino)methyl)thiophen-2-yl)

carbonyl]amino]-5-chlorobenzamide; NMR (DMSO-d$_6$) 11.1 (s, 1), 10.8 (s, 1), 8.3 (d, 1), 7.9 (d, 1), 7.8 (s, 1), 7.7 (d, 2), 7.6 (dd, 1), 7.4 (d, 2), 3.5 (s, 2), 2.5 (d, 2), 2.3 (d, 2), 2.2 (s, 3), 2.1 (s, 6) ppm;

N-(4-chlorophenyl)-2-[((3-chloro-4-((N'-methyl-N'-(ethoxycarbonylmethyl)amino)methyl)thiophen-2-yl)carbonyl)amino]-5-chlorobenzamide; NMR (CDCl$_3$) 11.1 (s, 1), 8.6 (s, 1), 8.3 (d, 1), 7.7 (d, 2), 7.6 (s, 1), 7.5 (d, 1), 7.4 (d, 2), 7.3 (dd, 1), 4.2 (q, 2), 3.7 (s, 2), 3.3 (s, 2), 2.5 (s, 3), 1.3 (t, 3) ppm;

N-(5-chloropyridin-2-yl)-2-[((4-((N'-methyl-N'-(3-(dimethylamino)propyl)amino)methyl)-3-chlorothiophen-2-yl)carbonyl)amino]-3-methoxy-5-chlorobenzamide; NMR (DMSO-d$_6$) 8.3 (d, 1), 8.1 (d, 1), 7.9 (dd, 1), 7.7 (s, 1), 7.4 (d, 1), 7.2 (d, 1), 3.9 (s, 3), 3.4 (s, 2), 2.4 (t, 2), 2.2 (t, 2), 2.1 (s, 3), 2.0 (s, 6), 1.5 (m, 2) ppm;

N-(5-chloropyridin-2-yl)-2-[((4-((4-ethylpiperazin-1-yl)methyl)-3-chlorothiophen-2-yl)carbonyl)amino]-3-methoxy-5-chlorobenzamide; NMR (DMSO-d$_6$/TFA) 10.9 (s, 1), 9.3 (s, 1), 8.4 (s, 1), 8.1 (d, 1), 7.9 (d, 1), 7.7 (s, 1), 7.4 (s, 1), 7.2 (s, 1), 3.9 (s, 3), 3.4 (s, 2), 3.3 (s, 3), 2.2–2.5 (br m, 11), 1.0 (t, 3) ppm;

N-(5-chloropyridin-2-yl)-2-[((4-((N'-methyl-N'-(2-hydroxyethyl)amino)methyl)-3-chlorothiophen-2-yl)carbonyl)amino]-3-methoxy-5-chlorobenzamide; NMR (DMSO-d$_6$/TFA) 10.9 (s, 1), 9.9 (s, 1), 9.4 (s, 1), 8.4 (s, 1), 8.1 (d, 1), 7.9 (d, 1), 7.8 (s, 1), 7.4 (s, 1), 7.2 (s, 1), 4.4 (t, 1), 3.9 (s, 3), 3.5 (m, 4), 3.3 (d, 2), 2.4 (m, 3) ppm;

5-(N-(5-chloropyridin-2-yl)amino)carbonyl-6-[4-((N'-methyl-N'-(2-hydroxyethyl)amino)methyl)-3-chlorothiophen-2-yl)carbonyl]amino-1,3-benzodioxole, NMR (DMSO-d$_6$/TFA) 11.5 (s, 1), 11.0 (s, 1), 9.6 (s, 1), 7.5–8.4 (m, 6), 6.1 (s, 2), 4.4 (m, 2), 3.8 (t, 2), 3.2 (m, 2), 2.8 (s, 3) ppm;

N-(5-chloropyridin-2-yl)-2-[((4-((N'-methyl-N'-(2,3-dihydroxypropyl)amino)methyl)-3-chlorothiophen-2-yl)carbonyl)amino]-3-hydroxy-5-chlorobenzamide; NMR (DMSO-d$_6$) 10.9 (br s, 1), 9.3 (br s, 1), 8.3 (s, 1), 8.1 (d, 1), 7.9 (d, 1), 7.8 (s, 1), 7.2 (s, 1), 7.1 (s, 1), 3.6 (m, 1), 3.5 (br s, 2), 3.3 (m, 2), 2.5 (m, 1), 2.3 (m, 1), 2.2 (s, 3) ppm;

N-(5-chloropyridin-2-yl)-2-[((4-(((t-butyl)amino)methyl)-3-chlorothiophen-2-yl)carbonyl)amino]-3-methoxy-5-chlorobenzamide; NMR (DMSO-d$_6$) 10.9 (br, 1), 9.4 (br, 1), 8.3 (d, 1), 8.1 (d, 1), 7.9 (dd, 1), 7.7 (s, 1), 7.4 (s, 1), 7.2 (s, 1), 3.9 (s, 3), 3.6 (s, 2), 1.1 (s, 9) ppm;

N-(5-chloropyridin-2-yl)-2-[((4-(((2-(dimethylamino)ethyl)amino)methyl)-3-chlorothiophen-2-yl)carbonyl)amino]-3-methoxy-5-chlorobenzamide;

N-(5-chloropyridin-2-yl)-2-[((4-(((2-(2-hydroxyethoxy)ethyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(2-(pyrrolidin-1-yl)ethyl)amino)methyl)-3-chlorothiophen-2-yl)carbonyl)amino]-3-hydroxy-5-chlorobenzamide;

N-(5-chloropyridin-2-yl)-2-[((4-(((2-(pyrrolidin-1-yl)ethyl)amino)methyl)-3-chlorothiophen-2-yl)carbonyl)amino]-3-(morpholin-4-yl)-5-chlorobenzamide;

N-(5-chloropyridin-2-yl)-2-[((4-(((4-hydroxycyclohexyl)amino)methyl)-3-chlorothiophen-2-yl)carbonyl)amino]-3-methoxy-5-chlorobenzamide;

N-(5-chloropyridin-2-yl)-2-[((4-((4-ethylpiperazin-1-yl)methyl)-3-chlorothiophen-2-yl)carbonyl)amino]-3-hydroxy-5-chlorobenzamide;

5-(N-(5-chloropyridin-2-yl)amino)carbonyl-6-[4-(((2-methoxyethyl)amino)methyl)-3-chlorothiophen-2-yl)carbonyl]amino-1,3-benzodioxole;

N-(5-chloropyridin-2-yl)-2-[((4-(((2-methoxyethyl)amino)methyl)-3-chlorothiophen-2-yl)carbonyl)amino]-3-methoxy-5-chlorobenzamide; NMR (DMSO-d$_6$/TFA) 10.8 (s, 1), 9.5 (br s, 1), 9.4 (s, 1), 8.2 (d, 1), 8.1 (s, 1), 8.0 (d, 1), 7.8 (dd, 1), 7.1 (s, 2), 4.3 (br d, 2), 3.75 (t, 2), 3.15 (br m, 4), 1.2 (t, 3) ppm;

N-(5-chloropyridin-2-yl)-2-[((4-((N'-ethyl-N'-(2-hydroxyethyl)amino)methyl)-3-chlorothiophen-2-yl)carbonyl)amino]-3-hydroxy-5-chlorobenzamide;

N-(5-chloropyridin-2-yl)-2-[((4-((N'-methyl-N'-(2-hydroxyethyl)amino)methyl)-3-chlorothiophen-2-yl)carbonyl)amino]-3,4,5-trimethoxybenzamide;

N-(5-chloropyridin-2-yl)-2-[((4-(ethylamino)methyl-3-chlorothiophen-2-yl)carbonyl)amino]-3-methoxy-5-chlorobenzamide; NMR (DMSO-d$_6$) 10.90 (s, 1H), 9.40 (s, 1H), 8.80 (br s, 2H), 8.75 (d, 1H), 8.20 (d, 1H), 8.10 (s, 1H), 7.80 (dd, 1H), 7.48 (d, 1H), 7.60 (d, 1H), 4.15 (s, 2H), 3.85 (s, 3H), 3.05 (br s, 2H), 1.20 (t, 3H) ppm;

N-(5-chloropyridin-2-yl)-2-[((4-((N'-ethyl-N'-methylamino)methyl)-3-chlorothiophen-2-yl)carbonyl)amino]-3-methoxy-5-chlorobenzamide; NMR (DMSO-d$_6$) 10.90 (s, 1H), 9.38 (s, 1H), 8.30 (d, 1H), 8.20 (d, 1H), 7.90 (dd, 1H), 7.70 (s, 1H), 7.40 (d, 1H), 7.25 (d, 1H), 3.90 (s, 3H), 3.30 (s, 2H), 2.40 (q, 2H), 2.10 (s, 3H), 1.00 (t, 3H) ppm;

N-(5-chloropyridin-2-yl)-2-[((4-((4-formylpiperazin-1-yl)methyl)-3-chlorothiophen-2-yl)carbonyl)amino]-3-methoxy-5-chlorobenzamide; NMR (DMSO-d$_6$) 10.9 (s, 1), 9.4 (s, 1), 8.3 (d, 1), 8.1 (d, 1), 8.0 (s, 1), 7.9 (dd, 1), 7.8 (s, 1), 7.4 (d, 1), 7.2 (d, 1), 3.9 (s, 3), 3.5 (s, 2), 3.3 (s, 4), 2.4 (m, 4) ppm;

N-(5-chloropyridin-2-yl)-2-[((4-((pyrrolidin-1-yl)methyl)-3-chlorothiophen-2-yl)carbonyl)amino]-3-methoxy-5-chlorobenzamide; NMR (CDCl$_3$) 9.1 (s, 1), 8.8 (s, 1), 8.3 (d, 1), 8.2 (d, 1), 7.7 (dd, 1), 7.5 (s, 1), 7.3 (d, 1), 7.1 (d, 1) 3.9 (s, 3), 3.6 (s, 2), 2.6 (m, 4), 1.8 (m, 4) ppm;

N-(5-chloropyridin-2-yl)-2-[((4-((2-(1-methylethyl)imidazol-1-yl)methyl)-3-chlorothiophen-2-yl)carbonyl)amino]-3-methoxy-5-chlorobenzamide; NMR (DMSO-d$_6$/TFA) 12.4 (s, 1), 10.9 (s, 1), 9.4 (s, 1), 8.3 (d, 1), 8.1 (d, 1), 7.9 (dd, 1), 7.8 (d, 2), 7.6 (s, 1), 7.3 (dd, 2), 7.0 (br d, 2), 5.1 (s, 2), 3.9 (s, 3), 3.8 (m, 1), 1.2 (d, 6) ppm;

N-(5-chloropyridin-2-yl)-2-[((4-((morpholin-4-yl)methyl)-3-chlorothiophen-2-yl)carbonyl)amino]-3-methoxy-5-chlorobenzamide; NMR (CDCl$_3$) 9.1 (s, 1), 8.7 (s, 1), 8.2 (d, 1), 8.1 (s, 1), 7.6 (dd, 1), 7.4 (s, 1), 7.2 (d, 1), 7.0 (s, 1), 3.9 (s, 3), 3.7 (bs, 4), 3.5 (s, 2), 2.5 (bs, 4) ppm;

N-(5-chloropyridin-2-yl)-2-[((4-((N'-(1-methylethyl)amino)methyl)-3-chlorothiophen-2-yl)carbonyl)amino]-3-methoxy-5-chlorobenzamide; NMR (CDCL$_3$) 9.1 (s, 1), 8.9 (s, 1), 8.3 (d, 1), 8.1 (d, 1), 7.6 (dd, 1), 7.4 (s, 1), 7.3 (s, 1), 7.05 (s, 1), 3.9 (s, 3), 3.8 (s, 2), 2.9 (m, 1), 1.0 (d, 6) ppm;

N-(5-chloropyridin-2-yl)-2-[((4-(diethylamino)methyl-3-chlorothiophen-2-yl)carbonyl)amino]-3-methoxy-5-chlorobenzamide; NMR (DMSO-d$_6$/TFA) 10.9 (s, 1), 9.5 (s, 1), 9.4 (s, 1), 8.4 (s, 1), 8.2 (s, 1), 8.1 (d, 1), 7.9 (d, 1), 7.3 (s, 1), 7.2 (s, 1), 4.2 (s, 2), 3.8 (s, 3), 3.1 (bs, 4), 1.2 (m, 6) ppm;

N-(5-chloropyridin-2-yl)-2-[((4-((2-imino-4-methyltetrahydrooxazol-3-yl)methyl)-3-chlorothiophen-2-yl)carbonyl)amino]-3-methoxy-5-chlorobenzamide; NMR (DMSO-d$_6$/TFA) 10.9 (s, 1), 9.6 (br s, 1), 9.4 (s, 1), 9.2 (br s, 1), 8.3 (d, 1), 8.1 (d, 1), 8.0 (s, 1), 7.8 (dd, 1), 7.2 (d, 2), 4.8 (t, 1), 4.6 (dd, 2), 4.3 (t, 1), 4.1 (m, 1), 3.8 (s, 3), 1.2 (d, 3) ppm;

N-(5-chloropyridin-2-yl)-2-[((4-((4-(methylsulfonyl)piperazin-1-yl)methyl)-3-chlorothiophen-2-yl)carbonyl)

amino]-3-methoxy-5-chlorobenzamide; NMR (DMSO-d$_6$) 10.9 (s, 1), 9.4 (s, 1), 8.4 (d, 1), 8.1 (d, 1), 7.9 (dd, 1), 7.8 (s, 1), 7.4 (d, 1), 7.2 (d, 1), 3.9 (s, 3), 3.5 (s, 2), 3.1 (s, 4), 2.9 (s, 3), 2.5 (s, 4) ppm;

N-(5-chloropyridin-2-yl)-2-[((4-(((2(S), 3(S)-3-hydroxybut-2-yl)amino)methyl)-3-chlorothiophen-2-yl)carbonyl)amino]-3-methoxy-5-chlorobenzamide;

N-(5-chloropyridin-2-yl)-2-[((4-(((2(R), 3(S)-3-hydroxybut-2-yl)amino)methyl)-3-chlorothiophen-2-yl)carbonyl)amino]-3-methoxy-5-chlorobenzamide;

N-(5-chloropyridin-2-yl)-2-[((4-(((aminocarbonylmethyl)amino)methyl)-3-chlorothiophen-2-yl)carbonyl)amino]-3-methoxy-5-chlorobenzamide;

N-(5-chloropyridin-2-yl)-2-[((4-(((2,3-dihydroxypropyl)amino)methyl)-3-chlorothiophen-2-yl)carbonyl)amino]-3-methoxy-5-chlorobenzamide;

N-(5-chloropyridin-2-yl)-2-[((4-(((3-aminopropyl)amino)methyl)-3-chlorothiophen-2-yl)carbonyl)amino]-3-methoxy-5-chlorobenzamide;

N-(5-chloropyridin-2-yl)-2-[((4-((N'-methyl-N'-(N"-methylpiperidin-4-yl)amino)methyl)-3-chlorothiophen-2-yl)carbonyl)amino]-3-(pyrrolin-1-yl)-5-chlorobenzamide;

N-(5-chloropyridin-2-yl)-2-[((4-((di(2-hydroxyethyl)amino)methyl)-3-chlorothiophen-2-yl)carbonyl)amino]-3-methoxy-5-chlorobenzamide.

C. In a manner similar to Paragraph A above, N-(5-chloropyridin-2-yl)-2-[((4-(chloromethyl)-3-chlorothiophen-2-yl)carbonyl)amino]-3-methoxy-5-chlorobenzamide (2.0 g, 4.0 mmol) was reacted with 2-aminoimidazole (1.3 g, 16 mmol) to give N-(5-chloropyridin-2-yl)-2-[((4-((2-aminoimidazol-1-yl)methyl)-3-chlorothiophen-2-yl)carbonyl)amino]-3-methoxy-5-chlorobenzamide, which was purified by HPLC on a C18 Vydac column with acetonitrile in water gradient with 0.1% trifluoroacetic acid to afford N-(5-chloropyridin-2-yl)-2-[((4-((2-aminoimidazol-1-yl)methyl)-3-chlorothiophen-2-yl)carbonyl)amino]-3-methoxy-5-chlorobenzamide, trifluoroacetic acid salt, as a white solid; NMR (DMSO-d$_6$/TFA) 10.9 (s, 1), 10.4 (s, 1), 8.3 (d, 1), 8.1 (d, 1), 7.9 (dd, 1), 7.8 (br, 1), 7.6 (s, 1), 4 (d, 1), 7.3 (d, 1), 6.9 (dt, 1), 5.0 (s, 2), 4.8 (s, 3) ppm.

D. In a similar manner, the following compounds were made:

N-(5-chloropyridin-2-yl)-2-[((4-((2-imino-5(S)-methyltetrahydrooxazol-3-yl)methyl)-3-chlorothiophen-2-yl)carbonyl)amino]-3-methoxy-5-chlorobenzamide, trifluoroacetic acid salt; NMR (DMSO-d$_6$/TFA) 10.9 (s, 1), 9.4 (s, 1), 8.3 (d, 1), 8.1 (d, 1), 8.0 (s, 1), 7.8 (dd, 1), 7.4 (s, 1), 7.3 (s, 1), 5.1 (m, 1), 4.6 (q, 2), 3.9 (s, 3), 3.9 (d, 1), 3.4 (t, 1), 1.4 (d, 3) ppm;

N-(5-chloropyridin-2-yl)-2-[((4-(((thiazol-2-yl)amino)methyl)-3-chlorothiophen-2-yl)carbonyl)amino]-3-methoxy-5-chlorobenzamide; trifluoroacetic acid salt; NMR (DMSO-d$_6$/TFA) 10.9 (s, 1), 9.4 (s, 1), 8.4 (d, 1), 8.1 (d, 1), 7.9 (dd, 1), 7.7 (s, 1), 7.4 (d, 1), 7.4 (d, 1), 7.3 (d, 1), 7.1 (d, 1), 5.2 (s, 2), 3.8 (s, 3) ppm;

N-(5-chloropyridin-2-yl)-2-[((4-((4-methylpiperazin-1-yl)methyl)-3-chlorothiophen-2-yl)carbonyl)amino]-3-(4-methylpiperazin-1-yl)-5-chlorobenzamide, trifluoroacetic acid salt; NMR (DMSO-d$_6$/TFA) 11.0 (s, 1), 9.5 (s, 1), 8.4 (d, 1), 8.1 (d, 1), 7.9 (dd, 1), 7.8 (s, 1), 7.5 (d, 2), 3.6 (s, 2), 3.5 (br m, 2), 3.4 (br m, 4), 3.2–2.8 (br m, 8), 2.8 (s, 3), 2.7 (s, 3), 2.6–2.4 (br m, 2) ppm;

N-(4-chlorophenyl)-2-[((3-chloro-4-((N'-methyl-N'-(2-diethylaminoethyl)amino)methyl)thiophen-2-yl)carbonyl)amino]-5-chlorobenzamide; NMR (DMSO-d$_6$/TFA) 11.2 (s, 1), 10.8 (s, 1), 8.3 (m, 2), 8.0 (s, 1), 7.7 (m, 3), 7.4 (d, 2), 4.4 (s, 2), 3.5 (m, 3), 3.2 (q, 4), 2.8 (s, 3), 1.2 (t, 6) ppm;

N-(5-chloropyridin-2-yl)-2-[((4-((N'-methyl-N'-(2-hydroxyethyl)amino)methyl)-3-chlorothiophen-2-yl)carbonyl)amino]-3-(4-methylpiperazin-1-yl)-5-chlorobenzamide, trifluoroacetic acid salt; NMR (DMSO-d$_6$/TFA) 11.0 (s, 1), 9.6 (s, 1), 8.4 (d, 1), 8.2 (s, 1), 8.1 (d, 1), 7.9 (dd, 1), 7.4 (d, 2), 4.4 (br d, 2), 3.8 (t, 2), 3.5 (m, 2), 3.3 (m, 2), 3.2 (m, 2), 3.1 (d, 4), 2.8 (s, 3), 2.7 (s, 3) ppm;

N-(5-chloropyridin-2-yl)-2-[((4-((2-imino-5-methyltetrahydrooxazol-3-yl)methyl)-3-chlorothiophen-2-yl)carbonyl)amino]-3-methoxy-5-chlorobenzamide, trifluoroacetic acid salt; NMR (DMSO-d$_6$/TFA) 10.9 (s, 1), 9.4 (s, 1), 8.3 (d, 1), 8.1 (d, 1), 8.0 (s, 1), 7.8 (dd, 1), 7.4 (s, 1), 7.3 (s, 1), 5.1 (m, 1), 4.6 (q, 2), 3.9 (s, 3), 3.9 (d, 1), 3.4 (t, 1), 1.4 (d, 3) ppm;

N-(5-chloropyridin-2-yl)-2-[((4-((2-imino-5,5-(dimethyl)tetrahydrooxazol-3-yl)methyl)-3-chlorothiophen-2-yl)carbonyl)amino]-3-methoxy-5-chlorobenzamide, trifluoroacetic acid salt; NMR (DMSO-d$_6$/TFA) 10.9 (s, 1), 9.4 (s, 1), 8.3 (d, 1), 8.1 (d, 1), 8.0 (s, 1), 7.8 (dd, 1), 7.4 (s, 1), 7.3 (s, 1), 4.6 (s, 2), 3.8 (s, 3), 3.5 (s, 2), 1.5 (s, 6) ppm;

N-(5-chloropyridin-2-yl)-2-[((4-((2-ethylimino-5,5-(dimethyl)tetrahydrooxazol-3-yl)methyl)-3-chlorothiophen-2-yl)carbonyl)amino]-3-methoxy-5-chlorobenzamide, trifluoroacetic acid salt; NMR (DMSO-d$_6$/TFA) 10.9 (s, 1), 9.4 (s, 1), 8.3 (d, 1), 8.1 (d, 1), 7.9 (s, 1), 7.8 (dd, 1), 7.3 (s, 1), 7.2 (s, 1), 4.6 (s, 2), 3.8 (s, 3), 3.5 (s, 2), 3.3 (q, 2), 1.4 (s, 6), 1.1 (t, 3) ppm;

N-(5-chloropyridin-2-yl)-2-[((4-((2-imino-5(R)-methyltetrahydrooxazol-3-yl)methyl)-3-chlorothiophen-2-yl)carbonyl)amino]-3-methoxy-5-chlorobenzamide, trifluoroacetic acid salt; NMR (DMSO-d6/TFA) 10.9 (s, 1), 9.4 (s, 1), 8.3 (d, 1), 8.1 (d, 1), 8.0 (s, 1), 7.8 (dd, 1), 7.4 (s, 1), 7.3 (s, 1), 5.1 (m, 1), 4.6 (q, 2), 3.9 (s, 3), 3.9 (d, 1), 3.4 (t, 1), 1.4 (d, 3) ppm;

N-(5-chloropyridin-2-yl)-2-[((4-((4-methylpiperazin-1-yl)methyl)-3-chlorothiophen-2-yl)carbonyl)amino]-3-(morpholin-4-yl)-5-chlorobenzamide, trifluoroacetic acid salt; NMR (DMSO-d$_6$/TFA) 10.9 (s, 1), 9.6 (s, 1), 7.3–8.5 (m, 6), 3.9 (s, 2), 3.7 (br d, 4), 3.0–3.7 (m, 8), 2.9 (br d, 2), 2.8 (s, 3) ppm;

N-(5-chloropyridin-2-yl)-2-[((4-((N'-methyl-N'-(2-(dimethylamino)ethyl)amino)methyl)-3-chlorothiophen-2-yl)carbonyl)amino]-3-(morpholin-4-yl)-5-chlorobenzamide, trifluoroacetic acid salt; NMR (DMSO-d$_6$/TFA) 10.9 (s, 1), 9.6 (s, 1), 7.3–8.4 (m, 6), 4.1 (br d, 2), 2.6–3.8 (m, 14) ppm;

N-(5-chloropyridin-2-yl)-2-[((4-((N'-(2-hydroxyethyl)amino)methyl)-3-chlorothiophen-2-yl)carbonyl)amino]-3-(morpholin-4-yl)-5-chlorobenzamide, trifluoroacetic acid salt; NMR (DMSO-d$_6$/TFA) 10.9 (s, 1), 9.6 (s, 1), 7.3–8.5 (m, 6), 4.1 (br d, 2), 2.8–3.8 (m, 14) ppm;

N-(5-chloropyridin-2-yl)-2-[((4-(N'-methyl-N'-(2-(dimethylamino)ethyl)amino)-3-chlorothiophen-2-yl)carbonyl)amino]-3-chloro-5-(N'-methyl-N'-(ethoxycarbonyl)methylamino)benzamide; trifluoroacetic acid salt; NMR (DMSO-d$_6$/TFA) 10.9 (s, 1), 9.6 (s, 1), 6.9–8.4 (m, 6), 5.6 (s, 2), 4.4 (s, 2), 4.3 (s, 2), 4.1 (q, 2), 3.5 (br d, 4), 3.0 (s, 3), 2.8 (s, 3), 2.7 (s, 3), 1.2 (t, 3) ppm;

N-(5-chloropyridin-2-yl)-2-[((4-((N'-methyl-N'-(2-hydroxyethyl)amino)methyl)-3-chlorothiophen-2-yl)carbonyl)amino]-3-(morpholin-4-yl)-5-chlorobenzamide, trifluoroacetic acid salt; NMR (DMSO-d$_6$/TFA) 10.9 (s, 1), 9.6 (s, 1), 7.3–8.5 (m, 6), 4.2 4.5 (m, 2), 3.6–3.9 (m, 6), 3.1–3.3 (m, 2), 2.9 (br d, 2), 2.8 (s, 3) ppm;

N-(5-chloropyridin-2-yl)-2-[((4-((N'-methyl-N'-(1-methylpiperidin-4-yl)amino)methyl)-3-chlorothiophen-2-yl)carbonyl)amino]-3-(morpholin-4-yl)-5-chlorobenzamide, trifluoroacetic acid salt; NMR (DMSO-$d_6$/TFA) 10.9 (s, 1), 9.5 (s, 1), 7.3–8.5 (m, 6), 3.0–4.2 (m, 14), 2.9 (s, 3), 2.5 (s, 3) ppm;

N-(5-chloropyridin-2-yl)-2-[((4-((N'-methyl-N'-(2-(morpholin-4-yl)ethyl)amino)methyl)-3-chlorothiophen-2-yl)carbonyl)amino]-3-(morpholin-4-yl)-5-chlorobenzamide, trifluoroacetic acid salt; NMR (DMSO-$d_6$/TFA) 11 (s, 1), 9.6 (s, 1), 7.3–8.5 (m, 6), 4.1 (br d, 2), 3.8 (br d, 4), 3.7 (br d, 4), 3.0–3.4 (m, 8), 2.9 (br d, 4), 2.5 (s, 3) ppm;

N-(5-chloropyridin-2-yl)-2-[((4-((N'-methyl-N'-(3-(dimethylamino)propyl)amino)methyl)-3-chlorothiophen-2-yl)carbonyl)amnino]-3-(morpholin-4-yl)-5-chlorobenzamide, trifluoroacetic acid salt; NMR (DMSO-$d_6$/TFA) 10.9 (s, 1), 9.5 (s, 1), 7.3–8.5 (m, 6), 2.9–3.7 (m, 14), 2.4 (m, 4), 2.1 (s, 3), 2.2 (s, 6), 1.6 (m, 2) ppm;

N-(5-chloropyridin-2-yl)-2-[((4-((N'-methyl-N'-(2-(pyrrolidin-1-yl)ethyl)amino)methyl)-3-chlorothiophen-2-yl)carbonyl)amino]-3-(morpholin-4-yl)-5-chlorobenzamide, trifluoroacetic acid salt; NMR (DMSO-$d_6$/TFA) 11 (s, 1), 9.6 (s, 1), 7.3–8.5 (m, 6), 2.8–4.2 (m, 14), 2.5 (s, 3), 1.8–2.0 (m, 4) ppm;

N-(5-chloropyridin-2-yl)-2-[((4-((N'-methyl-N'-(2-methoxyethyl)amino)methyl)-3-chlorothiophen-2-yl)carbonyl)amino]-3-(morpholin-4-yl)-5-chlorobenzamide, trifluoroacetic acid salt; NMR (DMSO-$d_6$/TFA) 10.9 (s, 1), 9.6 (s, 1), 7.3–8.5 (m, 6), 4.2–4.6 (m, 2), 3.6–3.8 (m, 6), 3.3 (s, 3H, 2.6–2.8 (m, 4) ppm;

N-(5-chloropyridin-2-yl)-2-[((4-((4-ethylpiperazin-1-yl)methyl)-3-chlorothiophen-2-yl)carbonyl)amino]-3-(morpholin-4-yl)-5-chlorobenzamide, trifluoroacetic acid salt; NMR (DMSO-$d_6$/TFA) 10.9 (s, 1), 9.6 (s, 1), 7.3–8.5 (m, 6), 2.9–3.9 (m, 18), 2.5 (s, 3), 1.2 (t, 3) ppm;

N-(5-chloropyridin-2-yl)-2-[((4-((N', N'-di(2-hydroxypropyl)amino)methyl)-3-chlorothiophen-2-yl)carbonyl)amino]-3-methoxy-5-chlorobenzamide, trifluoroacetic acid salt; NMR (DMSO-$d_6$/TFA) 10.9 (s, 1), 9.6 (s, 1), 7.2–8.5 (m, 6), 4.0–4.6 (m, 4), 3.1–3.4 (m, 4), 1.1 (s, 3), 1.2 (s, 3) ppm;

N-(5-chloropyridin-2-yl)-2-[((4-((N'-methyl-N'-(3-hydroxypropyl)amino)methyl)-3-chlorothiophen-2-yl)carbonyl)amino]-3-methoxy-5-chlorobenzamide, trifluoroacetic acid salt; NMR (DMSO-$d_6$/TFA) 10.9 (br d, 1), 9.6 (br d, 1), 7.2–8.5 (m, 6), 4.2–4.5 (m, 4), 3.9 (s, 3), 3.0–3.4 (m, 2), 2.7 (s, 3), 2.2 (m, 2) ppm;

N-(5-chloropyridin-2-yl)-2-[((4-((N'-(1-methylethyl)-N'-(2-(pyrrolidin-1-yl)ethyl)amino)methyl)-3-chlorothiophen-2-yl)carbonyl)amino]-3-(morpholin-4-yl)-5-chlorobenzamide, trifluoroacetic acid salt; NMR (DMSO-$d_6$/TFA) 10.9 (d, 1), 9.6 (d, 1), 7.3–8.5 (m, 6), 4.7 (m, 2), 3.3–3.8 (m, 13), 2.9 (s, 3), 2.1 (m, 4), 1.3 (m, 6) ppm;

N-(4-chlorophenyl)-2-[((4-((N'-methyl-N'-(2-hydroxyethyl)amino)methyl)-3-chlorothiophen-2-yl)carbonyl)amino]-3-(morpholin-4-yl)-5-chlorobenzamide, trifluoroacetic acid salt; NMR (DMSO-$d_6$/TFA) 10.5 (s, 1), 9.7 (s, 1), 7.2–8.3 (m, 7), 4.2–4.5 (m, 2), 3–3.9 (m, 8), 2.9 (br d, 4), 2.8 (s, 3) ppm;

N-(5-chloropyridin-2-yl)-2-[((4-((N'-methyl-N'-(2,2-dimethyl-2-hydroxyethyl)amino)methyl)-3-chlorothiophen-2-yl)carbonyl)amino]-3-methoxy-5-chlorobenzamide, trifluoroacetic acid salt; NMR (DMSO-$d_6$/TFA) 10.9 (s, 1), 9.6 (s, 1), 7.2–8.5 (m, 6), 4.2–4.6 (m, 2), 3.9 (s, 3), 3.0–3.3 (m, 2), 2.9 (s, 3), 1.3 (s, 3), 1.2 (s, 3) ppm;

N-(5-chloropyridin-2-yl)-2-[((4-((N'-methyl-N'-(2-hydroxyethyl)amino)methyl)-3-chlorothiophen-2-yl)carbonyl)amino]-3-(4-(ethoxycarbonyl)piperidin-1-yl)-5-chlorobenzamide, trifluoroacetic acid salt; NMR (DMSO-$d_6$/TFA) 10.9 (s, 1), 9.5 (s, 1), 7.3–8.5 (m, 6), 4.2– 4.5 (m, 2), 4.0 (q, 2), 3.7 (t, 2), 3.0–3.5 (m, 4), 2.6–2.9 (m, 5), 1.6–2.0 (m, 4), 1.1 (t, 3) ppm;

N-(5-chloropyridin-2-yl)-2-[((4-((N'-methyl-N'-(2,3-dihydroxypropyl)amino)methyl)-3-chlorothiophen-2-yl)carbonyl)amino]-3-(morpholin-4-yl)-5-chlorobenzamide, trifluoroacetic acid salt; NMR (DMSO-$d_6$/TFA) 10.9 (s, 1), 9.6 (s, 1), 7.3–8.5 (m, 6), 3.8–4.4 (m, 3), 3.7 (s, 3), 2.7–3.5 (m, 11) ppm;

N-(5-chloropyridin-2-yl)-2-[((4-((N'-methyl-N'-(2-hydroxyethyl)amino)methyl)-3-chlorothiophen-2-yl)carbonyl)amino]-3-(di(2-methoxyethyl)amino)-5-chlorobenzamide, trifluoroacetic acid salt; NMR (DMSO-$d_6$/TFA) 11.0 (s, 1), 9.7 (s, 1), 7.3–8.4 (m, 6), 4.2–4.5 (m, 2), 3.7 (t, 2), 3.2–3.4 (m, 10), 3.1 (s, 6) ppm;

N-(5-chloropyridin-2-yl)-2-[((4-((N'-methyl-N'-(1-methylpiperidin-4-yl)amino)methyl)-3-chlorothiophen-2-yl)carbonyl)amino]-3-hydroxy-5-chlorobenzamide, trifluoroacetic acid salt; NMR (DMSO-$d_6$/TFA) 10.9 (s, 1), 9.8 (br, 1), 9.4 (s, 1), 8.4 (s, 1), 8.2 (s, 1), 8.2 (d, 1), 7.9 (dd, 1), 4.4 (dd, 2), 3.6 (br, 2), 3.1 (br, 2), 2.9 (s, 3), 2.8 (s, 3), 2.4 (br, 2), 2.0 (q, 2) ppm;

N-(5-chloropyridin-2-yl)-2-[((4-((N'-methyl-N'-(2-(dimethylamino)ethyl)amino)methyl)-3-chlorothiophen-2-yl)carbonyl)amino]-3-hydroxy-5-chlorobenzamide, trifluoroacetic acid salt; NMR (DMSO-$d_6$/TFA) 10.9 (s, 1), 9.4 (s, 1), 8.3 (s, 1), 8.2 (s, 1), 8.1 (d, 1), 7.8 (dd, 1), 7.2 (2s, 2), 4.4 (s, 2), 3.6 (s, 4), 2.9 (s, 6), 2.8 (s, 3) ppm;

N-(5-chloropyridin-2-yl)-2-[((4-((N'-methyl-N'-(2-hydroxyethyl)amino)methyl)-3-chlorothiophen-2-yl)carbonyl)amino]-3-hydroxy-5-chlorobenzamide, trifluoroacetic acid salt; NMR (DMSO-$d_6$/TFA) 10.9 (s, 1), 9.6 (br, 1), 9.4 (s, 1), 8.4 (s, 1), 8.2 (s, 1), 8.1 (d, 1), 7.9 (dd, 1), 4.4 (d, 1), 4.3 (d, 1), 3.8 (t, 2), 3.2 (br, 2), 2.8 (s, 3) ppm;

N-(4-chlorophenyl)-2-[((4-((4-methylpiperazin-1-yl)methyl)-3-chlorothiophen-2-yl)carbonyl)amino]-5-fluorobenzamide, trifluoroacetic acid salt; NMR (DMSO-$d_6$/TFA) 11.0 (s, 1), 10.7 (s, 1), 8.3 (dd, 1), 7.9 (s, 1), 7.8 (m, 1), 7.7 (d, 2), 7.5 (m, 1), 7.4 (d, 2), 3.6 (s, 2), 3.4 (br, 2), 3.0 (br, 6), 2.8 (s, 3) ppm;

N-(4-chlorophenyl)-2-[((3-chloro-4-((((2-hydroxyethoxy)ethyl)amino)methyl)thiophen-2-yl)carbonyl)amino]-5-chlorobenzamide, trifluoroacetic acid salt; NMR (DMSO-$d_6$/TFA) 11.2 (s, 1), 10.8 (s, 1), 9.0 (br s, 2), 8.3 (d, 1), 8.2 (s, 1), 8.0 (s, 1), 7.8 (d, 2), 7.7 (d, 1), 7.4 (d, 2), 4.2 (s, 2), 3.7 (m, 2), 3.5 (m, 4), 3.2 (br s, 2) ppm;

N-(4-chlorophenyl)-2-[((3-chloro-4-((4-(2-(2-hydroxyethoxy)ethyl)piperazin-1-yl)methyl)thiophen-2-yl)carbonyl)amino]-5-chlorobenzamide, trifluoroacetic acid salt; NMR (DMSO-$d_6$/TFA) 11.2 (s, 1), 10.8 (s, 1), 8.4 (d, 1), 8.3 (s, 1), 8.0 (s, 1), 7.8 (d, 2), 7.6 (d, 1), 7.4 (d, 2), 4.4 (s, 2), 3.8 (br s, 2), 3.5 (m, 14) ppm;

N-(4-chlorophenyl)-2-[((3-chloro-4-((N'-(2-methylpropyl)amino)methyl)thiophen-2-yl)carbonyl)amino]-5-chlorobenzamide;

N-(5-chloropyridin-2-yl)-2-[((4-((N'-methyl-N'-(2-hydroxyethyl)amino)methyl)-3-chlorothiophen-2-yl)carbonyl)amino]-3-(pyrrolidin-1-yl)-5-chlorobenzamide, trifluoroacetic acid salt; NMR (DMSO-$d_6$/TFA) 10.8 (s, 1), 9.6 (s, 1), 9.6 (br s, 1), 8.4 (s, 1), 8.2 (s, 1), 8.1 (d, 1), 7.8 (d, 1), 7.0 (s, 1), 6.9 (s, 1), 4.4 (d, 1), 4.3 (d, 1), 3.8 (m, 2), 3.4 (m, 4), 3.2 (m, 2), 2.8 (s, 3), 1.9 (br s, 4) ppm;

N-(4-chlorophenyl)-2-[((3-chloro-4-((N'-methyl-N'-(3-(dimethylamino)propyl)amino)methyl)thiophen-2-yl)carbonyl)amino]-5-chlorobenzamide, trifluoroacetic acid salt; NMR (DMSO-d$_6$/TFA) 11.2 (s, 1), 10.8 (s, 1), 8.3 (d, 1), 8.2 (s, 1), 7.9 (d, 1), 7.7 (d, 2), 7.6 (dd, 1), 7.4 (d, 2), 4.4 (m, 2), 3.1 (m, 4), 2.8 (s, 9), 2.1 (m, 2) ppm;

N-(4-chlorophenyl)-2-[((3-chloro-4-((N'-methyl-N'-(2,3,4,5,6-pentahydroxyhexyl)amino)methyl)thiophen-2-yl)carbonyl)amino]-5-chlorobenzamide, trifluoroacetic acid salt; NMR (DMSO-d$_6$/TFA) 11.1 (s, 1), 10.4 (s, 1), 8.3 (d, 1), 8.2 (s, 1), 7.9 (d, 1), 7.6 (d, 2), 7.5 (dd, 1), 7.3 (d, 2), 4.3 (s, 2), 4.1 (m, 1), 3.9 (m, 1), 3.7 (d, 1), 3.6 (dd, 1), 3.5 (d, 1), 3.4 (dd, 1), 3.3 (m, 2), 3.0 (br, 1), 2.8 (s, 3), 2.5 (s, 1) ppm;

N-(4-chlorophenyl)-2-[((3-chloro-4-((N'-(2-hydroxyethyl)-N'-(1,1-di(hydroxymethyl)-2-hydroxyethyl)amino)methyl)thiophen-2-yl)carbonyl)amino]-5-chlorobenzamide, trifluoroacetic acid salt; NMR (DMSO-d$_6$/TFA) 11.2 (s, 1), 10.8 (s, 1), 8.7 (br, 1), 8.3 (d, 1), 8.1 (s, 1), 7.9 (d, 1), 7.7 (d, 2), 7.6 (dd, 1), 7.4 (d, 2), 4.3 (s, 2), 3.8 (s, 1), 3.6 (s, 8), 3.5 (s, 1) ppm;

N-(5-chloropyridin-2-yl)-2-[((4-((N'-methyl-N'-(pyridin-2-yl)methyl)amino)methyl)-3-chlorothiophen-2-yl)carbonyl)amino]-3-methoxy-5-chlorobenzamide, trifluoroacetic acid salt; NMR (DMSO-d$_6$/TFA) 10.9 (s, 1), 9.4 (s, 1), 8.6 (d, 1), 8.4 (d, 1), 8.2 (s, 1), 8.1 (d, 1), 7.9 (m, 2), 7.6 (d, 1), 7.5 (m, 1), 7.4 (s, 1), 7.2 (s, 1), 4.5 (s, 2), 4.3 (s, 2), 3.9 (s, 3), 2.8 (s, 3) ppm;

N-(4-chlorophenyl)-2-[((3-chloro-4-((N'-methyl-N'-(1-methylpiperidin4-yl)amino)methyl)thiophen-2-yl)carbonyl)amino]-5-chlorobenzamide, trifluoroacetic acid salt; NMR (DMSO-d$_6$/TFA) 11.2 (s, 1), 10.8 (s, 1), 8.4 (d, 2), 8.0 (s, 1), 7.7 (m, 3), 7.4 (d, 2), 3.6 (m, 2), 3.0 (m, 2), 2.8 (s, 3), 1.8–2.4 (br, 4) ppm;

N-(4-chlorophenyl)-2-[((3-chloro-4-((N'-(2-hydroxyethyl)-N'-(2-(morpholin-4-yl)ethyl)amino)methyl)thiophen-2-yl)carbonyl)amino]-5-chlorobenzamide, trifluoroacetic acid salt; NMR (DMSO-d$_6$/TFA) 11.2 (s, 1), 10.8 (s, 1), 8.3 (d, 1), 8.2 (s, 1), 8.0 (s, 1), 7.7 (m, 2), 7.4 (d, 2), 4.4 (s, 2), 3.8 (m, 4), 3.5 (m, 3), 3.2 (m, 5) ppm;

N-(4-chlorophenyl)-2-[((3-chloro-4-((4-ethylpiperazin-1-yl)methyl)thiophen-2-yl)carbonyl)amino]-5-chlorobenzamide, trifluoroacetic acid salt; NMR (DMSO-d$_6$/TFA) 11.1 (s, 1), 10.8 (s, 1), 8.3 (d, 1), 7.9 (d, 2), 7.7 (m, 3), 7.4 (d, 2), 3.6 (s, 2), 3.4 (br, 3), 3.2 (m, 2), 3.0 (m, 3), 2.4 (m, 2), 1.1 (t, 2) ppm;

N-(4-chlorophenyl)-2-[((3-chloro-4-((4-acetylpiperazin-1-yl)methyl)thiophen-2-yl)carbonyl)amino]-5-chlorobenzamide, trifluoroacetic acid salt; NMR (DMSO-d$_6$/TFA) 11.2 (s, 1), 10.8 (s, 1), 8.4 (d, 1), 8.2 (s, 1), 8.0 (s, 1), 7.7 (m, 3), 7.4 (d, 2), 4.3 (br, 2), 2.8–4.0 (br, 8), 2.0 (s, 3) ppm;

N-(4-chlorophenyl)-2-[((3-chloro-4-((N'-(4-methylpiperazin-1-yl)amino)methyl)thiophen-2-yl)carbonyl)amino]-5-chlorobenzamide;

N-(4-chlorophenyl)-2-[((3-chloro-4-((N'-methyl-N'-(2,3-dihydroxypropyl)amino)methyl)thiophen-2-yl)carbonyl)amino]-5-chlorobenzamide, trifluoroacetic acid salt; NMR (DMSO-d$_6$/TFA) 11.1 (s, 1), 10.8 (s, 1), 8.3 (d, 1), 8.0 (d, 2), 7.8 (d, 2), 7.7 (d, 1), 7.4 (d, 2), 4.4 (s, 2), 3.6 (m, 1), 3.5 (m, 1), 3.2–3.4 (br, 3), 2.5 (s, 3) ppm;

N-(5-chloropyridin-2-yl)-2-[((4-((4-methylpiperazin-1-yl)methyl)-3-chlorothiophen-2-yl)carbonyl)amino]-3-methoxy-5-chlorobenzamide, trifluoroacetic acid salt; NMR(DMSO-d$_6$/TFA) 10.9 (s, 1), 9.4 (s, 1), 8.3 (d, 1), 8.2 (s, 1), 8.1 (d, 1), 7.8 (dd, 1), 7.3 (d, 2), 4.4 (s, 2), 3.8 (s, 3), 3.1–3.8 (m, 8), 2.9 (s, 3) ppm;

N-(4-chlorophenyl)-2-[(((4-((4-methylpiperazin-1-yl)methyl)-3-chlorothiophen-2-yl)carbonyl)amino]-3-hydroxy-5-chlorobenzamide, trifluoroacetic acid salt; NMR (DMSO-d$_6$/TFA) 10.4 (s, 1), 9.4 (s, 1), 8.2 (s, 1), 7.5 (d, 2), 7.3 (d, 2), 7.1 (m, 2), 4.4 (s, 2), 3.1–3.9 (m, 8), 2.9 (s, 3) ppm;

N-(5-chloropyridin-2-yl)-2-[((4-((4-methylpiperazin-1-yl)methyl)-3-chlorothiophen-2-yl)carbonyl)amino]-3-hydroxy-5-chlorobenzamide, trifluoroacetic acid salt; NMR(DMSO-d$_6$/TFA) 10.8 (s, 1), 9.4 (s, 1), 8.3 (d, 1), 8.2 (s, 1), 8.1 (d, 1), 7.8 (dd, 1), 7.1 (m, 2), 4.4 (s, 2), 3.0–3.8 (br m, 8), 2.9 (s, 3) ppm;

N-(5-chloropyridin-2-yl)-2-[((4-(((2-hydroxyethyl)amino)methyl)-3-chlorothiophen-2-yl)carbonyl)amino]-3-methoxy-5-chlorobenzamide, trifluoroacetic acid salt; NMR(DMSO-d$_6$/TFA) 10.9 (br s, 1), 9.4 (s, 1), 8.9 (br s, 2), 8.3 (d, 1), 8.1 (d, 1), 8.0 (s, 1), 7.8 (dd, 1), 7.3 (s, 1), 7.2 (s, 1), 4.2 (t, 2), 3.8 (s, 3), 3.6 (t, 2), 3.0 (br s, 2) ppm;

N-(5-chloropyridin-2-yl)-2-[((4-((pyridinium-1-yl)methyl)-3-chlorothiophen-2-yl)carbonyl)amino]-3-methoxy-5-chlorobenzamide, trifluoroacetic acid salt; NMR(DMSO-d$_6$/TFA) 10.9 (br s, 1), 9.4 (s, 1), 9.1 (d, 2), 8.6 (t, 1), 8.3 (s, 1), 8.1 (m, 4), 7.8 (dd, 1), 7.3 (s, 1), 7.2 (s, 1), 5.8 (s, 2), 3.8 (s, 3) ppm;

N-(5-chloropyridin-2-yl)-2-[((4-((pyridinium-1-yl)methyl)-3-chlorothiophen-2-yl)carbonyl)amino]-3-hydroxy-5-chlorobenzamide, trifluoroacetic acid salt; NMR(DMSO-d$_6$/TFA) 10.8 (s, 1), 9.4 (s, 1), 9.1 (d, 2), 8.6 (dd, 1), 8.3 (s, 1), 8.2 (m, 3), 8.1 (d, 1), 7.8 (dd, 1), 7.1 (m, 2), 5.9 (s, 2) ppm;

N-(5-chloropyridin-2-yl)-2-[((4-((N'-methyl-N'-(2-hydroxypropyl)amino)methyl)-3-chlorothiophen-2-yl)carbonyl)amino]-3-methoxy-5-chlorobenzamide, trifluoroacetic acid salt; NMR (DMSO-d$_6$/TFA) 10.9 (s, 1), 9.5 (s, 1), 7.2–8.3 (m, 6), 4.0–4.5 (m, 2), 3.8 (s, 3), 2.3–3.3 (m, 5), 1.1 (m, 3) ppm;

N-(5-chloropyridin-2-yl)-2-[((4-((2-iminotetrahydrooxazol-3-yl)methyl)-3-chlorothiophen-2-yl)carbonyl)amino]-3-methoxy-5-chlorobenzamide, trifluoroacetic acid salt; NMR (DMSO-d$_6$/TFA) 10.9 (s, 1), 9.6 (br s, 1), 9.4 (s, 1), 9.2 (br s, 1), 7.2–8.3 (m, 6), 4.7 (t, 2), 4.6 (s, 2), 3.8 (s, 3), 3.7 (t, 2) ppm;

N-(4-chlorophenyl)-2-[((3-chloro-4-((N',N'-dimethyl-N'-(2-hydroxyethyl)ammonio)methyl)thiophen-2-yl)carbonyl)amino]-5-chlorobenzamide, trifluoroacetic acid salt, NMR (DMSO-d$_6$/TFA) 11.2 (s, 1), 10.8 (s, 1), 8.4 (s, 1), 8.3 (d, 1), 7.9 (s, 1), 7.7 (m, 3), 7.4 (d, 2), 4.6 (s, 2), 3.9 (br m, 2), 3.4 (br m, 2), 3.0 (s, 6) ppm;

N-(4-chlorophenyl)-2-[((3-chloro-4-((N',N'-dimethyl-N'-(3-hydroxypropyl)ammonio)methyl)thiophen-2-yl)carbonyl)amino]-5-chlorobenzamide, trifluoroacetic acid salt, NMR (DMSO-d$_6$/TFA) 11.2 (s, 1), 10.8 (s, 1), 8.4 (s, 1), 8.3 (d, 1), 8.0 (s, 1), 7.8 (m, 3), 7.4 (d, 2), 4.5 (s, 2), 3.5 (t, 1), 3.4 (m, 3), 3.0 (s, 6), 1.9 (m, 3) ppm;

N-(5-chloropyridin-2-yl)-2-[((4-((4-methylpiperazin-1-yl)methyl)-3-chlorothiophen-2-yl)carbonyl)amino]-3-chloro-5-(N'-methyl-N'-(ethoxycarbonyl)methylamino)benzamide, trifluoroacetic acid salt;

N-(4-methylphenyl)-2-[(((4-((4-methylpiperazin-1-yl)methyl)-3-chlorothiophen-2 -yl)carbonyl)amino]benzamide, trifluoroacetic acid salt;

N-(5-chloropyridin-2-yl)-2-[((4-((4-methylpiperazin-1-yl)methyl)-3-chlorothiophen-2-yl)carbonyl)amino]-3-amino-5-chlorobenzamide, trifluoroacetic acid salt;

N-(4-chlorophenyl)-2-[((4-((2-aminoimidazol-1-yl)methyl)-3-chlorothiophen-2-yl)carbonyl)amino]-3-methoxy-5-chlorobenzamide, trifluoroacetic acid salt;

NMR (DMSO-d₆/TFA) 12.18 (br s, 1), 10.45 (s, 1), 9.50 (s, 1), 7.75 (s, 1), 7.69 (s, 1), 7.65 (d, 2), 7.39 (d, 1), 7.36 (d, 2) 7.28 (d, 1), 6.98 (d, 1), 6.91 (d, 1), 5.05 (s, 1), 3.85 (s, 3) ppm.

N-(5-chloropyridin-2-yl)-2-[((4-((N'-methyl-N'-(2-(dimethylamino)ethyl)amino)methyl)-3-chlorothiophen-2-yl)carbonyl)amino]-3-methoxy-5-chlorobenzamide, trifluoroacetic acid salt; NMR (DMSO-d₆/TFA) 10.9 (s, 1), 9.5 (s, 1), 8.3 (d, 1), 8.2 (s, 1), 8.1 (d, 1), 7.9 (dd, 1), 7.4 (d, 1), 7.2 (d, 1), 4.4 (s, 2), 3.8 (s, 3), 3.5 (s, 4), 2.9 (s, 6), 2.8 (s, 3) ppm;

N-(4-chlorophenyl)-2-[((4-(((1,1-di(hydroxymethyl)-2-hydroxyethyl)amino)methyl)-3-chlorothiophen-2-yl)carbonyl)amino]-5-chlorobenzamide, trifluoroacetic acid salt; NMR (DMSO-d₆) 11.2 (s, 1), 10.8 (s, 1), 8.7 (br, 1), 8.4 (d, 1), 8.2 (s, 1), 7.9 (s, 1), 7.7 (m, 3), 7.4 (d, 2), 5.4 (br, 1), 4.3 (s, 2), 3.6 (s, 6) ppm;

N-(5-chloropyridin-2-yl)-2-[((4-((3-methyl-2-imino-2,3-dihydroimidazol-1-yl)methyl)-3-chlorothiophen-2-yl)carbonyl)amino]-3-methoxy-5-chlorobenzamide, trifluoroacetic acid salt; NMR (DMSO-d₆/TFA) 10.8 (s, 1), 9.4 (s, 1), 8.3 (d, 1), 8.1 (d, 1), 7.9 (br s, 2), 7.8 (dd, 1), 7.6 (s, 1), 7.3 (dd, 2), 7.0 (dd, 2), 5.0 (s, 2), 3.9 (s, 3), 3.4 (s, 3) ppm;

N-(5-chloropyridin-2-yl)-2-[((4-((1,4,5,6-tetrahydropyrimidin-1-yl)methyl)-3-chlorothiophen-2-yl)carbonyl)amino]-3-methoxy-5-chlorobenzamide, trifluoroacetic acid salt; NMR (DMSO-d₆/TFA) 10.9 (s, 1), 9.9 (s, 1), 9.4 (s, 1), 8.4 (d, 1), 8.3 (s, 1), 8.05 (d, 1), 8.0 (s, 1), 7.8 (dd, 1), 7.3 (s, 1), 7.2 (s, 1), 4.6 (s, 2), 3.9 (s, 3), 3.2 (bm, 4), 1.8 (bm, 3) ppm;

N-(5-chloropyridin-2-yl)-2-[((4-(hydroxy)methyl-3-chlorothiophen-2-yl)carbonyl)amino]-3-methoxy-5-chlorobenzamide, trifluoroacetic acid salt; NMR (DMSO-d₆/TFA-d) 10.9 (s, 1), 9.4 (s, 1), 8.4 (d, 1), 8.1 (dd, 1), 7.9 (dd, 1), 7.7 (d, 1), 7.3 (dd, 2), 4.4 (s, 2), 3.9 (s, 3) ppm;

N-(5-chloropyridin-2-yl)-2-[((4-((N'-(2-aminoethyl)amino)methyl)-3-chlorothiophen-2-yl)carbonyl)amino]-3-methoxy-5-chlorobenzamide, trifluoroacetic acid salt; NMR (DMSO-d₆/TFA) 10.9 (s, 1), 9.4 (d, 1), 9.2 (br s, 1), 8.4 (d, 1), 8.2 (d, 1), 8.1 (s, 1), 7.8~8.0 (m, 2), 7.4 (d, 1), 7.3 (d, 1), 4.3 (s, 2), 3.9 (s, 3), 3.2~3.4 (m, 4) ppm;

N-(5-chloropyridin-2-yl)-2-[((4-((2-(methoxymethyl)imidazolin-1-yl)methyl)-3-chlorothiophen-2-yl)carbonyl)amino]-3-methoxy-5-chlorobenzamide, trifluoroacetic acid salt; NMR (DMSO-d₆/TFA) 10.9 (s, 1), 10.4 (s, 1), 9.4 (d, 1), 8.4 (d, 1), 8.1 (d, 1), 8.0 (s, 1), 7.9 (dd, 1), 7.4 (d, 1), 7.3 (d, 1), 4.6 (s, 2), 4.55 (s, 2), 3.9 (s, 3), 3.8 (br s, 4), 3.4 (s, 3) ppm;

N-(5-chloropyridin-2-yl)-2-[((4-((4-(pyrimidin-2-yl)piperazin-1-yl)methyl)-3-chlorothiophen-2-yl)carbonyl)amino]-3-methoxy-5-chlorobenzamide, trifluoroacetic acid salt; NMR (DMSO-d₆/TFA) 10.9 (s, 1), 9.4 (d, 1), 9.0 (s, 1), 8.6 (d, 1), 8.4 (d, 1), 8.1 (d, 1), 7.9 (dd, 1), 7.8 (s, 1), 7.4 (d, 1), 7.3 (d, 1), 4.6 (s, 2), 3.9 (s, 3), 3.4 (m, 2), 2.6 (m, 2), 1.6~1.8 (m, 4) ppm;

N-(5-chloropyridin-2-yl)-2-[((4-(((5-hydroxymethyl-1-methylimidazol-2-yl)thio)methyl)-3-chlorothiophen-2-yl)carbonyl)amino]-3-methoxy-5-chlorobenzamide, trifluoroacetic acid salt; NMR (DMSO-d₆/TFA) 10.9 (s, 1), 9.4 (d, 1), 8.4 (d, 1), 8.1 (d, 1), 7.7 (dd, 1), 7.6 (s, 1), 7.5 (s, 1), 7.3 (d, 1), 7.2 (d, 1), 4.5 (s, 2), 4.3 (s, 2), 3.9 (s, 3), 3.6 (s, 3) ppm;

N-(5-chloropyridin-2-yl)-2-[((4-(((imidazol-2-yl)thio)methyl)-3-chlorothiophen-2-yl)carbonyl)amino]-3-methoxy-5-chlorobenzamide, trifluoroacetic acid salt; NMR (DMSO-d₆/TFA) 10.9 (s, 1), 9.4 (d, 1), 8.3 (d, 1), 8.1 (d, 1), 7.8 (dd, 1), 7.6 (s, 2), 7.5 (s, 1), 7.3 (d, 1), 7.2 (d, 1), 4.4 (s, 2), 3.8 (s, 3) ppm;

N-(5-chloropyridin-2-yl)-2-[((4-((4-methylimidazol-1-yl)methyl)-3-chlorothiophen-2-yl)carbonyl)amino]-3-methoxy-5-chlorobenzamide and N-(5-chloropyridin-2-yl)-2-[((4-((5-methylimidazol-1-yl)methyl)-3-chlorothiophen-2-yl)carbonyl)amino]-3-methoxy-5-chlorobenzamide (2:1 mixture), trifluoroacetic acid salt; NMR (DMSO-d₆) 10.77 (s, 0.3), 10.75 (s, 0.7), 9.37 (s, 0.3), 9.36 (s, 0.7), 9.04 (d, 0.7), 9.01 (d, 0.3), 8.32 (d, 1), 8.06 (d, 1), 7.98 (s, 0.7), 7.88 (dd, 1), 7.80 (s, 0.3), 7.45 (t, 0.3), 7.38 (t, 0.7), 7.35 (m, 1), 7.26 (d, 1), 5.36 (s, 0.6), 5.34 (s, 1.4), 3.84 (s, 3), 2.23 (s, 3) ppm;

N-(5-chloropyridin-2-yl)-2-[((4-((4-(hydroxymethyl)imidazol-1-yl)methyl)-3-chlorothiophen-2-yl)carbonyl)amino]-3-methoxy-5-chlorobenzamide and N-(5-chloropyridin-2-yl)-2-[((4-((5-(hydroxymethyl)imidazol-1-yl)-3-chlorothiophen-2-yl)carbonyl)amino]-3-methoxy-5-chlorobenzamide (2:1 mixture), trifluoroacetic acid salt; NMR (DMSO-d₆) 10.78 (s, 0.4), 10.77 (s, 0.6), 9.37 (s, 1), 9.10 (d, 0.6), 9.01 (d, 0.4), 8.32 (d, 1), 8.06 (dd, 1), 8.00 (s, 0.6), 7.88 (dd, 1), 7.81 (s, 0.4), 7.58 (s, 0.4), 7.52 (s, 0.6), 7.36 (m, 1), 7.26 (m, 1), 5.40 (s, 0.8), 5.38 (s, 1.2), 4.50 (s, 0.8), 4.47 (s, 1.2), 3.84 (1, 3) ppm;

N-(5-chloropyridin-2-yl-2-[((4-((N'-(imino(pyridin-4-yl)methyl)amino)methyl)-3-chlorothiophen-2-yl)carbonyl)amino]-3-methoxy-5-chlorobenzamide, trifluoroacetic acid salt; NMR (DMSO-d₆) 10.90 (s, 1), 10.38 (t, 1), 9.85 (s, 1), 9.70 (b, 1), 9.53 (s, 1), 9.40 (s, 1), 8.85 (ddd, 2), 8.35 (d, 1), 8.08 (d, 1), 7.95 (s, 1), 7.90 (dd, 1), 7.70 (ddd, 2), 7.38 (d, 1), 7.25 (d, 1), 4.60 (d, 2), 3.83 (s, 3) ppm;

N-(5-chloropyridin-2-yl)-2-[((4-((N'-(imino(pyrazin-2-yl)methyl)amino)methyl)-3-chlorothiophen-2-yl)carbonyl)amino]-3-methoxy-5-chlorobenzamide, trifluoroacetic acid salt; NMR (DMSO-d₆/TFA) 10.90 (s, 1), 10.60 (b, 1), 10.00 (s, 1), 9.70 (s, 1), 9.40 (d, 2), 9.00 (d, 1), 8.90 (d, 1), 8.30 (d, 1), 8.10 (d, 1), 7.90 (s, 1), 7.85 (dd, 1), 7.30 (d, 1), 7.25 (d, 1), 4.65 (d, 2), 3.80 (s, 3) ppm;

N-(5-chloropyridin-2-yl)-2-[((4-((N'-(2-(imidazol-4yl)ethyl)amino)methyl)-3-chlorothiophen-2-yl)carbonyl)amino]-3-methoxy-5-chlorobenzamide, trifluoroacetic acid salt; NMR (DMSO-d₆) 10.90 (s, 1), 9.40 (s, 1), 9.00 (s, 1), 8.35 (d, 1), 8.10 (d, 1), 8.00 (s, 1), 7.90 (dd, 1), 7.50 (s, 1), 7.40 (s, 1), 7.25 (s, 1), 4.20 (s, 2), 3.80 (s, 3), 3.30 (t, 2), 3.00 (t, 2) ppm;

N-(5-chloropyridin-2-yl)-2-[((4-((2,4-dimethylimidazol-1-yl)methyl)-3-chlorothiophen-2-yl)carbonyl)amino]-3-methoxy-5-chlorobenzamide and N-(5-chloropyridin-2-yl)-2-[((4-((2,5-dimethylimidazol-1-yl)methyl)-3-chlorothiophen-2-yl)carbonyl)amino]-3-methoxy-5-chlorobenzamide (9:1 mixture), trifluoroacetic acid salt; NMR (DMSO-d₆) 10.90 (s, 1), 9.42 (s, 0.2), 9.40 (s, 0.8), 8.35 (d, 1), 8.10 (d, 1), 7.90 (m, 2), 7.40 (d, 0.2), 7.35 (d, 1), 7.25 (d, 1), 7.20 (d, 0.8), 5.30 (s, 0.4), 5.25 (s, 1.6), 3.80 (s, 3), 2.58 (s, 2.5), 2.54 (s, 0.5), 2.18 (s, 2.5), 2.13 (d, 0.5) ppm;

N-(5-chloropyridin-2-yl)-2-[((4-((2-(N'-amino-N'-methylamino)imidazolin-1-yl)methyl)-3-chlorothiophen-2-yl)carbonyl)amino]-3-methoxy-5-chlorobenzamide, trifluoroacetic acid salt; NMR (DMSO-d₆) 10.80 (s, 1), 9.30 (s, 1), 8.30 (d, 1), 8.20 (s, 1), 8.05 (dd, 1), 7.90 (dd, 1), 7.80 (s, 1), 7.35 (dd, 1), 7.25 (d, 1), 4.90 (s, 2), 3.80 (s, 3), 3.65 (t, 2), 3.50 (t, 2), 3.15 (s, 3) ppm;

N-(5-chloropyridin-2-yl)-2-[((4-((2-aminoimidazol-1-yl)methyl)-3-chlorothiophen-2-yl)carbonyl)amino]-5-chlorobenzamide, trifluoroacetic acid salt; NMR (DMSO- $d_6$/TFA) 12.20 (s, 1), 11.30 (b, 1), 11.10 (s, 1), 8.35 (d, 1), 8.20 (d, 1), 8.10 (s, 1), 7.90 (m, 2), 7.70 (b, 2), 7.60 (s, 1), 7.55 (dd, 1), 6.85 (s, 1), 6.80 (s, 1), 5.05 (s, 2) ppm;

N-(5-chloropyridin-2-yl)-2-[((4-((2-(methylthio)imidazolin-1-yl)methyl)-3-chlorothiophen-2-yl)carbonyl)amino]-3-methoxy-5-chlorobenzamide, trifluoroacetic acid salt; NMR (DMSO-$d_6$/TFA) 10.9 (s, 1), 10.1 (s, 1), 9.4 (s, 1), 8.3 (s, 1), 8.1 (d, 1), 7.9 (s, 1), 7.8 (d, 1), 7.3 (s, 1), 7.2 (s, 1), 4.6 (s, 2), 3.8 (s, 3), 3.8 (s, 4), 2.6 (s, 3) ppm;

N-(5-chloropyridin-2-yl)-2-[((4-((imidazolin-2-yl)thio)methyl)-3-chlorothiophen-2-yl)carbonyl)amino]-3-methoxy-5-chlorobenzamide, trifluoroacetic acid salt; NMR (DMSO-$d_6$/TFA) 10.6 (s, 1), 10.3 (s, 2), 9.4 (s, 1), 8.3 (s, 1), 8.1 (d, 1), 7.9 (s, 1), 7.8 (d, 1), 7.4 (s, 1), 7.3 (s, 1), 4.5 (s, 2), 3.8 (s, 3), 3.8 (s, 4) ppm;

N-(5-chloropyridin-2-yl)-2-[((4-((2-(methylamino)imidazol-1-yl)methyl)-3-chlorothiophen-2-yl)carbonyl)amino]-3-methoxy-5-chlorobenzamide, trifluoroacetic acid salt; NMR (DMSO-$d_6$/TFA) 10.9 (s, 1), 9.4 (d, 1), 8.4 (d, 1), 8.1 (d, 1), 8.1 (d, 1), 7.8 (d, 1), 7.7 (d, 1), 7.3 (d, 1), 7.2 (d, 1), 4.6 (d, 2), 3.9 (s, 3), 3.6 (m, 2), 2.9~3.2 (m, 5), 2.2 (m, 2) ppm; and N-(5-chloropyridin-2-yl)-2-[((4-((2-(ethylamino)imidazol-1-yl)methyl)-3-chlorothiophen-2-yl)carbonyl)amino]-3-methoxy-5-chlorobenzamide, trifluoroacetic acid salt; NMR (DMSO-$d_6$/TFA) 10.9 (s, 1), 9.4 (d, 1), 8.3 (d, 1), 8.1 (d, 2), 7.8 (d, 1), 7.6 (s, 1), 7.35 (s, 1), 7.3 (s, 1), 7.0 (s, 1), 6.9 (s, 1), 5.1 (s, 2), 3.9 (s, 3), 3.2 (m, 2), 1.2 (t, 3) ppm.

E. To methylamine (2.0 M in tetrahydrofuran, 16 mL, 32 mmol) was added a solution of N-(5-chloropyridin-2-yl)-2-[((4-(chloromethyl)-3-chlorothiophen-2-yl)carbonyl)amino]-5-chlorobenzamide (3.0 g, 6.3 mmol) in DMF (10 mL) and the mixture stirred at ambient temperature. After 4 hours the reaction mixture was poured into water (100 mL), concentrated in vacuo to remove the tetrahydrofuran and extracted with ethyl acetate (2×75 mL). The combined organics were washed with brine (75 mL), dried over MgSO$_4$ and concentrated of all volatiles in vacuo. Purification by flash chromatography on silica gel afforded 1.1 g (38% yield) of N-(5-chloropyridin-2-yl)-2-[((4-((methylamino)methyl)-3-chlorothiophen-2-yl)carbonyl)amino]-5-chlorobenzamide as a yellow solid; NMR (DMSO-$d_6$/TFA) 11.4 (s, 1), 11.0 (s, 1), 8.9 (br s, 2), 7.6–8.4 (m, 7), 4.2 (m, 2), 2.6 (m, 3) ppm.

F. In a similar manner, the following compounds were made:

N-(5-chloropyridin-2-yl)-2-[((4-((methylamino)methyl)-3-chlorothiophen-2-yl)carbonyl)amino]-3-methoxy-5-chlorobenzamide; NMR (CDCl$_3$) 9.8 (br, 1), 9.1 (br, 1), 8.3 (d, 1), 7.9 (d, 1), 7.6 (dd, 1), 7.5 (s, 1), 7.1 (d, 1), 7.0 (d, 1), 3.9 (s, 3), 3.7 (s, 2), 2.4 (s, 3) ppm;

N-(5-chloropyridin-2-yl)-2-[((4-((methylamino)methyl)-3-chlorothiophen-2-yl)carbonyl)amino]-3-(4-methylpiperazin-1-yl)-5-chlorobenzamide; NMR (DMSO-$d_6$/TFA) 11.0 (s, 1), 9.6 (s, 1), 9.0 (s, 1), 8.3 (s, 1), 8.1 (d, 1), 8.0 (s, 1), 7.8 (dd, 1), 7.4 (d, 2), 4.1 (s, 2), 3.5 (d, 2), 3.3 (d, 2), 3.1 (d, 4), 2.8 (s, 3), 2.6 (s, 3) ppm;

N-(5-chloropyridin-2-yl)-2-[((4-((methylamino)methyl)-3-chlorothiophen-2-yl)carbonyl)amino]-3-(4-(tert-butoxycarbonyl)piperazin-1-yl)-5-chlorobenzamide; NMR (DMSO-$d_6$) 8.3 (s, 1), 8.1 (d, 1), 7.9 (s, 2), 7.8 (dd, 1), 7.6 (br, 1), 7.4 (s, 2), 7.3 (br, 1), 3.6 (s, 2), 2.9 (br, 8), 2.3 (s, 3), 1.4 (s, 9) ppm;

5-(N-(5-chloropyridin-2-yl)amino)carbonyl-6-[4-(((methyl)amino)methyl)-3-chlorothiophen-2-yl)carbonyl]amino-1,3-benzodioxole;

N-(5-chloropyridin-2-yl)-2-[((4-((methylamino)methyl)-3-chlorothiophen-2-yl)carbonyl)amino]-3-(morpholin-4-yl)-5-chlorobenzamide; NMR (DMSO-$d_6$) 10.9 (s, 1), 9.6 (s, 1), 7.2–8.4 (m, 6), 4.4 (s, 2), 3.7 (m, 4), 3.3 (m, 4), 2.9 (s, 3) ppm;

N-(5-chloropyridin-2-yl)-2-[((4-((ethylamino)methyl)-3-chlorothiophen-2-yl)carbonyl)amino]-3-methoxy-5-chlorobenzamide;

N-(5-chloropyridin-2-yl)-2-[((4-((ethylamino)methyl)-3-chlorothiophen-2-yl)carbonyl)amino]-3-(morpholin-4-yl)-5-chlorobenzamide;

N-(4-chlorophenyl)-2-[((4-((methylamino)methyl)-3-chlorothiophen-2-yl)carbonyl)amino]-3-methoxy-5-chlorobenzamide;

N-(4-chlorophenyl)-2-[((4-((methylamino)methyl)-3-chlorothiophen-2-yl)carbonyl)amino]-3-(morpholin-4-yl)-5-chlorobenzamide;

N-(5-chloropyridin-2-yl)-2-[((4-((N'-methyl-N'-((-1,2,4-oxadiazol-3-yl)methyl)amino)methyl)-3-chlorothiophen-2-yl)carbonyl)amino]-3-methoxy-5-chlorobenzamide; NMR (DMSO-$d_6$) 10.9 (s, 1), 9.6 (s, 1), 9.4 (s, 1), 8.4 (d, 1), 8.1 (d, 1), 7.9 (dd, 1), 7.8 (s, 1), 7.4 (d, 1), 7.2 (d, 1), 3.9 (s, 3), 3.8 (s, 2), 3.6 (s, 2), 2.2 (s, 3) ppm.

G. A suspension of N-(4-chlorophenyl)-2-[((4-(chloromethyl)-3-chlorothiophen-2-yl)carbonyl)amino]-5-chlorobenzamide (0.70 g, 1.6 mmol), N-hydroxy-N-methylamine hydrochloride (0.26 g, 3.2 mmol), K$_2$CO$_3$ (0.94 g, 3.2 mmol) and triethylamine (0.88 mL, 6.4 mmol) in DMF (30 mL) was stirred at ambient temperature. After 16 hours, the mixture was poured onto ice water (200 mL) and the resulting precipitate collected by filtration. Purification by HPLC on a C18 Dynamax column with acetonitrile in water gradient with 0.1% trifluoroacetic acid afforded N-(4-chlorophenyl)-2-[((3-chloro-4-((N'-methyl-N'-hydroxyamino)methyl)thiophen-2-yl)carbonyl)amino]-5-chlorobenzamide, trifluoroacetic acid salt as a white solid; NMR (DMSO-$d_6$/TFA) 11.2 (s, 1), 10.8 (s, 1), 8.4 (d, 1), 8.2 (s, 1), 7.9 (s, 1), 7.7 (d, 2), 7.6 (d, 1), 7.4 (d, 2), 4.6 (d, 1), 4.5 (d, 1), 3.1 (s, 3) ppm.

H. In a similar manner, the following compound was prepared:

N-(5-chloropyridin-2-yl)-2-[((4-(N'-methyl-N"-aminoguanidino)methyl-3-chlorothiophen-2-yl)carbonyl)amino]-3-methoxy-5-chlorobenzamide, trifluoroacetic acid salt; NMR (DMSO-$d_6$/TFA) 10.9 (s, 1), 9.4 (s, 1), 8.3 (s, 1), 8.1 (d, 1), 7.8 (d, 1), 7.7 (s, 1), 7.4 (s, 2), 7.3 (s, 1), 7.2 (s, 1), 4.6 (s, 2), 3.8 (s, 3) ppm.

I. To a solution of N-(5-chloropyridin-2-yl)-2-[((4-((methylamino)methyl)-3-chlorothiophen-2-yl)carbonyl)amino]-3-methoxy-5-chlorobenzamide (0.20 g, 0.4 mmol) in DMF (5 mL) were added methyl 2-chloro-4-(trifluoromethyl)pyrimidine-5-carboxylate (0.12 g, 0.48 mmol) and diisopropylethylamine (0.10 g, 0.8 mmol). The mixture was stirred at ambient temperature for 16 hours, and then poured onto brine (10 mL) and extracted with ethyl acetate (3×25 mL). The combined organics were washed with brine (10 mL), dried over Na$_2$SO$_4$ and concentrated in vacuo. Purification by chromatography on silica gel afforded 0.26 g (92% yield) of N-(5-chloropyridin-2-yl)-2-[((4-((N'-methyl-N'-(4-trifluoromethyl-5-(methoxycarbonyl)pyrimidin-2-yl)amino)methyl)-3-chlorothiophen-2-yl)carbonyl)amino]-3-methoxy-5-chlorobenzamide; NMR (DMSO-$d_6$/TFA) 10.9 (s, 1), 9.4 (s, 1), 7.3–8.9 (m, 7), 4.9 (m, 2), 3.9 (s, 3), 3.8 (s, 3), 3.2 (s, 3) ppm.

J. In a similar manner, the following compounds were made:

N-(5-chloropyridin-2-yl)-2-[((4-((N'-methyl-N'-(4-trifluoromethyl-5-(methoxycarbonyl)pyrimidin-2-yl)

amino)methyl)-3-chlorothiophen-2-yl)carbonyl)amino]-3-(morpholin-4-yl)-5-chlorobenzamide; NMR (DMSO-$d_6$/TFA) 10.9 (s, 1), 9.5 (s, 1), 7.3–9 (m, 7), 4.9 (s, 2), 3.8 (s, 3), 3.8 (br s, 4), 3.2 (s, 3), 2.9 (br s, 4), 2.8 (s, 3) ppm;

N-(5-chloropyridin-2-yl)-2-[((4-((N'-ethyl-N'-(4-methyloxazolin-2-yl)amino)methyl-3-chlorothiophen-2-yl)carbonyl)amino]-3-methoxy-5-chlorobenzamide; NMR (CDCl$_3$) 9.0 (s, 1), 8.6 (s, 1), 8.3 (d, 1), 8.2 (d, 1), 7.6 (d, 1), 7.4 (s, 1), 7.3 (d, 1), 7.1 (s, 1), 4.4 (m, 3), 4.1 (m, 1), 3.9 (s, 3), 3.8 (t, 1), 3.3 (q, 2), 1.2 (d, 3), 1.1 (t, 3) ppm;

N-(5-chloropyridin-2-yl)-2-[((4-((N'-methyl-N'-(cyanomethyl)amino)methyl)-3-chlorothiophen-2-yl)carbonyl)amino]-3-methoxy-5-chlorobenzamide; NMR (DMSO-$d_6$) 10.9 (s, 1), 9.4 (s, 1), 8.4 (d, 1), 8.1 (d, 1), 7.9 (dd, 1), 7.8 (s, 1), 7.4 (d, 1), 7.2 (d, 1), 3.9 (s, 3), 3.7 (s, 2), 3.5 (s, 2), 2.2 (s, 3) ppm;

N-(5-chloropyridin-2-yl)-2-[((4-((N'-(4-(ethoxycarbonyl)oxazolin-2-yl)amino)methyl)-3-chlorothiophen-2-yl)carbonyl)amino]-3-methoxy-5-chlorobenzamide; NMR (DMSO-$d_6$/TFA) 10.9 (s, 1), 9.9 (s, 1), 9.5 (s, 1), 9.4 (s, 1), 8.2 (d, 1), 8.1 (d, 2), 7.9 (dd, 1), 7.6 (m, 2), 7.2 (s, 2), 4.6 (s, 2), 3.9 (t, 2), 3.8 (s, 3), 34 (t, 2) ppm;

N-(5-chloropyridin-2-yl)-2-[((4-((N'-methyl-N'-(4-(ethoxycarbonyl)oxazolin-2-yl)amino)methyl)-3-chlorothiophen-2-yl)carbonyl)amino]-3-(morpholin-4-yl)-5-chlorobenzamide; NMR (DMSO-$d_6$/TFA) 10.9 (s, 1)7 9.5 (s, 1), 8.3 (d, 1), 8.1 (d, 1), 8.0 (s, 1), 7.8 (s, 1), 7.7 (dd, 1), 7.55 (m, 1), 7.3 (m, 2), 5.6 (s, 1), 5.4 (s, 1), 4.4 (s, 2), 4.1 (q, 2), 3.6 (m, 4), 2.95 (s, 2), 2.9 (m, 4), 1.2 (t, 3) ppm;

N-(5-chloropyridin-2-yl)-2-[((4-((N'-methyl-N'-((3-((methylthio)methyl)-1,2,4-oxadiazol-5-yl)methyl)amino)methyl)-3-chlorothiophen-2-yl)carbonyl)amino]-3-methoxy-5-chlorobenzamide; NMR (DMSO-$d_6$) 10.9 (s, 1), 9.4 (s, 1), 8.4 (d, 1), 8.1 (d, 1), 7.9 (dd, 1), 7.8 (s, 1), 7.4 (d, 1), 7.2 (d, 1), 4.0 (s, 2), 3.9 (s, 3), 3.8 (s, 2), 3.6 (s, 2), 2.3 (s, 3), 2.1 (s, 3) ppm; and N-(5-chloropyridin-2-yl)-2-[((4-((N'-methyl-N'-((3-(methoxymethyl)-1,2,4-oxadiazol-5-yl)methyl)amino)methyl)-3-chlorothiophen-2-yl)carbonyl)amino]-3-methoxy-5-chlorobenzamide; NMR (DMSO-$d_6$) 10.9 (s, 1), 9.4 (s, 1), 8.4 (d, 1), 8.1 (d, 1), 7.9 (dd, 1), 7.8 (s, 1), 7.4 (d, 1), 7.2 (d, 1), 4.5 (s, 2), 4.0 (s, 2), 3.9 (s, 3) ppm. 3.6 (s, 2), 3.3 (s, 3), 2.3 (s, 3) ppm.

K. In a manner similar to that described in Paragraph I above, N-(5-chloropyridin-2-yl)-2-[((4-((methylamino)methyl)-3-chlorothiophen-2-yl)carbonyl)amino]-3-methoxy-5-chlorobenzamide (1.5 g, 3 mmol) reacted with 2-chloro-5-methyl-4,5-dihydrooxazoline (2.7 g, 23 mmol) and triethylamine (0.78 mL, 5.6 mmol) to afford N-(5-chloropyridin-2-yl)-2-[((4-((N'-methyl-N'-(5-methyl-4,5-dihydrooxazolin-2-yl)amino)methyl)-3-chlorothiophen-2-yl)carbonyl)amino]-3-methoxy-5-chlorobenzamide. Purification by HPLC on a C18 Dynamax column with 20–80% acetonitrile in water gradient with 0.1% trifluoroacetic acid afforded the trifluoroacetic acid salt as a white solid: NMR (DMSO-$d_6$/TFA) 10.9 (s, 1), 9.4 (s, 1), 8.4 (d, 1), 8.1 (d, 1), 7.9 (dd, 1), 7.5 (s, 1), 7.4 (s, 1), 7.3 (s, 1), 4.4 (s, 2), 4.2 (m, 1), 3.8 (s, 3), 3.2 (m, 2), 2.8 (s, 3), 1.4 (d, 3) ppm.

L. In a similar manner, the following compound was made:

N-(5-chloropyridin-2-yl)-2-[((4-((N'-(3,4-dihydro-2H-pyrrol-5-yl)amino)methyl)-3-chlorothiophen-2-yl)carbonyl)amino]-3-methoxy-5-chlorobenzamide, trifluoroacetic acid salt; NMR (DMSO-$d_6$/TFA) 10.9 (s, 1), 9.4 (s, 1), 8.3 (d, 1), 8.2 (br s, 1), 8.1 (d, 1), 8.0 (br s, 1), 7.7 (dd, 1), 7.4 (d, 1), 7.3 (d, 1), 4.6 (s, 2), 3.9 (s, 3), 3.1~3.3 (m, 6) ppm.

M. To a solution of N-(5-chloropyridin-2-yl)-2-[((4-((methylamino)methyl)-3-chlorothiophen-2-yl)carbonyl)amino]-3-methoxy-5-chlorobenzamide (0.50 g, 1.0 mmol) in DMF (5 mL) were added 2-fluoropyridine (1 mL, 12 mmol) and cesium carbonate (0.33 g, 1.0 mmol) and the mixture was heated at 125° C. After 72 hours the mixture was cooled to ambient temperature, filtered and acidified with aqueous trifluoroacetic acid. Purification by HPLC on a C18 Vydac column with acetonitrile in water gradient with 0.1% trifluoroacetic acid afforded N-(5-chloropyridin-2-yl)-2-[((4-((N'-methyl-N'-(pyridin-2-yl)amino)methyl)-3-chlorothiophen-2-yl)carbonyl)amino]-3-methoxy-5-chlorobenzamide, trifluoroacetic acid salt as a white solid: NMR (DMSO-$d_6$/TFA) 10.9 (s, 1), 9.4 (s, 1), 8.4 (d, 1), 8.1 (d, 1), 8.0–7.9 (m, 3), 7.8 (dd, 1), 7.7 (s, 1), 7.4 (s, 1), 7.2 (d, 1), 7.1 (d, 1), 6.9 (t, 1), 4.8 (s, 2), 3.8 (s, 3), 3.2 (s, 3) ppm.

N. To a suspension of N-(4-chlorophenyl)-2-[((4,5-di(chloromethyl)-3-chlorothiophen-2-yl)carbonyl)amino]-5-chlorobenzamide (0.075 g, 0.14 mmol) in acetonitrile (3 mL) in a pressure vessel was added propylamine (0.025 mL, 0.30 mmol). The vessel was sealed and the suspension heated at 50° C. for 10 days, with additional 0.025 mL portions of propylamine being added after 3 and 9 days. The mixture was cooled to ambient temperature and concentrated of all volatiles in vacuo. The resulting solid was dissolved in acetonitrile, water and trifluoroacetic acid and purified by HPLC on a C18 Vydac column with 25–60% acetonitrile in water gradient with 0.1% trifluoroacetic acid to afford N-(4-chlorophenyl)-2-[((3-chloro-4,5-di((n-propyl)aminomethyl)thiophen-2-yl)carbonyl)amino]-5-chlorobenzamide, trifluoroacetic acid salt as a white solid; NMR (DMSO-$d_6$/TFA) 11.3 (s, 1), 10.8 (s, 1), 8.9 (br s, 2), 8.7 (br s, 2), 8.4 (d, 1), 7.4–8.0 (m, 6), 4.6 (s, 2), 4.3 (s, 2), 3.0 (m, 4), 1.6 (m, 4), 0.9 (m, 6) ppm.

O. In a manner similar to that described in Paragraph I above, N-(5-chloropyridin-2-yl)-2-[((4-((methylamino)methyl)-3-chlorothiophen-2-yl)carbonyl)amino]-3-methoxy-5-chlorobenzamide (0.86 g, 1.7 mmol) reacted with 2-methanesulfonyl-4-aminopyrimidine (0.60 g, 3.5 mmol) and diisopropylethylamine (0.90 mL, 5.2 mmol) in DMSO at 90° C. Purification by chromatography on silica gel afforded 0.78 g (76% yield) of N-(5-chloropyridin-2-yl)-2-[((4-((N'-methyl-N'-(4-aminopyrimidin-2-yl)amino)methyl)-3-chlorothiophen-2-yl)carbonyl)amino]-3-methoxy-5-chlorobenzamide, as a light brown solid; NMR (DMSO-$d_6$) 10.9 (s, 1), 9.4 (s, 1), 8.4 (d, 1), 8.1 (d, 1), 7.9 (dd, 1), 7.8 (d, 1), 7.5 (s, 1), 7.4 (d, 1), 7.3 (d, 1), 6.0 (br s, 1), 5.9 (d, 1), 4.8 (s, 2), 3.9 (s, 3), 3.0 (s, 3) ppm.

P. In a similar manner, the following compounds were made:

N-(5-chloropyridin-2-yl)-2-[((4-((N'-(4-aminopyrimidin-2-yl)amino)methyl)-3-chlorothiophen-2-yl)carbonyl)amino]-3-methoxy-5-chlorobenzamide; NMR (DMSO-$d_6$) 10.90 (s, 1H), 9.38 (s, 1H), 8.36 (d, 1H), 8.10 (d, 1H), 7.90 (dd, 1H), 7.69 (s, 1H), 7.62 (d, 1H), 7.38 (d, 1H), 7.28 (d, 1H), 5.96–5.92 (m, 2H), 5.80–5.74 (m, 2H), 4.35 (s, 2H), 3.90 (s, 3H) ppm;

N-(5-chloropyridin-2-yl)-2-[((4-((N'-(4-(methylamino)pyrimidin-2-yl)amino)methyl)-3-chlorothiophen-2-yl)carbonyl)amino]-3-methoxy-5-chlorobenzamide; NMR (DMSO-$d_6$) 11.90 (br s, 1H), 10.90 (s, 1H), 9.40 (s, 1H), 8.50 (s, 1H), 8.30 (d, 1H), 8.10 (d, 1H), 8.00–7.50 (m, 3H), 7.40 (d, 1H), 7.25 (d,$_1$ H), 6.20–6.00 (m, 2H), 4.604.35 (m, 2H), 4.00–3.80 (m, 3H), 2.90–2.80 (m, 3H) ppm.

Q. To a solution of N-(5-chloropyridin-2-yl)-2-[((4-(chloromethyl)-3-chlorothiophen-2-yl)carbonyl)amino]-3-methoxy-5-chlorobenzamide (2.1 g, 4.1 mmol) in DMF (20 mL) was added a 2,2,2-trifluoroethylamine (3.2 mL, 41 mmol). The mixture was heated at 75° C. for 18 hours, then cooled to ambient temperature and concentrated in vacuo to remove excess 2,2,2-trifluoroethylamine. Water was added and the mixture was extracted with methylene chloride. The organic layer was dried over $Na_2SO_4$ and concentrated in vacuo. Purification by flash chromatography on silica gel afforded 2.2 g (95% yield) of N-(5-chloropyridin-2-yl)-2-[((4-(((2,2,2-trifluoroethyl)amino)methyl)-3-chlorothiophen-2-yl)carbonyl)amino]-3-methoxy-5-chlorobenzamide; NMR (DMSO-$d_6$/TFA) 10.8 (s, 1) 9.4 (s, 1), 8.2 (d, 1), 8.1 (d, 1), 8.0 (s, 1), 7.8 (dd, 1), 7.2 (d, 2), 4.2 (s, 2), 4.1 (q, 2), 3.8 (s, 3) ppm.

R. To a solution of N-(5-chloropyridin-2-yl)-2-[((4-((methylamino)methyl)-3-chlorothiophen-2-yl)carbonyl)amino]-3-methoxy-5-chlorobenzamide (0.57 g, 1.1 mmol) in THF (23 mL) was added methyl chlorothiolformate (0.10 mL, 1.15 mmol) at 0° C. and the mixture stirred for 2 hours. The reaction was concentrated in vacuo and the residue dissolved in ethyl acetate and 1 M HCl. The layers were separated and the organic layer was washed with brine, dried over sodium sulfate and concentrated in vacuo. Purification by flash chromatography on silica gel afforded 0.26 g (42% yield) of N-(5-chloropyridin-2-yl)-2-[((4-((N'-methyl-N'-((methylthio)carbonyl)amino)methyl)-3-chlorothiophen-2-yl)carbonyl)amino]-3-methoxy-5-chlorobenzamide, as a white solid; NMR (DMSO-$d_6$) 10.9 (s, 1), 9.4 (s, 1), 8.4 (d, 1), 8.1 (d, 1), 7.9 (d, 1), 7.6 (s, 1), 7.4 (s, 1), 7.2 (s, 1), 4.4 (s, 2), 3.9 (s, 3), 3.0 (s, 3), 2.2 (s, 3) ppm.

S. In a similar manner, the following compound was made:

N-(5-chloropyridin-2-yl)-2-[((4-((N'-ethyl-N'-((phenylthio)carbonyl)amino)methyl)-3-chlorothiophen-2-yl)carbonyl)amino]-3-methoxy-5-chlorobenzamide; NMR (CDCl$_3$) 9.0 (s, 1), 8.8 (s, 1), 8.2 (d, 1), 8.1 (d, 1), 7.6 (d, 1), 7.5 (m, 3), 7.4 (m, 3), 7.0 (s, 1), 4.6 (s, 2), 3.9 (s, 3), 3.5 (q, 2), 1.2 (m, 3) ppm.

T. In a manner similar to that described in Paragraph C above, DMF (6 mL) was added to a mixture of N-(5-chloropyridin-2-yl)-2-[((4-(chloromethyl)-3-chlorothiophen-2-yl)carbonyl)amino]-3-methoxy-5-chlorobenzamide (0.87 g, 1.73 mmol) and imidazole (0.35 g, 5.18 mmol) at ambient temperature. The mixture was heated at 45° C. for 15 hours. After cooling, additional imidazole (0.25 g, 3.67 mmol) was added, and the heating was continued for 5 days. The mixture was cooled in an ice bath, and trifluoroacetic acid (0.5 mL) was added dropwise. Purification by HPLC on a C18 Dynamax column with 20–70% acetonitrile in water gradient with 0.1% trifluoroacetic acid gave 0.85 g of N-(5-chloropyridin-2-yl)-2-[((4-((imidazol-1-yl)methyl)-3-chlorothiophen-2-yl)carbonyl)amino]-3-methoxy-5-chlorobenzamide, trifluoroacetic acid salt, as a white solid; NMR (DMSO-$d_6$/TFA) 10.85 (s, 1), 9.40 (s, 1), 9.20 (s, 1), 8.25 (d 1), 8.05 (d, 1), 7.95 (s, 1), 7.80 (dd, 1), 7.70 (s, 1), 7.60 (s, 1), 7.30 (d, 1), 7.20 (d, 1), 5.40 (s, 2), 3.80 (s, 3) ppm.

U. In a similar manner, the following compounds were made:

N-(5-chloropyridin-2-yl)-2-[((4-((2-methylimidazol-1-yl)methyl)-3-chlorothiophen-2-yl)carbonyl)amino]-3-methoxy-5-chlorobenzamide, trifluoroacetic acid salt; NMR (DMSO-$d_6$/TFA) 10.85 (s, 1), 9.40 (s, 1), 8.25 (d, 1), 8.05 (d, 1), 7.80 (m, 2), 7.50 (s, 2), 7.30 (s, 1), 7.20 (d, 1), 5.30 (s, 2), 3.80 (s, 3), 2.60 (s, 3) ppm;

N-(5-chloropyridin-2-yl)-2-[((4-((N'-(1,2,4-triazol-4-yl)amino)methyl)-3-chlorothiophen-2-yl)carbonyl)amino]-3-methoxy-5-chlorobenzamide, trifluoroacetic acid salt; NMR (DMSO-$d_6$/TFA) 10.9 (s, 1), 10.3 (s., 1), 9.4 (s, 1), 9.2 (s, 1), 8.4 (d, 1), 8.1 (m, 2), 7.9 (m, 1), 7.3 (d, 1), 7.2 (d, 1), 5.6 (s, 2), 3.9 (s, 3), ppm;

N-(5-chloropyridin-2-yl)-2-[((4-((2,6-diaminopurin-9-yl)methyl)-3-chlorothiophen-2-yl)carbonyl)amino]-3-methoxy-5-chlorobenzamide, trifluoroacetic acid salt, and N-(5-chloropyridin-2-yl)-2-[((4-((2,6-diaminopurin-7-yl)methyl)-3-chlorothiophen-2-yl)carbonyl)amino]-3-methoxy-5-chlorobenzamide, trifluoroacetic acid salt; NMR (DMSO-$d_6$) 10.90 (s, 0.5), 10.85 (s, 0.5), 9.40 (s, 0.5), 9.38 (s, 0.5), 8.50 (b, 0.6), 8.34 (m, 1), 8.18 (b, 0.4), 8.14 (s, 1), 8.04–8.09 (m, 2), 7.94 (b, 1), 7.88 (dd, 1), 7.72 (b, 0.4), 7.56 (s, 0.6), 7.36 (m, 2), 7.26 (dd, 1), 5.28 (s, 1), 5.20 (s, 1), 3.85 (s, 1.5), 3.84 (s, 1.5) ppm;

N-(5-chloropyridin-2-yl)-2-[((4-((2-imino-1,2-dihydropyrimidin-1-yl)methyl)-3-chlorothiophen-2-yl)carbonyl)amino]-3-methoxy-5-chlorobenzamide, trifluoroacetic acid salt; NMR (DMSO-$d_6$/TFA) 10.85 (s, 1), 9.40 (s, 1), 8.85 (d, 1), 8.50 (d, 1), 8.30 (d, 1), 8.10 (d, 1), 7.80 (dd, 1), 7.75 (s, 1), 7.30 (s, 1), 7.25 (s, 1), 7.05 (dd, 1), 5.25 (s, 2), 3.80 (s, 3) ppm;

N-(5-chloropyridin-2-yl)-2-[((4-((2-imino-1(2H)-pyridin-1-yl)methyl)-3-chlorothiophen-2-yl)carbonyl)amino]-3-methoxy-5-chlorobenzamide, trifluoroacetic acid salt; NMR (DMSO-$d_6$/TFA) 10.90 (s, 1), 9.40 (s, 1), 8.60 (b, 2), 8.30 (d, 1), 8.10 (d, 1), 8.00 (d, 1), 7.80–7.90 (m, 2), 7.45 (s, 1), 7.30 (s, 1), 7.25 (s, 1), 7.10 (d, 1), 6.90 (m, 1), 5.30 (s, 2), 3.80 (s, 3) ppm;

N-(5-chloropyridin-2-yl)-2-[((4-((3,5-diamino-4H-1,2,4-triazol-4-yl)methyl)-3-chlorothiophen-2-yl)carbonyl)amino]-3-methoxy-5-chlorobenzamide, trifluoroacetic acid salt; NMR (DMSO-$d_6$/TFA) 10.9 (s, 1), 9.4 (s, 1), 8.3 (s, 1), 8.1 (d, 1), 8.1 (s, 1), 7.9 (d, 1), 7.8 (s, 1), 7.3 (s, 1), 7.2 (s, 1), 5 (s, 2), 3.8 (s, 3) ppm;

N-(5-chloropyridin-2-yl)-2-[((4-((2-iminotetrahydrothiazol-3-yl)methyl)-3-chlorothiophen-2-yl)carbonyl)amino]-3-methoxy-5-chlorobenzamide, trifluoroacetic acid salt; NMR (DMSO-$d_6$/TFA-d) 8.3 (s, 1), 8.1 (d, 1), 7.8 (s, 1), 7.8 (dd, 1), 7.3 (dd, 2), 4.7 (s, 2) 3.9 (t, 2), 3.8 (s, 3) 3.5 (t, 2) ppm; and N-(5-chloropyridin-2-yl)-2-[((4-((4-imino-1(4H)-pyridinyl)methyl)-3-chlorothiophen-2-yl)carbonyl)amino]-3-methoxy-5-chlorobenzamide, trifluoroacetic acid salt; NMR (DMSO-$d_6$) 10.85 (s, 1), 9.40 (s, 1), 8.30 (d, 1), 8.15 (m, 4), 8.05 (d, 1), 7.90 (s, 1), 7.85 (dd, 1), 7.35 (d, 1), 7.25 (d, 1), 6.80 (d, 2), 5.30 (s, 2), 3.80 (s, 3) ppm.

V. In a similar manner to that described above in Paragraph T, N-(5-chloropyridin-2-yl)-2-[((4-(chloromethyl)-3-chlorothiophen-2-yl)carbonyl)amino]-3-methoxy-5-chlorobenzamide (0.31 g, 0.6 mmol) and pyrazole (0.56 g, 6.7 mmol) were mixed in DMF (20 mL). The mixture was heated at 50° C. for 2 days. It was then added to water and the precipitate was isolated by filtration. The solid was dissolved in $CH_2Cl_2$ (200 mL) and washed with water (2×50 mL) and brine (2×50 mL), dried ($Na_2SO_4$) and concentrated. Purification by silica gel chromatography using 20:1 $CH_2Cl_2$:$CH_3OH$ as the eluent and precipitation afforded N-(5-chloropyridin-2-yl)-2-[((4-((N'-(pyrazol-3-yl)amino)methyl)-3-chlorothiophen-2-yl)carbonyl)amino]-3-methoxy-5-chlorobenzamide, as a white solid; NMR (DMSO-$d_6$) 11.55 (br s, 1H), 10.90 (s, 1H), 9.35 (s, 1H), 8.36 (d, 1H), 8.10 (d, 1H), 7.90 (dd, 1H), 7.64 (s, 1H), 7.40–7.25 (m, 3H), 5.60 (br s, 1H), 5.50 (s, 1H), 4.20 (s, 2H), 3.85 (s, 3H) ppm.

W. In a manner similar to that described in Paragraph I above, to a solution of 2-methoxy-3,4,5,6-tetrahydropyridine (0.27 g, 2.4 mmol), N-(5-chloropyridin-2-yl)-2-[((4 -((methylamino)methyl)-3-chlorothiophen-2-yl)carbonyl)amino]-3-methoxy-5-chlorobenzamide (1.0 g, 2.0 mmol) and DMF (10 mL) at ambient temperature was added N,N-diisopropylethylamine (0.65 g, 5.0 mmol). The solution was then warmed to 70° C. for 3 days. It was then poured into water. The mixture was extracted with ethyl acetate. The organic layer was washed with brine, dried ($Na_2SO_4$) and concentrated. Purification by HPLC on a C18 Dynamax column with acetonitrile in water gradient with 0.1% trifluoroacetic acid afforded the trifluoroacetic acid salt of N-(5-chloropyridin-2-yl)-2-[((4-((N'-methyl-N'-(3,4,5,6-tetrahydropyridin-2-yl)amino)methyl)-3-chlorothiophen-2-yl)carbonyl)amino]-3-methoxy-5-chlorobenzamide, as a white solid; NMR (DMSO-$d_6$/TFA) 10.9 (s, 1), 9.4 (d, 1), 8.4 (d, 1), 9.2 (br s, 1), 8.3 (d, 1), 8.2 (d, 1), 7.9 (m, 2), 7.4 (d, 1), 7.3 (d, 1), 4.6 (d, 2), 3.9 (s, 3), 2.6~3.4 (7), 1.6 (m, 3) ppm.

X. In a manner similar to that described in Paragraph O above, a mixture of 2-amino-4-chloro-6-methylpyrimidine (0.3 g, 2.1 mmol), N-(5-chloropyridin-2-yl)-2-[((4-((methylamino)methyl)-3-chlorothiophen-2-yl)carbonyl) amino]-3-methoxy-5-chlorobenzamide (0.25 g, 0.5 mmol), N,N-diisopropylethylamine (0.44 mL, 2.5 mmol), and DMSO (5 mL) was heated under $N_2$ at 100° C. for 15 hours. The mixture was cooled in ice bath, and trifluoroacetic acid (0.5 mL) was added dropwise. Purification by HPLC on a C18 Dynamax column with 20–70% acetonitrile in water gradient with 0.1% trifluoroacetic acid gave 0.24 g of N-(5-chloropyridin-2-yl)-2-[((4-((N'-methyl-N'-(2-amino-6-methylpyrimidin-4-yl)amino)methyl)-3-chlorothiophen-2-yl)carbonyl)amino]-3-methoxy-5-chlorobenzamide, trifluoroacetic acid salt, as a white solid; NMR (DMSO-$d_6$/TFA) 10.85 (s, 1), 9.40 (s, 1), 8.30 (1, 1), 8.10 (d, 1), 7.80 (d, 1), 7.60 (m, 2), 7.30 (s, 1), 7.25 (s, 1), 6.35 (s, 0.3), 6.30 (s, 0.7), 4.80 (s, 1.5), 4.60 (s, 0.5), 3.80 (s, 3), 2.22 (s, 2.2), 2.18 (s, 0.8) ppm.

Y. In a similar manner, the following compounds were made:

N-(5-chloropyridin-2-yl)-2-[((4-((N'-methyl-N'-(2-chloropyrimidin-4-yl)amino)methyl)-3-chlorothiophen-2-yl)carbonyl)amino]-3-methoxy-5-chlorobenzamide, trifluoroacetic acid salt; NMR (DMSO-$d_6$) 10.85 (s, 1), 9.40 (s, 1), 8.30 (d, 1), 8.10 (d, 1), 8.09 (b, 1), 7.90 (dd, 1), 7.60 (s, 1), 7.35 (s, 1), 7.25 (s, 1), 6.70 (d, 1), 4.65 (b, 2), 3.80 (s, 3), 3.30 (s, 3) ppm; and N-(5-chloropyridin-2-yl)-2-[((4-((N'-methyl-N'-(pyridin-4-yl)amino)methyl)-3-chlorothiophen-2-yl)carbonyl) amino]-3-methoxy-5-chlorobenzamide, trifluoroacetic acid salt; NMR (DMSO-$d_6$/TFA) 10.85 (s, 1), 9.40 (s, 1), 8.30 (d, 1), 8.20 (b, 2), 8.10 (d, 1), 7.80 (dd, 1), 7.60 (s, 1), 7.30 (s, 1), 7.25 (s, 1), 7.00 (d, 2), 4.75 (s, 2), 3.80 (s, 3), 3.20 (s, 3) ppm.

Z. In a manner similar to Paragraph E above, N-(5-chloropyridin-2-yl)-2-[((4-(chloromethyl)-3-chlorothiophen-2-yl)carbonyl)amino]-3-methoxy-5-chlorobenzamide (1.0 g, 2.0 mmol) in DMF (5 mL) was reacted with dimethylamine (1.33 M in tetrahydrofuran, 7.5 mL, 10 mmol) to give N-(5-chloropyridin-2-yl)-2-[((4-((dimethylamino)methyl)-3-chlorothiophen-2-yl)carbonyl) amino]-3-methoxy-5-chlorobenzamide; which was purified by lyophilization from aqueous HCl to afford N-(5-chloropyridin-2-yl)-2-[((4-((dimethylamino)methyl)-3-chlorothiophen-2-yl)carbonyl)amino]-3-methoxy-5-chlorobenzamide; hydrochloric acid salt, as a white solid; NMR (DMSO-$d_6$/TFA) 10.9 (s, 1), 10.1 (br s, 1), 9.5 (s, 1), 8.3 (d, 1), 8.2 (s, 1), 8.1 (d, 1), 7.8 (dd, 1), 7.3 (dd, 2), 4.3 (br s, 2), 3.9 (s, 3), 2.8 (br s, 6) ppm.

AA. Other compounds of the invention may be prepared by methods similar to those described in this Example and by methods known to those of ordinary skill in the art.

EXAMPLE 2

Compounds of Formula (Ic)

A. To a suspension of N-(4-chlorophenyl)-2-[((5-(bromomethyl)-3-chlorothiophen-2-yl)carbonyl)amino]-5-chlorobenzamide (0.75 g, 1.5 mmol) in methylene chloride (25 mL) was added 1-methylpiperazine (0.8 mL, 7.3 mmol). The resultant mixture was stirred at ambient temperature for 18 hours, then diluted with methylene chloride. The mixture was washed with saturated aqueous $NaHCO_3$ and the aqueous layer was back-extracted with methylene chloride. The combined organics were dried over $MgSO_4$ and concentrated in vacuo. The resulting solid was dissolved in acetonitrile, water and trifluoroacetic acid. Purification by HPLC on a C18 Dynamax column with 20–80% acetonitrile in water gradient with 0.1% trifluoroacetic acid afforded N-(4-chlorophenyl)-2-[((5-((4-methylpiperazin-1-yl) methyl)-3-chlorothiophen-2-yl)carbonyl)amino]-5-chlorobenzamide, trifluoroacetic acid salt; NMR (DMSO-$d_6$/TFA) 11.2 (s, 1), 10.7 (s, 1), 8.3 (d, 1), 7.7 (d, 2), 7.6 (dd, 1), 7.3 (s, 2), 7.2 (dd, 1), 4.5 (s, 2), 3.6–3.2 (br m, 8), 2.8 (s, 3) ppm.

B. In a similar manner to that described in Paragraph A above, N-(4-chlorophenyl)-2-[((5-(bromomethyl)-3-chlorothiophen-2-yl)carbonyl)amino]-5-chlorobenzamide (0.5 g, 1.0 mmol) was reacted with thiomorpholine (0.5 mL, 4.8 mmol). Purification by flash chromatography on silica gel afforded 0.4 g (73% yield) of N-(4-chlorophenyl)-2-[((5-((thiomorpholin-4-yl)methyl)-3-chlorothiophen-2-yl) carbonyl)amino]-5-chlorobenzamide; as a pale yellow powder; NMR ($CDCl_3$) 11.0 (s, 1), 9.0 (s, 1), 8.2 (d, 1), 7.8 (d, 2), 7.5 (d, 1), 7.4 (d, 2), 7.4 (s, 1), 7.2 (dd, 1), 3.7 (s, 2), 2.8 (m, 4), 2.7 (m, 4) ppm.

C. In a similar manner, the following compounds were made:

N-(4-chlorophenyl)-2-[((3-chloro-5-(((2-(dimethylamino) ethyl)thio)methyl)thiophen-2-yl)carbonyl)amino]-5-chlorobenzamide; NMR (DMSO-$d_6$) 11.1 (s, 1), 10.8 (s, 1), 8.3 (d, 1), 7.9 (s, 1), 7.7 (d, 2), 7.6 (dd, 1), 7.4 (d, 2), 7.2 (s, 1), 4.0 (s, 2), 3.3 (m, 2), 2.8–2.7 (m, 8) ppm;

N-(4-chlorophenyl)-2-[((3-chloro-5-((N'-methyl-N'-(2-dimethylaminoethyl)amino)methyl)thiophen-2-yl) carbonyl)amino]-5-chlorobenzamide; NMR (DMSO-$d_6$/TFA) 11.2 (s, 1), 10.8 (s, 1), 8.4 (d, 1), 7.9 (s, 1), 7.7 (d, 2), 7.6 (dd, 1), 7.4 (s, 1), 7.3 (d, 2), 4.6 (s, 2), 3.5 (s, 4), 2.8 (s, 6), 2.7 (s, 3) ppm;

N-(4-chlorophenyl)-2-[((3-chloro-5-((4-(ethoxycarbonylmethyl)piperazin-1-yl)methyl)thiophen-2-yl)carbonyl)amino]-5-chlorobenzamide; NMR (DMSO-$d_6$) 11.2 (s, 1), 10.8 (s, 1), 8.3 (d, 1), 7.3–8.0 (m, 7), 4.4 (s, 2), 4.2 (m, 4), 3.3 (br d, 8), 1.2 (t, 3) ppm;

N-(4-chlorophenyl)-2-[((3-((4-methylpiperazin-1-yl) methyl)thiophen-2-yl)carbonyl)amino]-5-chlorobenzamide;

N-(4-chlorophenyl)-2-[((3-chloro-5-(morpholin-4-yl) methylthiophen-2-yl)carbonyl)amino]-5-chlorobenzamide;

N-(4-chlorophenyl)-2-[((3-chloro-5-(N'-methyl-N'-(2-hydroxyethyl)amino)methylthiophen-2-yl)carbonyl) amino]-5-chlorobenzamide;

N-(4-chlorophenyl)-2-[((3-chloro-5-(N'-methyl-N'-(ethoxycarbonylmethyl)amino)methylthiophen-2-yl)carbonyl)amino]-5-chlorobenzamide;

N-(4-chlorophenyl)-2-[((3-chloro-5-(N',N'-di(2-hydroxyethyl)amino)methyl)thiophen-2-yl)carbonyl)amino]-5-chlorobenzamide;

N-(4-chlorophenyl)-2-[((3-chloro-5-((4-(((2-(2-methoxyethoxy)ethoxy)methyl)carbonyl)piperazin-1-yl)methyl)thiophen-2-yl)carbonyl)amino]-5-chlorobenzamide;

N-(4-chlorophenyl)-2-[((3-chloro-5-(((N'-(3-dimethylaminophenyl)amino)methyl)thiophen-2-yl)carbonyl)amino]-5-chlorobenzamide;

N-(4-fluorophenyl)-2-[((3-chlorobenzo[b]thien-2-yl)carbonyl)amino]-5-(pyrrolidin-1-yl)methylbenzamide;

N-(4-fluorophenyl)-2-[((3-chlorobenzo[b]thien-2-yl)carbonyl)amino]-5 -(dimethylamino)methylbenzamide;

N-(4-chlorophenyl)-2-[((3-(4-methylpiperazin-1-yl)methylbenzo[b]thien-2-yl)carbonyl)amino]-5-chlorobenzamide;

N-(4-fluorophenyl)-2-[((3-chlorobenzo[b]thien-2-yl)carbonyl)amino]-5-(amino)methylbenzamide;

N-(4-chlorophenyl)-2-[((3-chloro-6-(4-methylpiperazin-1-yl)methylbenzo[b]thien-2-yl)carbonyl)amino]-5-chlorobenzamide;

N-(4-chlorophenyl)-2-[((3-chloro-6-(4-(ethoxycarbonylmethyl)piperazin-1-yl)methylbenzo[b]thien-2-yl)carbonyl)amino]-5-chlorobenzamide; NMR (DMSO-d$_6$) 11.4 (s, 1), 10.8 (s, 1), 8.3 (d, 1), 7.4–8.0 (m, 9), 4.1 (m, 2), 3.6 (s, 2), 3.2 (s, 2), 3.1 (m, 1), 2.7 (m, 1), 2.4 (br m, 6), 1.2 (t, 3) ppm.

D. To a suspension of N-(4-chlorophenyl)-2-[((3-(bromomethyl)benzo[b]thien-2-yl)carbonyl)amino]-5-chlorobenzamide (0.075 g, 0.14 mmol) in methylene chloride (1.5 mL) in a pressure vessel was added dimethylamine hydrochloride (0.035 g, 0.43 mmol), followed by Bio-Rad AGI-X8 anion exchange resin (0.55 g, 0.7 mmol equivalents, OH$^-$ form). The vessel was sealed and the mixture was stirred at ambient temperature for 3.5 hours. The vessel was opened and the reaction mixture diluted with methylene chloride (25 mL) and acetonitrile (25 mL), filtered and concentrated in vacuo. Purification by flash chromatography on silica gel, followed by crystallization from acetonitrile afforded 0.030 g (43% yield) of N-(4-chlorophenyl)-2-[((3-(dimethylamino)methylbenzo[b]thien-2-yl)carbonyl)amino]-5-chlorobenzamide, as a crystalline solid; NMR (DMSO-d$_6$/TFA) 13.2 (s, 1), 10.7 (s, 1), 7.3–8.1 (m, 11), 3.9 (s, 2), 2.1 (s, 6) ppm.

E. In a similar manner, the following compounds were made:

N-(4-fluorophenyl)-2-[((3-chlorobenzo[b]thien-2-yl)carbonyl)amino]-5-(pyrrolidin-1-yl)methylbenzamide;

N-(4-fluorophenyl)-2-[((3-chlorobenzo[b]thien-2-yl)carbonyl)amino]-5-(dimethylamino)methylbenzamide;

N-(4-chlorophenyl)-2-[((3-chloro-6-(dimethylamino)methylbenzo[b]thien-2-yl)carbonyl)amino]-5-chlorobenzamide;

N-(4-chlorophenyl)-2-[((5-((dimethylamino)methyl)-3-chlorothiophen-2-yl)carbonyl)amino]-5-chlorobenzamid.

F. Other compounds of the invention may be prepared by methods similar to those described in this Example and by methods known to those of ordinary skill in the art.

EXAMPLE 3

Compounds of Formula (Id)

A. To a solution of N-(4-chlorophenyl)-2-[((4-(chloromethyl)-3-chlorothiophen-2-yl)carbonyl)amino]-3-methoxy-5-chlorobenzamide (0.52 g, 1.1 mmol) in DMF (12 mL) was added sodium thiomethoxide (0.39 g, 5.5 mmol) and the reaction mixture stirred at ambient temperature. After 16 hours, the mixture was poured into water (100 mL) and extracted with ethyl acetate (2×80 mL). The combined organics were washed with water (2×80 mL), 1 M hydrochloric acid (2×80 mL) and brine (80 mL), dried over MgSO$_4$ and concentrated of all volatiles in vacuo. Purification of the resulting solid by flash chromatography on silica gel afforded 0.36 g (68% yield) of N-(4-chlorophenyl)-2-[((3-chloro-4-((methylthio)methyl)thiophen-2-yl)carbonyl)amino]-5-chlorobenzamide; as a pale yellow solid; NMR (DMSO-d$_6$) 11.1 (s, 1), 10.8 (s, 1), 8.3 (d, 1), 7.9 (d, 1), 7.8 (s, 1), 7.7 (d, 2), 7.6 (dd, 1), 7.4 (d, 2), 3.7 (s, 2), 2.0 (s, 3) ppm.

B. In a similar manner, the following compounds were made:

N-(4-chlorophenyl)-2-[((3-chloro-5-((methylthio)methyl)thiophen-2-yl)carbonyl)amino]-5-chlorobenzamide; NMR (CDCl$_3$) 11.0 (s, 1), 9.2 (s, 1), 8.1 (d, 1), 7.8 (d, 2), 7.5 (d, 1), 7.4 (d, 2), 7.1 (dd, 1), 6.9 (s, 1), 3.8 (s, 2), 2.1 (s, 3) ppm;

N-(4-chlorophenyl)-2-[((3-chloro-5-((imidazol-1-yl)methyl)thiophen-2-yl)carbonyl)amino]-5-chlorobenzamide; NMR (DMSO-d$_6$) 11.1 (s, 1), 10.7 (s, 1), 9.2 (s, 1), 8.3 (d, 1), 7.9 (d, 1), 7.8 (s, 1), 7.3–7.2 (m, 4), 7.4 (s, 1), 7.3 (s, 2), 5.6 (s, 2) ppm;

N-(5-chloropyridin-2-yl)-2-[((4-cyanomethyl-3-chlorothiophen-2-yl)carbonyl)amino]-3-methoxy-5-chlorobenzamide; NMR (DMSO-d$_6$/TFA) 10.9 (s, 1), 9.4 (s, 1), 8.3 (s, 1), 8.1 (d, 1), 7.8 (m, 2), 7.3 (s, 1), 7.2 (s, 1), 3.9 (s, 2), 3.8 (s, 3) ppm.

C. In a manner similar to that described in Paragraph A above, N-(4-chlorophenyl)-2-[((4-(chloromethyl)-3-chlorothiophen-2-yl)carbonyl)amino]-5-chlorobenzamide (0.30 g, 0.64 mmol) reacted with sodium imidazole (0.17 g, 1.9 mmol) in DMF (10 mL) to afford N-(4-chlorophenyl)-2-[((3-chloro-4-((imidazol-1-yl)methyl)thiophen-2-yl)carbonyl)amino]-5-chlorobenzamide. Purification by HPLC on a C18 Dynamax column with acetonitrile in water gradient with 0.1% trifluoroacetic acid afforded two products: The earlier eluting material afforded N-(4-chlorophenyl)-2-[((3-chloro-4-((imidazol-1-yl)methyl)thiophen-2-yl)carbonyl)amino]-5-chlorobenzamide, trifluoroacetic acid salt as a cream-colored solid; NMR DMSO-d$_6$/TFA) 11.1 (s, 1), 10.8 (s, 1), 9.2 (s, 1), 8.3 (d, 1), 8.1 (s, 1), 7.9 (d, 1), 7.7 (m, 5), 7.4 d, 2), 5.4 (s, 2) ppm. The later eluting material afforded N-(4-chlorophenyl)-2-[((3-chloro-4-(hydroxymethyl)thiophen-2-yl)carbonyl)amino]-5-chlorobenzamide; as a white solid; NMR (DMSO-d$_6$/TFA) 11.1 (s, 1), 10.8 (s, 1), 8.3 (d, 1), 7.9 (d, 1), 7.8 (s, 1), 7.7 (d, 2), 7.6 (dd, 1), 7.4 (d, 2), 5.4 (br, 1), 4.4 (s, 2) ppm.

D. To a solution of 1,2,4-triazole (0.40 g, 5.7 mmol) in DMF (10 mL) was added NaH (60% dispersion in mineral oil, 0.23 g, 5.7 mmol) and the mixture stirred at ambient temperature. After 10 min, N-(4-chlorophenyl)-2-[((4-(chloromethyl)-3-chlorothiophen-2-yl)carbonyl)amino]-5-chlorobenzamide (0.90 g, 1.9 mmol) in DMF (5 mL) was added and stirring continued. After 18 hours, the mixture was poured onto water and extracted with methylene chloride. The organic layer was dried over MgSO$_4$ and concentrated in vacuo. Purification by flash chromatography on silica gel afforded 0.99 g (77% yield) of N-(4-chlorophenyl)-2-[((3-chloro-4-((1,2,4-triazol-1-yl)methyl)thiophen-2-yl)carbonyl)amino]-5-chlorobenzamide; as a white solid; NMR (DMSO-d$_6$/TFA) 11.2 (s, 1), 10.7 (s, 1), 9.3 (s, 1), 8.5 (s, 1), 8.3 (d, 1), 8.0 (s, 1), 7.9 (d, 1), 7.7 (d, 2), 7.6 (dd, 1), 7.4 (d, 2), 5.5 (s, 2) ppm.

E. In a similar manner, the following compounds were made:

N-(4-chlorophenyl)-2-[((3-chloro-4-((tetrazol-1-yl)methyl)thiophen-2-yl)carbonyl)amino]-5-chlorobenzamide; NMR (DMSO-d$_6$/TFA) 11.2 (s, 1), 10.7 (s, 1), 9.4 (s, 1), 8.3 (d, 1), 8.0 (s, 1), 7.85 (d, 1), 7.7 (d, 2), 7.5 (dd, 1), 7.3 (d, 2), 5.7 (s, 2) ppm;

N-(4-chlorophenyl)-2-[((3-chloro-4-((tetrazol-2-yl)methyl)thiophen-2-yl)carbonyl)amino]-5-chlorobenzamide; NMR (DMSO-d$_6$/TFA) 11.2 (s, 1), 10.7 (s, 1), 9.4 (s, 1), 8.3 (d, 1), 8.1 (s, 1), 7.9 (d, 1), 7.7 (d, 2), 7.6 (dd, 1), 7.4 (d, 2), 5.9 (s, 2) ppm;

N-(4-chlorophenyl)-2-[((3-chloro-4-((pyrazol-1-yl)methyl)thiophen-2-yl)carbonyl)amino]-5-chlorobenzamide; NMR (DMSO-d$_6$/TFA) 11.1 (s, 1), 10.7 (s, 1), 7.3–8.4 (m, 10), 6.3 (s, 1), 5.3 (s, 2) ppm;

N-(4-chlorophenyl)-2-[((3-chloro-4-((1,2,3-triazol-1-yl)methyl)thiophen-2-yl)carbonyl)amino]-5-chlorobenzamide; NMR (DMSO-d$_6$/TFA) 11.1 (s, 1), 10.7 (s, 1), 7.3–8.4 (m, 9), 5.3 (s, 2) ppm;

N-(4-chlorophenyl)-2-[((3-chloro-4-((1,2,3-triazol-2-yl)methyl)thiophen-2-yl)carbonyl)amino]-5-chlorobenzamide; NMR (DMSO-d$_6$/TFA) 11.2 (s, 1), 10.9 (s, 1), 7.3–8.5 (m, 10), 5.6 (br s, 2) ppm;

N-(5-chloropyridin-2-yl)-2-[((4-((N'-(2-imino-3-methyl-5-oxoimidazolin-2-yl)amino)methyl)-3-chlorothiophen-2-yl)carbonyl)amino]-3-methoxy-5-chlorobenzamide; NMR (DMSO-d$_6$/TFA) 10.9 (s, 1), 9.5 (br s., 1), 9.4 (s, 1), 8.4 (d, 1), 8.1 (d, 1), 7.9 (m, 2), 7.4 (s, 1), 7.3 (m, 2), 4.5 (d, 2), 4.2 (s, 2), 3.9 (s, 3), 3.1 (s, 3) ppm;

N-(5-chloropyridin-2-yl)-2-[((4-((4,5-dichloroimidazol-1-yl)methyl)-3-chlorothiophen-2-yl)carbonyl)amino]-3-methoxy-5-chlorobenzamide; NMR (DMSO-d$_6$/TFA) 10.85 (s, 1), 9.40 (s, 1), 8.30 (d, 1), 8.10 (d, 1), 7.80–7.86 (m, 2), 7.65 (s, 1), 7.30 (d, 1), 7.25 (d, 1), 5.20 (s, 2), 3.80 (s, 3) ppm;

N-(5-chloropyridin-2-yl)-2-[((4-((2-methyl-4-nitroimidazol-1-yl)methyl)-3-chlorothiophen-2-yl)carbonyl)amino]-3-methoxy-5-chlorobenzamide; NMR (DMSO-d$_6$/TFA) 10.85 (s, 1), 9.40 (s, 1), 8.30 (d, 1), 8.20 (s, 1), 8.10 (d, 1), 7.80 (dd, 1), 7.70 (s, 1), 7.30 (d, 1), 7.25 (d, 1), 5.20 (s, 2), 3.80 (s, 3), 2.30 (s, 3) ppm.

F. To a solution of N-(4-chlorophenyl)-2-[((4-(chloromethyl)-3-chlorothiophen-2-yl)carbonyl)amino]-5-chlorobenzamide (0.70 g, 1.5 mmol) in DMF (5 mL) was added 2-(dimethylamino)ethanethiol (2.1 g, 15 mmol), followed by potassium carbonate (1.0 g, 7.2 mmol) and the reaction stirred at ambient temperature. After 24 hours, the mixture was poured into water (100 mL) and the resulting solid collected by filtration, washed with water and dried in vacuo. Purification by flash chromatography on silica gel afforded 0.28 g (35% yield) of N-(4-chlorophenyl)-2-[((3-chloro-4-(((2-(dimethylamino)ethyl)thio)methyl)thiophen-2-yl)carbonyl)amino]-5-chlorobenzamide; as a cream-colored solid; NMR (DMSO-d$_6$) 11.1 (s, 1), 10.8 (s, 1), 8.3 (d, 1), 7.9 (d, 1), 7.8 (s, 1), 7.7 (d, 2), 7.6 (dd, 1), 7.4 (d, 2), 3.7 (s, 2), 2.5 (t, 2), 2.4 (t, 2), 2.1 (s, 6) ppm.

G. In a similar manner, the following compounds were made:

N-(4-chlorophenyl)-2-[((3-chloro-4-(((methoxycarbonylmethyl)thio)methyl)thiophen-2-yl)carbonyl)amino]-5-chlorobenzamide; NMR (DMSO-d$_6$) 11.1 (s, 1), 10.8 (s, 1), 8.3 (d, 1), 7.9 (d, 1), 7.8 (s, 1), 7.7 (d, 2), 7.6 (dd, 1), 7.4 (d, 2), 3.8 (s, 2), 3.6 (s, 3) ppm;

N-(5-chloropyridin-2-yl)-2-[((4-((4,5-dihydropyrazolin-1-yl)methyl)-3-chlorothiophen-2-yl)carbonyl)amino]-3-methoxy-5-chlorobenzamide; NMR (DMSO-d$_6$/TFA) 10.9 (s, 1), 9.4 (s, 1), 8, 4 (s, 1), 8.1 (d, 1), 7.9 (m, 2), 7.4 (s, 1), 7.2 (d, 2), 4.2 (s, 2), 3.9 (s, 3), 3.1 (t, 2), 2.7 (t, 2) ppm;

N-(4-chlorophenyl)-2-[((3-chloro-5-(((methoxycarbonylmethyl)thio)methyl)thiophen-2-yl)carbonyl)amino]-5-chlorobenzamide; NMR (DMSO-d$_6$) 11.0 (s, 1), 10.8 (s, 1), 8.3 (d, 1), 7.9 (s, 1), 7.8 (d, 2), 7.6 (dd, 1), 7.4 (d, 2), 7.1 (s, 1), 4.1 (s, 2), 3.6 (s, 3), 3.4 (s, 2) ppm;

N-(4-chlorophenyl)-2-[((3-chloro-6-((methoxycarbonyl)methylthio)methylbenzo[b]thien-2-yl)carbonyl)amino]-5-chlorobenzamide;

N-5-chloropyridin-2-yl)-2-[((4-((pyrazol-1-yl)methyl)-3-chlorothiophen-2-yl)carbonyl)amino]-3-methoxy-5-chlorobenzamide; NMR (DMSO-d$_6$) 10.9 (s, 1H), 9.40 (s, 1H), 8.36 (d, 1H), 8.10 (d, 1H), 7.90 (dd, 1H), 7.78 (d, 1H), 7.66 (s, 1H), 7.46 (d, 1H), 7.38 (d, 1H), 7.26 (d, 1H), 6.30 (s, 1H), 5.35 (s, 2H), 3.83 (s, 3H) ppm;

N-(5-chloropyridin-2-yl)-2-[((4-((hydantoin-3-yl)methyl)-3-chlorothiophen-2-yl)carbonyl)amino]-3-methoxy-5-chlorobenzamide; NMR (DMSO-d$_6$) 10.82 (s, 1H), 9.40 (s, 1H), 8.36 (d, 1H), 8.18 (s, 1H), 8.10 (d, 1H), 7.90 (dd, 1H), 7.70 (s, 1H), 7.38 (d, 1H), 7.27 (d, 1H), 4.46 (s, 2H), 3.97 (s, 2H), 3.88 (s, 3H) ppm;

N-(5-chloropyridin-2-yl)-2-[((4-((2-(ethylimino)pyrrolidin-1-yl) methyl)-3-chlorothiophen-2-yl)carbonyl)amino]-3-methoxy-5-chlorobenzamide; NMR (DMSO-d$_6$/TFA) 10.9 (s, 1), 9.4 (d, 1), 9.3 (m, 1), 8.4 (d, 1), 8.1 (d, 1), 8.0 (s, 1), 7.9 (m, 2), 7.4 (d, 1), 7.3 (d, 1), 4.6 (s, 2), 3.9 (s, 3), 3.6 (t, 2), 3.4 (m, 2), 3.0 (t, 3), 2.1 (m, 2), 1.2 (t, 3) ppm;

N-(5-chloropyridin-2-yl)-2-[((4-((2-iminopiperidin-1-yl)methyl)-3-chlorothiophen-2-yl)carbonyl)amino]-3-methoxy-5-chlorobenzamide; NMR (DMSO-d$_6$/TFA) 10.9 (s, 1), 9.3 (d, 1), 9.1 (s, 1), 8.6 (br s, 1), 8.3 (d, 1), 8.1 (d, 1), 7.9 (dd, 1), 7.6 (d, 1), 7.4 (d, 1), 7.3 (d, 1), 4.6 (s, 2), 3.9 (s, 3), 3.4 (m, 2), 2.7 (m, 2), 1.9 (m, 4) ppm.

H. To 2-methoxyethanol (20 mL) at 0° C. was added NaH (0.45 g, 11 mmol). The solution was warmed to ambient temperature and stirred for 16 hours. N-(5-chloropyridin-2-yl)-2-[((4-(chloromethyl)-3-chlorothiophen-2-yl)carbonyl)amino]-3-methoxy-5-chlorobenzamide (1.0 g, 2.3 mmol) was added and stirring continued for 3 hours. The mixture was then heated at 65° C. for 4 hours, then poured onto ice water (200 mL). The resulting solid was collected by filtration, washed with water and 50% ether/hexanes, and dried in vacuo to afford 0.65 g (52% yield) of N-(4-chlorophenyl)-2-[((3-chloro-4-((2-(2-methoxyethoxy)ethoxy)methyl)thiophen-2-yl)carbonyl)amino]-5-chlorobenzamide; as a pale yellow solid: NMR (DMSO-d$_6$/TFA) 11.1 (s, 1), 10.7 (s, 1), 8.3 (d, 1), 7.9 (d, 2), 7.7 (d, 2), 7.6 (d, 1), 7.4 (s, 1), 7.4 (s, 1), 4.4 (s, 2), 3.5 (m, 6), 3.4 (m, 2), 3.2 (s, 3) ppm.

I. In a similar manner, the following compounds were made:

N-(4-chlorophenyl)-2-[((3-chloro-4-((2-(2-(2-methoxyethoxy)ethoxy)ethoxy)methyl)thiophen-2-yl)carbonyl)amino]-5-chlorobenzamide; NMR (DMSO-d$_6$) 11.2 (s, 1), 10.8 (s, 1), 8.4 (d, 1), 7.9 (s, 1), 7.8 (s, 1), 7.7 (d, 2), 7.6 (d, 1), 7.4 (d, 2), 4.4 (d, 2), 3.6 (m, 4), 3.5 (m, 6), 3.4 (m, 2), 3.2 (s, 3) ppm;

N-(4-chlorophenyl)-2-[((3-chloro-4-((2-methoxyethoxy)methyl)thiophen-2-yl)carbonyl)amino]-5-chlorobenzamide;

N-(4-chlorophenyl)-2-[((3-chloro-4-(((2,2-dimethyldioxolan-4-yl)methoxy)methyl)thiophen-2-yl)carbonyl)amino]-5-chlorobenzamide; NMR (DMSO-d$_6$)

11.1 (s, 1), 10.8 (s, 1), 8.3 (d, 1), 8.0 (d, 2), 7.7 (d, 2), 7.6 (d, 1), 7.4 (d, 2), 4.5 (s, 2), 4.2 (t, 1)4.0 (t, 1), 3.6 (m, 1), 3.4 (d, 2), 1.2 (d, 6) ppm.

J. In a manner similar to that described in Paragraph F above, to a solution of 3-dimethylamino-5-methylpyrazole (0.38 g, 3.0 mmol), N-(5-chloropyridin-2-yl)-2-[((4-(chloromethyl)-3-chlorothiophen-2-yl)carbonyl)amino]-3-methoxy-5-chlorobenzamide (1.0 g, 2.0 mmol), and DMSO (10 mL) was added $K_2CO_3$ (1.0 g, 7.2 mmol). The mixture was stirred at ambient temperature for 16 hours, then it was poured into $H_2O$. The solid was isolated by filtration. Purification by HPLC on a C18 Dynamax column with 25–95% acetonitrile in water gradient with 0.1% trifluoroacetic acid afforded the trifluoroacetic acid salts of N-(5-chloropyridin-2-yl)-2-[((4-((3-dimethylamino-5-methylpyrazol-1-yl)methyl)-3-chlorothiophen-2-yl)carbonyl)amino]-3-methoxy-5-chlorobenzamide; NMR (DMSO-$d_6$) 10.90 (s, 1H), 9.50 (s, 1H), 8.40 (d, 1H), 8.10 (d, 1H), 7.90 (dd, 1H), 7.60 (s, 1H), 7.40 (d, 1H), 7.25 (d, 1H), 6.45 (s, 1H), 4.90 (s, 2H), 3.90 (s, 3H), 2.50 (s, 6H), 2.25 (s, 3H) ppm, and N-(5-chloropyridin-2-yl)-2-[((4-((3-dimethylamino-5-methylpyrazol-2-yl)methyl)-3-chlorothiophen-2-yl)carbonyl)amino]-3-methoxy-5-chlorobenzamide; NMR (DMSO-$d_6$) 10.90 (s, 1H), 9.40 (s, 1H), 8.40 (d, 1H), 8.10 (d, 1H), 7.90 (dd, 1H), 7.38 (s, 1H), 7.28 (d, 1H), 7.25 (d, 1H), 5.60 (s, 1H), 5.00 (s, 2H), 3.90 (s, 3H), 2.70 (s, 3H), 2.20 (s, 3H) ppm.

K. In a similar manner, the following compound was made:

N-(5-chloropyridin-2-yl)-2-[((4-((5-aminotetrazol-1-yl)methyl)-3-chlorothiophen-2-yl)carbonyl)amino]-3-methoxy-5-chlorobenzamide, trifluoroacetic acid salt; NMR (DMSO-$d_6$/TFA) 10.9 (s, 1), 9.4 (s., 1), 8.3 (d, 1), 8.1 (d, 1), 7.9 (dd, 2), 7.7 (s, 1), 7.3 (d, 1), 7.2 (d, 1), 5.3 (s, 1), 3.9 (s, 3) ppm.

L. In a manner similar to that described in Paragraph J above, to a solution of N,N-diethylhydroxylamine (0.45 g, 5.0 mmol), N-(5-chloropyridin-2-yl)-2-[((4-(chloromethyl)-3-chlorothiophen-2-yl)carbonyl)amino]-3-methoxy-5-chlorobenzamide (0.51 g, 1.0 mmol), and DMSO (10 mL) was added $K_2CO_3$ (0.68 g, 4.9 mmol). The mixture was stirred at 40° C. for 2 stirred at ambient temperature. After 0.5 hours, water (2 mL) was added resulting in a heterogeneous mixture. LiOH.$H_2O$ (large excess) was added and the mixture stirred for 2 hours, then concentrated in vacuo. Purification by HPLC on a C18 Dynamax column with acetonitrile in water gradient with 0.1% trifluoroacetic acid afforded N-(5-chloropyridin-2-yl)-2-[((4-((N'-methyl-N"-(2-carboxyethyl)ureido)methyl)-3-chlorothiophen-2-yl)carbonyl)amino]-3-methoxy-5-chlorobenzamide, trifluoroacetic acid salt, as a white solid: NMR (DMSO-$d_6$/TFA) 10.9 (s, 1), 9.4 (s, 1), 8.3 (s, 1), 8.1 (d, 1), 7.9 (d, 1), 7.5 (s, 1), 7.4 (s, 1), 7.3 (s, 1), 4.3 (s, 2), 3.9 (s, 3), 3.3 (t, 2), 2.8 (s, 3), 2.4 (t, 2) ppm.

J. Other compounds of the invention may be prepared by methods similar to those described in this Example and by methods known to those of ordinary skill in the art.

EXAMPLE 6

Compounds of Formula (Ij)

A. To a solution of N-(5-chloropyridin-2-yl)-2-[((4-((methylamino)methyl)-3-chlorothiophen-2-yl)carbonyl)amino]-3-methoxy-5-chlorobenzamide (1.6 g, 3.2 mmol) and diisopropylethylamine (1.7 mL, 9.6 mmol) in $CH_2Cl_2$ (10 mL) at 0° C. was added 2-chloroacetyl chloride (0.25 mL, 3.2 mmol). The mixture was stirred and allowed to warm to ambient temperature. After 7 hours, 4-hydroxypiperidine (0.65 g, 6.4 mmol) was added and the reaction stirred for 16 hours. The mixture was concentrated of all volatiles in vacuo and the resulting oil purified by HPLC on a C18 Dynamax column with acetonitrile in water gradient with 0.1% trifluoroacetic acid to afford N-(5-chloropyridin-2-yl)-2-[((4-((N'-methyl-N'-(((4-hydroxypiperidin-1-yl)methyl)carbonyl)amino)methyl)-3-chlorothiophen-2-yl)carbonyl)amino]-3-methoxy-5-chlorobenzamide, trifluoroacetic acid salt as a white solid; NMR (DMSO-$d_6$/TFA) 10.9 (s, 1), 9.5 (br s, 1), 9.4 (s, 1), 8.4 (s, 1), 8.1 (d, 1), 7.9 (d, 1), 7.7 (s, 1), 7.4 (s, 1), 7.3 (s, 1), 4.5 (m, 2), 4.3 (m, 2), 3.9 (m, 1), 3.9 (s, 3), 3.6 (m, 1), 3.4 (m, 1), 3.2 (m, 2), 3.0 (s, 3), 2.0 (m, 2), 1.7 (m, 2) ppm.

B. To a solution of N-(5-chloropyridin-2-yl)-2-[((4-((N'-methyl-N'-((2-chloroethyl)sulfonyl)amino)methyl)-3-chlorothiophen-2-yl)carbonyl)amino]-3-methoxy-5-chlorobenzamide (1.1 g, 1.8 mmol) in DMF (5 mL) was added $Cs_2CO_3$ (5.7 g, 18 mmol), followed by 4-hydroxypiperidine (0.27 g, 2.6 mmol). The mixture was stirred at ambient temperature for 16 hours, then filtered and concentrated in vacuo. Purification of the resulting oil by flash chromatography on silica gel afforded 1.0 g (82% yield) of N-(5-chloropyridin-2-yl)-2 -[((4-((N'-methyl-N'-((2-(4-hydroxypiperidin-1-yl)ethyl)sulfonyl)amino)methyl)-3-chlorothiophen-2-yl)carbonyl)amino]-3-methoxy-5-chlorobenzamide, as a white solid; NMR (DMSO-$d_6$/TFA) 10.9 (s, 1), 9.5 (br s, 1), 9.4 (s, 1), 8.4 (s, 1), 8.1 (d, 1), 7.9 (d, 1), 7.8 (s, 1), 7.4 (s, 1), 7.3 (s, 1), 4.3 (s, 2), 3.9 (m, 1), 3.9 (s, 3), 3.7 (m, 2), 3.5 (m, 2), 3.3 (m, 2), 3.2 (m, 1), 3.0 (m, 1), 2.8 (m, 3), 2.0 (m, 1), 1.8 (m, 2), 1.6 (m, 1) ppm.

C. In a similar manner, the following compounds were made:

N-(5-chloropyridin-2-yl)-2-[((4-((N'-methyl-N'-((2-(pyrrolidin-1-yl)ethyl)sulfonyl)amino)methyl)-3-chlorothiophen-2-yl)carbonyl)amino]-3-methoxy-5-chlorobenzamide; NMR (DMSO-$d_6$/TFA) 10.9 (s, 1), 9.4 (s, 1), 8.3 (s, 1), 8.1 (d, 1), 7.9 (d, 1), 7.8 (s, 1), 7.4 (s, 1), 7.3 (s, 1), 4.4 (s, 2), 3.9 (s, 3), 3.6 (m, 6), 3.1 (br m, 2), 2.8 (s, 3), 2.1 (m, 2), 1.9 (m, 2) ppm.

D. Other compounds of the invention may be prepared by methods similar to those described in this Example and by methods known to those of ordinary skill in the art.

EXAMPLE 7

Compounds of Formula (Ik)

A. To a solution of N-(5-chloropyridin-2-yl)-2-[((4-((methylamino)methyl)-3-chlorothiophen-2-yl)carbonyl)amino]-3-methoxy-5-chlorobenzamide (0.10 g, 0.20 mmol) in DMF (3 mL) were added triethylamine (0.28 mL, 2.0 mmol) and 1H -pyrazole-1-carboxamidine hydrochloride (0.30 g, 2.0 mmol). The mixture was stirred at ambient temperature for 15 hours, then heated at 45° C. for 3 hours. The cooled mixture was acidified with trifluoroacetic acid and purified by HPLC on a C18 Dynamax column with 20–70% acetonitrile in water gradient with 0.1% trifluoroacetic acid to afford N-(5-chloropyridin-2-yl)-2-[((4-(((amidino)(methyl)amino)methyl)-3-chlorothiophen-2-yl)carbonyl)amino]-3-methoxy-5-chlorobenzamide, trifluoroacetic acid salt as white solid; NMR (DMSO-$d_6$/TFA) 10.9 (s, 1), 9.4 (s, 1), 8.3 (d, 1), 8.1 (d, 1), 7.8 (dd, 1), 7.6 (s, 1), 7.4 (br s, 4), 7.3 (s, 1), 7.2 (s, 1), 4.5 (s, 2), 3.8 (s, 3), 2.9 (s, 3) ppm.

B. Other compounds of the invention may be prepared by methods similar to those described in this Example and by methods known to those of ordinary skill in the art.

EXAMPLE 8

Compounds of Formula (Im)

A. To a solution of N-(5-chloropyridin-2-yl)-2-[((4-((methylamino)methyl)-3 -chlorothiophen-2-yl)carbonyl)amino]-3-methoxy-5-chlorobenzamide (0.70 g, 1.4 mmol) in MeOH (30 mL) was added triethylamine (3 mL, 22 mmol) and ethyl acetimidate hydrochloride (large excess). The reaction was stirred at ambient temperature for 16 hours, then concentrated of all volatiles in vacuo. Purification of the residual oil by HPLC on a C18 Dynamax column with acetonitrile in water gradient with 0.1% trifluoroacetic acid afforded N-(5-chloropyridin-2-yl)-2-[((4-((N'-(1-iminoethyl)-N'-methylamino)methyl)-3-chlorothiophen-2-yl)carbonyl)amino]-3-methoxy-5-chlorobenzamide, trifluoroacetic acid salt as a white solid; NMR (DMSO-$d_6$/TFA) (rotational isomers observed) 10.9 (s, 1), 9.4 (s, 1), 9.3 (br s, 1), 8.6 (br s, 1), 8.4 (s, 1), 8.1 (d, 1), 7.9 (d, 1), 7.8 (s, 1), 7.4 (s, 1), 7.3 (s, 1), 4.6 (s, 2), 3.9 (s, 3), 3.1 (s, 3), 2.3 (s, 3) ppm.

B. To a solution of N-(5-chloropyridin-2-yl)-2-[((4-((methylamino)methyl)-3-chlorothiophen-2-yl)carbonyl)amino]-3-methoxy-5-chlorobenzamide (3.0 g, 6.0 mmol) in DMF (30 mL) were added N,N-diisopropylethylamine (1.94 g, 15 mmol) and 2-methylthioimidazoline hydroiodide (1.9 g, 7.8 mmol). The mixture was heated at 90° C. for 20 hours. The cooled mixture was poured into water, extracted with ethyl acetate, dried (MgSO$_4$) and concentrated in vacuo. Purification by HPLC on a C18 Dynamax column with 20–70% acetonitrile in water gradient with 0.1% trifluoroacetic acid afforded N-(5-chloropyridin-2-yl)-2-[((4-((N'-methyl-N'-(3,4-dihydro-2H-pyrrol-5-yl)amino)methyl)-3-chlorothiophen-2-yl)carbonyl)amino]-3-methoxy-5-chlorobenzamide, trifluoroacetic acid salt, as white solid; NMR (DMSO-$d_6$/TFA) 10.9 (s, 1), 9.7 (d, 1), 9.4 (d, 1), 8.3 (m, 1), 8.2 (d, 1), 8.1 (d, 1), 7.8 (d, 1), 7.7 (d, 1), 7.3 (d, 1), 7.2 (d, 1), 4.6 (d, 2), 3.9 (s, 3), 3.6 (m, 2), 2.9–3.2 (m, 5), 2.2 (m, 2) ppm.

C. Sodium hydride (60%, 0.1 g, 2.5 mmol) was added in portions to a mixture of ethyl (2-trifluoroethyl)acetimidate hydrochloride (0.53 g, 2.5 mmol) and DMF (4 mL), and stirred at 0° C. for 5 minutes, then at ambient temperature for 20 minutes. The mixture was re-cooled to 0° C., and N-(5-chloropyridin-2-yl)-2-[((4-((methylamino)methyl)-3-chlorothiophen-2-yl)carbonyl)amino]-3-methoxy-5-chlorobenzamide (0.25 g, 0.5 mmol) was added. After stirring at ambient temperature for 15 hours, cesium carbonate (0.6 g, 1.8 mmol) was added and the stirring was continued for 5 days. The mixture was cooled in an ice bath, and trifluoroacetic acid (0.5 mL) was added dropwise. Purification by HPLC on a C18 Dynamax column with 20–70% acetonitrile in water gradient with 0.1% trifluoroacetic acid gave 0.15 g of N-(5-chloropyridin-2-yl)-2-[((4-((N'-methyl-N'-(1-imino-4,4,4-trifluorobutyl)amino)methyl)-3-chlorothiophen-2-yl)carbonyl)amino]-3-methoxy-5-chlorobenzamide, trifluoroacetic acid salt, as a white solid; NMR (DMSO-$d_6$/TFA) 10.90 (s, 1), 9.3–9.4 (m, 2), 8.90 (d, 1), 8.30 (m, 1), 8.10 (d, 1), 7.75–7.85 (m, 2), 7.30 (s, 1), 7.25 (s, 1), 4.70 (s, 0.8), 4.60 (s, 1.2), 3.80 (s, 1), 3.20 (s, 1.8), 3.00 (s, 1.2), 2.90 (m, 2), 2.60 (m, 2) ppm.

D. In a similar manner, the following compounds were made:

N-(5-chloropyridin-2-yl)-2-[((4-((N'-ethyl-N'-(3-cyano-1-iminopropyl)amino)methyl)-3-chlorothiophen-2-yl)carbonyl)amino]-3-methoxy-5-chlorobenzamide, trifluoroacetic acid salt; NMR (DMSO-$d_6$) 10.90 (s, 1H), 9.90 (s, 1H), 9.70 (s, 1H), 9.40 (s, 1H), 8.40 (d, 1H), 8.10 (d, 1H), 7.90 (dd, 1H), 7.80 (s, 1H), 7.40 (d, 1H), 7.25 (d, 1H), 4.80 (s, 2H), 3.90 (s, 3H), 3.55 (q, 2H), 3.20–3.10 (m, 2H), 3.00–2.90 (m, 2H), 1.20 (t, 3H) ppm; and N-(5-chloropyridin-2-yl)-2-[((4-((N'-(1-imino-4,4,4-trifluorobutyl)amino)methyl)-3-chlorothlophen-2-yl)carbonyl)amino]-3-methoxy-5-chlorobenzamide, trifluoroacetic acid salt; NMR (DMSO-$d_6$/TFA) 10.85 (s, 1), 9.90 (b, 1), 9.40 (b, 1), 9.35 (s, 1), 9.00 (b, 1), 8.28 (d, 1), 8.08 (d, 1), 7.85 ( s, 1), 7.80 (dd, 1), 7.25 (d, 1), 4.40 (d, 2), 3.80 (s, 3), 2.60–2.70 (m, 4)

E. Other compounds of the invention may be prepared by methods similar to those described in this Example and by methods known to those of ordinary skill in the art.

EXAMPLE 9

Compounds of Formula (Io)

A. To a solution of N-(5-chloropyridin-2-yl)-2-[((4-((methylamino)methyl)-3-chlorothiophen-2-yl)carbonyl)amino]-5-chlorobenzamide (1.0 g, 2.1 mmol) in THF (30 mL) at 0° C. was added 2-bromoethylisocyanate (0.24 mL, 2.6 mmol) and the mixture stirred at ambient temperature. After 7 hours, an additional 0.12 mL (1.3 mmol) of 2-bromoethylisocyanate was added. After a further 16 h, the mixture was cooled to 0° C. and triethylamine (0.60 mL, 4.3 mmol) was added. The reaction mixture was warmed slowly to ambient temperature and stirred for 24 hours, then concentrated of all volatiles in vacuo. The resulting gum was dissolved in ethyl acetate (50 mL), washed with brine (50 mL), dried over MgSO$_4$ and concentrated in vacuo. Purification by flash chromatography on silica gel afforded 0.77 g (67%) of N-(5-chloropyridin-2-yl)-2-[((4-((N'-methyl-N'-(oxazolin-2-yl)amino)methyl)-3-chlorothiophen-2-yl)carbonyl)amino]-5-chlorobenzamide; as a white foam; NMR (CDCl$_3$) 11.2 (s, 1), 8.7 (s, 1), 8.6 (d, 1), 7.4–8.3 (m, 6), 4.4 (s, 2), 4.4 (t, 2), 3.8 (t, 2), 3.0 (s, 3) ppm.

B. In a similar manner, the following compounds were made: days, then it was poured into water. The resulting mixture was extracted with CH$_2$Cl$_2$ (2×50 mL). The organic layer was washed with 1% K$_2$CO$_3$, brine, treated with charcoal and concentrated. Purification by silica gel chromatography using 10:1 CH$_2$Cl$_2$:CH$_3$OH with 1% NH$_4$OH followed by precipitation from CH$_2$Cl$_2$ and hexane afforded N-(5-chloropyridin-2-yl)-2-[((4-(((diethylamino)oxy)methyl)-3-chlorothiophen-2-yl)carbonyl)amino]-3-methoxy-5-chlorobenzamide, as a white solid; NMR (DMSO-$d_6$) 8.35 (s, 1H), 8.20 (s, 1H), 8.10 (d, 1H), 7.90 (dd, 1H), 7.35 (s, 1H), 7.30 (s, 1H), 4.20 (s, 2H), 3.85 (s, 3H), 3.20–2.80 (m, 4H), 1.20 (t, 6H) ppm.

M. In a similar manner, the following compound was made:

N-(5-chloropyridin-2-yl)-2-[((4-((3-amino-1,2,4-triazol-1-yl)methyl)-3-chlorothiophen-2-yl)carbonyl)amino]-3-methoxy-5-chlorobenzamide; NMR (DMSO-$d_6$/TFA) 10.9 (s, 1), 9.4 (s., 1), 8.4 (d, 1), 8.3 (m, 2), 8.1 (d, 1), 7.9 (dd, 1), 7.7 (s, 1), 7.4 (s, 1), 7.3 (s, 1), 5.1 (s, 2), 3.9 (s, 3) ppm.

N. In a manner similar to that described above in Paragraph F, to a solution of 2-methyl-4,5-dihydroimidazole (1.50 g, 17.8 mmol), N,N-diethylhydroxylamine (0.45 g, 5.0 mmol), N-(5-chloropyridin-2-yl)-2-[((4-(chloromethyl)-3-chlorothiophen-2-yl)carbonyl)amino]-3-methoxy-5-chlorobenzamide (2.00 g, 4 mmol) and DMF (15 mL) was added K$_2$CO$_3$ (2.50 g, 18.1 mmol). The mixture was stirred at ambient temperature for 16 hours. Purification by HPLC on a C18 Dynamax column with 20–50% acetonitrile in water gradient with 0.1% trifluoroacetic acid afforded the trifluoroacetic acid salt of N-(5-chloropyridin-2-yl)-2-[((4-((2-methylimidazolin-1-yl)methyl)-3-chlorothiophen-2-yl)carbonyl)amino]-3-methoxy-5-chlorobenzamide, trifluoroacetic acid salt, as a white solid; NMR (DMSO-d$_6$/TFA) 10.9 (s, 1), 10.2 (s, 1), 9.4 (s, 1), 8.3 (s, 1), 8.1 (d, 1), 8.0 (s, 1), 7.8 (d, 1), 7.3 (s, 1), 7.2 (s, 1), 4.6 (s, 2), 3.8 (s, 3), 3.7 (s, 4), 2.3 (s, 3) ppm.

O. In a similar manner, the following compounds were made:

N-(5-chloropyridin-2-yl)-2-[((4-((4-amino-5-(aminocarbonyl)imidazol-1-yl)methyl)-3-chlorothiophen-2-yl)carbonyl)amino]-3-methoxy-5-chlorobenzamide, trifluoroacetic acid salt; NMR (DMSO-d$_6$/TFA) 10.9 (s, 1), 9.4 (s, 1), 8.8 (s, 1), 8.4 (d, 1), 8.1 (dd, 1), 7.9 (dd, 1), 7.8 (s, 1), 7.4 (d, 1), 7.3 (d, 1), 5.3 (s, 2), 3.9 (s, 3) ppm; and N-(5-chloropyridin-2-yl)-2-[((4-((2-iminopiperidin-1-yl)methyl)-3-chlorothiophen-2-yl)carbonyl)amino]-3-methoxy-5-chlorobenzamide, trifluoroacetic acid salt; NMR (DMSO-d$_6$/TFA) 10.9 (s, 1), 9.3 (d, 1), 9.1 (s, 1), 8.6 (br s, 1), 8.3 (d, 1), 8.1 (d, 1), 7.9 (dd, 1), 7.6 (d, 1), 7.4 (d, 1), 7.3 (d, 1), 4.6 (s, 2), 3.9 (s, 3), 3.4 (m, 2), 2.7 (m, 2), 1.9 (m, 4) ppm.

P. In a similar manner to that described in Paragraph F above, to a solution of theobromine (1.06 g, 5.9 mmol), N,N-diethylhydroxylamine (0.45 g, 5.0 mmol), N-(5-chloropyridin-2-yl)-2-[((4-(chloromethyl)-3-chlorothiophen-2-yl)carbonyl)amino]-3-methoxy-5-chlorobenzamide (0.32 g, 0.6 mmol), and DMF (40 mL) was added K$_2$CO$_3$ (0.74 g, 5.3 mmol). The mixture was stirred at 40° C. for 6 days, then it was poured into water. The solid was isolated by filtration. Purification by recrystallization from CH$_2$Cl$_2$ and CH$_3$OH afforded N-(5-chloropyridin-2-yl)-2-[((4-((2,3,4,5,6,7-hexahydro-3,7-dimethyl-2,6-dioxo-1H-purin-1-yl)methyl)-3-chlorothiophen-2-yl)carbonyl)amino]-3-methoxy-5-chlorobenzamide, as a white solid; NMR (DMSO-d$_6$) 10.90 (s, 1H), 9.40 (s, 1H), 8.36 (d, 1H), 8.12 (d, 1H), 8.06 (s, 1H), 7.90 (dd, 1H), 7.55 (s, 1H), 7.38 (d, 1H), 7.27 (d, 1H), 4.97 (s, 2H), 3.90 (s, 6H), 3.40 (s, 3H) ppm.

Q. In a manner similar to that described in Paragraph P above, a mixture of cytosine (0.3 g, 3.0 mmol), N-(5-chloropyridin-2-yl)-2-[((4-(chloromethyl)-3-chlorothiophen-2-yl)carbonyl)amino]-3-methoxy-5-chlorobenzamide (0.25 g, 0.5 mmol), cesium carbonate (0.5 g, 1.5 mmol), and DMF (5 mL) was heated under N$_2$ at 60° C. for 15 hours. The mixture was cooled in ice bath, and trifluoroacetic acid (0.5 mL) was added dropwise. Purification by HPLC on a C18 Dynamax column with 20–70% acetonitrile in water gradient with 0.1% trifluoroacetic acid gave 0.17 g of the trifluoroacetic acid salt of N-(5-chloropyridin-2-yl)-2-[((4-((5-amino-2-oxo-2H-pyrimidin-1-yl)methyl)-3-chlorothiophen-2-yl)carbonyl)amino]-3-methoxy-5-chlorobenzamide, trifluoroacetic acid salt, as a white solid; NMR (DMSO-d$_6$, 40° C.) 10.75 (s, 1), 9.35 (s, 1), 9.30 (b, 1), 8.35 (b, 1), 8.30 (d, 1), 8.05 (d, 1), 7.95 (d, 1), 7.85 (dd, 1), 7.90 (s, 1), 7.35 (d, 1), 7.25 (d, 1), 6.00 (d, 1), 4.90 (s, 2), 3.85 (s, 3) ppm.

R. In a similar manner, the following compounds were made:

N-(5-chloropyridin-2-yl)-2-[((4-((6-aminopurin-9-yl)methyl)-3-chlorothiophen-2-yl)carbonyl)amino]-3-methoxy-5-chlorobenzamide, trifluoroacetic acid salt, and N-(5-chloropyridin-2-yl)-2-[((4-((6-aminopurin-7-yl)methyl)-3-chlorothiophen-2-yl)carbonyl)amino]-3-methoxy-5-chlorobenzamide, trifluoroacetic acid salt; NMR (DMSO-d$_6$/TFA) 10.75 (s, 0.5), 10.74 (s, 0.5), 9.35 (m, 1.5), 8.83 (s, 0.5), 8.82 (b, 0.5), 8.55 (s, 0.5), 8.30 (m, 1.5), 8.27 (s, 0.5), 8.12 (b, 1), 8.06 (d, 1), 7.86 (m, 1, 5), 7.70 (s, 1), 7.34 (t, 1), 7.25 (t, 1), 5.56 (s, 1), 5.35 (s, 1), 3.80 (s, 3) ppm;

N-(5-chloropyridin-2-yl)-2-[((4-((2-amino-6-oxopurin-9-yl)methyl)-3-chlorothiophen-2-yl)carbonyl)amino]-3-methoxy-5-chlorobenzamide, trifluoroacetic acid salt, and N-(5-chloropyridin-2-yl)-2-[((4-((2-amino-6-oxopurin-7-yl)methyl)-3-chlorothiophen-2-yl)carbonyl)amino]-3-methoxy-5-chlorobenzamide, trifluoroacetic acid salt; NMR (DMSO-d$_6$) 10.75 (s, 1), 10.65 (s, 0.5), 9.33 (s, 1), 8.38 (s, 0.5), 8.31 (t, 1), 8.06 (dd, 1), 7.91 (s, 0.5), 7.88 (dd, 0.5), 7.86 (dd, 0.5), 7.69 (s, 0.5), 7.50 (s, 0.5), 7.34 (d, 1), 7.25 (d, 1), 6.75 (b, 1), 6.50 (b, 1), 5.40 (s, 1), 5.10 (s, 1), 3.85 (s, 3) ppm;

N-(5-chloropyridin-2-yl)-2-[((4-((2-amino-4-imino-1,4-dihydropyrimidin-1-yl)methyl)-3-chlorothiophen-2-yl)carbonyl)amino]-3-methoxy-5-chlorobenzamide, trifluoroacetic acid salt; NMR (DMSO-d$_6$/TFA) 10.80 (s, 1), 9.35 (s, 1), 8.33 (d, 1), 8.22 (s, 1), 8.10 (s, 1), 8.07 (d, 1), 8.10 (s, 2), 7.88 (dd, 1), 7.72 (d, 1), 7.65 (s, 1), 7.36 (d, 1), 7.26 (d, 1), 6.40 (d, 1), 5.00 (s, 2), 3.85 (s, 3) ppm;

N-(5-chloropyridin-2-yl)-2-[((4-((N'-(imino(thiophen-2-yl)methyl)amino)methyl)-3-chlorothiophen-2-yl)carbonyl)amino]-3-methoxy-5-chlorobenzamide, trifluoroacetic acid salt; NMR (DMSO-d$_6$/TFA) 10.85 (s, 1), 10.10 (s, 1), 9.60 (s, 1), 9.40 (s, 1), 9.20 (s, 1), 8.29 (d, 1), 8.10 (d, 1), 8.00 (dd, 1), 7.91 (dd, 1), 7.84 (s, 1), 7.82 (dd, 1), 7.30 (d, 1), 7.26 (m, 2), 4.55 (d, 2), 3.80 (s, 3) ppm; and N-(5-chloropyridin-2-yl)-2-[((4-((2,4-diamino-6-hydroxypyrimidin-5-yl)methyl)-3-chlorothiophen-2-yl)carbonyl)amino]-3-methoxy-5-chlorobenzamide, trifluoroacetic acid salt; NMR (DMSO-d$_6$/TFA) 10.85 (s, 1), 9.30 (s, 1), 8.30 (d, 1), 8.10 (d, 1), 8.00 (b, 1), 7.80 (dd, 1), 7.35 (s, 1), 7.30 (s, 1), 7.25 (s, 1), 3.80 (s, 3), 3.40 (s, 2) ppm.

S. In a manner similar to that described in Paragraph D, to a solution of benzamidine hydrochloride (0.78 mg, 5 mmol) and DMF (10 mL) was added NaH (0.21 g, 5.2 mmol). The mixture was stirred at ambient temperature for 30 minutes. The mixture was cooled to 0° C., then N,N-diethylhydroxylamine (0.45 g, 5.0 mmol), N-(5-chloropyridin-2-yl)-2-[((4-(chloromethyl)-3-chlorothiophen-2-yl)carbonyl)amino]-3-methoxy-5-chlorobenzamide (0.51 mg, 1 mmol) was added. The mixture was allowed to warm to ambient temperature and stirred for 5 days. The mixture was added to water and the resulting precipitate was isolated by filtration. Purification by HPLC on a C18 Dynamax column with 25–95% acetonitrile in water gradient with 0.1% trifluoroacetic acid afforded the trifluoroacetic acid salt of N-(5-chloropyridin-2-yl)-2-[((4-((N'-(imino(phenyl)methyl)amino)methyl)-3-chlorothiophen-2-yl)carbonyl)amino]-3-methoxy-5-chlorobenzamide; NMR (DMSO-d$_6$) 10.90 (s, 1H), 10.10 (br s, 1H), 9.65 (br s, 1H), 9.40 (s, 1H), 9.25 (br s, 1H), 8.40 (d, 1H), 9.10 (d, 1H), 7.95 (s, 1H), 7.90 (dd, 1H), 7.80–7.70 (m, 3H), 7.65–7.59 (m, 2H), 7.40 (d, 1 H), 7.30 (d, 1H), 4.55 (s, 2H), 3.85 (s, 3H) ppm.

T. In a similar manner, the following compounds were made:

N-(5-chloropyridin-2-yl)-2-[((4-((N'-(1-imino-2-(aminocarbonyl)ethyl)amino)methyl)-3-chlorothiophen-2-yl)carbonyl)amino]-3-methoxy-5-chlorobenzamide, trifluoroacetic acid salt; NMR (DMSO-d$_6$) 10.90 (s, 1H), 9.40 (s, 1H), 8.90 (s, 2H), 8.70 (s, 2H), 8.40 (d, 1H), 8.10 (d, 1H), 7.90 (dd, 1H), 7.70 (s, 1H), 7.60 (s, 1H), 7.58 (s, 1H), 7.40 (s, 1H), 7.25 (s, 1H), 3.90 (s, 3H), 3, 80 (m, 2H), 3.20 (m, 2H) ppm; and N-(5-chloropyridin-2-yl)-2-[((4-((N'-(cyclopropyl(imino)methyl)amino)methyl)-3-chlorothiophen-2-yl)carbonyl)amino]-3-methoxy-5-chlorobenzamide, trifluoroacetic acid salt; NMR (DMSO-d$_6$) 10.90 (s, 1H), 8.60 (br s, 1H), 9.38 (s, 1H), 8.70 (br s,1H), 8.38 (d, 1H), 8.10 (d, 1H), 8.00–7.80 (m, 2H), 7.40 (d, 1H), 7.25 (d, 1H), 4.40 (s, 2H), 3.90 (s, 3H), 1.98–1.85 (m, 1H), 1.20–1.10 (m, 4H) ppm.

U. Other compounds of the invention may be prepared by methods similar to those described in this Example and by methods known to those of ordinary skill in the art.

EXAMPLE 4

Compounds of Formula (If)

A. To a solution of N-(5-chloropyridin-2-yl)-2-[((4-((methylamino)methyl)-3-chlorothiophen-2-yl)carbonyl)amino]-3-methoxy-5-chlorobenzamide (1.3 g, 2.5 mmol) in pyridine (20 mL) at 0° C. was added methanesulfonyl chloride (0.20 mL, 2.8 mmol). The solution was allowed to warm to ambient temperature with stirring. After 16 hours, the pyridine was removed in vacuo. The resulting oil was purified by flash chromatography on silica gel to afford 1.1 g (75% yield) of N-(5-chloropyridin-2-yl)-2-[((4-((N'-methyl-N'-(methylsulfonyl)amino)methyl)-3-chlorothiophen-2-yl)carbonyl)amino]-3-methoxy-5-chlorobenzamide, as a white solid; NMR (DMSO-d$_6$/TFA) 10.9 (s, 1), 9.4 (s, 1), 8.3 (s, 1), 8.1 (d, 1), 7.9 (d, 1), 7.8 (s, 1), 7.4 (s, 1), 7.3 (s, 1), 4.2 (s, 2), 3.9 (s, 3), 3.0 (s, 3), 2.7 (s, 3) ppm.

B. In a similar manner, the following compounds were made:

N-(5-chloropyridin-2-yl)-2-[((4-((N'-methylsulfonyl-N'-(2-(pyrrolidin-1-yl)ethyl)amino)methyl)-3-chlorothiophen-2-yl)carbonyl)amino]-3-(morpholin-4-yl)-5-chlorobenzamide; NMR (DMSO-d$_6$/TFA) 10.9 (s, 1), 9.5 (s, 1), 7.3–8.5 (m, 6), 4.3 (s, 2), 2.8–4.1 (m, 14), 2.5 (s, 3), 2.2–2.5 (m, 2), 1.0–1.2 (m, 4) ppm;

N-(5-chloropyridin-2-yl)-2-[((4-((N'-methyl-N'-((dimethylamino)sulfonyl)amino)methyl)-3-chlorothiophen-2-yl)carbonyl)amino]-3-methoxy-5-chlorobenzamide; NMR (DMSO-d$_6$/TFA) 10.9 (s, 1), 9.4 (s, 1), 8.4 (s, 1), 8.1 (d, 1), 7.9 (d, 1), 7.8 (s, 1), 7.4 (s, 1), 7.3 (s, 1), 4.3 (s, 2), 3.9 (s, 3), 2.8 (s, 6), 2.7 (s, 3) ppm;

N-(5-chloropyridin-2-yl)-2-[((4-((N'-methyl-N'-((3,5-dimethylisoxazol-4-yl)sulfonyl)amino)methyl)-3-chlorothiophen-2-yl)carbonyl)amino]-3-methoxy-5-chlorobenzamide; NMR (DMSO-d$_6$/TFA) 10.9 (s, 1), 9.4 (s, 1), 8.4 (s, 1), 8.1 (d, 1), 7.9 (d, 1), 7.8 (s, 1), 7.4 (s, 1), 7.3 (s, 1), 4.3 (s, 2), 3.9 (s, 3), 2.7 (s, 3), 2.6 (s, 3), 2.4 (s, 3) ppm;

N-(5-chloropyridin-2-yl)-2-[((4-((N'-(methyl)sulfonyl-N'-(2-(dimethylamino)ethyl)amino)methyl)-3-chlorothiophen-2-yl)carbonyl)amino]-3-methoxy-5-chlorobenzamide; NMR (DMSO-d$_6$/TFA) 10.9 (s, 1), 9.5 (s, 1), 9.4 (s, 1), 8.4 (s, 1), 8.1 (d, 1), 7.9 (s, 1), 7.9 (d, 1), 7.4 (s, 1), 7.3 (s, 1), 4.2 (s, 2) 3.9 (s, 3), 3.6 (m, 2), 3.2 (m, 2), 3.1 (s, 3), 2.8 (s, 6) ppm; and N-(5-chloropyridin-2-yl)-2-[((4-((((2-chloroethyl)sulfonyl)amino)methyl)-3-chlorothiophen-2-yl)carbonyl)amino]-3-methoxy-5-chlorobenzamide.

C. In a similar manner to that described in Paragraph A above, N-(5-chloropyridin-2-yl)-2-[((4-((methylamino)methyl)-3-chlorothiophen-2-yl)carbonyl)amino]-3-(4-methylpiperazin-1-yl)-5-chlorobenzamide (0.7 g, 1.2 mmol) reacted with methanesulfonyl chloride (0.1 mL, 1.3 mmol) to afford N-(5-chloropyridin-2-yl)-2-[((4-((N'-methyl-N'-(methylsulfonyl)amino)methyl)-3-chlorothiophen-2-yl)carbonyl)amino]-3-(4-methylpiperazin-1-yl)-5-chlorobenzamide. Purification by HPLC on a C18 Dynamax column with 20–80% acetonitrile in water gradient with 0.1% trifluoroacetic acid afforded the trifluoroacetic acid salt as a white solid; NMR (DMSO-d$_6$/TFA) 10.9 (s, 1), 9.5 (s, 1), 8.4 (d, 1), 8.2 (d, 1), 7.9 (dd, 1), 7.8 (s, 1), 7.4 (d, 2), 4.3 (s, 2), 3.4 (d, 2), 3.0 (s, 2), 2.9 (s, 3), 2.7 (s, 3), 2.4 (br s, 3), 2.2 (s, 4) ppm.

D. In a similar manner, the following compounds were made:

N-(5-chloropyridin-2-yl)-2-[((4-((N'-methyl-N'-(methylsulfonyl)amino)methyl)-3-chlorothiophen-2-yl)carbonyl)amino]-3-(morpholin-4-yl)-5-chlorobenzamide, trifluoroacetic acid salt; NMR (DMSO-d$_6$/TFA) 9.8 (s, 1), 7.3–8.7 (m, 6), 3.9 (s, 2), 4.3 (s, 2), 3.8–4.0 (m, 4), 2.8–3.0 (m, 4), 2.9 (s, 3) ppm.

E. Other compounds of the invention may be prepared by methods similar to those described in this Example and by methods known to those of ordinary skill in the art.

EXAMPLE 5

Compounds of Formula (Ig)

A. To a solution of N-(5-chloropyridin-2-yl)-2-[((4-((methylamino)methyl)-3-chlorothiophen-2-yl)carbonyl)amino]-3-methoxy-5-chlorobenzamide (1.0 g, 2.0 mmol) in dioxane (20 mL) was added ethyl isocyanate (0.18 mL, 2.2 mmol) and the reaction stirred at ambient temperature. After 16 hours, the mixture was concentrated of all volatiles in vacuo. The residual solid was purified by flash chromatography on silica gel to afford 0.85 g (74% yield) of N-(5-chloropyridin-2-yl)-2-[((4-((N'-methyl-N"-ethylureido)methyl)-3-chlorothiophen-2-yl)carbonyl)amino]-3-methoxy-5-chlorobenzamide, as a white solid; NMR (DMSO-d$_6$/TFA) 10.9 (s, 1), 9.4 (s, 1), 8.4 (s, 1), 8.1 (d, 1), 7.9 (d, 1), 7.5 (s, 1), 7.4 (s, 1), 7.3 (s, 1), 4.4 (s, 2), 3.9 (s, 3), 3.1 (q, 2), 2.8 (s, 3), 1.0 (t, 3) ppm.

B. In a similar manner, the following compounds were made:

N-(5-chloropyridin-2-yl)-2-[((4-((N'-methyl-N"-ethylureido)methyl)-3-chlorothiophen-2-yl)carbonyl)amino]-3-(4-(tert-butoxycarbonyl)piperazin-1-yl)-5-chlorobenzamide; NMR (DMSO-d$_6$) 10.9 (s, 1), 9.5 (s, 1), 8.3 (d, 1), 8.1 (d, 1), 7.9 (dd, 1), 7.5 (s, 1), 7.4 (s, 1), 7.3 (s, 1), 6.4 (t, 1), 4.3 (s, 2), 3.3 (m, 4), 3.1 (m, 2), 2.9 (m, 4), 2.8 (s, 3), 1.4 (s, 9), 1.0 (t, 3) ppm.

C. In a manner similar to that described in Paragraph A above, N-(5-chloropyridin-2-yl)-2-[((4-((methylamino)methyl)-3-chlorothiophen-2-yl)carbonyl)amino]-3-methoxy-5-chlorobenzamide (1.0 g, 2.0 mmol) reacted with morpholinoethyl isothiocyanate (0.34 g, 2.0 mmol) in THF (20 mL) to afford N-(5-chloropyridin-2-yl)-2-[((4-((N'-methyl-N"-(2-(morpholin-4-yl)ethyl)thioureido)methyl)-3-chlorothiophen-2-yl)carbonyl)amino]-3-methoxy-5-chlorobenzamide. Purification by HPLC on a C18 Dynamax column with acetonitrile in water gradient with 0.1% trifluoroacetic acid afforded the trifluoroacetic acid salt as a white solid; NMR (DMSO-d$_6$/TFA) 10.9 (s, 1), 9.7 (br s, 1), 9.3 (s, 1), 7.2–8.3 (m, 7), 4.9 (s, 2), 3.9 (t, 4), 3.8 (s, 3), 3.7 (t, 2), 3.5 (d, 2), 3.3 (br, 2), 3.2 (br, 5) ppm.

D. In a similar manner, the following compounds were made:

N-(5-chloropyridin-2-yl)-2-[((4-((N"-methyl-N'-(2-(pyrrolidin-1-yl)ethyl)ureido)methyl)-3-chlorothiophen- 2-yl)carbonyl)amino]-3-(morpholin-4-yl)-5-chlorobenzamide, trifluoroacetic acid salt; NMR (DMSO-d$_6$/TFA) 10.9 (d, 1), 9.6 (d, 1), 7.3–8.5 (m, 6), 2.9–4.5 (m, 12), 2.8 (s, 3), 2.4 (br d, 2), 1.7–2.0 (m, 4) ppm.

E. A solution of potassium cyanate (0.70 g, 8.6 mmol) in methanol (4 mL) was added dropwise to a solution of N-(5-chloropyridin-2-yl)-2-[((4-((methylamino)methyl)-3-chlorothiophen-2-yl)carbonyl)amino]-3-methoxy-5-chlorobenzamide (0.10 g, 0.20 mmol) in acetic acid (1.5 mL), and the mixture was stirred at ambient temperature for 20 hours. Concentration and purification by HPLC on a C18 Dynamax column with 20–70% acetonitrile in water gradient with 0.1% trifluoroacetic acid afforded N-(5-chloropyridin-2-yl)-2-[((4-((N'-methylureido)methyl)-3-chlorothiophen-2-yl)carbonyl)amino]-3-methoxy-5-chlorobenzamide, trifluoroacetic acid salt as a white solid; NMR (DMSO-d$_6$/TFA) 10.9 (br s, 1), 9.3 (s, 1), 8.2 (s, 1), 8.1 (s, 1), 7.8 (d, 1), 7.5 (s, 1), 7.2 (s, 2), 4.4 (s, 2), 3.8 (s, 3), 2.9 (s, 3) ppm.

F. In a similar manner, the following compounds were made:

N-(5-chloropyridin-2-yl)-2-[((4-((N'-(2-hydroxyethyl)ureido)methyl)-3-chlorothiophen-2-yl)carbonyl)amino]-3-methoxy-5-chlorobenzamide; NMR (CDCl$_3$) 9.7 (br s, 1), 9.0 (s, 1), 8.3 (d, 1), 8.0 (d, 1), 7.7 (dd, 1), 7.4 (s, 1), 7.2 (d, 1), 7.0 (s, 1), 5.8 (br s, 2), 4.4 (s, 2), 3.9 (s, 3), 3.8 (br s, 1), 3.7 (t, 2), 3.4 (t, 2) ppm.

G. To a solution of bis(trichloromethyl) carbonate (0.15 g, 0.51 mmol) in CH$_2$Cl$_2$ (5 mL) at 0° C. was added N-(5-chloropyridin-2-yl)-2-[((4-((methylamino)methyl)-3-chlorothiophen-2-yl)carbonyl)amino]-3-methoxy-5-chlorobenzamide (0.10 g, 0.20 mmol), and the mixture stirred for 0.5 hour. Ethanolamine (0.40 mL, 6.6 mmol) was then added and the mixture was stirred at ambient temperature for 4 hours. Concentration in vacuo and purification by HPLC on a C18 Dynamax column with 20–70% acetonitrile in water gradient with 0.1% trifluoroacetic acid afforded N-(5-chloropyridin-2-yl)-2-[((4-((N'-methyl-N''-(2-hydroxyethyl)ureido)methyl)-3-chlorothiophen-2-yl)carbonyl)amino]-3-methoxy-5-chlorobenzamide, trifluoroacetic acid salt as a white solid; NMR (DMSO-d$_6$/TFA) 10.9 (br s, 1), 9.3 (s, 1), 8.3 (d, 1), 8.1 (d, 1), 7.8 (dd, 1), 7.7 (br s, 1), 7.5 (s, 1), 7.3 (s, 1), 7.2 (s, 1), 4.4 (s, 2), 3.8 (s, 3), 3.4 (t, 2), 3.1 (t, 2), 2.8 (s, 3) ppm.

H. In a similar manner, the following compounds were made:

N-(5-chloropyridin-2-yl)-2-[((4-((N'-methyl-N'-((4-(2-hydroxyethyl)piperazin-1-yl)carbonyl)amino)methyl)-3-chlorothiophen-2-yl)carbonyl)amino]-3-methoxy-5-chlorobenzamide, trifluoroacetic acid salt; NMR (DMSO-d$_6$/TFA) 10.9 (s, 1), 9.7 (s, 1), 9.3 (s, 1), 7.2–8.3 (m, 6), 4.3 (s, 2), 3.9 (s, 3), 3.0–3.7 (m, 12), 2.7 (s, 3) ppm.

I. To a solution of N-(5-chloropyridin-2-yl)-2-[((4-((methylamino)methyl)-3-chlorothiophen-2-yl)carbonyl)amino]-3-methoxy-5-chlorobenzamide (0.42 g, 0.87 mmol) in dioxane (5 mL) was added ethyl 3-isocyanatopropionate (0.15 mL, 1.0 mmol) and the mixture N-(5-chloropyridin-2-yl)-2-[((4-((N'-methyl-N'-(thiazolin-2-yl)amino)methyl)-3-chlorothiophen-2-yl)carbonyl)amino]-3-methoxy-5-chlorobenzamide; NMR (DMSO-d$_6$/TFA) 11.0 (s, 1), 10.1 (br d, 1), 9.5 (s, 1), 7.3–8.5 (m, 6), 4.7 (m, 2), 4 (m, 2), 3.9 (s, 3), 3.6 (m, 2), 3.2 (s, 3) ppm;

N-(4-chlorophenyl)-2-[((4-((N'-methyl-N'-(oxazolin-2-yl)amino)methyl)-3-chlorothiophen-2-yl)carbonyl)amino]-3-methoxy-5-chlorobenzamide; NMR (DMSO-d$_6$) 10.5 (s, 1), 10.3 (m, 1), 9.4 (s, 1), 7.3–8.0 (m, 7), 4.8 (m, 2), 4.6 (s, 2), 3.9 (m, 2), 3.8 (s, 3), 3.0 (s, 3) ppm;

N-(5-chloropyridin-2-yl)-2-[((4-((N'-methyl-N'-oxazolin-2-yl)amino)methyl)-3-chlorothiophen-2-yl)carbonyl)amino]-3-methoxy-5-chlorobenzamide; NMR (DMSO-d$_6$/TFA) 10.9 (s, 1), 10.3 (d, 1), 9.4 (s, 1), 7.3–8.4 (m, 6), 4.8 (t, 2), 4.5 (s, 2), 3.9 (t, 2), 3.8 (s; 3), 3.0 (s, 3) ppm;

N-(5-chloropyridin-2-yl)-2-[((4-((N'-ethyl-N'-(dihydro-4(H)-1,3-oxazin-2-yl)amino)methyl)-3-chlorothiophen-2-yl)carbonyl)amino]-3-methoxy-5-chlorobenzamide; NMR (DMSO-d$_6$) 10.9 (s, 1), 9.4 (s, 1), 9.3 (br s, 1), 8.4 (s, 1), 8.1 (d, 1), 7.9 (d, 1), 7.8 (s, 1), 7.4 (s, 1), 7.3 (s, 1), 4.6 (m, 2), 4.5 (s, 2), 3.9 (s, 3), 3.4 (m, 4), 2.0 (m, 2), 1.1 (t, 3) ppm;

N-(5-chloropyridin-2-yl)-2-[((4-((N'-ethyl-N'-(oxazolin-2-yl)amino)methyl)-3-chlorothiophen-2-yl)carbonyl)amino]-3-methoxy-5-chlorobenzamide; NMR (CDCl$_3$) 9.0 (s, 1), 8.9 (s, 1), 8.2 (d, 1), 8.1 (d, 1), 7.6 (dd, 1), 7.4 (s, 1), 7.3 (d, 1), 7.0 (d, 1), 4.4 (s, 2), 4.3 (t, 2), 3.9 (s, 3), 3.8 (t, 2), 3.3 (q, 2), 1.1 (t, 3) ppm;

N-(5-chloropyridin-2-yl)-2-[((4-((N'-(2,2,2-trifluoroethyl)-N'-(oxazolin-2-yl)amino)methyl)-3-chlorothiophen-2-yl)carbonyl)amino]-3-methoxy-5-chlorobenzamide; NMR (DMSO-d$_6$/TFA) 10.9 (s, 1), 9.4 (s, 1), 8.3 (d, 1), 8.1 (d, 1), 7.8 (d, 1), 7.75 (d, 1), 7.2 (d, 2), 4.9 (t, 2), 4.7 (s, 2), 4.4 (br s, 2), 3.9 (t, 2), 3.8 (s, 3) ppm.

C. In a similar manner to that described in Paragraph A above, N-(5-chloropyridin-2-yl)-2-[((4-((methylamino)methyl)-3-chlorothiophen-2-yl)carbonyl)amino]-3-methoxy-5-chlorobenzamide (1.5 g, 3.0 mmol) reacted with 3-bromopropylisocyanate (0.54 mL, 3.6 mmol), followed by triethylamine (2.0 mL, 15 mmol) to afford N-(5-chloropyridin-2-yl)-2-[((4-((N'-methyl-N'-(dihydro-4(H)-1,3-oxazin-2-yl)amino)methyl)-3-chlorothiophen-2-yl)carbonyl)amino]-3-methoxy-5-chlorobenzamide. Purification by HPLC on a C18 Dynamax column with acetonitrile in water gradient with 0.1% trifluoroacetic acid afforded the trifluoroacetic acid salt as a white solid; NMR (DMSO-d$_6$/TFA) 10.9 (s, 1), 9.4 (s, 1), 9.3 (br s, 1), 8.4 (s, 1), 8.1 (d, 1), 7.9 (d, 1), 7.9 (s, 1), 7.4 (s, 1), 7.3 (s, 1), 4.6 (m, 2), 4.5 (s, 2), 3.9 (s, 3), 3.4 (m, 2), 3.0 (s, 3), 2.0 (s, 2) ppm.

D. In a similar manner, the following compounds were made:

N-(5-chloropyridin-2-yl)-2-[((4-((N'-methyl-N'-(oxazolin-2-yl)amino)methyl)-3-chlorothiophen-2-yl)carbonyl)amino]-3-(morpholin-4-yl)-5-chlorobenzamide, trifluoroacetic acid salt; NMR (DMSO-d$_6$/TFA) 10.9 (s, 1), 10.3 (d, 1), 9.4 (s, 1), 7.2–8.4 (m$_1$ 6), 4.8 (t, 2), 4.6 (s, 2), 3.9 (t, 2), 3.8 (s, 3), 3.7 (br d, 4), 3.0 (s, 3), 2.9 (br d, 4) ppm;

N-(5-chloropyridin-2-yl)-2-[((4-((N'-ethyl-N'-(thiazolin-2-yl)amino)methyl)-3-chlorothiophen-2-yl)carbonyl)amino]-3-methoxy-5-chlorobenzamide, trifluoroacetic acid salt; NMR (DMSO-d$_6$/TFA) 10.9 (s, 1), 10.1 (br d, 1), 9.4 (d, 1), 7.2–8.4 (m, 6), 4.7 (d, 2), 4.0 (q, 2), 3.9 (s, 3), 3.4–3.7 (m, 4), 1.0–1.2 (m, 3) ppm;

N-(5-chloropyridin-2-yl)-2-[((4-((N'-methyl-N'-(4-(oxo)oxazolin-2-yl)amino)methyl)-3-chlorothiophen-2-yl)carbonyl)amino]-3-methoxy-5-chlorobenzamide, trifluoroacetic acid salt; NMR (DMSO-d$_6$/TFA) 10.9 (s, 1), 10.5 (s, 1), 9.4 (d, 1), 7.3–8.4 (m, 6), 4.5–4.8 (m, 4), 3.9 (s, 3), 3.4–3.7 (m, 4), 3.0 (d, 3) ppm;

N-(4-chlorophenyl)-2-[((4-((N'-methyl-N'-(oxazolin-2-yl)amino)methyl)-3-chlorothiophen-2-yl)carbonyl)amino]-3-(morpholin-4-yl)-5-chlorobenzamide, trifluoroacetic acid salt; NMR (DMSO-d$_6$/TFA) 10.5 (s, 1), 10.3 (d, 1), 9.6 (s, 1), 7.3–8.1 (m, 7), 4.9 (t, 2), 4.6 (s, 2), 3.9 (t, 2), 3.7 (br d, 4), 3.0 (s, 3), 2.9 (br d, 4) ppm;

N-(5-chloropyridin-2-yl)-2-[((4-((N'-ethyl-N'-(oxazolin-2-yl)amino)methyl)-3-chlorothiophen-2-yl)carbonyl)

amino]-3-(morpholin-4-yl)-5-chlorobenzamide, trifluoroacetic acid salt; NMR (DMSO-d$_6$/TFA) 10.9 (s, 1), 10.3 (s, 1), 9.5 (s, 1), 7.3–8.1 (m, 6), 4.9 (m, 2), 4.6 (s, 2), 3.9 (m, 2), 3.7 (m, 4), 3.4 (m, 2), 2.9 (m, 4), 1.0 (m, 3) ppm;

N-(5-chloropyridin-2-yl)-2-[((4-((N'-(t-butyl)-N'-(oxazolin-2-yl)amino)methyl)-3-chlorothiophen-2-yl)carbonyl)amino]-3-methoxy-5-chlorobenzamide, trifluoroacetic acid salt; NMR (DMSO-d$_6$/TFA) 10.9 (s, 1), 9.4 (s, 1), 8.4 (d, 1), 8.1 (d, 1), 7.9 (dd, 1), 7.5 (s, 1), 7.4 (d, 1), 7.2 (d, 1), 4.4 (s, 2), 4.1 (t, 2), 3.9 (s, 3), 3.6 (t, 2), 1.4 (s, 9) ppm;

5-(N-(5-chloropyridin-2-yl)amino)carbonyl-6-[4-((N'-methyl-N'-(oxazolin-2-yl)amino)methyl)-3-chlorothiophen-2-yl)carbonyl]amino-1,3-benzodioxole, trifluoroacetic acid salt; NMR (DMSO-d$_6$/TFA) 10.4 (s, 1), 10.0 (s, 1), 9.2 (s, 1), 6.5–7.4 (m, 6), 5.2 (s, 2), 3.8 (t, 2), 3.6 (s, 2), 2.8 (t, 2), 2.0 (s, 3) ppm;

N-(5-chloropyridin-2-yl)-2-[((4-((N'-(2-methoxyethyl)-N'-(oxazolin-2-yl)amino)methyl)-3 -chlorothiophen-2-yl)carbonyl)amino]-3-methoxy-5-chlorobenzamide, trifluoroacetic acid salt; NMR (DMSO-d$_6$/TFA) 11.0 (s, 1), 10.3 (d, 1), 9.4 (s, 1), 7.2–8.4(m, 6), 4.8 (m, 2), 4.6 (s, 2), 3.9 (s, 6), 3.5 (s, 2), 3.4 (s, 2), 3.2 (d, 2) ppm;

5-(N-(5-chloropyridin-2-yl)amino)carbonyl-6-[4-((N'-(2-methoxyethyl)-N'-(oxazolin-2-yl)amino)methyl)-3-chlorothiophen-2-yl)carbonyl]amino-1,3-benzodioxole, trifluoroacetic acid salt; NMR (DMSO-d$_6$/TFA) 11.5 (d, 1), 11.0 (s, 1), 10.3 (d, 1), 7.5–8.4 (m, 6), 6.1 (s, 2), 4.8 (s, 2), 4.6 (s, 2), 3.9 (m, 3), 3.4–3.6 (m, 4), 3.2 (d, 2) ppm.

E. Other compounds of the invention may be prepared by methods similar to those described in this Example and by methods known to those of ordinary skill in the art.

EXAMPLE 10

Compounds of Formula (Iq)

A. A mixture of N-(5-chloropyridin-2-yl)-2-[((4-((4-methylpiperazin-1-yl)methyl)-3-chlorothiophen-2-yl)carbonyl)amino]-3-hydroxy-5-chlorobenzamide (2.1 g, 3.7 mmol) and cesium carbonate (8 g, 25 mmol) in dimethyl formamide (50 mL) was stirred at ambient temperature for 1.0 hour. A solution of 1-chloro-3-iodopropane (1.1 g, 5.6 mmol) in dimethyl formamide (1.5 mL) was added dropwise, and stirring continued for 18 hours. 2-(methylamino)ethanol (1.5 mL, 18.7 mmol) was then added, and the mixture was heated at 65° C. for 12 hours. After cooling to ambient temperature the mixture was filtered, and the filtrate was acidified with trifluoroacetic acid. Purification by HPLC on a C18 Dynamax column with 20–70% acetonitrile in water gradient with 0.1% trifluoroacetic acid afforded N-(5-chloropyridin-2-yl)-2-[((4-((4-methylpiperazin-1-yl)methyl)-3-chlorothiophen-2-yl)carbonyl)amino]-3-(3-(N'-methyl-N'-(2-hydroxyethyl)amino)propoxy)-5-chlorobenzamide, trifluoroacetic acid salt as tan solid; NMR (DMSO-d$_6$/TFA) 11.0 (s, 1), 9.6 (s, 1), 9.4 (br, m, 1), 8.3 (s, 1), 8.2 (s, 1), 8.1 (d, 1), 7.8 (d, 1), 7.4 (s, 1), 7.3(s, 1), 4.4(s, 2), 4.2 (br t, 2), 3.0–4.0 (m, 14), 2.9 (s, 3), 2.8 (s, 3), 2.1 (m, 2) ppm.

B. In a similar manner, the following compounds were made:

N-(5-chloropyridin-2-yl)-2-[((4-((4-methylpiperazin-1-yl)methyl)-3-chlorothiophen-2-yl)carbonyl)amino]-3-(3-morpholinylpropoxy)-5-chlorobenzamide, trifluoroacetic acid salt; NMR (DMSO-d$_6$/TFA) 11.0 (s, 1), 9.9 (br s, 1), 9.6 (s, 1), 8.4 (d, 10), 8.2 (s, 1), 8.1 (d, 1), 7.9 (dd, 1), 7.4 (s, 1), 7.3 (s, 1), 4.4 (s, 2), 4.2 (t, 2), 3.9 (d, 2), 3.3–3.8 (m, 12), 3.3 (t, 2), 2.9–3.1 (m, 2), 2.9 (s, 3), 2.1 (m, 2) ppm;

N-5-chloropyridin-2-yl)-2-[((4-((4-methylpiperazin-1-yl)methyl)-3-chlorothiophen-2-yl)carbonyl)amino]-3-(3-(pyrrolidin-1-yl)propoxy)-5-chlorobenzamide, trifluoroacetic acid salt; NMR (DMSO-d$_6$/TFA) 11.0 (s, 1), 9.6 (s, 1), 8.4. (d, 1), 8.2 (s, 1), 8.15 (d, 1), 7.9 (dd, 1), 7.4 (s, 1), 7.3 (s, 1), 4.4 (s, 2), 4.2 (t, 2), 3.2–3.8 (m, 12), 3.0 (m, 2), 2.9 (s, 3), 2.1 (m, 2), 1.9 (m, 2), 1.8 (m, 2) ppm;

N-(5-chloropyridin-2-yl)-2-[((4-((N'-methyl-N'-(1-methylpiperidin4-yl)amino)methyl)-3-chlorothiophen-2-yl)carbonyl)amino]-3-(3-(morpholin-4-yl)propoxy)-5-chlorobenzamide, trifluoroacetic acid salt; NMR (DMSO-d$_6$/TFA) 11.0 (s, 1), 9.9 (br s, 1), 9.8 (br m, 1), 9.6 (s, 1), 8.4 (d, 1), 8.2(s, 1), 8.1 (d, 1), 7.8 (dd, 1), 7.4 (s, 1), 7.3 (s, 1), 4.4 (br m, 2), 4.2 (t, 2), 3.9 (d, 2), 3.5–3.7 (m, 5), 3.4 (d, 2), 3.3 (t, 2), 3.0 (m, 4), 2.8 (s, 3), 2.7 (s, 3), 2.3 (m, 2), 2.1 (m, 2), 2.0 (br q, 2) ppm;

N-(4-chlorophenyl)-2-[((4-((4-methylpiperazin-1-yl)methyl)-3-chlorothiophen-2-yl)carbonyl)amino]-3-(3-(morpholin-4-yl)propoxy)-5-chlorobenzamide, trifluoroacetic acid salt; NMR (DMSO-d$_6$/TFA) 10.6 (s, 1), 9.9 (br m, 1), 9.7 (s, 1), 8.2 (s, 1), 7.7 (d, 2), 7.4 (s, 1), 7.4 (s, 1), 7.3 (d, 2), 4.4 (s, 2), 4.2 (br t, 2), 3.9 (d, 2), 3.0–3.7 (m, 16), 2.9 (s, 3), 2.1 (m, 2) ppm;

N-(5-chloropyridin-2-yl)-2-[((4-((N'-methyl-N'-(2-hydroxyethyl)amino)methyl)-3-chlorothiophen-2-yl)carbonyl)amino]-3-(3-(pyrrolidin-1-yl)propoxy)-5-chlorobenzamide, trifluoroacetic acid salt; NMR (DMSO-d$_6$/TFA) 11.0 (s, 1), 9.7 (br s, 2), 9.6 (s, 1), 8.3 (d, 1), 8.2(s, 1), 8.1 (d, 1), 7.8 (dd, 1), 7.4 (s, 1), 7.3 (s, 1), 4.3 (br d, 2), 4.2 (t, 2), 3.7 (t, 2), 3.5 (m, 2), 3.3 (m, 2), 3.2 (m, 2), 2.9 (m, 2), 2.7 (s, 3), 2.1 (m, 2), 1.9 (m, 2), 1.8 (m, 2) ppm;

N-(5-chloropyridin-2-yl)-2-[((4-((N'-methyl-N'-(2-hydroxyethyl)amino)methyl)-3-chlorothiophen-2-yl)carbonyl)amino]-3-(3-(morpholin-4-yl)propoxy)-5-chlorobenzamide, trifluoroacetic acid salt; NMR (DMSO-d$_6$/TFA) 11.0 (s, 1), 9.8 (br s, 1), 9.7 (br s, 1), 9.6 (s, 1), 8.3 (d, 1), 8.2 (s, 1), 8.1 (d, 1), 7.8 (dd, 1), 7.4 (s, 1), 7.3 (s, 1), 4.3 (br d, 2), 4.2 (t, 2), 3.9 (d, 2), 3.7 (t, 2), 3.6 (t, 2), 3.4 (d, 2), 3.3 (m, 2), 3.2 (m, 2), 3.0 (m, 2), 2.7 (s, 3), 2.1 (m, 2) ppm;

N-(5-chloropyridin-2-yl)-2-[((4-((4-methylpiperazin-1-yl)methyl)-3-chlorothiophen-2-yl)carbonyl)amino]-3-(3-(imidazol-1-yl)propoxy)-5-chlorobenzamide, trifluoroacetic acid salt; NMR (DMSO-d$_6$/TFA) 11.0 (s, 1), 9.7 (s, 1), 9.0 (s, 1), 8.4 (d, 1), 8.2 (s, 1), 8.1 (d, 1), 7.9 (dd, 1), 7.7(s, 1), 7.6 (s, 1), 7.3 (s, 2), 4.4 (br m, 4), 4.0 (t, 2), 3.1–3.7 (m, 8), 2.8 (s, 3), 2.2 (m, 2) ppm;

N-(5-chloropyridin-2-yl)-2-[((4-((N'-methyl-N'-(2-hydroxyethyl)amino)methyl)-3-chlorothiophen-2-yl)carbonyt)amino]-3-(3-(imidazol-1-yl)propoxy)-5-chlorobenzamide, trifluoroacetic acid salt; NMR (DMSO-d$_6$/TFA) 11.0 (s, 1), 10.7 (s, 1), 9.1 (s, 1), 8.3 (d, 1), 8.2 (s, 1), 8.1 (d, 1), 7.8 (dd, 1), 7.7 (s, 1), 7.6 (s, 1), 7.3 (s, 2), 4.2–4.5 (m, 4), 4.0 (t, 2), 3.8 (t, 2), 3.2 (m, 2), 2.8 (s, 3), 2.2 (m, 2) ppm;

N-(5-chloropyridin-2-yl)-2-[((4-((N'-methyl-N'-(methylsulfonyl)amino)methyl)-3-chlorothiophen-2-yl)carbonyl)amino]-3-(3-(4-ethylpiperazin-1-yl)propoxy)-5-chlorobenzamide, trifluoroacetic acid salt; NMR (DMSO-d$_6$/TFA) 11.0 (br s, 1), 9.5 (s, 1), 8.3 (d, 1), 8.1 (d, 1), 7.9 (dd, 1), 7.8 (s, 1), 7.4 (s, 1), 7.3 (s, 1), 4.2 (br s, 2), 3.1–3.9 (m, 10), 2.9 (s, 3), 2.7 (s, 3), 2.2 (m, 2), 1.2 (t, 3) ppm;

N-(5-chloropyridin-2-yl)-2-[((4-((N'-methyl-N'-(2-hydroxyethyl)amino)methyl)-3-chlorothiophen-2-yl)carbonyl)amino]-3-(3-(pyridin-3-yloxy)propoxy)-5-chlorobenzamide, trifluoroacetic acid salt; NMR (DMSO-d$_6$) 11.0 (s, 1), 9.6 (s, 1), 7.9–8.7 (m, 8), 7.4 (d, 2), 4.4 (m, 6), 3.9 (m, 2), 2.8 (s, 3), 2.2 (m, 2) ppm.

C. To a solution of N-(5-chloropyridin-2-yl)-2-[((4-((N'-methyl-N'-(2-(pyrrolidin-1-yl)ethyl)amino)methyl)-3- chlorothiophen-2-yl)carbonyl)amino]-3-hydroxy-5-chlorobenzamide (1.3 g, 1.7 mmol) in DMF (30 mL) was added sodium hydride (60% dispersion in mineral oil, 0.16 g, 4.0 mmol), followed after 0.5 hour by 2-bromoethyl acetate (0.37 g, 2.2 mmol). The mixture was stirred at ambient temperature. After 24 hours NaOH (25% solution in water, 3 mL) was added, and the mixture was stirred for a further 4 hours. The mixture was acidified with trifluoroacetic acid, and purified by HPLC on a C18 Dynamax column with 20–70% acetonitrile in water gradient with 0.1% trifluoroacetic acid to afford N-(5-chloropyridin-2-yl)-2-[((4-((N'-methyl-N'-(2-(pyrrolidin-1-yl)ethyl)amino)methyl)-3-chlorothiophen-2-yl)carbonyl)amino]-3-(2-hydroxyethoxy)-5-chlorobenzamide, trifluoroacetic acid salt as white solid; NMR (DMSO-$d_6$/TFA) 10.9 (s, 1), 9.6 (s, 1), 8.3 (d, 1), 8.2 (s, 1), 8.1 (d, 1), 7.8 (dd, 1), 7.4 (s, 1), 7.3 (s, 1), 4.4 (s, 2), 4.2 (t, 2), 3.7 (t, 2), 3.6 (m, 2), 3.5 (m, 2), 3.0–3.8 (br m, 4), 2.8 (s, 3), 2.0 (br s, 4) ppm. Also obtained from this reaction was N-(5-chloropyridin-2-yl)-2-[((4-((N'-methyl-N'-(2-(pyrrolidin-1-yl)ethyl)amino)methyl)-3-chlorothiophen-2-yl)carbonyl)amino]-3-(2-acetoxyethoxy)-5-chlorobenzamide, trifluoroacetic acid salt; NMR (DMSO-$d_6$/TFA) 10.8 (s, 1), 9.4 (s, 1), 8.3 (s, 1), 8.2 (s, 1), 8.1 (d, 1), 7.8 (d, 1), 7.4 (s, 1), 7.3 (s, 1), 4.4 (s, 2), 4.3 (s, 4), 3.6 (m, 4), 3.5 (m, 4), 3.1–3.6 (br m, 4), 2.8 (s, 3), 1.9 (s, 3) ppm.

D. In a similar manner, the following compounds were made:

N-(5-chloropyridin-2-yl)-2-[((4-((4-methylpiperazin-1-yl)methyl)-3-chlorothiophen-2-yl)carbonyl)amino]-3-(2-hydroxyethoxy)-5-chlorobenzamide, trifluoroacetic acid salt; NMR (DMSO-$d_6$/TFA) 10.9 (s, 1), 9.6 (s, 1), 8.3 (d, 1), 8.2 (s, 1), 8.1 (d, 10), 7.8 (dd, 1), 7.4 (s, 1), 7.3 (s, 1), 4.4 (s, 2), 4.2 (t, 2), 3.7 (t, 2), 3.1–3.9 (br m, 8), 2.8 (s, 3) ppm;

N-(5-chloropyridin-2-yl)-2-[((4-((N'-methyl-N'-(2-(dimethylamino)ethyl)amino)methyl)-3-chlorothiophen-2-yl)carbonyl)amino]-3-(2-hydroxyethoxy)-5-chlorobenzamide, trifluoroacetic acid salt; NMR (DMSO-$d_6$/TFA) 10.9 (s, 1), 9.6 (s, 1), 8.3 (d, 1), 8.2 (s, 1), 8.1 (d, 1), 7.8 (dd, 1), 7.3 (s, 1), 7.2 (s, 1), 4.4 (s, 2), 4.1 (t, 2), 3.7 (t, 2), 3.5 (br s, 4), 2.9 (s, 6), 2.8 (s, 3) ppm;

N-(5-chloropyridin-2-yl)-2-[((4-((N'-methyl-N'-(1-methylpiperidin-4-yl)amino)methyl)-3-chlorothiophen-2-yl)carbonyl)amino]-3-(2-hydroxyethoxy)-5-chlorobenzamide, trifluoroacetic acid salt; NMR (DMSO-$d_6$/TFA) 11.0 (s, 1), 9.6 (s, 1), 8.4 (s, 1), 8.2 (s, 1), 8.1 (d, 1), 7.9 (dd, 1), 7.4 (s, 1), 7.3 (s, 1), 4.4 (br, 4), 4.2 (t, 2), 3.9–3.3 (m, 6), 3.2 (s, 3), 2.9 (s, 3), 2.4–2.2 (m, 4) ppm.

E. Other compounds of the invention may be prepared by methods similar to those described in this Example and by methods known to those of ordinary skill in the art.

EXAMPLE 11

Compounds of Formula (Ir)

A. To a solution of N-(5-chloropyridin-2-yl)-2-[((4-((4-methylpiperazin-1-yl)methyl)-3-chlorothiophen-2-yl)carbonyl)amino]-3-hydroxy-5-chlorobenzamide (1.0 g, 1.8 mmol) in DMF (15 mL) was added sodium hydride (0.051 g, 2.2 mmol) and the mixture stirred at ambient temperature. After 0.5 hours, ethyl bromoacetate (0.30 g, 1.8 mmol) was added and stirring continued. After 3 hours, the mixture was cooled to 0° C. and acidified with trifluoroacetic acid. Purification by HPLC on a C18 Vydac column with acetonitrile in water gradient with 0.1% trifluoroacetic acid afforded N-(5-chloropyridin-2-yl)-2-[((4-((4-methylpiperazin-1-yl)methyl)-3-chlorothiophen-2-yl)carbonyl)amino]-3-(ethoxycarbonyl)methoxy-5-chlorobenzamide, trifluoroacetic acid salt as a white solid; NMR (DMSO-$d_6$/TFA) 10.9 (s, 1), 9.4 (s, 1), 8.4 (dd, 1), 8.1 (d, 1), 8.0 (s, 1), 7.9 (dd, 1), 4.6 (s, 2), 4.3 (q, 2), 4.2 (s, 2), 3.8 (s, 4), 3.4 (s, 4), 3.4 (s, 3), 1.2 (t, 3) ppm.

B. In a similar manner, the following compounds were made:

N-(5-chloropyridin-2-yl)-2-[((4-((4-methylpiperazin-1-yl)methyl)-3-chlorothiophen-2 -yl)carbonyl)amino]-3-(methylthio)methoxy-5-chlorobenzamide, trifluoroacetic acid salt; NMR (DMSO-$d_6$/TFA) 10.8 (s, 1), 9.3 (s, 1), 8.3 (s, 1), 8.1 (d, 1), 8.1 (s, 1), 7.9 (dd, 1), 7.2 (s, 1), 7.12 (s, 1), 4.9 (s, 2), 4.3 (s, 2), 3.6 (s, 4), 3.5 (s, 4), 3.2 (s, 3), 2.4 (s, 3) ppm;

N-(5-chloropyridin-2-yl)-2-[((4-((N'-methyl-N'-(2-(pyrrolidin-1-yl)ethyl)amino)methyl)-3-chlorothiophen-2-yl)carbonyl)amino]-3-(2-methoxyethoxy)-5-chlorobenzamide, trifluoroacetic acid salt; NMR (DMSO-$d_6$/TFA) 10.9 (s, 1), 9.5 (s, 1), 8.4 (s, 1), 8.2 (s, 1), 8.1 (d, 1), 7.9 (br, 1), 7.2 (s, 1), 7.2 (s, 1), 4.4 (s, 2), 4.2 (br, 2), 3.7 (br, 2), 3.6 (br, 2), 3.5 (br, 2), 3.3 (s, 3), 2.8 (s, 3), 1.9 (br, 4) ppm;

N-(4-chlorophenyl)-2-[((4-((4-methylpiperazin-1-yl)methyl)-3-chlorothiophen-2-yl)carbonyl)amino]-3-(ethoxycarbonyl)methoxy-5-chlorobenzamide, trifluoroacetic acid salt; NMR (DMSO-$d_6$/TFA) 10.6 (s, ½), 10.5 (s, 1), 9.3 (s, ½), 7.8 (s, 1), 7.6 (d, 2), 7.4 (d, 2), 7.2 (s, 1), 7.1 (s, 1), 4.6 (s, 2), 4.2 (q, 2), 3.6 (s, 2), 3.4 (br, 8), 3.2 (t, 3), 3.1 (s, 3) ppm;

N-(4-chlorophenyl)-2-[((4-((4-methylpiperazin-1-yl)methyl)-3-chlorothiophen-2-yl)carbonyl)amino]-3-((acetoxy)ethoxy)-5-chlorobenzamide, trifluoroacetic acid salt; NMR (DMSO-$d_6$/TFA) 10.4 (s, 1), 9.5 (s, 1), 7.7 (d, 2), 7.4 (s, 1), 7.2 (d, 2), 7.1 (s, 1), 4.4 (s, 2), 4.4 (s, 4), 3.5 (br, 8), 2.9 (s, 3), 1.9 (s, 1) ppm;

N-(4-chlorophenyl)-2-[((4-((4-methylpiperazin-1-yl)methyl)-3-chlorothiophen-2-yl)carbonyl)amino]-3-(2-(morpholin-4-yl)ethoxy)-5-chlorobenzamide, trifluoroacetic acid salt; NMR (DMSO-$d_6$/TFA) 10.6 (s, 1), 9.7 (s, 1), 8.2 (s, 1), 7.7 (d, 2), 7.5 (s, 1), 7.4 (s, 1), 7.2 (d, 2), 4.5 (s, 2), 4.4 (s, 2), 3.9–3.1 (m, 20), 2.9 (s, 3) ppm;

N-(4-chlorophenyl)-2-[((4-((4-methylpiperazin-1-yl)methyl)-3-chlorothiophen-2-yl)carbonyl)amino]-3-((methylthio)methoxy)-5-chlorobenzamide, trifluoroacetic acid salt; NMR (DMSO-$d_6$/TFA) 10.6 (s, 1), 9.6 (s, 1), 8.2 (s, 1), 7.7 (d, 2), 7.5 (s, 1), 7.3 (d, 2), 5.4 (s, 2), 4.4 (s, 2), 3.2 (br, 8), 3.9 (s, 3), 2.2 (s, 3) ppm.

C. To a solution of N-(5-chloropyridin-2-yl)-2-[((4-((4-methylpiperazin-1-yl)methyl)-3-chlorothiophen-2-yl)carbonyl)amino]-3-hydroxy-5-chlorobenzamide (2.0 g, 3.6 mmol) in DMF (20 mL) were added cesium carbonate (8.0 g, 25 mmol) and 2-bromoethyl ethyl ether (0.71 g, 4.6 mmol). The suspension was heated at 60° C. for 16 hours. The mixture was cooled to ambient temperature and filtered, and the filtrate was acidified with trifluoroacetic acid. Purification by HPLC on a C18 Dynamax column acetonitrile in water gradient with 0.1% trifluoroacetic acid afforded N-(5-chloropyridin-2-yl)-2-[((4-((4-methylpiperazin-1-yl)methyl)-3 -clorothiophen-2-yl)carbonyl)amino]-3-(2-ethoxyethoxy)-5-chlorobenzamide trifluoroacetic acid salt as a white solid; NMR (DMSO-$d_6$/TFA) 11.9 (s, 1), 9.4 (s, 1), 8.3 (d, 1), 8.2 (s, 1), 8.1 (d, 1), 7.9 (dd, 1), 7.4 (s, 1), 7.3 (s, 1), 4.4 (s, 2), 4.2 (t, 2), 3.7 (t, 2), 3.5 (q, 2), 3.5 (br, 8), 2.9 (s, 3), 1.0 (t, 3) ppm.

D. In a similar manner, the following compounds were made:

N-(5-chloropyridin-2-yl)-2-[((4-((N'-methyl-N'-(2-hydroxyethyl)amino)methyl)-3-chlorothiophen-2-yl)

carbonyl)amino]-3-(2-methoxyethoxy)-5-chlorobenzamide, trifluoroacetic acid salt; NMR (DMSO-d$_6$/TFA) 10.9 (s, 1), 9.6 (br s, 1), 9.4 (s, 1), 8.3 (d, 1), 8.2 (s, 1), 8.1 (d, 1), 7.8 (d, 1), 7.4 (s, 1), 7.3 (s, 1), 4.3 (br d, 2), 4.2 (t, 2), 3.7 (t, 2), 3.6 (m, 2), 3.3 (s, 3), 3.2 (m, 2), 2.8 (s, 3) ppm;

N-(5-chloropyridin-2-yl)-2-[((4-((4-ethylpiperazin-1-yl)methyl)-3-chlorothiophen-2-yl)carbonyl)amino]-3-(2-(2-methoxyethoxy)ethoxy)-5-chlorobenzamide, trifluoroacetic acid salt; NMR (DMSO-d$_6$/TFA) 10.9 (s, 1), 9.4 (s, 1), 8.3 (d, 1), 8.2 (s, 1), 8.1 (d, 1), 7.8 (dd, 1), 7.4 (s, 1), 7.2 (s, 1), 4.5 (s, 2), 4.0 (t, 2), 3.0–3.8 (m, 16), 3.2 (s, 3), 1.2 (t, 3) ppm;

N-(5-chloropyridin-2-yl)-2-[((4-((N'-methyl-N'-(methylsulfonyl)amino)methyl)-3-chlorothiophen-2-yl)carbonyl)amino]-3-(2-aminoethoxy)-5-chlorobenzamide, trifluoroacetic acid salt; NMR (DMSO-d$_6$/TFA) 11.0 (s, 1), 9.6 (s, 1), 8.3 (d, 1), 8.1 (d, 1), 7.9 (br s, 3), 7.8 (dd, 1), 7.8 (s, 1), 7.4 (d, 1), 7.3 (s, 1), 4.3 (t, 2), 4.2 (s, 2), 3.2 (m, 2) ppm;

N-(5-chloropyridin-2-yl)-2-[((4-((N'-methyl-N'-(oxazolin-2-yl)amino)methyl)-3-chlorothiophen-2-yl)carbonyl)amino]-3-((2-(2-methoxyethoxy)ethoxy)-5-chlorobenzamide, trifluoroacetic acid salt; NMR (DMSO-d$_6$/TFA) 10.8 (br, 1), 10.3 (br, 1), 9.4 (br, 1), 8.3 (s, 1), 8.1 (d, 1), 7.9 (d, 1), 7.8 (d, 1), 7.4 (s, 1), 7.3 (s, 1), 4.8–4.4 (m, 3), 4.2 (m, 2), 3.9 (m, 2), 3.7 (m, 2), 3.5 (m, 2), 3.4 (m, 2), 3.2 (s, 3), 3.0 (s, 2), 2.8 (s, 2) ppm;

N-(5-chloropyridin-2-yl)-2-[((4-((N'-methyl-N'-(methylsulfonyl)amino)methyl)-3-chlorothiophen-2-yl)carbonyl)amino]-3-(2-(pyrrolidin-1-yl)ethoxy)-5-chlorobenzamide, trifluoroacetic acid salt; NMR (DMSO-d$_6$/TFA) 11.0 (br s, 1), 9.6 (br s, 2), 8.3( d, 1), 8.1 (d, 1), 7.8 (dd, 1), 7.7 (s, 1), 7.4 (s, 1), 7.3 (s, 1), 4.4 (m, 2), 4.2 (s,), 3.6 (m, 4), 3.1 (m, ), 2.9 (s, 3), 2.7 (s, 3), 1.9 (m, 2), 1.8 (m, 2) ppm;

N-(5-chloropyridin-2-yl)-2-[((4-((N'-methyl-N'-(2-hydroxyethyl)amino)methyl)-3-chlorothiophen-2-yl)carbonyl)amino]-3-(2-(imidazol-1-yl)ethoxy)-5-chlorobenzamide, trifluoroacetic acid salt; NMR (DMSO-d$_6$/TFA) 11.0 (s, 1), 9.6 (br s, 1), 9.5 (s, 1), 9.0 (s, 1), 8.3 (d, 1), 8.2 (s, 1), 8.1 (d, 1), 7.8 (dd, 1), 7.7 (s, 1), 7.5 (s, 1), 7.4 (s, 1), 7.3 (s, 1), 4.6 (m, 4), 4.4 (m, 1), 4.3 (m, 1), 3.8 (t, 2), 3.2 (m, 2), 2.8 (s, 3) ppm;

N-(5-chloropyridin-2-yl)-2-[((4-((N'-methyl-N'-(methylsulfonyl)amino)methyl)-3-chlorothiophen-2-yl)carbonyl)amino]-3-(2-(imidazol-1-yl)ethoxy)-5-chlorobenzamide, trifluoroacetic acid salt; NMR (DMSO-d$_6$/TFA) 10.9 (s, 1), 10.4 (s, 1), 9.0 (s, 1), 8.3 (d, 1), 8.1 (d, 1), 7.9 (dd, 1), 7.8 (s, 1), 7.7 (s, 1), 7.5 (s, 1), 7.4 (s, 1), 7.3 (d, 1), 4.6 (br, 4), 4.2 (s, 2), 2.9 (s, 3), 2.6 (s, 3) ppm;

N-(5-chloropyridin-2-yl)-2-[((4-((N'-methyl-N(2-hydroxyethyl)amino)methyl)-3-chlorothiophen-2-yl)carbonyl)amino]-3-(2-(pyrrolidin-1-yl)ethoxy)-5-chlorobenzamide; trifluoroacetic acid salt; NMR (DMSO-d$_6$/TFA) 11.0 (s, 1), 9.6 (s, 1), 8.4 (s, 1), 8.2 (s, 1), 8.1 (d, 1), 7.9 (dd, 1), 7.4 (s, 1), 7.4 (s, 1), 4.6 (s, 2), 4.9–3.6 (m, 8), 3.2 (dd, 4), 2.8 (s, 3), 2.0 (s, 3), 1.9 (br, 4) ppm;

N-(5-chloropyridin-2-yl)-2-[((4-((N'-methyl-N'-(2,3-dihydroxypropyl)amino)methyl)-3-chlorothiophen-2-yl)carbonyl)amino]-3-(2-methoxyethoxy)-5-chlorobenzamide, trifluoroacetic acid salt; NMR (DMSO-d$_6$/TFA) 10.9 (s, 1), 9.5 (br s, 1), 9.4 (s, 1), 8.4 (s, 1), 8.2 (m, 1), 8.1 (d, 1), 7.9 (d, 1), 7.4 (s, 1), 7.3 (s, 1), 4.4 (m, 2), 4.3 (m, 2), 4.0 (m, 1), 3.7 (m, 2), 3.4 (m, 2), 3.3 (s, 3), 3.1 (m, 2), 2.8 (brs, 3) ppm;

N-(5-chloropyridin-2-yl)-2-[((4-((N'-methyl-N'-(2-hydroxyethyl)amino)methyl)-3-chlorothiophen-2-yl)carbonyl)amino]-3-ethoxy-5-chlorobenzamide, trifluoroacetic acid salt; NMR (DMSO-d$_6$/TFA) 10.9 (s, 1), 9.4 (s, 1), 8.3 (s, 1), 8.1 (d, 1), 7.9 (d, 1), 7.8 (s, 1), 7.4 (s, 1), 7.3 (s, 1), 7.2 (s, 1), 4.24.5 (br, 2), 4.1 (q, 2), 3.7 (m, 2), 3.1 (m, 2), 2.8 (s, 3), 1.3 (t, 3) ppm;

N-(5-chloropyridin-2-yl)-2-[((4-((N'-ethyl-N(2-hydroxyethyl)amino)methyl)-3-chlorothiophen-2-yl)carbonyl)amino]-3-(2-methoxyethoxy)-5-chlorobenzamide, trifluoroacetic acid salt; NMR (DMSO-d$_6$/TFA) 10.9 (s, 1), 9.5 (s, 1), 8.4 (d, 1), 8.2 (s, 1), 8.1 (d, 1), 7.9 (dd, 1), 7.4 (d, 1), 7.3 (d, 1), 4.4 (br d, 2), 4.2 (br t, 2), 3.8 (t, 2), 3.6 (br t, 2), 3.2 (s, 3), 3.2–3.1 (brm, 4), 1.3 (t, 3) ppm.

E, In a manner similar to that described in Paragraph B above, N-(5-chloropyridin-2-yl)-2-[((4-((4-methylpiperazin-1-yl)methyl)-3-chlorothiophen-2-yl)carbonyl)amino]-3-hydroxy-5-chlorobenzamide (7.0 g, 13 mmol) reacted with cesium carbonate (29 g, 89 mmol) and 2-bromoethyl methyl ether (2.6 g, 19 mmol) in DMF (100 mL) at 60° C. Purification by flash chromatography on silica gel afforded 4.8 g (62% yield) of N-(5-chloropyridin-2-yl)-2-[((4-((4-methylpiperazin-1-yl)methyl)-3-chlorothiophen-2-yl)carbonyl)amino]-3-(2-methoxyethoxy)-5-chlorobenzamide, as a yellow solid; NMR (DMSO-d$_6$/TFA) 10.9 (s, 1), 9.4 (s, 1), 8.4 (s, 1), 8.1 (d, 2), 7.9 (d, 1), 7.4 (s, 1), 7.3 (s, 1), 4.2 (s, 2), 4.2 (br, 2), 3.6 (s, 2), 3.8-3.0 (br, 8), 3.2 (s, 3), 2.9 (s, 3) ppm.

F. In a similar manner, the following compounds were made:

N-(5-chloropyridin-2-yl)-2-[((4-((4-ethylpiperazin-1-yl)methyl)-3-chlorothiophen-2-yl)carbonyl)amino]-3-(2-methoxyethoxy)-5-chlorobenzamide; NMR (DMSO-d$_6$/TFA) 10.9 (s, 1), 9.5 (s, 1), 8.3 (s, 1), 8.2 (s, 1), 8.1 (d, 1), 7.8 (d, 1), 7.4 (s, 1), 7.2 (s, 1), 8.1 (d, 10, 7.8 (d, 1), 7.4 (s, 1), 7.2 (s, 1), 4.4 (s, 2), 4.3 (s, 2), 3.6 (s, 2), 3.2 (s, 3), 3.8–3.20 (br, 8), 3.2 (q, 2), 1.2 (t, 3) ppm;

N-(5-chloropyridin-2-yl)-2-[((4-((N'methyl-N'-(methylsulfonyl)amino)methyl)-3-chlorothiophen-2-yl)carbonyl)amino]-3-((2-(2-methoxyethoxy)ethoxy)-5-chlorobenzamide; (DMSO-d$_6$/TFA) 9.2 (s, 1), 9.0 (s, 1), 8.3 (d, 1), 8.1 (d, 1), 7.7 (dd, ), 7.6 (s, 1), 7.3 (d, 1), 7.1 (d, 1), 4.3 (s, 2), 4.2 (t, 2), 3.9 (t, 2), 3.7 (m, 2), 3.5 (m, 2), 3.4 (s, 3), 2.9 (s, 3), 2.85 (s, 3)ppm; and N-(4-chlorophenyl)-2-[((3-chlorobenzo[b]thien-2-yl)carbonyl)amino]-3-(ethoxycarbonyl)methoxybenzamide.

G. Other compounds of the invention may be prepared by methods similar to those described in this Example and by methods known to those of ordinary skill in the art.

EXAMPLE 12

Compounds of Formula (Is)

A. To a solution of N-(5-chloropyridin-2-yl)-2-[((4-((N'-methyl-N'-(methylsulfonyl)amino)methyl)-3-chlorothiophen-2-yl)carbonyl)amino]-3-(2,3-epoxypropoxy)-5-chlorobenzamide (0.20 g, 0.30 mmol) in DMF (20 mL) was added imidazole sodium salt (0.15 g, 1.6 mmol) and the mixture stirred at ambient temperature. After 18 hours, the mixture was concentrated of all volatiles in vacuo, and the residue dissolved in acetonitrile, water and trifluoroacetic acid. Purification by HPLC on a C18 Dynamax column with 20–80% acetonitrile in water gradient with 0.1% trifluoroacetic acid afforded N-(5-chloropyridin-2-yl)-2-[((4-((N'-methyl-N'-(methylsulfonyl)amino)methyl)-3-chlorothiophen-2-yl)carbonyl)amino]-3-

(2-hydroxy-3-(imidazol-1-yl)propoxy)-5-chlorobenzamide, trifluoroacetic acid salt as a white solid; NMR (DMSO-$d_6$/TFA) 11.0 (s, 1), 9.6 (s, 1), 9.0 (s, 1), 8.3 (d, 1), 8.1 (d, 1), 7.9 (dd, 1), 7.8 (s, 1), 7.6 (d, 2), 7.4 (d, 1), 7.3 (d, 1), 4.4-4.3 (m, 2), 4.25 (brm, 1), 4.2 (s, 2), 4.1-4.0 (brm, 2), 2.9 (s, 3), 2.7 (s, 3) ppm.

B. In a similar manner, the following compounds were made:

N-(5-chloropyridin-2-yl)-2-[((4-((N'-methyl-N'-((dimethylamino)sulfonyl)amino)methyl)-3-chlorothiophen-2-yl)carbonyl)amino]-3-(2-hydroxy-3-(pyrrolidin-1-yl)propoxy)-5-chlorobenzamide, trifluoroacetic acid salt; NMR (DMSO-$d_6$/TFA) 11.0 (s, 1), 9.6 (s, 1), 8.4 (d, 1), 8.1 (d, 1), 7.9 (dd, 1), 7.8 (s, 1), 7.4 (d, 1), 7.3 (d, 1), 4.3 (s, 2), 4.2 (br m, 1), 4.1 (br s, 2), 3.5 (br m, 2), 3.3 (br m, 2), 3.0 (br m, 2), 2.8 (s, 9), 2.7 (s, 3), 2.0–1.8 (br m, 4) ppm;

N-(5-chloropyridin-2-yl)-2-[((4-((N'-methyl-N'-(methylsulfonyl)amino)methyl)-3-chlorothiophen-2-yl)carbonyl)amino]-3-(2-hydroxy-3-(pyrrolidin-1-yl)propoxy)-5-chlorobenzamide, trifluoroacetic acid salt; NMR (DMSO-$d_6$/TFA) 11.0 (s, 1), 9.5 (s, 1), 8.3 (d, 1), 8.1 (d, 1), 7.8 (dd, 1), 7.7 (s, 1), 7.4 (d, 1), 7.3 (d, 1), 4.2 (s, 2), 4.2 (br m, 1), 4.1 (brs, 2), 3.5 (br m, 2), 3.3 (br m, 2), 3.0 (br m, 2), 2.9 (s, 3), 2.7 (s, 3), 2.0–1.8 (br m, 4) ppm.

C. Other compounds of the invention may be prepared by methods similar to those described in this Example and by methods known to those of ordinary skill in the art.

EXAMPLE 13

Compounds of Formula (It)

A. To a solution of N-(5-chloropyridin-2-yl)-2-[((4-((N'-methyl-N'-(methylsulfonyl)amino)methyl)-3-chlorothiophen-2-yl)carbonyl)amino]-3-(2,3-epoxypropoxy)-5-chlorobenzamide (0.20 g, 0.30 mmol) in methylene chloride (3 mL) was added methanol (5 mL), followed by 2,3-dichloro-5,6-dicyano-1,4-benzoquinone (DDQ) (0.040 g, 0.20 mmol) and the mixture stirred at ambient temperature. After 48 hours, the reaction was quenched with aqueous NaHCO$_3$ solution and extracted with methylene chloride. The organic layer was dried over Na$_2$SO$_4$ and concentrated in vacuo. Purification by flash chromatography on silica gel, followed by precipitation from methylene chloride-hexane afforded 0.080 g (38% yield) of N-(5-chloropyridin-2-yl)-2-[((4-((N'-methyl-N'-(methylsulfonyl)amino)methyl)-3-chlorothiophen-2-yl)carbonyl)amino]-3-(2-hydroxy-3-methoxypropoxy)-5-chlorobenzamide, as a pale brown solid; NMR (DMSO-$d_6$/TFA) 10.9 (s, 1), 9.4 (s, 1), 8.3 (d, 1), 8.1 (d, 1), 7.9 (dd, 1), 7.8 (s, 1), 7.4 (s, 1), 7.2 (s, 1), 4.2 (s, 2), 4.1–4.0 (br m, 2), 4.0-3.9 (m, 1), 3.4-3.3 (m, 1), 3.2 (s, 3), 2.9 (s, 3), 2.7 (s, 3) ppm.

B. Other compounds of the invention may be prepared by methods similar to those described in this Example and by methods known to those of ordinary skill in the art.

EXAMPLE 14

Compounds of Formula (Iv)

A. A solution of N-(4-chlorophenyl)-2-[((3-chlorobenzo[b]thien-2-yl)carbonyl)amino]-4,5-difluorobenzamide (0.045 g, 0.090 mmol) in 1-methylpiperazine (1 mL, 10.0 mmol) was heated at 85° C. for 15 hours. Concentration and purification by HPLC on a C18 Dynamax column with 20–70% acetonitrile in water gradient with 0.1% trifluoroacetic acid afforded N-(4-chlorophenyl)-2-[((3-chlorobenzo[b]thien-2-yl)carbonyl)amino]-4-(4-methylpiperazin-1-yl)-5-fluorobenzamide, trifluoroacetic acid salt as a white solid; NMR (DMSO-$d_6$/TFA) 12.0 (s, 1), 10.4 (s, 1), 9.9 (br s, 1), 8.3 (d, 1), 8.0 (m, 1), 7.9 (m, 1), 7.8 (d, 1), 7.7 (d, 2), 7.6 (m, 2), 7.3 (d, 2), 3.7 (d, 2), 3.6 (d, 2), 3.2 (m, 4), 2.9 (s, 3) ppm.

B. In a similar manner, the following compounds were made:

N-(4-chlorophenyl)-2-[((3-chlorobenzo[b]thien-2-yl)carbonyl)amino]4-((3-(4-methylpiperazin-1-yl)propyl)amino)-5-fluorobenzamide; NMR (DMSO-$d_6$/TFA) 12.5 (s, 1), 10.2 (s, 1), 8.1 (m, 1), 8.0 (d, 1), 7.9 (m, 1), 7.8 (d, 1), 7.7 (d, 2), 7.6 (m, 2), 7.4 (d, 2), 3.2–4.0 (m, 12), 2.9 (s, 3), 2.0 (m, 2) ppm;

N-(4-chlorophenyl)-2-[((3-chlorobenzo[b]thien-2-yl)carbonyl)amino]-4-(N'-methyl-N'(3-(dimethylamino)propylamino-5-fluorobenzamide;

C. 2-Dimethylaminoethanethiol hydrochloride (1.4 g, 10 mmol) was stirred in aqueous Na$_2$CO$_3$ (15% solution, 20 mL) for 0.5 hour. The solution was extracted with ethyl acetate (40 mL) and the organic layer was dried over Na$_2$SO$_4$, and concentrated in vacuo. To a solution of the residual oil in DMF (1.0 mL) was added N-(4-chlorophenyl)-2-[((3-chlorobenzo[b]thien-2-yl)carbonyl)amino]-4,5-difluorobenzamide (0.45 g, 0.09 mmol) and mixture was heated at 105° C. After 15 hours, the mixture was cooled to ambient temperature and concentrated in vacuo. Purification by HPLC on a C18 Dynamax column with 20–70% acetonitrile in water gradient with 0.1 % trifluoroacetic acid afforded N-(4-chlorophenyl)-2-[((3-((2-(dimethylamino)ethyl)thio)benzo[b]thien-2-yl)carbonyl)amino]4-((2-(dimethylamino)ethyl)thio)-5-fluorobenzamide, trifluoroacetic acid salt as tan solid; NMR (DMSO-$d_6$/TFA) 11.6 (s, 1), 10.7 (s, 1), 9.8 (brs, 1), 9.4 (brs, 1), 8.4 (d, 1), 8.0 (dd, 2), 7.8 (d, 1), 7.7 (d, 2), 7.5 (m, 2), 7.4 (d, 2), 3.4 (br m, 4), 3.2 (br m, 4), 2.8 (s, 6), 2.6 (s, 6) ppm.

D. Other compounds of the invention may be prepared by methods similar to those described in this Example and by methods known to those of ordinary skill in the art.

EXAMPLE 15

Compounds of Formula (Ip)

A. To a solution of N-(5-chloropyridin-2-yl)-2-[((4-((N'-methyl-N'-(methylsulfonyl)amino)methyl)-3-chlorothiophen-2-yl)carbonyl)amino]-3-methoxy-5-chlorobenzamide, (4.6 g, 8.0 mmol) in methylene chloride (120 mL) was added boron tribromide (1 M solution in methylene chloride, 80 mL, 80 mmol). After 18 hours, the mixture was poured slowly onto ice (ca. 300 g). Ethyl acetate (300 mL) was added, and the aqueous layer was adjusted to pH 7 with saturated aqueous NaHCO$_3$ solution. The layers were separated and the aqueous layer further extracted with ethyl acetate (300 mL). The combined organics were dried over Na$_2$SO$_4$ and concentrated in vacuo to afford 4.5 g (100% yield) of N-(5-chloropyridin-2-yl)-2-[((4-((N'-methyl-N'-(methylsulfonyl)amino)methyl)-3-chlorothiophen-2-yl)carbonyl)amino]-3-hydroxy-5-chlorobenzamide, as a tan solid; NMR (DMSO-$d_6$/TFA) 10.9 (s, 1), 9.3 (s, 1), 8.3 (d, 1), 8.1 (d, 1), 7.8 (dd, 1), 7.7 (s, 1), 7.1 (dd, 2), 4.2 (s, 2), 2.9 (s, 3), 2.7 (s, 3)ppm.

B. In a similar manner, the following compounds were made:

N-(4-chlorophenyl)-2-[((3-chlorobenzo[b]thien-2-yl)carbonyl)amino]-3-hydroxy-5-chlorobenzamide; NMR (DMSO-$d_6$) 10.6 (s, 1), 10.4 (s, 1), 9.6 (s, 1), 8.1 (m, 1), 7.9 (m, 1), 7.7 (d, 2), 7.6 (m, 2), 7.4 (d, 2), 7.1 (d, 2) ppm;

N-(5-chloropyridin-2-yl)-2-[((4-((N''-methyl-N'-(oxazolin-2-yl)amino)methyl)-3-chlorothiophen-2-yl)carbonyl)amino]-3-hydroxy-5-chlorobenzamide; NMR (DMSO-$d_6$/TFA) 11.0 (br s, 1), 9.4 (brs, 1), 8.3 (s, 1), 8.1 (d, 1), 7.9 (dd, 1), 7.8 (s, 1), 7.4 (s, 2), 7.3 (t, 2), 7.1 (s, 1), 7.0 (s, 1) 4.6 (t, 2), 3.9 (s, 3) ppm;

N-(5-chloropyridin-2-yl)-2-[((4-((N'-methyl-N'-((dimethylamino)sulfonyl)amino)methyl)-3-chlorothiophen-2-yl)carbonyl)amino]-3-hydroxy-5-chlorobenzamide; NMR (DMSO-$d_6$/TFA) 10.8 (s, 1), 9.3 (s, 1), 8.3 (d, 1), 8.1 (d, 1), 7.8 (dd, 1), 7.7 (s, 1), 7.1 (d, 2), 4.2 (s, 2), 2.7 (s, 6), 2.65 (s, 3) ppm;

N-phenyl-2-[((3-chlorobenzo[b]thien-2-yl)carbonyl)amino] 4,5-dihydroxybenzamide;

N-phenyl-2-[((3-chlorobenzo[b]thien-2-yl)carbonyl) amino]-3-hydroxybenzamide;

N-(4-chlorophenyl)-2-[((3-chlorobenzo[b]thien-2-yl) carbonyl)amino]-3-hydroxybenzamide; and N-(4-chlorophenyl)-2-[((3-chlorobenzo[b]thien-2-yl) carbonyl)amino]-4,5-dihydroxybenzamide.

C. Other compounds of the invention may be prepared by methods similar to those described in this Example and by methods known to those of ordinary skill in the art.

EXAMPLE 16

Compounds of Formula (Ib)

A. To a solution of N-(4-chlorophenyl)-2-amino-5-methylbenzamide (0.11 g, 0.42 mmol) in pyridine (5 mL) at 0° C. was added 2-chlorocarbonyl-3-chlorobenzo[b] thiophene (0.15 g, 0.64 mmol), and the mixture allowed to warm to ambient temperature with stirring. After 16 hours, the mixture was poured onto water (5 mL) and the resulting white solid collected by filtration and dried in vacuo. Recrystallization from acetonitrile afforded 0.095 g (50% yield) of N-(4-chlorophenyl)-2-[((3-chlorobenzo[b]thien-2-yl)carbonyl)amino]-5-methylbenzamide, as a white crystalline solid; NMR (DMSO-$d_6$/TFA) 11.4 (s, 1), 10.7 (s, 1), 8.2 (d, 1), 7.4–8.2 (m, 10), 2.4 (s, 3) ppm.

B. In a similar manner, the following compounds were made:

N-(4-bromophenyl)-2-[((3-chlorobenzorb]thien-2-yl) carbonyl)amino]-5-methylbenzamide; NMR (DMSO-$d_6$/TFA) 11.3 (s, 1), 10.7 (s, 1), 8.2 (d, 1), 7.4–8.2 (m, 10), 2.4 (s, 3) ppm;

N-(4-bromophenyl)-2-[((3-chlorobenzo[b]thien-2-yl) carbonyl)amino]-5-chlorobenzamide; NMR (DMSO-$d_6$/TFA) 11.4 (s, 1), 10.8 (s, 1), 8.4 (d, 1), 7.5–8.2 (m, 10) ppm;

N-(4-chlorophenyl)-2-[((3-chloro-6-methylbenzo[b]thien-2-yl)carbonyl)amino]-5-chlorobenzamide; NMR (DMSO-$d_6$/TFA) 11.3 (s, 1), 10.8 (s, 1), 8.3 (d, 1), 7.4–7.9 (m, 9), 2.5 (s, 3) ppm;

N-(4-chlorophenyl)-2-[((3-methylbenzo[b]thien-2-yl) carbonyl)amino]-5-chlorobenzamide; NMR (DMSO-$d_6$/TFA) 11.2 (s, 1), 10.7 (s,1), 8.4 (d, 1), 7.4-8.0 (m, 10), 2.8 (s, 3) ppm;

N-(5-chloropyridin-2-yl)-2-[((3-chlorobenzo[b]thien-2-yl) carbonyl)amino]-5-methylbenzamide; NMR (DMSO-$d_6$/TFA) 11.3 (s, 1), 11.2 (s, 1), 8.4 (d, 1), 7.4-8.2 (m, 9), 2.4 (s, 3) ppm;

N-(4-chlorophenyl)-2-[((5-methyl-3-chlorothiophen-2-yl) carbonyl)amino]-5-chlorobenzamide; NMR (DMSO-$d_6$/TFA) 11.0 (s, 1), 10.8 (s, 1), 8.3 (d, 1), 7.4-7.9 (m, 6), 7.0 (d, 2) 2.5 (d, 3) ppm;

N-(4-chlorophenyl)-2-[((3-chlorobenzo[b]thien-2-yl) carbonyl)amino]-5-fluorobenzamide; NMR (DMSO-d6/ TFA) 11.7 (s, 1), 11.2 (s, 1), 8.3 (dd, 1), 8.2 (m, 1), 7.9 (m, 1), 8.0 (d, 2), 7.7 (d, 1), 7.6 (m, 1), 7.5 (dt, 1), 7.4 (d, 2) ppm;

N-(4-chlorophenyl)-2-[((3-chlorobenzo[b]thien-2-yl) carbonyl)aminol-4-methylbenzamide; NMR (DMSO-$d_6$/TFA) 11.6 (s, 1), 10.6 (s, 1), 8.2 (s, 1), 8.1 (dd, 1), 7.9 (dd, 1), 7.8 (d, 1), 7.7 (d, 2), 7.6 (s, 1), 7.5 (d, 1), 7.4 (d, 2), 7.1 (d, 1), 2.4 (s, 3) ppm;

N-(4-chlorophenyl)-2-[((3-chlorobenzo[b]thien-2-yl) carbonyl)amino]-3-methyl-5-chlorobenzamide; NMR (DMSO-$d_6$/TFA) 10.6 (s, 1), 10.2 (s, 1), 8.1 (dd, 1), 7.9 (dd, 1), 7.7 (d, 2), 7.6–7.5 (m, 4), 7.4 (d, 2), 2.4 (s, 3) ppm;

N-(4-chlorophenyl)-2-[((3-chlorobenzo[b]thien-2-yl) carbonyl)amino]-5-chlorobenzamide; NMR (DMSO-$d_6$/TFA) 11.4 (s, 1), 10.8 (s, 1), 8.4 (d, 1), 7.4–8.1 (m, 10) ppm;

N-(4-chlorophenyl)-2-[((3-methoxybenzo[b]thien-2-yl) carbonyl)amino]-5-methylbenzamide; NMR (DMSO-$d_6$) 11.4 (s, 1), 10.7 (s, 1), 8.4 (d, 1), 8.0 (m, 2), 7.8 (d, 2), 7.6 (s, 1), 7.4 (m, 5), 4.2 (s, 3), 2.3 (s, 3) ppm;

N-(4-chlorophenyl)-2-[((3-chlorobenzo[b]thien-2-yl) carbonyl)amino]benzamide; NMR (DMSO-$d_6$) 11.4 (s, 1), 10.7 (s, 1), 8.4 (d, 2), 8.1 (m, 1), 7.9 (m, 1), 7.9 (d, 1), 7.8 (d, 2), 7.6 (m, 3), 7.4 (d, 2), 7.3 (t, 1) ppm;

N-(4-chlorophenyl)-2-[((3-chlorobenzo[b]thien-2-yl) carbonyl)amino]4,5-difluorobenzamide; NMR (DMSO-$d_6$) 11.6 (s, 1), 10.7 (s, 1), 8.4 (dd, 1), 8.1 (m, 2), 8.0 (d, 1), 7.8 (d, 2), 7.6 (m, 2), 7.4 (d, 2) ppm;

N-(4-chlorophenyl)-2-[((3-chlorobenzo[b]thien-2-yl) carbonyl)amino]-3-methoxy-5-chlorobenzamide; NMR (DMSO-$d_6$) 10.5 (s, 1), 9.8 (s, 1), 8.1 (m, 1), 7.9 (m, 1), 7.7 (d, 2), 7.6 (m, 2), 7.4 (s, 1), 7.4 (d, 2), 7.3 (s, 1), 3.9 (s, 3) ppm;

N-(4-chlorophenyl)-2-[((3-chlorobenzo[b]thien-2-yl) carbonyl)amino]-4-fluoro-5-chlorobenzamide; NMR (DMSO-$d_6$) 11.7 (s, 1), 10.8 (s, 1), 8.4 (d, 1), 8.2 (m, 2), 8.0 (d, 1), 7.7 (d, 2), 7.6 (m, 2), 7.4 (d, 2) ppm;

N-(4-chlorophenyl)-2-[((3-methylthiophen-2-yl)carbonyl) amino]-5-chlorobenzamide;

N-(4-chlorophenyl)-2-[((4-methyl-3-chlorothiophen-2-yl) carbonyl)amino]-5-chlorobenzamide;

N-phenyl-2-[((3-chlorobenzo[b]thien-2-yl)carbonyl) amino]-5-methylbenzamide;

N-(pyridin-3-yl)-2-[((3-chlorobenzo[b]thien-2-yl)carbonyl) amino]-5-methylbenzamide;

N-(2,4-difluorophenyl)-2-[((3-chlorobenzo[b]thien-2-yl) carbonyl)amino]-5-methylbenzamide;

N-(pyridin-2-yl)-2-[((3-chlorobenzo[]b]thien-2-yl) carbonyl)amino]-5-methylbenzamide;

N-(4-methoxyphenyl)-2-[((3-chlorobenzo[b]thien-2-yl) carbonyl)amino]-5-methylbenzamide;

N-(3-fluorophenyl)-2-[((3-chlorobenzo[b]thien-2-yl) carbonyl)amino]-5-methylbenzamide;

N-(3-chlorophenyl)-2-[((3-chlorobenzo[b]thien-2-yl) carbonyl)amino]-5-methylbenzamide;

N-(3-methylphenyl)-2-[((3-chlorobenzo[b]thien-2-yl) carbonyl)amino]-5-methylbenzamide;

N-(4-chloro-2-methylphenyl)-2-[((3-chlorobenzo[b]thien-2-yl)carbonyl)amino]-5-methylbenzamide;

N-(4-cyanophenyl)-2-[((3-chlorobenzo[b]thien-2-yl) carbonyl)amino]-5-methylbenzamide;

N-(4-fluorophenyl)-2-[((benzo[b]thien-2-yl)carbonyl) amino]-5-methylbenzamide;

N-(4-fluorophenyl)-2-[((3-chlorothiophen-2-yl)carbonyl) amino]-5-methylbenzamide;

N-(4-fluorophenyl)-2-[((3-methylbenzo[b]thien-2-yl) carbonyl)amino]-5-methylbenzamide;

N-(4-chlorophenyl)-2-[((3-chloro-4-(methylsulfonyl)
thiophen-2-yl)carbonyl)amino]-5-methylbenzamide;
N-(4-chlorophenyl)-2-[((3-chlorothiophen-2-yl)carbonyl)
amino]-5-methylbenzamide;
N-(4-chlorophenyl)-2-[((3-methoxybenzo[b]thien-2-yl)
carbonyl)amino]-5-methylbenzamide;
N-(4-chlorophenyl)-2-[((3-bromothiophen-2-yl)carbonyl)
amino]-5-methylbenzamide;
N-(4-chlorophenyl)-2-[((3-chloro-4-((1-methylethyl)
sulfonyl)thiophen-2-yl)carbonyl)amino]-5-
methylbenzamide;
N-(4-chlorophenyl)-2-[((4-bromo-3-methoxythiophen-2-yl)
carbonyl)amino]-5-methylbenzamide;
N-(4-chlorophenyl)-2-[((3-methoxythiophen-2-yl)carbonyl)
amino]-5-methylbenzamide;
N-(4-fluorophenyl)-2-[((3-chlorobenzo[b]thien-2-yl)
carbonyl)amino]benzamide;
N-(4-fluorophenyl)-2-[((3-chlorobenzo[b]thien-2-yl)
carbonyl)amino]-5-methoxybenzamide;
N-phenyl-2-[((3-chlorobenzo[b]thien-2-yl)carbonyl)
amino]-3-methylbenzamide;
N-(4-chlorophenyl)-2-[((3-chlorobenzo[b]thien-2-yl)
carbonyl)amino]4-(trifluoro)methylbenzamide;
N-(4-chlorophenyl)-2-[((3-chlorobenzo[b]thien-2-yl)
carbonyl)amino]-5-(4-methylpiperazin-1-yl)benzamide;
N-(4-chlorophenyl)-2-[((3-chlorobenzo[b]thien-2-yl)
carbonyl)amino]-5-hydroxybenzamide;
N-phenyl-2-[((3-chlorobenzo[b]thien-2-yl)carbonyl)
amino]-5-dimethoxybenzamide;
N-(4-chlorophenyl)-2-[((3-chlorobenzo[b]thien-2-yl)
carbonyl)amino]-3-chlorobenzamide;
N-phenyl-2-[((3-chlorobenzo[b]thien-2-yl)carbonyl)
amino]-3-methoxybenzamide;
N-(4-chlorophenyl)-2-[((3-chlorobenzo[b]thien-2-yl)
carbonyl)amino]-4-fluorobenzamide;
N-(4-chlorophenyl)-2-[((3-chlorobenzo[b]thien-2-yl)
carbonyl)amino]-4-chlorobenzamide;
N-(4-chlorophenyl)-2-[((3-chlorobenzo[b]thien-2-yl)
carbonyl)amino]-3-methoxybenzamide;
N-(4-chlorophenyl)-2-[((3-chlorobenzo[b]thien-2-yl)
carbonyl)amino]-6-fluorobenzamide;
N-(4-chlorophenyl)-2-[((3-chlorobenzo[b]thien-2-yl)
carbonyl)amino]-4,5-dimethoxybenzamide;
N-(4-chlorophenyl)-2-[((3-chlorobenzo[b]thien-2-yl)
carbonyl)amino]4-methyl-5-chlorobenzamide;
N-(4-chlorophenyl)-2-[((3-chlorobenzo[b]thien-2-yl)
carbonyl)amino]-3-methylbenzamide;
N-(5-chloropyridin-2-yl)-2-[((4-methyl-3-chlorothiophen-
2-yl)carbonyl)amino]-3-methoxy-5-chlorobenzamide;
NMR (DMSO-d$_6$/TFA) 10.8 (s, 1), 9.3 (s, 1), 8.3 (d, 1),
8.1 (d, 1), 7.8 (dd, 1), 7.5 (d, 1), 7.3 (dd, 2), 3.9 (s, 3), 2.2
(s, 3) ppm;
N-(5-chloropyridin-2-yl)-2-[((4-cyano-3-chlorothiophen-2-
yl)carbonyl)amino]-3-methoxy-5-chlorobenzamide;
N-(4-chlorophenyl)-2-[((5-nitro-3-methylthiophen-2-yl)
carbonyl)amino]-5-chlorobenzamide;
N-(4-chlorophenyl)-2-[((4-nitro-3-methylthiophen-2-yl)
carbonyl)amino]-5-chlorobenzamide;
N-(4-chlorophenyl)-3-[((3-chlorobenzo;b]thien-2-yl)
carbonyl)amino]pyridin-2-amide;
N-phenyl-2-[((1-bromonaphth-2-yl)carbonyl)amino]-5-
methylbenzamide; NMR (DMSO-d$_6$) 10.9 (s,1), 10.4 (s,
1), 8.26 (d, 1), 8.16 (d, 1), 8.06 (t, 2), 7.76 (m, 1), 7.6-7.7
(m, 5), 7.46 (d, 1), 7.30 (t, 2), 7.07 (t, 1), 2.4 (s, 3);
N-phenyl-2-[((naphth-2-yl)carbonyl)amino]-5-
methylbenzamide; NMR (DMSO-d$_6$) 11.45 (s, 1), 10.6 (s,
1), 8.5 (s, 1), 8.25 (d, 1), 8.05 (d, 2), 8.0 (d, 1), 7.95 (d,
1), 7.75 (m, 3), 7.6 (m, 2), 7.4 (m, 3), 2.4 (s, 3).

N-(4-chlorophenyl)-3-[((3-chlorobenzo[]b]thien-2-yl)
carbonyl)amino]pyridin-4-amide; NMR (DMSO-d$_6$) 11.1
(s, 1), 10.9 (s, 1), 9.4 (s, 1), 8.6 (d,$_1$), 8.2 (d, 1), 8.0 (d, 1),
7.8 (m, 3), 7.6 (m, 2), 7.4 (d, 2) ppm.

C. A suspension of 2-carboxy-3-chloro-4-(4-methylpiperazin-1-yl)methylthiophene HCl salt (2.0 g, 5.8 mmol) in thionyl chloride (50 mL) was heated at reflux. After 90 hours, the mixture was cooled to ambient temperature and concentrated of all volatiles in vacuo. To a suspension of the resulting solid in pyridine (20 mL) at 0° C was added N-(5-chloropyridin-2-yl)-2-amino-5-chlorobenzamide (1.5 g, 5.2 mmol) in pyridine (5 mL). The mixture was stirred and allowed to warm gradually to ambient temperature. After 16 hours, the mixture was concentrated of all volatiles in vacuo. Purification by flash chromatography on silica gel afforded 2.2 g (80% yield) of N-(5-chloropyridin-2-yl)-2-[((4-((4-methylpiperazin-1-yl)methyl)-3-chlorothiophen-2-yl)carbonyl)amino]-5-chlorobenzamide, as a tan foam; NMR (DMSO-d$_6$/TFA) 11.4 (s, 1), 11.0 (s, 1), 7.6–8.4 (m, 7), 4.4 (s, 2), 3.04.0 (br m, 8), 2.9 (s, 3) ppm.

D. In a similar manner, the following compounds were made:

N-(5-bromopyridin-2-yl)-2-[((4-((4-methylpiperazin-1-yl)
methyl)-3-chlorothiophen-2-yl)carbonyl)amino]-5-
chlorobenzamide; NMR (DMSO-d$_6$/ TFA) 11.4 (s, 1),
11.0 (s, 1), 7.6–8.5 (m, 7), 4.4 (s, 2), 3.0–3.8 (br s, 8), 2.9
(s, 3) ppm;
N-(4-chlorophenyl)-2-[((3-chloro-5-methyl-4-((4-
methylpiperazin-1-yl)methyl)thiophen-2-yl)carbonyl)
amino]-5-chlorobenzamide;
N-(4-chlorophenyl)-2-[((3-chloro4-methyl-5-((4-
methylpiperazin-1-yl)methyl)thiophen-2-5 yl)carbonyl)
amino]-5-chlorobenzamide; and
N-(4-chlorophenyl)-2-[((3-chloro-4-(thiomorpholin-4-yl)
methylthiophen-2-yl)carbonyl)amino]-5-
chlorobenzamide; NMR (DMSO-d$_6$) 11.1 (s, 1), 10.8 (s,
1), 8.3 (d, 1), 7.9 (s, 1), 7.8 (s, 1), 7.6 (m, 3), 7.4 (d, 2),
3.5 (s, 2), 2.6 (m, 8) ppm.

E. To a mixture of sodium 3-chloro-4-(morpholin-4-yl) methyl-2-thiophene carboxylate (1.0 g, 3.9 mmol) and N-(4-chlorophenyl)-2-amino-5-chlorobenzamide (0.88 g, 3.1 mmol) in pyridine (20 mL) at –10° C. was added POCl$_3$ (0.40 mL, 4.3 mmol). After 45 minutes, the mixture was poured onto ice-water and the resulting solid collected by filtration.

Crystallization from 1-butanol afforded 0.26 g (13% yield) of N-(4-chlorophenyl)-2-[((4-(morpholin-4-yl) methyl-3-chlorothiophen-2-yl)carbonyl)amino]-5-chlorobenzamide, as a tan solid; NMR (DMSO-d$_6$) 11.1 (s, 1), 10.8 (s, 1), 8.3 (d, 1), 7.9 (s, 1), 7.8 (s, 1), 7.7 (d, 2), 7.6 (d, 2), 7.4 (d, 3), 3.6 (s, 2), 3.3 (br, 4), 2.4 (br, 4) ppm.

F. In a similar manner, the following compounds were made:

N-(4-chlorophenyl)-2-[((4-(methylamino)sulfonyl-3-
methylthiophen-2-yl)carbonyl)amino]-5-
methylbenzamide; and
N-(4-chlorophenyl)-2-[((4-((4-methylpiperazin-1-yl)
sulfonyl)-3-chlorothiophen-2-yl)carbonyl)amino]-5-
chlorobenzamide.

G. To a solution of 2-chlorocarbonyl-3-chloro4-(2-(N-methyl-N-tert-butoxycarbonylamino)ethyl)thiophene (0.095 g, 0.28 mmol) in methylene chloride (10 mL) was added pyridine (0.056 mL, 0.56 mmol) and N-(5-chloropyridin-2-yl)-2-amino-3-methoxy-5-chlorobenzamide (0.096 g, 0.31 mmol) and the mixture was stirred at ambient temperature. After 4 days at ambient temperature, the reaction mixture was concentrated in vacuo and dissolved in methylene chloride. Trifluoroacetic acid was added and the reaction mixture was stirred for 2 days at ambient temperature. The reaction was quenched with saturated aqueous NaHCO$_3$ solution and extracted with methylene chloride. The combined extracts were dried over Na$_2$SO$_4$, filtered, and concentrated in vacuo. The product was purified by HPLC on a C18 Dynamax column with 25–95% acetonitrile in water gradient with 0.1% trifluoroacetic acid to afford 0.054 g of N-(5-chloropyridin-2-yl)-2-[((4-(2-methylaminoethyl)-3-chlorothiophen-2-yl)carbonyl)amino]-3-methoxy-5-chlorobenzamide, trifluoroacetic acid salt, as a white solid; NMR (DMSO-d$_6$/TFA) 10.9 (s, 1), 9.3 (s, 1), 8.4 (br s, 2), 8.2 (s, 1), 8.1 (d, 1), 7.8 (dd, 1), 7.6 (s, 1), 7.2 (s, 2), 3.8 (s, 3), 3.1 (brs, 2), 2.9 (m, 2), 2.5 (d, 3) ppm.

H. Other compounds of the invention may be prepared by methods similar to those described in this Example and by methods known to those of ordinary skill in the art.

EXAMPLE 17

A. To a solution of N-(5-chloropyridin-2-yl)-2-[((4-((methylamino)methyl)-3-chlorothiophen-2-yl)carbonyl)amino]-3-(morpholin-4-yl)-5-chlorobenzamide (0.20 g, 0.37 mmol) in methylene chloride (5 mL) were added potassium carbonate (0.10 g, 0.74 mmol) and cyanogen bromide (5.0 M in acetonitrile, 0.10 mL, 0.50 mmol) and the mixture stirred at ambient temperature. After 2 hours, water (10 mL) was added and the mixture extracted with ethyl acetate (3×20 mL). The combined organics were washed with brine (10 mL), dried over Na$_2$SO$_4$, and concentrated in vacuo. Purification by flash chromatography on silica gel afforded 0.1 g of N-(5-chloropyridin-2-yl)-2-[((4-((N'-methyl-N'-cyanoamino)methyl)-3-chlorothiophen-2-yl)carbonyl)amino]-3-(morpholin-4-yl)-5-chlorobenzamide. The resulting product material was dissolved in toluene (10 mL), and sodium azide (0.058 g, 0.88 mmol) and tributyltin chloride (0.29 g, 0.88 mmol) were added. The mixture was heated at reflux for 2 hours, then cooled to ambient temperature and poured onto brine (10 mL). The mixture was extracted with ethyl acetate (3×20 mL) and the combined organics washed with brine (10 mL), dried over Na$_2$SO$_4$, and concentrated in vacuo. Purification by HPLC on a C18 Dynamax column with 20–80% acetonitrile in water gradient with 0.1 % trifluoroacetic acid afforded N-(5-chloropyridin-2-yl)-2-[((4-((N'-methyl-N'-(tetrazol-5-yl)amino)methyl)-3-chlorothiophen-2-yl)carbonyl)amino]-3-(morpholin-4-yl)-5-chlorobenzamide, trifluoroacetic acid salt as a white solid; NMR (DMSO-d$_6$/TFA) 10.9 (s, 1), 9.5 (s, 1), 8.3 (s, 1), 8.1 (m, 1), 7.9 (m, 1), 7.7 (s, 1), 7.4 (m, 2), 4.6 (s, 2), 3.7 (m, 4), 3.0 (s, 3), 2.9 (m, 4) ppm.

B. In a similar manner, the following compounds were made:

N-(5-chloropyridin-2-yl)-2-[((4-((N'-methyl-N'-(tetrazol-5-yl)amino)methyl)-3-chlorothiophen-2-yl)carbonyl)amino]-3-methoxy-5-chlorobenzamide, trifluoroacetic acid salt; NMR (DMSO-d$_6$/TFA) 10.9 (s, 1), 9.3 (s, 1), 8.3 (s, 1), 8.0 (m, 1), 7.8 (m, 1), 7.6 (s, 1), 7.2 (m, 2), 4.5 (s, 2), 3.8 (s, 3), 3.0 (s, 3) ppm.

C. In a manner similar to that described in Paragraph A above, N-(5-chloropyridin-2-yl)-2-[((4-((ethylamino)methyl)-3-chlorothiophen-2-yl)carbonyl)amino]-3-methoxy-5-chlorobenzamide (0.60 g, 1.2 mmol) reacted with cyanogen bromide (5 M in acetonitrile, 0.6 mL, 3.0 mmol) and potassium carbonate (0.56 g, 4.0 mmol) in CH$_2$Cl$_2$ to afford N-(5-chloropyridin-2-yl)-2-[((4-((N'-ethyl-N'-cyanoamino)methyl)-3-chlorothiophen-2-yl)carbonyl)amino]-3-methoxy-5-chlorobenzamide. This material reacted with sodium azide (0.25 g, 3.8 mmol) and tributyltin chloride (1.3 g, 3.9 mmol) in toluene. Purification by flash chromatography on silica gel afforded 0.37 g (53% yield) of N-(5-chloropyridin-2-yl)-2-[((4-((N'-ethyl-N'-(tetrazol-5-yl)amino)methyl)-3-chlorothiophen-2-yl)carbonyl)amino]-3-methoxy-5-chlorobenzamide; NMR (DMSO-d$_6$/TFA) 10.9 (s, 1), 9.4 (s, 1), 8.3 (s, 1), 8.1 (m, 1), 7.9 (m, 1), 7.6 (s, 1), 7.2–7.4 (m, 2), 4.5 (s, 2), 4.0 (m, 2), 3.9 (s, 3), 1.1 (m, 3) ppm.

D. Other compounds of the invention may be prepared by methods similar to those described in this Example and by methods known to those of ordinary skill in the art.

EXAMPLE 18

A. To a solution of N-(5-chloropyridin-2-yl)-2-[((4-((N'-(2-hydroxyethyl)amino)methyl)-3-chlorothiophen-2-yl)carbonyl)amino]-3-(morpholin-4-yl)-5-chlorobenzamide (0.29 g, 0.50 mmol ) in MeOH were added cyanogen bromide (5 M in acetonitrile, 0.1 mL, 0.5 mmol) and K$_2$CO$_3$ (0.5 g, 3.6 mmol) and the reaction was stirred at ambient temperature. After 1 hour, the mixture was poured onto ethyl acetate and H$_2$O, and the layers separated. The organic layer was dried over MgSO$_4$, and concentrated in vacuo. Purification by flash chromatography on silica gel afforded 0.25 g (82% yield) of N-(5-chloropyridin-2-yl)-2-[((4-((2-iminotetrahydrooxazol-3-yl)methyl)-3-chlorothiophen-2-yl)carbonyl)amino]-3-(morpholin-4-yl)-5-chlorobenzamide, as a yellow solid; NMR (DMSO-d$_6$/TFA) 10.9 (s, 1), 9.6 (s,1), 9.5 (s, 1), 9.2 (s, 1), 7.4-8.4 (m, 6), 4.8 (t, 2), 4.6 (s, 2), 3.7 (t, 2), 3.6 (s, 4), 2.9 (s, 4) ppm.

B. To a solution of N-(5-chloropyridin-2-yl)-2-[((4-(chloromethyl)-3-chlorothiophen-2-yl)carbonyl)amino]-3-methoxy-5-chlorobenzamide (0.30 g, 0.59 mmol) in DMF (5 mL) was added 2-hydroxy-3-methoxypropylamine (1.0 g, 9.5 mmol) and the mixture was stirred at ambient temperature. After 16 hours, the mixture was acidified with trifluoroacetic acid and purified by HPLC on a C18 Dynamax column with 20–60% acetonitrile in water gradient with 0.1% trifluoroacetic acid. To a solution of the resulting material in methanol (5 mL) were added cyanogen bromide (5 M in acetonitrile, 0.1 mL, 0.5 mmol) and K$_2$CO$_3$ (0.3 g, 2.2) and the reaction was stirred at ambient temperature. After 3 hours, the mixture was partitioned between ethyl acetate and water, and the organic layer concentrated in vacuo. Purification by HPLC on a C18 Dynamax column with 20–60% acetonitrile in water gradient with 0.1 % trifluoroacetic acid afforded N-(5-chloropyridin-2-yl)-2-[((4-((2-imino-5-(methoxymethyl)oxazolidin-3-yl)methyl)-3-chlorothiophen-2-yl)carbonyl)amino]-3-methoxy-5-chlorobenzamide, trifluoroacetic acid salt as a white solid: NMR (DMSO-d$_6$/TFA) 10.9 (s, 1), 9.6 (s, 1), 9.4 (s, 1), 9.2 (s, 1), 7.2-8.3 (m, 6), 5.2 (s, 1), 4.6 (m, 2), 3.84.0 (m, 2), 3.9 (s, 3), 3.5–3.7 (m, 2), 3.3 (s, 3) ppm.

C. In a manner similar to that described in Paragraph A above, to a solution of N-(5-chloropyridin-2-yl)-2-[((4-((N'-(2-aminoethyl)amino)methyl)-3-chlorothiophen-2-yl)carbonyl)amino]-3-methoxy-5-chlorobenzamide (0.57 g, 1.08 mmol) in methanol (20 mL) - were added sodium acetate (0.18 g, 2.16 mmol) and cyanogen bromide (0.26 mL of 5 M -solution in acetonitrile, 1.29 mmol). After stirring for 3 hours at ambient temperature, the reaction mixture was concentrated and saturated NaHCO$_3$ (aq) was added. The reaction mixture was extracted with methylene chloride, and the combined extracts were dried over Na$_2$SO$_4$. The resulting product was filtered, concentrated, and purified by HPLC on a C18 Dynamax column with 20–95% acetonitrile in water gradient with 0.1 % trifluoroacetic acid to afford 0.37 g of N-(5-chloropyridin-2-yl)-2-[((4-((2-imino-tetrahydroimidazol-1-yl)methyl)-3-chlorothiophen-2-yl)carbonyl)amino]-3-methoxy-5-chlorobenzamide, trifluoroacetic acid salt, as a white solid; NMR (DMSO-$d_6$/TFA) 10.9 (s, 1), 9.4 (s, 1), 8.3 (s, 1), 8.1 (d, 2), 8.0 (br s, 1), 7.8 (dd, 1), 7.75 (s, 1), 7.3 (d, 2), 4.5 (s, 2), 3.8 (s, 3), 3.5 (s, 4) ppm.

D. In a similar manner, the following compounds were made:

N-(5-chloropyridin-2-yl)-2-[((4-((trans4,5-dimethyl-2-iminotetrahydrooxazol-3-yl)methyl)-3-chlorothiophen-2-yl)carbonyl)amino]-3-methoxy-5-chlorobenzamide, trifluoroacetic acid salt; NMR (DMSO-$d_6$/TFA) 9.1 (s, 1), 8.3 (d, 1), 8.0 (d, 1), 7.6 (dd, 1), 7.5 (s, 1), 7.4 (s, 1), 7.3 (s, 1), 7.2 (d, 1), 7.1 (d, 1), 3.9 (m, 5), 3.6 (d, 1), 3.3 (m, 1), 2.5 (m, 1), 1.2 (d, 3), 1.1 (d, 3) ppm;

N-(5-chloropyridin-2-yl)-2-[((4-((cis4,5-dimethyl-2-iminotetrahydrooxazol-3-yl)methyl)-3-chlorothiophen-2-yl)carbonyl)amino]-3-methoxy-5-chlorobenzamide, trifluoroacetic acid salt; NMR (DMSO-$d_6$/TFA) 9.1 (d, 2), 8.3 (d, 1), 8.0 (d, 1), 7.6 (dd, 1), 7.5 (s, 1), 7.4 (s, 1), 7.3 (s, 1), 7.2 (d, 1), 7.1 (d, 1), 3.9 (m, 6), 3.3 (m, 1), 2.7 (m, 1), 1.2 (d, 3), 1.1 (d, 3) ppm;

N-(5-chloropyridin-2-yl)-2-[((4-((2-imino-4-oxoimidazolin-1-yl)methyl)-3-chlorothiophen-2-yl)carbonyl)amino]-3-methoxy-5-chlorobenzamide, trifluoroacetic acid salt; NMR (DMSO-$d_6$/TFA) 10.9 (s, 1), 9.3 (s., 1), 8.3 (d, 1), 8.1 (m, 2), 7.7 (d, 1), 7.6 (d, 1), 7.5 (s, 1), 7.3 (d, 1), 7.2 (d, 1), 4.4 (s, 2), 4.3 (s, 2), 3.8 (s, 3) ppm;

N-(5-chloropyridin-2-yl)-2-[((4-((2-imino-4-(hydroxymethyl)tetrahydrooxazol-3-yl)methyl)-3-chlorothiophen-2-yl)carbonyl)amino]-3-methoxy-5-chlorobenzamide, trifluoroacetic acid salt; NMR (DMSO-$d_6$/TFA) 10.9 (s, 1), ), 9.5 (br s, 1), 9.4 (s, 1), 9.2 (br s, 1), 8.3 (s, 1), 8.1 (d, 1), 8.0 (s, 1), 7.8 (dd, 1), 7.3 (d, 2), 4.8 (m, 2), 4.5 (m, 2), 4.1 (m, 2), 3.8 (s, 3), 3.7 (d, 1), 3.4 (d, 2) ppm; and N-(5-chloropyridin-2-yl)-2-[((4-((tetrahydro-2-imino-2H-pyrimidin-1-yl)methyl)-3-chlorothiophen-2-yl)carbonyl)amino]-3-methoxy-5-chlorobenzamide, trifluoroacetic acid salt; NMR (DMSO-$d_6$/TFA) 10.85 (s, 1), 9.30 (s, 1), 8.30 (d, 1), 8.10 (d, 1), 7.80 (m, 2), 7.65 (s, 1), 7.20–7.30 (m, 4), 4.45 (s. 2), 3.80 (s, 3), 3.20–3.30 (m, 4), 1.90 (m, 2) ppm.

E. To a mixture of N-(5-chloropyridin-2-yl)-2-[((4-((methylamino)methyl)-3-chlorothiophen-2-yl)carbonyl)amino]-3-methoxy-5-chlorobenzamide (1.0 g, 2.0 mmol) and $K_2CO_3$ (0.97 g, 7.0 mmol) in acetonitrile (20 mL) was added cyanogen bromide (0.8 mL of a 5 M solution in acetonitrile, 4.0 mmol). After stirring at ambient temperature for 3 hours, the reaction was poured into water and extracted with ethyl acetate. The ethyl acetate extract was concentrated in vacuo and was purified by flash chromatography on silica gel to give 1.2 g of N-(5-chloropyridin-2-yl)-2-[((4-((N'-methyl-N'-cyanoamino)methyl)-3-chlorothiophen-2-yl)carbonyl)amino]-3-methoxy-5-chlorobenzamide; NMR (DMSO-$d_6$/ TFA) 10.9 (s, 1), 9.4 (s, 1), 8.3 (d, 1), 8.1 (m, 2), 7.8 (dd, 1), 7.7 (s, 1), 7.4 (d, 1), 7.3 (d, 1), 4.3 (s, 2), 3.9 (s, 3), 2.9 (s, 3) ppm.

F. Other compounds of the invention may be prepared by methods similar to those described in this Example and by methods known to those of ordinary skill in the art.

EXAMPLE 19

A. To a suspension of N-(5-chloropyridin-2-yl)-2-[((4-((N'-methylureido)methyl)-3-chlorothiophen-2-yl)carbonyl)amino]-3-methoxy-5-chlorobenzamide (0.10 g, 0.20 mmol) in ethanol (5 mL) was added chloroacetaldehyde diethylacetal (0.3 mL, 2.0 mmol). The mixture was heated at reflux for 4 days, then cooled to ambient temperature and poured onto water. The mixture was neutralized by addition of saturated $NaHCO_3$ solution and the solid collected by filtration. Purification by HPLC on a C18 Dynamax column with 20–80% acetonitrile in water gradient with 0.1% trifluoroacetic acid afforded N-(5-chloropyridin-2-yl)-2-[((4-((N'-methyl-N'-(oxazol-2-yl)amino)methyl)-3-chlorothiophen-2-yl)carbonyl)amino]-3-methoxy-5-chlorobenzamide, trifluoroacetic acid salt as a white solid: NMR (DMSO-$d_6$/TFA) 10.9 (s, 1), 9.4 (s, 1), 8.4 (d, 1), 8.1 (d, 1), 7.9 (dd, 1), 7.8 (s, 1), 7.6 (s, 1), 7.4 (d, 1), 7.3 (d, 1), 7.0 (s, 1), 4.5 (s, 2), 3.8 (s, 3), 3.0 (s, 3) ppm.

B. Other compounds of the invention may be prepared by methods similar to those described in this Example and by methods known to those of ordinary skill in the art.

EXAMPLE 20

A. To a solution of N-(4-chlorophenyl)-2-[((3-chloro4-((((2-hydroxyethoxy)ethyl)amino)methyl)thiophen-2-yl)carbonyl)amino]-5-chlorobenzamide (0.25 g, 0.46 mmol) in acetonitrile (5 mL) was added formaldehyde (0.19 mL of a 37% solution in water, 2.3 mmol), followed by $NaCNBH_3$ (0.045 g, 0.69 mmol) and the mixture stirred at ambient temperature. After 2 hours, the mixture was concentrated of all volatiles in vacuo. Purification by HPLC on a C18 Dynamax column with acetonitrile in water gradient with 0.1% trifluoroacetic acid afforded N-(4-chlorophenyl)-2-[((3-chloro-4-((N'-methyl-N'-(2-(hydroxyethoxy)ethyl)amino)methyl)thiophen-2-yl)carbonyl)amino]-5-chlorobenzamide, trifluoroacetic acid salt as a white solid; NMR (DMSO-$d_6$/TFA) 11.2 (s, 1), 10.8 (s, 1), 9.6 (br s, 1), 8.4 (d, 1), 8.3 (s, 1), 7.9 (s, 1), 7.7 (d, 2), 7.6 (d, 1), 7.4 (d, 2), 4.5 (d, 1), 4.3 (d, 1), 3.8 (m, 2), 3.5 (m, 4), 3.4 (br s, 1), 2.8 (s, 3) ppm.

B. In a similar manner, the following compounds were made:

N-(5-chloropyridin-2-yl)-2-[((4-((N'-methyl-N'-(2-(hydroxyethoxy)ethyl)amino)methyl)-3-chlorothiophen-2-yl)carbonyl)amino]-3-methoxy-5-chlorobenzamide, trifluoroacetic acid salt; NMR (DMSO-$d_6$/TFA) 10.9 (s, 1), 9.6 (br s, 1), 9.5 (s, 1), 8.4 (s, 1), 8.2 (s, 1), 8.1 (d, 1), 7.9 (d, 1), 7.4 (s, 1), 7.3 (s, 1), 4.5 (d, 1), 4.3 (d, 1), 3.9 (s, 3), 3.8 (m, 2), 3.5 (m, 4), 3.4 (br s, 2), 2.8 (s, 3) ppm;

N-(5-chloropyridin-2-yl)-2-[((4-((N'-methyl-N'-(4-hydroxycyclohexyl)amino)methyl)-3-chlorothiophen-2-yl)carbonyl)amino]-3-methoxy-5-chlorobenzamide; NMR ($CDCl_3$) 9.1 (s, 1), 9.0 (s, 1), 7.0–8.2 (m, 6), 4.4 (s, 2), 3.9 (s, 3), 3.6 (m, 1), 3.5 (s, 2), 2.5 (m, 1), 2.2 (s, 3), 1.8–2.1 (m, 4), 1.4 (m, 4) ppm;

N-(5-chloropyridin-2-yl)-2-[((4-((N'-ethyl-N'-((imidazol-2-yl)methyl)amino)methyl)-3-chlorothiophen-2-yl)carbonyl)amino]-3-methoxy-5-chlorobenzamide, trifluoroacetic acid salt; NMR (DMSO-$d_6$) 10.90 (S, 1H), 9.30 (s, 1H), 8.35 ($d_{,1}$ H), 8.10 (d, 1H), 7.90 (dd, 1H), 7.85 (s, 2H), 7.60 (s, 2H), 7.40 (d,1H), 7.25 (d, $_1$ H), 4.05 (s, 2H), 3.90 (s, 3H), 3.60 (s, 2H), 2.50 (q, 2H), 1.00 (t, 3H) ppm; and N-(5-chloropyridin-2-yl)-2-[((4-((N'-ethyl-N-(4-(dimethylamino)but-3-yn-2-yl)amino)methyl)-3-chlorothiophen-2-yl)carbonyl)amino]-3-methoxy-5-chlorobenzamide, trifluoroacetic acid salt; NMR (DMSO-$d_6$) 10.90–10.85 (m, 1H), 9.40–9.30 (m, 1HO, 8.38 (d, 1H), 8.10 (d, 1H), 7.90 (dd,1H), 7.65 (s,1H), 7.60 (s,1H), 7.39 (d, 1H), 7.25 (d,1H), 4.42–3.38 (m, 2H), 3.90 (s, 3H), 3.40–3.25 (m, 2H), 2.50 (s, 3H), 2.10–2.00 (m, 3H), 1.10–0.90 (m, 3H) ppm.

C. N-(5-chloropyridin-2-yl)-2-[((4-((N'-methyl-N"-ethylureido)methyl)-3-chlorothiophen-2-yl)carbonyl)amino]-3-(4-(tert-butoxycarbonyl)piperazin-1-yl)-5-chlorobenzamide, trifluoroacetic acid salt, (~2 g, 2.7 mmol) was dissolved in acetonitrile (40 mL), and acetaldehyde (~1 mL, 18 mmol) was added, followed by a few drops of acetic acid. After one hour, a few more drops of acetic acid were added. After several hours, more acetaldehyde and acetic acid were added and the reaction mixture allowed to stir for 16 hours at ambient temperature. More acetic acid (10 mL) was added and the reaction mixture stirred for one hour, then sodium cyanoborohydride (0.51 g, 8.0 mmol) was added to the reaction mixture. The reaction mixture was stirred for one hour, concentrated in vacuo, and the residue taken up in ethyl acetate (100 mL). The ethyl acetate layer was washed with 1 M sodium bicarbonate (2×5 mL), brine (50 mL), dried over $MgSO_4$, and concentrated in vacuo. The crude product was purified by reverse phase preparatory HPLC and lyophilized to give 0.69 g (28% yield) of the trifluoroacetic acid salt (monohydrate) of the compound, N-(5-chloropyridin-2-yl)-2-[((4-((N'-methyl-N"-ethylureido)methyl)-3-chlorothiophen-2-yl)carbonyl)amino]-3-(4-ethylpiperazin-1-yl)-5-chlorobenzamide, trifluoroacetic acid salt; NMR (DMSO-$d_6$/TFA) 10.9 (s, 1), 9.4 (s, 1), 8.4 (d, 1), 8.1 (d, 1), 7.9 (dd, 1), 7.5 (s, 1), 7.4 (d, 2), 6.4 (br, 1), 4.3 (s, 2), 3.6 (d, 2), 3.4 (d, 2), 3.2 (d, 3), 3.0 (d, 5), 2.8 (s, 3), 1.2 (t, 3), 1.0 (t, 3) ppm.

D. Other compounds of the invention may be prepared by methods similar to those described in this Example and by methods known to those of ordinary skill in the art.

EXAMPLE 21

A. To a solution of N-(4-chlorophenyl)-2-[((3-chloro-5-((4-(ethoxycarbonylmethyl)piperazin-1-yl)methyl)thiophen-2-yl)carbonyl)amino]-5-chlorobenzamide (0.61 g, 1.0 mmol) in 3:1:1 (volume ratio) tetrahydrofuran/methanol/water (35 mL) was added lithium hydroxide monohydrate (0.12 g, 3.0 mmol). The solution was stirred at ambient temperature for 1 hour, then diluted with water (25 mL), adjusted to pH 3 by addition of 1 N HCl and concentrated in vacuo to remove the tetrahydrofuran and methanol. The residual oil was diluted with acetonitrile, water and trifluoroacetic acid and purified by HPLC on a C18 Dynamax column with 50–65% acetonitrile in water gradient with 0.1 % trifluoroacetic acid to afford N-(4-chlorophenyl)-2-[((3-chloro-5-((4-(carboxymethyl)piperazin-1-yl)methyl)thiophen-2-yl)carbonyl)amino]-5-chlorobenzamide, trifluoroacetic acid salt as a white solid: NMR (DMSO-$d_6$/TFA) 11.2 (s, 1), 10.8 (s, 1), 8.3 (d, 1), 7.9 (d, 1), 7.3–7.7 (m, 6), 4.4 (s, 2) 4.2 (s, 2), 3.4 (br s, 4), 3.2 (br s, 4) ppm.

B. In a similar manner, the following compounds were made:

N-(4-chlorophenyl)-2-[((3-chloro-6-(4-(carboxymethyl)piperazin-1-yl)methyl benzo[b]thien-2-yl)carbonyl)amino]-5-chlorobenzamide; (DMSO-$d_6$/TFA) 11.4 (s, 1), 10.8 (s, 1), 8.4 (d, 1), 8.3 (br s, 1), 8.1 (d, 1), 8.0 (d, 1), 7.4–7.7 (m, 6), 4.6 (s, 2), 4.2 (s, 2), 3.5 (br s, 8) ppm;

N-(5-chloropyridin-2-yl)-2-[((4-((N'-methyl-N'-(2-hydroxyethyl)amino)methyl)-3-chlorothiophen-2-yl)carbonyl)amino]-3-(4-carboxy)piperidin-1-yl)-5-chlorobenzamide, trifluoroacetic acid salt; NMR (DMSO-$d_6$/TFA) 10.9 (s, 1), 9.6 (s, 1), 7.3–8.5 (m, 6), 4.2–4.5 (m, 2), 3.7 (t, 2), 3.6 (s, 3), 3.0–3.3 (m, 4), 2.6–2.9 (m, 4), 1.6–2.0 (m, 4) ppm;

N-(5-chlorpyridin-2-yl)-2-[((4-((N'-methyl-N'-(4-trifluoromethyl-5-carboxypyrimidin-2-yl)amino)methyl)-3-chlorothiophen-2-yl)carbonyl)amino]-3-(morpholin-4-yl)-5-chlorobenzamide, trifluoroacetic acid salt; NMR (DMSO-$d_6$/TFA) 10.9 (s, 1), 9.5 (s, 1), 8.9 (m, 1), 8.3 (br s, 1), 8.1 (m, 1), 7.8 (m, 1), 7.6 (m, 1), 7.6 (m, 1), 7.4 (s, 2), 4.8 (s, 2), 3.6 (m, 4), 3.2 (s, 3), 2.9 (m, 4) ppm;

N-(4-chlorophenyl)-2-[((3-chloro-5-carboxythiophen-2-yl)carbonyl)amino]-5-chlorobenzamide;

N-(4-chlorophenyl)-2-[((3-chloro-5-(N'-methyl-N'-(carboxymethyl)amino)methylthiophen-2-yl)carbonyl)amino]-5-chlorobenzamide; and N-(4-chlorophenyl)-2-[((3-chloro-5-(((carboxymethyl)thio)methyl)thiophen-2-yl)carbonyl)amino]-5-chlorobenzamide.

C. Other compounds of the invention may be prepared by methods similar to those described in this Example and by methods known to those of ordinary skill in the art.

EXAMPLE 22

A. To a suspension of N-(4-chlorophenyl)-2-[((3-chloro-5-(thiomorpholin-4-yl)methylthiophen-2-yl)carbonyl)amino]-5-chlorobenzamide (0.1 g, 0.2 mmol) in methanol (20 mL) at 0° C. was added a solution of potassium peroxymonosulfate (0.13 g, 0.2 mmol) in water (5 mL). After 5 minutes, the reaction was quenched by addition of aqueous 5% sodium bisulfite solution. The mixture was extracted with methylene chloride/methanol, and the organic phase dried over $Na_2SO_4$ and concentrated in vacuo. Purification by flash chromatography on silica gel afforded 0.064 g (62% yield) of N-(4-chlorophenyl)-2-[((3-chloro-5-(1-(oxo)thiomorpholin-4-yl)methylthiophen-2-yl)carbonyl)amino]-5-chlorobenzamide, as a pale yellow powder; NMR (DMSO-$d_6$/TFA) 11.2 (s, 1), 10.7 (s, 1), 8.3 (d, 1), 7.9 (s, 1), 7.7 (m, 2), 7.6 (m, 1), 7.4 (m, 3), 4.7 (s, 2), 3.7 (m, 2), 3.5 (m. 2), 2.9 (br s, 4) ppm.

B. In a similar manner, the following compounds were made:

N-(4-chlorophenyl)-2-[((3-chloro-5-((methylsulfinyl)methyl)thiophen-2-yl)carbonyl)amino]-5-chlorobenzamide; NMR (DMSO-$d_6$) 11.1 (s, 1), 10.8 (s, 1), 8.3 (dd, 1), 7.9 (d, 1), 7.8 (dd, 2), 7.7 (dd, 1), 7.4 (d, 2), 7.2 (s, 1), 4.4 (dd, 2), 3.3 (s, 3) ppm;

N-(4-chlorophenyl)-2-[((3-chloro-5-((methylsulfonyl)methyl)thiophen-2-yl)carbonyl)amino]-5-chlorobenzamide; NMR (DMSO-$d_6$) 11.1 (s, 1), 10.8 (s, 1), 8.3 (br d, 1), 7.9 (s, 1), 7.8–7.6 (br m, 3), 7.4 (br d, 2), 7.2 (s, 1), 4.8 (s, 2), 3.0 (s, 3) ppm;

N-(4-chlorophenyl)-2-[((3-chloro-5-(((2-(dimethylamino)ethyl)sulfinyl)methyl)thiophen-2-yl)carbonyl)amino]-5-chlorobenzamide; NMR (DMSO-$d_6$) 11.1 (s, 1), 10.8 (s, 1), 8.3 (d, 1), 7.9 (s, 1), 7.7 (d, 2), 7.5 (d, 1), 7.3 (d, 2), 7.2 (s, 1), 4.4 (dd, 2), 3.4 (m, 2), 3.2–2.8 (m, 2), 2.7 (s, 6) ppm;

N-(4-chlorophenyl)-2-[((3-chloro-4-((methylsulfonyl)methyl)thiophen-2-yl)carbonyl)amino]-5-chlorobenzamide; NMR (DMSO-$d_6$) 11.1 (s, 1), 10.8 (s, 1), 8.3 (d, 1), 8.1 (s, 1), 7.9 (s, 1), 7.7 (d, 2), 7.6 (dd, 1), 7.4 (d, 2), 4.6 (s, 2), 3.0 (s, 3) ppm;

N-(4-chlorophenyl)-2-[((3-chloro-4-((methylsulfinyl)methyl)thiophen-2-yl)carbonyl)amino]-5-chlorobenzamide; NMR (DMSO-$d_6$) 11.1 (s, 1), 10.7 (s, 1), 8.3 (d, 1), 7.9 (s, 1), 7.8 (s, 1), 7.7 (d, 2), 7.6 (dd, 1), 7.4 (d, 2), 4.1 (dd, 2), 2.5 (s, 3) ppm; and N-(4-chlorophenyl)-2-[((3-chloro-5-(1,1,4-tri(oxo)thiomorpholin-4-yl)methylthiophen-2-yl)carbonyl)amino]-5-chlorobenzamide.

C. To a solution of N-(5-chloropyridin-2-yl)-2-[((4-(chloromethyl)-3-chlorothiophen-2-yl)carbonyl)amino]-3-methoxy-5-chlorobenzamide (2.0 g, 4.0 mmol) in DMF (40 mL) was added sodium thiomethoxide (1.4 g, 20 mmol). The mixture was stirred at ambient temperature for 16 hours, then poured onto ice water (200 mL), filtered, and dried to give 1.55 g crude product, N-(5-chloropyridin-2-yl)-2-[((4-((methylthio)methyl)-3-chlorothiophen-2-yl)carbonyl)amino]-3-methoxy-5-chlorobenzamide. To a solution of the product in $CH_2Cl_2$ (30 mL) at $-20°$ C. was added 3-chloroperoxybenozic acid (mCPBA) (0.71 g, 3.3 mmol) in two equal portions. After 2 hours, the reaction was poured onto ice water (200 mL). The resulting solid was collected by filtration and washed with $CH_2Cl_2$ (30 mL) and THF (5 mL) to afford 0.72 g (34% yield) of N-(5-chloropyridin-2-yl)-2-[((4-((methylsulfinyl)methyl)-3-chlorothiophen-2-yl)carbonyl)amino]-3-methoxy-5-chlorobenzamide, as a tan solid; NMR (DMSO-$d_6$/TFA) 10.9 (s, 1), 9.4 (s, 1), 8.3 (s, 1), 8.1 (d, 1), 7.9 (d, 1), 7.8 (s, 1), 7.4 (s,1), 7.3 (s, 1), 4.2 (d, 1), 4.0 (d, 1), 3.9 (s, 3), 2.6 (s, 3) ppm.

D. In a similar manner, the following compound was made:

N-(4-chlorophenyl)-2-[((3-chloro-5-(((methoxycarbonylmethyl)sulfinyl)methyl)thiophen-2-yl)carbonyl)amino]-5-chlorobenzamide.

E. In a manner similar to that described in Paragraph C above, N-(5-chloropyridin-2-yl)-2-[((4-(chloromethyl)-3-chlorothiophen-2-yl)carbonyl)amino]-3-methoxy-5-chlorobenzamide (0.20 g, 0.42 mmol) reacted with morpholine (0.18 mL, 2.1 mmol), followed by mCPBA (0.24 g, 0.84 mmol) to afford N-(4-chlorophenyl)-2-[((3-chloro4-((4-oxomorpholin-4-yl)methyl)thiophen-2-yl)carbonyl)amino]-5-chlorobenzamide. Purification by HPLC on a C18 Dynamax column with 20–80% acetonitrile in water gradient with 0.1% trifluoroacetic acid afforded the trifluoroacetic acid salt as a white solid; NMR (DMSO-$d_6$/TFA) 11.2 (s, 1), 10.8 (s, 1), 8.4 (d, 1), 8.3 (s, 1), 7.9 (s, 1), 7.7 (d, 2), 7.6 (d, 1), 7.4 (d, 2), 4.9 (s, 2), 3.9 (m, 6), 3.5 (m, 2) ppm.

F. In a similar manner, the following compound was made:

N-(5-chloropyridin-2-yl)-2-[((4-(((2-hydroxyethyl)sulfinyl)methyl)-3-chlorothiophen-2-yl)carbonyl)amino]-3-methoxy-5-chlorobenzamide; NMR (DMSO-$d_6$/TFA) 10.8 (s, 1), 9.4 (s, 1), 8.3 (d, 1), 8.1 (d, 1), 7.8 (m, 1), 7.3 (s, 1), 7.2 (s, 1), 4.2 (d, 1), 4.0 (d, 1), 3.9 (s, 3), 3.8 (m, 2), 2.9 (m, 1), 2.8 (m, 1) ppm.

G. Other compounds of the invention may be prepared by methods similar to those described in this Example and by methods known to those of ordinary skill in the art.

EXAMPLE 23

A. A solution of N-(5-chloropyridin-2-yl)-2-[((4-((N'-methyl-N"-ethylureido)methyl)-3-chlorothiophen-2-yl)carbonyl)amino]-3-(4-(tert-butoxycarbonyl)piperazin-1-yl)-5-chlorobenzamide (4.7 g, 6.5 mmol) in methylene chloride (30 mL) and trifluoroacetic acid (3 mL) was stirred at ambient temperature. After one hour, additional trifluoroacetic acid (10 mL) was added and the reaction stirred for an additional 3 hours. The mixture was then concentrated and dried in vacuo to N-(5-chloropyridin-2-yl)-2-[((4-((N'-methyl-N'-ethylureido)methyl)-3-chlorothiophen-2-yl)carbonyl)amino]-3-(piperazin-1-yl)-5-chlorobenzamide, trifluoroacetic acid salt as a light brown oil; NMR (DMSO-$d_6$): 10.9 (s, 1), 9.4 (s, 1), 8.3 (d, 1), 8.1 (d, 1), 7.9 (dd, 1), 7.5 (s, 1), 7.4 (s, 2), 4.3 (s, 2), 3.1 (m, 10), 2.8 (s, 3), 1.0 (t, 3) ppm.

B. Other compounds of the invention may be prepared by methods similar to those described in this Example and by methods known to those of ordinary skill in the art.

EXAMPLE 24

A. N-(4-chlorophenyl)-2-[((3-chloro-4-(((2,2-dimethyldioxolan-4-yl)methoxy)methyl)thiophen-2-yl)carbonyl)amino]-5-chlorobenzamide 9955 (0.10 g, 0.17 mmol) was stirred in a mixture of 1 M HCl (1.0 mL) and THF (1.0 mL) at ambient temperature. After 16 hours, the mixture was poured onto water and extracted with ethyl acetate. The organic layer was dried over $Na_2SO_4$ and concentrated in vacuo. Purification by HPLC on a C18 Dynamax column with acetonitrile in water gradient with 0.1% trifluoroacetic acid afforded N-(4-chlorophenyl)-2-[((3-(2,3-dihydroxypropoxy)methylthiophen-2-yl)carbonyl)amino]-5-chlorobenzamide; NMR (DMSO-$d_6$) 11.0 (s, 1), 10.7 (s, 1), 8.3 (d, 1), 7.9 (d, 2), 7.7 (d, 2), 7.6 (d, 1), 7.4 (d, 2), 4.4 (s, 2), 3.5 (m, 1), 3.4 (m, 1), 3.3 (m, 2) ppm.

B. Other compounds of the invention may be prepared by methods similar to those described in this Example and by methods known to those of ordinary skill in the art.

EXAMPLE 25

A. A solution of N-(5-chloropyridin-2-yl)-2-[((4-cyano-3-chlorothiophen-2-yl)carbonyl)amino]-3-methoxy-5-chlorobenzamide (0.10 g, 0.21 mmol) in absolute ethanol (15 mL) was cooled to $-78°$ C. and HCl(g) was bubbled through the mixture for 15 minutes. The resultant mixture was stirred at ambient temperature in a sealed vessel for 20 hours, then concentrated of all volatiles in vacuo without heating. The residue was dissolved in absolute ethanol (10 mL) and treated with 1,2-diaminoethane (0.14 mL, 2.1 mmol) at $60°$ C. After 1 hour the mixture was cooled to ambient temperature and concentrated in vacuo. Purification by chromatography on silica gel, followed by lyophilization from aqueous trifluoroacetic acid afforded N-(5-chloropyridin-2-yl)-2-[((4-(imidazolin-2-yl)-3-chlorothiophen-2-yl)carbonyl)amino]-3-methoxy-5-chlorobenzamide, trifluoroacetic acid salt as a yellow solid; NMR (CDCl$_3$) 10.9 (s, 1), 10.4 (s, 1), 9.7 (s, 1), 8.6 (s, 1), 8.3 (d, 1), 8.1 (d, 1), 7.9 (d, 1), 7.3 (d, 2), 4.0 (s, 4), 3.9 (s, 3) ppm.

B. Other compounds of the invention may be prepared by methods similar to those described in this Example and by methods known to those of ordinary skill in the art.

EXAMPLE 26

A. To a solution of N-(5-chloropyridin-2-yl)-2-[((4-(chloromethyl)-3-chlorothiophen-2-yl)carbonyl)amino]-3-methoxy-5-chlorobenzamide (0.093 g, 0.19 mmol) in methylene chloride (4.0 mL) was added mCPBA (0.044 g, 0.20 mmol) The reaction mixture was stirred at ambient temperature for 16 hours. The mixture was poured into ethyl acetate (20 mL) and washed with saturated aqueous sodium bicarbonate (2×5 mL). The organic layer was dried and concentrated in vacuo to give the crude pyridine N-oxide. The crude material was dissolved in DMF (3.0 mL) and trimethylethylene diamine (0.115 mL, 0.9 mmol) was added. The reaction was stirred for 16 hours at ambient temperature and poured into water and ethyl acetate. The ethyl acetate layer was washed with water (2×2 mL) and concentrated. Purification by HPLC on a C18 Dynamax column with acetonitrile in water gradient with 0.1 % trifluoroacetica acid afforded 0.028 g of N-(5-chloropyridin-2-yl)-2-[((4-((N'-methyl-N'-(2-(dimethylamino)ethyl)amino)methyl)-3-chlorothiophen-2-yl)carbonyl)amino]-3-methoxy-5-chlorobenzamide N-oxide, trifluoroacetic acid salt; NMR (DMSO-d$_6$/TFA) 10.6 (br s, 1), 9.8 (s, 1), 8.6 (d, 1), 8.3 (d, 1), 8.2 (s, 1), 7.6 (dd, 1), 7.4 (dd, 2), 4.4 (s, 2), 3.9 (s, 3), 3.6 (s, 4), 2.9 (s, 6), 2.8 (s, 3) ppm.

B. Other compounds of the invention may be prepared by methods similar to those described in this Example and by methods known to those of ordinary skill in the art.

EXAMPLE 27

A. Hydroxylamine hydrochloride (0.58 g, 8.3 mmol) was dissolved in a solution of sodium methoxide prepared by dissolving sodium (0.17 g) in methanol (50 mL). N-(5-chloropyridin-2-yl)-2-[((4-cyanomethyl-3-chlorothiophen-2-yl)carbonyl)amino]-3-methoxy-5-chlorobenzamide (2.56 g, 5.2 mmol) and additional methanol (30 mL) were then added. The reaction mixture was refluxed for 16 hours, then a solution of hydroxylamine hydrochloride (0.67 g, 9.6 mmol) in sodium methoxide (0.20 g sodium, 25 mL methanol) was added. The reaction mixture was refluxed for 24 hours, then a solution of hydroxylamine hydrochloride (0.63 g, 9.1 mmol) in sodium methoxide (0.19 g sodium, 60 mL methanol) was added. The reaction mixture was refluxed for an additional 24 hours, filtered hot, concentrated in vacuo, and dried under vacuum. Purification by HPLC on a C18 Dynamax column with 20–70% acetonitrile in water gradient with 0.1 % trifluoroacetic acid gave N-(5-chloropyridin-2-yl)-2-[((4-(2-amino-2-(hydroxylmino)ethyl)-3-chlorothiophen-2-yl)carbonyl)amino]-3-methoxy-5-chlorobenzamide, trifluoroacetic acid salt, as a white solid; NMR (DMSO-d$_6$) 10.9 (s, 1), 9.4 (d, 1), 8.9 (br, 1), 8.4 (d, 1), 8.1 (d, 1), 7.9 (dd, 1), 7.8 (s, 0.5), 7.7 (s, 0.5), 7.4 (d, 1), 7.2 (d, 1), 3.9 (s, 3), 3.7 (s, 2) ppm.

B. In a similar manner, the following compound was made:

N-(5-chloropyridin-2-yl)-2-[((4-(N'-methyl-N'-hydroxyguanidino)methyl-3-chlorothiophen-2-yl)carbonyl)amino]-3-methoxy-5-chlorobenzamide, trifluoroacetic acid salt; NMR (DMSO-d$_6$/TFA) 10.9 (s, 1), 10.6 (s, 1), 9.4 (s., 1 ), 8.4 (d, 1), 8.1 (m, 2), 7.9 (dd, 1), 7.7 (s, 1), 7.4 (d, 1), 7.3 (d, 1), 4.5 (s, 2), 3.9 (s, 3), 3.0 (s, 3) ppm.

C. Other compounds of the invention may be prepared by methods similar to those described in this Example and by methods known to those of ordinary skill in the art.

EXAMPLE 28

A. To N-(5-chloropyridin-2-yl)-2-[((4-(chloromethyl)-3-chlorothiophen-2-yl)carbonyl)amino]-3-methoxy-5-chlorobenzamide (1.5 g, 3.0 mmol) in DMF (15 mL), was added ethylene diamine (0.09 g, 15 mmol) at ambient temperature. After 2 hours, the reaction was poured into water and extracted with ethyl acetate. The ethyl acetate solution was dried (NaSO$_4$) and concentrated in vacuo to afford the crude amine adduct. To the adduct was added triethyl orthoformate (1.33 g, 9 mmol) in acetic acid (20 mL). After stirring at ambient temperature for 1 hour, the reaction was poured into water and extracted with ethyl acetate. The ethyl acetate layer was dried (NaSO$_4$), concentrated in vacuo, and purified by HPLC on a C18 Dynamax column with acetonitrile in water gradient with 0.1 % trifluoroacetic acid to afford 0.87 g of N-(5-chloropyridin-2-yl)-2-[((4-((imidazolin-1-yl)methyl)-3-chlorothiophen-2-yl)carbonyl)amino]-3-methoxy-5-chlorobenzamide (870 mg), trifluoroacetic acid salt; NMR (DMSO-d$_6$/TFA) 10.9 (s, 1), 10.3 (s., 1 ), 9.4 (s, 1), 8.6 (d, 2), 8.3 (d, 1), 8.1 (d, 1), 7.8 (dd, 1), 7.3 (d, 1), 7.2 (d, 1), 4.6 (s, 2), 3.7~3.9 (m, 7) ppm.

B. In a similar manner, the following compound was made:

N-(5-chloropyridin-2-yl)-2-[((4-((5-hydroxy-1,4,5,6-tetrahydropyrimidin-1-yl)methyl)-3-chlorothiophen-2-yl) carbonyl)amino]-3-methoxy-5-chlorobenzamide, trifluoroacetic acid salt; NMR (DMSO-d$_6$/TFA) 10.9 (s, 1), 9.9 (s., 1), 9.4 (s, 1), 8.5 (d, 1), 8.4 (d, 1), 8.1 (d, 1), 8.0 (s, 1), 7.8 (dd, 1), 7.3 (d, 1), 7.2 (d, 1), 4.6 (m, 2), 4.62 (brs, 1), 3.9 (s, 3), 3.1~3.6 (m, 4) ppm.

C. Other compounds of the invention may be prepared by methods similar to those described in this Example and by methods known to those of ordinary skill in the art.

EXAMPLE 29

A. To a mixture of N-(5-chloropyridin-2-yl)-2-[((4-((2-aminoimidazol-1-yl)methyl)-3-chlorothiophen-2-yl)carbonyl)amino]-3-methoxy-5-chlorobenzamide (0.053 g, 0.96 mmol) and sulfuric acid (0.10 g, 1.06 mmol) in methanol (10 mL) was added N-chlorosuccinimide (0.192 g, 1.43 mmol). After stirring at ambient temperature for 6 hours, the reaction was poured into water and extracted with ethyl acetate. The ethyl acetate extract was dried over sodium sulfate, concentrated in vacuo, and purified by flash chromatography on silica gel to give 0.33 g of N-(5-chloropyridin-2-yl)-2-[((4-((cis4,5-dimethoxy-2-iminotetrahydroimidazol-1-yl)methyl)-3-chlorothiophen-2-yl)carbonyl)amino]-3-methoxy-5-chlorobenzamide; NMR (CDCl$_3$) 9.0 (d, 2), 8.3 (d, 1), 8.1 (d, 1), 7.7 (dd, 1), 7.5 (s, 1), 7.3 (d, 1), 7.1 (d, 1), 6.0 (brs, 1), 4.8 (m, 2), 4.6 (d, 1), 4.3 (d, 1), 3.9 (s, 3), 3.4 (s, 3), 3.3 (s, 3) ppm.

B. Other compounds of the invention may be prepared by methods similar to those described in this Example and by methods known to those of ordinary skill in the art.

EXAMPLE 30

A. To a solution of N-(5-chloropyridin-2-yl)-2-[((4-((N'-(2-aminoethyl)amino)methyl)-3-chlorothiophen-2-yl) carbonyl)amino]-3-methoxy-5-chlorobenzamide (0.64 g, 1.2 mmol) and triethylamine (0.31 g, 3.1 mmol) in dichloromethane (20 mL) at 0° C. was added POCl$_3$ (0.14 g, 0.923 mmol). The reaction was allowed to warm to ambient temperature and stirred for 16 hours. The reaction was quenched with methanol, concentrated in vacuo, and purified by HPLC on a C18 Dynamax column with acetonitrile in water gradient with 0.1% trifluoroacetic acid to afford 0.13 g of N-(5-chloropyridin-2-yl)-2-[((4-(((2-dimethylphosphoramidoethyl)amino)methyl)-3-chlorothiophen-2-yl)carbonyl)amino]-3-methoxy-5-chlorobenzamide, trifluoroacetic acid salt; NMR (DMSO-d$_6$/TFA) 10.9 (s, 1), 9.4 (s, 1), 8.9 (br s, 1), 8.4 (d, 1), 8.2 (d, 1), 8.1 (s, 1), 7.9 (dd, 1), 7.4 (s, 1), 7.3 (s, 1), 4.2 (s, 2), 3.9 (s, 3), 3.6 (s, 3), 3.55 (s, 3), 3.1 (m, 4) ppm.

B. Other compounds of the invention may be prepared by methods similar to those described in this Example and by methods known to those of ordinary skill in the art.

EXAMPLE 31

A. To a mixture of N-(5-chloropyridin-2-yl)-2-[((4-((methylamino)methyl)-3-chlorothiophen-2-yl)carbonyl) amino]-3-methoxy-5-chlorobenzamide (0.70 g, 1.4 mmol)

and triethylamine (0.16 g, 1.5 mmol) in dichloromethane (7 mL) was added ethylene chlorophosphate (0.19 g, 1.5 mmol) at 0° C. The reaction was allowed to warm to ambient temperature and stirred for 2 hours. The reaction was then quenched with methanol. The reaction mixture was poured into water and extracted with ethyl acetate. The ethyl acetate extract was concentrated in vacuo and purified by flash chromatography on silica gel to give 0.70 g of N-(5-chloropyridin-2-yl)-2-[((4-((N'-methyl-N'-(1,3,2-dioxaphospholan-2-yl)amino)methyl)-3-chlorothiophen-2-yl)carbonyl)amino]-3-methoxy-5-chlorobenzamide; NMR (DMSO-$d_6$/TFA) 10.9 (s, 1), 9.4 (d, 1), 8.3 (d, 1), 8.1 (d, 1), 7.9 (dd, 1), 7.7 (s, 1), 7.4 (d, 1), 7.3 (d, 1), 4.4 (m, 4), 4.2 (d, 2), 3.9 (s, 3), 2.6 (d, 3) ppm.

B. Other compounds of the invention may be prepared by methods similar to those described in this Example and by methods known to those of ordinary skill in the art.

EXAMPLE 32

A. A mixture of N-(5-chloropyridin-2-yl)-2-[((4-((N'-(2-aminoethyl)amino)methyl)-3-chlorothiophen-2-yl)carbonyl)amino]-3-methoxy-5-chlorobenzamide (1.5 g, 2.9 mmol) and triethyl orthochloroacetate (1.3 g, 8.6 mmol) in acetic acid (10 mL) was stirred at ambient temperature for 16 hours. The solvent was removed in vacuo and the resulting residue was purified by HPLC on a C18 Dynamax column with acetonitrile in water gradient with 0.1% trifluoroacetic acid to afford 0.14 g of N-(5-chloropyridin-2-yl)-2-[((4-((2-(chloromethyl)imidazolin-1-yl)methyl)-3-chlorothiophen-2-yl)carbonyl)amino]-3-methoxy-5-chlorobenzamide, trifluoroacetic acid salt. The product (0.14 g, 0.24 mmol) was treated with tetrabutylammonium cyanide (0.097 g, 0.36 mmol) in acetonitrile (3 mL) and the mixture stirred at ambient temperature for 16 hours. It was then purified directly by HPLC on a C18 Dynamax column with acetonitrile in water gradient-with 0.1 % trifluoroacetic acid to afford 0.020 g of N-(5-chloropyridin-2-yl)-2-[((4-((2-(cyanomethyl)imidazolin-1-yl)methyl)-3-chlorothiophen-2-yl)carbonyl)amino]-3-methoxy-5-chlorobenzamide, trifluoroacetic acid salt; NMR (DMSO-$d_6$/TFA) 10.9 (s, 1), 9.8 (br s, 1), 9.4 (d, 1), 8.4 (d, 1), 8.2 (d, 1), 8.1 (s, 1), 7.9 (dd, 1), 7.4 (d, 1), 7.3 (d, 1), 4.7 (s, 2), 4.5 (brs, 2), 3.7–3.9 (m, 7) ppm.

B. Other compounds of the invention may be prepared by methods similar to those described in this Example and by methods known to those of ordinary skill in the art.

EXAMPLE 33

A. A mixture of N-(5-chloropyridin-2-yl)-2-[((4-((2-(methylthio)imidazolin-1-yl)methyl)-3-chlorothiophen-2-yl)carbonyl)amino]-3-methoxy-5-chlorobenzamide (0.60 g, 1.03 mmol) and 2-aminoethanol (0.18 g, 3.1 mmol) was refluxed in isopropanol for 16 hours. After removal of the solvent in vacuo, the resulting crude product was purified by HPLC on a C18 Dynamax column with acetonitrile in water gradient with 0.1% trifluoroacetic acid to afford 0.13 g of N-(5-chloropyridin-2-y)-2-[((4-((2-((2-hydroxyethyl)imino)tetrahydroimidazol-1-yl)methyl)-3-chlorothiophen-2-yl)carbonyl)amino]-3-methoxy-5-chlorobenzamide, trifluoroacetic acid salt; NMR (DMSO-$d_6$/TFA) 10.9 (s, 1), 9.4 (d, 1), 8.4 (brs, 2), 8.3 (d, 1), 8.1 (d, 1), 7.7 (m, 1), 7.6 (s, 1), 7.3 (d, 1), 7.2 (d, 1), 4.5 (s, 2), 3.9 (s, 3), 3.4 3. 7 (m, 6), 3.2–3.35 (m, 2) ppm.

B. A mixture of N-(5-chloropyridin-2-yl)-2-[((4-((2-(methylthio)imidazolin-1-yl)methyl)-3-chlorothiophen-2-yl)carbonyl)amino]-3-methoxy-5-chlorobenzamide (0.88 g, 1.5 mmol), glycinamide hydrochloride (0.33 g, 3.0 mmol) and diisopropylethylamine (0.49 g, 3.8 mmol) in DMF was stirred at 75–80° C. for 10 hours. The reaction was then poured into water and extracted with ethyl acetate. The ethyl acetate layer was dried over sodium sulfate, concentrated in vacuo, and purified by HPLC on a C18 Dynamax column with acetonitrile in water gradient with 0.1 % trifluoroacetic acid to afford 0.47 g of N-(5-chloropyridin-2-yl)-2-[((4-((2-(((aminocarbonyl)methyl)imino)tetrahydroimidazol-1-yl)methyl)-3-chlorothiophen-2-yl)carbonyl)amino]-3-methoxy-5-chlorobenzamide, trifluoroacetic acid salt; NMR (DMSO-$d_6$/TFA) 9.4 (d, 1), 8.6 (br s, 2), 8.2 (d, 1), 8.1 (d, 1), 7.6 (m, 2), 7.4 (br s, 1), 7.2 (br s, 1), 4.5 (s, 2), 3.9 (s, 5), 3.6 (m, 4) ppm.

C. Other compounds of the invention may be prepared by methods similar to those described in this Example and by methods known to those of ordinary skill in the art.

EXAMPLE 34

A. A mixture of N-(5-chloropyridin-2-yl)-2-[((4-(chloromethyl)-3-chlorothiophen-2-yl)carbonyl)amino]-3-methoxy-5-chlorobenzamide (1.0 g, 2.0 mmol) and 2-formylimidazole (1.2 g, 12.5 mmol) in DMF was stirred at 110° C. for 10 hours. After cooling to ambient temperature, the reaction mixture was poured into water and extracted with ethyl acetate. The ethyl acetate extract was concentrated in vacuo and purified by flash chromatography on silica gel to give the imidazole adduct. To the imidazole adduct in methanol (10 mL) at 0° C. was added NaBH$_4$ until thin layer chromatography indicated the completion of the reaction. The reaction was poured into water and extracted with ethyl acetate. The ethyl acetate extract concentrated in vacuo and purified by HPLC on a C18 Dynamax column with acetonitrile in water gradient with 0.1% trifluoroacetic acid to afford to give 0.21 g of N-(5-chloropyridin-2-yl)-2-[((4-((2-(hydroxymethyl)imidazol-1-yl)methyl)-3-chlorothiophen-2-yl)carbonyl)amino]-3-methoxy-5-chlorobenzamide, trifluoroacetic acid salt; NMR (DMSO-$d_6$/ TFA) 10.9 (s,1), 9.4 (d, 1), 8.3 (d, 1), 8.1 (d, 1), 7.9 (m, 2), 7.6 (s, 2), 7.35 (d, 1), 7.25 (d, 1), 5.4 (s, 2), 4.8 (s, 2), 3.9 (s, 3) ppm.

B. Other compounds of the invention may be prepared by methods similar to those described in this Example and by methods known to those of ordinary skill in the art.

EXAMPLE 35

A. N-(5-Chloropyridin-2-yl)-2-[((4-((N'-methyl-N'-(2-nitro-1-methylthioethenyl)amino)methyl)-3-chlorothiophen-2-yl)carbonyl)amino]-3-methoxy-5-chlorobenzamide (0.185 g, 0.30 mmol) was dissolved in DMF (3 mL) under nitrogen. A 2.0 M solution of methylamine in THF (0.75 mL, 1.5 mmol) was added. The reaction mixture was stirred at ambient temperature for 16 hours, then poured into water (50 mL). The aqueous layer was extracted with ethyl acetate (3×30 mL). The combined organic layers were washed with water (3×40 mL), brine (40 mL), dried over magnesium sulfate, concentrated in vacuo, and dried under vacuum. Purification by HPLC on a C18 Dynamax column with acetonitrile in water gradient with 0.1 % trifluoroacetic acid afforded N-(5-chloropyridin-2-yl)-2-[((4-((N'-methyl-N'-(2-nitro-1-(methylamino)ethenyl)amino)methyl)-3-chlorothiophen-2-yl)carbonyl)amino]-3-methoxy-5-chlorobenzamide, trifluoroacetic acid salt, as a mixture of geometric isomers; NMR (DMSO-$d_6$) 10.9 (d, 1), 9.6 (br, 0.5), 9.4 (s, 1), 8.8 (br, .5), 8.4 (d, 1), 8.1 (d, 1), 7.9 (dd, 1), 7.85 (s, 0.33), 7.75 (s, 0.33), 7.7 (s, 0.33), 7.4 (d, 1), 7.2 (d, 1), 6.2 (s, 1), 4.9 (s, .67), 4.7 (s, 0.67), 4.4 (s, 0.67), 3.9 (s, 3), 3.3 (s, 1), 3.2 (s, 1), 3.1 (d, 1), 3.0 (d, 1), 2.9 (d, 1), 2.8 (s, 1) ppm.

B. In a similar manner the following compound was made:

N-(5-chloropyridin-2-yl)-2-[((4-(N'-methyl-N"-(2-aminoethyl)-N'"-cyanoguanidino)methyl-3-chlorothiophen-2-yl)carbonyl)amino]-3-methoxy-5-chlorobenzamide, trifluoroacetic acid salt; NMR (DMSO-$d_6$/TFA) 10.9 (s, 1), 9.4 (s, 1), 8.3 (s, 1), 8.1 (d, 1), 7.9 (dd, 1), 7.8 (br s, 2), 7.7 (s, 1), 7.3 (d, 2), 7.2 (s, 1), 4.6 (s, 2), 3.8 (s, 3), 3.5 (m, 2), 2.9 (br s, 5) ppm.

C. To a solution of
N-(5-chloropyridin-2-yl)-2-[((4-((N'-methyl-N'-(methylthio(cyanoimino)methyl)amino)methyl)-3-chlorothiophen-2-yl)carbonyl)amino]-3-methoxy-5-chlorobenzamide (0.1 g, 0.17 mmol) in DMF (10 mL) was added methylamine (0.84 mL of a 2 M solution in THF, 1.7 mmol). After stirring for 16 hours at ambient temperature, the reaction mixture was concentrated in vacuo to remove THF, poured into water and filtered. The resulting solid was purified by silica gel chromatography using 1–8% methanol in methylene chloride gradient followed by precipitation from $CH_2Cl_2$ and hexane to afford 0.072 g of N-(5-chloropyridin-2-yl)-2-[((4-(N',N"-dimethyl-N'"-cyanoguanidino)methyl-3-chlorothiophen-2-yl)carbonyl)amino]-3-methoxy-5-chlorobenzamide, as a white solid; NMR (DMSO-$d_6$/TFA) 10.9 (s, 1), 9.4 (s,1), 8.3 (s, 1), 8.1 (d, 1), 7.9 (dd, 1), 7.6 (s, 1), 7.4 (s, 1), 7.3 (s, 1), 7.2 (br d, 1), 4.5 (s, 2), 3.8 (s, 3), 2.9 (d, 3), 2.85 (s, 3) ppm.

D. Other compounds of the invention may be prepared by methods similar to those described in this Example and by methods known to those of ordinary skill in the art.

EXAMPLE 36

A. Dimethylamine (40% aqueous, 0.51 mL, 4.1 mmol) was dissolved in DMF (2 mL) under nitrogen, and N-(5-chloropyridin-2-yl)-2-[((4-((5-trichloromethyl-1,2,4-oxadiazol-3-yl)methyl)-3-chlorothiophen-2-yl)carbonyl)amino]-3-methoxy-5-chlorobenzamide (0.151 g, 0.23 mmol) was added. The reaction mixture was stirred for 40 minutes at ambient temperature, then poured into water (40 mL). The aqueous layer was extracted with ethyl acetate (3×25 mL). The combined organic layers were washed with water (3×25 mL), brine (25 mL), dried over magnesium sulfate, concentrated in vacuo, and dried under vacuum. The crude product was purified by flash chromatography on silica gel, eluting with 75% ethyl acetate/hexanes to afford N-(5-chloropyridin-2-yl)-2-[((4-((5-(dimethylamino)-1,2,4-oxadiazol-3-yl)methyl)-3-chlorothiophen-2-yl)carbonyl)amino]-3-methoxy-5-chlorobenzamide; NMR (DMSO-$d_6$) 10.9 (br, 1), 9.4 (br, 1), 8.4 (d, 1), 8.1 (d, 1), 7.9 (dd, 1), 7.8 (s, 1), 7.4 (d, 1), 7.2 (d, 1), 3.9 (s, 3), 3.8 (s, 2), 3.0 (s, 6) ppm.

B. In a similar manner, the following compound was prepared,

N-(5-chloropyridin-2-yl)-2-[((4-((5-amino-1,2,4-oxadiazol-3-yl)methyl)-3-chlorothiophen-2-yl)carbonyl)amino]-3-methoxy-5-chlorobenzamide; NMR (DMSO-$d_6$) 10.9 (s, 1), 9.4 (s, 1), 8.4 (d, 1), 8.1 (d, 1), 7.9 (dd, 1), 7.7 (s, 3), 7.4 (d, 1), 7.2 (d, 1), 3.9 (s, 3), 3.8 (s, 2) ppm.

C. Other compounds of the invention may be prepared by methods similar to those 10 described in this Example and by methods known to those of ordinary skill in the art.

EXAMPLE 37

A. N-(4-chlorophenyl)-2-[(((4,5)-nitro-3-methylthiophen-2-yl)carbonyl)amino]-5-chlorobenzamide (1 g, 2.1 mmol) was stirred in a 4:1 ethanol/water solution (43 mL). To this 15 solution was added iron (0.59 g, 10.6 mmol), and ammonium chloride (5.0 eq.) and the reaction mixture was refluxed for 1 hour. The reaction mixture was cooled to ambient temperature, filtered through Celite®, and the Celite® layer was washed with methylene chloride and ethyl acetate. The filtrate was washed with aqueous sodium bicarbonate, water and dried over sodium sulfate to afford a rust-colored solid, 0.71 g (75% yield). Purification by flash chromatography on silica, eluting with 1:1 ethyl acetate/hexanes afforded
N-(4-chlorophenyl)-2-[((5-amino-3-methylthiophen-2-yl)carbonyl)amino]-5-chlorobenzamide; NMR (DMSO-$d_6$/TFA) 10.7 (s, 1), 10.6 (s, 1), 8.4 (d, 1), 8.0 (s, 1), 7.8 (d, 2), 7.6 (d, 1), 7.4 (d, 2), 5.8 (s, 1) 2.4 (s, 3) ppm, and N-(4-chlorophenyl)-2-[((4-amino-3-methylthiophen-2-yl)carbonyl)amino]-5-chlorobenzamide.

B. To a solution of N-(4-chlorophenyl)-2-[((5-amino-3-methylthiophen-2-yl)carbonyl)amino]-5-chlorobenzamide (0.05 g, 0.114 mmol) in pyridine (3 mL) at 0° C. was added acetyl chloride (0.009 mL, 0.125 mmol) and the reaction was warmed to ambient temperature. The reaction was stirred 3 hours and was poured into water and ice. The resulting solid was collected by filtration, washed with water and dried in vacuo to afford 0.03 g 30 (55%) of
N-(4-chlorophenyl)-2-[((5-acetamido-3-chlorothiophen-2-yl)carbonyl)amino]-5-chlorobenzamide; NMR (DMSO-$d_6$) 11.4 (s, 1), 10.8 (s, 1), 10.7 (s, 1), 8.3 (d, 1), 7.9 (s, 1), 7.8 (d, 2), 7.6 (d, 1), 7.4 (d, 2), 6.5 (s, 1), 2.4 (s, 3), 2.0 (d, 3) ppm.

C. Other compounds of the invention may be prepared by methods similar to those described in this Example and by methods known to those of ordinary skill in the art.

EXAMPLE 38

A. A suspension of N-(5-chloropyridin-2-yl)-2-[((4-(N',N"-dimethyl-N'"-cyanoguanidino)methyl-3-chlorothiophen-2-yl)carbonyl)amino]-3-methoxy-5-chlorobenzamide (0.3 g, 0.52 mmol) in 3 M HCl (10 mL) was stirred for 24 hours at ambient temperature. The reaction mixture was made pH basic with 2 N NaOH and saturated aqueous $NaHCO_3$. The reaction mixture was filtered, and the solid was dissolved in methylene chloride. The solution was dried over $Na_2SO_4$, filtered, concentrated, and purified by flash chromatography on silica using 1–8% methanol in methylene chloride gradient followed by precipitation from $CH_2Cl_2$ and hexane to afford 0.115 g of N-(5-chloropyridin-2-yl)-2-[((4-(N'N"-dimethyl-N'"-(aminocarbonyl)guanidino)methyl-3-chlorothiophen-2-yl)carbonyl)amino]-3-methoxy-5-chlorobenzamide, as a white solid; NMR (DMSO-$d_6$/TFA) 10.9 (s, 1), 9.4 (s, 1), 8.8 (br s, 1), 8.3 (s, 1), 8.1 (d, 1), 7.8 (m, 2), 7.3 (d, 2), 6.9 (br m, 1), 4.6 (s, 2), 3.8 (s, 3), 3.0 (s, 3), 2.9 (d, 3) ppm.

B. Other compounds of the invention may be prepared by methods similar to those described in this Example and by methods known to those of ordinary skill in the art.

EXAMPLE 39

A. To a solution of
N-(5-chloropyridin-2-yl)-2-[((4-((N'-(2-aminoethyl)amino)methyl)-3-chlorothiophen-2-yl)carbonyl)amino]-3-methoxy-5-chlorobenzamide (0.9 g, 1.7 mmol) in DMF (50 mL) was added excess of dimethyl N-cyanodithioimidocarbonate. After stirring for 16 hours at ambient temperature, the reaction mixture was concentrated in vacuo. Water was added, and the reaction mixture was extracted with methylene chloride. The combined extracts were dried over Na₂SO₄, filtered, concentrated, and purified by flash chromatography on silica using 1–8% methanol in methylene chloride to afford a white solid. The solid was dissolved in acetonitrile and heated at reflux for for 16 hours. The solution was concentrated and purified by HPLC on a C18 Dynamax column with 25–95% acetonitrile in water gradient with 0.1% trifluoroacetic acid to afford 0.084 g of N-(5-chloropyridin-2-yl)-2-[((4-((2-(cyanoimino) tetrahydroimidazol-1-yl)methyl)-3-chlorothiophen-2-yl) carbonyl)amino]-3-methoxy-5-chlorobenzamide, trifluoroacetic acid salt, as a white solid; NMR (DMSO-d₆/TFA) 10.9 (s, 1), 9.4 (s, 1), 8.4 (s, 1), 8.1 (d, 1), 8.0 (s, 1), 7.9 (dd, 1), 7.8 (s, 1), 7.4 (s, 1), 7.3 (s, 1), 4.3 (s, 2), 3.8 (s, 3), 3.4 (m, 4) ppm.

B. Other compounds of the invention may be prepared by methods similar to those described in this Example and by methods known to those of ordinary skill in the art.

EXAMPLE 40

A. To a solution of N-(4-chlorophenyl)-2-[((5-bromomethyl-3-chlorothiophen-2-yl)carbonyl)amino]-5-chlorobenzamide (0.3 g, 0.58 mmol) in dioxane (10 mL) and water (2 mL) was added CaCO₃ (0.29 g, 2.89 mmol). The resulting turbid solution was heated to reflux for 64 hours, and then cooled to ambient temperature. The reaction mixture was concentrated to remove dioxane and purified by flash chromatography on silica followed by precipitation from CH₂Cl₂ and hexane to afford 0.15 g of N-(4-chlorophenyl)-2-[((5-hydroxymethyl-3-chlorothiophen-2-yl)carbonyl)amino]-5-chlorobenzamide, as a yellow solid; NMR (DMSO-d₆/ TFA) 11.1 (s, 1), 10.7 (s, 1), 8.4 (d, 1), 7.9 (s, 1), 7.7 (d, 2), 7.5 (d, 1), 7.3 (d, 2), 7.0 (s, 1), 4.6 (s, 2) ppm.

B. To a solution of N-(4-chlorophenyl)-2-[((5-hydroxymethyl-3-chlorothiophen-2-yl)carbonyl)amino]-5-chlorobenzamide (0.085 g, 0.19 mmol) in DMF (6 mL) was added pyridinium dichromate (PDC) (0.25 g, 0.65 mmol) at ambient temperature. After stirring for 20 hours, water was added and the reaction mixture was extracted with methylene chloride. The combined extracts were dried over Na₂SO₄, filtered, concentrated in vacuo, and purified by flash chromatography on silica to afford 0.035 g of N-(4-chlorophenyl)-2-[((5-formyl-3-chlorothiophen-2-yl) carbonyl)amino]-5-chlorobenzamide, as a pale yellow solid; NMR (DMSO-d₆) 11.3 (s, 1), 10.8(s, 1), 9.9 (s, 1),8.3 (d, 1), 8.1 (s, 1), 7.9 (s, 1), 7.7 (d, 2), 7.6 (d, 1), 7.4 (d, 2) ppm.

C. To a solution of N-(4-chlorophenyl)-2-[((5-formyl-3-chlorothiophen-2-yl)carbonyl)amino]-5-chlorobenzamide (0.31 g, 0.69 mmol) in CCl₄ (10 mL) and benzene (15 mL) was added N-bromosuccinimide (NBS) (0.18 g, 1.03 mmol) and 2,2'-azobisisobutyronitrile (AIBN) (0.011 g, 0.068 mmol). The reaction mixture was heated to reflux for 1 hour, and the resulting clear yellow solution was cooled to 0° C. Methanol (0.1 mL) was added and the reaction mixture was stirred for 14 hours at ambient temperature. Water was added and the reaction mixture was extracted with methylene chloride. The combined extracts were dried over Na₂SO₄, filtered, concentrated in vacuo, and purified by flash chromatography on silica to afford 0.27 g of N-(4-chlorophenyl)-2-[((5-methoxycarbonyl-3-chlorothiophen-2-yl)carbonyl) amino]-5-chlorobenzamide. as a pale yellow solid; NMR (DMSO-d₆/TFA) 11.3 (s,1), 10.8 (s, 1), 8.3 (d, 1), 7.9 (s, 1), 7.7 (m, 3), 7.6 (d, 1), 7.4 (d, 2), 3.8 (s, 3) ppm.

D. In a similar manner, the following compound was made:

N-(4-chlorophenyl)-2-[((5-(diethylamino)carbonyl-3-chlorothiophen-2-yl)carbonyl)amino]-5-chlorobenzamide; NMR (CDCl₃) 11.0 (s, 1), 9.2 (s, 1), 8.4 (d, 1), 7.7 (d, 2), 7.5 (s,1), 7.4 (d, 1), 7.3 (d, 1), 7.2 (d, 1), 7.0 (s, 1), 3.5 (q, 4), 1.2 (t, 6) ppm.

E. Other compounds of the invention may be prepared by methods similar to those described in this Example and by methods known to those of ordinary skill in the art.

EXAMPLE 41

A. To a solution of N-(5-chloropyridin-2-yl)-2-[((4-((N'-methyl-N'-oxazolin-2-yl)amino)methyl)-3-chlorothiophen-2-yl)carbonyl)amino]-3-methoxy-5-chlorobenzamide (5.0 g, 8.03 mmol) in ethanol (50 mL) at 40° C. was added salicylic acid (1.22 g, 8.03 mmol) followed by the addition of ethyl acetate (125 mL). The solution was seeded with previously prepared crystals of the salicylic acid salt of N-(5-chloropyridin-2-yl)-2-[((4-((N'-methyl-N'-oxazolin-2-yl)amino)methyl)-3-chlorothiophen-2-yl)carbonyl)amino]-3-methoxy-5-chlorobenzamide. Crystallization occurred as the solution cooled to ambient temperature. After 1 hour at ambient temperature the crystalline product was isolated by filtration. The solid was washed with ethyl acetate (50 mL), then dried in vacuo at 35° C. for 24 hours to afford 5.4 g (87%) of the salicylic acid salt of N-(5-chloropyridin-2-yl)-2-[((4-((N'-methyl-N'oxazolin-2-yl)amino)methyl)-3-chlorothiophen-2-yl)carbonyl)amino]-3-methoxy-5-chlorobenzamide, as a white solid. A vial was charged with salicylic acid salt of N-(5-chloropyridin-2-yl)-2-[((4-((N'-methyl-N'-oxazolin-2-yl)amino)methyl)-3-chlorothiophen-2-yl)carbonyl)amino]-3-methoxy-5-chlorobenzamide (200 mg). The vial was placed in an oil bath at 145° C. to melt the solid then allowed to cool to ambient temperature to afford N-(5-chloropyridin-2-yl)-2-[((4-((N'-methyl-N''-(2-(((2-hydroxyphenyl)carbonyl)oxy)ethyl)ureido)-methyl)-3-chlorothiophen-2-yl)carbonyl)amino]-3-methoxy-5-chlorobenzamide, in quantitative yield as an off-white solid; NMR (DMSO-d₆) 10.9 (s, 0.5), 10.5 (s, 0.5), 9.3 (s, 0.5), 8.4 (d, 1), 8.1 (d, 1), 7.9 (dd, 1), 7.8 (dd, 1), 7.5 ( m, 2), 7.4 (d, 1) 7.3 (d, 1), 6.9 (m, 2), 6.7 (t, 1), 4.3 (m, 4), 3.9 (s, 3), 3.4 (d, 2), 3.3 (d, 4), 2.7 (s, 3) ppm.

B. In a similar manner, the following compound was made:

N-(5-chloropyridin-2-yl)-2-[((4-((N'-methyl-N!-(2-(acetoxy)ethyl)ureido)methyl)-3-chlorothiophen-2-yl) carbonyl)amino]-3-methoxy-5-chlorobenzamide; NMR (DMSO-d₆) 10.9 (s, 0.5), 9.3 (s, 0.5), 8.4 (s, 1), 8.1 (d, 1), 7.9 (dd, 1), 7.5 (s, 1), 7.4 (d, 1) 7.3 (d, 1), 6.6 (t, 1), 4.4 (s, 2), 4.0 (t, 2), 3.9 (s, 3), 3.4 (d, 2), 3.3 (m, 2), 2.8 (s, 3), 2.0 (s, 3) ppm.

C. Other compounds of the invention may be prepared by methods similar to those described in this Example and by methods known to those of ordinary skill in the art.

EXAMPLE 42

A. To a solution of N-(5-chloropyridin-2-yl)-2-[((4-((methylamino)methyl)-3-chlorothiophen-2-yl)carbonyl) amino]-3-methoxy-5-chlorobenzamide (0.70 g, 1.4 mmol) in THF (10 mL) at 0° C. was added 2-bromoethylisocyanate (0.63 mL, 4.2 mmol) and the mixture stirred at ambient temperature. After 30 minutes, the mixture was cooled, concentrated in vacuo and the residue dissolved in DMF (4 mL). Pyrrolidine (0.50 g, 7.0 mmol) was added. The reaction was stirred for 1 hour and poured into water and ethyl acetate. The ethyl acetate layer was dried over $MgSO_4$ and concentrated in vacuo. Purification by flash chromatography on silica gel afforded 0.050 g of N-(5-chloropyridin-2-yl)-2-[((4-((N'-methyl-N'-(2-(pyrrolidin-1-yl)ethyl)ureido)methyl)-3-chlorothiophen-2-yl)carbonyl)amino]-3-methoxy-5-chlorobenzamide; NMR (DMSO-$d_6$/TFA) 10.9 (s, 1), 9.6 (m,1), 9.4 (s, 1), 8.3 (d, 1), 8.1 (d, 1), 7.9 (dd, 1), 7.5 (s, 1), 7.4 (s, 1), 7.3 (s, 1), 4.4 (s, 2), 3.9 (s, 3), 3.6 (m, 2), 3.4 (m, 2), 3.2 (m, 2), 3.0 (m, 2), 2.9 (s, 3), 2 (m, 2), 1.8 (m, 2) ppm.

B. Other compounds of the invention may be prepared by methods similar to those described in this Example and by methods known to those of ordinary skill in the art.

EXAMPLE 43

A. To a mixture of N-(5-chloropyridin-2-yl)-2-[((4-((2-iminotetrahydroimidazol-1-yl)methyl)-3-chlorothiophen-2-yl)carbonyl)amino]-3-methoxy-5-chlorobenzamide (0.072 g, 1.3 mmol) and triethyl amine (0.13 g, 1.3 mmol) in dichloromethane (100 mL) was added methylchloroformate (0.12 g, 1.3 mmol) at 0° C. The reaction was allowed to warm and stirred at ambient temperature for 1 hour. The reaction was then quenched with methanol, and extracted between ethyl acetate and water. The ethyl acetate extract was purified by HPLC on a C18 Dynamax column with acetonitrile in water gradient with 0.1% trifluoroacetic acid to afford 0.12 g of N-(5-chloropyridin-2-yl)-2-[((4-((2-(methoxycarbonylamino)imidazolin-1-yl)methyl)-3-chlorothiophen-2-yl)carbonyl)amino]-3-methoxy-5-chlorobenzamide, trifluoroacetic acid salt; NMR (DMSO-$d_6$/TFA) 10.9 (s, 1), 9.5 (s.,$_1$ ), 9.4 (s, 1), 8.3 (d, 2), 8.1 (d, 1), 7.9 (m, 2), 7.4 (d, 1), 7.3 (d, 1), 4.6 (s, 2), 3.9 (s, 3), 3.8 (s, 3), 3.6 (m, 4) ppm.

B. In a similar manner, to a mixture of N-(5-chloropyridin-2-yl)-2-[((4-((2-iminotetrahydroimidazol-1-yl)methyl)-3-chlorothiophen-2-yl)carbonyl)amino]-3-methoxy-5-chlorobenzamide (0.56 g, 1.0 mmol) and triethyl amine (0.41 g, 3.0 mmol) in dichloromethane (100 mL) was added phenylisocyanate (0.36 g, 3.0 mmol) at 0C. The reaction was allowed to warm and stirred at ambient temperature for 1 hour. The reaction was then quenched with methanol, and extracted between ethyl acetate and water. The ethyl acetate extract was purified by HPLC on a C18 Dynamax column with acetonitrile in water gradient with 0.1 % trifluoroacetic acid to afford 0.12 g of N-(5-chloropyridin-2-yl)-2-[((4-((2-imino-3-((phenylamino)carbonyl)tetrahydroimidazol-1-yl)methyl)-3-chlorothiophen-2-yl)carbonyl)amino]-3-methoxy-5-chlorobenzamide, trifluoroacetic acid salt; NMR (DMSO-$d_6$/TFA) 10.9 (s, 1), 9.7 (s.,1 ), 9.6 (s, 1), 9.4 (s, 1), 8.3 (s, 1), 8.1 (d, 1), 7.9 (s, 1), 7.8 (dd, 1), 7.1~7.5 (m, 7), 4.6 (s, 2), 3.9 (s, 3), 3.6~3.8 (m, 4) ppm.

C. Other compounds of the invention may be prepared by methods similar to those described in this Example and by methods known to those of ordinary skill in the art.

EXAMPLE 44

A. 3-Methyl-2-formylbenzo[b]thiophene (0.68 g, 3.83 mmol) and N'-(4-chlorophenyl)-2-amino-5-benzamide (1.0 g, 3.83 mmol) were stirred at 0° C. in acetic acid (20 mL) for 2 hours. Sodium cyanoborohydride (0.48 g, 7.64 mmol) was added and the reaction stirred for 16 hours at ambient temperature. The reaction was poured into water and the resulting pale yellow precipitate was collected by filtration. Purification by flash chromatography in ethyl acetate/hexanes afforded 0.14 g (10%) of N'-(4-chlorophenyl)-2-((3-methylbenzo[b]thien-2yl)methyl)amino-5-benzamide as a white solid; NMR (CDCl$_3$) 7.8 (s, 1), 7.7 (s, 1), 7.6 (s, 1), 7.5 (d, 2), 7.4 (m, 3), 7.2 (d, 2), 6.8 (d, 2), 4.6 (s, 2), 2.4 (s, 3), 2.3 (s, 3) ppm.

B. Other compounds of the invention may be prepared by methods similar to those described in this Example and by methods known to those of ordinary skill in the art.

EXAMPLE 45

A. To a solution of N-phenyl-2-[((3-chlorobenzo[b]thien-2-yl)carbonyl)amino]-4,5-dihydroxybenzamide (0.09 g, 0.21 mmol) in $CH_2Cl_2$ (1 mL) and pyridine.(1 mL) at 0° C. was added trimethylacetyl chloride (0.027 mL, 0.22 mmol). The solution was allowed to warm to ambient temperature with stirring. After 16 hours, the reaction mixture was partitioned between ethyl acetate and dilute HCl. The organic layer was dried over $Na_2SO_4$ and concentrated in vacuo. The resulting oil was purified by flash chromatography on silica gel to afford 0.038 g (40% yield) of N-phenyl-2-[((3-chlorobenzo[b]thien-2-yl)carbonyl)amino]-5-hydroxy4-((1,1-dimethylethyl)carbonyl)oxybenzamide as a white solid; NMR(DMSO-$d_6$) 12.2 (s, 1), 10.8 (s, 1), 10.4 (s, 1), 8.3 (s, 1), 8.2 (d, 1), 8.0 (d, 1), 7.6–7.7 (m, 4), 7.4 (t, 2), 7.1 (t, 1), 1.3 (s, 9) ppm.

B. Other compounds of the invention may be prepared by methods similar to those described in this Example and by methods known to those of ordinary skill in the art.

EXAMPLE 46

This example illustrates the preparation of representative pharmaceutical compositions for oral administration containing a compound of the invention, or a pharmaceutically acceptable salt thereof, e.g., N-(5-chloropyridin-2-yl)-2-[((4-((pyridinium-1-yl)methyl)-3-chlorothiophen-2-yl)carbonyl)amino]-3-hydroxy-5-chlorobenzamide:

| A. | Ingredients | % wt./wt. |
|---|---|---|
| | Compound of the invention | 20.0% |
| | Lactose | 79.5% |
| | Magnesium stearate | 0.5% |

The above ingredients are mixed and dispensed into hard-shell gelatin capsules containing 100 mg each, one capsule would approximate a total daily dosage.

| B. | Ingredients | % wt./wt. |
|---|---|---|
| | Compound of the invention | 20.0% |
| | Magnesium stearate | 0.9% |
| | Starch | 8.6% |
| | Lactose | 69.6% |
| | PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. | Ingredients | |
|---|---|---|
| | Compound of the invention | 0.1 g |
| | Propylene glycol | 20.0 g |
| | Polyethylene glycol 400 | 20.0 g |
| | Polysorbate 80 | 1.0 g |
| | Water | qs. 100 mL |

The compound of the invention is dissolved in propylene glycol, polyethylene glycol 400 and polysorbate 80. A sufficient quantity of water is then added with stirring to provide 100 mL of the solution which is filtered and bottled.

| D. | Ingredients | % wt./wt. |
|---|---|---|
| | Compound of the invention | 20.0% |
| | Peanut Oil | 78.0% |
| | Span 60 | 2.0% |

The above ingredients are melted, mixed and filled into soft elastic capsules.

| E. | Ingredients | % wt./wt. |
|---|---|---|
| | Compound of the invention | 1.0% |
| | Methyl or carboxymethyl cellulose | 2.0% |
| | 0.9% saline | q.s. 100 mL |

The compound of the invention is dissolved in the cellulose/saline solution, filtered and bottled for use.

EXAMPLE 47

This example illustrates the preparation of a representative pharmaceutical formulation for parenteral administration containing a compound of the invention, or a pharmaceutically acceptable salt thereof, e.g., N-(5-chloropyridin-2-yl)-2-[((4-((N'-methyl-N'-ethylureido)methyl)-3-chlorothiophen-2-yl)carbonyl)amino]-3-methoxy-5-chlorobenzamide:

| Ingredients | |
|---|---|
| Compound of the invention | 0.02 g |
| Propylene glycol | 20.0 g |
| Polyethylene glycol 400 | 20.0 g |
| Polysorbate 80 | 1.0 g |
| 0.9% Saline solution | q.s. 100 mL |

The compound of the invention is dissolved in propylene glycol, polyethylene glycol 400 and polysorbate 80. A sufficient quantity of 0.9% saline solution is then added with stirring to provide 100 mL of the I.V. solution which is filtered through a 0.2 m membrane filter and packaged under sterile conditions.

EXAMPLE 48

This example illustrates the preparation of a representative pharmaceutical composition in suppository form containing a compound of the invention, or a pharmaceutically acceptable salt thereof, e.g., N-(4-chlorophenyl)-2-[((3-chlorobenzo[b]thien-2-yl)carbonyl)amino]-5-methylbenzamide:

| Ingredients | % wt./wt. |
|---|---|
| Compound of the invention | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 49

This example illustrates the preparation of a representative pharmaceutical formulation for insufflation containing a compound of the invention, or a pharmaceutically acceptable salt thereof, e.g., N-(5-chloropyridin-2-yl)-2-[((4-((N'-methyl-N'-(2-(pyrrolidin-1-yl)ethyl)amino)methyl)-3-chlorothiophen-2-yl)carbonyl)amino]-3-(2-acetoxyethoxy)-5-chlorobenzamide:

| Ingredients | % wt./wt. |
|---|---|
| Micronized compound of the invention | 1.0% |
| Micronized lactose | 99.0% |

The ingredients are milled, mixed, and packaged in an insufflator equipped with a dosing pump.

EXAMPLE 50

This example illustrates the preparation of a representative pharmaceutical formulation in nebulized form containing a compound of the invention, or a pharmaceutically acceptable salt thereof, e.g., N-(5-chloropyridin-2-yl)-2-[((4-((N'-methyl-N'-(dihydro-4(H)-1,3-oxazin-2-yl)amino)methyl)-3-chlorothiophen-2-yl)carbonyl)amino]-3-methoxy-5-chlorobenzamide:

| Ingredients | % wt./wt. |
|---|---|
| Compound of the invention | 0.005% |
| Water | 89.995% |
| Ethanol | 10.000% |

The compound of the invention is dissolved in ethanol and blended with water. The formulation is then packaged in a nebulizer equipped with a dosing pump.

EXAMPLE 51

This example illustrates the preparation of a representative pharmaceutical formulation in aerosol form containing a compound of the invention, or a pharmaceutically acceptable salt thereof, e.g., N-(4-chlorophenyl)-2-[((4-((N'-methyl-N'-(oxazolin-2-yl)amino)methyl)-3-chlorothiophen-2-yl)carbonyl)amino]-3-(morpholin-4-yl)-5-chlorobenzamide:

| Ingredients | % wt./wt. |
|---|---|
| Compound of the invention | 0.10% |
| Propellant 11/12 | 98.90% |
| Oleic acid | 1.00% |

The compound of the invention is dispersed in oleic acid and the propellants. The resulting mixture is then poured into an aerosol container fitted with a metering valve.

EXAMPLE 52

(In vitro assay for Factor Xa and Thrombin)

This assay demonstrates the activity of the compounds of the invention towards factor Xa, thrombin and tissue plasminogen activator. The activities were determined as an initial rate of cleavage of the peptide p-nitroanilide by the enzyme. The cleavage product, p-nitroaniline, absorbs at 405 nm with a molar extinction coefficient of 9920 $M^{-1}cm^{-1}$.

Reagents and Solutions:
Dimethyl sulfoxide (DMSO) (Baker analyzed grade).
Assay buffer:
  50 mM TrisHCl, 150 mM NaCl, 2.5 mM $CaCl_2$, and
  0.1% polyethylene glycol 6000, pH 7.5.
Enzymes (Enzyme Research Lab.):
  1. Human factor Xa stock solution: 0.281 mg/mL in assay buffer, stored at −80° C. (working solution (2X): 106 ng/mL or 2 nM in assay buffer, prepare prior to use).
  2. Human thrombin stock solution: Concentration as specified by the supplier, stored at −80° C. (working solution (2X): 1200 ng/mL or 32 nM in assay buffer, prepare prior to use).
  3. Human tissue plasminogen activator (tPA) (Two chains, Sigma or American Diagnostica Inc.) stock solution: Concentration as specified by the supplier, stored at −80° C. (working solution (2X): 1361 ng/mL or 20 nM in assay buffer, prepare prior to use).
Chromogenic substrates (Pharmacia Hepar Inc.):
  1. S2222 (FXa assay) stock solution: 6 mM in deionized $H_2O$, store at 4° C. (working solution (4X): 656 $\mu M$ in assay buffer).
  2. S2302 (Thrombin assay) stock solution: 10 mM in deionized $H_2O$, stored at 4° C. (working solution (4X): 1200 $\mu M$ in assay buffer).
  3. S2288 (tPA assay) stock solution: 10 mM in deionized $H_2O$, stored at 4° C. (working solution (4X): 1484 $\mu M$ in assay buffer for Sigma tPA, or 1120 $\mu M$ for American Diagnostica tPA).
Standard inhibitor compound stock solution:
  5 mM in DMSO, stored at −20° C.
Test compounds (compounds of the invention) stock solutions:
  10 mM in DMSO, stored at −20° C.
Assay procedure:

Assays were performed in 96-well microtiter plates in a total volume of 200 $\mu l$. Assay components were in final concentration of 50 mM TrisHCl, 150 mM NaCl, 2.5 mM $CaCl_2$, 0.1 % polyethylene glycol 6000, pH 7.5, in the absence or presence of the standard inhibitor or the test compounds and enzyme and substrate at following concentrations: (1) 1 nM factor Xa (0.1 nM or 0.2 nM factor Xa for compounds with $K_i$Xa in low picomolar range) and 164 $\mu M$ S2222; (2) 16 nM thrombin and 300 $\mu M$ S2302; and (3) 10 nM tPA and 371 $\mu M$ or 280 $\mu M$ S2288. Concentrations of the standard inhibitor compound in the assay were from 5 $\mu M$ to 0.021 $\mu M$ in 1 to 3 dilution. Concentration of the test compounds in the assay typically were from 10 $\mu M$ to 0.041 $\mu M$ in 1 to 3 dilution. For potent test compounds, the concentrations used in the factor Xa assay were further diluted 100 fold (100 nM to 0.41 nM) or 1000 fold (10 nM to 0.041 nM). All substrate concentrations used are equal to their Km values under the present assay conditions. Assays were performed at ambient temperature.

The first step in the assay was the preparation of 10 mM test compound stock solutions in DMSO (for potent test compounds, 10 mM stock solutions were further diluted to 0.1 or 0.01 mM for the factor Xa assay), followed by the preparation of test compound working solutions (4X) by a serial dilutions of 10 mM stock solutions with Biomek 1000 in 96 deep well plates as follows:

(a) Prepare a 40 $\mu M$ working solution by diluting the 10 mM stock 1 to 250 in assay buffer in 2 steps: 1 to 100, and 1 to 2.5.

(b) Make another five serial dilutions (1:3) of the 40 $\mu M$ solution (600 $\mu L$ for each concentration). A total of six diluted test compound solutions were used in the assay.

Standard inhibitor compound (5 mM stock) or DMSO (control) went through the same dilution steps as those described above for test compounds.

The next step in the assay was to dispense 50 $\mu L$ of the test compound working solutions (4X) (from 40 $\mu M$ to 0.164 $\mu M$) in duplicate to microtiter plates with Biomek. To this was added 100 $\mu L$ of enzyme working solution (2X) with Biomek. The resulting solutions were incubated at ambient temperature for 10 minutes.

To the solutions was added 50 $\mu L$ of substrate working solution (4X) with Biomek.

The enzyme kinetics were measured at 405 nm at 10 seconds intervals for five minutes in a THERMOmax plate reader at ambient temperature. When a lower concentration of factor Xa was needed in the factor Xa assay, the enzyme kinetics were measured for fifteen minutes (0.2 nM factor Xa) or thirty minutes (0.1 nM factor Xa) at ambient temperature.

Calculation of $K_i$ of the Test compounds

Enzyme initial rates were calculated as mOD/min based on the first two minutes readings. The $IC_{50}$ values were determined by fifting the data to the log-logit equation (linear) or the Morrison equation (non-linear) with an EXCEL spread-sheet. $K_i$ values were then obtained by dividing the $IC_{50}$ by 2. Routinely, $K_i$(factor Xa) values less than 3 nM were calculated from the Morrison equation.

Compounds of the invention, when tested in this assay, demonstrated the selective ability to inhibit human factor Xa and human thrombin.

EXAMPLE 53

(In vitro assay for Human Prothrombinase)

This assay demonstrates the ability of the compounds of the invention to inhibit prothrombinase. Prothrombinase (PTase) catalyzes the activation of prothrombin to yield fragment 1.2 plus thrombin with meizothrombin as the intermediate. This assay is an end point assay. Activity of the prothrombinase is measured by activity of thrombin (one of the reaction products) or by the amount of thrombin formed/time based on a thrombin standard curve ( nM vs mOD/min). For determination of $IC_{50}$ (PTase) of the compounds of the invention, PTase activity was expressed by thrombin activity (mOD/min).

Materials:

Enzymes:
1. Human factor Va (Haematologic Technologies Inc., Cat# HCVA-0110) working solution: 1.0 mg/mL in 50% glycerol, 2 mM $CaCl_2$, stored at $-20°$ C.
2. Human factor Xa (Enzyme Res. Lab. cat# HFXal011) working solution: 0.281 mg/mL in assay buffer (without BSA), stored at $-80°$ C.
3. Human prothrombin (Fll) (Enzyme Res. Lab., Cat# HP1002) working solution: Diluted Fll to 4.85 mg/mL in assay buffer (without BSA), stored at $-80°$ C.

Phospholipid (PCPS) vesicles
PCPS vesicles (80%PC, 20%PS) were prepared by modification of the method reported by Barenholz et al., *Biochemistry* (1977), Vol. 16, pp. 2806–2810.

Phosphatidyl serine (Avanti Polar Lipids, Inc., Cat#840032)
10 mg/mL in chloroform, purified from brain, stored $-20°$ C. under nitrogen or argon.

Phosphatidyl Choline (Avanti Polar Lipids, Inc., Cat# 850457)
50 mg/ml in chloroform, synthetic 16:0–18:1 Palmitoyl-Oleoyl, stored at $-20°$ C. under nitrogen or argon.

Spectrozyme-TH (American Diagnostica Inc., Cat# 238L, 50 μmoles, stored at ambient temperature) working solution: Dissolved 50 μmoles in 10 mL $dH_2O$.

BSA (Sigma Chem Co., Cat# A-7888, FractionV, RIA grade).

Assay buffer: 50 mM TrisHCl, pH 7.5,150 mM NaCl, 2.5 mM $CaCl_2$, 0.1% PEG 6000 (BDH), 0.05% BSA (Sigma, Fr.V, RIA grade).

For one plate assay, prepare the following working solutions:
1. Prothrombinase complex:
   (a) 100 μM PCPS (27.5 μL of PCPS stock (4.36 mM) diluted to final 1200 μL with assay buffer.
   (b) 25 nM Human factor Va: 5.08 μL of Va stock(1 mg/mL) was diluted to final 1200 μL with assay buffer.
   (c) 5 pM Human factor Xa: Dilute factor Xa stock (0.281 mg/mL) 1:1,220,000 with assay buffer. Prepare at least 1200 μL.

Combine equal volumes (1100 μL) of each component in the order of PCPS, Va and Xa. Use immediately or store in ice (bring to ambient temperature before use).

2. 6 μM Human prothrombin (Fll): dilute 124 μL of Fll stock (4.85 mg/mL) to final 1400 μL with assay buffer.
3. 20 mM EDTA/Assay buffer: 0.8 mL of 0.5 M EDTA (pH 8.5) plus 19.2 mL assay buffer.
4. 0.2 mM Spectrozyme-TH/EDTA buffer: 0.44 mL of SPTH stock (5 mM) plus 10.56 mL of 20 mM EDTA/ assay buffer.
5. Test compounds (compounds of the invention):
   Prepare a working solution (5X) from 10 mM stock (DMSO) and make a series of 1:3 dilution. Compounds were assayed at 6 concentrations in duplicate.

Assay conditions and procedure

Prothrombinase reaction was performed in final 50 μL of mixture containing PTase (20 μM PCPS, 5 nM hFVa, and 1 pM hFXa), 1.2 μM human factor ll and varied concentration of the test compounds (5 μM to 0.021 μM or lower concentration range). Reaction was started by addition of PTase and incubated for 6 minutes at ambient temperature. Reaction was stopped by addition of EDTA/buffer to final 10 mM. Activity of thrombin (product) was then measured in the presence of 0.1 mM of Spectrozyme-TH as substrate at 405 nm for 5 minutes (10 seconds intervals) at ambient temperature in a THEROmax microplate reader. Reactions were performed in 96-well microtiter plates.

In the first step of the assay, 10 μL of diluted test compound (5X) or buffer was added to the plates in duplicate. Then 10 μL of prothrombin (hFll) (5X) was added to each well. Next 30 μL PTase was added to each well, mix for about 30 seconds. The plates were then incubated at ambient temperature for 6 minutes.

In the next step, 50 μL of 20 mM EDTA (in assay buffer) was added to each well to stop the reaction. The resulting solutions were then mixed for about 10 seconds. Then 100 μL of 0.2 mM spectrozyme was added to each well. The thrombin reaction rate was then measured at 405 nm for 5 minutes at 10 seconds intervals in a Molecular Devices microplate reader.

Calculations

Thrombin reaction rate was expressed as mOD/min. using OD readings from the five minute reaction. $IC_{50}$ values were calculated with the log-logit curve fit program.

The compounds of the invention demonstrated the ability to inhibit pro-hrombinase when tested in this assay.

EXAMPLE 54

(In vivo assay)

The following assay demonstrates the ability of the compounds to act as anti-coagulants.

Male rats (250–330 g) were anesthetized with sodium pentobarbital (90 mg/kg, i.p.) and prepared for surgery. The left carotid artery was cannulated for the measurement of blood pressure as well as for taking blood samples to monitor clotting variables (prothrombin time (PT) and activated partial thromboplastin time (aPTT)). The tail vein was cannulated for the purpose of administering the test compounds (i.e., the compounds of the invention and standards) and the thromboplastin infusion. The abdomen was opened via a mid-line incision and the abdominal vena cava was isolated for 2–3 cm distal to the renal vein. All venous branches in this 2–3 cm segment of the abdominal vena cava were ligated. Following all surgery, the animals were allowed to stabilize prior to beginning the experiment. Test icompounds were administered as an intravenous bolus (t=0). Three minutes later (t=3), a 5-minute infusion of thromboplastin was begun. Two minutes into the infusion (t=5), the abdominal vena cava was ligated at both the proximal and distal ends. The vessel was left in place for 60 minutes, after which it was excised from the animal, slit open, the clot (if any) carefully removed, and weighed. Statistical analysis on the results was performed using a Wilcoxin-matched-pairs signed rank test.

The compounds of the invention, when tested in this assay, demonstrated the ability to inhibit the clotting of the blood.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:
1. A compound of formula (I):

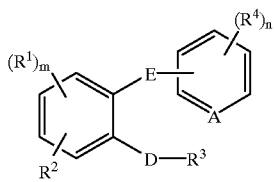

wherein:
A is =N—;
m is 1 to 3;
n is 1 to 4;
D is —N($R^5$)—C(Z)— or —N($R^5$)—S(O)$_p$— (where p is 0 to 2; Z is oxygen, sulfur or H$_2$; and the nitrogen atom is directly bonded to the phenyl ring having the $R^1$ and $R^2$ substituents);
E is —C(Z)—N($R^5$)— or —S(O)$_p$—N($R^5$)— (where p is 0 to 2; Z is oxygen, sulfur or H$_2$; and the nitrogen atom can be bonded to the phenyl ring having the $R^1$ and the $R^2$ substituents or to the aromatic ring having the $R^4$ substituent);
each $R^1$ is independently hydrogen, alkyl, aryl, aralkyl, halo, haloalkyl, cyano, —OR$^5$, —S(O)$_p$—R$^9$ (where p is 0 to 2), —C(O)OR$^5$, —C(O)N(R$^5$)R$^6$, —N(R$^5$)R$^6$, —O—C(O)R$^5$, or —N(R$^5$)—CH(R$^{12}$)—C(O)OR$^5$;
or two adjacent $R^1$'s together with the carbons to which they are attached form a heterocyclic ring fused to the phenyl ring wherein the heterocyclic ring is optionally substituted by one or more substituents selected from the group consisting of alkyl, aryl and aralkyl;
$R^2$ is hydrogen, alkyl, aryl, aralkyl, halo, haloalkyl, cyano, —OR$^5$, —S(O)$_p$—R$^9$ (where p is 0 to 2), —C(O)OR$^5$, —OC(O)—R$^5$, —C(O)N(R$^5$)R$^6$, —N(R$^{10}$)R$^{11}$, —C(R$^7$)H—N(R$^{10}$)R$^{11}$, —C(R$^7$)H—R$^8$—N(R$^{10}$)R$^{11}$, —C(R$^7$)H—OR$^5$, —C(R$^7$)H—R$^8$—OR$^5$, —C(R$^7$)H—S(O)$_p$—R$^9$ (where p is 0 to 2), —C(R$^7$)H—R$^8$—S(O)$_p$—R$^9$ (where p is 0 to 2), —O—R$^8$—S(O)$_p$—R$^9$ (where p is 0 to 2), —C(R$^7$)H—N(R$^5$)R$^6$, —C(R$^7$)H—R$^8$—N(R$^5$)R$^6$, —O—R$^8$—CH(OH)—CH$_2$—N(R$^{10}$)R$^{11}$, —O—R$^8$—N(R$^{10}$)R$^{11}$, —O—R$^8$—O—C(O)R$^5$, —O—R$^8$—CH(OH)—CH$_2$—OR$^5$, —O—(R$^8$—O)$_t$—R$^5$ (where t is 1 to 6), —O—(R$^8$—O)$_t$—R$^{19}$ (where t is 1 to 6), —O—R$^8$—C(O)R5, —O—R$^8$—C(O)R$^{19}$, —O—R$^8$—C(O)OR$^5$, —N(R$^5$)—R$^8$—N(R$^{10}$)R$^{11}$, —S(O)$_p$—R$^8$—N(R$^5$)R$^6$ (where p is 0 to 2), —S(O)$_p$—R$^8$—C(O)OR$^5$ (where p is 0 to 2), or —N(R$^5$)—CH(R$^{12}$)—C(O)OR$^5$;
$R^3$ is a radical of formula (i):

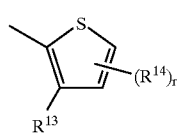

where:
r is 1 or 2;
$R^{13}$ is hydrogen, alkyl, halo, haloalkyl, —N(R$^5$)R$^6$, —C(R$^7$)H—N(R$^5$)R$^6$, O—R$^5$, —R$^8$—OR$^5$, —S(O)$_p$—R$^8$—N(R$^5$)R$^6$ (where p is 0 to 2) or heterocyclylalkyl (where the heterocyclic ring is optionally substituted by one or more substituents selected from the group consisting of alkyl, halo, aralkyl, nitro and cyano); and each $R^{14}$ is independently hydrogen, alkyl, halo, formyl, acetyl, cyano, —R$^8$—CN, —N(R$^{10}$)R$^{11}$, —C(R$^7$)H—N(R$^{10}$)R$^{11}$, —C(R$^7$)H—R$^8$—N(R$^{10}$)R$^{11}$, —C(R$^7$)H—N$^\oplus$(R$^9$)(R$^{16}$)$_2$, —C(R$^7$)H—R$^8$—N$^\oplus$(R$^9$)(R$^{16}$)$_2$, —C(O)OR$^5$, —C(R$^7$)H—C(O)OR$^5$, —C(R$^7$)H—R$^8$—C(O)OR$^5$, —OR$^5$, —C(R$^7$)H—OR$^5$, —C(R$^7$)H—R$^8$—OR$^5$, —C(R$^7$)H—O—R$^{15}$, —S(O)$_p$—R$^{15}$ (where p is 0 to 2), —C(R$^7$)H—S(O)$_p$—R$^{15}$ (where p is 0 to 2), —C(R$^7$)H—R$^8$—S(O)$_p$—R$^{15}$ (where p is 0 to 2), —S(O)$_p$—N(R$^5$)R$^6$ (where p is 0 to 2), —C(O)N(R$^5$)R$^6$, —C(R$^7$)H—C(O)N(R$^5$)R$^6$, —C(R$^7$)H—R$^8$—C(O)N(R$^5$)R$^6$, —C(R$^7$)H—N(R$^5$)—(R$^8$—O)$_t$—R$^5$ (where t is 1 to 6), —C(R$^7$)H—R$^8$—N(R$^5$)—(R$^8$—O)$_t$—R$^5$ (where t is 1 to 6), —C(R$^7$)H—O—(R$^8$—O)$_t$—R$^5$ (where t is 1 to 6), —C(R$^7$)H—R$^8$—O—(R$^8$—O)$_t$—R$^5$ (where t is 1 to 6), —O—R$^8$—CH(OH)—CH$_2$—OR$^5$, —C(R$^7$)H—O—R$^8$—CH(OH)—CH$_2$—OR$^5$, —C(R$^7$)H—N(R$^5$)—R$^8$—[CH(OH)]$_t$—CH$_2$—OR$^5$ (where t is 1 to 6), —C(R$^7$)H—N(R$^5$)—S(O)$_2$—N(R$^{10}$)R$^{11}$, —C(R$^7$)H—N(R$^{10}$)—C(NR$^{17}$)—N(R$^{10}$)R$^{11}$, —C(R$^7$)H—N(R$^{10}$)—C(N R$^{17}$)—R$^{10}$, —C(NR$^{17}$)—N(R$^5$)R$^6$, —C(R$^7$)H—C(NR$^{17}$)—N(R$^5$)R$^6$, —C(R$^7$)H—O—N(R$^5$)R$^6$, heterocyclyl (wherein the heterocyclyl radical is not attached to the radical of formula (i) through a nitrogen atom and is optionally substituted by alkyl, aryl, aralkyl, halo, haloalkyl, oxo, —OR$^5$, —C(O)OR$^5$, —N(R$^5$)R$^6$ or —C(O)N(R$^5$)R$^6$), or heterocyclylalkyl (wherein the heterocyclyl radical is not attached to the alkyl radical through a nitrogen atom and is optionally substituted by one or more substituents selected from the group consisting of alkyl, aryl, aralkyl, halo, haloalkyl, oxo, —OR$^5$, —C(O)OR$^5$, —N(R$^5$)R$^6$ and —C(O)N(R$^5$)R$^6$);
each $R^4$ is independently hydrogen, alkyl, halo, haloalkyl, cyano, nitro, —OR$^5$, —C(O)OR$^5$, —N(R$^5$)R$^6$, —C(O)N(R$^5$)R$^6$, or —R$^8$—N(R$^5$)R$^6$;
$R^5$ and $R^6$ are each independently hydrogen, alkyl, aryl or aralkyl;
each $R^7$ is independently hydrogen or alkyl;
each $R^8$ is independently a straight or branched alkylene, alkylidene or alkylidyne chain;
each $R^9$ is independently alkyl, aryl or aralkyl;
$R^{10}$ and $R^{11}$ are each independently hydrogen, alkyl, haloalkyl, aryl, aralkyl, formyl, cyano, —R$^8$—CN, —OR$^5$, —R$^8$—OR$^5$, —S(O)$_p$—R$^{15}$ (where p is 0 to 2), —R$^8$—S(O)p—R$^{15}$ (where p is 0 to 2), —N(R$^5$)R$^6$, —R$^8$—N(R$^5$)R$^6$, —R$^8$—C(O)OR$^5$, —C(O)—R$^{15}$, —C(O)NH$_2$, —R$^8$—C(O)NH$_2$, —C(S)NH$_2$, —C(O)—S—R$^5$, —C(O)—N(R$^5$)R$^{15}$, —R$^8$—C(O)—N(R$^5$)R$^{15}$, —C(S)—N(R$^5$)R$^{15}$, —R$^8$—N(R$^5$)—C(O)H, —R$^8$—N(R$^5$)—C(O)R$^{15}$, —C(O)O—R$^8$—N(R$^5$)R$^6$, —C(N(R$^5$)R$^6$)=C(R$^{18}$)R$^{10}$, —R$^8$—N(R$^5$)-P(O)(OR$^5$)$_2$, cycloalkyl (optionally substituted by one or more substituents selected from the group consisting of alkyl, halo and —OR$^5$), heterocyclyl (optionally substituted by one or more substituents selected from alkyl, aryl, aralkyl, halo, haloalkyl, oxo, —OR$^5$, —R$^8$—OR$^5$, —C(O)OR$^5$, —S(O)$_p$—R$^9$ (where p is 0 to 2), —R$^8$—S(O)$_p$—R$^9$ (where p is 0 to 2), —N(R$^5$)R$^6$ and —C(O)N(R$^5$)R$^6$), or heterocyclylalkyl (optionally substituted by one or more substituents selected from the group consisting of alkyl, aryl, aralkyl, halo, haloalkyl, oxo, —OR$^5$, —R$^8$—OR$^5$, —C(O)OR$^5$, —S(O)$_p$—R$^9$ (where p is 0 to 2), —R$^8$—S(O)$_p$—R$^9$ (where p is 0 to 2), —N(R$^5$)R$^6$ and —C(O)N(R$^5$)R$^6$);
or $R^{10}$ and $R^{11}$ together with the nitrogen to which they are attached form a N-heterocyclic ring containing zero to three additional hetero atoms, where the N-heterocyclic ring is optionally substituted by one or more substituents selected from the group consisting of alkyl, halo, haloalkyl, aryl, aralkyl, oxo, nitro, cyano, —$R^8$—CN, =N($R^{17}$), —$OR^5$, —C(O)$OR^5$, —$R^8$—C(O)$OR^5$, —N($R^5$)$R^6$, —$R^8$—N($R^5$)$R^6$, —C(O)N($R^5$)$R^6$, —$R^8$—C(O)N($R^5$)$R^6$, —N($R^5$)—N($R^5$)$R^6$, —C(O)$R^5$, —C(O)—($R^8$—O)$_t$—$R^5$ (where t is 1 to 6), —S(O)p—$R^9$ (where p is 0 to 2), —$R^8$—S(O)$_p$—$R^9$ (where p is 0 to 2), —($R^8$—O)$_t$—$R^5$ (where t is 1 to 6), and heterocyclyl (optionally substituted by one or more substituents selected from the group consisting of alkyl, aryl, aralkyl, halo, haloalkyl, —$OR^5$, —C(O)$OR^5$, —N($R^5$)$R^6$, and —C(O)N($R^5$)$R^6$);

$R^{12}$ is a side chain of an α-amino acid;

each $R^{15}$ is independently alkyl, cycloalkyl, haloalkyl, aryl, aralkyl, —$R^8$—O—C(O)—$R^5$, —$R^8$—$OR^5$, —N($R^5$)$R^6$, —$R^8$—N($R^5$)$R^6$, —$R^8$—C(O)$OR^5$, heterocyclyl (optionally substituted by one or more substituents selected from the group consisting of alkyl, aryl, aralkyl, halo, haloalkyl, —$OR^5$, —$R^8$—$OR^5$, —C(O)$OR^5$, —N($R^5$)$R^6$, and —C(O)N($R^5$)$R^6$), or heterocyclylalkyl (optionally substituted by one or more substituents selected from the group consisting of alkyl, aryl, aralkyl, halo, haloalkyl, —$OR^5$, —$R^8$—$OR^5$, —C(O)$OR^5$, —N($R^5$)$R^6$, and —C(O)N($R^5$)$R^6$);

or $R^5$ and $R^{15}$ together with the nitrogen to which they are attached form a N-heterocyclic ring containing zero to three additional hetero atoms, where the N-heterocyclic ring is optionally substituted by one or more substituents selected from the group consisting of alkyl, aryl, aralkyl, amino, monoalkylamino, dialkylamino, —$OR^5$, —C(O)$OR^5$, aminocarbonyl, monoalkylaminocarbonyl, and dialkylaminocarbonyl;

each $R^{16}$ is independently alkyl, aryl, aralkyl, —$R^8$—$OR^5$, —$R^8$—N($R^5$)$R^6$, cycloalkyl (optionally substituted by one or more substituents selected from the group consisting of alkyl, halo and —$OR^5$), heterocyclyl (optionally substituted by alkyl, aryl, aralkyl, halo, haloalkyl, —$OR^5$, —C(O)$OR^5$, —N($R^5$)$R^6$ or —C(O)N($R^5$)$R^6$), or heterocyclylalkyl (optionally substituted by one or more substituents selected from the group consisting of alkyl, aryl, aralkyl, halo, —$OR^5$, —C(O)$OR^5$, —N($R^5$)$R^6$ and —C(O)N($R^5$)$R^6$); or both $R^{16}$'s together with the nitrogen to which they are attached (and wherein the $R^9$ substituent is not present) form an aromatic N-heterocyclic ring containing zero to three additional hetero atoms, where the N-heterocyclic ring is optionally substituted by one or more substituents selected from the group consisting of alkyl, aryl, aralkyl, —$OR^5$, —C(O)$OR^5$, —$R^8$—C(O)$OR^5$, —N($R^5$)$R^6$, —$R^8$—N($R^5$)$R^6$, —C(O)$R^5$, —C(O)—($R^8$—O)$_t$—$R^5$ (where t is 1 to 6), and —($R^8$—O)$_t$—$R^5$ (where t is 1 to 6);

each $R^{17}$ is independently hydrogen, alkyl, aryl, aralkyl, cyano, —$OR^5$, —$R^8$—$OR^5$, —C(O)$OR^5$, —$R^8$—C(O)$OR^5$, —C(O)—N($R^5$)$R^6$, or —$R^8$—C(O)—N($R^5$)$R^6$;

$R^{18}$ is hydrogen, alkyl, aryl, aralkyl, cyano, —C(O)$OR^5$, or —$NO_2$; and each $R^{19}$ is cycloalkyl, haloalkyl, —$R^8$—$OR^5$, —$R^8$—N($R^5$)$R^6$, —$R^8$—C(O)$OR^5$, —$R^8$—C(O)N($R^5$)$R^6$, heterocyclyl (optionally substituted by alkyl, aryl, aralkyl, halo, haloalkyl, —$OR^5$, —C(O)$OR^5$, —N($R^5$)$R^6$ or —C(O)N($R^5$)$R^6$), or heterocyclylalkyl (optionally substituted by one or more substituents selected from the group consisting of alkyl, aryl, aralkyl, halo, haloalkyl, —$OR^5$, —C(O)$OR^5$, —N($R^5$)$R^6$ and —C(O)N($R^5$)$R^6$);

as a single stereoisomer or a mixture thereof; or a pharmaceutically acceptable salt thereof.

2. A pharmaceutical composition useful in treating a human having a disease-state characterized by thrombotic activity, which composition comprises a pharmaceutically acceptable excipient and a therapeutically effective amount of a compound of formula (I):

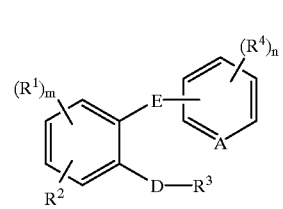

(I)

wherein:

A is =N—;

m is 1 to 3;

n is 1 to 4;

D is —N($R^5$)—C(Z)— or —N($R^5$)—S(O)$_p$—(where p is 0 to 2; Z is oxygen, sulfur or $H_2$; and the nitrogen atom is directly bonded to the phenyl ring having the $R^1$ and $R^2$ substituents);

E is —C(Z)—N($R^5$)— or —S(O)$_p$—N($R^5$)—(where p is 0 to 2; Z is oxygen, sulfur or $H_2$; and the nitrogen atom can be bonded to the phenyl ring having the $R^1$ and the $R^2$ substituents or to the aromatic ring having the $R^4$ substituent);

each $R^1$ is independently hydrogen, alkyl, aryl, aralkyl, halo, haloalkyl, cyano, —$OR^5$, —S(O)$_p$—$R^9$ (where p is 0 to 2), —C(O)$OR^5$, —C(O)N($R^5$)$R^6$, —N($R^5$)$R^6$, —O—C(O)$R^5$, or —N($R^5$)—CH($R^{12}$)—C(O)$OR^5$;

or two adjacent $R^1$'s together with the carbons to which they are attached form a heterocyclic ring fused to the phenyl ring wherein the heterocyclic ring is optionally substituted by one or more substituents selected from the group consisting of alkyl, aryl and aralkyl;

$R^2$ is hydrogen, alkyl, aryl, aralkyl, halo, haloalkyl, cyano, —$OR^5$, —S(O)$_p$—$R^9$ (where p is 0 to 2), —C(O)$OR^5$, —OC(O)—$R^5$, —C(O)N($R^5$)$R^6$, —N($R^{10}$)$R^{11}$, —C($R^7$)H—N($R^{10}$)$R^{11}$, —C($R^7$)H—$R^8$—N($R^{10}$)$R^{11}$, —C($R^7$)H—$OR^5$, —C($R^7$)H—$R^8$—$OR^5$, —C($R^7$)H—S(O)$_p$—$R^9$ (where p is 0 to 2), —C($R^7$)H—$R^8$—S(O)$_p$—$R^9$ (where p is 0 to 2), —O—$R^8$—S(O)$_p$—$R^9$ (where p is 0 to 2), —C($R^7$)H—N($R^5$)$R^6$, —C($R^7$)H—$R^8$—N($R^5$)$R^6$, —O—$R^8$—CH(OH)—$CH_2$—N($R^{10}$)$R^{11}$, —O—$R^8$—N($R^{10}$)$R^{11}$, —O—$R^8$—O—C(O)$R^5$, —O—$R^8$—CH(OH)—$CH_2$—$OR^5$, —O—($R^8$—O)$_t$—$R^5$ (where t is 1 to 6), —O—($R^8$—O)$_t$—$R^{19}$ (where t is 1 to 6), —O—$R^8$—C(O)$R^5$, —O—$R^8$—C(O)$R^{19}$, —O—$R^8$—C(O)$OR^5$, —N($R^5$)—$R^8$—N($R^{10}$)$R^{11}$, —S(O)$_p$—$R^8$—N($R^5$)$R^6$ (where p is 0 to 2), —S(O)p—$R^8$—C(O)$OR^5$ (where p is 0 to 2), or —N($R^5$)—CH($R^{12}$)—C(O)$OR^5$;

$R^3$ is a radical of formula (i):

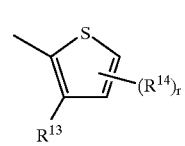

(i)

where:

r is 1 or 2;

$R^{13}$ is hydrogen, alkyl, halo, haloalkyl, —N($R^5$)$R^6$, —C($R^7$)H—N($R^5$)$R^6$, —$OR^5$, —$R^8$—$OR^5$, —S(O)$_p$—

$R^8$—$N(R^5)R^6$ (where p is 0 to 2) or heterocyclylalkyl (where the heterocyclic ring is optionally substituted by one or more substituents selected from the group consisting of alkyl, halo, aralkyl, nitro and cyano); and each $R^{14}$ is independently hydrogen, alkyl, halo, formyl, acetyl, cyano, —$R^8$—CN, —$N(R^{10})R^{11}$, —$C(R^7)H$—$N(R^{10})R^{11}$, —$C(R^7)H$—$R^8$—$N(R^{10})R^{11}$, —$C(R7)H$—$N^\oplus(R^9)(R^{16})_2$, —$C(R^7)H$—$R^8$—$N^\oplus(R^9)(R^{16})_2$, —$C(O)OR^5$, —$C(R^7)H$—$C(O)OR^5$, —$C(R^7)H$—$R^8$—$C(O)OR^5$, —$OR^5$, —$C(R^7)H$—$OR^5$, —$C(R^7)H$—$R^8$—$OR^5$, —$C(R^7)H$—$O$—$R^{15}$, —$S(O)_p$—$R^{15}$ (where p is 0 to 2), —$C(R^7)H$—$S(O)_p$—$R^{15}$ (where p is 0 to 2), —$C(R^7)H$—$R^8$—$S(O)_p$—$R^{15}$ (where p is 0 to 2), —$S(O)_p$—$N(R^5)R^6$ (where p is 0 to 2), —$C(O)N(R^5)R^6$, —$C(R^7)H$—$C(O)N(R^5)R^6$, —$C(R^7)H$—$R^8$—$C(O)N(R^5)R^6$, —$C(R^7)H$—$N(R^5)$—$(R^8$—$O)_t$—$R^5$ (where t is 1 to 6), —$C(R^7)H$—$R^8$—$N(R^5)$—$(R^8$—$O)_t$—$R^5$ (where t is 1 to 6), —$C(R^7)H$—$O$—$(R^8$—$O)_t$—$R^5$ (where t is 1 to 6), —$C(R^7)H$—$R^8$—$O$—$(R^8$—$O)_t$—$R^5$ (where t is 1 to 6), —$O$—$R^8$—CH(OH)—$CH_2$—$OR^5$, —$C(R^7)H$—$O$—$R^8$—CH(OH)—$CH_2$—$OR^5$, —$C(R^7)H$—$N(R^5)$—$R^8$-[CH(OH)]$_t$—$CH_2$—$OR^5$ (where t is 1 to 6), —$C(R^7)H$—$N(R^5)$—$S(O)_2$—$N(R^{10})R^{11}$, —$C(R^7)H$—$N(R^{10})$—$C(NR^{17})$—$N(R^{10})R^{11}$, —$C(R^7)H$—$N(R^{10})$—$C(NR^{17})$—$R^{10}$, —$C(NR^{17})$—$N(R^5)R^6$, —$C(R^7)H$—$C(NR^{17})$—$N(R^5)R^6$, —$C(R^7)H$—$O$—$N(R^5)R^6$, heterocyclyl (wherein the heterocyclyl radical is not attached to the radical of formula (i) through a nitrogen atom and is optionally substituted by alkyl, aryl, aralkyl, halo, haloalkyl, oxo, —$OR^5$, —$C(O)OR^5$, —$N(R^5)R^6$ or —$C(O)N(R^5)R^6$), or heterocyclylalkyl (wherein the heterocyclyl radical is not attached to the alkyl radical through a nitrogen atom and is optionally substituted by one or more substituents selected from the group consisting of alkyl, aryl, aralkyl, halo, haloalkyl, oxo, —$OR^5$, —$C(O)OR^5$, —$N(R^5)R^6$ and —$C(O)N(R^5)R^6$);

each $R^4$ is independently hydrogen, alkyl, halo, haloalkyl, cyano, nitro, —$OR^5$, —$C(O)OR^5$, —$N(R^5)R^6$, —$C(O)N(R^5)R^6$, or —$R^8$—$N(R^5)R^6$;

$R^5$ and $R^6$ are each independently hydrogen, alkyl, aryl or aralkyl;

each $R^7$ is independently hydrogen or alkyl;

each $R^8$ is independently a straight or branched alkylene, alkylidene or alkylidyne chain;

each $R^9$ is independently alkyl, aryl or aralkyl;

$R^{10}$ and $R^{11}$ are each independently hydrogen, alkyl, haloalkyl, aryl, aralkyl, formyl, cyano, —$R^8$—CN, —$OR^5$, —$R^8$—$OR^5$, —$S(O)_p$—$R^{15}$ (where p is 0 to 2), —$R^8$—$S(O)_p$—$R^{15}$ (where p is 0 to 2), —$N(R^5)R^6$, —$R^8$—$N(R^5)R$, —$R^8$—$C(O)OR^5$, —$C(O)$—$R^{15}$, —$C(O)NH_2$, —$R^8$—$C(O)NH_2$, —$C(S)NH_2$, —$C(O$—$S$—$R^5$, —$C(O)$—$N(R^5)R^{15}$, —$R^8$—$C(O)$—$N(R^5)R^{15}$, —$C(S)$—$N(R^5)R^{15}$, —$R^8$—$N(R^5)$—$C(O)H$, —$R^8$—$N(R^5)$—$C(O)R^{15}$, —$C(O)O$—$R^8$—$N(R^5)R^6$, —$C(N(R^5)R^6)=C(R^{18})R^{10}$, —$R^8$—$N(R^5)$-$P(O)(OR^5)_2$, cycloalkyl (optionally substituted by one or more substituents selected from the group consisting of alkyl, halo and —$OR^5$), heterocyclyl (optionally substituted by one or more substituents selected from the group consisting of alkyl, aryl, aralkyl, halo, haloalkyl, oxo, —$OR^5$, —$R^8$—$OR^5$, —$C(O)OR^5$, —$S(O)_p$—$R^9$ (where p is 0 to 2), —$R^8$—$S(O)_p$—$R^9$ (where p is 0 to 2), —$N(R^5)R^6$ or —$C(O)N(R^5)R^6$), or heterocyclylalkyl (optionally substituted by one or more substituents selected from the group consisting of alkyl, aryl, aralkyl, halo, haloalkyl, oxo, —$OR^5$, —$R^8$—$OR^5$, —$C(O)OR^5$, —$S(O)_p$—$R^9$ (where p is 0 to 2), —$R^8$—$S(O)_p$—$R^9$ (where p is 0 to 2), —$N(R^5)R^6$ and —$C(O)N(R^5)R^6$);

or $R^{10}$ and $R^{11}$ together with the nitrogen to which they are attached form a N-heterocyclic ring containing zero to three additional hetero atoms, where the N-heterocyclic ring is optionally substituted by one or more substituents selected from the group consisting of alkyl, halo, haloalkyl, aryl, aralkyl, oxo, nitro, cyano, —$R^8$—CN, =$N(R^{17})$, —$OR^5$, —$C(O)OR^5$, —$R^8$—$C(O)OR^5$, —$N(R^5)R^6$, —$R^8$—$N(R^5)R^6$, —$C(O)N(R^5)R^6$, —$R^8$—$C(O)N(R^5)R^6$, —$N(R^5)$—$N(R^5)R^6$, —$C(O)R^5$, —$C(O)$—$(R^8$—$O)_t$—$R^5$ (where t is 1 to 6), —$S(O)_p$—$R^9$ (where p is 0 to 2), —$R^8$—$S(O)_p$—$R^9$ (where p is 0 to 2), —$(R^8$—$O)_t$—$R^5$ (where t is 1 to 6), and heterocyclyl (optionally substituted by one or more substituents selected from the group consisting of alkyl, aryl, aralkyl, halo, haloalkyl, —$OR^5$, —$C(O)OR^5$, —$N(R^5)R^6$, and —$C(O)N(R^5)R^6$);

$R^{12}$ is a side chain of an α-amino acid;

each $R^{15}$ is independently alkyl, cycloalkyl, haloalkyl, aryl, aralkyl, —$R^8$—$O$—$C(O)$—$R^5$, —$R^8$—$OR^5$, —$N(R^5)R^6$, —$R^8$—$N(R^5)R^6$, —$R^8$—$C(O)OR^5$, heterocyclyl (optionally substituted by one or more substituents selected from the group consisting of alkyl, aryl, aralkyl, halo, haloalkyl, —$OR^5$, —$R^8$—$OR^5$, —$C(O)OR^5$, —$N(R^5)R^6$, and —$C(O)N(R^5)R^6$), or heterocyclylalkyl (optionally substituted by one or more substituents selected from the group consisting of alkyl, aryl, aralkyl, halo, haloalkyl, —$OR^5$, —$R^8$—$OR^5$, —$C(O)OR^5$, —$N(R^5)R^6$, and —$C(O)N(R^5)R^6$);

or $R^5$ and $R^{15}$ together with the nitrogen to which they are attached form a N-heterocyclic ring containing zero to three additional hetero atoms, where the N-heterocyclic ring is optionally substituted by one or more substituents selected from the group consisting of alkyl, aryl, aralkyl, amino, monoalkylamino, dialkylamino, —$OR^5$, —$C(O)OR^5$, aminocarbonyl, monoalkylaminocarbonyl, and dialkylaminocarbonyl;

each $R^{16}$ is independently alkyl, aryl, aralkyl, —$R^8$—$OR^5$, —$R^8$—$N(R^5)R^6$, cycloalkyl (optionally substituted by one or more substituents selected from the group consisting of alkyl, halo and —$OR^5$), heterocyclyl (optionally substituted by alkyl, aryl, aralkyl, halo, haloalkyl, —$OR^5$, —$C(O)OR^5$, —$N(R^5)R^6$ or —$C(O)N(R^5)R^6$), or heterocyclylalkyl (optionally substituted by one or more substituents selected from the group consisting of alkyl, aryl, aralkyl, halo, haloalkyl, —$OR^5$, —$C(O)OR^5$, —$N(R^5)R^6$ and —$C(O)N(R^5)R^6$); or both $R^{16}$'s together with the nitrogen to which they are attached (and wherein the $R^9$ substituent is not present) form an aromatic N-heterocyclic ring containing zero to three additional hetero atoms, where the N-heterocyclic ring is optionally substituted by one or more substituents selected from the group consisting of alkyl, aryl, aralkyl, —$OR^5$, —$C(O)OR^5$, $R^8$—$C(O)OR^5$, —$N(R^5)R^6$, —$R^8$—$N(R^5)R^6$, —$C(O)R^5$, —$C(O)$—$(R^8$—$O)_t$—$R^5$ (where t is 1 to 6), and —$(R^8$—$O)_t$—$R^5$ (where t is 1 to 6);

each $R^{17}$ is independently hydrogen, alkyl, aryl, aralkyl, cyano, —$OR^5$, —$R^8$—$OR^5$, —$C(O)OR^5$, —$R^8$—$C(O)OR^5$, —$C(O)$—$N(R^5)R^6$, or —$R^8$—$C(O)$—$N(R^5)R^6$;

$R^{18}$ is hydrogen, alkyl, aryl, aralkyl, cyano, —$C(O)OR^5$, or —$NO_2$; and each $R^{19}$ is cycloalkyl, haloalkyl, —$R^8$—$OR^5$, —$R^8$—$N(R^5)R^6$, —$R^8$—$C(O)OR^5$, —$R^8$—$C(O)N(R^5)R^6$, heterocyclyl (optionally substituted by alkyl, aryl, aralkyl, halo, haloalkyl, —$OR^5$, —$C(O)OR^5$, —$N(R^5)R^6$ or —$C(O)N(R^5)R^6$), or heterocyclylalkyl (optionally substituted by one or more substituents selected from the group consisting of alkyl, aryl, aralkyl, halo, haloalkyl, —$OR^5$, —$C(O)OR^5$, —$N(R^5)R^6$ and —$C(O)N(R^5)R^6$);

3. The compound of claim 1 wherein:
A is =N—;
m is 1 to 3;
n is 1 to 4;
D is —N(R$^5$)—C(Z)— (where Z is oxygen, sulfur or H$_2$, and R$^5$ is hydrogen or alkyl);
E is —C(Z)—N(R$^5$)— (where Z is oxygen, sulfur or H$_2$, R$^5$ is hydrogen or alkyl, and the nitrogen is attached to the pyridinyl ring);
R$^1$ is halo or haloalkyl;
R$^2$ is —N(R$^{10}$)R$^{11}$, —O—R$^8$—S(O)p—R$^9$ (where p is 0), —O—R$^8$—C(O)OR$^5$, —O—(R$^8$—O)$_t$—R$^5$ (where t is 1) or —O—R$^8$—N(R$^{10}$)R$^{11}$ where:
  each R$^5$ is independently hydrogen or alkyl;
  each R$^8$ is independently a straight or branched alkylene chain;
  R$^9$ is alkyl; and
  R$^{10}$ and R$^{11}$ are each independently hydrogen, alkyl, or —R$^8$—O—R$^5$ (where R$^8$ is a straight or branched alkylene chain and R$^5$ is hydrogen or alkyl);
  or R$^{10}$ and R$^{11}$ together with the nitrogen to which they are attached form a N-heterocyclic ring containing zero to one additional hetero atoms, where the N-heterocyclic ring is optionally substituted by alkyl;
R$^3$ is a radical of the formula (i):

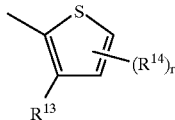

(i)

where r is 1;
R$^{13}$ is halo; and
R$^{14}$ is —C(R$^7$)H—N(R$^{10}$)R$^{11}$ where:
  R$^7$ is hydrogen; and
  R$^{10}$ and R$^{11}$ together with the nitrogen to which they are attached form piperazinyl optionally substituted by one or more substituents selected from the group consisting of alkyl and —C(O)R$^5$; and
R$^4$ is hydrogen or halo.

4. The compound of claim 3 wherein:
m is 1;
n is 1;
D is —N(H)—C(O)—;
E is —C(O)—N(H)— (where the nitrogen is bonded to the 2-position of the pyridinyl ring);
R$^1$ is halo in the 5-position;
R$^2$ is —N(R$^{10}$)R$^{11}$, —O—R$^8$—S(O)$_p$—R$^9$ (where p is 0), —O—R$^8$—C(O)OR$^5$, —O—(R$^8$—O)$_t$—R$^5$ (where t is 1) or —O—R$^8$—N(R$^{10}$)R$^{11}$ where:
  each R$^5$ is independently hydrogen, methyl or ethyl;
  each R$^8$ is independently a methylene, ethylene or propylene chain;
  R$^9$ is methyl or ethyl; and
  R$^{10}$ and R$^{11}$ are each independently hydrogen, methyl, ethyl, or —R$^8$—O—R$^5$ (where R$^8$ is ethylene and R$^5$ is hydrogen, methyl or ethyl); or
  R$^{10}$ and R$^{11}$ together with the nitrogen to which they are attached form a N-heterocyclic ring containing zero to one additional hetero atoms, where the N-heterocyclic ring is optionally substituted by alkyl;

R$^3$ is a radical of the formula (i):

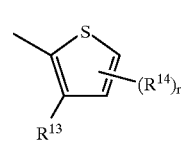

(i)

where r is 1;
R$^{13}$ is chloro; and
R$^{14}$ is in the 4-position and is —C(R$^7$)H—N(R$^{10}$)R$^{11}$ where:
  R$^7$ is hydrogen; and
  R$^{10}$ and R$^{11}$ together with the nitrogen to which they are attached form piperazinyl optionally substituted by methyl or ethyl; and
R$^4$ is hydrogen, bromo or chloro in the 5-position.

5. The compound of claim 4 wherein:
R$^1$ is chloro;
R$^2$ is —O—R$^8$—S(O)$_p$—R$^9$ (where p is 0), —O—R$^8$—C(O)OR$^5$ or —O—(R$^8$—O)$_t$—R$^5$ (where t is 1 or 2) where:
  each R$^5$ is independently hydrogen, methyl or ethyl;
  each R$^8$ is independently a methylene, ethylene or propylene chain; and
  R$^9$ is methyl or ethyl.

6. The compound of claim 5 which is selected from the group consisting of:
N-(5-chloropyridin-2-yl)-2-[((4-((4-methylpiperazin-1-yl)methyl)-3-chlorothiophen-2-yl)carbonyl)amino]-3-(methylthio)methoxy-5-chlorobenzamide;
N-(5-chloropyridin-2-yl)-2-[((4-((4-methylpiperazin-1-yl)methyl)-3-chlorothiophen-2-yl)carbonyl)amino]-3-(ethoxycarbonyl)methoxy-5-chlorobenzamide;
N-(5-chloropyridin-2-yl)-2-[((4-((4-methylpiperazin-1-yl)methyl)-3-chlorothiophen-2-yl)carbonyl)amino]-3-(2-hydroxyethoxy)-5-chlorobenzamide;
N-(5-chloropyridin-2-yl)-2-[((4-((4-methylpiperazin-1-yl)methyl)-3-chlorothiophen-2-yl)carbonyl)amino]-3-(2-methoxyethoxy)-5-chlorobenzamide; and
N-(5-chloropyridin-2-yl)-2-[((4-((4-methylpiperazin-1-yl)methyl)-3-chlorothiophen-2-yl)carbonyl)amino]-3-(2-ethoxyethoxy)-5-chlorobenzamide;
N-(5-chloropyridin-2-yl)-2-[((4-((4-ethylpiperazin-1-yl)methyl)-3-chlorothiophen-2-yl)carbonyl)amino]-3-(2-methoxyethoxy)-5-chlorobenzamide, and
N-(5-chloropyridin-2-yl)-2-[((4-((4-ethylpiperazin-1-yl)methyl)-3-chlorothiophen-2-yl)carbonyl)amino]-3-(2-(2-methoxyethoxy)ethoxy)-5-chlorobenzamide.

7. The compound of claim 4 wherein
R$^1$ is chloro; and
R$^2$ is —N(R$^{10}$)R$^{11}$ or —O—R$^8$—N(R$^{10}$)R$^{11}$ where:
  R$^8$ is a methylene, ethylene or propylene chain; and
  R$^{10}$ and R$^{11}$ are each independently hydrogen, methyl, ethyl, or —R$^8$—O—R$^5$ (where R$^8$ is ethylene and R$^5$ is hydrogen, methyl or ethyl).

8. The compound of claim 7 which is selected from the group consisting of:
N-(5-chloropyridin-2-yl)-2-[((4-((4-methylpiperazin-1-yl)methyl)-3-chlorothiophen-2-yl)carbonyl)amino]-3-(dimethyl)amino-5-chlorobenzamide;
N-(5-chloropyridin-2-yl)-2-[((4-((4-methylpiperazin-1-yl)methyl)-3-chlorothiophen-2-yl)carbonyl)amino]-3-(3-(N'-methyl-N'-(2-hydroxyethyl)amino)propoxy)-5-chlorobenzamide; and N-(5-chloropyridin-2-yl)-2-[((4-((4-methylpiperazin-1-yl)methyl)-3-chlorothiophen-2-yl)carbonyl)amino]-3-amino-5-chlorobenzamide.

9. The compound of claim 4 wherein
$R^1$ is chloro;
$R^2$ is $—N(R^{10})R^{11}$ or $—O—R^8—N(R^{10})R^{11}$ where:
   $R^8$ is methylene, ethylene or propylene; and
   $R^{10}$ and $R^{11}$ together with the nitrogen to which they are attached form a N-heterocyclic ring containing zero to one additional hetero atoms, where the N-heterocyclic ring is optionally substituted by alkyl and is selected from the group consisting of morpholinyl, piperazinyl, pyrrolidinyl or imidazolyl.

10. The compound of claim 9 selected from the group consisting of:
N-(5-chloropyridin-2-yl)-2-[((4-((4-methylpiperazin-1-yl)methyl)-3-chlorothiophen-2-yl)carbonyl)amino]-3-(morpholin-4-yl)-5-chlorobenzamide;
N-(5-chloropyridin-2-yl)-2-[((4-((4-methylpiperazin-1-yl)methyl)-3-chlorothiophen-2-yl)carbonyl)amino]-3-(4-methylpiperazin-1-yl)-5-chlorobenzamide;
N-(5-chloropyridin-2-yl)-2-[((4-((4-methylpiperazin-1-yl)methyl)-3-chlorothiophen-2-yl)carbonyl)amino]-3-(3-morpholinylpropoxy)-5-chlorobenzamide;
N-(5-chloropyridin-2-yl)-2-[((4-((4-methylpiperazin-1-yl)methyl)-3-chlorothiophen-2-yl)carbonyl)amino]-3-(3-(pyrrolidin-1-yl)propoxy)-5-chlorobenzamide;
N-(5-chloropyridin-2-yl)-2-[((4-((4-methylpiperazin-1-yl)methyl)-3-chlorothiophen-2-yl)carbonyl)amino]-3-(pyrrolidin-1-yl)-5-chlorobenzamide;
N-(5-chloropyridin-2-yl)-2-[((4-((4-methylpiperazin-1-yl)methyl)-3-chlorothiophen-2-yl)carbonyl)amino]-3-(3-(imidazol-1-yl)propoxy)-5-chlorobenzamide; and
N-(5-chloropyridin-2-yl)-2-[((4-((4-ethylpiperazin-1-yl)methyl)-3-chlorothiophen-2-yl)carbonyl)amino]-3-(morpholin-4-yl)-5-chlorobenzamide.

11. The compound of claim 1 wherein:
A is =N—;
m is 1 to 3;
n is 1 to 4;
D is $—N(R^5)—C(Z)—$ (where Z is oxygen, sulfur or $H_2$, and $R^5$ is hydrogen or alkyl);
E is $—C(Z)—N(R^5)—$ (where Z is oxygen, sulfur or $H_2$, $R^5$ is hydrogen or alkyl, and the nitrogen is attached to the pyridinyl ring);
$R^1$ is halo or haloalkyl;
$R^2$ is hydrogen, haloalkyl, or $—OR^5$ where $R^5$ is hydrogen or alkyl;
$R^3$ is a radical of the formula (i):

(i)

where r is 1;
$R^{13}$ is halo; and
each $R^{14}$ is independently hydrogen, alkyl, halo, formyl, acetyl, cyano, $—R^8—CN$, $—N(R^{10})R^{11}$, $—C(R^7)H—N(R^{10})R^{11}$, $—C(R^7)H—R^8—N(R^{10})R^{11}$, $—C(R^7)H—N^{\oplus}(R^9)(R^{16})_2$, $—C(R^7)H—R^8—N^{\oplus}(R^9)(R^{16})_2$, $—C(O)OR^5$, $—C(R^7)H—C(O)OR^5$, $—C(R^7)H—R^8—C(O)OR^5$, $—OR^5$, $—C(R^7)H—OR^5$, $—C(R^7)H—R^8—OR^5$, $—C(R^7)H—O—R^{15}$, $—S(O)_p—R^{15}$ (where p is 0 to 2), $—C(R^7)H—S(O)_p—R^{15}$ (where p is 0 to 2), $—C(R^7)H—R^8—S(O)_p—R^{15}$ (where p is 0 to 2), $—S(O)_p—N(R^5)R^6$ (where p is 0 to 2), $-C(O)N(R^5)R^6$, $—C(R^7)H—C(O)N(R^5)R^6$, $—C(R^7)H—R^8—C(O)N(R^5)R^6$, $—C(R^7)H—N(R^5)—(R^8-O)_t—R^5$ (where t is 1 to 6), $—C(R^7)H—R—N(R^5)-(R^8—O)_t—R^5$ (where t is 1 to 6), $—C(R^7)H—O—(R^8—O)_t—R^5$ (where t is 1 to 6), $—C(R^7)H—R^8—O—(R^8—O)_t—R^5$ (where t is 1 to 6), $—O—R^8—CH(OH)—CH_2—OR^5$, $—C(R^7)H—O—R^8—CH(OH)—CH_2—OR^5$, $—C(R^7)H—N(R^5)—R^8—[CH(OH)]_t—CH_2—OR^5$ (where t is 1 to 6), $—C(R^7)H—N(R^5)—S(O)_2—N(R^{10})R^{11}$, $—C(R^7)H—N(R^{10})—C(NR^{17})—N(R^{16})R^{11}$, $—C(R^7)H—N(R^{10})—C(NR^{17})—R^{10}$, $—C(NR^{17})—N(R^5)R^6$, $—C(R^7)H—C(NR^{17})—N(R^5)R^6$, $—C(R^7)H—O—N(R^5)R^6$, heterocyclyl (wherein the heterocyclyl radical is not attached to the radical of formula (i) through a nitrogen atom and is optionally substituted by alkyl, aryl, aralkyl, halo, haloalkyl, oxo, $—OR^5$, $—C(O)OR^5$, $—N(R^5)R^6$ or $—C(O)N(R^5)R^6$), or heterocyclylalkyl (wherein the heterocyclyl radical is not attached to the alkyl radical through a nitrogen atom and is optionally substituted by one or more substituents selected from the group consisting of alkyl, aryl, aralkyl, halo, haloalkyl, oxo, $—OR^5$, $—C(O)OR^5$, $—N(R^5)R^6$ and $—C(O)N(R^5)R^6$); where $R^5$ and $R^6$ are each independently hydrogen, alkyl, aryl or aralkyl;
each $R^7$ is independently hydrogen or alkyl;
each $R^8$ is independently a straight or branched alkylene, alkylidene or alkylidyne chain;
each $R^9$ is independently alkyl, aryl or aralkyl;
$R^{10}$ and $R^{11}$ are each independently hydrogen, alkyl, haloalkyl, aryl, aralkyl, formyl, cyano, $—R^8—CN$, $—OR^5$, $—R^8—OR^5$, $—S(O)_p—R^{15}$ (where p is 0 to 2), $—R^8—S(O)_p—R^{15}$ (where p is 0 to 2), $—N(R)R^6$, $—R^8—N(R^5)R^6$, $—R^8—C(O)OR^5$, $—C(O)—R^{15}$, $—C(O)NH_2$, $—R^8—C(O)NH_2$, $—C(S)NH_2$, $—C(O)—S—R^5$, $—C(O)—N(R^5)R^{15}$, $R^8—C(O)—N(R^5)R^{15}$, $—C(S)—N(R^5)R^{15}$, $—R^8—N(R^5)—C(O)H$, $—R^8—N(R^5)—C(O)R_{15}$, $—C(O)O—R—N(R^8)R^6$, $—C(N(R^5)R^6)=C(R^{18})R^{10}$, $—R^8—N(R^5)-P(O)(OR^5)_2$, cycloalkyl (optionally substituted by one or more substituents selected from the group consisting of alkyl, halo and $—OR^5$), heterocyclyl (optionally substituted by alkyl, aryl, aralkyl, halo, haloalkyl, oxo, $—OR^5$, $—R^8—OR^5$, $—C(O)OR^5$, $—S(O)p—R^9$ (where p is 0 to 2), $—R^8—S(O)_p—R^9$ (where p is 0 to 2), $—N(R^5)R^6$ or $—C(O)N(R^5)R^6$), or heterocyclylalkyl (optionally substituted by one or more substituents selected from the group consisting of alkyl, aryl, aralkyl, halo, haloalkyl, oxo, $—OR^5$, $—R^8—OR^5$, $—C(O)OR^5$, $—S(O)_p—R^9$ (where p is 0 to 2), $—R^8—S(O)p—R^9$ (where p is 0 to 2), $—N(R^5)R^6$ and $—C(O)N(R^5)R^6$), where
$R^5$ and $R^6$ are each independently hydrogen, alkyl, aryl or aralkyl;
each $R^8$ is independently a straight or branched alkylene, alkylidene or alkylidyne chain;
each $R^9$ is independently alkyl, aryl or aralkyl;
each $R^{15}$ is independently alkyl, cycloalkyl, haloalkyl, aryl, aralkyl,
   $—R^8—O—C(O)—R^5$, $—R^8—OR^5$, $—N(R^5)R^6$, $—R^8—N(R^5)R^6$,
   $—R^8—C(O)OR^5$, heterocyclyl (optionally substituted by one or more substituents selected from the group consisting of alkyl, aryl, aralkyl, halo, haloalkyl, $—OR^5$, $—R^8—OR^5$, $—C(O)OR^5$, —N($R^5$)$R^6$, and —C(O)N($R^5$)$R^6$), or heterocyclylalkyl (optionally substituted by one or more substituents selected from the group consisting of alkyl, aryl, aralkyl, halo, haloalkyl, —$OR^5$, —$R^8$—$OR^5$, —C(O)$OR^5$, —N($R^5$)$R^6$, and —C(O)N($R^5$)$R^6$), where $R^5$ and $R^6$ are independently each hydrogen, alkyl, aryl or aralkyl, and each $R^8$ is independently a straight or branched alkylene, alkylidene or alkylidyne chain;

or $R^5$ and $R^{15}$ together with the nitrogen to which they are attached form a N-heterocyclic ring containing zero to three additional hetero atoms, where the N-heterocyclic ring is optionally substituted by one or more substituents selected from the group consisting of alkyl, aryl, aralkyl, amino, monoalkylamino, dialkylamino, —$OR^5$, —C(O)$OR^5$, aminocarbonyl, monoalkylaminocarbonyl, and dialkylaminocarbonyl, where each $R^5$ is hydrogen, alkyl, aryl or aralkyl; and $R^{18}$ is hydrogen, alkyl, aryl, aralkyl, cyano, —C(O)$OR^5$, or —$NO_2$;

or $R^{10}$ and $R^{11}$ together with the nitrogen to which they are attached form a N-heterocyclic ring containing zero to three additional hetero atoms, where the N-heterocyclic ring is optionally substituted by one or more substituents selected from the group consisting of alkyl, halo, haloalkyl, aryl, aralkyl, oxo, nitro, cyano, —$R^8$—CN, =N($R^{17}$), —$OR^5$, —C(O)$OR^5$, —$R^8$—C(O)$OR^5$, —N($R^5$)$R^6$, —$R^8$—N($R^5$)$R^6$, —C(O)N($R^5$)$R^6$, —$R^8$—C(O)N($R^5$)$R^6$, —N($R^5$)—N($R^5$)$R^6$, —C(O)$R^5$, —C(O)—($R^8$—O)$_t$$R^5$ (where t is 1 to 6), —S(O)$_p$—$R^9$ (where p is 0 to 2), —$R^8$—S(O)$_p$—$R^9$ (where p is 0 to 2), —($R^8$—O)$_t$—$R^5$ (where t is 1 to 6), and heterocyclyl (optionally substituted by one or more substituents selected from the group consisting of alkyl, aryl, aralkyl, halo, haloalkyl, —$OR^5$, —C(O)$OR^5$, —N($R^5$)$R^6$, and —C(O)N($R^5$)$R^6$), where $R^5$ and $R^6$ are each independently hydrogen, alkyl, aryl or aralkyl;

each $R^8$ is independently a straight or branched alkylene, alkylidene or alkylidyne chain;

each $R^9$ is independently alkyl, aryl or aralkyl;

each $R^{17}$ is independently hydrogen, alkyl, aryl, aralkyl, cyano, —$OR^5$, —$R^8$—$OR^5$, —C(O)$OR^5$, —$R^8$—C(O)$OR^5$, —C(O)—N($R^5$)$R^6$, or —$R^8$—C(O)—N($R^5$)$R^6$, where $R^5$ and $R^6$ are independently each hydrogen, alkyl, aryl or aralkyl, and each $R^8$ is independently a straight or branched alkylene, alkylidene or alkylidyne chain;

each $R^{16}$ is independently alkyl, aryl, aralkyl, —R —$OR^5$, —$R^8$—N($R^5$)$R^6$, cycloalkyl (optionally substituted by one or more substituents selected from the group consisting of alkyl, halo and —$OR^5$), heterocyclyl (optionally substituted by alkyl, aryl, aralkyl, halo, haloalkyl, —$OR^5$, —C(O)$OR^5$, —N($R^5$)$R^6$ or —C(O)N($R^5$)$R^6$), or heterocyclylalkyl (optionally substituted by one or more substituents selected from the group consisting of alkyl, aryl, aralkyl, halo, haloalkyl, —$OR^5$, —C(O)$OR^5$, —N($R^5$)$R^6$ and —C(O)N($R^5$)$R^6$), where $R^5$ and $R^6$ are independently each hydrogen, alkyl, aryl or aralkyl, and each $R^8$ is independently a straight or branched alkylene, alkylidene or alkylidyne chain; or both $R^{16}$'s together with the nitrogen to which they are attached (and wherein the $R^9$ substituent is not present) form an aromatic N-heterocyclic ring containing zero to three additional hetero atoms, where the N-heterocylic ring is optionally substituted by one or more substituents selected from the group consisting of alkyl, aryl, aralkyl, —$OR^5$, —C(O)$OR^5$, —$R^8$—C(O)$OR^5$, —N($R^5$)$R^6$, —$R^8$—N($R^5$)$R^6$, —C(O)$R^5$, —C(O)—($R^8$—O)$_t$—$R^5$ (where t is 1 to 6), and —($R^8$—O)$_t$—$R^5$ (where t is 1 to 6), where $R^5$ and $R^6$ are independently each hydrogen, alkyl, aryl or aralkyl, and each $R^8$ is independently a straight or branched alkylene, alkylidene or alkylidyne chain;

each $R^{17}$ is independently hydrogen, alkyl, aryl, aralkyl, cyano, —$OR^5$, —$R^8$—$OR^5$, —C(O)$OR^5$, —$R^8$—C(O)$OR^5$, —C(O)—N($R^5$)$R^6$, or —$R^8$—C(O)—N($R^5$)$R^6$, where $R^5$ and $R^6$ are independently each hydrogen, alkyl, aryl or aralkyl, and each $R^8$ is independently a straight or branched alkylene, alkylidene or alkylidyne chain;

and $R^4$ is hydrogen or halo.

12. The compound of claim 11 wherein:

m is 1;

n is 1;

D is —N(H)—C(O)—;

E is —C(O)—N(H)— (where the nitrogen is bonded to the 2-position of the pyridinyl ring);

$R^2$ is hydrogen, haloalkyl, or —$OR^5$ where $R^5$ is hydrogen or alkyl;

$R^3$ is a radical of the formula (i):

where r is 1;

$R^{13}$ is halo; and

R is —C($R^7$)H—N($R^{10}$)$R^{11}$ where:

$R^7$ is hydrogen;

$R^{10}$ and $R^{11}$ are each independently hydrogen, alkyl, haloalkyl, aryl, aralkyl, formyl, cyano, —$R^8$—CN, —$OR^5$, —$R^8$—$OR^5$, —S(O)$_p$—$R^{15}$ (where p is 0 to 2), —$R^8$—S(O)$_p$—$R^{15}$ (where p is 0 to 2), —N($R^5$)$R^6$, —$R^8$—N($R^5$)$R^6$, —$R^8$—C(O)$OR^5$, —C(O)—$R^{15}$, —C(O)$NH_2$, —$R^8$—C(O)$NH_2$, —C(S)$NH_2$, —C(O)—S—$R^5$, —C(O)—N($R^5$)$R^5$, —R—C(O)—N($R^5$)$R^{15}$, —C(S)—N($R^5$)$R^{15}$, —$R^8$—N($R^5$)—C(O)H, —$R^8$—N($R^5$)—C(O)$R^{15}$, —C(O)O—$R^8$—N($R^5$)$R^6$, —C(N($R^5$)$R^6$)=C($R^{18}$)$R^{10}$, —$R^8$—N($R^5$)-P(O)(OR^5$)$_2$, cycloalkyl (optionally substituted by one or more substituents selected from the group consisting of alkyl, halo and —$OR^5$), heterocyclyl (optionally substituted by alky, aryl, aralkyl, halo, haloalkyl, oxo, —$OR^5$, —$R^8$—$OR^5$, —C(O)$OR^5$, —S(O)p—$R^9$ (where p is 0 to 2), —$R^8$—S(O)$_p$—$R^9$ (where p is 0 to 2), —N($R^5$)$R^6$ or —C(O)N($R^5$)$R^6$), or heterocyclylalkyl (optionally substituted by one or more substituents selected from the group consisting of alkyl, aryl, aralkyl, halo, haloalkyl, oxo, —$OR^5$, —$R^8$—$OR^5$, —C(O)$OR^5$, —S(O)$_p$—$R^9$ (where p is 0 to 2), —R8—S(O)p—$R^9$ (where p is 0 to 2), —N($R^5$)$R^6$ and —C(O)N($R^5$)$R^6$), where $R^5$ and $R^6$ are each independently hydrogen, alkyl, aryl or aralkyl;

each $R^8$ is independently a straight or branched alkylene, alkylidene or alkylidyne chain;

each $R^9$ is independently alkyl, aryl or aralkyl;

each $R^{15}$ is independently alkyl, cycloalkyl, haloalkyl, aryl, aralkyl, $-R^8-O-C(O)-R^5$, $-R^8-OR^5$, $-N(R^5)R^6$, $-R^8-N(R^5)R^6$, $-R^8-C(O)OR^5$, heterocyclyl (optionally substituted by one or more substituents selected from the group consisting of alkyl, aryl, aralkyl, halo, haloalkyl, $-OR^5$, $-R^8-OR^5$, $-C(O)OR^5$, $-N(R^5)R^6$, and $-C(O)N(R^5)R^6$), or heterocyclylalkyl (optionally substituted by one or more substituents selected from the group consisting of alkyl, aryl, aralkyl, halo, haloalkyl, $-OR^5$, $-R^8-OR^5$, $-C(O)OR^5$, $-N(R^5)R^6$, and $-C(O)N(R^5)R^6$), where $R^5$ and $R^6$ are independently each hydrogen, alkyl, aryl or aralkyl, and each $R^8$ is independently a straight or branched alkylene, alkylidene or alkylidyne chain;

or $R^5$ and $R^{15}$ together with the nitrogen to which they are attached form a N-heterocyclic ring containing zero to three additional hetero atoms, where the N-heterocyclic ring is optionally substituted by one or more substituents selected from the group consisting of alkyl, aryl, aralkyl, amino, monoalkylamino, dialkylamino, $-OR^5$, $-C(O)OR^5$, aminocarbonyl, monoalkylaminocarbonyl, and dialkylaminocarbonyl, where each $R^5$ is hydrogen, alkyl, aryl or aralkyl; and $R^{18}$ is hydrogen, alkl, aryl, aralkyl, cyano, $-C(O)OR^5$, or $-NO_2$;

or $R^{10}$ and $R^{11}$ together with the nitrogen to which they are attached form a N-heterocyclic ring containing zero to three additional hetero atoms, where the N-heterocylic ring is optionally substituted by one or more substituents selected from the group consisting of alkyl, halo, haloalkyl, aryl, aralkyl, oxo, nitro, cyano, $-R^8-CN$, $=N(R^{17})$, $-OR^5$, $-C(O)OR^5$, $-R^8-C(O)OR^5$, $-N(R^5)R^6$, $-R^8-N(R^5)R^6$, $-C(O)N(R^5)R^6$, $-R^8-C(O)N(R^5)R^6$, $-N(R^5)-N(R^5)R^6$, $-C(O)R^5$, $-C(O)-(R^8-O)_t-R^5$ (where t is 1 to 6), $-S(O)_p-R^9$ (where p is 0 to 2), $-R^8-S(O)_p-R^9$ (where p is 0 to 2), $-(R^8-O)_t-R^5$ (where t is 1 to 6), and heterocyclyl (optionally substituted by one or more substituents selected from the group consisting of alkyl, aryl, aralkyl, halo, haloalkyl, $-OR^5$, $-C(O)OR^5$, $-N(R^5)R^6$, and $-C(O)N(R^5)R^6$), where $R^5$ and $R^6$ are each independently hydrogen, alkyl, aryl or aralkyl;

each $R^8$ is independently a straight or branched alkylene, alkylidene or alkylidyne chain;

each $R^9$ is independently alkyl, aryl or aralkyl;

each $R^{17}$ is independently hydrogen, alkyl, aryl, aralkyl, cyano, $-OR^5$, $-R^8-OR^5$, $-C(O)OR^5$, $-R^8-C(O)OR^5$, $-C(O)-N(R^5)R^6$, or $-R^8-C(O)-N(R^5)R^6$ where $R^5$ and $R^6$ are independently each hydrogen, alkyl, aryl or aralkyl, and each $R^8$ is independently a straight or branched alkylene, alkylidene or alkylidyne chain;

and $R^4$ is in the 5-position.

13. The compound of claim 12 wherein:

$R^{10}$ and $R^{11}$ are each independently hydrogen, alkyl, haloalkyl, aryl, aralkyl, formyl, cyano, $-R^8-CN$, $-OR^5$, $-R^8-OR^5$, $-S(O)_p-R^{15}$ (where p is 0 to 2), $-R^8-S(O)p-R^{15}$ (where p is 0 to 2), $-N(R^5)R^6$, $-R^8-N(R^5)R^6$, $-R^8-C(O)OR^5$, $-C(O)-R^{15}$, $-C(O)NH_2$, $-R^8-C(O)NH_2$, $-C(S)NH_2$, $-C(O)-S-R^5$, $-C(O)-N(R^5)R^{15}$, $-R^8-C(O)-N(R^5)R^{15}$, $-C(S)-N(R^5)R^{15}$, $-R^8-N(R^5)-C(O)H$, $-R^8-N(R^5)-C(O)R^{15}$, $-C(O)O-R^8-N(R^5)R^6$, $-C(N(R^5)R^6)=C(R^{18})R^{10}$, $-R^8-N(R^5)-P(O)(OR^5)_2$, cycloalkyl (optionally substituted by one or more substituents selected from the group consisting of alkyl, halo and $-OR^5$), heterocyclyl (optionally substituted by alkyl, aryl, aralkyl, halo, haloalkyl, oxo, $-OR^5$, $-R^8-OR^5$, $-C(O)OR^5$, $-S(O)p-R9$ (where p is 0 to 2), $-R^8-S(O)_pR^9$ (where p is 0 to 2), $-N(R^5)R^6$ or $-C(O)N(R^5)R^6$), or heterocyclylalkyl (optionally substituted by one or more substituents selected from the group consisting of alkyl, aryl, aralkyl, halo, haloalkyl, oxo, $-OR^5$, $-R^8-OR^5$, $-C(O)OR^5$, $-S(O)_p-R9$ (where p is 0 to 2), $-R-S(O)p-R^9$ (where p is 0 to 2), $-N(R^5)R^6$ and $-C(O)N(R^5)R^6$), where $R^5$ and R6 are each independently hydrogen, alkyl, aryl or aralkyl;

each $R^8$ is independently a straight or branched alkylene, alkylidene or alkylidyne chain;

each $R^9$ is independently alkyl, aryl or aralkyl;

each $R^{15}$ is independently alkyl, cycloalkyl, haloalkyl, aryl, aralkyl, $-R^8-O-C(O)-R^5$, $-R^8-OR^5$, $-N(R^5)R^6$, $-R^8-N(R^5)R^6$, $-R^8-C(O)OR^5$, heterocyclyl (optionally substituted by one or more substituents selected from the group consisting of alkyl, aryl, aralkyl, halo, haloalkyl, $-OR^5$, $-R^8-OR^5$, $-C(O)OR^5$, $-N(R^5)R^6$, and $-C(O)N(R^5)R^6$), or heterocyclylalkyl (optionally substituted by one or more substituents selected from the group consisting of alkyl, aryl, aralkyl, halo, haloalkyl, $-OR^5$, $-R-OR^5$, $-C(O)OR^5$, $-N(R^5)R^6$, and $-C(O)N(R^5)R^6$) where $R^5$ and $R^6$ are independently each hydrogen, alkyl, aryl or aralkyl, and each $R^8$ is independently a straight or branched alkylene, alkylidene or alkylidyne chain;

or $R^5$ and $R^{15}$ together with the nitrogen to which they are attached form a N-heterocyclic ring containing zero to three additional hetero atoms, where the N-heterocyclic ring is optionally substituted by one or more substituents selected from the group consisting of alkyl, aryl, aralkyl, amino, monoalkylamino, dialkylamino, $-OR^5$, $-C(O)OR^5$, aminocarbonyl, monoalkylaminocarbonyl, and dialkylaminocarbonyl, where each $R^5$ is independently hydrogen, alkyl, aryl or aralkyl; and $R^{18}$ is hydrogen, alkyl, aryl, aralkyl, cyano, $-C(O)OR^5$, or $-NO_2$.

14. The compound of claim 13 wherein:

$R^{10}$ is hydrogen, alkyl, or $-R^8-OR^5$; and $R^{11}$ is hydrogen, alkyl or $-R^8-OR^5$;

where each $R^8$ is independently a straight or branched alkylene chain, and each $R^5$ is hydrogen or alkyl.

15. The compound of claim 14 selected from the group consisting of:

N-(5-chloropyridin-2-yl)-2-[((4-((N'-methyl—N'-(2-hydroxyethyl)amino)methyl)-3-chlorothiophen-2-yl)carbonyl)amino]-3-methoxy-5-chlorobenzamide;

N-(5-chloropyridin-2-yl)-2-[((4-((N methyl—N'-(2-hydroxyethyl)amino)methyl)-3-chlorothiophen-2-yl)carbonyl)amino]-3-hydroxy-5-chlorobenzamide;

N-(5-chloropyridin-2-yl)-2-[((4-((N'N'-di(2-hydroxypropyl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(3-hydroxypropyl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(2-hydroxypropyl)amino)methyl)-3-chlorothiophen-2-yl)carbonyl)amino]-3-methoxy-5-chlorobenzamide;

N-(5-chloropyridin-2-yl)-2-[((4-((N'-ethyl—N'-(2-hydroxyethyl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(2,2-dimethyl-2-hydroxyethyl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(2-hydroxyethyl)amino)methyl)-3-chlorothiophen-2-yl)carbonyl)amino]-3-ethoxy-5-chlorobenzamide;

N-(5-chloropyridin-2-yl)-2-[((4-(((2-hydroxyethyl)amino)methyl)-3-chlorothiophen-2-yl)carbonyl)amino]-3-methoxy-5-chlorobenzamide;

N-(5-chloropyridin-2-yl)-2-[((4-((methylamino)methyl)-3-chlorothiophen-2-yl)carbonyl)amino]-3-methoxy-5-chlorobenzamide;

N-(5-chloropyridin-2-yl)-2-[((4-(amino)methyl-3-chlorothiophen-2-yl)carbonyl)amino]-3-methoxy-5-chlorobenzamide;

N-(5-chloropyridin-2-yl)-2-[((4-((dimethylamino)methyl)-3-chlorothiophen-2-yl)carbonyl)amino]-3-methoxy-5-chlorobenzamide;

N-(5-chloropyridin-2-yl)-2-[((4-((N'-ethyl—N'-methylamino)methyl)-3-chlorothiophen-2-yl)carbonyl)amino]-3-methoxy-5-chlorobenzamide;

N-(5-chloropyridin-2-yl)-2-[((4-((N'-(1-methylethyl)amino)methyl)-3-chlorothiophen-2-yl)carbonyl)amino]-3-methoxy-5-chlorobenzamide;

N-(5-chloropyridin-2-yl)-2-[((4-(ethylamino)methyl-3-chlorothiophen-2-yl)carbonyl)amino]-3-methoxy-5-chlorobenzamide; and N-(5-chloropyridin-2-yl)-2-[((4-(diethylamino)methyl-3-chlorothiophen-2-yl)carbonyl)amino]-3-methoxy-5-chlorobenzamide.

16. The compound of claim 13 wherein:
$R^{10}$ is hydrogen, alkyl, or —$R^8$—$N(R^5)R^6$, and
$R^{11}$ is —$S(O)_p$—$R^{15}$ (where p is 0 to 2) or —$R^8$—$N(R^5)R^6$
where:
$R^5$ and $R^6$ are independently hydrogen or alkyl;
each $R^8$ is independently a straight or branched alkylene, alkylidene or alkylidyne chain; and
$R^{15}$ is independently alkyl, cycloalkyl, haloalkyl, aryl, aralkyl, —$R^8$—O—C(O)—$R^5$, —$R^8$—$OR^5$, —$N(R^5)R^6$, —$R^8$—$N(R^5)R^6$, —$R^8$—$C(O)OR^5$, heterocyclyl (optionally substituted by one or more substituents selected from the group consisting of alkyl, aryl, aralkyl, halo, haloalkyl, —$OR^5$, —$R^8$—$OR^5$, —C(O)$OR^5$, —$N(R^5)R^6$, and —C(O)$N(R^5)R^6$), or heterocyclylalkyl (optionally substituted by one or more substituents selected from the group consisting of alkyl, aryl, aralkyl, halo, haloalkyl, —$OR^5$, —$R^8$—$OR^5$, —C(O)$OR^5$, —$N(R^5)R^6$, and —C(O)$N(R^5)R^6$) where $R^5$ and $R^6$ are independently each hydrogen, alkyl, aryl or aralkyl, and
each $R^8$ is independently a straight or branched alkylene, alkylidene or alkylidyne chain.

17. The compound of claim 16 selected from the group consisting of.

N-(5-chloropyridin-2-yl)-2-[((4-((N'-methyl—N'-(3-(dimethylamino)propyl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(methylsulfonyl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(2-(dimethylamino)ethyl)amino)methyl)-3-chlorothiophen-2-yl)carbonyl)amino]-3-hydroxy-5-chlorobenzamide;

N-(5-chloropyridin-2-yl)-2-[((4-((N'-(methyl)sulfonyl—N'-(2-(dimethylamino)ethyl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(2-(dimethylamino)ethyl)amino)methyl)-3-chlorothiophen-2-yl)carbonyl)amino]-3-methoxy-5-chlorobenzamide;

N-(5-chloropyridin-2-yl)-2-[((4-((N'-methyl—N'-((3,5-dimethylisoxazol4-yl)sulfonyl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(methylsulfonyl)amino)methyl)-3-chlorothiophen-2-yl)carbonyl)amino]-3-hydroxy-5-chlorobenzamide;

N-(5-chloropyridin-2-yl)-2-[((4-((N'-methyl—N'-((2-(4-hydroxypiperidin-1-yl)ethyl)sulfonyl)amino)methyl)-3-chlorothiophen-2-yl)carbonyl)amino]-3-methoxy-5-chlorobenzamide;

N-(5-chloropyridin-2-yl)-2-[((4-((N'-methyl—N'-((2-(pyrrolidin-1-yl)ethyl)sulfonyl)amino)methyl)-3-chlorothiophen-2-yl)carbonyl)amino]-3-methoxy-5-chlorobenzamide;

N-(5-chloropyridin-2-yl)-2-[((4-((Nt-methyl—N'-((dimethylamino)sulfonyl)amino)methyl)-3-chlorothiophen-2-yl)carbonyl)amino]-3-methoxy-5-chlorobenzamide;

N-(5-chloropyridin-2-yl)-2-[((4-((N'-(2-aminoethyl)amino)methyl)-3-chlorothiophen-2-yl)carbonyl)amino]-3-methoxy-5-chlorobenzamide; and N-(5-chloropyridin-2-yl)-2-[((4-((N'-ethyl—N'-(4-(dimethylamino)but-3-yn-2-yl)amino)methyl)-3-chlorothiophen-2-yl)carbonyl)amino]-3-methoxy-5-chlorobenzamide.

18. The compound of claim 13 wherein:
R10 is hydrogen, alkyl or —$R^8$—$OR^5$; and
$R^{11}$ is formyl, cyano, —C(O)—$R^{15}$, —C(O)$NH_2$, —C(S)$NH_2$, —C(O)—S—$R^5$, —C(O)—$N(R^5)R^{15}$, —$R^8(R^5)$—C(O)$R^{15}$, —C(O)O—$R^8$—$N(R^5)R^6$, —C(S)—$N(R^5)R^{15}$, —$R^8$—$N(R^5)$-P(O)($OR^5$)$_2$, or —C($N(R^5)R^6$)=C($R^{18}$)$R^{10}$,
where:
each $R^5$ and $R^6$ is independently hydrogen or alkyl;
$R^8$ is a straight or branched alkylene chain;
each $R^{15}$ is independently alkyl, cycloalkyl, haloalkyl, aryl, aralkyl, —$R^8$—O—C(O)—$R^5$, —$R^8$—$OR^5$, —$N(R^5)R^6$, —$R^8$—$N(R^5)R^6$, —$R^8$—$C(O)OR^5$, heterocyclyl (optionally substituted by one or more substituents selected from the group consisting of alkyl, aryl, aralkyl, halo, haloalkyl, —$OR^5$, —$R^8$—$OR^5$, —C(O)$OR^5$, —$N(R^5)R^6$, and —C(O)$N(R^5)R^6$), or heterocyclylalkyl (optionally substituted by one or more substituents selected from the group consisting of alkyl, aryl, aralkyl, halo, haloalkyl, —$OR^5$, —$R^8$—$OR^5$, —C(O)$OR^5$, —$N(R^5)R^6$, and —C(O)$N(R^5)R^6$) where $R^5$ and $R^6$ are independently each hydrogen, alkyl, aryl or aralkyl, and
each $R^8$ is independently a straight or branched alkylene, alkylidene or alkylidyne chain; and
$R^{18}$ is hydrogen, alkyl aryl, aralkyl, cyano, —C(O)$OR^5$, or —$NO_2$.

19. The compound of claim 18 selected from the group consisting of:

N-(5-chloropyridin-2-yl)-2-[((4-((N'-methyl—N"-ethylureido)methyl)-3-chlorothiophen-2-yl)carbonyl)amino]-3-methoxy-5-chlorobenzamide;

N-(5-chloropyridin-2-yl)-2-[((4-((N'-methyl—N"-(2-carboxyethyl)ureido)methyl)-3-chlorothiophen-2-yl)carbonyl)amino]-3-methoxy-5-chlorobenzamide;

N-(5-chloropyridin-2-yl)-2-[((4-((N'-methyl—N'-((4-(2-hydroxyethyl)piperazin-1-yl)carbonyl)amino)methyl)-3-chlorothiophen-2-yl)carbonyl)amino]-3-methoxy-5-chlorobenzamide;

N-(5-chloropyridin-2-yl)-2-[((4-((N'-methyl—N"-(2-(morpholin-4-yl)ethyl)thioureido)methyl)-3-chlorothiophen-2-yl)carbonyl)amino]-3-methoxy-5-chlorobenzamide;

N-(5-chloropyridin-2-yl)-2-[((4-((N'-methyl—N'-(((4-hydroxypiperidin-1-yl)methyl)carbonyl)amino)methyl)-3-chlorothiophen-2-yl)carbonyl)amino]-3-methoxy-5-chlorobenzamide;

N-(5-chloropyridin-2-yl)-2-[((4-((N'-methyl—N"-(2-hydroxyethyl)ureido)methyl)-3-chlorothiophen-2-yl)carbonyl)amino]-3-methoxy-5-chlorobenzamide;

N-(5-chloropyridin-2-yl)-2-[((4-(N'-methylureido)methyl)-3-chlorothiophen-2-yl)carbonyl)amino]-3-methoxy-5-chlorobenzamide; and N-(5-chloropyridin-2-yl)-2-[((4-((N'-(2-hydroxyethyl)ureido)methyl)-3-chlorothiophen-2-yl)carbonyl)amino]-3-methoxy-5-chlorobenzamide;

N-(5-chloropyridin-2-yl)-2-[((4-((N'-methyl—N"-(2-(chloro)ethyl)ureido)methyl)-3-chlorothiophen-2-yl)carbonyl)amino]-3-methoxy-5-chlorobenzamide;

N-(5-chloropyridin-2-yl)-2-[((4-((N'-methyl—N"-(2-(acetoxy)ethyl)ureido)methyl)-3-chlorothiophen-2-yl)carbonyl)amino]-3-methoxy-5-chlorobenzamide;

N-(5-chloropyridin-2-yl)-2-[((4-((N'-methyl—N"-(2-(pyrrolidin-1-yl)ethyl)ureido)methyl)-3-chlorothiophen-2-yl)carbonyl)amino]-3-methoxy-5-chlorobenzamide;

N-(5-chloropyridin-2-yl)-2-[((4-((N"-(2-(chloro)ethyl)ureido)methyl)-3-chlorothiophen-2-yl)carbonyl)amino]-3-methoxy-5-chlorobenzamide;

N-(5-chloropyridin-2-yl)-2-[((4-((N'-methyl—N'-(2-(((2-hydroxyphenyl)carbonyl)oxy)ethyl)ureido)-methyl)-3-chlorothiophen-2-yl)carbonyl)amino]-3-methoxy-5-chlorobenzamide;

N-(5-chloropyridin-2-yl)-2-[((4-((N'-methyl—N'-cyanoamino)methyl)-3-chlorothiophen-2-yl)carbonyl)amino]-3-methoxy-5-chlorobenzamide;

N-(5-chloropyridin-2-yl)-2-[((4-((N'-(2-((fluoromethylcarbonyl)amino)ethyl)amino)methyl)-3-chlorothiophen-2-yl)carbonyl)amino]-3-methoxy-5-chlorobenzamide;

N-(5-chloropyridin-2-yl)-2-[((4-((N'-methyl—N'-((2-aminoethoxy)carbonyl)amino)methyl)-3-chlorothiophen-2-yl)carbonyl)amino]-3-methoxy-5-chlorobenzamide;

N-(5-chloropyridin-2-yl)-2-[((4-((N'-methyl—N'-((methylthio)carbonyl)amino)methyl)-3-chlorothiophen-2-yl)carbonyl)amino]-3-methoxy-5-chlorobenzamide;

N-(5-chloropyridin-2-yl)-2-[((4-((N'-ethyl—N'-((phenylthio)carbonyl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(2-nitro-1-(methylamino)ethenyl)amino)methyl)-3-chlorothiophen-2-yl)carbonyl)amino]-3-methoxy-5-chlorobenzamide;

N-(5-chloropyridin-2-yl)-2-[((4-(((2-dimethylphosphoramidoethyl)amino)methyl)-3-chlorothiophen-2-yl)carbonyl)amino]-3-methoxy-5-chlorobenzamide.

20. The compound of claim 13 wherein:

$R^{10}$ is hydrogen, alkyl, haloalkyl, or —$R^8$—$OR^5$;

$R^{11}$ is cycloalkyl (optionally substituted by one or more substituents selected from the group consisting of alkyl, halo and —$OR^5$), heterocyclyl (optionally substituted by alkyl, aryl, aralkyl, halo, haloalkyl, oxo, —$OR^5$, —$R^8$—$OR^5$, —$C(O)OR^5$, —$S(O)_p$—$R^9$ (where p is 0 to 2), —$R^8$—$S(O)_p$—$R^9$ (where p is 0 to 2), —$N(R^5)R^6$ or —$C(O)N(R^5)R^6$), or heterocyclylalkyl (optionally substituted by one or more substituents selected from the group consisting of alkyl, aryl, aralkyl, halo, haloalkyl, oxo, —$OR^5$, —$R^8$—$OR^5$, —$C(O)OR^5$, —$S(O)_p$—$R^9$ (where p is 0 to 2), —$R^8$—$S(O)_p$—$R^9$ (where p is 0 to 2), —$N(R^5)R^6$ and —$C(O)N(R^5)R^6$), where $R^5$ and $R^6$ are each independently hydrogen, alkyl, aryl or aralkyl;

each $R^8$ is independently a straight or branched alkylene, alkylidene or alkylidyne chain; and each $R^9$ is independently alkyl, aryl or aralkyl;

each $R^{15}$ is independently alkyl, cycloalkyl, haloalkyl, aryl, aralkyl, —$R^8$—O—$C(O)$—$R^5$, —$R^8$—$OR^5$, —$N(R^5)R^6$, —$R^8$—$N(R^5)R^6$, —R —$C(O)OR^5$, heterocyclyl (optionally substituted by one or more substituents selected from the group consisting of alkyl, aryl, aralkyl, halo, haloalkyl, —$OR^5$, —$R^8$—$OR^5$, —$C(O)OR^5$, —$N(R^5)R^6$, and —$C(O)N(R^5)R^6$), or heterocyclylalkyl (optionally substituted by one or more substituents selected from the group consisting of alkyl, aryl, aralkyl, halo, haloalkyl, —$OR^5$, —$R^8$—$OR^5$, —$C(O)OR^5$, —$N(R^5)R^6$, and —$C(O)N(R^5)R^6$) where $R^5$ and $R^6$ are independently each hydrogen, alkyl, aryl or aralkyl, and each $R^8$ is independently a straight or branched alkylene, alkylidene or alkylidyne chain.

21. The compound of claim 20 selected from the group consisting of:

N-(5-chloropyridin-2-yl)-2-[((4-((N'-(2-(morpholin-4-yl)ethyl)amino)methyl)-3-chlorothiophen-2-yl)carbonyl)amino]-5-chlorobenzamide;

N-(5-chloropyridin-2-yl)-2-[((4-((N'-methyl—N'-(2-(pyrrolidin-1-yl)ethyl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(1-methylpiperidin-4-yl)amino)methyl)-3-chlorothiophen-2-yl)carbonyl)amino]-3-hydroxy-5-chlorobenzamide;

N-(5-chloropyridin-2-yl)-2-[((4-((N'-methyl—N'-(4-hydroxycyclohexyl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(pyridin-2-yl)methyl)amino)methyl)-3-chlorothiophen-2-yl)carbonyl)amino]-3-methoxy-5-chlorobenzamide;

N-(5-chloropyridin-2-yl)-2-[((4-((N'-methyl—N'oxazolin-2-yl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(thiazolin-2-yl)amino)methyl)-3-chlorothiophen-2-yl)carbonyl)amino]-3-methoxy-5-chlorobenzamide;

N-(5-chloropyridin-2-yl)-2-[((4-((N'-ethyl—N'-(oxazolin-2-yl)amino)methyl)-3-chlorothiophen-2-yl)carbonyl)amino]-3-methoxy-5-chlorobenzamide;

N-(5-chloropyridin-2-yl)-2-[((4-((N'-ethyl—N'-(thiazolin-2-yl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(4-(oxo)oxazolin-2-yl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(pyridin-2-yl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(dihydro-4(H)-1,3-oxazin-2-yl)amino)methyl)-3-chlorothiophen-2-yl)carbonyl)amino]-3-methoxy-5-chlorobenzamide;

N-(5-chloropyridin-2-yl)-2-[((4-((N'-methyl—Nt-(oxazolin-2-yl)amino)methyl)-3-chlorothiophen-2-yl)carbonyl)amino]-5-chlorobenzamide;

N-(5-chloropyridin-2-yl)-2-[((4-((N'-methyl—N'-(oxazolin-2-yl)amino)methyl)-3-chlorothiophen-2-yl)carbonyl)amino]-3-hydroxy-5-chlorobenzamide;

N-(5-chloropyridin-2-yl)-2-[((4-((N'-(t-butyl)—N'-(oxazolin-2-yl)amino)methyl)-3-chlorothiophen-2-yl)carbonyl)amino]-3-methoxy-5-chlorobenzamide;

N-(5-chloropyridin-2-yl)-2-[((4-(((thiazol-2-yl)amino)methyl)-3-chlorothiophen-2-yl)carbonyl)amino]-3-methoxy-5-chlorobenzamide;

N-(5-chloropyridin-2-yl)-2-[((4-((N'-(2-methoxyethyl)-N-(oxazolin-2-yl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(oxazol-2-yl)amino)methyl)-3-chiorothiophen-2-yl)carbonyl)amino]-3-methoxy-5-chlorobenzamide;

N-(5-chloropyridin-2-yl)-2-[((4-((N'-methyl—N-(4-trifluoromethyl-5-(methoxycarbonyl)pyrimidin-2-yl)amino)methyl)-3-chlorothiophen-2-yl)carbonyl)amino]-3-methoxy-5-chlorobenzamide;

N-(5-chloropyridin-2-yl)-2-[((4-((N'-ethyl—N'-(dihydro-4(H)-1,3-oxazin-2-yl)amino)methyl)-3-chlorothiophen-2-yl)carbonyl)amino]-3-methoxy-5-chlorobenzamide;

N-(5-chloropyridin-2-yl)-2-[((4-((N-methyl—Nt-(5-methyloxazolin-2-yl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(tetrazol-5-yl)amino)methyl)-3-chlorothiophen-2-yl)carbonyl)amino]-3-methoxy-5-chlorobenzamide;

N-(5-chloropyridin-2-yl)-2-[((4-((N'-ethyl—N (tetrazol-5-yl)amino)methyl-3-chiorothiophen-2-yl)carbonyl)amino]-3-methoxy-5-chlorobenzamide;

N-(5-chloropyridin-2-yl)-2-[((4-((N'-ethyl—N'-(4-methyloxazolin-2-yl)amino)methyl-3-chlorothiophen-2-yl)carbonyl)amino]-3-methoxy-5-chlorobenzamide;

N-(5-chloropyridin-2-yl)-2-[((4-((N'-(pyrazol-3-yl)amino)methyl)-3-chlorothiophen-2-yl)carbonyl)amino]-3-methoxy-5-chlorobenzamide;

N-(5-chloropyridin-2-yl)-2-[((4-((N'-(2,2,2-trifluoroethyl)—N'-(oxazolin-2-yl)amino)methyl)-3-chlorothiophen-2-yl)carbonyl)amino]-3-methoxy-5-chlorobenzamide;

N-(5-chloropyridin-2-yl)-2-[((4-((N'-(4-(ethoxycarbonyl)oxazolin-2-yl)amino)methyl)-3-chlorothiophen-2-yl)carbonyl)amino]-3-methoxy-5-chlorobenzamide;

N-(5-chloropyridin-2-yl)-2-[((4-((Nt-(3,4-dihydro-2H-pyrrol-5-yl)amino)methyl)-3-chlorothiophen-2-yl)carbonyl)amino]-3-methoxy-5-chlorobenzamide;

N-(5-chloropyridin-2-yl)-2-[((4-((N'-(1,2,4-triazol4-yl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(3,4-dihydro-2H-pyrrol-5-yl)amino)methyl)-3-chlorothiophen-2-yl)carbonyl)amino]-3-methoxy-5-chlorobenzamide;

N-(5-chloropyridin-2-yl)-2-[((4-((N'-methyl-N-(pyridin-4-yl)amino)methyl)-3-chlorothiophen-2-yl)carbonyl)amino]-3-methoxy-5-chlorobenzamide;

N-(5-chloropyridin-2-yl)-2-[((4-((N'-methyl—N!-(2-amino-6-methylpyrimidin-4-yl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(1,2,4-oxadiazol-3-yl)methyl)amino)methyl)-3-chlorothiophen-2-yl)carbonyl)amino]-3-methoxy-5-chlorobenzamide;

N-(5-chloropyridin-2-yl)-2-[((4-((N'-(2-(imidazol-4-yl)ethyl)amino)methyl)-3-chlorothiophen-2-yl)carbonyl)amino]-3-methoxy-5-chlorobenzamide;

N-(5-chloropyridin-2-y)-2-[((4-((N'-methyl—N'-(3,4,5,6-tetrahydropyridin-2-yl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(2-chloropyrimidin-4-yl)amino)methyl)-3-chlorothiophen-2-yl)carbonyl)amino]-3-methoxy-5-chlorobenzamide;

N-(5-chloropyridin-2-yl)-2-[((4-((N'ethyl—N'-((imidazol-2-yl)methyl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(4-aminopyrimidin-2-yl)amino)methyl)-3-chlorothiophen-2-yl)carbonyl)amino]-3-methoxy-5-chlorobenzamide;

N-(5-chloropyridin-2-yl)-2-[((4-((Nt-(4-aminopyrimidin-2-yl)amino)methyl)-3-chlorothiophen-2-yl)carbonyl)amino]-3-methoxy-5-chlorobenzamide;

N-(5-chloropyridin-2-yl)-2-[((4-((N'-(4-(methylamino)pyrimidin-2-yl)amino)methyl)-3-chlorothiophen-2-yl)carbonyl)amino]-3-methoxy-5-chlorobenzamide;

N-(5-chloropyridin-2-yl)-2-[((4-((N'-methyl—N'-((3-(methoxymethyl)-1,2,4-oxadiazol-5-yl)methyl)amino)methyl)-3-chlorothiophen-2-yl)carbonyl)amino]-3-methoxy-5-chlorobenzamide;

N-(5-chloropyridin-2-yl)-2-[((4-((N'-methyl—N'-((3-((methylthio)methyl)-1,2,4-oxadiazol-5-yl)methyl)amino)methyl)-3-chlorothiophen-2-yl)carbonyl)amino]-3-methoxy-5-chlorobenzamide; and N-(5-chloropyridin-2-yl)-2-[((4-((N'-methyl—N'-(1,3,2-dioxaphospholan-2-yl)amino)methyl)-3-chlorothiophen-2-yl)carbonyl)amino]-3-methoxy-5-chlorobenzamide.

22. The compound of claim 12 wherein:

$R^{10}$ and $R^{11}$ together with the nitrogen to which they are attached form a N-heterocyclic ring containing zero to three additional hetero atoms, where the N-heterocylic ring is optionally substituted by one or more substituents selected from the group consisting of alkyl, halo, haloalkyl, aryl, aralkyl, oxo, nitro, cyano, —$R^8$—CN, =N($R^{17}$), —O$R^5$, —C(O)O$R^5$, —$R^8$—C(O)O$R^5$, —N($R^5$)$R^6$, —$R^8$—N($R^5$)$R^6$, —C(O)N($R^5$)$R^6$, —$R^8$—C(O)N($R^5$)$R^6$, —N($R^5$)—N($R^5$)$R^6$, —C(O)$R^5$, —C(O)—($R^8$—O)$_t$—$R^5$ (where t is 1 to 6), —S(O)p—$R^9$ (where p is 0 to 2), —$R^8$—S(O)$_p$—$R^9$ (where p is 0 to 2), —($R^8$—O)$_t R^5$ (where t is 1 to 6), and heterocyclyl (optionally substituted by one or more substituents selected from the group consisting of alkyl, aryl, aralkyl, halo, haloalkyl, —O$R^5$, —C(O)O$R^5$, —N($R^5$)$R^6$, and —C(O)N($R^5$)$R^6$), where $R^5$ and $R^6$ are each independently hydrogen, alkyl, aryl or aralkyl;

each $R^8$ is independently a straight or branched alkylene, alkylidene or alkylidyne chain;

each $R^9$ is independently alkyl, aryl or aralkyl;

each $R^{17}$ is independently hydrogen, alkyl, aryl, aralkyl, cyano, —O$R^5$, —$R^8$—O$R^5$, —C(O)O$R^5$, —$R^8$—C(O)O$R^5$, —C(O)—N($R^5$)$R^6$, or —$R^8$—C(O)—N($R^5$)$R^6$ where $R^5$ and $R^6$ are independently each hydrogen, alkyl, aryl or aralkyl, and each $R^8$ is independently a straight or branched alkylene, alkylidene or alkylidyne chain.

23. The compound of claim 22 wherein the N-heterocylic ring is optionally substituted by one or more substituents selected from the group consisting of alkyl, halo, haloalkyl, aryl, aralkyl, oxo, and nitro.

24. The compound of claim 23 selected from the group consisting of:

N-(5-chloropyridin-2-yl)-2-[((4-((4,5-dihydropyrazolin-1-yl)methyl)-3-chlorothiophen-2-yl)carbonyl)amino]-3-methoxy-5-chlorobenzamide;

N-(5-chloropyridin-2-yl)-2-[((4-((imidazol-1-yl)methyl)-3-chlorothiophen-2-yl)carbonyl)amino]-3-methoxy-5-chlorobenzamide;

N-(5-chloropyridin-2-yl)-2-[((4-((morpholin-4-yl)methyl)-3-chlorothiophen-2-yl)carbonyl)amino]-3-methoxy-5-chlorobenzamide;

N-(5-chloropyridin-2-yl)-2-[((4-((pyrazol-1-yl)methyl)-3-chlorothiophen-2-yl)carbonyl)amino]-3-methoxy-5-chlorobenzamide;

N-(5-chloropyridin-2-yl)-2-[((4-((hydantoin-3-yl)methyl)-3-chlorothiophen-2-yl)carbonyl)amino]-3-methoxy-5-chlorobenzamide;

N-(5-chloropyridin-2-yl)-2-[((4-((1,4,5,6-tetrahydropyrimidin-1-yl)methyl)-3-chlorothiophen-2-yl)carbonyl)amino]-3-methoxy-5-chlorobenzamide;

N-(5-chloropyridin-2-yl)-2-[((4-((imidazolin-1-yl)methyl)-3-chlorothiophen-2-yl)carbonyl)amino]-3-methoxy-5-chlorobenzamide;

N-(5-chloropyridin-2-yl)-2-[((4-((pyrrolidin-1-yl)methyl)-3-chlorothiophen-2-yl)carbonyl)amino]-3-methoxy-5-chlorobenzamide;

N-(5-chloropyridin-2-yl)-2-[((4-((2,3,4,5,6,7-hexahydro-3,7-dimethyl-2,6-dioxo-1H-purin-1-yl)methyl)-3-chlorothiophen-2-yl)carbonyl)amino]-3-methoxy-5-chlorobenzamide;

N-(5-chloropyridin-2-yl)-2-[((4-((4-methylpiperazin-1-yl)methyl)-3-chlorothiophen-2-yl)carbonyl)amino]-3-methoxy-5-chlorobenzamide;

N-(5-chloropyridin-2-yl)-2-[((4-((4-methylpiperazin-1-yl)methyl)-3-chlorothiophen-2-yl)carbonyl)amino]-3-hydroxy-5-chlorobenzamide;

N-(5-chloropyridin-2-yl)-2-[((4-((4-methylpiperazin-1-yl)methyl)-3-chlorothiophen-2-yl)carbonyl)amino]-5-chlorobenzamide;

N-(pyridin-2-yl)-2-[((4-((4-methylpiperazin-1-yl)methyl)-3-chlorothiophen-2-yl)carbonyl)amino]-5-chlorobenzamide;

N-(5-bromopyridin-2-yl)-2-[((4-((4-methylpiperazin-1-yl)methyl)-3-chlorothiophen-2-yl)carbonyl)amino]-5-chlorobenzamide;

N-(5-chloropyridin-2-yl)-2-[((4-((4-ethylpiperazin-1-yl)methyl)-3-chlorothiophen-2-yl)carbonyl)amino]-3-methoxy-5-chlorobenzamide;

N-(5-chloropyridin-2-yl)-2-[((4-((2-methylimidazol-1-yl)methyl)-3-chlorothiophen-2-yl)carbonyl)amino]-3-methoxy-5-chlorobenzamide;

N-(5-chloropyridin-2-yl)-2-[((4-((4-methylimidazol-1-yl)methyl)-3-chlorothiophen-2-yl)carbonyl)amino]-3-methoxy-5-chlorobenzamide;

N-(5-chloropyridin-2-yl)-2-[((4-((5-methylimidazol-1-yl)methyl)-3-chlorothiophen-2-yl)carbonyl)amino]-3-methoxy-5-chlorobenzamide;

N-(5-chloropyridin-2-yl)-2-[((4-((2-methylimidazolin-1-yl)methyl)-3-chlorothiophen-2-yl)carbonyl)amino]-3-methoxy-5-chlorobenzamide;

N-(5-chloropyridin-2-yl)-2-[((4-((2,4-dimethylimidazol-1-yl)methyl)-3-chlorothiophen-2-yl)carbonyl)amino]-3-methoxy-5-chlorobenzamide;

N-(5-chloropyridin-2-yl)-2-[((4-((2,5-dimethylimidazol-1-yl)methyl)-3-chlorothiophen-2-yl)carbonyl)amino]-3-methoxy-5-chlorobenzamide;

N-(5-chloropyridin-2-yl)-2-[((4-((2-methyl-4-nitroimidazol-1-yl)methyl)-3-chlorothiophen-2-yl)carbonyl)amino]-3-methoxy-5-chlorobenzamide;

N-(5-chloropyridin-2-yl)-2-[((4-((4,5-dichloroimidazol-1-yl)methyl)-3-chlorothiophen-2-yl)carbonyl)amino]-3-methoxy-5-chlorobenzamide;

N-(5-chloropyridin-2-yl)-2-[((4-((2-(chloromethyl)imidazolin-1-yl)methyl)-3-chlorothiophen-2-yl)carbonyl)amino]-3-methoxy-5-chlorobenzamide; and N-(5-chloropyridin-2-yl)-2-[((4-((2-(fluoromethyl)imidazolin-1-yl)methyl)-3-chlorothiophen-2-yl)carbonyl)amino]-3-methoxy-5-chlorobenzamide.

25. The compound of claim 22 wherein the N-heterocylic ring is substituted by one or more substituents selected from the group consisting of alkyl, nitro, —$R^8$—CN, —$OR^5$, —$N(R^5)$—$N(R^5)R^6$, —$C(O)R^5$, —$S(O)_p$—$R^9$ (where p is 0 to 2), —$(R^8$—O$)_tR^5$ (where t is 1 to 6), and heterocyclyl (optionally substituted by one or more substituents selected from the group consisting of alkyl, aryl, aralkyl, halo, haloalkyl, —$OR^5$, —$C(O)OR^5$, —$N(R^5)R^6$, and —$C(O)N(R^5)R^6$), where $R^5$ and $R^6$ are each independently hydrogen, alkyl, aryl or aralkyl;

each $R^8$ is independently a straight or branched alkylene, alkylidene or alkylidyne chain;

each $R^9$ is independently alkyl, aryl or aralkyl.

26. The compound of claim 25 selected from the group consisting of:

N-(5-chloropyridin-2-yl)-2-[((4-((4-(hydroxymethyl)imidazol-1-yl)methyl)-3-chlorothiophen-2-yl)carbonyl)amino]-3-methoxy-5-chlorobenzamide;

N-(5-chloropyridin-2-yl)-2-[((4-((5-(hydroxymethyl)imidazol-1-yl)-3-chlorothiophen-2-yl)carbonyl)amino]-3-methoxy-5-chlorobenzamide;

N-(5-chloropyridin-2-yl)-2-[((4-((2-(methoxymethyl)imidazolin-1-yl)methyl)-3-chlorothiophen-2-yl)carbonyl)amino]-3-methoxy-5-chlorobenzamide;

N-(5-chloropyridin-2-yl)-2-[((4-((2-(hydroxymethyl)imidazol-1-yl)methyl)-3-chlorothiophen-2-yl)carbonyl)amino]-3-methoxy-5-chlorobenzamide;

N-(5-chloropyridin-2-yl)-2-[((4-((4-formylpiperazin-1-yl)methyl)-3-chlorothiophen-2-yl)carbonyl)amino]-3-methoxy-5-chlorobenzamide;

N-(5-chloropyridin-2-yl)-2-[((4-((2-(N amino—N'-methylamino)imidazolin-1-yl)methyl)-3-chlorothiophen-2-yl)carbonyl)amino]-3-methoxy-5-chlorobenzamide;

N-(5-chloropyridin-2-yl)-2-[((4-((4-hydroxypiperidin-1-yl)methyl)-3-chlorothiophen-2-yl)carbonyl)amino]-3-methoxy-5-chlorobenzamide;

N-(5-chloropyridin-2-yl)-2-[((4-((2-(methylthio)imidazolin-1-yl)methyl)-3-chlorothiophen-2-yl)carbonyl)amino]-3-methoxy-5-chlorobenzamide;

N-(5-chloropyridin-2-yl)-2-[((4-((4-(methylsulfonyl)piperazin-1-yl)methyl)-3-chlorothiophen-2-yl)carbonyl)amino]-3-methoxy-5-chlorobenzamide;

N-(5-chloropyridin-2-yl)-2-[((4-((2-methyl-4-nitroimidazol-1-yl)methyl)-3-chlorothiophen-2-yl)carbonyl)amino]-3-methoxy-5-chlorobenzamide;

N-(5-chloropyridin-2-yl)-2-[((4-((2-(cyanomethyl)imidazolin-1-yl)methyl)-3-chlorothiophen-2-yl)carbonyl)amino]-3-methoxy-5-chlorobenzamide; and N-(5-chloropyridin-2-yl)-2-[((4-((4-(pyrimidin-2-yl)piperazin-1-yl)methyl)-3-chlorothiophen-2-yl)carbonyl)amino]-3-methoxy-5-chlorobenzamide.

27. The compound of claim 22 wherein the N-heterocylic ring is substituted by one or more substituents selected from the group consisting of alkyl, oxo, —$OR^5$=$N(R^{17})$, —C(O)

OR$^5$, —N(R$^5$)R$^6$, —C(O)N(R$^5$)R$^6$, —(R$^8$—O)$_r$R$^5$, and heterocyclyl (optionally substituted by one or more substituents selected from the group consisting of alkyl, aryl, aralkyl, halo, haloalkyl, —OR$^5$, —C(O)OR$^5$, —N(R$^5$)R$^6$, and —C(O)N(R$^5$)R$^6$), where R$^5$ and R$^6$ are each independently hydrogen, alkyl, aryl or aralkyl;

each R$^8$ is independently a straight or branched alkylene, alkylidene or alkylidyne chain;

each R$^{17}$ is independently hydrogen, alkyl, aryl, aralkyl, cyano, —OR$^5$, —R$^8$—OR$^5$, or —C(O)OR$^5$, —R$^8$—C(O)OR$^5$, —C(O)—N(R$^5$)R$^6$, —R$^8$—C(O)—N(R$^5$)R$^6$ where R$^5$ and R$^6$ are independently each hydrogen, alkyl, aryl or aralkyl, and each R$^8$ is independently a straight or branched alkylene, alkylidene or alkylidyne chain.

28. The compound of claim 27 wherein the N-heterocylic ring is substituted by =N(R$^{17}$) and is optionally substituted by one or more substituents selected from the group consisting of alkyl, oxo, —OR$^5$, —C(O)OR$^5$, —N(R$^5$)R$^6$, —C(O)N(R$^5$)R$^6$, and —(R$^8$—O)$_r$—R$^5$, where R$^5$ and R$^6$ are each independently hydrogen, alkyl, aryl or aralkyl;

each R$^8$ is independently a straight or branched alkylene, alkylidene or alkylidyne chain;

each R$^{17}$ is independently hydrogen, alkyl, aryl, aralkyl, cyano, —OR$^5$, —R$^8$—OR$^5$, —C(O)OR$^5$, —R$^8$—C(O)OR$^5$, —C(O)—N(R$^5$)R$^6$, or —R$^8$—C(O)—N(R$^5$)R$^6$ where R$^5$ and R$^6$ are independently each hydrogen, alkyl, aryl or aralkyl, and each R$^8$ is independently a straight or branched alkylene, alkylidene or alkylidyne chain.

29. The compound of claim 28 selected from the group consisting of:

N-(5-chloropyridin-2-yl)-2-[((4-((2-imino-5-methyltetrahydrooxazol-3-yl)methyl)-3-chlorothiophen-2-yl)carbonyl)amino]-3-methoxy-5-chlorobenzamide;

N-(5-chloropyridin-2-yl)-2-[((4-((2-imino-5,5(dimethyl)tetrahydrooxazol-3-yl)methyl)-3-chlorothiophen-2-yl)carbonyl)amino]-3-methoxy-5-chlorobenzamide;

N-(5-chloropyridin-2-yl)-2-[((4-((2-ethylimino-5,5-(dimethyl)tetrahydrooxazol-3-yl)methyl)-3-chlorothiophen-2-yl)carbonyl)amino]-3-methoxy-5-chlorobenzamide;

N-(5-chloropyridin-2-yl)-2-[((4-((2- imino-5,5-methyltetrahydrooxazol-3-yl)methyl)-3-chlorothiophen-2-yl)carbonyl)amino]-3-methoxy-5-chlorobenzamide;

N-(5-chloropyridin-2-yl)-2-[((4-((2-imino-5(S)-methyltetrahydrooxazol-3-yl)methyl)-3-chlorothiophen-2-yl)carbonyl)amino]-3-methoxy-5-chlorobenzamide;

N-(5-chloropyridin-2-yl)-2-[((4-((2-imino tetrahydrooxazol-3-yl) methyl)-3-yl)carbonyl)amino]-3-methoxy-5-chlorobenzamide;

N-(5-chloropyridin-2-yl)-2-[((4-((2-iminotetrahydrooxazol-3-yl)methyl)-3-chlorothiophen-2-yl)carbonyl)amino]-3-methoxy-5-chlorobenzamide;

N-(5-chloropyridin-2-yl)-2-[((4-((2-imino-4-methyltetrahydrooxazol-3-yl)methyl)-3-chlorothiophen-2-yl)carbonyl)amino]-3-methoxy-5-chlorobenzamide;

N-(5-chloropyridin-2-yl)-2-[((4-((trans4,5-dimethyl-2-iminotetrahydrooxazol-3-yl)methyl)-3-chlorothiophen-2-yl)carbonyl)amino]-3-methoxy-5-chlorobenzamide;

N-(5-chloropyridin-2-yl)-2-[((4-((cis4,5-dimethyl-2-iminotetrahydrooxazol-3-yl)methyl)-3-chlorothiophen-2-yl)carbonyl)amino]-3-methoxy-5-chlorobenzamide;

N-(5-chloropyridin-2-yl)-2-[((4-((3-methyl-2-imino-2,3-dihydroimidazol-1-yl)methyl)-3-chlorothiophen-2-yl)carbonyl)amino]-3-methoxy-5-chlorobenzamide;

N-(5-chloropyridin-2-yl)-2-[((4-((2-imino-tetrahydroimidazol-1-yl)methyl)-3-chlorothiophen-2-yl)carbonyl)amino]-3-methoxy-5-chlorobenzamide;

N-(5-chloropyridin-2-yl)-2-[((4-((2-imino-1,2-dihydropyrimidin-1-yl)methyl)-3-chlorothiophen-2-yl)carbonyl)amino]-3-methoxy-5-chlorobenzamide;

N-(5-chloropyridin-2-yl)-2-[((4-((2-imino-4-(hydroxymethyl)tetrahydrooxazol-3-yl)methyl)-3-chlorothiophen-2-yl)carbonyl)amino]-3-methoxy-5-chlorobenzamide;

N-(5-chloropyridin-2-yl)-2-[((4-((2-iminotetrahydrothiazol-3-yl)methyl)-3-chlorothiophen-2-yl)carbonyl)amino]-3-methoxy-5-chlorobenzamide;

N-(5-chloropyridin-2-yl)-2-[((4-((2-imino-4-oxoimidazolin-1-yl)methyl)-3-chlorothiophen-2-yl)carbonyl)amino]-3-methoxy-5-chlorobenzamide;

N-(5-chloropyridin-2-yl)-2-[((4-((tetrahydro-2-imino-2H-pyrimidin-1-yl)methyl)-3-chlorothiophen-2-yl)carbonyl)amino]-3-methoxy-5-chlorobenzamide;

N-(5-chloropyridin-2-yl)-2-[((4-((2-(methoxycarbonylamino)imidazolin-1-yl)methyl)-3-chlorothiophen-2-yl)carbonyl)amino]-3-methoxy-5-chlorobenzamide;

N-(5-chloropyridin-2-yl)-2-[((4-((2-(cyanoimino)tetrahydroimidazol-1-yl)methyl)-3-chlorothiophen-2-yl)carbonyl)amino]-3-methoxy-5-chlorobenzamide;

N-(5-chloropyridin-2-yl)-2-[((4-((2-imino-3-((phenylamino)carbonyl)tetrahydroimidazol-1-yl)methyl)-3-chlorothiophen-2-yl)carbonyl)amino]-3-methoxy-5-chlorobenzamide;

N-(5-chloropyridin-2-yl)-2-[((4-((cis4,5-dimethoxy-2-iminotetrahydroimidazol-1 -yl)methyl)-3-chlorothiophen-2-yl)carbonyl)amino]-3-methoxy-5-chlorobenzamide;

N-(5-chloropyridin-2-yl)-2-[((4-((2-amino4-imino-1,4-dihydropyrimidin-1-yl)methyl)-3-chlorothiophen-2-yl)carbonyl)amino]-3-methoxy-5-chlorobenzamide;

N-(5-chloropyridin-2-yl)-2-[((4-((2-((2-hydroxyethyl)imino)tetrahydroimidazol-1 -yl)methyl)-3-chlorothiophen-2-yl)carbonyl)amino]-3-methoxy-5-chlorobenzamide;

N-(5-chloropyridin-2-yl)-2-[((4-((2-iminopiperidin-1-yl)methyl)-3-chlorothiophen-2-yl)carbonyl)amino]-3-methoxy-5-chlorobenzamide;

N-(5-chloropyridin-2-yl)-2-[((4-((4-imino-1 (4H)-pyridinyl)methyl)-3-chlorothiophen-2-yl)carbonyl)amino]-3-methoxy-5-chlorobenzamide;

N-(5-chloropyridin-2-yl)-2-[((4-((2-imino-1 (2M)-pyridin-1-yl)methyl)-3-chlorothiophen-2-yl)carbonyl)amino]-3-methoxy-5-chlorobenzamide;

N-(5-chloropyridin-2-yl)-2-[((4-((2-(ethylimino)pyrrolidin-1-yl)methyl)-3-chlorothiophen-2-yl)carbonyl)amino]-3-methoxy-5-chlorobenzamide; and N-(5-chloropyridin-2-yl)-2-[((4-((2-(((aminocarbonyl)methyl)imino)tetrahydroimidazol-1-yl)methyl)-3-chlorothiophen-2-yl)carbonyl)amino]-3-methoxy-5-chlorobenzamide.

30. The compound of claim 22 wherein the N-heterocylic ring is substituted by —N(R$^5$)R$^6$ and optionally substituted by one or more substituents selected from the group consisting of alkyl, oxo, —N(R$^5$)R$^6$, —OR$^5$, and —C(O)N(R$^5$)R$^6$, where R$^5$ and R$^6$ are each independently hydrogen, alkyl, aryl or aralkyl.

31. The compound of claim 30 selected from the group consisting of:

N-(5-chloropyridin-2-yl)-2-[((4-((2-aminoimidazol-1-yl)methyl)-3-chlorothiophen-2-yl)carbonyl)amino]-3-methoxy-5-chlorobenzamide;

N-(5-chloropyridin-2-yl)-2-[((4-((5-aminotetrazol-1-yl)methyl)-3-chlorothiophen-2-yl)carbonyl)amino]-3-methoxy-5-chlorobenzamide;

N-(5-chloropyridin-2-yl)-2-[((4-((3-amino-1,2,4-triazol-1-yl)methyl)-3-chlorothiophen-2-yl)carbonyl)amino]-3-methoxy-5-chlorobenzamide;

N-(5-chloropyridin-2-yl)-2-[((4-((3,5-diamino-4H-1,2,4-triazol-4-yl)methyl)-3-chlorothiophen-2-yl)carbonyl)amino]-3-methoxy-5-chlorobenzamide;

N-(5-chloropyridin-2-yl)-2-[((4-((4-amino-5-(aminocarbonyl)imidazol-1-yl)methyl)-3-chlorothiophen-2-yl)carbonyl)amino]-3-methoxy-5-chlorobenzamide;

N-(5-chloropyridin-2-yl)-2-[((4-((2,6-diaminopurin-9-yl)methyl)-3-chlorothiophen-2-yl)carbonyl)amino]-3-methoxy-5-chlorobenzamide;

N-(5-chloropyridin-2-yl)-2-[((4-((2,6-diaminopurin-7-yl)methyl)-3-chlorothiophen-2-yl)carbonyl)amino]-3-methoxy-5-chlorobenzamide;

N-(5-chloropyridin-2-yl)-2-[((4-((5-amino-2-oxo-2H-pyrimidin-1-yl)methyl)-3-chlorothiophen-2-yl)carbonyl)amino]-3-methoxy-5-chlorobenzamide;

N-(5-chloropyridin-2-yl)-2-[((4-((6-aminopurin-9-yl)methyl)-3-chlorothiophen-2-yl)carbonyl)amino]-3-methoxy-5-chlorobenzamide;

N-(5-chloropyridin-2-yl)-2-[((4-((6-aminopurin-7-yl)methyl)-3-chlorothiophen-2-yl)carbonyl)amino]-3-methoxy-5-chlorobenzamide;

N-(5-chloropyridin-2-yl)-2-[((4-((2-amino-6-oxopurin-9-yl)methyl)-3-chlorothiophen-2-yl)carbonyl)amino]-3-methoxy-5-chlorobenzamide;

N-(5-chloropyridin-2-yl)-2-[((4-((2-amino-6-oxopurin-7-yl)methyl)-3-chlorothiophen-2-yl)carbonyl)amino]-3-methoxy-5-chlorobenzamide;

N-(5-chloropyridin-2-yl)-2-[((4-((5-(dimethylamino)-1,2,4-oxadiazol-3-yl)methyl)-3-chlorothiophen-2-yl)carbonyl)amino]-3-methoxy-5-chlorobenzamide;

N-(5-chloropyridin-2-yl)-2-[((4-((5-amino-1,2,4-oxadiazol-3-yl)methyl)-3-chlorothiophen-2-yl)carbonyl)amino]-3-methoxy-5-chlorobenzamide;

N-(5-chloropyridin-2-yl)-2-[((4-((2-(methylamino)imidazol-1-yl)methyl)-3-chlorothiophen-2-yl)carbonyl)amino]-3-methoxy-5-chlorobenzamide;

N-(5-chloropyridin-2-yl)-2-[((4-((2,4-diamino-6-hydroxypyrimidin-5-yl)methyl)-3-chlorothiophen-2-yl)carbonyl)amino]-3-methoxy-5-chlorobenzamide;

N-(5-chloropyridin-2-yl)-2-[((4-((2-(ethylamino)imidazol-1-yl)methyl)-3-chlorothiophen-2-yl)carbonyl)amino]-3-methoxy-5-chlorobenzamide;

N-(5-chloropyridin-2-yl)-2-[((4-((2-(1-methylethyl)aminolmidazol-1-yl)methyl)-3-chlorothiophen-2-yl)carbonyl)amino]-3-methoxy-5-chlorobenzamide;

N-(5-chloropyridin-2-yl)-2-[((4-((3-dimethylamino-5-methylpyrazol-1-yl)methyl)-3-chlorothiophen-2-yl)carbonyl)amino]-3-methoxy-5-chlorobenzamide; and N-(5-chloropyridin-2-yl)-2-[((4-((3-dimethylamino-5-methylpyrazol-2-yl)methyl)-3-chlorothiophen-2-yl)carbonyl)amino]-3-methoxy-5-chlorobenzamide.

32. The compound of claim 11 wherein:

each $R^{14}$ is independently alkyl, —$R^8$—CN, —C($R^7$)H—$R^8$—N($R^{10}$)$R^{11}$, —C($R^7$)H—$R^8$—N$^{\oplus}$($R^9$)($R^{16}$)$_2$, —C($R^7$)H—O$R^5$, —C($R^7$)H—$R^8$—O$R^5$, —C($R^7$)H—O—$R^{15}$, —C($R^7$)H—S(O)$_p$—$R^{15}$ (where p is 0 to 2), —C($R^7$)H—N($R^5$)—($R^5$)$_t$—$R^5$ (where t is 1 to 6), —C($R^7$)H—N($R^5$)—$R^8$—[CH(OH)]$_t$CH$_2$—O$R^5$ (where t is 1 to 6), —C($R^7$)H—N($R^5$)—S(O)$_2$—N($R^{10}$)$R^{11}$, —C($R^7$)H—O—N($R^5$)$R^6$, or heterocyclyl (wherein the heterocyclyl radical is not attached to the radical of formula (i) through a nitrogen atom and is optionally substituted by alkyl, aryl, aralkyl, halo, haloalkyl, oxo, —O$R^5$, —C(O)O$R^5$, —N($R^5$)$R^6$ or —C(O)N($R^5$)$R^6$), where $R^5$ and $R^6$ are each independently hydrogen, alkyl, aryl or aralkyl;

each $R^7$ is independently hydrogen or alkyl;

each $R^8$ is independently a straight or branched alkylene, alkylidene or alkylidyne chain;

$R^{10}$ and $R^{11}$ are each independently hydrogen, alkyl, haloalkyl, aryl, aralkyl, formyl, cyano, —$R^8$—CN, —O$R^5$, —$R^8$—O$R^5$, —S(O)$_p$—$R^{15}$ (where p is 0 to 2), —$R^8$—S(O)$_p$—$R^{15}$ (where p is 0 to 2), —N($R^5$)$R^6$, —$R^8$—N($R^5$)$R^6$, —$R^5$—C(O)O$R^5$, —C(O)—$R^{15}$, —C(O)NH$_2$, —$R^8$—C(O)NH$_2$, —C(S)NH$_2$, —C(O)—S—$R^5$, —C(O)—N($R^5$)$R^{15}$, —$R^8$—C(O)—N($R^5$)$R^{15}$, —C(S)—N($R^5$)$R^{15}$, —$R^8$—N($R^5$)—C(O)H, —$R^8$—N($R^5$)—C(O)$R^{15}$, —C(O)O—$R^8$—N($R^5$)$R^6$, —C(N($R^5$)$R^6$)=C($R^{18}$)$R^{10}$, —$R^8$—N($R^5$)-P(O)(O$R^5$)$_2$, cycloalkyl (optionally substituted by one or more substituents selected from the group consisting of alkyl, halo and —O$R^5$), heterocyclyl (optionally substituted by alkyl, aryl, aralkyl, halo, haloalkyl, oxo, —O$R^5$, —$R^8$—O$R^5$, —C(O)O$R^5$, —S(O)$_p$—$R^9$ (where p is 0 to 2), —$R^8$—S(O)$_p$—$R^9$ (where p is 0 to 2), —N($R^5$)$R^6$ or —C(O)N($R^5$)$R^6$), or heterocyclylalkyl (optionally substituted by one or more substituents selected from the group consisting of alkyl, aryl, aralkyl, halo, haloalkyl, oxo, —O$R^5$, —$R^8$—O$R^5$, —C(O)O$R^5$, —S(O)$_p$—$R^9$ (where p is 0 to 2), —$R^8$—S(O)$_p$—$R^9$ (where p is 0 to 2), —N($R^5$)$R^6$ and —C(O)N($R^5$)$R^6$), where $R^5$ and $R^6$ are each independently hydrogen, alkyl, aryl or aralkyl;

each $R^8$ is independently a straight or branched alkylene, alkylidene or alkylidyne chain;

each $R^9$ is independently alkyl, aryl or aralkyl;

each $R^{15}$ is independently alkyl, cycloalkyl, haloalkyl, aryl, aralkyl, —$R^8$—O—C(O)—$R^5$, —$R^8$—O$R^5$, —N($R^5$)$R^6$, —R N($R^5$)$R^6$, —$R^8$—C(O)O$R^5$, heterocyclyl (optionally substituted by one or more substituents selected from the group consisting of alkyl, aryl, aralkyl, halo, haloalkyl, —O$R^5$, —$R^8$—O$R^5$, —C(O)O$R^5$, —N($R^5$)$R^6$, and —C(O)N($R^5$)$R^6$), or heterocyclylalkyl (optionally substituted by one or more substituents selected from the group consisting of alkyl, aryl, aralkyl, halo, haloalkyl, —O$R^5$, —$R^8$—O$R^5$, —C(O)O$R^5$, —N($R^5$)$R^6$, and —C(O)N($R^5$)$R^6$), where $R^5$ and $R^6$ are independently each hydrogen, alkyl, aryl or aralkyl, and each $R^8$ is independently a straight or branched alkylene, alkylidene or alkylidyne chain;

or $R^5$ and $R^{15}$ together with the nitrogen to which they are attached form a N-heterocyclic ring containing zero to three additional hetero atoms, where the N-heterocyclic ring is optionally substituted by one or more substituents selected from the group consisting of alkyl, aryl, aralkyl, amino, monoalkylamino, dialkylamino, —O$R^5$, —C(O)O$R^5$, aminocarbonyl, monoalkylaminocarbonyl, and dialkylaminocarbonyl, where each $R^5$ is hydrogen, alkyl, aryl or aralkyl; and $R^{18}$ is hydrogen, alkyl, aryl, aralkyl, cyano, —C(O)O$R^5$, or —NO$_2$;

or $R^{10}$ and $R^{11}$ together with the nitrogen to which they are attached form a N-heterocyclic ring containing zero to three additional hetero atoms, where the N-heterocylic ring is optionally substituted by one or more substituents selected from the group consisting of alkyl, halo, haloalkyl, aryl, aralkyl, oxo, nitro, cyano, $-R^8-CN$, $=N(R^{17})$, $-OR^5$, $-C(O)OR^5$, $-R^8-C(O)OR^5$, $-N(R^5)R^6$, $-R^8-N(R^5)R^6$, $-C(O)N(R^5)R^6$, $-R^8-C(O)N(R^5)R^6$, $-N(R^5)-N(R^5)R^6$, $-C(O)R^5$, $-C(O)-(R^8-O)_t-R^5$ (where t is 1 to 6), $-S(O)_p-R^9$ (where p is 0 to 2), $-R^8-S(O)_p-R^9$ (where p is 0 to 2), $-(R^8-O)_t-R^5$ (where t is 1 to 6), and heterocyclyl (optionally substituted by one or more substituents selected from the group consisting of alkyl, aryl, aralkyl, halo, haloalkyl, $-OR^5$, $-C(O)OR^5$, $-N(R^5)R^6$, and $-C(O)N(R^5)R^6$), where $R^5$ and $R^6$ are each independently hydrogen, alkyl, aryl or aralkyl;

each $R^8$ is independently a straight or branched alkylene, alkylidene or alkylidyne chain;

each $R^9$ is independently alkyl, aryl or aralkyl;

each $R^{17}$ is independently hydrogen, alkyl, aryl, aralkyl, cyano, $-OR^5$, $-R^8-OR^5$, $-C(O)OR^5$, $-R^8-C(O)OR^5$, $-C(O)-N(R^5)R^6$, or $-R^8-C(O)-N(R^5)R^6$, where $R^5$ and $R^6$ are independently each hydrogen, alkyl, aryl or aralkyl, and each $R^8$ is independently a straight or branched alkylene, alkylidene or alkylidyne chain;

each $R^{16}$ is independently alkyl, aryl, aralkyl, $-R^8-OR^5$, $-R^8-N(R^5)R^6$, cycloalkyl (optionally substituted by one or more substituents selected from the group consisting of alkyl, halo and $-OR^5$), heterocyclyl (optionally substituted by alkyl, aryl, aralkyl, halo, haloalkyl, $-OR^5$, $-C(O)OR^5$, $-N(R^5)R^6$ or $-C(O)N(R^5)R^6$), or heterocyclylalkyl (optionally substituted by one or more substituents selected from the group consisting of alkyl, aryl, aralkyl, halo, haloalkyl, $-OR^5$, $-C(O)OR^5$, $-N(R^5)R^6$ and $-C(O)N(R^5)R^6$), where $R^5$ and $R^6$ are independently each hydrogen, alkyl, aryl or aralkyl, and each $R^8$ is independently a straight or branched alkylene, alkylidene or alkylidyne chain; or both R16,s together with the nitrogen to which they are attached (and wherein the $R^9$ substituent is not present) form an aromatic N-heterocyclic ring containing zero to three additional hetero atoms, where the N-heterocyclic ring is optionally substituted by one or more substituents selected from the group consisting of alkyl, aryl, aralkyl, $-OR^5$, $-R^8OR^5$, $-C(O)OR^5$, $-R^8-C(O)OR^5$, $-N(R^5)R^6$, $-R^8-N(R^5)R^6$, $-C(O)R^5$, $-C(O)-(R^8-O)_tR^5$ (where t is 1 to 6), and $-(R^8-O)_t-R^5$ (where t is I to 6), where $R^5$ and $R^6$ are independently each hydrogen, alkyl, aryl or aralkyl, and each $R^8$ is independently a straight or branched alkylene, alkylidene or alkylidyne chain.

33. The compound of claim 32 selected from the group consisting of:

N-(5-chloropyridin-2-yl)-2-[((4-((pyridinium-1-yl)methyl)-3-chlorothiophen-2-yl)carbonyl)amino]-3-hydroxy-5-chlorobenzamide;

N-(5-chloropyridin-2-yl)-2-[((4-((N'-methyl—N'-(2-(hydroxyethoxy)ethyl)amino)methyl)-3-chlorothiophen-2-yl)carbonyl)amino]-3-methoxy-5-chlorobenzamide;

N-(5-chloropyridin-2-yl)-2-[((4-((methylsulfinyl)methyl)-3-chlorothiophen-2-yl)carbonyl)amino]-3-methoxy-5-chlorobenzamide;

N-(5-chloropyridin-2-yl)-2-[((4-((N'-methyl—N'-(2,3-dihydroxypropyl)amino)methyl)-3-chlorothiophen-2-yl)carbonyl)amino]-3-methoxy-5-chlorobenzamide;

N-(5-chloropyridin-2-yl)-2-[((4-(((2-hydroxyethyl)sulfinyl)methyl)-3-chlorothiophen-2-yl)carbonyl)amino]-3-methoxy-5-chlorobenzamide;

N-(5-chloropyridin-2-yl)-2-[((4-((pyridinium-1-yl)methyl)-3-chlorothiophen-2-yl)carbonyl)amino]-3-methoxy-5-chlorobenzamide;

N-(5-chloropyridin-2-yl)-2-[((4-methyl-3-chlorothiophen-2-yl)carbonyl)amino]-3-methoxy-5-chlorobenzamide;

N-(5-chloropyridin-2-yl)-2-[((4-cyanomethyl-3-chlorothiophen-2-yl)carbonyl)amino]-3-methoxy-5-chlorobenzamide;

N-(5-chloropyridin-2-yl)-2-[((4-(2-methylaminoethyl)-3-chlorothiophen-2-yl)carbonyl)amino]-3-methoxy-5-chlorobenzamide;

N-(5-chloropyridin-2-yl)-2-[((4-(hydroxy)methyl-3-chlorothiophen-2-yl)carbonyl)amino]-3-methoxy-5-chlorobenzamide;

N-(5-chloropyridin-2-yl)-2-[((4-(((imidazol-2-yl)thio)methyl)-3-chlorothiophen-2-yl)carbonyl)amino]-3-methoxy-5-chlorobenzamide;

N-(5-chloropyridin-2-yl)-2-[((4-((imidazolin-2-yl)thio)methyl)-3-chlorothiophen-2-yl)carbonyl)amino]-3-methoxy-5-chlorobenzamide;

N-(5-chloropyridin-2-yl)-2-[((4-(((5-hydroxymethyl-1-methylimidazol-2-yl)thio)methyl)-3-chlorothiophen-2-yl)carbonyl)amino]-3-methoxy-5-chlorobenzamide;

N-(5-chloropyridin-2-yl)-2-[((4-(((diethylamino)oxy)methyl)-3-chlorothiophen-2-yl)carbonyl)amino]-3-methoxy-5-chlorobenzamide; and N-(5-chloropyridin-2-yl)-2-[((4-(imidazolin-2-yl)-3-chlorothiophen-2-yl)carbonyl)amino]-3-methoxy-5-chlorobenzamide.

34. The compound of claim 11 wherein:

each $R^{14}$ is independently $-C(R^7)H-N(R^{10})-C(NR^{17})-N(R^{10})R^{11}$ $-C(R^7)H-N(R^{10})-C(NR^{17})-R^{10}$, or $-C(R^7)H-C(NR^{17})-N(R^5)R^6$, where $R^5$ and $R^6$ are each independently hydrogen, alkyl, aryl or aralkyl;

each $R^7$ is independently hydrogen or alkyl;

each $R^9$ is independently alkyl, aryl or aralkyl;

$R^{10}$ and $R^{1"}$ are each independently hydrogen, alkyl, haloalkyl, aryl, aralkyl, formyl, cyano, $-R^8-CN$, $-OR^5$, $-R^8-OR^5$, $-S(O)p-R^{15}$ (where p is 0 to 2), $-R^8-S(O)_p-R^{15}$ (where p is 0 to 2), $-N(R^5)R^6$, $-R^8-N(R^5)R^6$, $-R^8-C(O)OR^5$, $-C(O)-R^{15}$, $-C(O)NH_2$, $-R^8-C(O)NH_2$, $-C(S)NH_2$, $-C(O)-S-R^5$, $-C(O)-N(R^5)R^{15}$, $-R^8-C(O)-N(R^5)R^{15}$, $-C(S)-N(R^5)R^{15}$, $-R^8-N(R^5)-C(O)H$, $-R^8-N(R^5)-C(O)R^{15}$, $-C(O)O-R^8-N(R^5)R^6$, $-C(N(R^5)R^6)=C(R^{18})R^{10}$, $-R^8-N(R^5)-P(O)(OR^5)_2$, cycloalkyl (optionally substituted by one or more substituents selected from the group consisting of alkyl, halo and $-OR^5$), heterocyclyl (optionally substituted by alkyl, aryl, aralkyl, halo, haloalkyl, oxo, $-OR^5$, $-R^8-OR^5$, $-C(O)OR^5$, $-S(O)p-R9$ (where p is 0 to 2), $-R^8-S(O)_p-R^9$ (where p is 0 to 2), $-N(R^5)R^6$ or $-C(O)N(R^5)R^6$), or heterocyclylalkyl (optionally substituted by one or more substituents selected from the group consisting of alkyl, aryl, aralkyl, halo, haloalkyl, oxo, $-OR^5$, $-R^8-OR$, $-C(O)OR^5$, $-S(O)_p-R^9$ (where p is 0 to 2), $-R^8-S(O)_p-R^9$ (where p is 0 to 2), $-N(R^5)R^6$ and $-C(O)N(R^5)R^6$), where $R^5$ and $R^6$ are each independently hydrogen, alkyl, aryl or aralkyl;

each $R^8$ is independently a straight or branched alkylene, alkylidene or alkylidyne chain;

each $R^9$ is independently alkyl, aryl or aralkyl;

each $R^{15}$ is independently alkyl, cycloalkyl, haloalkyl, aryl, aralkyl, —$R^8$—O—C(O)—$R^5$, —$R^8$—O$R^5$, —N($R^5$)$R^6$, —$R^8$—N($R^5$)$R^6$, —$R^8$—C(O)O$R^5$, heterocyclyl (optionally substituted by one or more substituents selected from the group consisting of alkyl, aryl, aralkyl, halo, haloalkyl, —O$R^5$, —$R^8$—O$R^5$, —C(O)O$R^5$, —N($R^5$)$R^6$, and —C(O)N($R^5$)$R^6$), or heterocyclylalkyl (optionally substituted by one or more substituents selected from the group consisting of alkyl, aryl, aralkyl, halo, haloalkyl, —O$R^5$, —$R^8$—O$R^5$, —C(O)O$R^5$, —N($R^5$)$R^6$, and —C(O)N($R^5$)$R^6$), where $R^5$ and $R^6$ are independently each hydrogen, alkyl, aryl or aralkyl, and each $R^8$ is independently a straight or branched alkylene, alkylidene or alkylidyne chain;

or $R^5$ and $R^{15}$ together with the nitrogen to which they are attached form a N-heterocyclic ring containing zero to three additional hetero atoms, where the N-heterocyclic ring is optionally substituted by one or more substituents selected from the group consisting of alkyl, aryl, aralkyl, amino, monoalkylamino, dialkylamino, —O$R^5$, —C(O)O$R^5$, aminocarbonyl, monoalkylaminocarbonyl, and dialkylaminocarbonyl, where each $R^5$ is hydrogen, alkyl, aryl or aralkyl; and $R^{18}$ is hydrogen, alkyl, aryl, aralkyl, cyano, —C(O)O$R^5$, or —NO$_2$; or $R^{10}$ and $R^{11}$ together with the nitrogen to which they are attached form a N-heterocyclic ring containing zero to three additional hetero atoms, where the N-heterocylic ring is optionally substituted by one or more substituents selected from the group consisting of alkyl, halo, haloalkyl, aryl, aralkyl, oxo, nitro, cyano, —$R^8$—CN, =N($R^{17}$), —O$R^5$, —C(O)O$R^5$, —$R^8$—C(O)O$R^5$, —N($R^5$)$R^6$, —$R^8$—N($R^5$)$R^6$, —C(O)N($R^5$)$R^6$, —$R^8$—C(O)N($R^5$)$R^6$, —N($R^5$)—N($R^5$)$R^6$, —C(O)$R^5$, —C(O)—($R^8$—O)$_t$—$R^5$ (where t is 1 to 6), —S(O)$_p$—$R^9$ (where p is 0 to 2), —$R^8$—S(O)$_p$—$R^9$ (where p is 0 to 2), —($R^8$—O)$_t$—$R^5$ (where t is 1 to 6), and heterocyclyl (optionally substituted by one or more substituents selected from the group consisting of alkyl, aryl, aralkyl, halo, haloalkyl, —O$R^5$, —C(O)O$R^5$, —N($R^5$)$R^6$, and —C(O)N($R^5$)$R^6$), where $R^5$ and $R^6$ are each independently hydrogen, alkyl, aryl or aralkyl;

each R8 is independently a straight or branched alkylene, alkylidene or alkylidyne chain;

each $R^9$ is independently alkyl, aryl or aralkyl;

each $R^{17}$ is independently hydrogen, alkyl, aryl, aralkyl, cyano, —O$R^5$, —$R^8$—O$R^5$, —C(O)O$R^5$, —$R^8$—C(O)O$R^5$, —C(O)—N($R^5$)$R^6$, or —$R^8$—C(O)—N($R^5$)$R^6$, where $R^5$ and $R^6$ are independently each hydrogen, alkyl, aryl or aralkyl, and each $R^8$ is independently a straight or branched alkylene, alkylidene or alkylidyne chain;

each $R^{17}$ is independently hydrogen, alkyl, aryl, aralkyl, cyano, —O$R^5$, —$R^8$—O$R^5$, —C(O)O$R^5$, —$R^8$—C(O)O$R^5$, —C(O)—N($R^5$)$R^6$, or —$R^8$—C(O)—N($R^5$)$R^6$, where $R^5$ and $R^6$ are independently each hydrogen, alkyl, aryl or aralkyl, and each R8 is independently a straight or branched alkylene, alkylidene or alkylidyne chain.

35. The compound of claim 34 selected from the group consisting of:

N-(5-chloropyridin-2-yl)-2-[((4-(((amidino)(methyl)amino)methyl)-3-chlorothiophen-2-yl)carbonyl)amino]-3-methoxy-5-chlorobenzamide;

N-(5-chloropyridin-2-yl)-2-[((4-((N'-(1-iminoethyl)—N'-methylamino)methyl)-3-chlorothiophen-2-yl)carbonyl)amino]-3-methoxy-5-chlorobenzamide;

N-(5-chloropyridin-2-yl)-2-[((4-(N',N''-dimethyl—N'''-cyanoguanidino)methyl-3-chlorothiophen-2-yl)carbonyl)amino]-3-methoxy-5-chlorobenzamide;

N-(5-chloropyridin-2-yl)-2-[((4-(N'-methyl-N''-hydroxyguanidino)methyl-3-chlorothiophen-2-yl)carbonyl)amino]-3-methoxy-5-chlorobenzamide;

N-(5-chloropyridin-2-yl)-2-[((4-(N'-methyl-N''-(2-aminoethyl)-N'''-cyanoguanidino)methyl-3-chlorothiophen-2-yl)carbonyl)amino]-3-methoxy-5-chlorobenzamide;

N-(5-chloropyridin-2-yl)-2-[((4-(N'-methyl-N''-aminoguanidino)methyl-3-chlorothiophen-2-yl)carbonyl)amino]-3-methoxy-5-chlorobenzamide;

N-(5-chloropyridin-2-yl)-2-[((4-(N',N''-dimethyl—N'''-(aminocarbonyl)guanidino)methyl-3-chlorothiophen-2-yl)carbonyl)amino]-3-methoxy-5-chlorobenzamide;

N-(5-chloropyridin-2-yl)-2-[((4-((N'-(imino(phenyl)methyl)amino)methyl)-3-chlorothiophen-2-yl)carbonyl)amino]-3-methoxy-5-chlorobenzamide;

N-(5-chloropyridin-2-yl)-2-[((4-((N'-(i-imino-2-(aminocarbonyl)ethyl)amino)methyl)-3-chlorothiophen-2-yl)carbonyl)amino]-3-methoxy-5-chlorobenzamide;

N-(5-chloropyridin-2-yl)-2-[((4-((N'-(1-imino4,4,4-trifluorobutyl)amino)methyl)-3-chlorothiophen-2-yl)carbonyl)amino]-3-methoxy-5-chlorobenzamide;

N-(5-chloropyridin-2-yl)-2-[((4-((N'-(imino(pyridin4-yl)methyl)amino)methyl)-3-chlorothiophen-2-yl)carbonyl)amino]-3-methoxy-5-chlorobenzamide;

N-(5-chloropyridin-2-yl)-2-[((4-((N'-(imino(thiophen-2-yl)methyl)amino)methyl)-3-chlorothiophen-2-yl)carbonyl)amino]-3-methoxy-5-chlorobenzamide;

N-(5-chloropyridin-2-yl)-2-[((4-((N'-(imino(pyrazin-2-yl)methyl)amino)methyl)-3-chlorothiophen-2-yl)carbonyl)amino]-3-methoxy-5-chlorobenzamide;

N-(5-chloropyridin-2-yl)-2-[((4-((N'-(cyclopropyl(imino)methyl)amino)methyl)-3-chlorothiophen-2-yl)carbonyl)amino]-3-methoxy-5-chlorobenzamide;

N-(5-chloropyridin-2-yl)-2-[((4-((N'-ethyl—N'-(3-cyano-1-iminopropyl)amino)methyl)-3-chlorothiophen-2-yl)carbonyl)amino]-3-methoxy-5-chlorobenzamide;

N-(5-chloropyridin-2-yl)-2-[((4-((N'-methyl—N'-(1-imino-4,4,4-trifluorobutyl)amino)methyl)-3-chlorothiophen-2-yl)carbonyl)amino]-3-methoxy-5-chlorobenzamide; and N-(5-chloropyridin-2-yl)-2-[((4-(2-amino-2-(hydroxylmino)ethyl)-3-chlorothiophen-2-yl)carbonyl)amino]-3-methoxy-5-chlorobenzamide.

36. The compound of claim 1 wherein:

A is =N—;

m is 1;

n is 1;

D is —N(H)—C(O)—;

E is —C(O)—N(H)— (where the nitrogen is bonded to the 2-position of the pyridinyl ring);

$R^2$ is —N($R^{10}$)$R^{11}$ where:

$R^{10}$ and $R^{11}$ are each independently hydrogen, alkyl or —$R^8$—O—$R^5$ where $R^8$ is an alkylene chain, and $R^5$ is hydrogen or alkyl; or $R^{10}$ and $R^{11}$ together with the nitrogen to which they are attached form a N-heterocyclic ring containing zero to three additional hetero atoms, where the N-heterocylic ring is optionally substituted by one or more substituents selected from the group consisting of alkyl and —C(O)OR$^5$ where R$^5$ is hydrogen or alkyl;

$R^3$ is a radical of the formula (i):

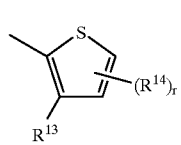

(i)

where r is 1;
$R^{13}$ is halo; and
$R^{14}$ is —C(R$^7$)H—N(R$^{10}$)R$^{11}$ or —C(R$^7$)H—N(R$^5$)—R$^8$—[CH(OH)]$_t$—CH$_2$—OR$^5$ (where t is 1 to 3) where:
  each R$^5$ is independently hydrogen or alkyl;
  R$^7$ is hydrogen;
  R$^8$ is a straight or branched alkylene chain;
  $R^{10}$ and $R^{11}$ are each independently hydrogen, alkyl, formyl, —R$^8$—OR$^5$, —S(O)$_p$—R$^{15}$ (where p is 0 to 2), —R$^8$—N(R$^5$)R$^6$, —R$^8$—C(O)OR$^5$, —C(O)—R$^{15}$, —C(O)NH$_2$, —C(S)NH$_2$, —C(O)—N(R$^5$)R$^{11}$, —C(S)—N(R$^5$)R$^{15}$, cycloalkyl (optionally substituted by —OR$^5$), heterocyclyl (optionally substituted by one or more substituents selected from the group consisting of alkyl, haloalkyl, oxo, —OR$^5$, and —C(O)OR$^5$), or heterocyclylalkyl (optionally substituted by one or more substituents selected from the group consisting of alkyl, haloalkyl, oxo, —OR$^5$, and —C(O)OR$^5$), where:
    each R$^5$ and R$^6$ is independently hydrogen or alkyl;
    each R$^8$ is independently a straight or branched alkylene chain; and
    each R$^{15}$ is alkyl, —R$^8$—OR$^5$, —R$^8$—C(O)OR$^5$, heterocyclyl (optionally substituted by —R$^8$—OR$^5$), or heterocyclylalkyl (optionally substituted by —OR$^5$);
  or $R^{10}$ and $R^{10}$ together with the nitrogen to which they are attached form a N-heterocyclic ring containing zero to three additional hetero atoms, where the N-heterocylic ring is optionally substituted by one or more substituents selected from the group consisting of alkyl, oxo, =N(R$^{17}$), —OR$^5$, —R$^8$—OR$^5$, and —N(R$^5$)R$^6$; where
    each R$^5$ and R$^6$ is independently hydrogen or alkyl;
    R$^8$ is a straight or branched alkylene chain; and
    each R$^{17}$ is independently hydrogen, alkyl, aryl, aralkyl, cyano, —OR$^5$, —R$^8$—OR$^5$, —C(O)OR$^5$, —R$^8$—C(O)OR$^5$, —C(O)—N(R$^5$)R$^6$, or —R$^8$—C(O)—N(R$^5$)R$^6$;

and R$^4$ is in the 5-position and is hydrogen or halo.

37. The compound of claim 36 wherein:
R$^2$ is —N(R$^{10}$)R$^{11}$ where:
  $R^{10}$ and $R^{11}$ are each independently hydrogen, alkyl or —R$^8$—O—R$^5$ where R$^8$ is an alkylene chain, and R$^5$ is hydrogen or alkyl.

38. The compound of claim 37 wherein:
$R^{14}$ is —C(R$^7$)H—N(R$^{10}$)R$^{11}$ where:
  R$^7$ is hydrogen;
  $R^{10}$ and $R^{11}$ are each independently hydrogen, alkyl, formyl, —R$^8$—OR$^5$, —S(O)$_p$—R$^{15}$ (where p is 0 to 2), —R$^8$—N(R$^5$)R$^6$, —R$^8$—C(O)OR$^5$, —C(O)—R$^{15}$, —C(O)NH$_2$, —C(S)NH$_2$, —C(O)—N(R$^5$)R$^{15}$, —C(S)—N(R$^5$)R$^{15}$, cycloalkyl (optionally substituted by —OR$^5$), heterocyclyl (optionally substituted by one or more substituents selected from the group consisting of alky, haloalkyl, oxo, —OR$^5$, and —C(O)OR$^5$), or heterocyclylalkyl (optionally substituted by one or more substituents selected from the group consisting of alkyl, haloalkyl, oxo, —OR$^5$, and —C(O)OR$^5$); where:
    each R$^5$ and R$^6$ is independently hydrogen or alkyl;
    each R$^8$ is independently a straight or branched alkylene chain; and
    each R$^{15}$ is alkyl, —R$^8$—OR$^5$, —R$^8$—C(O)OR$^5$, heterocyclyl (optionally substituted by —R$^8$—OR$^5$), or heterocyclylalkyl (optionally substituted by —OR$^5$);
  or $R^{10}$ and $R^{11}$ together with the nitrogen to which they are attached form a N-heterocyclic ring containing zero to three additional hetero atoms, where the N-heterocylic ring is optionally substituted by one or more substituents selected from the group consisting of alkyl, oxo, =N(R$^{17}$), —OR$^5$, —R$^8$—OR$^5$, and —N(R$^5$)R$^6$; where:
    each R$^5$ and R$^6$ is independently hydrogen or alkyl;
    R$^8$ is straight or branched alkylene chain; and
    each R$^{17}$ is independently hydrogen, alkyl, aryl, aralkyl, cyano, —OR$^5$, —R$^8$OR$^5$, —C(O)OR$^5$, —R$^8$—C(O)OR$^5$, —C(O)—N(R$^5$)R$^6$, or —R$^8$—C(O)—N(R$^5$)R$^6$.

39. The compound of claim 38 selected from the group consisting of:
N-(5-chloropyridin-2-yl)-2-[((4-((N'-methyl—N'-(3-(dimethylamino)propyl)amino)methyl)-3-chlorothiophen-2-yl)carbonyl)amino]-3-(dimethyl)amino-5-chlorobenzamide;
N-(5-chloropyridin-2-yl)-2-[((4-((N'-methyl—N'-(2-(dimethylamino)ethyl)amino)methyl)-3-chlorothiophen-2-yl)carbonyl)amino]-3-(dimethyl)amino-5-chlorobenzamide;
N-(5-chloropyridin-2-yl)-2-[((4-((N'-methyl—N'-(1-methylpiperidin4-yl)amino)methyl)-3-chlorothiophen-2-yl)carbonyl)amino]-3-(dimethyl)amino-5-chlorobenzamide; and
N-(5-chloropyridin-2-yl)-2-[((4-((N'-methyl—N(2-hydroxyethyl)amino)methyl)-3-chlorothiophen-2-yl)carbonyl)amino]-3-(di(2-methoxyethyl)amino)-5-chlorobenzamide.

40. The compound of claim 36 wherein
R$^2$ is —N(R$^{10}$)R$^{11}$ where:
  $R^{10}$ and $R^{11}$ together with the nitrogen to which they are attached form a N-heterocyclic ring containing zero to three additional hetero atoms, where the N-heterocylic ring is optionally substituted by one or more substituents selected from the group consisting of alkyl and —C(O)OR$^5$ where R$^5$ is hydrogen or alkyl.

41. The compound of claim 40 selected from the group consisting of:
N-(5-chloropyridin-2-yl)-2-[((4-((N'-methyl-N-(2-(dimethylamino)ethyl)amino)methyl)-3-chlorothiophen-2-yl)carbonyl)amino]-3-(morpholin-4-yl)-5-chlorobenzamide;
N-(5-chloropyridin-2-yl)-2-[((4-((N'-(2-hydroxyethyl)amino)methyl)-3-chlorothiophen-2-yl)carbonyl)amino]-3-(morpholin-4-yl)-5-chlorobenzamide;
N-(5-chloropyridin-2-yl)-2-[((4-((N'-methyl—N'-(2-hydroxyethyl)amino)methyl)-3-chlorothiophen-2-yl)carbonyl)amino]-3-(morpholin-4-yl)-5-chlorobenzamide;

N-(5-chloropyridin-2-yl)-2-[((4-((N'-methyl—N'-(1-methylpiperidin-4-yl)amino)methyl)-3-chlorothiophen-2-yl)carbonyl)amino]-3-(morpholin-4-yl)-5-chlorobenzamide;

N-(5-chloropyridin-2-yl)-2-[((4-((N'-methyl—N'-(2-(morpholin-4-yl)ethyl)amino)methyl)-3-chlorothiophen-2-yl)carbonyl)amino]-3-(morpholin-4-yl)-5-chlorobenzamide;

N-(5-chloropyridin-2-yl)-2-[((4-((N'-methyl-N'-(methylsulfonyl)amino)methyl)-3-chlorothiophen-2-yl)carbonyl)amino]-3-(morpholin-4-yl)-5-chlorobenzamide;

N-(5-chloropyridin-2-yl)-2-[((4-((N'-methyl-N'-(3-(dimethylamino)propyl)amino)methyl)-3-chlorothiophen-2-yl)carbonyl)amino]-3-(morpholin-4-yl)-5-chlorobenzamide;

N-(5-chloropynidin-2-yl)-2-[((4-((N'-methyl—N'-(2-(pyrrolidin-1-yl)ethyl)amino)methyl)-3-chlorothiophen-2-yl)carbonyl)amino]-3-(morpholin4-yl)-5-chlorobenzamide;

N-(5-chloropyridin-2-yl)-2-[((4-((N'-methyl—N'-(2-methoxyethyl)amino)methyl)-3-chlorothiophen-2-yl)carbonyl)amino]-3-(morpholin-4-yl)-5-chlorobenzamide;

N-(5-chloropyridin-2-yl)-2-[((4-((N'-methylsulfonyl—N'-(2-(pyrrolidin-1-yl)ethyl)amino)methyl)-3-chlorothiophen-2-yl)carbonyl)amino]-3-(morpholin-4-yl)-5-chlorobenzamide;

N-(5-chloropyridin-2-yl)-2-[((4-((N'-methyl—N'-(2-(pyrrolidin-1-yl)ethyl)ureido)methyl)-3-chlorothiophen-2-yl)carbonyl)amino]-3-(morpholin-4-yl)-5-chlorobenzamide;

N-(5-chloropyridin-2-yl)-2-[((4-((N'-methyl—N'-(methylsulfonyl)amino)methyl)-3-chlorothiophen-2-yl)carbonyl)amino]-3-(4-methylpiperazin-1-yl)-5-chlorobenzamide;

N-(5-chloropyridin-2-yl)-2-[((4-((N'-methyl—N'-(2-hydroxyethyl)amino)methyl)-3-chlorothiophen-2-yl)carbonyl)amino]-3-(4-methylpiperazin-1-yl)-5-chlorobenzamide;

N-(5-chloropyridin-2-yl)-2-[((4-((N'-methyl-N-(2-hydroxyethyl)amino)methyl)-3-chlorothiophen-2-yl)carbonyl)amino]-3-(pyrrolidin-1-yl)-5-chlorobenzamide;

N-(5-chloropyridin-2-yl)-2-[((4-((N'-(1-methylethyl)—N'-(2-(pyrrolidin-1-yl)ethyl)amino)methyl)-3-chlorothiophen-2-yl)carbonyl)amino]-3-(morpholin-4-yl)-5-chlorobenzamide;

N-(5-chloropyridin-2-yl)-2-[((4-((N'-methyl—N'-(2-hydroxyethyl)amino)methyl)-3-chlorothiophen-2-yl)carbonyl)amino]-3-(4-(ethoxycarbonyl)piperidin-1-yl)-5-chlorobenzamide;

N-(5-chloropyridin-2-yl)-2-[((4-((N'-methyl—Nt-(2-hydroxyethyl)amino)methyl)-3-chlorothiophen-2-yl)carbonyl)amino]-3-(4-(carboxy)piperidin-1-yl)-5-chlorobenzamide;

N-(5-chloropyridin-2-yl)-2-[((4-((N'-methyl—Nt-(2,3-dihydroxypropyl)amino)methyl)-3-chlorothiophen-2-yl)carbonyl)amino]-3-(morpholin4-yl)-5-chlorobenzamide;

N-(5-chloropyridin-2-yl)-2-[((4-((N'-methyl—N'-ethylureido)methyl)-3-chlorothiophen-2-yl)carbonyl)amino]-3-(4-ethylpiperazin-1-yl)-5-chlorobenzamide;

N-(5-chloropyridin-2-yl)-2-[((4-((N'-methyl—N'-(oxazolin-2-yl)amino)methyl)-3-chlorothiophen-2-yl)carbonyl)amino]-3-(morpholin4-yl)-5-chlorobenzamide;

N-(5-chloropyridin-2-yl)-2-[((4-((N'-ethyl—Nt-(oxazolin-2-yl)amino)methyl)-3-chlorothiophen-2-yl)carbonyl)amino]-3-(morpholin-4-yl)-5-chlorobenzamide;

N-(5-chloropyridin-2-yl)-2-[((4-((Nt-methyl—Nt-(4-trifluoromethyl-5-(methoxycarbonyl)pyrimidin-2-yl)amino)methyl)-3-chlorothiophen-2-yl)carbonyl)amino]-3-(morpholin-4-yl)-5-chlorobenzamide;

N-(5-chloropyridin-2-yl)-2-[((4-((N'-methyl—N'-(4-trifluoromethyl-5-carboxypyrimidin-2-yl)amino)methyl)-3-chlorothiophen-2-yl)carbonyl)amino]-3-(morpholin-4-yl)-5-chlorobenzamide;

N-(5-chloropyridin-2-yl)-2-[((4-((2-iminotetrahydrooxazol-3-yl)methyl)-3-chlorothiophen-2-yl)carbonyl)amino]-3-(morpholin4-yl)-5-chlorobenzamide; and N-(5-chloropyridin-2-yl)-2-[((4-((N'-methyl—N'-(tetrazol-5-yl)amino)methyl)-3-chlorothiophen-2-yl)carbonyl)amino]-3-(morpholin4-yl)-5-chlorobenzamide.

42. The compound of claim 1 wherein:

A is =N—;

m is 1;

n is 1;

D is —N(H)—C(O)—;

E is —C(O)—N(H)— (where the nitrogen is bonded to the 2-position of the pyridinyl ring);

$R^2$ is —O—$(R^8$—O$)_t R^5$ (where t is 1 to 3) or —O—$(R^8$—O$)_t$—$R^{19}$ where $R^5$ is hydrogen or alkyl, each $R^8$ is independently a straight or branched alkylene chain, and $R^{19}$ is heterocyclyl (optionally substituted by alkyl, aryl, aralkyl, halo, or haloalkyl);

$R^3$ is a radical of the formula (i):

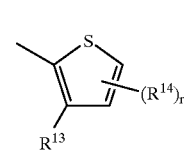

(i)

where r is 1;

$R^{13}$ is halo; and $R^{14}$ is —C($R^7$)H—N($R^{10}$)$R^{11}$ or —C($R^7$)H—N($R^5$)—$R^8$—[CH(OH)], —CH$_2$—O$R^5$ (where t is 1 to 6) where:

each $R^5$ is independently hydrogen or alkyl;

$R^8$ is a straight or branched alkylene chain;

$R^7$ is hydrogen;

$R^{10}$ and $R^{11}$ are each independently hydrogen, alkyl, formyl, —$R^8$—O$R^5$, —S(O)$_p$—$R^{15}$ (where p is 0 to 2), —R —N($R^5$)$R^6$, —$R^8$—C(O)O$R^5$, —C(O)—$R^{15}$, —C(O)NH$_2$, —C(S)NH$_2$, —C(O)—N($R^5$)$R^{15}$, —C(S)—N($R^5$)$R^{15}$, cycloalkyl (optionally substituted by —O$R^5$), heterocyclyl (optionally substituted by one or more substituents selected from the group consisting of alkyl, haloalkyl, oxo, —O$R^5$, and —C(O)O$R^5$), or heterocyclylalkyl (optionally substituted by one or more substituents selected from the group consisting of alkyl, haloalkyl, oxo, —O$R^5$, and —C(O)O$R^5$); where:

each $R^5$ and $R^6$ is independently hydrogen or alkyl;

each $R^8$ is independently a straight or branched alkylene chain; and each $R^{15}$ is alkyl, —$R^8$—O$R^5$, —$R^8$—C(O)O$R^5$, heterocyclyl (optionally substituted by —$R^8$—O$R^5$), or heterocyclylalkyl (optionally substituted by —O$R^5$);

or $R^{10}$ and $R^{11}$ together with the nitrogen to which they are attached form a N-heterocyclic ring containing zero to three additional hetero atoms, where the N-heterocylic ring is optionally substituted by one or more substituents selected from the group consisting of alkyl, oxo, =N($R^{17}$), —O$R^5$, —$R^8$—O$R^5$, and —N($R^5$)$R^6$; where each R⁵ and R⁶ is independently hydrogen or alkyl;
R⁸ is straight or branched alkylene chain; and
each R¹⁷ is independently hydrogen, alkyl, aryl, aralkyl, cyano, —OR⁵, —R⁸—OR⁵, —C(O)OR⁵, —R⁸—C(O)OR⁵, —C(O)—N(R⁵)R⁶, or —R⁸—C(O)—N(R⁵)R⁶; and
R⁴ is in the 5-position and is hydrogen or halo.

43. The compound of claim 42 selected from the group consisting of:

N-(5-chloropyridin-2-yl)-2-[((4-((N'-methyl—N'-(2-(dimethylamino)ethyl)amino)methyl)-3-chlorothiophen-2-yl)carbonyl)amino]-3-(2-hydroxyethoxy)-5-chlorobenzamide;

N-(5-chloropyridin-2-yl)-2-[((4-((N'-methyl—N'-(1-methylpiperidin-4-yl)amino)methyl)-3-chlorothiophen-2-yl)carbonyl)amino]-3-(2-hydroxyethoxy)-5-chlorobenzamide;

N-(5-chloropyridin-2-yl)-2-[((4-((N'-methyl—N'-(2-(pyrrolidin-1-yl)ethyl)amino)methyl)-3-chlorothiophen-2-yl)carbonyl)amino]-3-(2-methoxyethoxy)-5-chlorobenzamide, N-(5-chloropyridin-2-yl)-2-[((4-((N'-methyl—N'-(2-(pyrrolidin-1-yl)ethyl)amino)methyl)-3-chlorothiophen-2-yl)carbonyl)amino]-3-(2-hydroxyethoxy)-5-chlorobenzamide;

N-(5-chloropyridin-2-yl)-2-[((4-((N'-methyl—N'-(2,3-dihydroxypropyl)amino)methyl)-3-chlorothiophen-2-yl)carbonyl)amino]-3-(2-methoxyethoxy)-5-chlorobenzamide;

N-(5-chloropyridin-2-yl)-2-[((4-((N'-ethyl—N'-(2-hydroxyethyl)amino)methyl)-3-chlorothiophen-2-yl)carbonyl)amino]-3-(2-methoxyethoxy)-5-chlorobenzamide;

N-(5-chloropyridin-2-yl)-2-[((4-((N'-methyl—N'-(2-hydroxyethyl)amino)methyl)-3-chlorothiophen-2-yl)carbonyl)amino]-3-(2-methoxyethoxy)-5-chlorobenzamide, N-(5-chloropyridin-2-yl)-2-[((4-((N'-methyl—N'-(oxazolin-2-yl)amino)methyl)-3-chlorothiophen-2-yl)carbonyl)amino]-3-((2-(2-methoxyethoxy)ethoxy)-5-chlorobenzamide;

N-(5-chloropyridin-2-yl)-2-[((4-((N'-methyl—N'-(methylsulfonyl)amino)methyl)-3-chlorothiophen-2-yl)carbonyl)amino]-3-((2-(2-methoxyethoxy)ethoxy)-5-chlorobenzamide; and N-(5-chloropyridin-2-yl)-2-[((4-((N'-methyl—Nt-(2-hydroxyethyl)amino)methyl)-3-chlorothiophen-2-yl)carbonyl)amino]-3-(3-(pyridin-3-yloxy)propoxy)-5-chlorobenzamide.

44. The compound of claim 1 wherein:
A is =N—;
m is 1;
n is 1;
D is —N(H)—C(O)—;
E is —C(O)—N(H)— (where the nitrogen is bonded to the 2-position of the pyridinyl ring);
R² is —O—R —N(R¹⁰)R¹¹ where:
R⁸ is a straight or branched alkylene chain; and
R¹⁰ and R¹¹ are each independently hydrogen, alkyl or —R⁸—O—R⁵ where R⁸ is an alkylene chain, and R⁵ is hydrogen or alkyl; or
R¹⁰ and R¹¹ together with the nitrogen to which they are attached form a N-heterocyclic ring containing zero to three additional hetero atoms, where the N-heterocylic ring is optionally substituted by one or more substituents selected from the group consisting of alkyl and —C(O)OR⁵ where R⁵ is hydrogen or alkyl;

R³ is a radical of the formula (i):

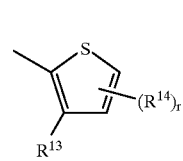

(i)

where r is 1;
R¹³ is halo; and
R¹⁴ is —C(R⁷)H—N(R¹⁰)R¹¹ where:
R⁷ is hydrogen;
R¹⁰ and R¹¹ are each independently hydrogen, alkyl, formyl, —R⁸—OR⁵, —S(O)ₚ—R¹⁵ (where p is 0 to 2), —R⁸—N(R⁵)R⁶, —R⁸—C(O)OR⁵, —C(O)—R₁₅, —C(O)NH₂, —C(S)NH₂, —C(O)—N(R⁵)R¹⁵, —C(S)—N(R⁵)R¹⁵, cycloalkyl (optionally substituted by —OR⁵), heterocyclyl (optionally substituted by one or more substituents selected from the group consisting of alkyl, haloalkyl, oxo, —OR⁵, and —C(O)OR⁵), or heterocyclylalkyl (optionally substituted by one or more substituents selected from the group consisting of alkyl, haloalkyl, oxo, —OR⁵ and —C(O)OR⁵), where:
each R⁵ and R⁶ is independently hydrogen or alkyl;
each R⁸ is independently a straight or branched alkylene chain; and
each R¹⁵ is alkyl, —R⁸—OR⁵, —R⁸—C(O)OR⁵, heterocyclyl (optionally substituted by —R⁸—OR⁵), or heterocyclylalkyl (optionally substituted by —OR⁵); and
R⁴ is in the 5-position and is hydrogen or halo.

45. The compound of claim 44 selected from the group consisting of:

N-(5-chloropyridin-2-yl)-2-[((4-((N'-methyl—N'-(1-methylpiperidin-4-yl)amino)methyl)-3-chlorothiophen-2-yl)carbonyl)amino]-3-(3-(morpholin-4-yl)propoxy)-5-chlorobenzamide;

N-(5-chloropyridin-2-yl)-2-[((4-((N'-methyl—N'-(2-hydroxyethyl)amino)methyl)-3-chlorothiophen-2-yl)carbonyl)amino]-3-(3-(pyrrolidin-1-yl)propoxy)-5-chlorobenzamide;

N-(5-chloropyridin-2-yl)-2-[((4-((N'-methyl—N'-(2-hydroxyethyl)amino)methyl)-3-chlorothiophen-2-yl)carbonyl)amino]-3-(3-(morpholin-4-yl)propoxy)-5-chlorobenzamide;

N-(5-chloropyridin-2-yl)-2-[((4-((N'-methyl—N'-(2-hydroxyethyl)amino)methyl)-3-chlorothiophen-2-yl)carbonyl)amino]-3-(2-(imidazol-1-yl)ethoxy)-5-chlorobenzamide;

N-(5-chloropyridin-2-yl)-2-[((4-((N'-methyl—N'-(2-hydroxyethyl)amino)methyl)-3-chlorothiophen-2-yl)carbonyl)amino]-3-(3-(imidazol-I -yl)propoxy)-5-chlorobenzamide;

N-(5-chloropyridin-2-yl)-2-[((4-((N'-methyl—N'-(methylsulfonyl)amino)methyl)-3-chlorothiophen-2-yl)carbonyl)amino]-3-(2-(pyrrolidin-1-yl)ethoxy)-5-chlorobenzamide;

N-(5-chloropyridin-2-yl)-2-[((4-((N'-methyl—N'-(methylsulfonyl)amino)methyl)-3-chlorothiophen-2-yl)carbonyl)amino]-3-(2-(imidazol-I -yl)ethoxy)-5-chlorobenzamide;

N-(5-chloropyridin-2-yl)-2-[((4-((N'-methyl—N'-(2-hydroxyethyl)amino)methyl)-3-chlorothiophen-2-yl)carbonyl)amino]-3-(2-(pyrrolidin-1-yl)ethoxy)-5-chlorobenzamide;

N-(5-chloropyridin-2-yl)-2-[((4-((N'-methyl—Nt-(methylsulfonyl)amino)methyl)-3-chlorothiophen-2-yl)carbonyl)amino]-3-(3-(4-ethylpiperazin-1-yl)propoxy)-5-chlorobenzamide; and N-(5-chloropyridin-2-yl)-2-[((4-((N'-methyl—N'-(methylsulfonyl)amino)methyl)-3-chlorothiophen-2-yl)carbonyl)amino]-3-(2-aminoethoxy)-5-chlorobenzamide.

46. The compound of claim 1 wherein:

A is =N—;
m is 1;
n is 1;
D is —N(H)—C(O)—;
E is —C(O)—N(H)— (where the nitrogen is bonded to the 2-position of the pyridinyl ring);
$R^2$ is —O—$R^8$—O—C(O)$R^5$, —O—$R^8$—CH(OH)—$CH_2$—N($R^{10}$)$R^{11}$, or —O—$R^8$—CH(OH)—$CH_2$—O$R^5$ where
  each $R^5$ is hydrogen or alkyl;
  $R^8$ is a straight or branched alkylene chain; and
  $R^{10}$ and $R^{11}$ are each independently hydrogen, alkyl or —$R^8$—O—$R^5$ where $R^8$ is an alkylene chain, and $R^5$ is hydrogen or alkyl; or
  $R^{10}$ and $R^{11}$ together with the nitrogen to which they are attached form a N-heterocyclic ring containing zero to three additional hetero atoms, where the N-heterocylic ring is optionally substituted by one or more substituents selected from the group consisting of alkyl and —C(O)O$R^5$ where $R^5$ is hydrogen or alkyl;
$R^3$ is a radical of the formula (i):

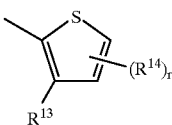

(i)

where r is 1;
$R^{13}$ is halo; and
$R^{14}$ is —C($R^7$)H—N($R^{10}$)$R^{11}$ or —C($R^7$)H—N($R^5$)—S(O)$_2$—N($R^{10}$)$R^{11}$ where:
  $R^5$ is hydrogen or alkyl;
  $R^7$ is hydrogen;
  $R^{10}$ and $R^{11}$ are each independently hydrogen, alkyl, formyl, —$R^8$—O$R^5$, —S(O)$_p$—$R^{15}$ (where p is 0 to 2), —$R^8$—N($R^5$)$R^6$, —$R^8$—C(O)O$R^5$, —C(O)—$R^{15}$, —C(O)NH$_2$, —C(S)NH$_2$, —C(O)—N($R^5$)$R^{15}$, —C(S)—N($R^5$)$R^{15}$, cycloalkyl (optionally substituted by —O$R^5$), heterocyclyl (optionally substituted by one or more substituents selected from the group consisting of alkyl, haloalkyl, oxo, —O$R^5$, and —C(O)O$R^5$), or heterocyclylalkyl (optionally substituted by one or more substituents selected from the group consisting of alkyl, haloalkyl, oxo, —O$R^5$, and —C(O)O$R^5$); where:
    each $R^5$ and $R^6$ is independently hydrogen or alkyl;
    each $R^8$ is independently a straight or branched alkylene chain; and
    each R is alkyl, —$R^8$—O$R^5$, —$R^8$—C(O)O$R^5$, heterocyclyl (optionally substituted by —$R^8$—O$R^5$), or heterocyclylalkyl (optionally substituted by —O$R^5$); and
$R^4$ is in the 5-position and is hydrogen or halo.

47. The compound of claim 46 selected from the group consisting of:

N-(5-chloropyridin-2-yl)-2-[((4-((N'-methyl—N'-(2-(pyrrolidin-1-yl)ethyl)amino)methyl)-3-chlorothiophen-2-yl)carbonyl)amino]-3-(2-acetoxyethoxy)-5-chlorobenzamide;

N-(5-chloropyridin-2-yl)-2-[((4-((N'-methyl-N'-(methylsulfonyl)amino)methyl)-3-chlorothiophen-2-yl)carbonyl)amino]-3-(2-hydroxy-3-(pyrrolidin-1-yl)propoxy)-5-chlorobenzamide;

N-(5-chloropyridin-2-yl)-2-[((4-((N'-methyl—N'-((dimethylamino)sulfonyl)amino)methyl)-3-chlorothiophen-2-yl)carbonyl)amino]-3-(2-hydroxy-3-(pyrrolidin-1-yl)propoxy)-5-chlorobenzamide;

N-(5-chloropyridin-2-yl)-2-[((4-((N'-methyl—N'-(methylsulfonyl)amino)methyl)-3-chlorothiophen-2-yl)carbonyl)amino]-3-(2-hydroxy-3-(imidazol-1-yl)propoxy)-5-chlorobenzamide; and N-(5-chloropyridin-2-yl)-2-[((4-((N'-methyl—N'-(methylsulfonyl)amino)methyl)-3-chlorothiophen-2-yl)carbonyl)amino]-3-(2-hydroxy-3-methoxypropoxy)-5-chlorobenzamide.

48. The compound of claim 1 wherein:

A is =N—;
m is 1 to 3;
n is 1;
D is —N($R^5$)—C()—(where Z is oxygen and $R^5$ is hydrogen or alkyl);
E is —C(Z)—N($R^5$)—(where Z is oxygen, $R^5$ is hydrogen or alkyl, and the nitrogen is attached to the pyridinyl ring);
each $R^1$ is independently hydrogen, halo or —O$R^5$;
or two adjacent $R^1$'s together with the carbons to which they are attached form a dioxole ring fused to the phenyl ring wherein the dioxole ring is optionally substituted by alkyl;
$R^2$ is hydrogen;
$R^3$ is a radical of the formula (i):

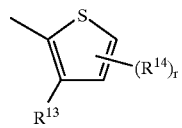

(i)

where r is 1;
$R^{13}$ is halo; and
$R^{14}$ is —C($R^7$)H—N($R^{10}$)$R^{11}$ where:
  $R^7$ is hydrogen; and
  $R^{10}$ and $R^{11}$ are each independently hydrogen, alkyl, formyl, —$R^8$—O$R^5$, —S(O)$_p$—$R^{15}$ (where p is 0 to 2), —$R^8$—N($R^5$)$R^6$, —$R^8$—C(O)O$R^5$, —C(O)—$R^{15}$, —C(O)NH$_2$, —C(S)NH$_2$, —C(O)—N($R^5$)$R^{15}$, —C(S)—N($R^5$)$R^{15}$, cycloalkyl (optionally substituted by —O$R^5$), heterocyclyl (optionally substituted by one or more substituents selected from the group consisting of alkyl, haloalkyl, oxo, —O$R^5$, and —C(O)O$R^5$), or heterocyclyalkyl (optionally substituted by one or more substituents selected from the group consisting of alkyl, haloalkyl, oxo, —O$R^5$, and —C(O)O$R^5$); where:
    each $R^5$ and $R^6$ is independently hydrogen or alkyl;
    each $R^8$ is independently a straight or branched alkylene chain; and
    each $R^{15}$ is alkyl, —$R^8$—O$R^5$, —$R^8$—C(O)O$R^5$, heterocyclyl (optionally substituted by —$R^8$—O$R^5$), or heterocyclyalkyl (optionally substituted by —O$R^5$); and
$R^4$ is in the 5-position and is hydrogen or halo.

49. The compound of claim 48 selected from the group consisting of:

219

N-(5-chloropyridin-2-yl)-2-[((4-((N'-methyl—N'-(2-hydroxyethyl)amino)methyl)-3-chlorothiophen-2-yl)carbonyl)amino]-3,4,5-trimethoxybenzamide;

5-(N-(5-chloropyridin-2-yl)amino)carbonyl-6-[4-((N'-methyl—N'-(oxazolin-2-yl)amino)methyl)-3-chlorothiophen-2-yl)carbonyl]amino-1,3-benzodioxole;

5-(N-(5-chloropyridin-2-yl)amino)carbonyl-6-[4-((N'-methyl—N'-(2-hydroxyethyl)amino)methyl)-3-chlorothiophen-2-yl)carbonyl]amino-1,3-benzodioxole; and 5-(N-(5-chloropyridin-2-yl)amino)carbonyl-6-[4-((N'-(2-methoxyethyl)—N'-(oxazolin-2-yl)amino)methyl)-3-chlorothiophen-2-yl)carbonyl]amino-1,3-benzodioxole.

50. A method of treating a human having a disease-state characterized by thrombotic activity, wherein the method comprises administering to a human in need thereof a therapeutically effective amount of a compound of formula (I):

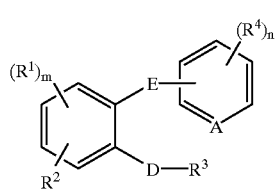

wherein:

A is =N—;
m is 1 to 3;
n is 1 to 4;
D is —N(R$^5$)—C(Z)— or —N(R$^5$)—S(O)$_p$— (where p is 0 to 2; Z is oxygen, sulfur or H$_2$; and the nitrogen atom is directly bonded to the phenyl ring having the R$^1$ and R$^2$ substituents);
E is —C(Z)—N(R$^5$)— or —S(O)$_p$—N(R$^5$)—(where p is 0 to 2; Z is oxygen, sulfur or H$_2$; and the nitrogen atom can be bonded to the phenyl ring having the R$^1$ and the R$^2$ substituents or to the aromatic ring having the R$^4$ substituent);
each R$^1$ is independently hydrogen, alkyl, aryl, aralkyl, halo, haloalkyl, cyano, —OR$^5$, —S(O)$_p$—R$^9$ (where p is 0 to 2), —C(O)OR$^5$, —C(O)N(R$^5$)R$^6$, —N(R$^5$)R$^6$, —O—C(O)R$^5$, or —N(R$^5$)—CH(R$^{12}$)—C(O)OR$^5$;
or two adjacent R$^1$'s together with the carbons to which they are attached form a heterocyclic ring fused to the phenyl ring wherein the heterocyclic ring is optionally substituted by one or more substituents selected from the group consisting of alkyl, aryl and aralkyl;
R$^2$ is hydrogen, alkyl, aryl, aralkyl, halo, haloalkyl, cyano, —OR$^5$, —S(O)$_p$—R$^9$ (where p is 0 to 2), —C(O)OR$^5$, —OC(O)—R$^5$, —C(O)N(R$^5$)R$^6$, —N(R$^{10}$)R$^{11}$, —C(R$^7$)H—N(R$^{10}$)R$^{11}$, —C(R$^7$)H—R$^8$—N(R$^{10}$)R$^{11}$, —C(R$^7$)H—OR$^5$, —C(R$^7$)H—R$^8$—OR$^5$, —C(R$^7$)H—S(O)$_p$—R$^9$ (where p is 0 to 2), —C(R$^7$)H—R$^8$—S(O)$_p$—R$^9$ (where p is 0 to 2), —O—R$^8$—S(O)$_p$—R$^9$ (where p is 0 to 2), —C(R$^7$)H—N(R$^5$)R$^6$, —C(R$^7$)H—R$^8$—N(R$^5$)R$^6$, —O—R$^8$—CH(OH)—CH$_2$—N(R$^{10}$)R$^{11}$, —O—R$^8$—N(R$^{10}$)R$^{11}$, —O—R$^8$—O—C(O)R$^5$, —O—R$^8$—CH(OH)—CH$_2$—OR$^5$, —O—(R$^8$—O)$_t$—R$^5$ (where t is 1 to 6), —O—(R$^8$—O)$_t$—R$^{19}$ (where t is 1 to 6), —O—R$^8$—C(O)R$^5$, —O—R$^8$—C(O)R$^{19}$, —O—R$^8$—C(O)OR$^5$, —N(R$^5$)—R$^8$—N(R$^{10}$)R$^{11}$, —S(O)$_p$—R$^8$—N(R$^5$)R$^6$ (where p is 0 to 2), —S(O)$_p$—R$^8$—C(O)OR$^5$ (where p is 0 to 2), or —N(R$^5$)—CH(R$^{12}$)—C(O)OR$^5$;

220

R$^3$ is a radical of formula (i):

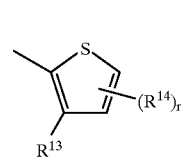

where:
r is 1 or 2;
R$^{13}$ is hydrogen, alkyl, halo, haloalkyl, —N(R$^5$)R$^6$, —C(R$^7$)H—N(R$^5$)R$^6$, OR$^5$, —R$^8$—OR$^5$, —S(O)$_p$—R$^8$—N(R$^5$)R$^6$ (where p is 0 to 2) or heterocyclylalkyl (where the heterocyclic ring is optionally substituted by one or more substituents selected from the group consisting of alkyl, halo, aralkyl, nitro and cyano); and
each R$^{14}$ is independently hydrogen, alkyl, halo, formyl, acetyl, cyano, —R$^8$—CN, —N(R$^{10}$)R$^{11}$, —C(R$^7$)H—N(R$^{10}$)R$^{11}$, —C(R$^7$)H—R$^8$—N(R$^{10}$)R$^{11}$, —C(R$^7$)H—N$^{\oplus}$(R$^9$)(R$^{16}$)$_2$, —C(R$^7$)H—R$^8$—N$^{\oplus}$(R$^9$)(R$^{16}$)$_2$, —C(O)OR$^5$, —C(R$^7$)H—C(O)OR$^5$, —C(R$^7$)H—R$^8$—C(O)OR$^5$, —OR$^5$, —C(R$^7$)H—OR$^5$, —C(R$^7$)H—R$^8$—OR$^5$, —C(R$^7$)H—O—R$^{15}$, —S(O)$_p$—R$^{15}$ (where p is 0 to 2), —C(R$^7$)H—S(O)$_p$—R$^{15}$ (where p is 0 to 2), —C(R$^7$)H—R$^8$—S(O)$_p$—R$^{15}$ (where p is 0 to 2), —S(O)$_p$—N(R$^5$)R$^6$ (where p is 0 to 2), —C(O)N(R$^5$)R$^6$, —C(R$^7$)H—C(O)N(R$^5$)R$^6$, —C(R$^7$)H—R$^8$—C(O)N(R$^5$)R$^6$, —C(R$^7$)H—N(R$^5$)—(R$^8$—O)t—R$^5$ (where t is 1 to 6), —C(R$^7$)H—R$^8$—N(R$^5$)—(R$^8$-O)$_t$—R$^5$ (where t is 1 to 6), —C(R$^7$)H—O—(R$^8$—O)$_t$—R$^5$ (where t is 1 to 6), —C(R$^7$)H—R—O—(R$^8$—O)$_t$—R$^5$ (where t is 1 to 6), —O—R$^8$—CH(OH)—CH$_2$—OR$^5$, —C(R$^7$)H—O—R$^8$—CH(OH)—CH$_2$—OR$^5$, —C(R$^7$)H—N(R$^5$)—R$^8$-[CH(OH)]$_t$—CH$_2$—OR$^5$ (where t is 1 to 6), —C(R$^7$)H—N(R$^5$)—S(O)$_2$—N(R$^{10}$)R$^{11}$, —C(R$^7$)H—N(R$^{10}$)—C(NR$^{17}$)—N(R$^{10}$)R$^{11}$, —C(R$^7$)H—N(R$^{10}$)—C(NR$^{17}$)—R$^{10}$, —C(NR$^{17}$)—N(R$^5$)R$^6$, —C(R$^7$)H—C(NR$^{17}$)—N(R$^5$)R$^6$, —C(R$^7$)H—O—N(R$^5$)R$^6$, heterocyclyl (wherein the heterocyclyl radical is not attached to the radical of formula (i) through a nitrogen atom and is optionally substituted by alkyl, aryl, aralkyl, halo, haloalkyl, oxo, —OR$^5$, —C(O)OR$^5$, —N(R$^5$)R$^6$ or —C(O)N(R$^5$)R$^6$), or heterocyclylalkyl (wherein the heterocyclyl radical is not attached to the alkyl radical through a nitrogen atom and is optionally substituted by one or more substituents selected from the group consisting of alkyl, aryl, aralkyl, halo, haloalkyl, oxo, —OR$^5$, —C(O)OR$^5$, —N(R$^5$)R$^6$ and —C(O)N(R$^5$)R$^6$);
each R$^4$ is independently hydrogen, alkyl, halo, haloalkyl, cyano, nitro, —OR$^5$, —C(O)OR$^5$, —N(R$^5$)R$^6$, —C(O)N(R$^5$)R$^6$, or —R$^8$—N(R$^5$)R$^6$;
R$^5$ and R$^6$ are each independently hydrogen, alkyl, aryl or aralkyl;
each R$^7$ is independently hydrogen or alkyl;
each R$^8$ is independently a straight or branched alkylene, alkylidene or alkylidyne chain;
each R$^9$ is independently alkyl, aryl or aralkyl;
R$^{10}$ and R$^{11}$ are each independently hydrogen, alkyl, haloalkyl, aryl, aralkyl, formyl, cyano, —R$^8$—CN, —OR$^5$, —R$^8$—OR$^5$, —S(O)$_p$—R$^{15}$ (where p is 0 to 2), —R$^8$—S(O)$_p$—R$^{15}$ (where p is 0 to 2), —N(R$^5$)R$^6$, —R$^8$—N(R$^5$)R$^6$, —R$^8$—C(O)OR$^5$, —C(O)—R$^{15}$, —C(O)NH$_2$, —R$^8$—C(O)NH$_2$, —C(S)NH$_2$, —C(O)—S—R$^5$, —C(O)—N(R$^5$)R$^{15}$, —R$^8$—C(O)—N(R$^5$)R$^{15}$, —C(S)—N($R^5$)$R^{15}$, —$R^8$—N($R^5$)—C(O)H, —$R^8$—N($R^5$)—C(O)$R^{15}$, —C(O)O—$R^8$—N($R^5$)$R^6$, —C(N($R^5$)$R^6$)=C($R^{18}$)$R^{10}$, —$R^8$—N($R^5$)-P(O)(O$R^5$)$_2$, cycloalkyl (optionally substituted by one or more substituents selected from the group consisting of alkyl, halo and —O$R^5$), heterocyclyl (optionally substituted by one or more substituents selected from the group consisting of alkyl, aryl, aralkyl, halo, haloalkyl, oxo, —O$R^5$, —$R^8$—O$R^5$, —C(O)O$R^5$, —S(O)$_p$—R9 (where p is 0 to 2), —R—S(O)$_p$—$R^9$ (where p is 0 to 2), —N($R^5$)$R^6$ and —C(O)N($R^5$)$R^6$), or heterocyclylalkyl (optionally substituted by one or more substituents selected from the group consisting of alkyl, aryl, aralkyl, halo, haloalkyl, oxo, —O$R^5$, —$R^8$—O$R^5$, —C(O)O$R^5$, —S(O)$_p$—$R^9$ (where p is 0 to 2), —$R^8$—S(O)$_p$—$R^9$ (where p is 0 to 2), —N($R^5$)$R^6$ and —C(O)N($R^5$)$R^6$);

or $R^{10}$ and $R^{11}$ together with the nitrogen to which they are attached form a N-heterocyclic ring containing zero to three additional hetero atoms, where the N-heterocyclic ring is optionally substituted by one or more substituents selected from the group consisting of alkyl, halo, haloalkyl, aryl, aralkyl, oxo, nitro, cyano, —$R^8$—CN, =N($R^{17}$), —O$R^5$, —C(O)O$R^5$, —$R^8$—C(O)O$R^5$, —N($R^5$)$R^6$, —$R^8$—N($R^5$)$R^6$, —C(O)N($R^5$)$R^6$, —$R^8$—C(O)N($R^5$)$R^6$, —N($R^5$)—N($R^5$)$R^6$, —C(O)$R^5$, —C(O)—($R^8$—O)$_t$—$R^5$ (where t is 1 to 6), —S(O)p—R9 (where p is 0 to 2), —$R^8$—S(O)$_p$—$R^9$ (where p is 0 to 2), —($R^8$-O)$_t$—$R^5$ (where t is 1 to 6), and heterocyclyl (optionally substituted by one or more substituents selected from the group consisting of alkyl, aryl, aralkyl, halo, haloalkyl, —O$R^5$, —C(O)O$R^5$, —N($R^5$)$R^6$, and —C(O)N($R^5$)$R^6$);

$R^{12}$ is a side chain of an α-amino acid;

each $R^{15}$ is independently alkyl, cycloalkyl, haloalkyl, aryl, aralkyl, —$R^8$—O—C(O)—$R^5$, —$R^8$—O$R^5$, —N($R^5$)$R^6$, —$R^8$—N($R^5$)$R^6$, —$R^8$—C(O)O$R^5$, heterocyclyl (optionally substituted by one or more substituents selected from the group consisting of alkyl, aryl, aralkyl, halo, haloalkyl, —O$R^5$, —$R^8$—O$R^5$, —C(O)O$R^5$, —N($R^5$)$R^6$, and —C(O)N($R^5$)$R^6$), or heterocyclylalkyl (optionally substituted by one or more substituents selected from the group consisting of alkyl, aryl, aralkyl, halo, haloalkyl, —O$R^5$, —$R^8$—O$R^5$, —C(O)O$R^5$, —N($R^5$)$R^6$, and —C(O)N($R^5$)$R^6$);

or $R^5$ and $R^{15}$ together with the nitrogen to which they are attached form a N-heterocyclic ring containing zero to three additional hetero atoms, where the N-heterocyclic ring is optionally substituted by one or more substituents selected from the group consisting of alkyl, aryl, aralkyl, amino, monoalkylamino, dialkylamino, —O$R^5$, —C(O)O$R^5$, aminocarbonyl, monoalkylaminocarbonyl, and dialkylaminocarbonyl;

each $R^{16}$ is independently alkyl, aryl, aralkyl, —$R^8$—O$R^5$, —$R^8$—N($R^5$)$R^6$, cycloalkyl (optionally substituted by one or more substituents selected from the group consisting of alkyl, halo and —O$R^5$), heterocyclyl (optionally substituted by alkyl, aryl, aralkyl, halo, haloalkyl, —O$R^5$, —C(O)O$R^5$, —N($R^5$)$R^6$ or —C(O)N($R^5$)$R^6$), or heterocyclylalkyl (optionally substituted by one or more substituents selected from the group consisting of alkyl, aryl, aralkyl, halo, haloalkyl, —O$R^5$, —C(O)O$R^5$, —N($R^5$)$R^6$ and —C(O)N($R^5$)$R^6$); or both $R^{16}$'s together with the nitrogen to which they are attached (and wherein the $R^9$ substituent is not present) form an aromatic N-heterocyclic ring containing zero to three additional hetero atoms, where the N-heterocyclic ring is optionally substituted by one or more substituents selected from the group consisting of alkyl, aryl, aralkyl, —O$R^5$, —C(O)O$R^5$, —$R^8$—C(O)O$R^5$, —N($R^5$)$R^6$, —$R^8$—N($R^5$)$R^6$, —C(O)$R^5$, —C(O)—($R^8$—O)$_t$—$R^5$ (where t is 1 to 6), and —($R^8$—O)$_t$—$R^5$ (where t is 1 to 6);

each $R^{17}$ is independently hydrogen, alkyl, aryl, aralkyl, cyano, —O$R^5$, —$R^8$—O$R^5$, —C(O)O$R^5$, —$R^8$—C(O)O$R^5$, —C(O)—N($R^5$)$R^6$, or —$R^8$—C(O)—N($R^5$)$R^6$;

$R^{18}$ is hydrogen, alkyl, aryl, aralkyl, cyano, —C(O)O$R^6$, or —NO$_2$; and each $R^{19}$ is cycloalkyl, haloalkyl, —$R^8$—O$R^5$, —$R^8$—N($R^5$)$R^6$, —$R^8$—C(O)O$R^5$, —$R^8$—C(O)N($R^5$)$R^6$, heterocyclyl (optionally substituted by alkyl, aryl, aralkyl, halo, haloalkyl, —O$R^5$, —C(O)O$R^5$, —N($R^5$)$R^6$ or —C(O)N($R^5$)$R^6$), or heterocyclylalkyl (optionally substituted by one or more substituents selected from the group consisting of alkyl, aryl, aralkyl, halo, haloalkyl, —O$R^5$, —C(O)O$R^5$, —N($R^5$)$R^6$ and —C(O)N($R^5$)$R^6$); as a single stereoisomer or a mixture thereof; or a pharmaceutically acceptable salt thereof.

\* \* \* \* \*